US012790295B2

(12) United States Patent
Arve et al.

(10) Patent No.: US 12,790,295 B2
(45) Date of Patent: Nov. 10, 2026

(54) SUBSTITUTED PYRROLIDIN-2-ONES, SALTS THEREOF AND THEIR USE AS HERBICIDALLY ACTIVE SUBSTANCES

(71) Applicant: Bayer Aktiengesellschaft, Leverkusen (DE)

(72) Inventors: Lars Arve, Leverkusen (DE); Jens Frackenpohl, Leverkusen (DE); Hansjörg Dietrich, Leverkusen (DE); Ines Heinemann, Leverkusen (DE); Jan Dittgen, Leverkusen (DE); Dirk Schmutzler, Leverkusen (DE); Elmar Gatzweiler, Leverkusen (DE); Anna Maria Reingruber, Leverkusen (DE); Birgit Bollenbach-Wahl, Leverkusen (DE)

(73) Assignee: BAYER AKTIENGESELLSCHAFT, Leverkusen (DE)

( * ) Notice: Subject to any disclaimer, the term of this patent is extended or adjusted under 35 U.S.C. 154(b) by 455 days.

(21) Appl. No.: 18/551,766

(22) PCT Filed: Mar. 18, 2022

(86) PCT No.: PCT/EP2022/057153

§ 371 (c)(1),
(2) Date: Sep. 21, 2023

(87) PCT Pub. No.: WO2022/200208

PCT Pub. Date: Sep. 29, 2022

(65) Prior Publication Data

US 2024/0199542 A1 Jun. 20, 2024

(30) Foreign Application Priority Data

Mar. 22, 2021 (EP) .................................... 21163986

(51) Int. Cl.

| | |
|---|---|
| ***C07D 207/46*** | (2006.01) |
| ***A01N 43/36*** | (2006.01) |
| ***A01N 43/40*** | (2006.01) |
| ***A01N 43/653*** | (2006.01) |
| ***A01N 43/82*** | (2006.01) |
| ***A01P 13/00*** | (2006.01) |
| ***C07D 401/12*** | (2006.01) |
| ***C07D 403/12*** | (2006.01) |
| ***C07D 405/06*** | (2006.01) |
| ***C07D 409/12*** | (2006.01) |
| ***C07D 413/12*** | (2006.01) |
| ***C07D 417/12*** | (2006.01) |

(52) U.S. Cl.

CPC ........... *C07D 207/46* (2013.01); *A01N 43/36* (2013.01); *A01N 43/40* (2013.01); *A01N 43/653* (2013.01); *A01N 43/82* (2013.01); *A01P 13/00* (2021.08); *C07D 401/12* (2013.01); *C07D 403/12* (2013.01); *C07D 405/06* (2013.01); *C07D 409/12* (2013.01); *C07D 413/12* (2013.01); *C07D 417/12* (2013.01)

(58) Field of Classification Search

CPC ....... C07D 207/46; A01P 13/00; A01N 43/36; A01N 43/40; A01N 43/653; A01N 43/82

See application file for complete search history.

(56) References Cited

U.S. PATENT DOCUMENTS

| | | | |
|---|---|---|---|
| 7,491,748 B2 | 2/2009 | Tani et al. | |
| 2003/0171218 A1 | 9/2003 | Bojack et al. | |
| 2019/0225575 A1 * | 7/2019 | Fischl .................. | C07D 207/27 |

FOREIGN PATENT DOCUMENTS

| | | | | |
|---|---|---|---|---|
| DE | 1925198 A1 | 11/1970 | | |
| EP | 0055215 A1 | 6/1982 | | |
| GB | 2015521 A * | 9/1979 | ........... | C07D 207/27 |
| JP | H04270283 A | 9/1992 | | |
| JP | 4529119 B2 | 8/2010 | | |

(Continued)

OTHER PUBLICATIONS

Du, J.X., et al., "A novel approach to the Geissman-Waiss lactone and a key intermediate in the synthesis of pyrrolidine trans-lactones," Tetrahedron: Asymmetry, 15: 3461-3466 (2004).

(Continued)

*Primary Examiner* — Michael B. Pallay

(74) *Attorney, Agent, or Firm* — Paul D. Tietz; Alexandria Quezada

(57) ABSTRACT

The present invention relates to substituted pyrrolidin-2-ones of the general formula (I) or salts thereof, (I)

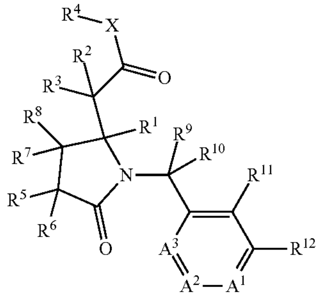

where the radicals in the general formula (I) correspond to the definitions given in the description, and to their use as herbicides, in particular for controlling broad-leaved weeds and/or weed grasses in crops of useful plants and/or as plant growth regulators for influencing the growth of crops of useful plants.

20 Claims, No Drawings

(56) References Cited

FOREIGN PATENT DOCUMENTS

| | | | |
|---|---|---|---|
| WO | 9720838 | A1 | 6/1997 |
| WO | 2009038412 | A2 | 3/2009 |
| WO | 2009077559 | A2 | 6/2009 |
| WO | 2019068841 | A1 | 4/2019 |
| WO | 2019185868 | A1 | 10/2019 |

OTHER PUBLICATIONS

Homerin, G., et al., "Pyroglutamide-Based P2X7 Receptor Antagonists Targeting Inflammatory Bowel Disease," J. Med. Chem., 63: 2074-2094 (2020).

Kono, M., et al., "Rhodium-Catalyzed Stereospecific C—H Amination for the Construction of Spiroaminal Cores: Reactivity Difference between Nitrenoid and Carbenoid Species against Amide Functionality," Chem. Eur. J., 23: 7428-7432 (2017).

* cited by examiner

SUBSTITUTED PYRROLIDIN-2-ONES, SALTS THEREOF AND THEIR USE AS HERBICIDALLY ACTIVE SUBSTANCES

The present application is a 35 U.S.C. § 371 national phase entry of International Application No. PCT/EP2022/057153, filed on Mar. 18, 2022, which claims priority to European Patent Application No. 21163986.9, filed Mar. 22, 2021, the contents of each of which are hereby incorporated by reference in their entirety.

The invention relates to the technical field of crop protection agents, in particular that of herbicides for the selective control of broad-leaved weeds and weed grasses in crops of useful plants. Specifically, the present invention relates to substituted pyrrolidin-2-ones and salts thereof, to processes for their preparation and to their use as herbicides.

In their application, crop protection agents known to date for the selective control of harmful plants in crops of useful plants or active compounds for controlling unwanted vegetation sometimes have disadvantages, be it (a) that they have no or insufficient herbicidal activity against particular harmful plants, (b) that the spectrum of harmful plants which can be controlled with an active compound is not broad enough, (c) that their selectivity in crops of useful plants is too low and/or (d) that they have a toxicologically unfavourable profile.

Furthermore, some active compounds which can be used as plant growth regulators for a number of useful plants cause unwanted reduced harvest yields in other useful plants or are not compatible with the crop plant, or only within a narrow application rate range. Some of the known active compounds cannot be produced economically on an industrial scale owing to precursors and reagents which are difficult to obtain, or they have only insufficient chemical stabilities. In the case of other active compounds, the activity is too highly dependent on environmental conditions, such as weather and soil conditions.

The herbicidal activity of these known compounds, in particular at low application rates, and/or their compatibility with crop plants remain deserving of improvement.

Various documents describe substituted pyrrolidin-2-ones as having useful biological properties and uses. WO 2009/077559 and WO 2019/185868 demonstrate that substituted pyrrolidine-2-one carboxamides can modulate the P2X7 receptor function and are therefore useful in the treatment of pain, inflammation, cancer and neurodegenerative diseases. In addition, WO 2009/038412 discloses that substituted pyrrolidin-2-ones or pharmaceutically acceptable salts thereof can be used as a method for treating neurodegenerative diseases, in particular Alzheimer's disease, via inhibition of beta-secretase.

WO2019/068841 concerns the preparation of pyrrolidin-2-one-substituted beta-oxocarboxamides and their use for the treatment of viral infections by acting as PLA2G16. WO 2003/016254 relates to substituted 2,3-Dihydro-2-(1-naphthalenylmethyl)-3-oxo-1H-isoindole-1-acetic acids and other compounds and their use as antagonists of prostaglandin E2 (PEG2) receptors. Furthermore, JP04270283 discloses dimeric pyrrolidin-2-one motifs forming a diazabicyclo[3.3.0]octane dione core that can be used as peptidic antiulcer agents.

The publication entitled "Pyroglutamide-based P2X7 receptor antagonists targeting inflammatory Bowel Disease" (J. Med. Chem. 2020, 63, 2074-2094) shows methods to prepare compounds containing a pyrrolidin-2-one core, as well as their potential for the treatment of inflammatory diseases. Further procedures to prepare compounds containing a pyrrolidin-2-one moiety are outlined in the publications entitled "Rhodim-catalyzed stereospecific C—H amination for the construction of spiroaminal cores: Reactivity difference between nitrenoid and carbenoid species against amide functionality" (Chemistry—a European Journal 2017, 23, 7428) and "A novel approach to the Geissman-Waiss lactone and a key intermediate in the synthesis of pyrrolidine trans-lactones" (Tetrahedron: Asymmetry 2004, 15, 3461).

However, the use of substituted pyrrolidin-2-ones or salts thereof as herbicidally active compounds has not been previously described. Surprisingly, it has now been found that certain substituted pyrrolidin-2-ones or salts thereof are particularly suitable as herbicides.

In their application, herbicides that are known to date for controlling harmful plants in crops of useful plants or herbicides for controlling unwanted vegetation sometimes have disadvantages, be it (a) that they have no or insufficient herbicidal activity against particularly harmful plants, (b) that the spectrum of harmful plants which can be controlled with an active compound is not broad enough, and/or (c) that the selectivity of the herbicides in and their compatibility with crop plants is too low, thereby causing unwanted damage and/or unwanted reduced harvest yields of the crops.

Thus, there is still a need for alternative herbicides, in particular highly active herbicides that are useful at low application rates and/or having good compatibility with crop plants, for the selective application in plant crops or use on non-crop land. It is also desirable to provide alternative chemical active compounds which may be used in an advantageous manner as herbicides or plant growth regulators.

It is therefore an objective of the present invention to provide compounds having herbicidal activity which are highly effective against economically important harmful plants even at relatively low application rates and that can be used selectively in crop plants. It has now been found that the compounds following general formula (I) or the salts thereof meet the said objectives.

Accordingly, the present invention provides substituted pyrrolidin-2-ones of the general formula (I) or salts thereof (I)

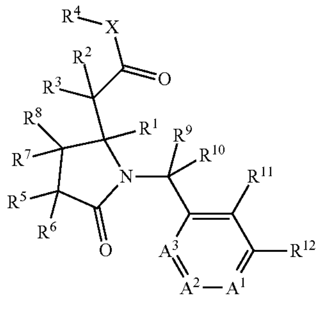

in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, $(C_1$-$C_8)$-alkyl, $(C_1$-$C_{10})$-haloalkyl, $(C_2$-$C_8)$-alkenyl, $(C_2$-$C_8)$-alkynyl, $(C_3$-$C_8)$-cycloalkyl, $(C_3$-$C_8)$-cycloalkyl-$(C_1$-$C_8)$-alkyl, aryl-$(C_1$-

$C_8$)-alkyl, $R^{19}$—O—($C_1$-$C_8$)-alkyl, heteroaryl-($C_1$-$C_8$)-alkyl, heterocyclyl-($C_1$-$C_8$)-alkyl, $R^2$ and $R^3$ independently of one another represent hydrogen, halogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, $OR^{19}$, $R^{17}R^{18}$N—($C_1$-$C_8$)-alkyl, ($C_3$-$C_{10}$)-cycloalkyl-($C_1$-$C_8$)-alkyl, C(═O)$R^{19}$, C(═O)O$R^{19}$, C(═O)N$R^{17}R^{18}$, $R^{20}S(O)_m$—($C_1$-$C_8$)-alkyl, $R^4$ represents hydrogen, ($C_1$-$C_8$)-alkyl, ($C_1$-$C_{10}$)-haloalkyl, cyano-($C_1$-$C_8$)-alkyl, nitro-($C_1$-$C_8$)-alkyl, ($C_3$-$C_8$)-cycloalkyl, ($C_3$-$C_8$)-cycloalkyl-($C_1$-$C_8$)-alkyl, ($C_2$-$C_8$)-alkenyl, ($C_2$-$C_8$)-alkynyl, ($C_2$-$C_8$)-haloalkenyl, ($C_2$-$C_8$)-haloalkynyl, ($C_3$-$C_{10}$)-halocycloalkyl, ($C_4$-$C_{10}$)-cycloalkenyl, ($C_4$-$C_{10}$)-halocycloalkenyl, aryl-($C_1$-$C_8$)-alkyl, $R^{19}$O—($C_1$-$C_8$)-alkyl, $R^{19}$O—($C_1$-$C_8$)-alkoxy-($C_1$-$C_8$)-alkyl, $R^{20}S(O)_m$—($C_1$-$C_8$)-alkyl, $R^{17}R^{18}$N—($C_1$-$C_8$)-alkyl, $R^{19}$O(O)C—($C_1$-$C_8$)-alkyl, $R^{19}$(O═)C—($C_1$-$C_8$)-Alkyl, $R^{17}R^{18}$N(O)C—($C_1$-$C_8$)-alkyl, heteroaryl-($C_1$-$C_8$)-alkyl, heterocyclyl-($C_1$-$C_8$)-alkyl, aryl, heteroaryl, heterocyclyl, ($C_1$-$C_8$)-alkoxy-($C_1$-$C_8$)-haloalkyl, ($C_1$-$C_8$)-alkylthio-($C_1$-$C_8$)-haloalkyl, tris-[($C_1$-$C_8$)-alkyl]silyl-($C_1$-$C_8$)-alkyl, $R^5$, $R^6$, $R^7$ and $R^8$ independently of one another represent hydrogen, halogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, $OR^{19}$, N$R^{17}R^{18}$, $R^{17}R^{18}$N—($C_1$-$C_8$)-alkyl, ($C_3$-$C_{10}$)-cycloalkyl-($C_1$-$C_8$)-alkyl, C(═O)$R^{19}$, C(═O)O$R^{19}$, C(═O)N$R^{17}R^{18}$, $S(O)_mR^{20}$, $R^{20}S(O)_m$—($C_1$-$C_8$)-alkyl, $R^9$ and $R^{10}$ independently of one another represent hydrogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{11}$ and $R^{12}$ independently of one another represent halogen, cyano, nitro, thiocyanato, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, cyano-($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, N$R^{17}R^{18}$, $S(O)_mR^{20}$, N—O—$R^{19}$, C(═N—O—$R^{19}$)H, C(═O)H, C(═O)$R^{19}$, C(═O)O$R^{19}$, C(═O)N$R^{17}R^{18}$, tris-[($C_1$-$C_8$)-alkyl]silyl, ($C_1$-$C_8$)-alkoxy-($C_1$-$C_8$)-haloalkyl, ($C_1$-$C_8$)-alkylthio-($C_1$-$C_8$)-haloalkyl, m is 0, 1, 2, X represents O (oxygen), S (sulfur), N$R^{13}$, or a group C$R^{14}R^{15}$, $R^{13}$ represents hydrogen, amino, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, $R^{19}$O—($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, N$R^{17}R^{18}$, $S(O)_mR^{20}$, C(═O)$R^{19}$, C(═O)O$R^{19}$, C(═O)N$R^{17}R^{18}$, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, heterocyclyl, heterocyclyl-($C_1$-$C_8$)-alkyl, $R^{14}$ and $R^{15}$ are equal or different and independently of one another represent ($C_1$-$C_8$)-alkyl, ($C_1$-$C_{10}$)-haloalkyl, ($C_3$-$C_8$)-cycloalkyl, ($C_3$-$C_8$)-cycloalkyl-($C_1$-$C_8$)-alkyl, aryl, heteroaryl, heterocyclyl, aryl-($C_1$-$C_8$)-alkyl, $R^{19}$—O—($C_1$-$C_8$)-alkyl, heteroaryl-($C_1$-$C_8$)-alkyl, heterocyclyl-($C_1$-$C_8$)-alkyl, C(═O)$R^{19}$, C(═O)O$R^{19}$, C(═O)N$R^{17}R^{18}$, $R^{19}$O(O)C—($C_1$-$C_8$)-alkyl, $R^{19}$(O═)C—($C_1$-$C_8$)-Alkyl, $R^{17}R^{18}$N(O)C—($C_1$-$C_8$)-alkyl, cyano-($C_1$-$C_8$)-alkyl, $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution.

$R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution.

$R^{14}$ and $R^{15}$ together with the carbon atom to which they are bonded form an unsaturated 5- to 6-membered heteroaromatic or aromatic ring optionally having further substituents.

$R^{16}$ represents hydrogen, halogen, cyano, nitro, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, N$R^{17}R^{18}$, $S(O)_m R^{20}$, C(═O)$R^{19}$, C(═N—O—$R^{19}$)H, C(═O)H, C(═O)O$R^{19}$, C(═O)N$R^{17}R^{18}$, ($C_1$-$C_8$)-alkoxy-($C_1$-$C_8$)-haloalkyl, ($C_1$-$C_8$)-alkylthio-($C_1$-$C_8$)-haloalkyl, $R^{17}$ and $R^{18}$ are equal or different and independently of one another represent hydrogen, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkyl, ($C_1$-$C_8$)-haloalkoxy-($C_1$-$C_8$)-alkyl, ($C_1$-$C_8$)-alkylthio-($C_1$-$C_8$)-alkyl, ($C_1$-$C_8$)-haloalkylthio-($C_1$-$C_8$)-alkyl, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, CO$R^{19}$, $SO_2R^{20}$, heterocyclyl, ($C_1$-$C_8$)-alkoxycarbonyl, bis-[($C_1$-$C_8$)-alkyl]aminocarbonyl-($C_1$-$C_8$)-alkyl, ($C_1$-$C_8$)-alkyl-aminocarbonyl-($C_1$-$C_8$)-alkyl, aryl-($C_1$-$C_8$)-alkyl-aminocarbonyl-($C_1$-$C_8$)-alkyl, ($C_1$-$C_8$)-alkoxycarbonyl-($C_1$-$C_8$)-alkyl, ($C_2$-$C_8$)-alkenyloxycarbonyl-($C_1$-$C_8$)-alkyl, ($C_2$-$C_8$)-alkynyloxycarbonyl-($C_1$-$C_8$)-alkyl, aryl-($C_1$-$C_8$)-alkoxycarbonyl-($C_1$-$C_8$)-alkyl, heteroaryl-($C_1$-$C_8$)-alkoxycarbonyl-($C_1$-$C_8$)-alkyl, heterocyclyl-($C_1$-$C_8$)-alkoxycarbonyl-($C_1$-$C_8$)-alkyl, aryl-($C_1$-$C_8$)-alkoxycarbonyl, heteroaryl-($C_1$-$C_8$)-alkoxycarbonyl, ($C_2$-$C_8$)-alkenyloxycarbonyl, ($C_2$-$C_8$)-alkynyloxycarbonyl, heterocyclyl-($C_1$-$C_8$)-alkyl, or $R^{17}$ and $R^{18}$ together with the carbon atom to which they are bonded form a fully saturated or partly saturated 3- to 10-membered monocyclic or bicyclic ring optionally interrupted by heteroatoms and optionally having further substitution, $R^{19}$ represents hydrogen, ($C_1$-$C_8$)-alkyl, ($C_2$-$C_8$)-alkenyl, ($C_2$-$C_8$)-alkinyl, ($C_1$-$C_8$)-cyanoalkyl, ($C_1$-$C_{10}$)-haloalkyl, ($C_2$-$C_8$)-haloalkenyl, ($C_3$-$C_8$)-haloalkinyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-haloalkoxy-($C_1$-$C_8$)-alkyl, ($C_1$-$C_8$)-alkoxy-($C_1$-$C_8$)-haloalkyl, ($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkoxy-($C_1$-$C_8$)-alkyl, aryl, aryl-($C_1$-$C_8$)-alkyl, aryl-($C_1$-$C_8$)-alkoxy-($C_1$-$C_8$)-alkyl, aryloxy-($C_1$-$C_8$)-alkyl, heteroaryl-($C_1$-$C_8$)-alkoxy-($C_1$-$C_8$)-alkyl, heteroaryloxy-($C_1$-$C_8$)-alkyl, heteroaryl, heteroaryl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, bis-[($C_1$-$C_8$)-alkyl]aminocarbonyl-($C_1$-$C_8$)-alkyl, ($C_1$-$C_8$)-alkyl-aminocarbonyl-($C_1$-$C_8$)-alkyl, aryl-($C_1$-$C_8$)-alkyl-aminocarbonyl-($C_1$-$C_8$)-alkyl, bis-[($C_1$-$C_8$)-alkyl]amino-($C_2$-$C_6$)-alkyl, ($C_1$-$C_8$)-alkyl-amino-($C_2$-$C_6$)-alkyl, aryl-($C_1$-$C_8$)-alkylamino-($C_2$-$C_6$)-alkyl, $R^{20}O)_m$S—($C_1$-$C_8$)-alkyl, hydroxycarbonyl-($C_1$-$C_8$)-alkyl, heterocyclyl, heterocyclyl-($C_1$-$C_8$)-alkyl, heterocyclyl-($C_1$-$C_8$)-alkoxy-($C_1$-$C_8$)-alkyl, heterocyclyloxy-($C_1$-$C_8$)-alkyl, tris-[($C_1$-$C_8$)-alkyl]silyl-($C_1$-$C_8$)-alkyl, bis-[($C_1$-$C_8$)-alkyl](aryl)silyl($C_1$-$C_8$)-alkyl, [($C_1$-$C_8$)-alkyl]-bis-(aryl)silyl-($C_1$-$C_8$)-alkyl, ($C_1$-$C_8$)-alkylcarbonyloxy-($C_1$-$C_8$)-alkyl, ($C_3$-$C_8$)-cycloalkylcarbonyloxy-($C_1$-$C_8$)-alkyl, arylcarbonyloxy-($C_1$-$C_8$)-alkyl, heteroarylcarbonyloxy-($C_1$-$C_8$)-alkyl, Heterocyclylcarbonyloxy-($C_1$-$C_8$)-alkyl, ($C_1$-$C_8$)-alkoxycarbonyl, ($C_1$-$C_8$)-alkoxycarbonyl-($C_1$-$C_8$)-alkyl, ($C_2$-$C_8$)-alkenyloxycarbonyl-($C_1$-$C_8$)-alkyl, ($C_2$-$C_8$)-alkynyloxycarbonyl-($C_1$-$C_8$)-alkyl, aryl-($C_1$-$C_8$)-alkoxycarbonyl-($C_1$-$C_8$)-alkyl, heteroaryl-($C_1$-$C_8$)-alkoxycarbonyl-($C_1$-$C_8$)-alkyl, heterocyclyl-($C_1$-$C_8$)-alkoxycarbonyl-($C_1$-$C_8$)-alkyl, and $R^{20}$ represents hydrogen, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, heterocyclyl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, bis-[($C_1$-$C_8$)-alkyl]amino, ($C_1$-$C_8$)-alkyl-amino, aryl-($C_1$-$C_8$)-amino, aryl-($C_1$-$C_6$)-alkyl-amino, aryl-[($C_1$-$C_8$)-alkyl]amino; heteroaryl-($C_1$-$C_8$)-amino, heteroaryl-($C_1$-$C_6$)-alkyl-amino, heteroaryl-[($C_1$-$C_8$)-alkyl]amino; Heterocyclyl-($C_1$-$C_8$)-amino, heterocyclyl-($C_1$-$C_6$)-alkyl-amino, heterocyclyl-[($C_1$-$C_8$)-alkyl]amino; ($C_3$-$C_8$)-cycloalkyl-amino, ($C_3$-$C_8$)-cycloalkyl-[($C_1$-$C_8$)-alkyl]amino; N-azetidinyl, N-pyrrolidinyl, N-piperidinyl, N-morpholinyl.

The compounds of the general formula (I) can form salts by addition of a suitable inorganic or organic acid, for example mineral acids, for example HCl, HBr, $H_2SO_4$, $H_3PO_4$ or $HNO_3$, or organic acids, for example carboxylic acids such as formic acid, acetic acid, propionic acid, oxalic acid, lactic acid or salicylic acid or sulfonic acids, for example p-toluenesulfonic acid, onto a basic group, for example amino, alkylamino, dialkylamino, piperidino, morpholino or pyridino. In such a case, these salts will comprise the conjugated base of the acid as the anion. Suitable substituents in deprotonated form, for example sulfonic acids, particular sulfonamides or carboxylic acids, are capable of forming internal salts with groups, such as amino groups, which are themselves protonatable. Salts may also be formed by action of a base on compounds of the general formula (I). Suitable bases are, for example, organic amines such as trialkylamines, morpholine, piperidine and pyridine, and the hydroxides, carbonates and bicarbonates of ammonium, alkali metals or alkaline earth metals, especially sodium hydroxide, potassium hydroxide, sodium carbonate, potassium carbonate, sodium bicarbonate and potassium bicarbonate. These salts are compounds in which the acidic hydrogen is replaced by an agriculturally suitable cation, for example metal salts, especially alkali metal salts or alkaline earth metal salts, in particular sodium and potassium salts, or else ammonium salts, salts with organic amines or quaternary ammonium salts, for example with cations of the formula $[NR^aR^bR^cR^d]^+$ in which $R^a$ to $R^d$ are each independently an organic radical, especially alkyl, aryl, arylalkyl or alkylaryl. Also suitable are alkylsulfonium and alkylsulfoxonium salts, such as ($C_1$-$C_4$)-trialkylsulfonium and ($C_1$-$C_4$)-trialkylsulfoxonium salts.

The substituted pyrrolidin-2-ones of the general formula (I) according to the invention can, depending on external conditions such as pH, solvent and temperature, be present in various tautomeric structures, all of which are embraced by the general formula (I).

The compounds of the formula (I) used in accordance with the invention and salts thereof are also referred to hereinafter as "compounds of the general formula (I)".

The invention preferably provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, ($C_1$-$C_7$)-alkyl, ($C_1$-$C_7$)-haloalkyl, ($C_3$-$C_7$)-cycloalkyl, ($C_3$-$C_7$)-cycloalkyl-($C_1$-$C_7$)-alkyl, aryl-($C_1$-$C_7$)-alkyl, $R^{19}$—O—($C_1$-$C_7$)-alkyl, heteroaryl-($C_1$-$C_7$)-alkyl, heterocyclyl-($C_1$-$C_7$)-alkyl, $R^2$ and $R^3$ independently of one another represent hydrogen, halogen, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}$O—($C_1$-$C_7$)-alkyl, $OR^{19}$, $R^{17}R^{18}$N—($C_1$-$C_7$)-alkyl, ($C_3$-$C_7$)-cycloalkyl-($C_1$-$C_7$)-alkyl, C(═O)$R^{19}$, C(═O)O$R^{19}$, C(═O)N$R^{17}R^{18}$, $R^{20}S(O)_m$—($C_1$-$C_7$)-alkyl, $R^4$ represents hydrogen, ($C_1$-$C_7$)-alkyl, ($C_1$-$C_7$)-haloalkyl, cyano-($C_1$-$C_7$)-alkyl, nitro-($C_1$-$C_7$)-alkyl, ($C_3$-$C_7$)-cycloalkyl, ($C_3$-$C_7$)-cycloalkyl-($C_1$-$C_7$)-alkyl, ($C_2$-$C_7$)-alkenyl, ($C_2$-$C_7$)-alkynyl, ($C_2$-$C_7$)-haloalkenyl, ($C_2$-$C_7$)-haloalkynyl, ($C_3$-$C_7$)-halocycloalkyl, ($C_4$-$C_7$)-cycloalkenyl, ($C_4$-$C_7$)-halocycloalkenyl, aryl-($C_1$-$C_7$)-alkyl, $R^{19}$O—($C_1$-$C_7$)-alkyl, $R^{19}$O—($C_1$-$C_7$)-alkoxy-($C_1$-$C_7$)-alkyl, $R^{20}S(O)_m$—($C_1$-$C_7$)-alkyl, $R^{17}R^{18}$N—($C_1$-$C_7$)-alkyl, $R^{19}$O(O)C—($C_1$-$C_7$)-alkyl, $R^{19}$(O═)C—($C_1$- $C_7$)-Alkyl, $R^{17}R^{18}$N(O)C—($C_1$-$C_7$)-alkyl, heteroaryl-($C_1$-$C_7$)-alkyl, heterocyclyl-($C_1$-$C_7$)-alkyl, aryl, heteroaryl, heterocyclyl, ($C_1$-$C_7$)-alkoxy-($C_1$-$C_7$)-haloalkyl, ($C_1$-$C_7$)-alkylthio-($C_1$-$C_7$)-haloalkyl, tris-[($C_1$-$C_7$)-alkyl]silyl-($C_1$-$C_7$)-alkyl, $R^5$, $R^6$, $R^7$ and $R^8$ independently of one another represent hydrogen, halogen, ($C_1$-$C_7$)-alkyl, ($C_2$-$C_7$)-alkenyl, $(C_2\text{-}C_7)$-alkynyl, $(C_1\text{-}C_7)$-haloalkyl, $(C_3\text{-}C_7)$-cycloalkyl, aryl-$(C_1\text{-}C_7)$-alkyl, aryl, heteroaryl, heteroaryl-$(C_1\text{-}C_7)$-alkyl, heterocyclyl, heterocyclyl-$(C_1\text{-}C_7)$-alkyl, $R^{19}O$—$(C_1\text{-}C_7)$-alkyl, $OR^{19}$, $NR^{17}R^{18}$, $R^{17}R^{18}N$—$(C_1\text{-}C_7)$-alkyl, $(C_3\text{-}C_7)$-cycloalkyl-$(C_1\text{-}C_7)$-alkyl, $C(=O)R^{19}$, $C(=O)OR^{19}$, $C(=O)NR^{17}R^{18}$, $S(O)_mR^{20}$, $R^{20}S(O)_m$—$(C_1\text{-}C_7)$-alkyl, $R^9$ and $R^{10}$ independently of one another represent hydrogen, $(C_1\text{-}C_7)$-alkyl, $(C_2\text{-}C_7)$-alkenyl, $(C_2\text{-}C_7)$-alkynyl, $(C_1\text{-}C_7)$-haloalkyl, $(C_3\text{-}C_7)$-cycloalkyl, aryl-$(C_1\text{-}C_7)$-alkyl, aryl, heteroaryl, heteroaryl-$(C_1\text{-}C_7)$-alkyl, heterocyclyl, heterocyclyl-$(C_1\text{-}C_7)$-alkyl, $R^{19}O$—$(C_1\text{-}C_7)$-alkyl, $(C_3\text{-}C_{10})$-cycloalkyl-$(C_1\text{-}C_7)$-alkyl, $R^{20}S(O)_m$—$(C_1\text{-}C_7)$-alkyl, $R^{11}$ and $R^{12}$ independently of one another represent halogen, cyano, nitro, thiocyanato, $(C_1\text{-}C_7)$-alkyl, $(C_2\text{-}C_7)$-alkenyl, $(C_2\text{-}C_7)$-alkynyl, $(C_1\text{-}C_7)$-haloalkyl, $(C_3\text{-}C_7)$-cycloalkyl, aryl-$(C_1\text{-}C_7)$-alkyl, aryl, heteroaryl, heteroaryl-$(C_1\text{-}C_7)$-alkyl, heterocyclyl, heterocyclyl-$(C_1\text{-}C_7)$-alkyl, $R^{19}O$—$(C_1\text{-}C_7)$-alkyl, cyano-$(C_1\text{-}C_7)$-alkyl, $(C_3\text{-}C_7)$-cycloalkyl-$(C_1\text{-}C_7)$-alkyl, $R^{20}S(O)_m$—$(C_1\text{-}C_7)$-alkyl, $R^{17}R^{18}N$—$(C_1\text{-}C_7)$-alkyl, $OR^{19}$, $NR^{17}R^{18}$, $S(O)_mR^{20}$, $C(=O)R^{19}$, $C(=O)OR^{19}$, $C(=O)NR^{17}R^{18}$, tris-$[(C_1\text{-}C_7)$- alkyl]silyl, $(C_1\text{-}C_7)$-alkoxy-$(C_1\text{-}C_7)$-haloalkyl, $(C_1\text{-}C_7)$-alkylthio-$(C_1\text{-}C_7)$-haloalkyl, m is 0, 1, 2, X represents O (oxygen), S (sulfur), $NR^{13}$, or a group $CR^{14}R^{15}$, $R^{13}$ represents hydrogen, amino, $(C_1\text{-}C_7)$-alkyl, $(C_2\text{-}C_7)$-alkenyl, $(C_2\text{-}C_7)$-alkynyl, $(C_1\text{-}C_7)$-cyanoalkyl, $(C_1\text{-}C_7)$-haloalkyl, $(C_2\text{-}C_7)$-haloalkenyl, $(C_3\text{-}C_7)$-haloalkynyl, $(C_3\text{-}C_7)$-cycloalkyl, $(C_3\text{-}C_7)$-halocycloalkyl, $(C_4\text{-}C_7)$-cycloalkenyl, $(C_4\text{-}C_7)$-halocycloalkenyl, $R^{19}O$—$(C_1\text{-}C_7)$-alkyl, $(C_3\text{-}C_7)$-cycloalkyl-$(C_1\text{-}C_7)$-alkyl, $R^{20}S(O)_m$—$(C_1\text{-}C_7)$-alkyl, $R^{17}R^{18}N$—$(C_1\text{-}C_7)$-alkyl, $OR^{19}$, $NR^{17}R^{18}$, $S(O)_mR^{20}$, $C(=O)R^{19}$, $C(=O)OR^{19}$, $C(=O)NR^{17}R^{18}$, $(C_1\text{-}C_7)$-alkoxy-$(C_1\text{-}C_7)$-haloalkyl, aryl, aryl-$(C_1\text{-}C_7)$-alkyl, heteroaryl, heteroaryl-$(C_1\text{-}C_7)$-alkyl, heterocyclyl, heterocyclyl-$(C_1\text{-}C_7)$-alkyl, $R^{14}$ and $R^{15}$ are equal or different and independently of one another represent $(C_1\text{-}C_7)$-alkyl, $(C_1\text{-}C_7)$-haloalkyl, $(C_3\text{-}C_7)$-cycloalkyl, $(C_3\text{-}C_7)$-cycloalkyl-$(C_1\text{-}C_7)$-alkyl, aryl, heteroaryl, heterocyclyl, aryl-$(C_1\text{-}C_7)$-alkyl, $R^{19}$—O—$(C_1\text{-}C_7)$-alkyl, heteroaryl-$(C_1\text{-}C_7)$-alkyl, heterocyclyl-$(C_1\text{-}C_7)$-alkyl, $C(=O)R^{19}$, $C(=O)OR^{19}$, $C(=O)NR^{17}R^{18}$, $R^{19}O(O)C$—$(C_1\text{-}C_7)$-alkyl, $R^{19}(O=)C$—$(C_1\text{-}C_7)$-Alkyl, $R^{17}R^{18}N(O)C$—$(C_1\text{-}C_7)$-alkyl, cyano-$(C_1\text{-}C_7)$-alkyl, $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution.

$R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution.

$R^{14}$ and $R^{15}$ together with the carbon atom to which they are bonded form an unsaturated 5- to 6-membered heteroaromatic or aromatic ring optionally having further substituents.

$R^{16}$ represents hydrogen, halogen, cyano, nitro, $(C_1\text{-}C_7)$-alkyl, $(C_2\text{-}C_7)$-alkenyl, $(C_2\text{-}C_7)$-alkynyl, $(C_1\text{-}C_7)$-haloalkyl, $(C_3\text{-}C_7)$-cycloalkyl, aryl-$(C_1\text{-}C_7)$-alkyl, aryl, heteroaryl, heteroaryl-$(C_1\text{-}C_7)$-alkyl, heterocyclyl, heterocyclyl-$(C_1\text{-}C_7)$-alkyl, $R^{19}O$—$(C_1\text{-}C_7)$-alkyl, $(C_3\text{-}C_{10})$-cycloalkyl-$(C_1\text{-}C_7)$-alkyl, $R^{20}S(O)_m$—$(C_1\text{-}C_7)$-alkyl, $R^{17}R^{18}N$—$(C_1\text{-}C_5)$-alkyl, $OR^{19}$, $NR^{17}R^{18}$, $S(O)_m R^{20}$, $C(=O)R^{19}$, $C(=O)OR^{19}$, $C(=O)NR^{17}R^{18}$, $(C_1\text{-}C_7)$-alkoxy-$(C_1\text{-}C_7)$-haloalkyl, $(C_1\text{-}C_7)$-alkylthio-$(C_1\text{-}C_7)$-haloalkyl, $R^{17}$ and $R^{18}$ are equal or different and independently of one another represent hydrogen, $(C_1\text{-}C_7)$-alkyl, $(C_2\text{-}C_7)$-alkenyl, $(C_2\text{-}C_7)$-alkynyl, $(C_1\text{-}C_7)$-cyanoalkyl, $(C_1\text{-}C_7)$-haloalkyl, $(C_2\text{-}C_7)$-haloalkenyl, $(C_3\text{-}C_7)$-haloalkynyl, $(C_3\text{-}C_7)$-cycloalkyl, $(C_3\text{-}C_7)$-halocycloalkyl, $(C_4\text{-}C_7)$-cycloalkenyl, $(C_4\text{-}C_7)$-halocycloalkenyl, $(C_1\text{-}C_7)$-alkoxy-$(C_1\text{-}C_7)$-alkyl, $(C_1\text{-}C_7)$-alkoxy-$(C_1\text{-}C_7)$-alkoxy-$(C_1\text{-}C_7)$-alkyl, $(C_1\text{-}C_7)$-alkoxy-$(C_1\text{-}C_7)$-alkoxy-$(C_1\text{-}C_7)$-alkoxy-$(C_1\text{-}C_7)$-alkyl, $(C_1\text{-}C_7)$-haloalkoxy-$(C_1\text{-}C_7)$-alkyl, $(C_1\text{-}C_7)$-alkylthio-$(C_1\text{-}C_7)$-alkyl, $(C_1\text{-}C_7)$-haloalkylthio-$(C_1\text{-}C_7)$-alkyl, $(C_1\text{-}C_7)$-alkoxy-$(C_1\text{-}C_7)$-haloalkyl, aryl, aryl-$(C_1\text{-}C_7)$-alkyl, heteroaryl, heteroaryl-$(C_1\text{-}C_7)$-alkyl, $(C_3\text{-}C_7)$-cycloalkyl-$(C_1\text{-}C_7)$-alkyl, $(C_4\text{-}C_7)$-cycloalkenyl-$(C_1\text{-}C_7)$-alkyl, $COR^{19}$, $SO_2R^{20}$, heterocyclyl, $(C_1\text{-}C_7)$-alkoxycarbonyl, bis-$[(C_1\text{-}C_7)$-alkyl]aminocarbonyl-$(C_1\text{-}C_7)$-alkyl, $(C_1\text{-}C_7)$-alkyl-aminocarbonyl-$(C_1\text{-}C_7)$-alkyl, aryl-$(C_1\text{-}C_7)$-alkyl-aminocarbonyl-$(C_1\text{-}C_7)$-alkyl, $(C_1\text{-}C_7)$-alkoxycarbonyl-$(C_1\text{-}C_7)$-alkyl, $(C_2\text{-}C_7)$-alkenyloxycarbonyl-$(C_1\text{-}C_7)$-alkyl, $(C_2\text{-}C_7)$-alkynyloxycarbonyl-$(C_1\text{-}C_7)$-alkyl, aryl-$(C_1\text{-}C_7)$-alkoxycarbonyl-$(C_1\text{-}C_7)$-alkyl, heteroaryl-$(C_1\text{-}C_7)$-alkoxycarbonyl-$(C_1\text{-}C_7)$-alkyl, heterocyclyl-$(C_1\text{-}C_7)$-alkoxycarbonyl-$(C_1\text{-}C_7)$-alkyl, aryl-$(C_1\text{-}C_7)$-alkoxycarbonyl, heteroaryl-$(C_1\text{-}C_7)$-alkoxycarbonyl, $(C_2\text{-}C_7)$-alkenyloxycarbonyl, $(C_2\text{-}C_7)$-alkynyloxycarbonyl, heterocyclyl-$(C_1\text{-}C_7)$-alkyl, or $R^{17}$ and $R^{18}$ together with the carbon atom to which they are bonded form a fully saturated or partly saturated 3- to 10-membered monocyclic or bicyclic ring optionally interrupted by heteroatoms and optionally having further substitution, $R^{19}$ represents hydrogen, $(C_1\text{-}C_7)$-alkyl, $(C_2\text{-}C_7)$-alkenyl, $(C_2\text{-}C_7)$-alkinyl, $(C_1\text{-}C_7)$-cyanoalkyl, $(C_1\text{-}C_7)$-haloalkyl, $(C_2\text{-}C_7)$-haloalkenyl, $(C_3\text{-}C_7)$-haloalkinyl, $(C_3\text{-}C_7)$-cycloalkyl, $(C_3\text{-}C_7)$-halocycloalkyl, $(C_4\text{-}C_7)$-cycloalkenyl, $(C_4\text{-}C_7)$-halocycloalkenyl, $(C_1\text{-}C_7)$-alkoxy-$(C_1\text{-}C_7)$-alkyl, $(C_1\text{-}C_7)$-haloalkoxy-$(C_1\text{-}C_7)$-alkyl, $(C_1\text{-}C_7)$-alkoxy-$(C_1\text{-}C_7)$-haloalkyl, $(C_1\text{-}C_7)$-alkoxy-$(C_1\text{-}C_7)$-alkoxy-$(C_1\text{-}C_7)$-alkyl, $(C_1\text{-}C_7)$-alkoxy-$(C_1\text{-}C_7)$-alkoxy-$(C_1\text{-}C_7)$-alkoxy-$(C_1\text{-}C_7)$-alkyl, $(C_1\text{-}C_7)$-alkoxy-$(C_1\text{-}C_7)$-alkoxy-$(C_1\text{-}C_7)$-alkoxy-$(C_1\text{-}C_7)$-alkoxy-$(C_1\text{-}C_7)$-alkyl, aryl, aryl-$(C_1\text{-}C_7)$-alkyl, aryl-$(C_1\text{-}C_7)$-alkoxy-$(C_1\text{-}C_7)$-alkyl, aryloxy-$(C_1\text{-}C_7)$-alkyl, heteroaryl-$(C_1\text{-}C_7)$-alkoxy-$(C_1\text{-}C_7)$-alkyl, heteroaryloxy-$(C_1\text{-}C_7)$-alkyl, heteroaryl, heteroaryl-$(C_1\text{-}C_7)$-alkyl, $(C_3\text{-}C_7)$-cycloalkyl-$(C_1\text{-}C_7)$-alkyl, $(C_4\text{-}C_7)$-cycloalkenyl-$(C_1\text{-}C_7)$-alkyl, bis-$[(C_1\text{-}C_7)$-alkyl]aminocarbonyl-$(C_1\text{-}C_7)$-alkyl, $(C_1\text{-}C_7)$-alkyl-aminocarbonyl-$(C_1\text{-}C_7)$-alkyl, aryl-$(C_1\text{-}C_7)$-alkyl-aminocarbonyl-$(C_1\text{-}C_7)$-alkyl, bis-$[(C_1\text{-}C_7)$-alkyl]amino-$(C_2\text{-}C_6)$-alkyl, $(C_1\text{-}C_7)$-alkyl-amino-$(C_2\text{-}C_6)$-alkyl, aryl-$(C_1\text{-}C_7)$-alkylamino-$(C_2\text{-}C_6)$-alkyl, $R^{20}O)_m$S—$(C_1\text{-}C_7)$-alkyl, hydroxycarbonyl-$(C_1\text{-}C_7)$-alkyl, heterocyclyl, heterocyclyl-$(C_1\text{-}C_7)$-alkyl, heterocyclyl-$(C_1\text{-}C_7)$-alkoxy-$(C_1\text{-}C_7)$-alkyl, heterocyclyloxy-$(C_1\text{-}C_7)$-alkyl, tris-$[(C_1\text{-}C_7)$-alkyl]silyl-$(C_1\text{-}C_7)$-alkyl, bis-$[(C_1\text{-}C_7)$-alkyl](aryl)silyl$(C_1\text{-}C_7)$-alkyl, $[(C_1\text{-}C_7)$-alkyl]-bis-(aryl)silyl-$(C_1\text{-}C_7)$-alkyl, $(C_1\text{-}C_7)$-alkylcarbonyloxy-$(C_1\text{-}C_7)$-alkyl, $(C_3\text{-}C_7)$-cycloalkylcarbonyloxy-$(C_1\text{-}C_7)$-alkyl, arylcarbonyloxy-($C_1$-$C_7$)-alkyl, heteroarylcarbonyloxy-($C_1$-$C_7$)-alkyl, Heterocyclylcarbonyloxy-($C_1$-$C_7$)-alkyl, ($C_1$-$C_7$)-alkoxycarbonyl, ($C_1$-$C_7$)-alkoxycarbonyl-($C_1$-$C_7$)-alkyl, ($C_2$-$C_7$)-alkenyloxycarbonyl-($C_1$-$C_7$)-alkyl, ($C_2$-$C_7$)-alkynyloxycarbonyl-($C_1$-$C_7$)-alkyl, aryl-($C_1$-$C_7$)-alkoxycarbonyl-($C_1$-$C_7$)-alkyl, heteroaryl-($C_1$-$C_7$)-alkoxycarbonyl-($C_1$-$C_7$)-alkyl, heterocyclyl-($C_1$-$C_7$)-alkoxycarbonyl-($C_1$-$C_7$)-alkyl, and $R^{20}$ represents hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_{10}$)-haloalkyl, ($C_2$-$C_7$)-haloalkenyl, ($C_3$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, heterocyclyl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, bis-[($C_1$-$C_7$)-alkyl]amino, ($C_1$-$C_7$)-alkyl-amino, aryl-($C_1$-$C_7$)-amino, aryl-($C_1$-$C_6$)-alkyl-amino, aryl-[($C_1$-$C_7$)-alkyl]amino; heteroaryl-($C_1$-$C_7$)-amino, heteroaryl-($C_1$-$C_6$)-alkyl-amino, heteroaryl-[($C_1$-$C_7$)-alkyl]amino; Hetercyclyl-($C_1$-$C_7$)-amino, heterocyclyl-($C_1$-$C_6$)-alkyl-amino, heterocyclyl-[($C_1$-$C_7$)-alkyl]amino; ($C_3$-$C_7$)-cycloalkyl-amino, ($C_3$-$C_7$)-cycloalkyl-[($C_1$-$C_7$)-alkyl]amino; N-azetidinyl, N-pyrrolidinyl, N-piperidinyl, N-morpholinyl.

The invention more preferably provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, ($C_1$-$C_6$)-alkyl, ($C_1$-$C_6$)-haloalkyl, ($C_3$-$C_6$)-cycloalkyl, $R^{19}$—O—($C_1$-$C_6$)-alkyl, heterocyclyl-($C_1$-$C_6$)-alkyl, $R^2$ and $R^3$ independently of one another represent hydrogen, fluorine, chlorine, bromine, iodine, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, $OR^{19}$, $R^{17}R^{18}$N—($C_1$-$C_6$)-alkyl, ($C_3$-$C_6$)-cycloalkyl-($C_1$-$C_6$)-alkyl, C(═O)$R^{19}$, C(═O)O$R^{19}$, C(═O)N$R^{17}R^{18}$, $R^{20}S(O)_m$—($C_1$-$C_6$)-alkyl, $R^4$ represents hydrogen, ($C_1$-$C_6$)-alkyl, ($C_1$-$C_6$)-haloalkyl, cyano-($C_1$-$C_6$)-alkyl, nitro-($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_2$-$C_6$)-haloalkenyl, ($C_2$-$C_6$)-haloalkynyl, ($C_3$-$C_6$)-halocycloalkyl, ($C_4$-$C_6$)-cycloalkenyl, ($C_4$-$C_6$)-halocycloalkenyl, aryl-($C_1$-$C_6$)-alkyl, $R^{19}$O—($C_1$-$C_6$)-alkyl, $R^{19}$O—($C_1$-$C_6$)-alkoxy-($C_1$-$C_6$)-alkyl, $R^{20}S(O)_m$—($C_1$-$C_6$)-alkyl, $R^{17}R^{18}$N—($C_1$-$C_6$)-alkyl, $R^{19}$O(O)C—($C_1$-$C_6$)-alkyl, $R^{19}$(O═)C—($C_1$-$C_6$)-Alkyl, $R^{17}R^{18}$N(O)C—($C_1$-$C_6$)-alkyl, heteroaryl-($C_1$-$C_6$)-alkyl, heterocyclyl-($C_1$-$C_6$)-alkyl, aryl, heteroaryl, heterocyclyl, ($C_1$-$C_6$)-alkoxy-($C_1$-$C_6$)-haloalkyl, ($C_1$-$C_6$)-alkylthio-($C_1$-$C_6$)-haloalkyl, tris-[($C_1$-$C_6$)-alkyl]silyl-($C_1$-$C_6$)-alkyl, $R^5$, $R^6$, $R^7$ and $R^8$ independently of one another represent hydrogen, fluorine, chlorine, bromine, iodine, ($C_1$-$C_6$)-alkyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, $OR^{19}$, N$R^{17}R^{18}$, $R^{17}R^{18}$N—($C_1$-$C_6$)-alkyl, ($C_3$-$C_6$)-cycloalkyl-($C_1$-$C_6$)-alkyl, C(═O)$R^{19}$, C(═O)O$R^{19}$, C(═O)N$R^{17}R^{18}$, $S(O)_mR^{20}$, $R^{20}S(O)_m$—($C_1$-$C_6$)-alkyl, $R^9$ and $R^{10}$ independently of one another represent hydrogen, ($C_1$-$C_6$)-alkyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, $R^{11}$ and $R^{12}$ independently of one another represent fluorine, chlorine, bromine, iodine, cyano, nitro, thiocyanato, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, cyano-($C_1$-$C_6$)-alkyl, ($C_3$-$C_6$)-cycloalkyl-($C_1$-$C_6$)-alkyl, $R^{20}S(O)_m$—($C_1$-$C_6$)-alkyl, $R^{17}R^{18}$N—($C_1$-$C_6$)-alkyl, $OR^{19}$, N$R^{17}R^{18}$, $S(O)_mR^{20}$, C(═O)$R^{19}$, C(═O)O$R^{19}$, C(═O)N$R^{17}R^{18}$, ($C_1$-$C_6$)-alkoxy-($C_1$-$C_6$)-haloalkyl, ($C_1$-$C_6$)-alkylthio-($C_1$-$C_6$)-haloalkyl, m is 0, 1, 2, X represents O (oxygen), S (sulfur), N$R^{13}$, or a group C$R^{14}R^{15}$, $R^{13}$ represents hydrogen, amino, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_6$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, $R^{19}$O—($C_1$-$C_6$)-alkyl, ($C_3$-$C_6$)-cycloalkyl-($C_1$-$C_6$)-alkyl, $R^{20}S(O)_m$—($C_1$-$C_6$)-alkyl, $R^{17}R^{18}$N—($C_1$-$C_6$)-alkyl, $OR^{19}$, N$R^{17}R^{18}$, $S(O)_mR^{20}$, C(═O)$R^{19}$, C(═O)O$R^{19}$, C(═O)N$R^{17}R^{18}$, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, heterocyclyl, heterocyclyl-($C_1$-$C_6$)-alkyl, $R^{14}$ and $R^{15}$ are equal or different and independently of one another represent ($C_1$-$C_6$)-alkyl, ($C_1$-$C_6$)-haloalkyl, ($C_3$-$C_6$)-cycloalkyl, ($C_3$-$C_6$)-cycloalkyl-($C_1$-$C_6$)-alkyl, aryl, heteroaryl, heterocyclyl, aryl-($C_1$-$C_6$)-alkyl, $R^{19}$—O—($C_1$-$C_6$)-alkyl, heteroaryl-($C_1$-$C_6$)-alkyl, heterocyclyl-($C_1$-$C_6$)-alkyl, C(═O)$R^{19}$, C(═O)O$R^{19}$, C(═O)N$R^{17}R^{18}$, $R^{19}$O(O)C—($C_1$-$C_6$)-alkyl, $R^{19}$(O═)C—($C_1$-$C_6$)-Alkyl, $R^{17}R^{18}$N(O)C—($C_1$-$C_6$)-alkyl, cyano-($C_1$-$C_6$)-alkyl, $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution.

$R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution.

$R^{14}$ and $R^{15}$ together with the carbon atom to which they are bonded form an unsaturated 5- to 6-membered heteroaromatic or aromatic ring optionally having further substituents.

$R^{16}$ represents hydrogen, fluorine, chlorine, bromine, iodine, cyano, nitro, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, ($C_3$-$C_{10}$)-cycloalkyl-($C_1$-$C_6$)-alkyl, $R^{20}S(O)_m$—($C_1$-$C_6$)-alkyl, $R^{17}R^{18}$N—($C_1$-$C_5$)-alkyl, $OR^{19}$, N$R^{17}R^{18}$, $S(O)_mR^{20}$, C(═O)$R^{19}$, C(═O)O$R^{19}$, C(═O)N$R^{17}R^{18}$, ($C_1$-$C_6$)-alkoxy-($C_1$-$C_6$)-haloalkyl, ($C_1$-$C_6$)-alkylthio-($C_1$-$C_6$)-haloalkyl, $R^{17}$ and $R^{18}$ are equal or different and independently of one another represent hydrogen, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_6$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkyl, ($C_1$-$C_6$)-haloalkoxy-($C_1$-$C_6$)-alkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, $COR^{19}$, $SO_2R^{20}$, heterocyclyl, ($C_1$-$C_6$)-alkoxycarbonyl, bis-[($C_1$-$C_6$)-alkyl]aminocarbonyl-($C_1$-$C_6$)-alkyl, ($C_1$-$C_6$)-alkyl-aminocarbonyl-($C_1$-$C_6$)-alkyl, aryl-($C_1$-$C_6$)-alkyl-aminocarbonyl-($C_1$-$C_6$)-alkyl, ($C_1$-$C_6$)-alkoxycarbonyl-($C_1$-$C_6$)-alkyl, ($C_2$-$C_6$)-alkenyloxycarbonyl-($C_1$-$C_6$)-alkyl, ($C_2$-$C_6$)-alkynyloxycarbonyl-($C_1$-$C_6$)-alkyl, aryl-($C_1$-$C_6$)-alkoxycarbonyl-($C_1$-$C_6$)-alkyl, heteroaryl-($C_1$-$C_6$)-alkoxycarbonyl-($C_1$-$C_6$)-alkyl, heterocyclyl-($C_1$-$C_6$)-alkoxycarbonyl-($C_1$-$C_6$)-alkyl, aryl-($C_1$-$C_6$)-alkoxycarbonyl, heteroaryl-($C_1$-$C_6$)-alkoxycarbonyl, ($C_2$-$C_6$)-alkenyloxycarbonyl, ($C_2$-$C_6$)-alkynyloxycarbonyl, heterocyclyl-($C_1$-$C_6$)-alkyl, or $R^{17}$ and $R^{18}$ together with the carbon atom to which they are bonded form a fully saturated or partly saturated 3- to 10-membered monocyclic or bicyclic ring optionally interrupted by heteroatoms and optionally having further substitution, $R^{19}$ represents hydrogen, ($C_1$-$C_6$)-alkyl, ($C_2$-$C_6$)-alkenyl, ($C_2$-$C_6$)-alkinyl, ($C_1$-$C_6$)-cyanoalkyl, ($C_1$-$C_6$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-haloalkoxy-($C_1$-$C_6$)-alkyl, ($C_1$-$C_6$)-alkoxy-($C_1$-$C_6$)-haloalkyl, ($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkoxy-($C_1$-$C_6$)-alkyl, aryl, aryl-($C_1$-$C_6$)-alkyl, aryl-($C_1$-$C_6$)-alkoxy-($C_1$-$C_6$)-alkyl, aryloxy-($C_1$-$C_6$)-alkyl, heteroaryl-($C_1$-$C_6$)-alkoxy-($C_1$-$C_6$)-alkyl, heteroaryloxy-($C_1$-$C_6$)-alkyl, heteroaryl, heteroaryl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, bis-[($C_1$-$C_6$)-alkyl]aminocarbonyl-($C_1$-$C_6$)-alkyl, ($C_1$-$C_6$)-alkyl-aminocarbonyl-($C_1$-$C_6$)-alkyl, aryl-($C_1$-$C_6$)-alkyl-aminocarbonyl-($C_1$-$C_6$)-alkyl, bis-[($C_1$-$C_6$)-alkyl]amino-($C_2$-$C_6$)-alkyl, ($C_1$-$C_6$)-alkyl-amino-($C_2$-$C_6$)-alkyl, aryl-($C_1$-$C_6$)-alkylamino-($C_2$-$C_6$)-alkyl, $R^{20}O)_m$S—($C_1$-$C_6$)-alkyl, hydroxycarbonyl-($C_1$-$C_6$)-alkyl, heterocyclyl, heterocyclyl-($C_1$-$C_6$)-alkyl, heterocyclyl-($C_1$-$C_6$)-alkoxy-($C_1$-$C_6$)-alkyl, heterocyclyloxy-($C_1$-$C_6$)-alkyl, tris-[($C_1$-$C_6$)-alkyl]silyl-($C_1$-$C_6$)-alkyl, bis-[($C_1$-$C_6$)-alkyl](aryl)silyl($C_1$-$C_6$)-alkyl, [($C_1$-$C_6$)-alkyl]-bis-(aryl)silyl-($C_1$-$C_6$)-alkyl, ($C_1$-$C_6$)-alkylcarbonyloxy-($C_1$-$C_6$)-alkyl, ($C_3$-$C_6$)-cycloalkylcarbonyloxy-($C_1$-$C_6$)-alkyl, arylcarbonyloxy-($C_1$-$C_6$)-alkyl, heteroarylcarbonyloxy-($C_1$-$C_6$)-alkyl, Heterocyclylcarbonyloxy-($C_1$-$C_6$)-alkyl, ($C_1$-$C_6$)-alkoxycarbonyl, ($C_1$-$C_6$)-alkoxycarbonyl-($C_1$-$C_6$)-alkyl, ($C_2$-$C_6$)-alkenyloxycarbonyl-($C_1$-$C_6$)-alkyl, ($C_2$-$C_6$)-alkynyloxycarbonyl-($C_1$-$C_6$)-alkyl, aryl-($C_1$-$C_6$)-alkoxycarbonyl-($C_1$-$C_6$)-alkyl, heteroaryl-($C_1$-$C_6$)-alkoxycarbonyl-($C_1$-$C_6$)-alkyl, heterocyclyl-($C_1$-$C_6$)-alkoxycarbonyl-($C_1$-$C_6$)-alkyl, and $R^{20}$ represents hydrogen, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_{10}$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, heterocyclyl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, bis-[($C_1$-$C_6$)-alkyl]amino, ($C_1$-$C_6$)-alkyl-amino, aryl-($C_1$-$C_6$)-amino, aryl-($C_1$-$C_6$)-alkyl-amino, aryl-[($C_1$-$C_6$)-alkyl]amino; heteroaryl-($C_1$-$C_6$)-amino, heteroaryl-($C_1$-$C_6$)-alkyl-amino, heteroaryl-[($C_1$-$C_6$)-alkyl]amino; Hetercyclyl-($C_1$-$C_6$)-amino, heterocyclyl-($C_1$-$C_6$)-alkyl-amino, heterocyclyl-[($C_1$-$C_6$)-alkyl]amino; ($C_3$-$C_6$)-cycloalkyl-amino, ($C_3$-$C_6$)-cycloalkyl-[($C_1$-$C_6$)-alkyl]amino; N-azetidinyl, N-pyrrolidinyl, N-piperidinyl, N-morpholinyl.

The invention particularly provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, methyl, ethyl, prop-1-yl, prop-2-yl, but-1-yl, difluoromethyl, trifluoromethyl, 2,2-difluoroethyl, 2,2,2-trifluoroethyl, cyclopropyl, cyclobutyl, cyclopentyl, cyclohexyl, methoxymethyl, methoxyethyl, ethoxymethyl, ethoxyethyl, $R^2$ and $R^3$ independently of one another represent hydrogen, fluorine, chlorine, bromine, iodine, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl and 1-ethyl-2-methylprop-1-yl, cyclopropylmethyl, cyclobutylmethyl, cyclopentylmethyl, cyclohexylmethyl, ethenyl, prop-1-en-1-yl, prop-2-en-1-yl, 1-methyl-eth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-1-yl, 1-ethylprop-2-en-1-yl, hexen-1-yl, hexen-2-yl, hexen-3-yl, hexen-4-yl, hexen-5-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, cyclopropyl, cyclobutyl, cyclopentyl, cyclohexyl, cyclopropylmethyl, cyclobutylmethyl, cyclopentylmethyl, cyclohexylmethyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, 3,3,3-trifluoro-n-propyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, trifluoromethoxymethyl, methoxy, ethoxy, 1-methylethoxy, benzyloxy, methylcarbonyloxy, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 4-Cl-phenyl, 3-Cl-phenyl, 2-Cl-phenyl, methylthiomethyl, trifluoromethylthiomethyl, pyridin-2-yl, pyridin-3-yl, pyridin-4-yl, pyridin-2-ylmethyl, pyridin-3-ylmethyl, pyridin-4-ylmethyl, hydroxycarbonyl, methoxycarbonyl, ethoxycarbonyl, 1-methylethoxycarbonyl, 1,1-dimethylethoxycarbonyl, $R^5$, $R^6$, $R^7$ and $R^8$ independently of one another represent hydrogen, fluorine, chlorine, bromine, iodine, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl and 1-ethyl-2-methylprop-1-yl, cyclopropyl, cyclobutyl, cyclopentyl, cyclohexyl, cyclopropylmethyl, cyclobutylmethyl, cyclopentylmethyl, cyclohexylmethyl, difluoromethyl, trifluoromethyl, 2,2-difluoroethyl, 2,2,2-trifluoroethyl, pentafluorethyl, methoxy, ethoxy, trifluoromethoxy, 2,2-difluoroethoxy, 2,2,2-trifluoroethoxy, methoxymethyl, ethoxymethyl, methoxyethyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 4-Cl-phenyl, 3-Cl-phenyl, 2-Cl-phenyl, methylthiomethyl, trifluoromethylthiomethyl, pyridin-2-yl, pyridin-3-yl, pyridin-4-yl, pyridin-2-ylmethyl, pyridin-3-ylmethyl, pyridin-4-ylmethyl, $R^9$ and $R^{10}$ independently of one another represent hydrogen, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, cyclopropyl, cyclobutyl, cyclopentyl, cyclohexyl, difluoromethyl, trifluoromethyl, 2,2-difluoroethyl, 2,2,2-trifluoroethyl, pentafluorethyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, methoxymethyl, ethoxymethyl, methoxyethyl, ethoxyethyl, $R^{11}$ and $R^{12}$ independently of one another represent fluorine, chlorine, bromine, iodine, cyano, nitro, thiocyanato, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl and 1-ethyl-2-methylprop-1-yl, cyclopropylmethyl, cyclobutylmethyl, cyclopentylmethyl, cyclohexylmethyl, ethenyl, prop-1-en-1-yl, prop-2-en-1-yl, 1-methyleth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-1-yl, 1-ethylprop-2-en-1-yl, hexen-1-yl, hexen-2-yl, hexen-3-yl, hexen-4-yl, hexen-5-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, methoxymethyl, ethoxymethyl, ethoxyethyl, methoxyethyl, methoxy-n-propyl, ethoxy-n-propyl, methoxy-n-butyl, iso-propoxymethyl, iso-propoxyethyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, pentafluoroethoxymethyl, pentafluoroethoxyethyl, pentafluoroethoxy-n-propyl, methylthiomethyl, methylthioethyl, ethylthioethyl, methylthio-n-propyl, ethylthio-n-propyl, trifluoromethylthiomethyl, trifluoromethylthioethyl, trifluoromethylthio-n-propyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, ethoxyethoxyethyl, hydroxymethyl, methylcarbonyloxymethyl, hydroxyethyl, hydroxyethoxy, hydroxy, methoxy, ethoxy, 1-methylethoxy, 1,1-dimethylethoxy, benzyloxy, phenoxy, methylcarbonyloxy, hydrothio, methylthio, ethylthio, difluoromethoxy, trifluoromethoxy, 2,2-difluoroethoxy, 2,2,2-trifluoroethoxy, trifluoromethylthio, cyclopropyl, cyclobutyl, cyclopentyl, cyclohexyl, cyclopropylmethyl, cyclobutylmethyl, cyclopentylmethyl, cyclohexylmethyl, 1-methylcycloprop-1-yl, 2-methylcycloprop-1-yl, 2,2-dimethylcycloprop-1-yl, 2,3-dimethylcycloprop-1-yl, 1,1'-bi(cyclopropyl)-1-yl, 1,1'-bi(cyclopropyl)-2-yl, 2'-methyl-1,1'-bi(cyclopropyl)-2-yl, 1-cyanocycloprop-1-yl, 2-cyanocycloprop-1-yl, methylamino, ethylamino, dimethylamino, diethylamino, methyl(ethyl)amino, methoxycarbonylamino, ethoxycarbonylamino, 1,1-dimethylethoxycarbonylamino, N-azetidinyl, N-pyrrolidinyl, N-piperidinyl, N-morpholinyl, dimethylaminomethyl, diethylaminomethyl, hydroxycarbonyl, methoxycarbonyl, ethoxycarbonyl, 1-methylethoxycarbonyl, 1,1-dimethylethoxycarbonyl, aminocarbonyl, methylaminocarbonyl, ethylaminocarbonyl, cyclopropylaminocarbonyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, $R^{16}$ represents hydrogen, fluorine, chlorine, bromine, iodine, cyano, nitro, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl and 1-ethyl-2-methylprop-1-yl, cyclopropyl, cyclobutyl, cyclopentyl, cyclohexyl, cyclopropylmethyl, cyclobutylmethyl, cyclopentylmethyl, cyclohexylmethyl, hydroxy, methoxy, ethoxy, 1-methylethoxy, 1,1-dimethylethoxy, benzyloxy, phenoxy, methylcarbonyloxy, hydrothio, methylthio, ethylthio, difluoromethoxy, trifluoromethoxy, 2,2-difluoroethoxy, 2,2,2-trifluoroethoxy, trifluoromethylthio, ethenyl, prop-1-en-1-yl, prop-2-en-1-yl, 1-methyleth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, difluoromethyl, trifluoromethyl, 2,2-difluoroethyl, 2,2,2-trifluoroethyl, pentafluoroethyl, methoxymethyl, ethoxymethyl, ethoxyethyl, hydroxymethyl, methylamino, ethylamino, dimethylamino, diethylamino, methyl(ethyl)amino, methoxycarbonylamino, ethoxycarbonylamino, 1,1-dimethylethoxycarbonylamino, N-azetidinyl, N-pyrrolidinyl, N-piperidinyl, N-morpholinyl, dimethylaminomethyl, diethylaminomethyl, hydroxycarbonyl, methoxycarbonyl, ethoxycarbonyl, 1-methylethoxycarbonyl, 1,1-dimethylethoxycarbonyl, aminocarbonyl, methylaminocarbonyl, ethylaminocarbonyl, cyclopropylaminocarbonyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, and $R^4$—X represents OH, (1-methyl-1H-1,2,4-triazol-5-yl)amino, (1-ethyl-1H-1,2,4-triazol-5-yl)amino, (1-methyl-1H-tetrazol-5-yl)amino, (1-ethyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl]amino, [(1R,2R)-1-carboxy-2-methylbutyl]amino, [(1S,2R)-1-carboxy-2-methylbutyl]amino, (5-methoxy-2,5-dioxopentyl)amino, 2-(4-fluorophenoxy)ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl)sulfinylethoxy, butan-2-yloxy, 2-(4-methoxyphenoxy)ethoxy, 2-(benzenesulfonyl)ethoxy, 2-(4-chlorophenoxy) ethoxy, 2-(4-methylphenoxy)ethoxy, 3-methylbutan-2-yloxy, [3-(1H-imidazol-4-yl)-1-methoxy-1-oxopropan-2-yl]amino, [(2R)-3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl] amino, [(1R)-1-carboxy-2-phenylethyl]amino, [(1S)-1-carboxy-2-phenylethyl]amino, [1-carboxy-2-(4-hydroxyphenyl)ethyl]amino, [(1R)-1-carboxy-2-(4-hydroxyphenyl)ethyl]amino, [(1S)-1-carboxy-2-(4-hydroxyphenyl)ethyl]amino, [1-carboxy-2-(4-methoxyphenyl)ethyl]amino, [(1R)-1-carboxy-2-(4-methoxyphenyl)ethyl]amino, [(1S)-1-carboxy-2-(4-methoxyphenyl)ethyl]amino, 2-[(4-methoxyphenyl) thio]ethoxy, 2-[(4-methylphenyl)thio]ethoxy, [1-carboxy-3-methylbutyl]amino, [(1R)-1-carboxy-3-methylbutyl]amino, [(1S)-1-carboxy-3-methylbutyl] amino, (4-methyl-1,2,5-oxadiazol-3-yl)amino, 2-(4-methylphenyl)sulfinylethoxy, [1-(methoxycarbonyl) cyclopropyl]amino, 2-hydroxyethylamino, [3-(1H-imidazol-4-yl)-1-methoxy-1-oxopropan-2-yl]amino, [(2S)-3-(1H-imidazol-4-yl)-1-methoxy-1-oxopropan-2-yl]amino, [(2R)-3-(1H-imidazol-4-yl)-1-methoxy-1-oxopropan-2-yl]amino, [1-carboxy-2-methoxyethyl] amino, [(1R)-1-carboxy-2-methoxyethyl]amino, [(1S)-1-carboxy-2-methoxyethyl]amino, [1-carboxy-2-methylthioethyl]amino, [(1R)-1-carboxy-2-methylthioethyl]amino, [(1S)-1-carboxy-2-methylthioethyl]amino, [1-carboxyethyl]amino, [(1R)-1-carboxyethyl]amino, [(1S)-1-carboxyethyl]amino, [1-carboxy-2-methylpropyl]amino, [(1R)-1-carboxy-2-methylpropyl]amino, [(1S)-1-carboxy-2-methylpropyl] amino, trifluoromethylsulfonylamino, (2-methoxy-2-oxoethyl)-methylamino, 2-(4-methoxyphenyl) sulfonylethoxy, benzylamino, 2-methylpropylamino, amino, 2,2-dimethylhydrazino, hydrazino, prop-2-en-1-ylamino, 2-(4-methoxyphenyl)sulfinylethoxy, 2-phenylethylamino, (6-chloropyridin-3-yl)methyl-methylamino, (4-methoxy-4-oxobutan-2-yl)amino, [(2S)-4-methoxy-4-oxobutan-2-yl)]amino, [(2R)-4-methoxy-4-oxobutan-2-yl)]amino, [2-isopropyl-5-methylcyclohexyl]oxy, [(1S,2R,5S)-2-isopropyl-5-methylcyclohexyl]oxy, [(1S,2R,5R)-2-isopropyl-5-methylcyclohexyl]oxy, [(1R,2R,5S)-2-isopropyl-5-methylcyclohexyl]oxy, [(1R,2R,5R)-2-isopropyl-5-methylcyclohexyl]oxy, [(1S,2S,5S)-2-isopropyl-5-methylcyclohexyl]oxy, [(1S,2S,5R)-2-isopropyl-5-methylcyclohexyl]oxy, [(1R,2S,5S)-2-isopropyl-5-methylcyclohexyl]oxy, [(1R,2S,5R)-2-isopropyl-5-methylcyclohexyl]oxy, 1,2,3,4-tetrahydronaphthalen-1-ylamino, [1-carboxy-2-(1H-indol-3-yl)ethyl]amino, [(1S)-1-carboxy-2-(1H-indol-3-yl)ethyl]amino, [(1R)-1-carboxy-2-(1H-indol-3-yl)ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl)anilino, 2-(3,4-dichlorophenyl) ethylamino, 2,2,2-trifluoroethylsulfonylamino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, ethoxyethylamino, prop-2-yn-1-ylamino, (2-ethylphenyl)methylamino, (1-ethyl-3-methyl-1H-pyrazol-4-yl)methylamino, 3-methylbutylamino, 2-(2-bromophenyl)ethylamino, ethylamino, 2-(3,5-dimethoxyphenyl)ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, [(1R,2R)-2,6-dimethylindan-1-yl]amino, [(1S,2S)-2,6-dimethylindan-1-yl]amino, [(1S,2R)-2,6-dimethylindan-1-yl]amino, 2-(1,3-benzodioxol-5-yl) ethylamino, butan-2-ylamino, 2-(1H-indol-3-yl) ethylamino, propylamino, 2-(2,6-difluorophenyl) ethylamino, 2-(3-methylphenyl)ethylamino, 2-[3-(trifluoromethoxy)phenyl]ethylamino, indan-1-ylamino, quinolin-6-ylmethylamino, [1-tert-butoxy-3-(4-hydroxyphenyl)-1-oxopropan-2-yl]amino, [(2S)-1-tert-butoxy-3-(4-hydroxyphenyl)-1-oxopropan-2-yl] amino, [(2R)-1-tert-butoxy-3-(4-hydroxyphenyl)-1-oxopropan-2-yl]amino, [1-methoxy-3-(4-hydroxyphenyl)-1-oxopropan-2-yl]amino, [(2S)-1-methoxy-3-(4-hydroxyphenyl)-1-oxopropan-2-yl] amino, [(2R)-1-methoxy-3-(4-hydroxyphenyl)-1-oxopropan-2-yl]amino, [1-tert-butoxy-3-phenyl-1-oxopropan-2-yl]amino, [(2S)-1-tert-butoxy-3-phenyl-1-oxopropan-2-yl]amino, [(2R)-1-tert-butoxy-3-phenyl-1-oxopropan-2-yl]amino, [1-methoxy-3-phenyl-1-oxopropan-2-yl]amino, [(2S)-1-methoxy-3-phenyl-1-oxopropan-2-yl]amino, [(2R)-1-methoxy-3-(4-hydroxyphenyl)-1-oxopropan-2-yl]amino, 2-(4-tert-butylphenyl)ethylamino, cyclopropylamino, isopropylamino, 2-(ethoxycarbonyl)piperidin-1-yl, (1-n-propyl-1H-1,2,4-triazol-5-yl)amino, 2-(2-fluorophenyl)ethylamino, (2-methoxy-2-oxoethyl)-methylamino, 2-(ethoxycarbonyl)piperidin-1-yl, benzhydrylamino, N-propylanilino, cyclobutylamino, cyclohexylmethylamino, N-ethylanilino, (2-methoxy-2-oxoethyl)-methylamino, 2-(ethoxycarbonyl)piperidin-1-yl, 3-(diethylamino)propylamino, (2,4-difluorophenyl)methylamino, 2-(5-hydroxy-1H-indol-3-yl) ethylamino, anilino, cyclopentylamino, cyclohexylamino, 2-[3-(trifluoromethyl)phenyl]ethylamino, 2-(diethylamino)ethylamino, isoquinolin-5-ylmethylamino, carboxymethyl(methyl)amino, 2-(4-fluorophenyl)ethylamino, 2-(5-methoxy-1H-indol-3-yl)ethylamino, carboxymethyl(ethyl)amino, 2-[4-(trifluoromethoxy)phenyl]ethylamino, 2-(3-bromophenyl)ethylamino, 2-(2,5-dichlorophenyl) ethylamino, 2-thiophen-2-ylethylamino, 2-(2-methoxyphenyl)ethylamino, 2-(3,4-dimethoxyphenyl) ethylamino, (4-methoxy-4-oxobutyl)amino, 2-(4-chlorophenyl)ethylamino, 2-pyridin-3-ylethylamino, 2-[3-chloro-5-(trifluoromethyl)pyridin-2-yl]ethylamino, cyclopentylsulfonylamino, 2-(4-methoxyphenyl)ethylamino, 2-(3-methoxyphenyl)ethylamino, 2-(2,3-dichlorophenyl)ethylamino, 2-[3,5-bis(trifluoromethyl)phenyl]ethylamino, 2-(4-methylphenyl)ethylamino, 2-(3-chlorophenyl) ethylamino, 2-(2-chlorophenyl)ethylamino, 2-pyridin-2-ylethylamino, 2-(2,4-dichlorophenyl)ethylamino, 2-(3-fluorophenyl)ethylamino, 2,2-difluoroethylamino, 1,3-dimethoxy-1,3-dioxopropan-2-yl, 5-hydroxy-1,3-dimethyl-1H-pyrazol-4-yl, 3,3-dimethyl-2,6-dioxocyclohexyl, 4,4-dimethyl-2,6-dioxocyclohexyl, 4-methyl-2,6-dioxocyclohexyl, 2,5-dioxocyclopentyl, dicyanomethyl, 2,4-dioxo-3-bicyclo[3.2.1]octanyl, 3,3,5,5-tetramethyl-2,4,6-trioxocyclohexyl, 2,6-dioxocyclohexyl, 2,2-dimethyl-4,6-dioxo-1,3-dioxan-5-yl, 5-hydroxy-1-methyl-1H-pyrazol-4-yl, 1-cyano-2-methoxy-2-oxoethyl, 1-methoxy-1,3-dioxobutan-2-yl, 2,4-dioxo-3-bicyclo[3.2.1]oct-6-enyl, phenylsulfonyl, ethoxyethoxy, methoxyethoxyethoxy, hydroxyethoxy, hydroxyethoxyethoxy, hydroxyethoxyethoxyethoxy, cyclopropylmethoxy, cyclobutylmethoxy, cyclopentylmethoxy, cyclohexylmethoxy, cyclopropylmethylamino, cyclobutylmethylamino, cyclopentylmethylamino, cyclohexylmethylamino, oxetan-3-yloxy, oxetan-3-ylamino, tetrahydrofuran-2-yloxy, tetrahydrofuran-3-yloxy, tetrahydrofuran-2-ylmethoxy, tetrahydrofuran-3-ylmethoxy, tetrahydrofuran-2-ylamino, tetrahydrofuran-3-ylamino, tetrahydrofuran-2-ylmethylamino, tetrahydrofuran-3-ylmethylamino, benzyloxy, 4-fluorobenzyloxy, 4-chlorobenzyloxy, 3-fluorobenzyloxy, 3-chlorobenzyloxy, 2-fluorobenzyloxy, 2-chlorobenzyloxy, 4-fluorobenzylamino, 4-chlorobenzylamino, 3-fluorobenzylamino, 3-chlorobenzylamino, 2-fluorobenzylamino, 2-chlorobenzylamino, pyridin-3-ylmethylamino, pyridin-4-ylmethylamino, 4-chloro-pyridin-2-ylmethylamino, 4-chloro-pyridin-3-ylmethylamino, 4-trifluoromethyl-pyridin-3-ylmethylamino, pyridin-2-ylmethoxy, pyridin-3-ylmethoxy, pyridin-4-ylmethoxy, 4-chloro-pyridin-2-ylmethoxy, 4-chloro-pyridin-3-ylmethoxy, cyanomethylamino, cyanomethoxy, cyanoethoxy, hydroxycarbonylmethylamino, hydroxycarbonylmethoxy, hydroxycarbonylethoxy, hydroxycarbonylethylamino, methoxycarbonylmethylamino, ethoxycarbonylmethylamino, azetidin-1-yl-amino, pyrrolidin-1-ylamino, piperidin-1-ylamino, ethylthioethoxy, 1,2,4-thiadiazol-5-ylamino, 5-(difluoromethyl)-1,3,4-thiadiazol-2-ylamino, 5-tert-butyl-1,2-oxazol-3-ylamino, 4-(trifluoromethyl)pyridin-2-ylamino, 5-chloro-4-(trifluoromethyl)pyridin-2-ylamino, (pyridin-4-ylmethoxy)amino, hydroxyamino, methoxyamino, ethoxyamino, benzyloxyamino, methyl(methoxy)amino, methoxycarbonylmethoxyamino, ethoxycarbonylmethoxyamino, methoxycarbonylethoxyamino, ethoxycarbonylethoxyamino, hydroxycarbonylmethoxyamino, hydroxycarbonylethoxyamino, benzyloxycarbonylmethoxyamino, benzyloxycarbonylmethoxyamino, (1,1-dimethyleth-1-yl)oxycarbonylmethoxyamino, (1,1-dimethyleth-1-yl)oxycarbonylmethoxyamino.

The invention especially provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, methyl, ethyl, prop-1-yl, prop-2-yl, difluoromethyl, trifluoromethyl, 2,2-difluoroethyl, 2,2,2-trifluoroethyl, cyclopropyl, methoxymethyl, $R^2$ and $R^3$ independently of one another represent hydrogen, fluorine, chlorine, bromine, methyl, ethyl, n-propyl, 1-methylethyl, n-butyl, 1-methylprop-1-yl, 2-methylprop-1-yl, 1,1-dimethylethyl, ethenyl, prop-1-en-1-yl, prop-2-en-1-yl, 1-methyl-eth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, ethynyl, prop-1-yn-1-yl, prop-2-yn-1-yl, but-1-yn-1-yl, but-2-yn-1-yl, but-3-yn-1-yl, cyclopropyl, cyclobutyl, cyclopentyl, cyclohexyl, cyclopropylmethyl, cyclobutylmethyl, cyclopentylmethyl, cyclohexylmethyl, trifluoromethyl, difluoromethyl, 2,2-difluoroethyl, 2,2,2-trifluoroethyl, methoxymethyl, trifluoromethoxymethyl, methoxy, ethoxy, benzyloxy, benzyl, phenyl, methylthiomethyl, trifluoromethylthiomethyl, $R^5$, $R^6$, $R^7$ and $R^8$ independently of one another represent hydrogen, fluorine, chlorine, bromine, iodine, methyl, ethyl, n-propyl, 1-methylethyl, n-butyl, 1-methylprop-1-yl, 2-methylprop-1-yl, 1,1-dimethylethyl, cyclopropyl, cyclobutyl, cyclopentyl, cyclohexyl, difluoromethyl, trifluoromethyl, methoxy, ethoxy, trifluoromethoxy, benzyl, phenyl, methylthiomethyl, trifluoromethylthiomethyl, pyridin-2-yl, pyridin-3-yl, pyridin-4-yl, $R^9$ and $R^{10}$ independently of one another represent hydrogen, methyl, ethyl, n-propyl, 1-methylethyl, cyclopropyl, cyclobutyl, difluoromethyl, trifluoromethyl, $R^{11}$ and $R^{12}$ independently of one another represent fluorine, chlorine, bromine, iodine, cyano, nitro, methyl, ethyl, n-propyl, 1-methylethyl, n-butyl, 1-methylprop-1-yl, 2-methylprop-1-yl, 1,1-dimethylethyl, ethenyl, prop-1-en-1-yl, prop-2-en-1-yl, 1-methyleth-1-en-1-yl, ethynyl, prop-1-yn-1-yl, prop-2-yn-1-yl, but-1-yn-1-yl, methoxymethyl, ethoxymethyl, ethoxyethyl, methoxyethyl, trifluoromethyl, pentafluoroethyl, heptafluoropropyl, chlorodifluoromethyl, difluoromethyl, 2,2-difluoroethyl, 2,2,2-trifluoroethyl, trifluoromethoxymethyl, trifluoromethoxyethyl, difluoromethoxymethyl, difluoromethoxyethyl, 2,2-difluoroethoxymethyl, 2,2,2-trifluoroethoxymethyl, methylthiomethyl, methylthioethyl, trifluoromethylthiomethyl, methoxymethoxymethyl, methoxyethoxymethyl, hydroxymethyl, methylcarbonyloxymethyl, hydroxy, methoxy, ethoxy, 1-methylethoxy, 1,1-dimethylethoxy, benzyloxy, phenoxy, methylcarbonyloxy, hydrothio, methylthio, difluoromethoxy, trifluoromethoxy, 2,2-difluoroethoxy, 2,2,2-trifluoroethoxy, trifluoromethylthio, cyclopropyl, cyclobutyl, cyclopentyl, cyclohexyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, $R^{16}$ represents hydrogen, fluorine, chlorine, bromine, iodine, cyano, nitro, methyl, ethyl, n-propyl, 1-methylethyl, n-butyl, 1-methylprop-1-yl, 2-methylprop-1-yl, 1,1-dimethylethyl, cyclopropyl, cyclobutyl, cyclopentyl, cyclohexyl, hydroxy, methoxy, ethoxy, 1-methylethoxy, 1,1-dimethylethoxy, benzyloxy, phenoxy, methylcarbonyloxy, hydrothio, methylthio, ethylthio, difluoromethoxy, trifluoromethoxy, 2,2-difluoroethoxy, 2,2,2-trifluoroethoxy, trifluoromethylthio, ethenyl, prop-1-en-1-yl, prop-2-en-1-yl, 1-methyleth-1-en-1-yl, ethynyl, prop-1-yn-1-yl, prop-2-yn-1-yl, but-1-yn-1-yl, difluoromethyl, trifluoromethyl, 2,2-difluoroethyl, 2,2,2-trifluoroethyl, pentafluoroethyl, methoxymethyl, ethoxymethyl, ethoxyethyl, hydroxymethyl, hydroxycarbonyl, methoxycarbonyl, ethoxycarbonyl, 1-methylethoxycarbonyl, 1,1-dimethylethoxycarbonyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, and the group $R^4$—X— represents OH, (1-methyl-1H-1,2,4-triazol-5-yl)amino, (1-ethyl-1H-1,2,4-triazol-5-yl) amino, (1-methyl-1H-tetrazol-5-yl)amino, (1-ethyl-1H-tetrazol-5-yl)amino, [1-carboxy-2-methylbutyl] amino, [(1S,2S)-1-carboxy-2-methylbutyl]amino, [(1R,2S)-1-carboxy-2-methylbutyl]amino, [(1R,2R)-1-carboxy-2-methylbutyl]amino, [(1S,2R)-1-carboxy-2-methylbutyl]amino, (5-methoxy-2,5-dioxopentyl) amino, 2-(4-fluorophenoxy)ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethyl-propoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxy-ethoxy, pentan-2-yloxy, 2-(4-chlorophenyl)sulfinylethoxy, butan-2-yloxy, 2-(4-methoxyphenoxy)ethoxy, 2-(benzenesulfonyl)ethoxy, 2-(4-chlorophenoxy) ethoxy, 2-(4-methylphenoxy)ethoxy, 3-methylbutan-2-yloxy, [3-(1H-imidazol-4-yl)-1-methoxy-1-oxopropan-2-yl]amino, [(2R)-3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl] amino, [(1R)-1-carboxy-2-phenylethyl]amino, [(1S)-1-carboxy-2-phenylethyl]amino, [1-carboxy-2-(4-hydroxyphenyl)ethyl]amino, [(1R)-1-carboxy-2-(4-hydroxyphenyl)ethyl]amino, [(1S)-1-carboxy-2-(4-hydroxyphenyl)ethyl]amino, [1-carboxy-2-(4-methoxyphenyl)ethyl]amino, [(1R)-1-carboxy-2-(4-methoxyphenyl)ethyl]amino, [(1S)-1-carboxy-2-(4-methoxyphenyl)ethyl]amino, 2-[(4-methoxyphenyl) thio]ethoxy, 2-[(4-methylphenyl)thio]ethoxy, [1-carboxy-3-methylbutyl]amino, [(1R)-1-carboxy-3-methylbutyl]amino, [(1S)-1-carboxy-3-methylbutyl] amino, (4-methyl-1,2,5-oxadiazol-3-yl)amino, 2-(4-methylphenyl)sulfinylethoxy, [1-(methoxycarbonyl) cyclopropyl]amino, 2-hydroxyethylamino, [3-(1H-imidazol-4-yl)-1-methoxy-1-oxopropan-2-yl]amino, [(2S)-3-(1H-imidazol-4-yl)-1-methoxy-1-oxopropan-2-yl]amino, [(2R)-3-(1H-imidazol-4-yl)-1-methoxy-1-oxopropan-2-yl]amino, [1-carboxy-2-methoxyethyl] amino, [(1R)-1-carboxy-2-methoxyethyl]amino, [(1S)-1-carboxy-2-methoxyethyl]amino, [1-carboxy-2-methylthioethyl]amino, [(1R)-1-carboxy-2-methylthioethyl]amino, [(1S)-1-carboxy-2-methylthioethyl]amino, [1-carboxyethyl]amino, [(1R)-1-carboxyethyl]amino, [(1S)-1-carboxyethyl]amino, [1-carboxy-2-methylpropyl]amino, [(1R)-1-carboxy-2-methylpropyl]amino, [(1S)-1-carboxy-2-methylpropyl] amino, trifluoromethylsulfonylamino, (2-methoxy-2-oxoethyl)-methylamino, 2-(4-methoxyphenyl) sulfonylethoxy, benzylamino, 2-methylpropylamino, amino, 2,2-dimethylhydrazino, hydrazino, prop-2-en-1-ylamino, 2-(4-methoxyphenyl)sulfinylethoxy, 2-phenylethylamino, (6-chloropyridin-3-yl)methyl-methyl-amino, (4-methoxy-4-oxobutan-2-yl)amino, [(2S)-4-methoxy-4-oxobutan-2-yl)]amino, [(2R)-4-methoxy-4-oxobutan-2-yl)]amino, [2-isopropyl-5-methylcyclohexyl]oxy, [(1S,2R,5S)-2-isopropyl-5-methylcyclohexyl]oxy, [(1S,2R,5R)-2-isopropyl-5-methylcyclohexyl]oxy, [(1R,2R,5S)-2-isopropyl-5-methylcyclohexyl]oxy, [(1R,2R,5R)-2-isopropyl-5-methylcyclohexyl]oxy, [(1S,2S,5S)-2-isopropyl-5-methylcyclohexyl]oxy, [(1S,2S,5R)-2-isopropyl-5-methylcyclohexyl]oxy, [(1R,2S,5S)-2-isopropyl-5-methylcyclohexyl]oxy, [(1R,2S,5R)-2-isopropyl-5-methylcyclohexyl]oxy, 1,2,3,4-tetrahydronaphthalen-1-ylamino, [1-carboxy-2-(1H-indol-3-yl)ethyl]amino, [(1S)-1-carboxy-2-(1H-indol-3-yl)ethyl]amino, [(1R)-1-carboxy-2-(1H-indol-3-yl)ethyl]amino, pyrrolidin-1-yl, ethylsulfonylamino, diethylamino, difluoromethyl-sulfonylamino, isopropylsulfonylamino, pyridin-2-ylmethylamino, quinolin-5-ylmethylamino, 2-(methoxycarbonyl)anilino, 2-(3,4-dichlorophenyl) ethylamino, 2,2,2-trifluoroethylsulfonylamino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, ethoxyethylamino, prop-2-yn-1-ylamino, (2-ethylphenyl)methylamino, (1-ethyl-3-methyl-1H-pyrazol-4-yl)methylamino, 3-methylbutylamino, 2-(2-bromophenyl)ethylamino, ethylamino, 2-(3,5-dimethoxyphenyl)ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, [(1R,2R)-2,6-dimethylindan-1-yl]amino, [(1S,2S)-2,6-dimethylindan-1-yl]amino, [(1S,2R)-2,6-dimethylindan-1-yl]amino, 2-(1,3-benzodioxol-5-yl) ethylamino, butan-2-ylamino, 2-(1H-indol-3-yl) ethylamino, propylamino, 2-(2,6-difluorophenyl) ethylamino, 2-(3-methylphenyl)ethylamino, 2-[3-(trifluoromethoxy)phenyl]ethylamino, indan-1-ylamino, quinolin-6-ylmethylamino, [1-tert-butoxy-3-(4-hydroxyphenyl)-1-oxopropan-2-yl]amino, [(2S)-1-tert-butoxy-3-(4-hydroxyphenyl)-1-oxopropan-2-yl] amino, [(2R)-1-tert-butoxy-3-(4-hydroxyphenyl)-1-oxopropan-2-yl]amino, [1-methoxy-3-(4-hydroxyphenyl)-1-oxopropan-2-yl]amino, [(2S)-1-methoxy-3-(4-hydroxyphenyl)-1-oxopropan-2-yl] amino, [(2R)-1-methoxy-3-(4-hydroxyphenyl)-1-oxopropan-2-yl]amino, [1-tert-butoxy-3-phenyl-1-oxopropan-2-yl]amino, [(2S)-1-tert-butoxy-3-phenyl-1-oxopropan-2-yl]amino, [(2R)-1-tert-butoxy-3-phenyl-1-oxopropan-2-yl]amino, [1-methoxy-3-phenyl-1-oxopropan-2-yl]amino, [(2S)-1-methoxy-3-phenyl-1-oxopropan-2-yl]amino, [(2R)-1-methoxy-3-(4-hydroxyphenyl)-1-oxopropan-2-yl]amino, 2-(4-tert-butylphenyl)ethylamino, cyclopropylamino, isopropylamino, 2-(ethoxycarbonyl)piperidin-1-yl, (1-n-propyl-1H-1,2,4-triazol-5-yl)amino, 2-(2-fluorophenyl)ethylamino, (2-methoxy-2-oxoethyl)-methylamino, 2-(ethoxycarbonyl)piperidin-1-yl, benzhydrylamino, N-propylanilino, cyclobutylamino, cyclohexylmethylamino, N-ethylanilino, (2-methoxy-2-oxoethyl)-methylamino, 2-(ethoxycarbonyl)piperidin-1-yl, 3-(diethylamino)propylamino, (2,4-difluorophenyl)methylamino, 2-(5-hydroxy-1H-indol-3-yl) ethylamino, anilino, cyclopentylamino, cyclohexylamino, 2-[3-(trifluoromethyl)phenyl]ethylamino, 2-(diethylamino)ethylamino, isoquinolin-5-ylmethylamino, carboxymethyl(methyl)amino, 2-(4-fluorophenyl)ethylamino, 2-(5-methoxy-1H-indol-3-yl)ethylamino, carboxymethyl(ethyl)amino, 2-[4-(trifluoromethoxy)phenyl]ethylamino, 2-(3-bromophenyl)ethylamino, 2-(2,5-dichlorophenyl) ethylamino, 2-thiophen-2-ylethylamino, 2-(2-methoxyphenyl)ethylamino, 2-(3,4-dimethoxyphenyl) ethylamino, (4-methoxy-4-oxobutyl)amino, 2-(4-chlorophenyl)ethylamino, 2-pyridin-3-ylethylamino, 2-[3-chloro-5-(trifluoromethyl)pyridin-2-yl]ethylamino, cyclopentylsulfonylamino, 2-(4-methoxyphenyl)ethylamino, 2-(3-methoxyphenyl)ethylamino, 2-(2,3-dichlorophenyl)ethylamino, 2-[3,5-bis(trifluoromethyl)phenyl]ethylamino, 2-(4-methylphenyl)ethylamino, 2-(3-chlorophenyl)ethylamino, 2-(2-chlorophenyl)ethylamino, 2-pyridin-2-ylethylamino, 2-(2,4-dichlorophenyl)ethylamino, 2-(3-fluorophenyl)ethylamino, 2,2-difluoroethylamino, 1,3-dimethoxy-1,3-dioxopropan-2-yl, 5-hydroxy-1,3-dimethyl-1H-pyrazol-4-yl, 3,3-dimethyl-2,6-dioxocyclohexyl, 4,4-dimethyl-2,6-dioxocyclohexyl, 4-methyl-2,6-dioxocyclohexyl, 2,5-dioxocyclopentyl, dicyanomethyl, 2,4-dioxo-3-bicyclo[3.2.1]octanyl, 3,3,5,5-tetramethyl-2,4,6-trioxocyclohexyl, 2,6-dioxocyclohexyl, 2,2-dimethyl-4,6-dioxo-1,3-dioxan-5-yl, 5-hydroxy-1-methyl-1H-pyrazol-4-yl, 1-cyano-2-methoxy-2-oxoethyl, 1-methoxy-1,3-dioxobutan-2-yl, 2,4-dioxo-3-bicyclo[3.2.1]oct-6-enyl, phenylsulfonyl, ethoxyethoxy, methoxyethoxyethoxy, hydroxyethoxy, hydroxyethoxyethoxy, hydroxyethoxyethoxyethoxy, cyclopropylmethoxy, cyclobutylmethoxy, cyclopentylmethoxy, cyclohexylmethoxy, cyclopropylmethylamino, cyclobutylmethylamino, cyclopentylmethylamino, cyclohexylmethylamino, oxetan-3-yloxy, oxetan-3-ylamino, tetrahydrofuran-2-yloxy, tetrahydrofuran-3-yloxy, tetrahydrofuran-2-ylmethoxy, tetrahydrofuran-3-ylmethoxy, tetrahydrofuran-2-ylamino, tetrahydrofuran-3-ylamino, tetrahydrofuran-2-ylmethylamino, tetrahydrofuran-3-ylmethylamino, benzyloxy, 4-fluorobenzyloxy, 4-chlorobenzyloxy, 3-fluorobenzyloxy, 3-chlorobenzyloxy, 2-fluorobenzyloxy, 2-chlorobenzyloxy, 4-fluorobenzylamino, 4-chlorobenzylamino, 3-fluorobenzylamino, 3-chlorobenzylamino, 2-fluorobenzylamino, 2-chlorobenzylamino, pyridin-3-ylmethylamino, pyridin-4-ylmethylamino, 4-chloro-pyridin-2-ylmethylamino, 4-chloro-pyridin-3-ylmethylamino, 4-trifluoromethyl-pyridin-3-ylmethylamino, pyridin-2-ylmethoxy, pyridin-3-ylmethoxy, pyridin-4-ylmethoxy, 4-chloro-pyridin-2-ylmethoxy, 4-chloro-pyridin-3-ylmethoxy, cyanomethylamino, cyanomethoxy, cyanoethoxy, hydroxycarbonylmethylamino, hydroxycarbonylmethoxy, hydroxycarbonylethoxy, hydroxycarbonylethylamino, methoxycarbonylmethylamino, ethoxycarbonylmethylamino, azetidin-1-yl-amino, pyrrolidin-1-ylamino, piperidin-1-ylamino, ethylthioethoxy, 1,2,4-thiadiazol-5-ylamino, 5-(difluoromethyl)-1,3,4-thiadiazol-2-ylamino, 5-tert-butyl-1,2-oxazol-3-ylamino, 4-(trifluoromethyl)pyridin-2-ylamino, 5-chloro-4-(trifluoromethyl)pyridin-2-ylamino, (pyridin-4-ylmethoxy)amino, hydroxyamino, methoxyamino, ethoxyamino, benzyloxyamino, methyl(methoxy)amino, methoxycarbonylmethoxyamino, ethoxycarbonylmethoxyamino, methoxycarbonylethoxyamino, ethoxycarbonylethoxyamino, hydroxycarbonylmethoxyamino, hydroxycarbonylethoxyamino, benzyloxycarbonylmethoxyamino, benzyloxycarbonylmethoxyamino, (1,1-dimethyleth-1-yl)oxycarbonylmethoxyamino, (1,1-dimethyleth-1-yl)oxycarbonylmethoxyamino.

The invention more especially provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, methyl, $R^2$ and $R^3$ independently of one another represent hydrogen, methyl, $R^5$, $R^6$, $R^7$ and $R^8$ independently of one another represent hydrogen, methyl, phenyl, $R^9$ and $R^{10}$ independently of one another represent hydrogen, methyl, $R^{11}$ and $R^{12}$ independently of one another represent fluorine, chlorine, bromine, iodine, cyano, methyl, ethyl, 1-methylethyl, trifluoromethyl, difluoromethyl, ethenyl, 1-methylethenyl, ethynyl, hydroxy, methoxy, ethoxy, benzyloxy, phenoxy, methylthio, difluoromethoxy, trifluoromethoxy, trifluoromethylthio, cyclopropyl, $R^{16}$ represents hydrogen, fluorine, chlorine, bromine, iodine, cyano, methyl, ethyl, 1-methylethyl, hydroxy, methoxy, ethoxy, methylthio, difluoromethoxy, trifluoromethoxy, trifluoromethylthio, ethenyl, 1-methyleth-1-en-1-yl, ethynyl, difluoromethyl, trifluoromethyl, and $R^4$—X represents OH, (1-methyl-1H-1,2,4-triazol-5-yl)amino, (1-ethyl-1H-1,2,4-triazol-5-yl)amino, (1-methyl-1H-tetrazol-5-yl)amino, (1-ethyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl]amino, [(1R,2R)-1-carboxy-2-methylbutyl]amino, [(1S,2R)-1-carboxy-2-methylbutyl]amino, (5-methoxy-2,5-dioxopentyl)amino, 2-(4-fluorophenoxy)ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl)sulfinylethoxy, butan-2-yloxy, 2-(4-methoxyphenoxy)ethoxy, 2-(benzenesulfonyl)ethoxy, 2-(4-chlorophenoxy)ethoxy, 2-(4-methylphenoxy)ethoxy, 3-methylbutan-2-yloxy, [3-(1H-imidazol-4-yl)-1-methoxy-1-oxopropan-2-yl]amino, [(2R)-3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl]amino, [(1R)-1-carboxy-2-phenylethyl]amino, [(1S)-1-carboxy-2-phenylethyl]amino, [1-carboxy-2-(4-hydroxyphenyl)ethyl]amino, [(1R)-1-carboxy-2-(4-hydroxyphenyl)ethyl]amino, [(1S)-1-carboxy-2-(4-hydroxyphenyl)ethyl]amino, [1-carboxy-2-(4-methoxyphenyl)ethyl]amino, [(1R)-1-carboxy-2-(4-methoxyphenyl)ethyl]amino, [(1S)-1-carboxy-2-(4-methoxyphenyl)ethyl]amino, 2-[(4-methoxyphenyl)thio]ethoxy, 2-[(4-methylphenyl)thio]ethoxy, [1-carboxy-3-methylbutyl]amino, [(1R)-1-carboxy-3-methylbutyl]amino, [(1S)-1-carboxy-3-methylbutyl]amino, (4-methyl-1,2,5-oxadiazol-3-yl)amino, 2-(4-methylphenyl)sulfinylethoxy, [1-(methoxycarbonyl)cyclopropyl]amino, 2-hydroxyethylamino, [3-(1H-imidazol-4-yl)-1-methoxy-1-oxopropan-2-yl]amino, [(2S)-3-(1H-imidazol-4-yl)-1-methoxy-1-oxopropan-2-yl]amino, [(2R)-3-(1H-imidazol-4-yl)-1-methoxy-1-oxopropan-2-yl]amino, [1-carboxy-2-methoxyethyl]amino, [(1R)-1-carboxy-2-methoxyethyl]amino, [(1S)-1-carboxy-2-methoxyethyl]amino, [1-carboxy-2-methylthioethyl]amino, [(1R)-1-carboxy-2-methylthioethyl]amino, [(1S)-1-carboxy-2-methylthioethyl]amino, [1-carboxyethyl]amino, [(1R)-1-carboxyethyl]amino, [(1S)-1-carboxyethyl]amino, [1-carboxy-2-methylpropyl]amino, [(1R)-1-carboxy-2-methylpropyl]amino, [(1S)-1-carboxy-2-methylpropyl] amino, trifluoromethylsulfonylamino, (2-methoxy-2-oxoethyl)-methylamino, 2-(4-methoxyphenyl) sulfonylethoxy, benzylamino, 2-methylpropylamino, amino, 2,2-dimethylhydrazino, hydrazino, prop-2-en-1-ylamino, 2-(4-methoxyphenyl)sulfinylethoxy, 2-phenylethylamino, (6-chloropyridin-3-yl)methyl-methylamino, (4-methoxy-4-oxobutan-2-yl)amino, [(2S)-4-methoxy-4-oxobutan-2-yl)]amino, [(2R)-4-methoxy-4-oxobutan-2-yl)]amino, [2-isopropyl-5-methylcyclohexyl]oxy, [(1S,2R,5S)-2-isopropyl-5-methylcyclohexyl]oxy, [(1S,2R,5R)-2-isopropyl-5-methylcyclohexyl]oxy, [(1R,2R,5S)-2-isopropyl-5-methylcyclohexyl]oxy, [(1R,2R,5R)-2-isopropyl-5-methylcyclohexyl]oxy, [(1S,2S,5S)-2-isopropyl-5-methylcyclohexyl]oxy, [(1S,2S,5R)-2-isopropyl-5-methylcyclohexyl]oxy, [(1R,2S,5S)-2-isopropyl-5-methylcyclohexyl]oxy, [(1R,2S,5R)-2-isopropyl-5-methylcyclohexyl]oxy, 1,2,3,4-tetrahydronaphthalen-1-ylamino, [1-carboxy-2-(1H-indol-3-yl)ethyl]amino, [(1S)-1-carboxy-2-(1H-indol-3-yl)ethyl]amino, [(1R)-1-carboxy-2-(1H-indol-3-yl)ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl)anilino, 2-(3,4-dichlorophenyl) ethylamino, 2,2,2-trifluoroethylsulfonylamino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, ethoxyethylamino, prop-2-yn-1-ylamino, (2-ethylphenyl)methylamino, (1-ethyl-3-methyl-1H-pyrazol-4-yl)methylamino, 3-methylbutylamino, 2-(2-bromophenyl)ethylamino, ethylamino, 2-(3,5-dimethoxyphenyl)ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, [(1R,2R)-2,6-dimethylindan-1-yl]amino, [(1S,2S)-2,6-dimethylindan-1-yl]amino, [(1S,2R)-2,6-dimethylindan-1-yl]amino, 2-(1,3-benzodioxol-5-yl) ethylamino, butan-2-ylamino, 2-(1H-indol-3-yl) ethylamino, propylamino, 2-(2,6-difluorophenyl) ethylamino, 2-(3-methylphenyl)ethylamino, 2-[3-(trifluoromethoxy)phenyl]ethylamino, indan-1-ylamino, quinolin-6-ylmethylamino, [1-tert-butoxy-3-(4-hydroxyphenyl)-1-oxopropan-2-yl]amino, [(2S)-1-tert-butoxy-3-(4-hydroxyphenyl)-1-oxopropan-2-yl] amino, [(2R)-1-tert-butoxy-3-(4-hydroxyphenyl)-1-oxopropan-2-yl]amino, [1-methoxy-3-(4-hydroxyphenyl)-1-oxopropan-2-yl]amino, [(2S)-1-methoxy-3-(4-hydroxyphenyl)-1-oxopropan-2-yl] amino, [(2R)-1-methoxy-3-(4-hydroxyphenyl)-1-oxopropan-2-yl]amino, [1-tert-butoxy-3-phenyl-1-oxopropan-2-yl]amino, [(2S)-1-tert-butoxy-3-phenyl-1-oxopropan-2-yl]amino, [(2R)-1-tert-butoxy-3-phenyl-1-oxopropan-2-yl]amino, [1-methoxy-3-phenyl-1-oxopropan-2-yl]amino, [(2S)-1-methoxy-3-phenyl-1-oxopropan-2-yl]amino, [(2R)-1-methoxy-3-(4-hydroxyphenyl)-1-oxopropan-2-yl]amino, 2-(4-tert-butylphenyl)ethylamino, cyclopropylamino, isopropylamino, 2-(ethoxycarbonyl)piperidin-1-yl, (1-n-propyl-1H-1,2,4-triazol-5-yl)amino, 2-(2-fluorophenyl)ethylamino, (2-methoxy-2-oxoethyl)-methylamino, 2-(ethoxycarbonyl)piperidin-1-yl, benzhydrylamino, N-propylanilino, cyclobutylamino, cyclohexylmethylamino, N-ethylanilino, (2-methoxy-2-oxoethyl)-methylamino, 2-(ethoxycarbonyl)piperidin-1-yl, 3-(diethylamino)propylamino, (2,4-difluorophenyl)methylamino, 2-(5-hydroxy-1H-indol-3-yl) ethylamino, anilino, cyclopentylamino, cyclohexylamino, 2-[3-(trifluoromethyl)phenyl]ethylamino, 2-(diethylamino)ethylamino, isoquinolin-5-ylmethylamino, carboxymethyl(methyl)amino, 2-(4-fluorophenyl)ethylamino, 2-(5-methoxy-1H-indol-3-yl)ethylamino, carboxymethyl(ethyl)amino, 2-[4-(trifluoromethoxy)phenyl]ethylamino, 2-(3-bromophenyl)ethylamino, 2-(2,5-dichlorophenyl) ethylamino, 2-thiophen-2-ylethylamino, 2-(2-methoxyphenyl)ethylamino, 2-(3,4-dimethoxyphenyl) ethylamino, (4-methoxy-4-oxobutyl)amino, 2-(4-chlorophenyl)ethylamino, 2-pyridin-3-ylethylamino, 2-[3-chloro-5-(trifluoromethyl)pyridin-2-yl]ethylamino, cyclopentylsulfonylamino, 2-(4-methoxyphenyl)ethylamino, 2-(3-methoxyphenyl)ethylamino, 2-(2,3-dichlorophenyl)ethylamino, 2-[3,5-bis(trifluoromethyl)phenyl]ethylamino, 2-(4-methylphenyl)ethylamino, 2-(3-chlorophenyl) ethylamino, 2-(2-chlorophenyl)ethylamino, 2-pyridin-2-ylethylamino, 2-(2,4-dichlorophenyl)ethylamino, 2-(3-fluorophenyl)ethylamino, 2,2-difluoroethylamino, 1,3-dimethoxy-1,3-dioxopropan-2-yl, 5-hydroxy-1,3-dimethyl-1H-pyrazol-4-yl, 3,3-dimethyl-2,6-dioxocyclohexyl, 4,4-dimethyl-2,6-dioxocyclohexyl, 4-methyl-2,6-dioxocyclohexyl, 2,5-dioxocyclopentyl, dicyanomethyl, 2,4-dioxo-3-bicyclo[3.2.1]octanyl, 3,3,5,5-tetramethyl-2,4,6-trioxocyclohexyl, 2,6-dioxocyclohexyl, 2,2-dimethyl-4,6-dioxo-1,3-dioxan-5-yl, 5-hydroxy-1-methyl-1H-pyrazol-4-yl, 1-cyano-2-methoxy-2-oxoethyl, 1-methoxy-1,3-dioxobutan-2-yl, 2,4-dioxo-3-bicyclo[3.2.1]oct-6-enyl, phenylsulfonyl, ethoxyethoxy, methoxyethoxyethoxy, hydroxyethoxy, hydroxyethoxyethoxy, hydroxyethoxyethoxyethoxy, cyclopropylmethoxy, cyclobutylmethoxy, cyclopentylmethoxy, cyclohexylmethoxy, cyclopropylmethylamino, cyclobutylmethylamino, cyclopentylmethylamino, cyclohexylmethylamino, oxetan-3-yloxy, oxetan-3-ylamino, tetrahydrofuran-2-yloxy, tetrahydrofuran-3-yloxy, tetrahydrofuran-2-ylmethoxy, tetrahydrofuran-3-ylmethoxy, tetrahydrofuran-2-ylamino, tetrahydrofuran-3-ylamino, tetrahydrofuran-2-ylmethylamino, tetrahydrofuran-3-ylmethylamino, benzyloxy, 4-fluorobenzyloxy, 4-chlorobenzyloxy, 3-fluorobenzyloxy, 3-chlorobenzyloxy, 2-fluorobenzyloxy, 2-chlorobenzyloxy, 4-fluorobenzylamino, 4-chlorobenzylamino, 3-fluorobenzylamino, 3-chlorobenzylamino, 2-fluorobenzylamino, 2-chlorobenzylamino, pyridin-3-ylmethylamino, pyridin-4-ylmethylamino, 4-chloro-pyridin-2-ylmethylamino, 4-chloro-pyridin-3-ylmethylamino, 4-trifluoromethyl-pyridin-3-ylmethylamino, pyridin-2-ylmethoxy, pyridin-3-ylmethoxy, pyridin-4-ylmethoxy, 4-chloro-pyridin-2-ylmethoxy, 4-chloro-pyridin-3-ylmethoxy, cyanomethylamino, cyanomethoxy, cyanoethoxy, hydroxycarbonylmethylamino, hydroxycarbonylmethoxy, hydroxycarbonylethoxy, hydroxycarbonylethylamino, methoxycarbonylmethylamino, ethoxycarbonylmethylamino, azetidin-1-yl-amino, pyrrolidin-1-ylamino, piperidin, -1-ylamino, ethylthioethoxy, 1,2,4-thiadiazol-5-ylamino, 5-(difluoromethyl)-1,3,4-thiadiazol-2-ylamino, 5-tert-butyl-1,2-oxazol-3-ylamino, 4-(trifluoromethyl)pyridin-2-ylamino, 5-chloro-4-(trifluoromethyl)pyridin-2-ylamino, (pyridin-4-ylmethoxy)amino, hydroxyamino, methoxyamino, ethoxyamino, benzyloxyamino, methyl(methoxy)amino, methoxycarbonylmethoxyamino, ethoxycarbonylmethoxyamino, methoxycarbonylethoxyamino, ethoxycarbonylethoxyamino, hydroxycarbonylmethoxyamino, hydroxycarbonylethoxyamino, benzyloxycarbonylmethoxyamino, benzyloxycarbonylmethoxyamino, (1,1-dimethyleth-1-yl)oxycarbonylmethoxyamino, (1,1-dimethyleth-1-yl) oxycarbonylmethoxyamino.

The invention very especially provides compounds of the general formula (I) in which $A^1$, $A^2$, and $A^3$ are the same or different and independently from one another represent N (nitrogen) or the C—$R^{16}$ moiety, with a maximum of two adjacent nitrogen atoms, and where $R^{16}$ in each C—$R^{16}$ moiety is the same or different as defined below, $R^1$ represents hydrogen, $R^2$ and $R^3$ independently of one another represent hydrogen, $R^5$, $R^6$, $R^7$ and $R^8$ independently of one another represent hydrogen, $R^9$ and $R^{10}$ independently of one another represent hydrogen, $R^{11}$ and $R^{12}$ independently of one another represent fluorine, chlorine, methyl, $R^{16}$ represents hydrogen, fluorine, chlorine, methyl and $R^4$—X represents OH, (1-methyl-1H-1,2,4-triazol-5-yl) amino, (1-methyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl] amino, [(1R,2R)-1-carboxy-2-methylbutyl]amino, [(1S,2R)-1-carboxy-2-methylbutyl]amino, (5-methoxy-2,5-dioxopentyl)amino, 2-(4-fluorophenoxy)ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl)sulfinylethoxy, butan-2-yloxy, 2-(4-methoxyphenoxy)ethoxy, 2-(benzenesulfonyl)ethoxy, 2-(4-chlorophenoxy)ethoxy, 2-(4-methylphenoxy)ethoxy, 3-methylbutan-2-yloxy, [3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl] amino, [(1R)-1-carboxy-2-phenylethyl]amino, [(1S)-1-carboxy-2-phenylethyl]amino, [1-carboxy-3-methylbutyl]amino, [(1R)-1-carboxy-3-methylbutyl] amino, 2-[(4-methoxyphenyl)thio]ethoxy, 2-[(4-methylphenyl)thio]ethoxy, (4-methyl-1,2,5-oxadiazol-3-yl)amino, 2-(4-methylphenyl)sulfinylethoxy, [1-(methoxycarbonyl)cyclopropyl]amino, 2-hydroxyethylamino, trifluoromethylsulfonylamino, (2-methoxy-2-oxoethyl)-methylamino, 2-(4-methoxyphenyl)sulfonylethoxy, benzylamino, 2-methylpropylamino, amino, 2,2-dimethylhydrazino, hydrazino, prop-2-en-1-ylamino, 2-(4-methoxyphenyl)sulfinylethoxy, 2-phenylethylamino, [1-carboxy-2-(1H-indol-3-yl)ethyl]amino, [(1S)-1-carboxy-2-(1H-indol-3-yl) ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl)anilino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, prop-2-yn-1-ylamino, ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, propylamino, 2-[3-(trifluoromethyl)phenyl]ethylamino, 2-pyridin-2-ylethylamino, 2,2-difluoroethylamino, 1,3-dimethoxy-1,3-dioxopropan-2-yl, 3,3-dimethyl-2,6-dioxocyclohexyl, 4,4-dimethyl-2,6-dioxocyclohexyl, 4-methyl-2,6-dioxocyclohexyl, 3,3,5,5-tetramethyl-2,4,6-trioxocyclohexyl, 2,2-dimethyl-4,6-dioxo-1,3-dioxan-5-yl, pyrrolidin-1-ylamino, piperidin, -1-ylamino, 1,2,4-thiadiazol-5-ylamino.

The definitions of radicals listed above in general terms or within areas of preference apply both to the end products of the general formula (I) and correspondingly to the starting materials or intermediates required for preparation in each case. These radical definitions can be combined with one another as desired, i.e. including combinations between the given preferred ranges.

Primarily for reasons of higher herbicidal activity, better selectivity and/or better producibility, compounds of the abovementioned general formula (I) according to the invention or their salts or their use according to the invention are of particular interest in which individual radicals have one of the preferred meanings already specified or specified below, or in particular those in which one or more of the preferred meanings already specified or specified below occur in combination.

With regard to the compounds according to the invention, the terms used above and further below will be elucidated. These are familiar to the person skilled in the art and especially have the definitions elucidated hereinafter.

Unless defined differently, names of chemical groups are generally to be understood such that attachment to the skeleton or the remainder of the molecule is via the structural element mentioned last, i.e. for example in the case of ($C_2$-$C_8$)-alkenyloxy via the oxygen atom and in the case of ($C_1$-$C_8$)-alkoxy-($C_1$-$C_4$)-alkyl or ($C_1$-$C_8$)-alkoxycarbonyl-($C_1$-$C_8$)-alkyl, in each case via the carbon atom of the alkyl group. In the case of specified groups, such as $OR^{19}$, $NR^{17}R^{18}$, $S(O)_mR^{20}$, C(═O)$R^{19}$, C(═O)$OR^{19}$, or C(═O) $NR^{17}R^{18}$ the attachment to the skeleton is via the structural element mentioned first, i.e. for example in the case of $OR^{19}$ via the oxygen atom and in the case of C(═O)$OR^{19}$ via the carbonyl atom.

According to the invention, "alkylsulfonyl"—alone or as part of a chemical group—refers to straight-chain or branched alkylsulfonyl, preferably having 1 to 8 or 1 to 6 carbon atoms, for example (but not limited to) ($C_1$-$C_6$)-alkylsulfonyl such as methylsulfonyl, ethylsulfonyl, propylsulfonyl, 1-methylethylsulfonyl, butylsulfonyl, 1-methylpropylsulfonyl, 2-methylpropylsulfonyl, 1,1-dimethylethylsulfonyl, pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropylsulfonyl and 1-ethyl-2-methylpropylsulfonyl.

According to the invention, "alkylthio"—alone or as part of a chemical group—denotes straight-chain or branched S-alkyl, preferably having 1 to 8 or 1 to 6 carbon atoms, such as $(C_1-C_{10})$—, $(C_1-C_6)$- or $(C_1-C_4)$-alkylthio, for example (but not limited to) $(C_1-C_6)$-alkylthio such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 1,1-dimethylpropylthio, 1,2-dimethylpropylthio, 2,2-dimethylpropylthio, 1-ethylpropylthio, hexylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio.

According to the invention, "alkylsulfinyl (alkyl-S(═O)—)", unless defined differently elsewhere, denotes alkyl radicals which are attached to the skeleton via —S(═O)—, such as $(C_1-C_{10})$—, $(C_1-C_6)$- or $(C_1-C_4)$-alkylsulfinyl, for example (but not limited to) $(C_1-C_6)$-alkylsulfinyl such as methylsulfinyl, ethylsulfinyl, propylsulfinyl, 1-methylethylsulfinyl, butylsulfinyl, 1-methylpropylsulfinyl, 2-methylpropylsulfinyl, 1,1-dimethylethylsulfinyl, pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

"Alkoxy" denotes an alkyl radical bonded via an oxygen atom, for example (but not limited to) $(C_1-C_6)$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Alkenyloxy denotes an alkenyl radical attached via an oxygen atom, and alkynyloxy denotes an alkynyl radical attached via an oxygen atom, such as $(C_2-C_{10})$—, $(C_2-C_6)$- or $(C_2-C_4)$-alkenoxy and $(C_3-C_{10})$—, $(C_3-C_6)$- or $(C_3-C_4)$-alkynoxy.

"Cycloalkoxy" denotes a cycloalkyl radical attached via an oxygen atom and cycloalkenyloxy denotes a cycloalkenyl radical attached via an oxygen atom.

According to the invention, "alkylcarbonyl" (alkyl-C(═O)—), unless defined differently elsewhere, represents alkyl radicals attached to the skeleton via —C(═O)—, such as $(C_1-C_{10})$—, $(C_1-C_6)$- or $(C_1-C_4)$-alkylcarbonyl. Here, the number of the carbon atoms refers to the alkyl radical in the alkylcarbonyl group.

Analogously, "alkenylcarbonyl" and "alkynylcarbonyl", unless defined differently elsewhere, in accordance with the invention, respectively represent alkenyl and alkynyl radicals attached to the skeleton via —C(═O)—, such as $(C_2-C_{10})$—, $(C_2-C_6)$- or $(C_2-C_4)$-alkenylcarbonyl and $(C_2-C_{10})$—, $(C_2-C_6)$- or $(C_2-C_4)$-alkynylcarbonyl. Here, the number of the carbon atoms refers to the alkenyl or alkynyl radical in the alkenyl or alkynyl group.

"Alkoxycarbonyl (alkyl-O—C(═O)—)," unless defined differently elsewhere: alkyl radicals attached to the skeleton via —O—C(═O)—, such as $(C_1-C_{10})$—, $(C_1-C_6)$- or $(C_1-C_4)$-alkoxycarbonyl. Here, the number of the carbon atoms refers to the alkyl radical in the alkoxycarbonyl group. Analogously, "alkenyloxycarbonyl" and "alkynyloxycarbonyl", unless defined differently elsewhere, in accordance with the invention, respectively represent alkenyl and alkynyl radicals attached to the skeleton via —O—C(═O)—, such as $(C_2-C_{10})$—, $(C_2-C_6)$- or $(C_2-C_4)$-alkenyloxycarbonyl and $(C_3-C_{10})$—, $(C_3-C_6)$- or $(C_3-C_4)$- alkynyloxycarbonyl. Here, the number of the carbon atoms refers to the alkenyl or alkynyl radical in the alkenyloxycarbonyl or alkynyloxycarbonyl group.

The term "aryl" denotes an optionally substituted mono-, bi- or polycyclic aromatic system having preferably 6 to 14, especially 6 to 10, ring carbon atoms, for example phenyl, naphthyl, anthryl, phenanthrenyl and the like, preferably phenyl.

The term "optionally substituted aryl" also embraces polycyclic systems, such as tetrahydronaphthyl, indenyl, indanyl, fluorenyl, biphenylyl, where the bonding site is on the aromatic system. In systematic terms, "aryl" is generally also encompassed by the term "optionally substituted phenyl". Preferred aryl substituents here are, for example, hydrogen, halogen, alkyl, cycloalkyl, cycloalkylalkyl, cycloalkenyl, halocycloalkyl, alkenyl, alkynyl, aryl, arylalkyl, arylalkenyl, heteroaryl, heteroarylalkyl, heterocyclyl, heterocyclylalkyl, alkoxyalkyl, alkylthio, haloalkylthio, haloalkyl, alkoxy, haloalkoxy, cycloalkoxy, cycloalkylalkoxy, aryloxy, heteroraryloxy, alkoxyalkoxy, alkynylalkoxy, alkenyloxy, dialkylamino-alkoxy, tris-[alkyl]silyl, di-[alkyl]arylsilyl, di-[alkyl]alkylsilyl, tris-[alkyl]silylalkynyl, arylalkynyl, heteroarylalkynyl, alkylalkynyl, cycloalkylalkynyl, haloalkylalkynyl, heterocyclyl-N-alkoxy, nitro, cyano, amino, alkylamino, dialkylamino, alkylcarbonylamino, cycloalkylcarbonylamino, arylcarbonylamino, alkoxycarbonylamino, alkoxycarbonylalkylamino, arylalkoxycarbonylalkylamino, hydroxycarbonyl, alkoxycarbonyl, aminocarbonyl, alkylaminocarbonyl, cycloalkylaminocarbonyl, di-alkylaminocarbonyl, heteroarylalkoxy, arylalkoxy.

A heterocyclic radical (heterocyclyl) contains at least one heterocyclic ring (=carbocyclic ring in which at least one carbon atom has been replaced by a heteroatom, preferably by a heteroatom from the group of N, O, S, P) which is saturated, unsaturated, partially saturated or heteroaromatic and may be unsubstituted or substituted, in which case the bonding site is localized on a ring atom. If the heterocyclyl radical or the heterocyclic ring is optionally substituted, it may be fused to other carbocyclic or heterocyclic rings. In the case of optionally substituted heterocyclyl, polycyclic systems are also included, for example 8-azabicyclo[3.2.1]octanyl, 8-azabicyclo[2.2.2]octanyl or 1-azabicyclo[2.2.1]heptyl. Optionally substituted heterocyclyl also includes spirocyclic systems, such as, for example, 1-oxa-5-aza-spiro[2.3]hexyl. Unless defined otherwise, the heterocyclic ring preferably contains 3 to 9 ring atoms, in particular 3 to 6 ring atoms, and one or more, preferably 1 to 4, in particular 1, 2 or 3 heteroatoms in the heterocyclic ring, preferably from the group N, O and S, where, however, two oxygen atoms must not be directly adjacent to one another, for example having one heteroatom from the group consisting of N, O and S 1- or 2- or 3-pyrrolidinyl, 3,4-dihydro-2H-pyrrol-2- or -3-yl, 2,3-dihydro-1H-pyrrol-1- or -2- or -3- or -4- or -5-yl; 2,5-dihydro-1H-pyrrol-1- or -2- or -3-yl, 1- or 2- or 3- or 4-piperidinyl; 2,3,4,5-tetrahydropyridin-2- or -3- or -4- or -5-yl or -6-yl; 1,2,3,6-tetrahydropyridin-1- or -2- or -3- or -4- or -5- or -6-yl; 1,2,3,4-tetrahydropyridin-1- or -2- or -3- or -4- or -5- or -6-yl; 1,4-dihydropyridin-1- or -2- or -3- or -4-yl; 2,3-dihydropyridin-2- or -3- or -4- or -5- or -6-yl; 2,5-dihydropyridin-2- or -3- or -4- or -5- or -6-yl, 1- or 2- or 3- or 4-azepanyl; 2,3,4,5-tetrahydro-1H-azepin-1- or -2- or -3- or -4- or -5- or -6- or -7-yl; 2,3,4,7-tetrahydro-1H-azepin-1- or -2- or -3- or -4- or -5- or -6- or -7-yl; 2,3,6,7-tetrahydro-1H-azepin-1- or -2- or -3- or -4-yl; 3,4,5,6-tetrahydro-2H-azepin-2- or -3- or -4- or -5- or -6- or -7-yl; 4,5-dihydro-1H-azepin-1- or -2- or -3- or -4-yl; 2,5-dihydro-1H-azepin-1- or -2- or -3- or -4- or -5- or -6- or -7-yl; 2,7-dihydro-1H-azepin-1- or -2- or -3- or -4-yl; 2,3-dihydro-1H-azepin-1- or -2- or -3- or -4- or -5- or -6- or -7-yl; 3,4-dihydro-2H-azepin-2- or -3- or -4- or -5- or -6- or -7-yl; 3,6-dihydro-2H-azepin-2- or -3- or -4- or -5- or -6- or -7-yl; 5,6-dihydro-2H-azepin-2- or -3- or -4- or -5- or -6- or -7-yl; 4,5-dihydro-3H-azepin-2- or -3- or -4- or -5- or -6- or -7-yl; 1H- azepin-1- or -2- or -3- or -4- or -5- or -6- or -7-yl; 2H-azepin-2- or -3- or -4- or -5- or -6- or -7-yl; 3H-azepin-2- or -3- or -4- or -5- or -6- or -7-yl; 4H-azepin-2- or -3- or -4- or -5- or -6- or -7-yl, 2- or 3-oxolanyl (=2- or 3-tetrahydrofuranyl); 2,3-dihydrofuran-2- or -3- or -4- or -5-yl; 2,5-dihydrofuran-2- or -3-yl, 2- or 3- or 4-oxanyl (=2- or 3- or 4-tetrahydropyranyl); 3,4-dihydro-2H-pyran-2- or -3- or -4- or -5- or -6-yl; 3,6-dihydro-2H-pyran-2- or -3- or -4- or -5- or -6-yl; 2H-pyran-2- or -3- or -4- or -5- or -6- yl; 4H-pyran-2- or -3- or -4-yl, 2- or -3- or -4-oxepanyl; 2,3,4,5-tetrahydrooxepin-2- or -3- or -4- or -5- or -6- or -7-yl; 2,3,4,7-tetrahydrooxepin-2- or -3- or -4- or -5- or -6- or -7-yl; 2,3,6,7-tetrahydrooxepin-2- or -3- or -4-yl; 2,3-dihydrooxepin-2- or -3- or -4- or -5- or -6- or -7-yl; 4,5-dihydrooxepin-2- or -3- or -4-yl; 2,5-dihydrooxepin-2- or -3- or -4- or -5- or -6- or -7-yl; oxepin-2- or -3- or -4- or -5- or -6- or -7-yl; 2- or 3-tetrahydrothiophenyl; 2,3-dihydrothiophen-2- or -3- or -4- or -5-yl; 2,5-dihydrothiophen-2- or -3-yl; tetrahydro-2H-thiopyran-2- or -3- or -4-yl; 3,4-dihydro-2H-thiopyran-2- or -3- or -4- or -5- or -6-yl; 3,6-dihydro-2H-thiopyran-2- or -3- or -4- or -5- or -6-yl; 2H-thiopyran-2- or -3- or -4- or -5- or -6-yl; 4H-thiopyran-2- or -3- or -4-yl. Preferred 3-membered and 4-membered heterocycles are, for example, 1- or 2-aziridinyl, oxiranyl, thiiranyl, 1- or 2- or 3-azetidinyl, 2- or 3-oxetanyl, 2- or 3-thietanyl, 1,3-dioxetan-2-yl. Further examples of "heterocyclyl" are a partially or fully hydrogenated heterocyclic radical having two heteroatoms from the group of N, O and S, for example 1- or 2- or 3- or 4-pyrazolidinyl; 4,5-dihydro-3H-pyrazol-3- or -4- or -5-yl; 4,5-dihydro-1H-pyrazol-1- or -3- or -4- or -5-yl; 2,3-dihydro-1H-pyrazol-1- or -2- or -3- or -4- or -5-yl; 1- or -2- or -3- or -4-imidazolidinyl; 2,3-dihydro-1H-imidazol-1- or -2- or -3- or -4-yl; 2,5-dihydro-1H-imidazol-1- or -2- or -4- or -5-yl; 4,5-dihydro-1H-imidazol-1- or -2- or -4- or -5-yl; hexahydropyridazin-1- or -2- or -3- or -4-yl; 1,2,3,4-tetrahydropyridazin-1- or -2- or -3- or -4- or -5- or -6-yl; 1,2,3,6-tetrahydropyridazin-1- or -2- or -3- or -4- or -5- or -6-yl; 1,4,5,6-tetrahydropyridazin-1- or -3- or -4- or -5- or -6-yl; 3,4,5,6-tetrahydropyridazin-3- or -4- or -5-yl; 4,5-dihydropyridazin-3- or -4-yl; 3,4-dihydropyridazin-3- or -4- or -5- or -6-yl; 3,6-dihydropyridazin-3- or -4-yl; 1,6-dihydropyridazin-1- or -3- or -4- or -5- or -6-yl; hexahydropyrimidin-1- or -2- or -3- or -4-yl; 1,4,5,6-tetrahydropyrimidin-1- or -2- or -4- or -5- or -6-yl; 1,2,5,6-tetrahydropyrimidin-1- or -2- or -4- or -5- or -6-yl; 1,2,3,4-tetrahydropyrimidin-1- or -2- or -3- or -4- or -5- or -6-yl; 1,6-dihydropyrimidin-1- or -2- or -4- or -5- or -6-yl; 1,2-dihydropyrimidin-1- or -2- or -4- or -5- or -6-yl; 2,5-dihydropyrimidin-2- or -4- or -5-yl; 4,5-dihydropyrimidin-4- or -5- or -6-yl; 1,4-dihydropyrimidin-1- or -2- or -4- or -5- or -6-yl; 1- or -2- or -3-piperazinyl; 1,2,3,6-tetrahydropyrazin-1- or -2- or -3- or -5- or -6-yl; 1,2,3,4-tetrahydropyrazin-1- or -2- or -3- or -4- or -5- or -6-yl; 1,2-dihydropyrazin-1- or -2- or -3- or -5- or -6-yl; 1,4-dihydropyrazin-1- or -2- or -3-yl; 2,3-dihydropyrazin-2- or -3- or -5- or -6-yl; 2,5-dihydropyrazin-2- or -3-yl; 1,3-dioxolan-2- or -4- or -5-yl; 1,3-dioxol-2- or -4-yl; 1,3-dioxan-2- or -4- or -5-yl; 4H-1,3-dioxin-2- or -4- or -5- or -6-yl; 1,4-dioxan-2- or -3- or -5- or -6-yl; 2,3-dihydro-1,4-dioxin-2- or -3- or -5- or -6-yl; 1,4-dioxin-2- or -3-yl; 1,2-dithiolan-3- or -4-yl; 3H-1,2-dithiol-3- or -4- or -5-yl; 1,3-dithiolan-2- or -4-yl; 1,3-dithiol-2- or -4-yl; 1,2-dithian-3- or -4-yl; 3,4-dihydro-1,2-dithiin-3- or -4- or -5- or -6-yl; 3,6-dihydro-1,2-dithiin-3- or -4-yl; 1,2-dithiin-3- or -4-yl; 1,3-dithian-2- or -4- or -5-yl; 4H-1,3-dithiin-2- or -4- or -5- or -6-yl; isoxazolidin-2- or -3- or -4- or -5-yl; 2,3-dihydroisoxazol-2- or -3- or -4- or -5-yl; 2,5-dihydroisoxazol-2- or -3- or -4- or -5-yl; 4,5-dihydroisoxazol-3- or -4- or -5-yl; 1,3-oxazolidin-2- or -3- or -4- or -5-yl; 2,3-dihydro-1,3-oxazol-2- or -3- or -4- or -5-yl; 2,5-dihydro-1,3-oxazol-2- or -4- or -5-yl; 4,5-dihydro-1,3-oxazol-2- or -4- or -5-yl; 1,2-oxazinan-2- or -3- or -4- or -5- or -6-yl; 3,4-dihydro-2H-1,2-oxazin-2- or -3- or -4- or -5- or -6-yl; 3,6-dihydro-2H-1,2-oxazin-2- or -3- or -4- or -5- or -6-yl; 5,6-dihydro-2H-1,2-oxazin-2- or -3- or -4- or -5- or -6-yl; 5,6-dihydro-4H-1,2-oxazin-3- or -4- or -5- or -6-yl; 2H-1,2-oxazin-2- or -3- or -4- or -5- or -6-yl; 6H-1,2-oxazin-3- or -4- or -5- or -6-yl; 4H-1,2-oxazin-3- or -4- or -5- or -6-yl; 1,3-oxazinan-2- or -3- or -4- or -5- or -6-yl; 3,4-dihydro-2H-1,3-oxazin-2- or -3- or -4- or -5- or -6-yl; 3,6-dihydro-2H-1,3-oxazin-2- or -3- or -4- or -5- or -6-yl; 5,6-dihydro-2H-1,3-oxazin-2- or -4- or -5- or -6-yl; 5,6-dihydro-4H-1,3-oxazin-2- or -4- or -5- or -6-yl; 2H-1,3-oxazin-2- or -4- or -5- or -6-yl; 6H-1,3-oxazin-2- or -4- or -5- or -6-yl; 4H-1,3-oxazin-2- or -4- or -5- or -6-yl; morpholin-2- or -3- or -4-yl; 3,4-dihydro-2H-1,4-oxazin-2- or -3- or -4- or -5- or -6-yl; 3,6-dihydro-2H-1,4-oxazin-2- or -3- or -5- or -6-yl; 2H-1,4-oxazin-2- or -3- or -5- or -6-yl; 4H-1,4-oxazin-2- or -3-yl; 1,2-oxazepan-2- or -3- or -4- or -5- or -6- or -7-yl; 2,3,4,5-tetrahydro-1,2-oxazepin-2- or -3- or -4- or -5- or -6- or -7-yl; 2,3,4,7-tetrahydro-1,2-oxazepin-2- or -3- or -4- or -5- or -6- or -7-yl; 2,3,6,7-tetrahydro-1,2-oxazepin-2- or -3- or -4- or -5- or -6- or -7-yl; 2,5,6,7-tetrahydro-1,2-oxazepin-2- or -3- or -4- or -5- or -6- or -7-yl; 4,5,6,7-tetrahydro-1,2-oxazepin-3- or -4- or -5- or -6- or -7-yl; 2,3-dihydro-1,2-oxazepin-2- or -3- or -4- or -5- or -6- or -7-yl; 2,5-dihydro-1,2-oxazepin-2- or -3- or -4- or -5- or -6- or -7-yl; 2,7-dihydro-1,2-oxazepin-2- or -3- or -4- or -5- or -6- or -7-yl; 4,5-dihydro-1,2-oxazepin-3- or -4- or -5- or -6- or -7-yl; 4,7-dihydro-1,2-oxazepin-3- or -4- or -5- or -6- or -7-yl; 6,7-dihydro-1,2-oxazepin-3- or -4- or -5- or -6- or -7-yl; 1,2-oxazepin-3- or -4- or -5- or -6- or -7-yl; 1,3-oxazepan-2- or -3- or -4- or -5- or -6- or -7-yl; 2,3,4,5-tetrahydro-1,3-oxazepin-2- or -3- or -4- or -5- or -6- or -7-yl; 2,3,4,7-tetrahydro-1,3-oxazepin-2- or -3- or -4- or -5- or -6- or -7-yl; 2,3,6,7-tetrahydro-1,3-oxazepin-2- or -3- or -4- or -5- or -6- or -7-yl; 2,5,6,7-tetrahydro-1,3-oxazepin-2- or -4- or -5- or -6- or -7-yl; 4,5,6,7-tetrahydro-1,3-oxazepin-2- or -4- or -5- or -6- or -7-yl; 2,3-dihydro-1,3-oxazepin-2- or -3- or -4- or -5- or -6- or -7-yl; 2,5-dihydro-1,3-oxazepin-2- or -4- or -5- or -6- or -7-yl; 2,7-dihydro-1,3-oxazepin-2- or -4- or -5- or -6- or -7-yl; 4,5-dihydro-1,3-oxazepin-2- or -4- or -5- or -6- or -7-yl; 4,7-dihydro-1,3-oxazepin-2- or -4- or -5- or -6- or -7-yl; 6,7-dihydro-1,3-oxazepin-2- or -4- or -5- or -6- or -7-yl; 1,3-oxazepin-2- or -4- or -5- or -6- or -7-yl; 1,4-oxazepan-2- or -3- or -5- or -6- or -7-yl; 2,3,4,5-tetrahydro-1,4-oxazepin-2- or -3- or -4- or -5- or -6- or -7-yl; 2,3,4,7-tetrahydro-1,4-oxazepin-2- or -3- or -4- or -5- or -6- or -7-yl; 2,3,6,7-tetrahydro-1,4-oxazepin-2- or -3- or -5- or -6- or -7-yl; 2,5,6,7-tetrahydro-1,4-oxazepin-2- or -3- or -5- or -6- or -7-yl; 4,5,6,7-tetrahydro-1,4-oxazepin-2- or -3- or -4- or -5- or -6- or -7-yl; 2,3-dihydro-1,4-oxazepin-2- or -3- or -5- or -6- or -7-yl; 2,5-dihydro-1,4-oxazepin-2- or -3- or -5- or -6- or -7-yl; 2,7-dihydro-1,4-oxazepin-2- or -3- or -5- or -6- or -7-yl; 4,5-dihydro-1,4-oxazepin-2- or -3- or -4- or -5- or -6- or -7-yl; 4,7-dihydro-1,4-oxazepin-2- or -3- or -4- or -5- or -6- or -7-yl; 6,7-dihydro-1,4-oxazepin-2- or -3- or -5- or -6- or -7-yl; 1,4-oxazepin-2- or -3- or -5- or -6- or -7-yl; isothiazolidin-2- or -3- or -4- or -5-yl; 2,3-dihydroisothiazol-2- or -3- or -4- or -5-yl; 2,5-dihydroisothiazol-2- or -3- or -4- or -5-yl; 4,5-dihydroisothiazol-3- or -4- or -5-yl; 1,3-thiazolidin-2- or -3- or -4- or -5-yl; 2,3-dihydro-1,3-thiazol-2- or -3- or -4- or -5-yl; 2,5-dihydro-1,3-thiazol-2- or -4- or -5-yl; 4,5-dihydro-1,3-thiazol-2- or -4- or -5-yl; 1,3-thiazinan-2- or -3- or -4- or -5- or -6-yl; 3,4-dihydro-2H-1,3-thiazin-2- or -3- or -4- or -5- or -6-yl; 3,6-dihydro-2H-1,3-thiazin-2- or -3- or -4- or -5- or -6-yl; 5,6-dihydro-2H-1,3-thiazin-2- or -4- or -5- or -6-yl; 5,6-dihydro-4H-1,3-thiazin-2- or -4- or -5- or -6-yl; 2H-1,3-thiazin-2- or -4- or -5- or -6-yl; 6H-1,3-thiazin-2- or -4- or -5- or -6-yl; 4H-1,3-thiazin-2- or - 4- or -5- or -6-yl. Further examples of "heterocyclyl" are a partially or fully hydrogenated heterocyclic radical having 3 heteroatoms from the group of N, O and S, for example 1,4,2-dioxazolidin-2- or -3- or -5-yl; 1,4,2-dioxazol-3- or -5-yl; 1,4,2-dioxazinan-2- or -3- or -5- or -6-yl; 5,6-dihydro-1,4,2-dioxazin-3- or -5- or -6-yl; 1,4,2-dioxazin-3- or -5- or -6-yl; 1,4,2-dioxazepan-2- or -3- or -5- or -6- or -7-yl; 6,7-dihydro-5H-1,4,2-dioxazepin-3- or -5- or -6- or -7-yl; 2,3-dihydro-7H-1,4,2-dioxazepin-2- or -3- or -5- or -6- or -7-yl; 2,3-dihydro-5H-1,4,2-dioxazepin-2- or -3- or -5- or -6- or -7-yl; 5H-1,4,2-dioxazepin-3- or -5- or -6- or -7-yl; 7H-1,4,2-dioxazepin-3- or -5- or -6- or -7-yl. Structural examples of heterocycles which are optionally substituted further are also listed below:

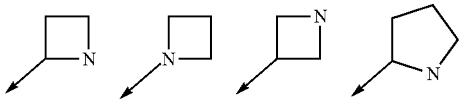
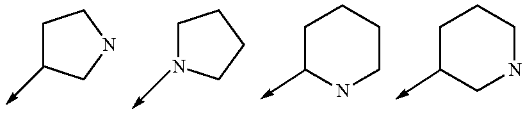
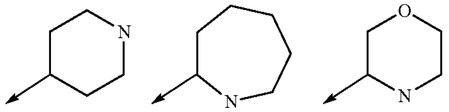
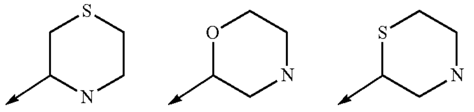

-continued

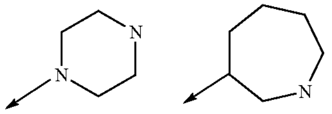
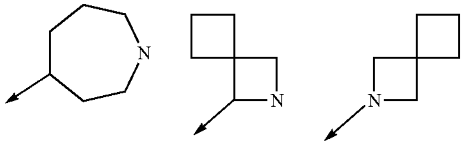
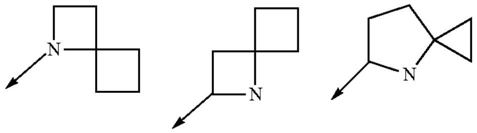
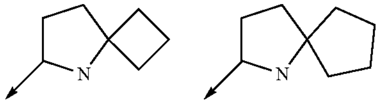
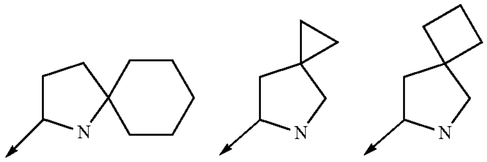
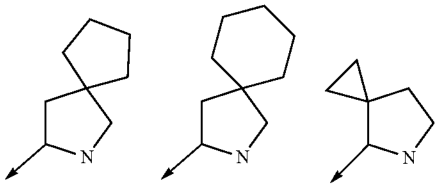
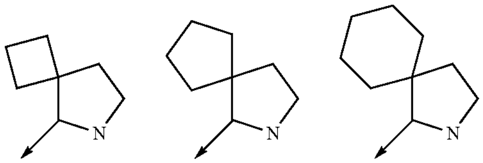
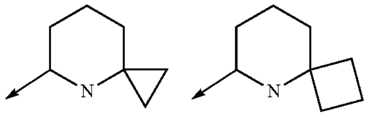
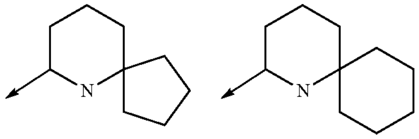
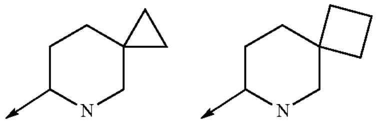
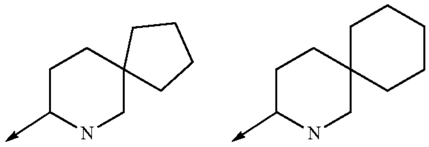
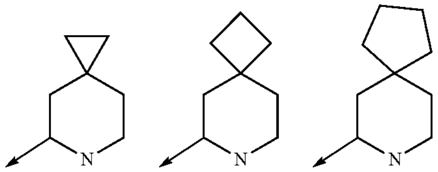

-continued
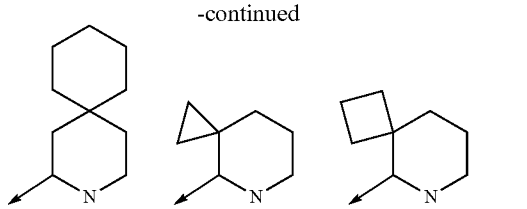
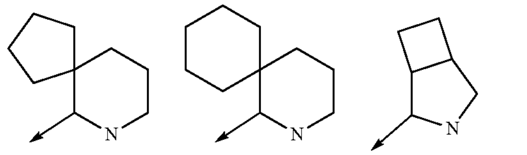
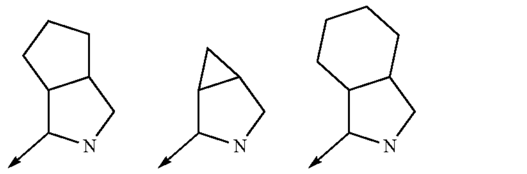
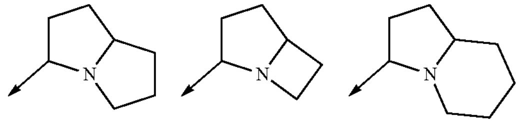
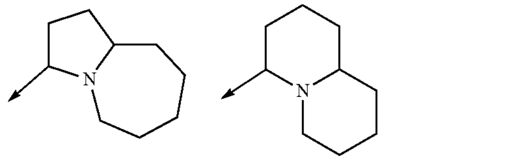
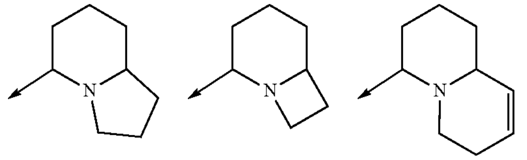
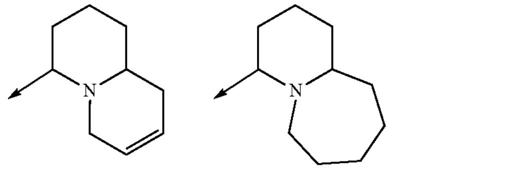
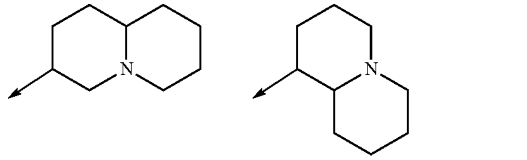
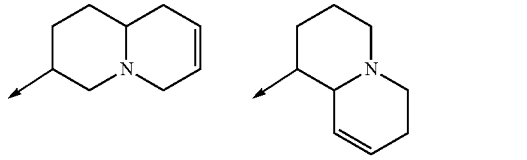
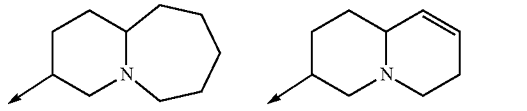
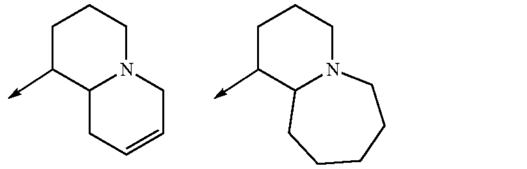
-continued
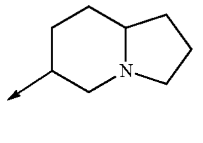
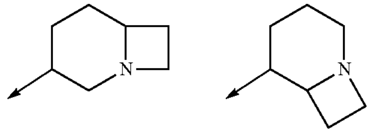
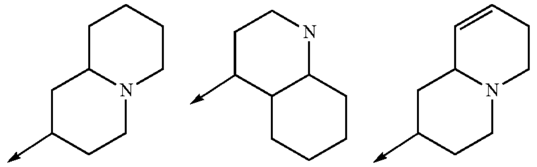
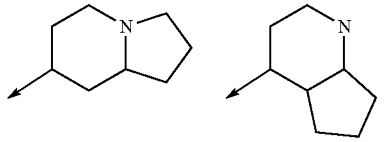
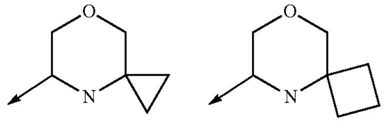
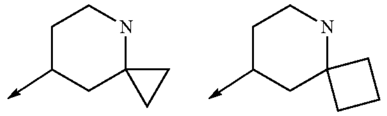
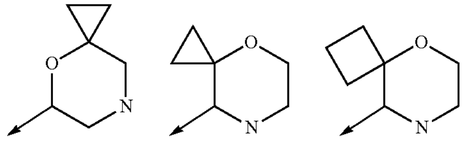
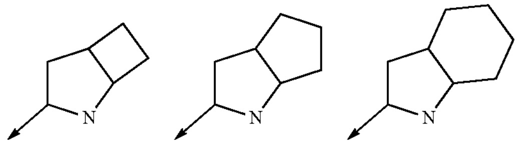
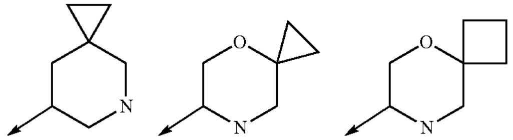
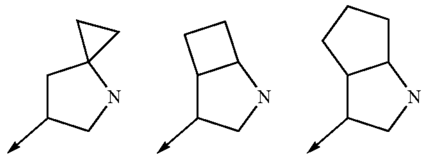
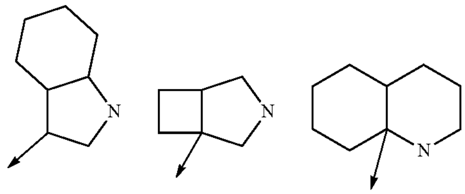
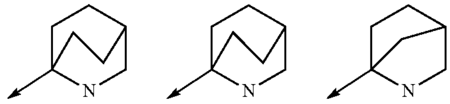

-continued

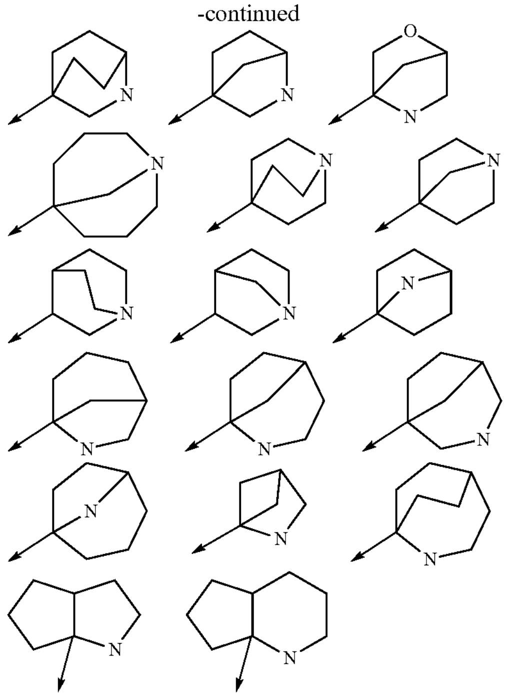

The heterocycles listed above are preferably substituted, for example, by hydrogen, halogen, alkyl, haloalkyl, hydroxyl, alkoxy, cycloalkoxy, aryloxy, alkoxyalkyl, alkoxyalkoxy, cycloalkyl, halocycloalkyl, aryl, arylalkyl, heteroaryl, heterocyclyl, alkenyl, alkylcarbonyl, cycloalkylcarbonyl, arylcarbonyl, heteroarylcarbonyl, alkoxycarbonyl, hydroxycarbonyl, cycloalkoxycarbonyl, cycloalkylalkoxycarbonyl, alkoxycarbonylalkyl, arylalkoxycarbonyl, arylalkoxycarbonylalkyl, alkynyl, alkynylalkyl, alkylalkynyl, trisalkylsilylalkynyl, nitro, amino, cyano, haloalkoxy, haloalkylthio, alkylthio, hydrothio, hydroxyalkyl, oxo, heteroarylalkoxy, arylalkoxy, heterocyclylalkoxy, heterocyclylalkylthio, heterocyclyloxy, heterocyclylthio, heteroaryloxy, dialkylamino, alkylamino, cycloalkylamino, hydroxycarbonylalkylamino, alkoxycarbonylalkylamino, arylalkoxycarbonylalkylamino, alkoxycarbonylalkyl(alkyl)amino, aminocarbonyl, alkylaminocarbonyl, dialkylaminocarbonyl, cycloalkylaminocarbonyl, hydroxycarbonylalkylaminocarbonyl, alkoxycarbonylalkylaminocarbonyl, arylalkoxycarbonylalkylaminocarbonyl.

When a base structure is substituted "by one or more substituents" from a list of radicals (=group) or a generically defined group of radicals, this in each case includes simultaneous substitution by a plurality of identical and/or structurally different radicals.

In the case of a partially or fully saturated nitrogen heterocycle, this may be joined to the remainder of the molecule either via carbon or via the nitrogen.

Suitable substituents for a substituted heterocyclic radical are the substituents specified further down, and additionally also oxo and thioxo. The oxo group as a substituent on a ring carbon atom is then, for example, a carbonyl group in the heterocyclic ring. As a result, lactones and lactams are preferably also included. The oxo group may also occur on the ring heteroatoms, which may exist in different oxidation states, for example in the case of N and S, and in that case form, for example, the divalent —N(O)—, —S(O)— (also SO for short) and —$S(O)_2$— (also $SO_2$ for short) groups in the heterocyclic ring. In the case of —N(O)— and —S(O)— groups, both enantiomers in each case are included.

According to the invention, the expression "heteroaryl" refers to heteroaromatic compounds, i.e. fully unsaturated aromatic heterocyclic compounds, preferably 5- to 7-membered rings having 1 to 4, preferably 1 or 2, identical or different heteroatoms, preferably O, S or N. Inventive heteroaryls are, for example, 1H-pyrrol-1-yl; 1H-pyrrol-2-yl; 1H-pyrrol-3-yl; furan-2-yl; furan-3-yl; thien-2-yl; thien-3-yl, 1H-imidazol-1-yl; 1H-imidazol-2-yl; 1H-imidazol-4-yl; 1H-imidazol-5-yl; 1H-pyrazol-1-yl; 1H-pyrazol-3-yl; 1H-pyrazol-4-yl; 1H-pyrazol-5-yl, 1H-1,2,3-triazol-1-yl, 1H-1,2,3-triazol-4-yl, 1H-1,2,3-triazol-5-yl, 2H-1,2,3-triazol-2-yl, 2H-1,2,3-triazol-4-yl, 1H-1,2,4-triazol-1-yl, 1H-1,2,4-triazol-3-yl, 4H-1,2,4-triazol-4-yl, 1,2,4-oxadiazol-3-yl, 1,2,4-oxadiazol-5-yl, 1,3,4-oxadiazol-2-yl, 1,2,3-oxadiazol-4-yl, 1,2,3-oxadiazol-5-yl, 1,2,5-oxadiazol-3-yl, azepinyl, pyridin-2-yl, pyridin-3-yl, pyridin-4-yl, pyrazin-2-yl, pyrazin-3-yl, pyrimidin-2-yl, pyrimidin-4-yl, pyrimidin-5-yl, pyridazin-3-yl, pyridazin-4-yl, 1,3,5-triazin-2-yl, 1,2,4-triazin-3-yl, 1,2,4-triazin-5-yl, 1,2,4-triazin-6-yl, 1,2,3-triazin-4-yl, 1,2,3-triazin-5-yl, 1,2,4-, 1,3,2-, 1,3,6- and 1,2,6-oxazinyl, isoxazol-3-yl, isoxazol-4-yl, isoxazol-5-yl, 1,3-oxazol-2-yl, 1,3-oxazol-4-yl, 1,3-oxazol-5-yl, isothiazol-3-yl, isothiazol-4-yl, isothiazol-5-yl, 1,3-thiazol-2-yl, 1,3-thiazol-4-yl, 1,3-thiazol-5-yl, oxepinyl, thiepinyl, 1,2,4-triazolonyl and 1,2,4-diazepinyl, 2H-1,2,3,4-tetrazol-5-yl, 1H-1,2,3,4-tetrazol-5-yl, 1,2,3,4-oxatriazol-5-yl, 1,2,3,4-thiatriazol-5-yl, 1,2,3,5-oxatriazol-4-yl, 1,2,3,5-thiatriazol-4-yl. The heteroaryl groups according to the invention may also be substituted by one or more identical or different radicals. If two adjacent carbon atoms are part of a further aromatic ring, the systems are fused heteroaromatic systems, such as benzofused or polyannealed heteroaromatics. Preferred examples are quinolines (e.g. quinolin-2-yl, quinolin-3-yl, quinolin-4-yl, quinolin-5-yl, quinolin-6-yl, quinolin-7-yl, quinolin-8-yl); isoquinolines (e.g. isoquinolin-1-yl, isoquinolin-3-yl, isoquinolin-4-yl, isoquinolin-5-yl, isoquinolin-6-yl, isoquinolin-7-yl, isoquinolin-8-yl); quinoxaline; quinazoline; cinnoline; 1,5-naphthyridine; 1,6-naphthyridine; 1,7-naphthyridine; 1,8-naphthyridine; 2,6-naphthyridine; 2,7-naphthyridine; phthalazine; pyridopyrazines; pyridopyrimidines; pyridopyridazines; pteridines; pyrimidopyrimidines. Examples of heteroaryl are also 5- or 6-membered benzofused rings from the group of 1H-indol-1-yl, 1H-indol-2-yl, 1H-indol-3-yl, 1H-indol-4-yl, 1H-indol-5-yl, 1H-indol-6-yl, 1H-indol-7-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1H-indazol-1-yl, 1H-indazol-3-yl, 1H-indazol-4-yl, 1H-indazol-5-yl, 1H-indazol-6-yl, 1H-indazol-7-yl, 2H-indazol-2-yl, 2H-indazol-3-yl, 2H-indazol-4-yl, 2H-indazol-5-yl, 2H-indazol-6-yl, 2H-indazol-7-yl, 2H-isoindol-2-yl, 2H-isoindol-1-yl, 2H-isoindol-3-yl, 2H-isoindol-4-yl, 2H-isoindol-5-yl, 2H-isoindol-6-yl; 2H-isoindol-7-yl, 1H-benzimidazol-1-yl, 1H-benzimidazol-2-yl, 1H-benzimidazol-4-yl, 1H-benzimidazol-5-yl, 1H-benzimidazol-6-yl, 1H-benzimidazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,2-benzisoxazol-3-yl, 1,2-benzisoxazol-4-yl, 1,2-benzisoxazol-5-yl, 1,2-benzisoxazol-6-yl, 1,2-benzisoxazol-7-yl, 1,2-benzisothiazol-3-yl, 1,2-benzisothiazol-4-yl, 1,2-benzisothiazol-5-yl, 1,2-benzisothiazol-6-yl, 1,2-benzisothiazol-7-yl.

The term "halogen" denotes, for example, fluorine, chlorine, bromine or iodine. If the term is used for a radical, "halogen" denotes, for example, a fluorine, chlorine, bromine or iodine atom.

According to the invention, "alkyl" denotes a straight-chain or branched open-chain, saturated hydrocarbon radical which is optionally mono- or polysubstituted, and in the latter case is referred to as "substituted alkyl". Preferred substituents are halogen atoms, alkoxy, haloalkoxy, cyano, alkylthio, haloalkylthio, amino or nitro groups, particular preference being given to methoxy, methyl, fluoroalkyl, cyano, nitro, fluorine, chlorine, bromine or iodine.

The prefix "di" includes the combination of equal or different alkyl radicals, e.g. dimethyl or methyl(ethyl) or ethyl(methyl).

"Haloalkyl", "-alkenyl" and "-alkynyl" respectively denote alkyl, alkenyl and alkynyl partially or fully substituted by identical or different halogen atoms, for example monohaloalkyl such as $CH_2CH_2C_1$, $CH_2CH_2Br$, $CHClCH_3$, $CH_2Cl$, $CH_2F$; perhaloalkyl such as $CCl_3$, $CClF_2$, $CFCl_2$, $CF_2CClF_2$, $CF_2CClFCF_3$; polyhaloalkyl such as $CH_2CHFCl$, $CF_2CClFH$, $CF_2CBrFH$, $CH_2CF_3$; the term perhaloalkyl also encompasses the term perfluoroalkyl.

"Haloalkoxy" is, for example, $OCF_3$, $OCHF_2$, $OCH_2F$, $OCF_2CF_3$, $OCH_2CF_3$ and $OCH_2CH_2Cl$; this applies correspondingly to haloalkenyl and other halogen-substituted radicals.

The expression "($C_1$-$C_4$)-alkyl" mentioned here by way of example is a brief notation for straight-chain or branched alkyl having one to 4 carbon atoms according to the range stated for carbon atoms, i.e. encompasses the methyl, ethyl, 1-propyl, 2-propyl, 1-butyl, 2-butyl, 2-methylpropyl or tert-butyl radicals. General alkyl radicals with a larger specified range of carbon atoms, e.g. "($C_1$-$C_6$)-alkyl", correspondingly also encompass straight-chain or branched alkyl radicals with a greater number of carbon atoms, i.e. according to the example also the alkyl radicals having 5 and 6 carbon atoms.

Unless stated specifically, preference is given to the lower carbon skeletons, for example having from 1 to 6 carbon atoms, or having from 2 to 6 carbon atoms in the case of unsaturated groups, in the case of the hydrocarbyl radicals such as alkyl, alkenyl and alkynyl radicals, including in composite radicals. Alkyl radicals, including in composite radicals such as alkoxy, haloalkyl, etc., are, for example, methyl, ethyl, n-propyl or i-propyl, n-, i-, t- or 2-butyl, pentyls, hexyls such as n-hexyl, i-hexyl and 1,3-dimethylbutyl, heptyls such as n-heptyl, 1-methylhexyl and 1,4-dimethylpentyl; alkenyl and alkynyl radicals are defined as the possible unsaturated radicals corresponding to the alkyl radicals, where at least one double bond or triple bond is present. Preference is given to radicals having one double bond or triple bond.

The term "alkenyl" also includes, in particular, straight-chain or branched open-chain hydrocarbon radicals having more than one double bond, such as 1,3-butadienyl and 1,4-pentadienyl, but also allenyl or cumulenyl radicals having one or more cumulated double bonds, for example allenyl (1,2-propadienyl), 1,2-butadienyl and 1,2,3-pentatrienyl. Alkenyl denotes, for example, vinyl which may optionally be substituted by further alkyl radicals, for example (but not limited thereto) ($C_2$-$C_6$)-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "alkynyl" also includes, in particular, straight-chain or branched open-chain hydrocarbon radicals having more than one triple bond, or else having one or more triple bonds and one or more double bonds, for example 1,3-butatrienyl or 3-penten-1-yn-1-yl. ($C_2$-$C_6$)-Alkynyl denotes, for example, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

The term "cycloalkyl" denotes a carbocyclic saturated ring system having preferably 3-8 ring carbon atoms, for example cyclopropyl, cyclobutyl, cyclopentyl or cyclohexyl, which optionally has further substitution, preferably by hydrogen, alkyl, alkoxy, cyano, nitro, alkylthio, haloalkylthio, halogen, alkenyl, alkynyl, haloalkyl, amino, alkylamino, dialkylamino, alkoxycarbonyl, hydroxycarbonyl, arylalkoxycarbonyl, aminocarbonyl, alkylaminocarbonyl, cycloalkylaminocarbonyl. In the case of optionally substituted cycloalkyl, cyclic systems with substituents are included, also including substituents with a double bond on the cycloalkyl radical, for example an alkylidene group such as methylidene. In the case of optionally substituted cycloalkyl, polycyclic aliphatic systems are also included, for example bicyclo[1.1.0]butan-1-yl, bicyclo[1.1.0]butan-2-yl, bicyclo[2.1.0]pentan-1-yl, bicyclo[1.1.1]pentan-1-yl, bicyclo[2.1.0]pentan-2-yl, bicyclo[2.1.0]pentan-5-yl, bicyclo[2.1.1]hexyl, bicyclo[2.2.1]hept-2-yl, bicyclo[2.2.2]octan-2-yl, bicyclo[3.2.1]octan-2-yl, bicyclo[3.2.2]nonan-2-yl, adamantan-1-yl and adamantan-2-yl, but also systems such as 1,1'-bi(cyclopropyl)-1-yl, 1,1'-bi(cyclopropyl)-2-yl, for example. The term "($C_3$-$C_7$)-cycloalkyl" is a brief notation for cycloalkyl having three to 7 carbon atoms, corresponding to the range specified for carbon atoms.

In the case of substituted cycloalkyl, spirocyclic aliphatic systems are also included, for example spiro[2.2]pent-1-yl, spiro[2.3]hex-1-yl, spiro[2.3]hex-4-yl, 3-spiro[2.3]hex-5-yl, spiro[3.3]hept-1-yl, spiro[3.3]hept-2-yl.

"Cycloalkenyl" denotes a carbocyclic, nonaromatic, partially unsaturated ring system having preferably 4-8 carbon atoms, e.g. 1-cyclobutenyl, 2-cyclobutenyl, 1-cyclopentenyl, 2-cyclopentenyl, 3-cyclopentenyl, or 1-cyclohexenyl, 2-cyclohexenyl, 3-cyclohexenyl, 1,3-cyclohexadienyl or 1,4-cyclohexadienyl, also including substituents with a double bond on the cycloalkenyl radical, for example an alkylidene group such as methylidene. In the case of optionally substituted cycloalkenyl, the elucidations for substituted cycloalkyl apply correspondingly.

According to the invention, "haloalkylthio"—on its own or as constituent part of a chemical group—represents straight-chain or branched S-haloalkyl, preferably having 1 to 8, or having 1 to 6 carbon atoms, such as ($C_1$-$C_8$)—, ($C_1$-$C_6$)- or ($C_1$-$C_4$)-haloalkylthio, for example (but not limited thereto)trifluoromethylthio, pentafluoroethylthio, difluoromethyl, 2,2-difluoroeth-1-ylthio, 2,2,2-difluoroeth-1-ylthio, 3,3,3-prop-1-ylthio.

"Halocycloalkyl" and "halocycloalkenyl" denote cycloalkyl and cycloalkenyl, respectively, which are partially or fully substituted by identical or different halogen atoms, such as F, Cl and Br, or by haloalkyl, such as trifluoromethyl or difluoromethyl, for example 1-fluorocycloprop-1-yl, 2-fluorocycloprop-1-yl, 2,2-difluorocycloprop-1-yl, 1-fluorocyclobut-1-yl, 1-trifluoromethylcycloprop-1-yl, 2-trifluoromethylcycloprop-1-yl, 1-chlorocycloprop-1-yl, 2-chlorocycloprop-1-yl, 2,2-dichlorocycloprop-1-yl, 3,3-difluorocyclobutyl.

According to the invention, "trialkylsilyl"—on its own or as constituent part of a chemical group—represents straight-chain or branched Si-alkyl, preferably having 1 to 8, or having 1 to 6 carbon atoms, such as tri[($C_1$-$C_5$)—, ($C_1$-$C_6$)- or ($C_1$-$C_4$)-alkyl]silyl, for example (but not limited thereto) trimethylsilyl, triethylsilyl, tri(n-propyl)silyl, tri(isopropyl)silyl, tri(n-butyl)silyl, tri(1-methylprop-1-yl)silyl, tri(2-methylprop-1-yl)silyl, tri(1,1-dimethyleth-1-yl)silyl, tri(2,2-dimethyleth-1-yl)silyl.

If the compounds can form, through a hydrogen shift, tautomers whose structure is not formally covered by the general formula (I), these tautomers are nevertheless covered by the definition of the inventive compounds of the general formula (I), unless a particular tautomer is under consideration. For example, many carbonyl compounds may be present both in the keto form and in the enol form, both forms being encompassed by the definition of the compound of the general formula (I).

Depending on the nature of the substituents and the manner in which they are attached, the compounds of the general formula (I) may be present as stereoisomers. The general formula (I) embraces all possible stereoisomers defined by the specific three-dimensional form thereof, such as enantiomers, diastereomers, Z and E isomers. If, for example, one or more alkenyl groups are present, diastereomers (Z and E isomers) may occur. If, for example, one or more asymmetric carbon atoms are present, enantiomers and diastereomers may occur. Stereoisomers can be obtained from the mixtures obtained in the preparation by customary separation methods. The chromatographic separation can be affected either on the analytical scale to find the enantiomeric excess or the diastereomeric excess, or else on the preparative scale to produce test specimens for biological testing. It is likewise possible to selectively prepare stereoisomers by using stereoselective reactions with use of optically active starting materials and/or auxiliaries. The invention thus also relates to all stereoisomers which are embraced by the general formula (I) but are not shown in their specific stereomeric form, and to mixtures thereof.

If the compounds are obtained as solids, the purification can also be carried out by recrystallization or digestion. If individual compounds of general formula (I) cannot be obtained in a satisfactory manner by the routes described below, they can be prepared by derivatization of other compounds of general formula (I).

Suitable isolation methods, purification methods and methods for separating stereoisomers of compounds of the general formula (I) are methods generally known to the person skilled in the art from analogous cases, for example by physical processes such as crystallization, chromatographic methods, in particular column chromatography and HPLC (high pressure liquid chromatography), distillation, optionally under reduced pressure, extraction and other methods, any mixtures that remain can generally be separated by chromatographic separation, for example on chiral solid phases. Suitable for preparative amounts or on an industrial scale are processes such as crystallization, for example of diastereomeric salts which can be obtained from the diastereomer mixtures using optically active acids and, if appropriate, provided that acidic groups are present, using optically active bases.

Synthesis of Substituted Pyrrolidine-2-Ones of the General Formula (I).

The substituted pyrrolidin-2-ones of the general formula (I) according to the invention can be prepared using known processes (cf. J. Org. Chem. 1950, 2727). The ring-closing reaction was carried out in a sealed tube under microwave irradiation. The synthesis routes used and examined proceed from commercially available or easily synthesized substituted benzyl amines or substituted aminomethyl pyridines. In the following schemes, the groups $R^1$, $R^2$, $R^3$, $R^4$, $R^5$, $R^6$, $R^7$, $R^8$, $R^9$, $R^{10}$, $R^{10}$, $R^{12}$, $A^1$, $A^2$, and $A^3$ of the general formula (I) have the meanings defined above, unless exemplary, but not limiting definitions are given. The synthesis route for substituted pyrrolidin-2-ones of the general formula (I) proceeds via a ring-closing reaction between hexene dicarboxylic acid (A) and a suitably substituted benzyl amine or a corresponding aminomethyl pyridine (B) (scheme (I):

Scheme 1.

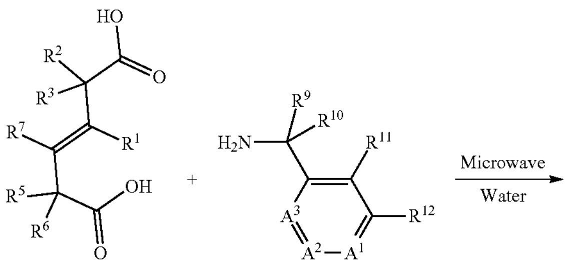

(A) (B)

-continued

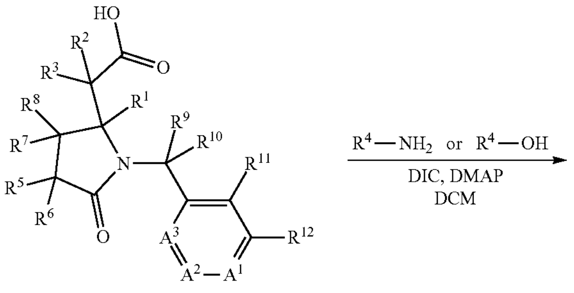

(Ia)

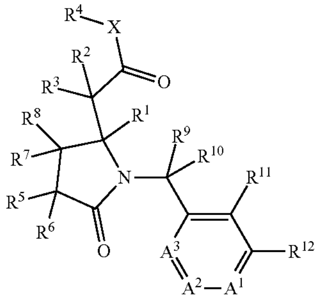

(Ib)

The resulting pyrrolidin-2-ones (Ia) are subsequently transformed to the derivatives (Ib) by standard methods (exemplary but not limited to esterification, amidation, sulfonamidation). Alternatively, oxopyrrolidinyl acetic acid esters (Ic) can be prepared via a two step chain elongation procedure of corresponding oxopyrrolidinyl carboxylates (D) (Scheme 2) using firstly a boron hydride mediated reduction of the carboxylate (e.g. with $LiBH_4$ or $NaBH_4$), and secondly treatment of the intermediate alcohol (D) with triethyl phosphonoacetate and a suitable base, e.g. sodium hydride (Chemistry—A European Journal (2017) 23, 7428-74321). In the following scheme 2, the groups $R^2$ and $R^3$ are represented in an exemplary, but not limiting way by hydrogen.

Scheme 2.

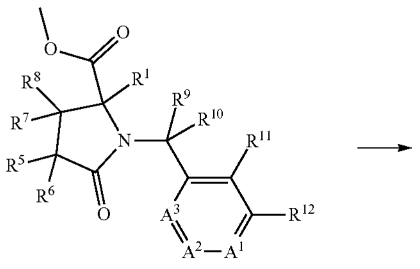

(C)

-continued

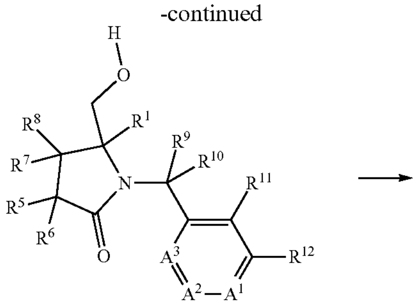

(D)

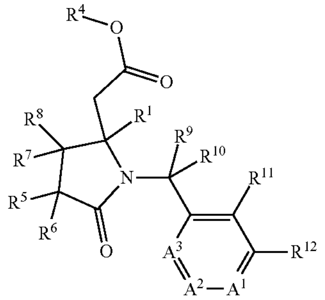

(Ic)

Selected detailed synthesis examples for the compounds of the general formula (I) according to the invention are given below. The example numbers mentioned correspond to the numbering scheme in Schemes 1 to 2 and Table 1 below. The $^1$H NMR spectroscopy data reported for the chemical examples described in the sections that follow were obtained on Bruker instruments at 600 MHz, 400 MHz or 300 MHz using $CDCl_3$ or $d_6$-DMSO as the solvent with tetramethylsilane (δ=0.00 ppm) as the internal standard. The signals listed have the meanings given below: br=broad; s=singlet, d=doublet, t=triplet, dd=doublet of doublets, ddd=doublet of a doublet of doublets, m=multiplet, q=quartet, qu=quintet, sext=sextet, sept=septet, dq=doublet of quartets, dt=doublet of triplets.

SYNTHESIS EXAMPLES

I-001: 2-[1-[(3-chloro-2-fluorophenyl)methyl]-5-oxo-pyrrolidin-2-yl]acetic acid

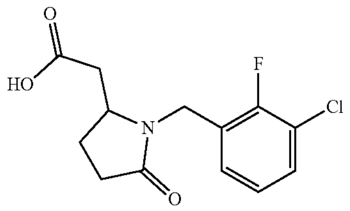 [SMILES: O=C(O)CC1CCC(=O)N1Cc1cccc(Cl)c1F]

3-Chloro-2-fluorobenzylamine (221 mg, 1.39 mmol, 1.0 eq.) and (E)-hexenoic acid (200 mg, 1.39 mmol, 1.0 eq.) were suspended in water (5.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford I-001 (135 mg, 34% yield) as a colorless oil. $^1$H-NMR (400.0 MHz, $CDCl_3$) δ ppm 7.36-

7.32 (m, 1H), 7.22-7.18 (m, 1H), 7.09-7.04 (m, 1H), 4.91-4.87 (d, 1H), 4.27-4.23 (d, 1H), 3.94-3.88 (m, 1H), 2.78-2.73 (dd, 1H), 2.62-2.42 (m, 3H), 2.37-2.26 (m, 1H), 1.93-1.85 (m, 1H).

No. I-204 and No. I-205: (+)- and (−)-2-[1-[(3-chloro-2-fluorophenyl)methyl]-5-oxo-pyrrolidin-2-yl]acetic acid:

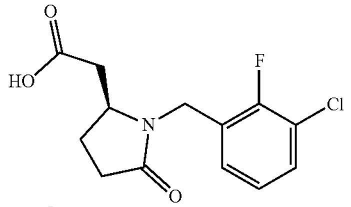

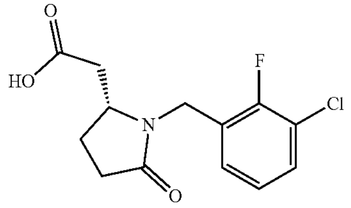

The reaction outlined above was repeated using the same amount of reagents, and a combined amount of racemic 2-[1-[(3-chloro-2-fluorophenyl)methyl]-5-oxo-pyrrolidin-2-yl]acetic acid (I-001, 200 mg) was separated via chiral preparative SFC using a chiral Opti Prep ODB column (Gradient Chir_C3_IE_B1_90_CO2_MeOH_6 min_CD) into the enantiomers Ent-1 I-204 (85 mg, retention time 1.177, optical rotation 28.50°-20 mg/10 mL), $^1$H-NMR (400.0 MHz, $CDCl_3$) δ ppm 7.38-7.33 (m, 1H), 7.22-7.17 (m, 1H), 7.09-7.03 (m, 1H), 4.92-4.88 (d, 1H), 4.27-4.23 (d, 1H), 3.94-3.88 (m, 1H), 2.78- 2.73 (dd, 1H), 2.62-2.42 (m, 3H), 2.39-2.25 (m, 1H), 1.93-1.85 (m, 1H) and Ent-2 I-205 (91 mg, retention time 1.862, optical rotation −36.00°-22 mg/100 mL), $^1$H-NMR (400.0 MHz, $CDCl_3$) δ ppm 7.36-7.31 (m, 1H), 7.23-7.15 (m, 1H), 7.09-7.04 (m, 1H), 4.91-4.85 (d, 1H), 4.27-4.23 (d, 1H), 3.93- 3.87 (m, 1H), 2.77-2.72 (dd, 1H), 2.64-2.43 (m, 3H), 2.37-2.26 (m, 1H), 1.93-1.84 (m, 1H).

I-003: 2-[1-[(2,3-difluorophenyl)methyl]-5-oxo-pyrrolidin-2-yl]acetic acid

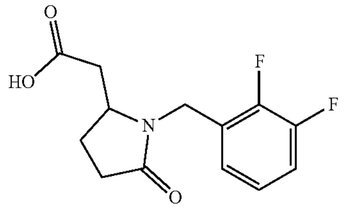 [SMILES: O=C(O)CC1CCC(=O)N1Cc1cccc(F)c1F]

2,3-Difluorobenzylamine (993 mg, 6.93 mmol, 1.0 eq.) and (E)-hexenoic acid (1.00 g, 6.93 mmol, 1.0 eq.) were suspended in water (10.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford I-003 (182.0 mg, 23% yield) as a colorless oil. $^1$H-NMR (600.0 MHz, $d_6$-DMSO): δ=1.69-1.76 (m, 1H), 2.14-2.29 (m, 2H), 2.34-2.45 (m, 2H), 2.69 (dd, J=15.97, 4.05 Hz, 1H), 3.76 (tt, J=8.31, 4.14 Hz, 1H), 4.24 (d, J=15.85 Hz, 1H), 4.73 (d, J=15.85 Hz, 1H), 7.08 (t, J=7.03 Hz, 1H), 7.16-7.21 (m, 1H), 7.36 (q, J=8.42 Hz, 1H).

I-034: 2-(4-methylphenoxy)ethyl 2-[1-[(2,3-difluorophenyl)methyl]-5-oxo-pyrrolidin-2-yl]acetate

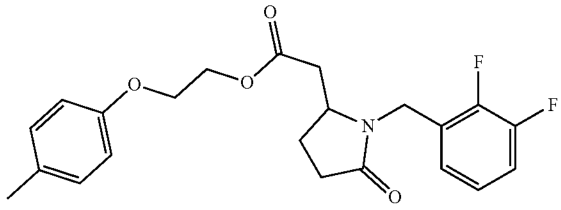 [SMILES: Cc1ccc(OCCOC(=O)CC2CCC(=O)N2Cc2cccc(F)c2F)cc1]

To a solution of 2-[1-[(2,3-difluorophenyl)methyl]-5-oxo-pyrrolidin-2-yl]acetic acid (150.0 mg, 0.55 mmol, 1.0 eq.) in dichloromethane (20 mL) was added 2-(4-methylphenoxy) ethanol (170.0 mg, 1.11 mmol, 2.0 eq.), DMAP (0.7 mg, 0.05 mmol, 0.1 eq.) and EDAC (117.0 mg, 0.61 mmol, 1.1 eq.). The reaction mixture was stirred at ambient temperature for 5 h. Following addition of water (20 mL) the mixture was extracted with dichloromethane (3×50 mL). The combined organic layers were dried over magnesium sulfate, filtered and concentrated under reduced pressure. The crude product was purified by flash chromatography on silica gel eluting with heptane/EtOAc (4:1) to afford I-034 (141.0 mg, 62% yield) as a colorless oil. $^1$H-NMR (400.1 MHz, $CDCl_3$): δ ppm 1.79-1.89 (m, 1H), 2.22-2.31 (m, 4H), 2.34-2.52 (m, 3H), 2.75 (dd, J=15.57, 3.99 Hz, 1H), 3.88 (dt, J=8.31, 4.16 Hz, 1H), 4.09-4.15 (m, 2H), 4.24 (d, J=15.49 Hz, 1H), 4.37-4.44 (m, 2H), 4.86 (dd, J=15.57, 1.55 Hz, 1H), 6.75-6.82 (m, 2H), 7.00-7.12 (m, 5H).

I-046: 2-[1-[(2,3-difluorophenyl)methyl]-5-oxo-pyrrolidin-2-yl]-N-(4-methyl-1,2,5-oxadiazol-3-yl) acetamide

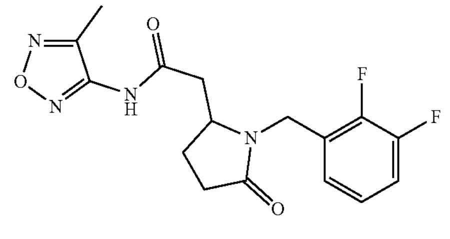 [SMILES: Cc1nonc1NC(=O)CC1CCC(=O)N1Cc1cccc(F)c1F]

To a solution of 4-methyl-1,2,5-oxadiazol-3-amine (74.0 mg, 0.74 mmol, 1.0 eq.) in dichloromethane (6 mL) was added 2-[1-[(2,3-difluorophenyl)methyl]-5-oxo-pyrrolidin-2-yl]acetic acid (200.0 mg, 0.74 mmol, 1.0 eq.) and 1-Propylphosphonic acid cyclic anhydride (T3P®, 709.0 mg, 0.663 mL, 1.11 mmol, 1.5 eq., 50%-solution in EtOAc). The mixture was stirred at ambient temperature for 1 h. Triethylamine (376.0 mg, 0.52 mL, 3.71 mmol, 5.0 eq.) was added dropwise followed by DMAP (18.0 mg, 0.14 mmol. 0.2 eq.). The reaction mixture was stirred at ambient temperature for 16 h. Following addition of water (20 mL) the mixture was extracted with dichloromethane (3×50 mL). The combined organic layers were dried over magnesium sulfate, filtered and concentrated under reduced pressure. The crude product was purified by preparative HPLC to afford I-046 (114.0 mg, 43% yield) as a yellowish oil. $^{1}$H-NMR (400.1 MHz, $d_6$-DMSO): δ ppm 1.77-1.87 (m, 1H), 2.18-2.37 (m, 5H), 2.37-2.44 (m, 1H), 2.54-2.62 (m, 1H), 2.88 (dd, J=14.92, 4.16 Hz, 1H), 3.90 (br d, J=3.91 Hz, 1H), 4.28 (d, J=15.98 Hz, 1H), 4.73 (d, J=16.14 Hz, 1H), 7.05-7.11 (m, 1H), 7.15-7.22 (m, 1H), 7.30-7.39 (m, 1H).

I-077: 2-[1-[(2,3-dichlorophenyl)methyl]-5-oxo-pyrrolidin-2-yl]acetic acid

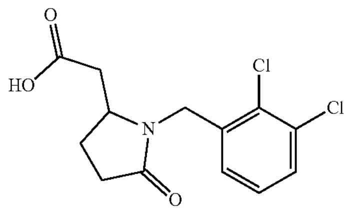

2,3-Dichlorobenzylamine (1.21 g, 6.93 mmol, 1.0 eq.) and (E)-hexenoic acid (1.00 g, 6.93 mmol, 1.0 eq.) were suspended in water (10.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford I-077 (847.0 mg, 40% yield) as a white solid. $^{1}$H-NMR (400.1 MHz, $d_6$-DMSO): δ ppm 1.72-1.82 (m, 1H), 2.19-2.34 (m, 2H), 2.36-2.45 (m, 2H), 2.65 (dd, J=16.06, 4.32 Hz, 1H), 3.81 (tt, J=8.09, 4.22 Hz, 2H), 4.29 (d, J=16.47 Hz, 1H), 4.68 (d, J=16.47 Hz, 1H), 7.22 (dd, J=7.66, 1.47 Hz, 1H), 7.35 (t, J=7.91 Hz, 1H), 7.57 (dd, J=7.99, 1.47 Hz, 1H).

I-130: 2-[1-[(2,3-dichlorophenyl)methyl]-5-oxo-pyrrolidin-2-yl]-N-(dimethylsulfamoyl)acetamide

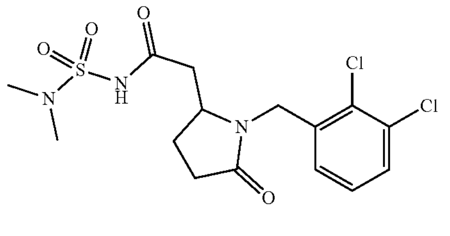 [SMILES: CN(C)S(=O)(=O)NC(=O)CC1CCC(=O)N1Cc1cccc(Cl)c1Cl]

To a solution of 2-[1-[(2,3-dichlorophenyl)methyl]-5-oxo-pyrrolidin-2-yl]acetic acid (250.0 mg, 0.82 mmol, 1.0 eq.) in dichloromethane (30 mL) was added N,N-dimethylsulfamide (205.0 mg, 1.65 mmol, 2.0 eq.), DMAP (0.1 mg, 0.08 mmol, 0.1 eq.) and EDAC (174.0 mg, 0.91 mmol, 1.1 eq.). The reaction mixture was stirred at ambient temperature for 5 h. Following addition of water (20 mL) the mixture was extracted with dichloromethane (3x50 mL). The combined organic layers were dried over magnesium sulfate, filtered and concentrated under reduced pressure. The crude product was purified by preparative HPLC to afford I-130 (151.0 mg, 44% yield) as a white solid. 1H-NMR (400 MHz, $d_6$-DMSO) δ ppm 1.75-1.83 (m, 1H), 2.18-2.46 (m, 4H), 2.66-2.73 (m, 1H), 3.85 (tt, J=8.15, 4.08 Hz, 1H), 4.27 (d, J=16.63 Hz, 1H), 4.66 (d, J=16.63 Hz, 1H), 7.17-7.21 (m, 1H), 7.36 (t, J=15.81 Hz, 1H), 7.56-7.60 (m, 1H).

I-191: [5-Oxo-1-(2,3,6-trifluorobenzyl)pyrrolidin-2-yl]acetic acid

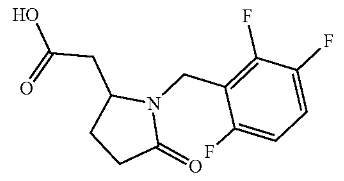 [SMILES: O=C(O)CC1CCC(=O)N1Cc1c(F)ccc(F)c1F]

1-(2,3,6-Trifluorophenyl)methylamine (335 mg, 2.08 mmol, 1.0 equiv.) and (E)-hexenoic acid (300 mg, 2.08 mmol, 1.0 eq.) were suspended in water (5.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford [5-Oxo-1-(2,3,6-trifluorobenzyl)pyrrolidin-2-yl]acetic acid I-191 (144 mg, 25% yield of theory) as a white solid. $^{1}$H-NMR (400 MHz, $CDCl_3$) δ ppm 7.18-7.10 (m, 1H), 6.90-6.84 (m, 1H), 5.19 (d, 1H), 4.17 (d, 1H), 3.86-3.80 (m, 1H), 2.84-2.79 (dd, 1H), 2.62-2.43 (m, 3H), 2.33-2.25 (m, 1H), 1.934-1.86 (m, 1H).

I-192: [5-Oxo-1-(2,3,4-trifluorobenzyl)pyrrolidin-2-yl]acetic acid

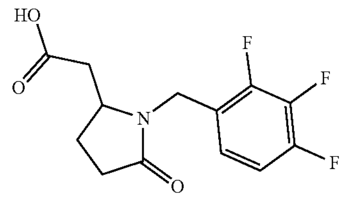 [SMILES: O=C(O)CC1CCC(=O)N1Cc1ccc(F)c(F)c1F]

1-(2,3,4-Trifluorophenyl)methylamine (112 mg, 0.69 mmol, 1.0 equiv.) and (E)-hexenoic acid (100 mg, 0.69 mmol, 1.0 eq.) were suspended in water (5.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford [5-Oxo-1-(2,3,4-trifluorobenzyl)pyrrolidin-2-yl]acetic acid I-191 (52 mg, 27% yield of theory) as a white solid. $^{1}$H-NMR (400 MHz, $CDCl_3$) δ ppm 7.09-7.03 (m, 1H), 6.98-6.92 (m, 1H), 4.87 (d, 1H), 4.21 (d, 1H), 3.93-3.87 (m, 1H), 2.80-2.75 (dd, 1H), 2.61-2.40 (m, 3H), 2.38-2.27 (m, 1H), 1.94-1.86 (m, 1H).

I-193: 2-[1-[(2,3-difluorophenyl)methyl]-5-oxo-pyrrolidin-2-yl]-N-(1,2,4-thiadiazol-5-yl)acetamide

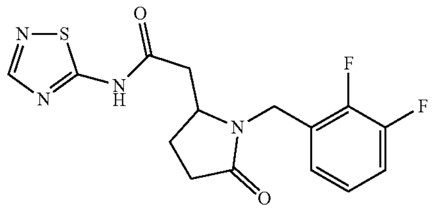 [SMILES: O=C(CC1CCC(=O)N1Cc1cccc(F)c1F)Nc1ncns1]

To a solution of 5-amino-1,2,4-thiazole hydrochloride (120 mg, 0.87 mmol, 1.0 eq.) in dichloromethane (5 mL) was added 2-[1-[(2,3-difluorophenyl)methyl]-5-oxo-pyrrolidin-2-yl]acetic acid (235 mg, 0.87 mmol, 1.0 eq.) and 1-Propylphosphonic acid cyclic anhydride (T3P®, 722 mg, 0.68 mL, 1.13 mmol, 1.3 eq., 50%-solution in tetrahydrofuran). The mixture was stirred at ambient temperature for 1 h, and triethylamine (0.37 mL, 2.62 mmol, 3.0 eq.) was added dropwise. The reaction mixture was stirred at room temperature for 8 h. Following addition of water (20 mL) the mixture was extracted thoroughly with dichloromethane (3×50 mL). The combined organic layers were dried over magnesium sulfate, filtered and concentrated under reduced pressure. The crude product was then purified by preparative HPLC to afford I-193 (110 mg, 35% yield) as a colourless solid. $^1$H-NMR (400.0 MHz, $CDCl_3$) δ ppm 11.77 (br. s, 1H, NH), 8.21 (s, 1H), 7.08-7.01 (m, 3H), 4.84-4.80 (d, 1H), 4.36-4.32 (d, 1H), 4.16-4.12 (m, 1H), 3.04-2.99 (dd, 1H), 2.72-2.66 (dd, 1H), 2.62-2.48 (m, 2H), 2.44-2.37 (m, 1H), 1.95-1.88 (m, 1H).

I-200: 2-[1-[(2,3-difluorophenyl)methyl]-5-oxo-pyrrolidin-2-yl]-N-(pyrrolidin-1-yl)acetamide

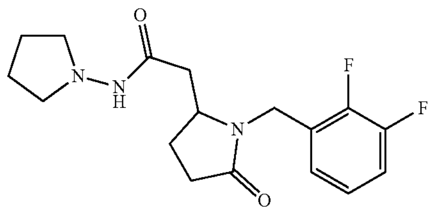 [SMILES: O=C(CC1CCC(=O)N1Cc1cccc(F)c1F)NN1CCCC1]

To a solution of pyrrolidin-1-ylamine (150 mg, 1.74 mmol, 1.0 eq.) in dichloromethane (5 mL) was added 2-[1-[(2,3-difluorophenyl)methyl]-5-oxo-pyrrolidin-2-yl] acetic acid (400.0 mg, 1.74 mmol, 1.0 eq.) and 1-Propylphosphonic acid cyclic anhydride (T3P®, 1441 mg, 1.35 mL, 2.26 mmol, 1.3 eq., 50%-solution in tetrahydrofuran). The mixture was stirred at ambient temperature for 1 h, and triethylamine (0.73 mL, 5.22 mmol, 3.0 eq.) was added dropwise. The reaction mixture was stirred at ambient temperature for 8 h. Following addition of water (20 mL) the mixture was extracted thoroughly with dichloromethane (3×50 mL). The combined organic layers were dried over magnesium sulfate, filtered and concentrated under reduced pressure. The crude product was then purified by preparative HPLC to afford I-200 (150 mg, 25% yield) as a yellowish oil. $^1$H-NMR (400.0 MHz, $CDCl_3$) δ ppm 7.12-7.03 (m, 3H), 6.07 (br. s, 1H, NH), 4.93-4.89/4.88-4.84 (d, 1H), 4.30-4.27/4.26-4.23 (d, 1H), 3.97-3.89 (m, 1H), 3.22-3.18 (m, 1H), 2.96-2.92 (dd, 1H), 2.60-2.48 (m, 3H), 2.46-2.38 (m, 1H), 2.32-2.18 (m, 2H), 2.04-1.98 (m, 1H), 1.92-1.85 (m, 1H), 1.84-1.78 (m, 4H).

I-202: [5-Oxo-1-(2,4-difluoro-3-methoxybenzyl) pyrrolidin-2-yl]acetic acid

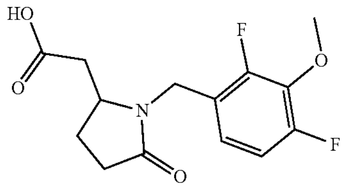 [SMILES: COc1c(F)ccc(CN2C(=O)CCC2CC(=O)O)c1F]

1-(2,4-Difluoro-3-methoxyphenyl)methylamine (180 mg, 1.04 mmol, 1.0 equiv.) and (E)-hexenoic acid (150 mg, 1.04 mmol, 1.0 eq.) were suspended in water (5.0 mL) and placed in a sealed microwave tube. The mixture was heated to 190° C. for 1 h under microwave conditions (pressure inside the tube rose to 18 bar). After the reaction the water was concentrated under reduced pressure. The resulting residue was purified by preparative HPLC to afford [5-Oxo-1-(2,4-trifluoro-3-methoxybenzyl)pyrrolidin-2-yl]acetic acid I-202 (88 mg, 27% yield of theory) as a white solid. $^1$H-NMR (400 MHz, $CDCl_3$) δ ppm 9.12-8.80 (br. s, 1H, OH), 6.97-6.92 (m, 1H), 6.91-6.86 (m, 1H), 4.88-4.84 (d, 1H), 4.20-4.17 (d, 1H), 4.00 (s, 3H), 3.94-3.89 (m, 1H), 2.81-2.76 (dd, 1H), 2.69-2.59 (m, 1H), 2.57-2.48 (m, 2H), 2.35-2.30 (m, 1H), 1.94-1.88 (m, 1H).

In analogy to the preparation examples cited above and recited at the appropriate point, and taking account of the general details relating to the preparation of substituted pyrrolidin-2-ones of the general formula (I), the compounds cited below are obtained. In table 1 below, $R^1$, $R^3$, $R^5$, $R^6$, $R^8$, $R^9$ and $R^{10}$ represent a hydrogen.

TABLE 1

Examples of preferred compounds of the general formula (I), with "Rac" representing a racemic mixture and "Ent-1" and "Ent-2" representing the specific stereoconfiguration at carbon C-2.

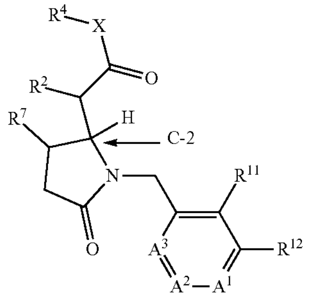

| Ex. No. | $R^4$—X— | C-2 Stereo-chemistry | $R^2$ | $R^7$ | $R^{11}$ | $R^{12}$ | $A^1$ | $A^2$ | $A^3$ |
|---|---|---|---|---|---|---|---|---|---|
| I-001 | OH | Rac | H | H | fluoro | chloro | C—H | C—H | C—H |
| I-002 | (1-methyl-1H-1,2,4-triazol-5-yl)amino | Rac | H | H | fluoro | fluoro | C—H | C—H | C—H |
| I-003 | OH | Rac | H | H | fluoro | fluoro | C—H | C—H | C—H |
| I-004 | (1-methyl-1H-tetrazol-5-yl)amino | Rac | H | H | fluoro | fluoro | C—H | C—H | C—H |
| I-005 | [(1S,2S)-1-carboxy-2-methylbutyl]amino | Ent-1 | H | H | fluoro | fluoro | C—H | C—H | C—H |
| I-006 | (5-methoxy-2,4-dioxopentyl)amino | Rac | H | H | fluoro | fluoro | C—H | C—H | C—H |
| I-007 | 2-(4-fluorophenoxy)ethoxy | Rac | H | H | fluoro | fluoro | C—H | C—H | C—H |
| I-008 | methoxy | Rac | H | H | fluoro | fluoro | C—H | C—H | C—H |
| I-009 | 2-methylsulfonylethoxy | Rac | H | H | fluoro | fluoro | C—H | C—H | C—H |
| I-010 | 2-methylsulfanylethoxy | Rac | H | H | fluoro | fluoro | C—H | C—H | C—H |
| I-011 | [(1S,2S)-1-carboxy-2-methylbutyl]amino | Ent-2 | H | H | fluoro | fluoro | C—H | C—H | C—H |
| I-012 | methanesulfonamido | Rac | H | H | fluoro | fluoro | C—H | C—H | C—H |
| I-013 | 2-carboxypyrrolidin-1-yl | Rac | H | H | fluoro | fluoro | C—H | C—H | C—H |
| I-014 | OH | Ent-2 | H | H | fluoro | fluoro | C—H | C—H | C—H |
| I-015 | 2-methoxyethoxy | Rac | H | H | fluoro | fluoro | C—H | C—H | C—H |
| I-016 | [(1R,2R)-1-carboxy-2-methylbutyl]amino | Ent-2 | H | H | fluoro | fluoro | C—H | C—H | C—H |
| I-017 | Cyclopentyloxy | Rac | H | H | fluoro | fluoro | C—H | C—H | C—H |
| I-018 | 2,2-dimethylpropoxy | Rac | H | H | fluoro | fluoro | C—H | C—H | C—H |
| I-019 | ethoxy | Rac | H | H | fluoro | fluoro | C—H | C—H | C—H |
| I-020 | cyclopropylmethoxy | Rac | H | H | fluoro | fluoro | C—H | C—H | C—H |
| I-021 | prop-2-ene-1-yloxy | Rac | H | H | fluoro | fluoro | C—H | C—H | C—H |
| I-022 | 2-phenylsulfanylethoxy | Rac | H | H | fluoro | fluoro | C—H | C—H | C—H |
| I-023 | prop-2-yne-1-yloxy | Rac | H | H | fluoro | fluoro | C—H | C—H | C—H |
| I-024 | cyclobutyloxy | Rac | H | H | fluoro | fluoro | C—H | C—H | C—H |
| I-025 | isopropyloxy | Rac | H | H | fluoro | fluoro | C—H | C—H | C—H |
| I-026 | but-3-enoxy | Rac | H | H | fluoro | fluoro | C—H | C—H | C—H |
| I-027 | 2-phenoxyethoxy | Rac | H | H | fluoro | fluoro | C—H | C—H | C—H |
| I-028 | pentan-2-yloxy | Rac | H | H | fluoro | fluoro | C—H | C—H | C—H |
| I-029 | 2-(4-chlorophenyl)sulfinylethoxy | Rac | H | H | fluoro | fluoro | C—H | C—H | C—H |
| I-030 | butan-2-yloxy | Rac | H | H | fluoro | fluoro | C—H | C—H | C—H |
| I-031 | 2-(4-methoxyphenoxy)ethoxy | Rac | H | H | fluoro | fluoro | C—H | C—H | C—H |
| I-032 | 2-(benzenesulfonyl)ethoxy | Rac | H | H | fluoro | fluoro | C—H | C—H | C—H |
| I-033 | 2-(4-chlorophenoxy)ethoxy | Rac | H | H | fluoro | fluoro | C—H | C—H | C—H |
| I-034 | 2-(4-methylphenoxy)ethoxy | Rac | H | H | fluoro | fluoro | C—H | C—H | C—H |
| I-035 | OH | Rac | H | H | fluoro | fluoro | C-methyl | C—H | C—H |
| I-036 | 3-methylbutan-2-yloxy | Rac | H | H | fluoro | fluoro | C—H | C—H | C—H |
| I-037 | [(2S)-3-(1H-imidazol-4-yl)-1-methoxy-1-oxopropan-2-yl]amino | Ent-2 | H | H | fluoro | fluoro | C—H | C—H | C—H |
| I-038 | 2-[(4-chlorophenyl)thio]ethoxy | Rac | H | H | fluoro | fluoro | C—H | C—H | C—H |
| I-039 | [(1R)-1-carboxy-2-phenylethyl]amino | Ent-2 | H | H | fluoro | fluoro | C—H | C—H | C—H |
| I-040 | 2-[(4-methoxyphenyl)thio]ethoxy | Rac | H | H | fluoro | fluoro | C—H | C—H | C—H |
| I-041 | 2-[(4-methylphenyl)thio]ethoxy | Rac | H | H | fluoro | fluoro | C—H | C—H | C—H |
| I-042 | methoxy | Rac | H | H | fluoro | chloro | C—H | C—H | C—H |
| I-043 | [(1R,2R)-1-carboxy-2-methylbutyl]amino | Ent-1 | H | H | fluoro | fluoro | C—H | C—H | C—H |
| I-044 | [(1R)-1-carboxy-2-phenylethyl]amino | Rac | H | H | fluoro | fluoro | C—H | C—H | C—H |
| I-045 | [(1R)-1-carboxy-3-methylbutyl]amino | Rac | H | H | fluoro | fluoro | C—H | C—H | C—H |
| I-046 | (4-methyl-1,2,5-oxadiazol-3-yl)amino | Rac | H | H | fluoro | fluoro | C—H | C—H | C—H |
| I-047 | 2-(4-methylphenyl)sulfinylethoxy | Rac | H | H | fluoro | fluoro | C—H | C—H | C—H |
| I-048 | [1-(methoxycarbonyl)cyclopropyl]amino | Rac | H | H | fluoro | fluoro | C—H | C—H | C—H |
| I-049 | 2-hydroxyethylamino | Rac | H | H | fluoro | fluoro | C—H | C—H | C—H |
| I-050 | [(2S)-3-(1H-imidazol-4-yl)-1-methoxy-1-oxopropan-2-yl]amino | Ent-1 | H | H | fluoro | fluoro | C—H | C—H | C—H |

TABLE 1-continued

Examples of preferred compounds of the general formula (I), with “Rac” representing a racemic mixture and “Ent-1” and “Ent-2” representing the specific stereoconfiguration at carbon C-2.

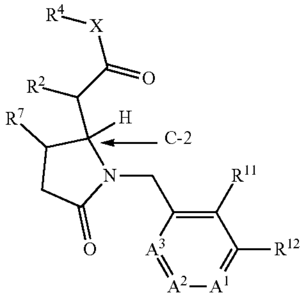

| Ex. No. | $R^4$—X— | C-2 Stereo-chemistry | $R^2$ | $R^7$ | $R^{11}$ | $R^{12}$ | $A^1$ | $A^2$ | $A^3$ |
|---|---|---|---|---|---|---|---|---|---|
| I-051 | [(1S)-1-carboxy-2-phenylethyl]amino | Rac | H | H | fluoro | fluoro | C—H | C—H | C—H |
| I-052 | trifluoromethylsulfonylamino | Rac | H | H | fluoro | fluoro | C—H | C—H | C—H |
| I-053 | (2-methoxy-2-oxoethyl)-methylamino | Rac | H | H | fluoro | fluoro | C—H | C—H | C—H |
| I-054 | 2-(4-methoxyphenyl)sulfonylethoxy | Rac | H | H | fluoro | fluoro | C—H | C—H | C—H |
| I-055 | benzylamino | Rac | H | H | fluoro | fluoro | C—H | C—H | C—H |
| I-056 | 2-methylpropylamino | Rac | H | H | fluoro | fluoro | C—H | C—H | C—H |
| I-057 | amino | Rac | H | H | fluoro | fluoro | C—H | C—H | C—H |
| I-058 | 2,2-dimethylhydrazino | Rac | H | H | fluoro | fluoro | C—H | C—H | C—H |
| I-059 | allylamino | Rac | H | H | fluoro | fluoro | C—H | C—H | C—H |
| I-060 | 2-(4-methoxyphenyl)sulfinylethoxy | Rac | H | H | fluoro | fluoro | C—H | C—H | C—H |
| I-061 | 2-phenylethylamino | Rac | H | H | fluoro | fluoro | C—H | C—H | C—H |
| I-062 | (6-chloropyridin-3-yl)methyl-methylamino | Rac | H | H | fluoro | fluoro | C—H | C—H | C—H |
| I-063 | (4-methoxy-4-oxobutan-2-yl)amino | Rac | H | H | fluoro | fluoro | C—H | C—H | C—H |
| I-064 | [(1S,2R,5R)-2-isopropyl-5-methylcyclohexyl]oxy | Ent-2 | H | H | fluoro | fluoro | C—H | C—H | C—H |
| I-065 | OH | Ent-1 | H | H | fluoro | fluoro | C—H | C—H | C—H |
| I-066 | 1,2,3,4-tetrahydronaphthalen-1-ylamino | Rac | H | H | fluoro | fluoro | C—H | C—H | C—H |
| I-067 | [(1S,2R,5S)-2-isopropyl-5-methylcyclohexyl]oxy | Ent-2 | H | H | fluoro | fluoro | C—H | C—H | C—H |
| I-068 | [(1S)-1-carboxy-2-(1H-indol-3-yl)ethyl]amino | Rac | H | H | fluoro | fluoro | C—H | C—H | C—H |
| I-069 | [(1R)-1-carboxy-2-(1H-indol-3-yl)ethyl]amino | Rac | H | H | fluoro | fluoro | C—H | C—H | C—H |
| I-070 | methanesulfonamido | Rac | H | H | fluoro | chloro | C—H | C—H | C—H |
| I-071 | pyrrolidin-1-yl | Rac | H | H | fluoro | fluoro | C—H | C—H | C—H |
| I-072 | ethylsulfonylamino | Rac | H | H | fluoro | fluoro | C—H | C—H | C—H |
| I-073 | Diethylamino | Rac | H | H | fluoro | fluoro | C—H | C—H | C—H |
| I-074 | difluoromethylsulfonylamino | Rac | H | H | fluoro | fluoro | C—H | C—H | C—H |
| I-075 | (1-methyl-1H-1,2,4-triazol-5-yl)amino | Ent-2 | H | H | fluoro | fluoro | C—H | C—H | C—H |
| I-076 | isopropylsulfonylamino | Rac | H | H | fluoro | fluoro | C—H | C—H | C—H |
| I-077 | OH | Rac | H | H | chloro | chloro | C—H | C—H | C—H |
| I-078 | pyridin-2-ylmethylamino | Rac | H | H | fluoro | fluoro | C—H | C—H | C—H |
| I-079 | quinolin-5-ylmethylamino | Rac | H | H | fluoro | fluoro | C—H | C—H | C—H |
| I-080 | 2-(methoxycarbonyl)anilino | Rac | H | H | fluoro | fluoro | C—H | C—H | C—H |
| I-081 | 2-(3,4-dichlorophenyl)ethylamino | Rac | H | H | fluoro | fluoro | C—H | C—H | C—H |
| I-082 | 2,2,2-trifluoroethylsulfonylamino | Rac | H | H | fluoro | fluoro | C—H | C—H | C—H |
| I-083 | dimethylsulfamoylamino | Rac | H | H | fluoro | fluoro | C—H | C—H | C—H |
| I-084 | (3-methoxy-3-oxopropyl)amino | Rac | H | H | fluoro | fluoro | C—H | C—H | C—H |
| I-085 | (1-ethyl-1H-pyrazol-3-yl)methylamino | Rac | H | H | fluoro | fluoro | C—H | C—H | C—H |
| I-086 | cyclopropylsulfonylamino | Rac | H | H | fluoro | fluoro | C—H | C—H | C—H |
| I-087 | Methanesulfonamido | Rac | H | H | fluoro | fluoro | C-methyl | C—H | C—H |
| I-089 | tert-butoxy | Rac | H | H | fluoro | fluoro | C—H | C—H | C—H |
| I-090 | 2,2,2-trifluoroethylamino | Rac | H | H | fluoro | fluoro | C—H | C—H | C—H |
| I-091 | 2-methoxyethylamino | Rac | H | H | fluoro | fluoro | C—H | C—H | C—H |
| I-092 | prop-2-yn-1-ylamino | Rac | H | H | fluoro | fluoro | C—H | C—H | C—H |
| I-093 | (2-ethylphenyl)methylamino | Rac | H | H | fluoro | fluoro | C—H | C—H | C—H |
| I-094 | (1-ethyl-3-methyl-1H-pyrazol-4-yl)methylamino | Rac | H | H | fluoro | fluoro | C—H | C—H | C—H |
| I-095 | difluoromethylsulfonylamino | Rac | H | H | chloro | chloro | C—H | C—H | C—H |
| I-096 | 3-methylbutylamino | Rac | H | H | fluoro | fluoro | C—H | C—H | C—H |
| I-097 | 2-(2-bromophenyl)ethylamino | Rac | H | H | fluoro | fluoro | C—H | C—H | C—H |
| I-098 | Ethylamino | Rac | H | H | fluoro | fluoro | C—H | C—H | C—H |
| I-099 | 2-(3,5-dimethoxyphenyl)ethylamino | Rac | H | H | fluoro | fluoro | C—H | C—H | C—H |
| I-100 | N-methylanilino | Rac | H | H | fluoro | fluoro | C—H | C—H | C—H |
| I-101 | methylsulfonylazanidyl | Rac | H | H | fluoro | fluoro | C—H | C—H | C—H |
| I-102 | (6-chloropyridin-3-yl)methylamino | Rac | H | H | fluoro | fluoro | C—H | C—H | C—H |

TABLE 1-continued

Examples of preferred compounds of the general formula (I), with "Rac" representing a racemic mixture and "Ent-1" and "Ent-2" representing the specific stereoconfiguration at carbon C-2.

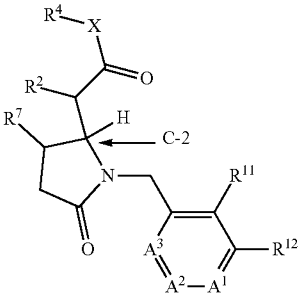

| Ex. No. | $R^4$—X— | C-2 Stereo-chemistry | $R^2$ | $R^7$ | $R^{11}$ | $R^{12}$ | $A^1$ | $A^2$ | $A^3$ |
|---|---|---|---|---|---|---|---|---|---|
| I-103 | 2-(2,4-difluorophenyl)ethylamino | Rac | H | H | fluoro | fluoro | C—H | C—H | C—H |
| I-104 | Methylamino | Rac | H | H | fluoro | fluoro | C—H | C—H | C—H |
| I-105 | Methanesulfonamido | Rac | H | H | chloro | chloro | C—H | C—H | C—H |
| I-106 | [(1R,2S)-2,6-dimethylindan-1-yl]amino | Rac | H | H | fluoro | fluoro | C—H | C—H | C—H |
| I-107 | 2-(1,3-benzodioxol-5-yl)ethylamino | Rac | H | H | fluoro | fluoro | C—H | C—H | C—H |
| I-108 | butan-2-ylamino | Rac | H | H | fluoro | fluoro | C—H | C—H | C—H |
| I-109 | 2-(1H-indol-3-yl)ethylamino | Rac | H | H | fluoro | fluoro | C—H | C—H | C—H |
| I-110 | Propylamino | Rac | H | H | fluoro | fluoro | C—H | C—H | C—H |
| I-111 | 2-(2,6-difluorophenyl)ethylamino | Rac | H | H | fluoro | fluoro | C—H | C—H | C—H |
| I-112 | 2-(3-methylphenyl)ethylamino | Rac | H | H | fluoro | fluoro | C—H | C—H | C—H |
| I-113 | [(1S,2R,5S)-2-isopropyl-5-methylcyclohexyl]oxy | Ent-1 | H | H | fluoro | fluoro | C—H | C—H | C—H |
| I-114 | 2-[3-(trifluoromethoxy)phenyl]ethylamino | Rac | H | H | fluoro | fluoro | C—H | C—H | C—H |
| I-115 | OH | Rac | H | H | tri-fluoro methyl | fluoro | C—H | C—H | C—H |
| I-116 | indan-1-ylamino | Rac | H | H | fluoro | fluoro | C—H | C—H | C—H |
| I-117 | quinolin-5-ylmethylamino | Rac | H | H | fluoro | fluoro | C—H | C—H | C—H |
| I-118 | [(2S)-1-tert-butoxy-3-(4-hydroxyphenyl)-1-oxopropan-2-yl]amino | Rac | H | H | fluoro | fluoro | C—H | C—H | C—H |
| I-119 | 2-(4-tert-butylphenyl)ethylamino | Rac | H | H | fluoro | fluoro | C—H | C—H | C—H |
| I-120 | methanesulfonamido | Ent-2 | H | H | fluoro | fluoro | C—H | C—H | C—H |
| I-121 | cyclopropylamino | Rac | H | H | fluoro | fluoro | C—H | C—H | C—H |
| I-122 | isopropylamino | Rac | H | H | fluoro | fluoro | C—H | C—H | C—H |
| I-123 | 2-(ethoxycarbonyl)piperidin-1-yl | Rac | H | H | fluoro | fluoro | C—H | C—H | C—H |
| I-124 | (1-methyl-1H-1,2,4-triazol-5-yl)amino | Ent-1 | H | H | fluoro | fluoro | C—H | C—H | C—H |
| I-125 | 2-(2-fluorophenyl)ethylamino | Rac | H | H | fluoro | fluoro | C—H | C—H | C—H |
| I-126 | (2-methoxy-2-oxoethyl)-methylamino | Ent-1 | H | H | fluoro | fluoro | C—H | C—H | C—H |
| I-127 | methanesulfonamido | Ent-1 | H | H | fluoro | fluoro | C—H | C—H | C—H |
| I-128 | 2-(ethoxycarbonyl)piperidin-1-yl | Ent-2 | H | H | fluoro | fluoro | C—H | C—H | C—H |
| I-129 | benzhydrylamino | Ent-1 | H | H | fluoro | fluoro | C—H | C—H | C—H |
| I-130 | dimethylsulfamoylamino | Rac | H | H | chloro | chloro | C—H | C—H | C—H |
| I-131 | N-methylanilino | Ent-2 | H | H | fluoro | fluoro | C—H | C—H | C—H |
| I-132 | cyclopropylamino | Ent-1 | H | H | fluoro | fluoro | C—H | C—H | C—H |
| I-133 | cyclohexylmethylamino | Rac | H | H | fluoro | fluoro | C—H | C—H | C—H |
| I-134 | N-methylanilino | Ent-1 | H | H | fluoro | fluoro | C—H | C—H | C—H |
| I-135 | (2-methoxy-2-oxoethyl)-methylamino | Ent-2 | H | H | fluoro | fluoro | C—H | C—H | C—H |
| I-136 | 2-(ethoxycarbonyl)piperidin-1-yl | Ent-1 | H | H | fluoro | fluoro | C—H | C—H | C—H |
| I-137 | benzhydrylamino | Ent-2 | H | H | fluoro | fluoro | C—H | C—H | C—H |
| I-138 | 3-(diethylamino)propylamino | Rac | H | H | fluoro | fluoro | C—H | C—H | C—H |
| I-139 | (2,4-difluorophenyl)methylamino | Rac | H | H | fluoro | fluoro | C—H | C—H | C—H |
| I-140 | 2-(5-hydroxy-1H-indol-3-yl)ethylamino | Rac | H | H | fluoro | fluoro | C—H | C—H | C—H |
| I-141 | [(1S,2R,5R)-2-isopropyl-5-methylcyclohexyl]oxy | Ent-1 | H | H | fluoro | fluoro | C—H | C—H | C—H |
| I-142 | Anilino | Rac | H | H | fluoro | fluoro | C—H | C—H | C—H |
| I-143 | cyclopropylamino | Ent-2 | H | H | fluoro | fluoro | C—H | C—H | C—H |
| I-144 | 2-[3-(trifluoromethyl)phenyl]ethylamino | Rac | H | H | fluoro | fluoro | C—H | C—H | C—H |
| I-145 | 2-(diethylamino)ethylamino | Rac | H | H | fluoro | fluoro | C—H | C—H | C—H |
| I-146 | isoquinolin-5-ylmethylamino | Rac | H | H | fluoro | fluoro | C—H | C—H | C—H |
| I-147 | carboxymethyl(methyl)amino | Ent-1 | H | H | fluoro | fluoro | C—H | C—H | C—H |
| I-148 | benzhydrylamino | Rac | H | H | fluoro | fluoro | C—H | C—H | C—H |
| I-149 | 2-(4-fluorophenyl)ethylamino | Rac | H | H | fluoro | fluoro | C—H | C—H | C—H |
| I-150 | OH | Rac | H | Ph | fluoro | fluoro | C—H | C—H | C—H |

TABLE 1-continued

Examples of preferred compounds of the general formula (I), with "Rac" representing a racemic mixture and "Ent-1" and "Ent-2" representing the specific stereoconfiguration at carbon C-2.

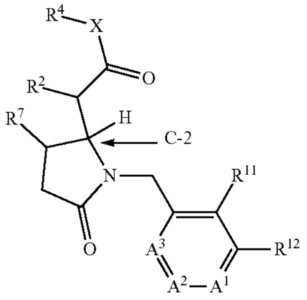

| Ex. No. | $R^4$—X— | C-2 Stereo-chemistry | $R^2$ | $R^7$ | $R^{11}$ | $R^{12}$ | $A^1$ | $A^2$ | $A^3$ |
|---|---|---|---|---|---|---|---|---|---|
| I-151 | 2-(5-methoxy-1H-indol-3-yl)ethylamino | Rac | H | H | fluoro | fluoro | C—H | C—H | C—H |
| I-152 | carboxymethyl(methyl)amino | Ent-2 | H | H | fluoro | chloro | C—H | C—H | C—H |
| I-153 | 2-[4-(trifluoromethoxy)phenyl]ethylamino | Rac | H | H | fluoro | fluoro | C—H | C—H | C—H |
| I-154 | 2-(3-bromophenyl)ethylamino | Rac | H | H | fluoro | fluoro | C—H | C—H | C—H |
| I-155 | 2-(2,5-dichlorophenyl)ethylamino | Rac | H | H | fluoro | fluoro | C—H | C—H | C—H |
| I-156 | 2-thiophen-2-ylethylamino | Rac | H | H | fluoro | fluoro | C—H | C—H | C—H |
| I-157 | 2-(2-methoxyphenyl)ethylamino | Rac | H | H | fluoro | fluoro | C—H | C—H | C—H |
| I-158 | 2-(3,4-dimethoxyphenyl)ethylamino | Rac | H | H | fluoro | fluoro | C—H | C—H | C—H |
| I-159 | (4-methoxy-4-oxobutyl)amino | Rac | H | H | fluoro | fluoro | C—H | C—H | C—H |
| I-160 | 2-(4-chlorophenyl)ethylamino | Rac | H | H | fluoro | fluoro | C—H | C—H | C—H |
| I-161 | 2-pyridin-3-ylethylamino | Rac | H | H | fluoro | fluoro | C—H | C—H | C—H |
| I-162 | OH | Rac | methyl | H | fluoro | fluoro | C—H | C—H | C—H |
| I-163 | 2-[3-chloro-5-(trifluoromethyl)pyridin-2-yl]ethylamino | Rac | H | H | fluoro | fluoro | C—H | C—H | C—H |
| I-164 | Methanesulfonamido | Rac | H | Ph | fluoro | fluoro | C—H | C—H | C—H |
| I-165 | 2-(4-methoxyphenyl)ethylamino | Rac | H | H | fluoro | fluoro | C—H | C—H | C—H |
| I-166 | 2-(3-methoxyphenyl)ethylamino | Rac | H | H | fluoro | fluoro | C—H | C—H | C—H |
| I-167 | 2-(2,3-dichlorophenyl)ethylamino | Rac | H | H | fluoro | fluoro | C—H | C—H | C—H |
| I-168 | 2-[3,5-bis(trifluoromethyl)phenyl]ethylamino | Rac | H | H | fluoro | fluoro | C—H | C—H | C—H |
| I-169 | 2-(4-methylphenyl)ethylamino | Rac | H | H | fluoro | fluoro | C—H | C—H | C—H |
| I-170 | 2-(3-chlorophenyl)ethylamino | Rac | H | H | fluoro | fluoro | C—H | C—H | C—H |
| I-171 | 2-(2-chlorophenyl)ethylamino | Rac | H | H | fluoro | fluoro | C—H | C—H | C—H |
| I-172 | 2-pyridin-2-ylethylamino | Rac | H | H | fluoro | fluoro | C—H | C—H | C—H |
| I-173 | 2-(2,4-dichlorophenyl)ethylamino | Rac | H | H | fluoro | fluoro | C—H | C—H | C—H |
| I-174 | 2-(3-fluorophenyl)ethylamino | Rac | H | H | fluoro | fluoro | C—H | C—H | C—H |
| I-175 | 2,2-difluoroethylamino | Rac | H | H | fluoro | fluoro | C—H | C—H | C—H |
| I-176 | 1,3-dimethoxy-1,3-dioxopropan-2-yl | Rac | H | H | fluoro | fluoro | C—H | C—H | C—H |
| I-177 | 5-hydroxy-1,3-dimethyl-1H-pyrazol-4-yl | Rac | H | H | fluoro | fluoro | C—H | C—H | C—H |
| I-178 | 3,3-dimethyl-2,6-dioxocyclohexyl | Rac | H | H | fluoro | fluoro | C—H | C—H | C—H |
| I-179 | 4,4-dimethyl-2,6-dioxocyclohexyl | Rac | H | H | fluoro | fluoro | C—H | C—H | C—H |
| I-180 | 4-methyl-2,6-dioxocyclohexyl | Rac | H | H | fluoro | fluoro | C—H | C—H | C—H |
| I-181 | 2,5-dioxocyclopentyl | Rac | H | H | fluoro | fluoro | C—H | C—H | C—H |
| I-182 | dicyanomethyl | Rac | H | H | fluoro | fluoro | C—H | C—H | C—H |
| I-183 | 2,4-dioxo-3-bicyclo[3.2.1]octanyl | Rac | H | H | fluoro | fluoro | C—H | C—H | C—H |
| I-184 | 3,3,5,5-tetramethyl-2,4,6-trioxocyclohexyl | Rac | H | H | fluoro | fluoro | C—H | C—H | C—H |
| I-185 | 2,6-dioxocyclohexyl | Rac | H | H | fluoro | fluoro | C—H | C—H | C—H |
| I-186 | 2,2-dimethyl-4,6-dioxo-1,3-dioxan-5-yl | Rac | H | H | fluoro | fluoro | C—H | C—H | C—H |
| I-187 | 5-hydroxy-1-methyl-1H-pyrazol-4-yl | Rac | H | H | fluoro | fluoro | C—H | C—H | C—H |
| I-188 | 1-cyano-2-methoxy-2-oxoethyl | Rac | H | H | fluoro | fluoro | C—H | C—H | C—H |
| I-189 | 1-methoxy-1,3-dioxobutan-2-yl | Rac | H | H | fluoro | fluoro | C—H | C—H | C—H |
| I-190 | 2,4-dioxo-3-bicyclo[3.2.1]oct-6-enyl | Rac | H | H | fluoro | fluoro | C—H | C—H | C—H |
| I-191 | OH | Rac | H | H | fluoro | fluoro | C—H | C—H | C—F |
| I-192 | OH | Rac | H | H | fluoro | fluoro | C—F | C—H | C—H |
| I-193 | 1,2,4-thiadiazol-5-ylamino | Rac | H | H | fluoro | fluoro | C—H | C—H | C—H |
| I-194 | OH | Rac | H | H | methyl | methyl | C—H | C—H | C—H |
| I-195 | 5-(difluoromethyl)-1,3,4-thiadiazol-2-ylamino | Rac | H | H | fluoro | fluoro | C—H | C—H | C—H |
| I-196 | 5-tert-butyl-1,2-oxazol-3-ylamino | Rac | H | H | fluoro | fluoro | C—H | C—H | C—H |
| I-197 | 4-(trifluoromethyl)pyridin-2-ylamino | Rac | H | H | fluoro | fluoro | C—H | C—H | C—H |
| I-198 | 5-chloro-4-(trifluoromethyl)pyridin-2-ylamino | Rac | H | H | fluoro | fluoro | C—H | C—H | C—H |

TABLE 1-continued

Examples of preferred compounds of the general formula (I), with "Rac" representing a racemic mixture and "Ent-1" and "Ent-2" representing the specific stereoconfiguration at carbon C-2.

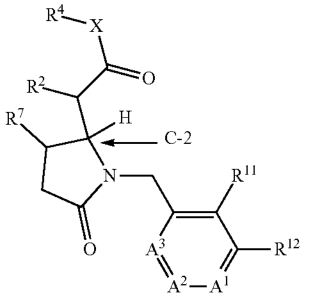

| Ex. No. | $R^4$—X— | C-2 Stereo-chemistry | $R^2$ | $R^7$ | $R^{11}$ | $R^{12}$ | $A^1$ | $A^2$ | $A^3$ |
|---|---|---|---|---|---|---|---|---|---|
| I-199 | (pyridin-4-ylmethoxy)amino | Rac | H | H | fluoro | fluoro | C—H | C—H | C—H |
| I-200 | pyrrolidin-1-ylamino | Rac | H | H | fluoro | fluoro | C—H | C—H | C—H |
| I-201 | OH | Rac | H | H | fluoro | fluoro | C—H | C—F | C—H |
| I-202 | OH | Rac | H | H | fluoro | methoxy | C—F | C—H | C—H |
| I-203 | piperidin-1-ylamino | Rac | H | H | fluoro | fluoro | C—H | C—H | C—H |
| I-204 | OH | Ent-1 | H | H | fluoro | chloro | C—H | C—H | C—H |
| I-205 | OH | Ent-2 | H | H | fluoro | chloro | C—H | C—H | C—H |

Spectroscopic data of selected table examples:

The spectroscopic data listed hereinafter for selected table examples were evaluated via conventional $^1$H-NMR interpretation or via NMR peak list methods.

a) Conventional $^1$H-NMR interpretation

No. 1-007: $^1$H-NMR (400.1 MHz, $CDCl_3$): δ ppm 1.79-1.89 (m, 1H), 2.22-2.31 (m, 4H), 2.34-2.52 (m, 3H), 2.75 (dd, J=15.57, 3.99 Hz, 1H), 3.88 (dt, J=8.31, 4.16 Hz, 1H), 4.09-4.15 (m, 2H), 4.24 (d, J=15.49 Hz, 1H), 4.37-4.44 (m, 2H), 4.86 (dd, J=15.57, 1.55 Hz, 1H), 6.85-6.92 (in, 2H), 7.00-7.12 (in, 5H).

No. 1-194: $^1$H-NMR (400 MHz, $CDCl_3$): $\delta_H$ ppm 7.13-7.11 (d, 1H), 7.09-7.05 (dd, 1H), 6.98-6.96 (d, 1H), 5.04 (d, 1H), 4.08 (d, 1H), 3.80-3.75 (m, 1H), 2.68-2.50 (m, 3H), 2.48-2.41 (dd, 1H), 2.31-2.23 (m, 1H), 2.28 (s, 3H), 2.15 (s, 3H), 1.95-1.88 (in, 1H).

No. I-195: $^1$H-NMR (400.0 MHz, $CDCl_3$) δ ppm 7.10-6.84 (br. t, 1H, $CHF_2$), 7.06-6.97 (m, 4H), 4.88-4.84 (d, 1H), 4.40-4.36 (d, 1H), 4.14-4.10 (m, 1H), 3.14-3.09 (m, 1H), 2.87-2.81 (dd, 1H), 2.63-2.58 (m, 1H), 2.48-2.44 (m, 1H), 2.42-2.32 (m, 1H), 2.01-1.93 (m, 1H).

No. I-201: $^1$H-NMR (400 MHz, $CDCl_3$): $\delta_H$ ppm 6.90-6.79 (m, 2H), 4.85 (d, 1H), 4.29 (d, 1H), 3.95-3.88 (m, 1H), 2.78-2.74 (dd, 1H), 2.61-2.42 (m, 3H), 2.39-2.30 (m, 1H), 1.94-1.86 (m, 1H).

No. I-203: $^1$H-NMR (400.0 MHz, $CDCl_3$) δ ppm 7.12-7.04 (m, 3H), 6.15 (br. s, 1H, NH), 4.91-4.87/4.88-4.84 (d, 1H), 4.33-4.29/4.26-4.22 (d, 1H), 3.96-3.89 (m, 1H), 3.22-3.18 (m, 1H), 3.04-2.81 (m, 1H), 2.90-2.86 (dd, 1H), 2.62-2.35 (m, 5H), 2.32-2.18 (m, 3H), 2.04-1.98 (m, 1H), 1.90-1.79 (m, 2H), 1.60-1.48 (m, 2H).

b) NMR peak list method $^1$H-NMR data of selected examples are written in form of $^1$H-NMR-peak lists. To each signal peak are listed the δ-value in ppm and the signal intensity in round brackets. Between the δ-value—signal intensity pairs are semicolons as delimiters. The peak list of an example has therefore the form:

$$\delta_1(\text{intensity}_1);\delta_2(\text{intensity}_2); \ldots ;\delta_i(\text{intensity}_n); \ldots ; \delta_n(\text{intensity}_n)$$

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown. For calibrating chemical shift for $^1$H spectra, we use tetramethylsilane and/or the chemical shift of the solvent used, especially in the case of spectra measured in DMSO. Therefore in NMR peak lists, tetramethylsilane peak can occur but not necessarily. The $^1$H-NMR peak lists are similar to classical $^1$H-NMR prints and contains therefore usually all peaks, which are listed at classical NMR-interpretation. Additionally they can show like classical $^1$H-NMR prints signals of solvents, stereoisomers of the target compounds, which are also object of the invention, and/or peaks of impurities. To show compound signals in the delta-range of solvents and/or water the usual peaks of solvents, for example peaks of DMSO in DMSO-$D_6$ and the peak of water are shown in our $^1$H-NMR peak lists and have usually on average a high intensity. The peaks of stereoisomers of the target compounds and/or peaks of impurities have usually on average a lower intensity than the peaks of target compounds (for example with a purity >90%). Such stereoisomers and/or impurities can be typical for the specific preparation process. Therefore, their peaks can help to recognize the reproduction of our preparation process via "side-products-fingerprints". An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking done in the course of a classical $^1$H-NMR interpretation. Further details of NMR-data description with peak lists can be found in the publication "Citation of NMR Peaklist Data within Patent Applications" of the Research Disclosure Database Number 564025.

I-001: $^1$H-NMR(400.0 MHz, $d_6$-DMSO):
δ = 7.5273 (2.0); 7.5223 (2.0); 7.5084 (3.3); 7.5029 (3.8); 7.4915 (2.3); 7.4850 (2.1); 7.2549 (0.9); 7.2500 (1.3); 7.2354 (3.2); 7.2306 (2.6); 7.2210 (4.2); 7.2169 (11.7); 7.1976 (6.6); 7.1784 (1.9); 4.7268 (3.0); 4.6869 (3.5); 4.2494 (3.9); 4.2092 (3.3); 3.7943 (0.8); 3.7839 (1.2); 3.7730 (1.8); 3.7635 (2.0); 3.7532 (1.8); 3.7426 (1.4); 3.7323 (0.5); 3.3770 (8.7); 3.1663 (3.3); 2.7741 (0.6); 2.7116 (3.2); 2.7014 (3.2); 2.6717 (4.3); 2.6615 (4.0); 2.5239 (2.2); 2.5192 (3.2); 2.5105 (50.3); 2.5059 (111.3); 2.5013 (155.7); 2.4967 (108.8); 2.4921 (48.1); 2.4468 (1.3); 2.4301 (1.1); 2.4057 (6.4); 2.3889 (2.1); 2.3835 (5.6); 2.3658 (4.0); 2.3517 (0.7); 2.3437 (3.4); 2.3328 (0.7); 2.3280 (1.0); 2.3234 (0.7); 2.2930 (1.5); 2.2801 (1.6); 2.2685 (2.8); 2.2557 (2.7); 2.2269 (3.6); 2.2171 (2.2); 2.2045 (1.4); 2.1993 (1.2); 2.1869 (1.8); 2.1803 (0.9); 2.1746 (0.7); 2.1677 (1.2); 2.1620 (1.0); 2.1432 (0.6); 1.7575 (1.7); 1.7466 (1.7); 1.7357 (1.9); 1.7284 (1.0); 1.7228 (1.0); 1.7180 (1.1); 1.7039 (1.1); 1.6914 (0.8); 1.6346 (0.6); 1.6181 (0.8); 1.6008 (0.6); 1.4445 (0.9); 1.4247 (1.2); 1.4052 (1.2); 1.3877 (0.7); 0.8894 (16.0); 0.8729 (15.3); −0.0002 (15.0)
I-002: $^1$H-NMR(400.1 MHz, $d_6$-DMSO):
δ = 12.5234 (0.5); 12.4463 (0.6); 12.4011 (0.6); 12.3590 (0.6); 12.3360 (0.6); 12.3258 (0.6); 12.2780 (0.7); 12.1966 (0.5); 12.1506 (0.6); 12.1440 (0.7); 12.0718 (0.6); 11.9413 (0.6); 7.8181 (1.0); 7.3820 (2.6); 7.3781 (2.8); 7.3614 (5.7); 7.3576 (6.4); 7.3516 (3.8); 7.3354 (6.3); 7.3318 (5.8); 7.3157 (3.7); 7.3111 (3.4); 7.2096 (2.9); 7.2057 (3.4); 7.1967 (3.7); 7.1897 (6.5); 7.1858 (6.7); 7.1770 (6.4); 7.1734 (7.0); 7.1693 (4.9); 7.1654 (4.3); 7.1564 (3.9); 7.1531 (4.1); 7.1289 (0.6); 7.0951 (6.4); 7.0791 (8.9); 7.0600 (4.8); 7.0447 (0.9); 4.7423 (9.6); 4.7028 (11.4); 4.6780 (0.5); 4.2544 (12.5); 4.2148 (10.8); 3.8881 (0.5); 3.7898 (2.2); 3.7796 (4.0); 3.7687 (5.6); 3.7581 (6.4); 3.7484 (5.9); 3.7379 (4.7); 3.7278 (2.4); 3.6940 (0.7); 3.6517 (0.6); 3.6114 (0.7); 3.5977 (3.7); 3.5672 (0.9); 3.5600 (1.0); 3.5540 (1.1); 3.5249 (1.3); 3.5026 (1.4); 3.3613 (79.3); 3.1682 (10.0); 3.1265 (0.8); 3.1082 (0.8); 3.0944 (0.8); 3.0342 (0.6); 2.9971 (0.6); 2.7039 (9.7); 2.6935 (9.8); 2.6743 (4.0); 2.6698 (5.5); 2.6642 (14.6); 2.6538 (12.4); 2.5566 (2.4); 2.5520 (2.6); 2.5472 (1.4); 2.5398 (2.5); 2.5232 (7.9); 2.5185 (11.8); 2.5099 (249.1); 2.5053 (560.3); 2.5007 (795.0); 2.4961 (586.7); 2.4916 (296.0); 2.4499 (7.0); 2.4287 (5.2); 2.4192 (4.3); 2.4042 (10.1); 2.4007 (16.0); 2.3876 (7.2); 2.3788 (15.7); 2.3724 (4.6); 2.3609 (12.0); 2.3520 (2.9); 2.3388 (11.3); 2.3323 (4.7); 2.3274 (5.6); 2.3232 (4.1); 2.3185 (2.5); 2.2891 (5.3); 2.2761 (5.7); 2.2646 (8.5); 2.2516 (9.1); 2.2366 (1.7); 2.2205 (8.2); 2.2116 (6.6); 2.2067 (5.9); 2.1966 (5.3); 2.1914 (4.4); 2.1859 (3.1); 2.1791 (6.2); 2.1721 (3.4); 2.1663 (2.6); 2.1594 (4.1); 2.1537 (3.7); 2.1346 (2.1); 2.0720 (4.0); 1.8683 (0.7); 1.7841 (1.0); 1.7612 (2.6); 1.7562 (5.6); 1.7451 (5.6); 1.7328 (6.1); 1.7268 (3.6); 1.7212 (3.5); 1.7149 (4.2); 1.7023 (3.7); 1.6901 (2.5); 1.2552 (0.6); 0.9771 (0.6); 0.0082 (3.3)
I-003: $^1$H-NMR(400.0 MHz, $d_6$-DMSO):
δ = 12.3726 (10.8); 7.3860 (2.9); 7.3820 (3.1); 7.3656 (6.0); 7.3615 (6.6); 7.3554 (3.4); 7.3458 (4.3); 7.3395 (6.5); 7.3354 (5.7); 7.3193 (3.6); 7.3153 (3.4); 7.2112 (4.0); 7.2073 (4.3); 7.1985 (4.1); 7.1946 (4.9); 7.1913 (7.5); 7.1875 (8.0); 7.1785 (7.3); 7.1750 (8.2); 7.1710 (5.1); 7.1670 (5.0); 7.1582 (4.3); 7.1545 (4.7); 7.0958 (7.8); 7.0799 (10.5); 7.0765 (9.7); 7.0604 (5.4); 4.7435 (12.3); 4.7039 (14.3); 4.2546 (16.0); 4.2150 (13.8); 3.7886 (2.6); 3.7781 (4.9); 3.7672 (6.9); 3.7572 (7.4); 3.7472 (6.8); 3.7367 (5.4); 3.7261 (2.2); 3.3520 (1.4); 3.3265 (262.8); 3.2764 (1.3); 2.7083 (13.1); 2.6981 (13.3); 2.6756 (1.7); 2.6684 (17.1); 2.6582 (16.1); 2.5414 (0.6); 2.5246 (2.6); 2.5199 (4.1); 2.5112 (54.6); 2.5066 (116.9); 2.5020 (160.6); 2.4974 (109.1); 2.4928 (47.5); 2.4478 (3.6); 2.4304 (4.2); 2.4210 (2.6); 2.4064 (10.6); 2.4021 (19.0); 2.3892 (7.7); 2.3801 (19.3); 2.3723 (3.8); 2.3622 (14.6); 2.3508 (1.9); 2.3402 (14.1); 2.3289 (1.6); 2.3242 (1.1); 2.3197 (0.6); 2.2899 (6.2); 2.2770 (6.9); 2.2655 (11.3); 2.2526 (11.0); 2.2374 (1.1); 2.2241 (9.0); 2.2209 (9.6); 2.2188 (9.2); 2.2129 (6.6); 2.2103 (6.2); 2.2069 (6.6); 2.1965 (5.9); 2.1909 (4.6); 2.1858 (2.6); 2.1787 (7.2); 2.1721 (3.7); 2.1665 (2.6); 2.1594 (4.7); 2.1533 (4.2); 2.1350 (2.4); 2.0748 (0.8); 1.7822 (1.1); 1.7601 (3.1); 1.7543 (7.0); 1.7431 (7.2); 1.7355 (4.6); 1.7301 (7.2); 1.7250 (4.2); 1.7194 (4.0); 1.7136 (5.0); 1.7005 (4.4); 1.6878 (2.9); 0.0080 (1.6); 0.0063 (0.5); 0.0055 (0.6); 0.0047 (0.7); 0.0039 (0.8); 0.0022 (2.2); −0.0002 (53.4); −0.0051 (1.0); −0.0059 (0.7); −0.0068 (0.6); −0.0085 (1.6)
I-004: $^1$H-NMR(400.1 MHz, $d_6$-DMSO):
δ = 11.1978 (0.8); 7.3828 (0.5); 7.3780 (0.4); 7.3621 (1.2); 7.3577 (1.1); 7.3414 (1.2); 7.3370 (1.3); 7.3163 (0.7); 7.2178 (0.3); 7.2142 (0.4); 7.2056 (0.7); 7.1942 (1.1); 7.1858 (1.4); 7.1774 (1.2); 7.1738 (1.3); 7.1653 (0.9); 7.1532 (0.6); 7.0797 (1.4); 7.0636 (0.7); 4.7699 (1.0); 4.7432 (1.3); 4.7300 (1.2); 4.7031 (1.4); 4.3015 (1.2); 4.2554 (1.8); 4.2153 (1.4); 3.9266 (0.4); 3.9162 (0.5); 3.9053 (0.6); 3.8949 (0.6); 3.8846 (0.4); 3.8383 (16.0); 3.7797 (0.5); 3.7701 (0.8); 3.7600 (0.9); 3.7491 (0.8); 3.7392 (0.6); 3.3704 (18.0); 3.1686 (1.1); 2.9541 (0.6); 2.9442 (0.6); 2.9160 (0.8); 2.9060 (0.7); 2.7041 (1.2); 2.6938 (1.2); 2.6747 (0.5); 2.6699 (0.7); 2.6645 (1.8); 2.6540 (1.6); 2.6354 (0.7); 2.6128 (0.7); 2.5970 (0.6); 2.5747 (0.7); 2.5616 (0.6); 2.5576 (0.6); 2.5530 (0.4); 2.5234 (1.0); 2.5185 (1.7); 2.5101 (31.6); 2.5055 (68.7); 2.5009 (96.0); 2.4964 (70.2); 2.4919 (35.2); 2.4548 (1.0); 2.4497 (1.2); 2.4457 (1.3); 2.4315 (1.2); 2.4141 (1.1); 2.4060 (1.6); 2.4012 (2.0); 2.3887 (1.1); 2.3792 (2.0); 2.3736 (0.7); 2.3611 (1.5); 2.3509 (0.4); 2.3391 (1.4); 2.3328 (1.0); 2.3277 (0.8); 2.3201 (0.7); 2.3085 (0.8); 2.2962 (0.8); 2.2898 (0.8); 2.2765 (0.7); 2.2649 (1.4); 2.2520 (1.3); 2.2481 (1.0); 2.2352 (0.6); 2.2206 (1.3); 2.2119 (1.1); 2.1969 (1.0); 2.1918 (0.9); 2.1788 (0.8); 2.1723 (0.6); 2.1664 (0.4); 2.1604 (0.5); 2.1544 (0.5); 1.8706 (0.4); 1.8587 (0.5); 1.8479 (0.5); 1.8428 (0.5); 1.8363 (0.4); 1.8293 (0.4); 1.8166 (0.3); 1.7621 (0.3); 1.7568 (0.7); 1.7458 (0.7); 1.7329 (0.8); 1.7275 (0.5); 1.7218 (0.4); 1.7157 (0.5); 1.7030 (0.5); 0.0082 (0.5); 0.0000 (17.0)
I-005: $^1$H-NMR(400.1 MHz, $d_6$-DMSO):
δ = 8.1838 (0.6); 8.1628 (0.7); 8.1443 (0.5); 8.1236 (0.5); 8.1049 (1.0); 8.0829 (1.1); 7.3769 (0.6); 7.3571 (1.3); 7.3337 (1.3); 7.3113 (0.7); 7.2067 (0.6); 7.1868 (1.4); 7.1742 (1.4); 7.1538 (0.7); 7.0893 (1.0); 7.0733 (1.6); 7.0571 (0.8); 4.7542 (1.4); 4.7372 (0.6); 4.7145 (1.6); 4.6965 (0.8); 4.3978 (1.0); 4.3862 (1.0); 4.3755 (1.0); 4.3640 (1.0); 4.2659 (1.2); 4.2543 (0.9); 4.2457 (0.8); 4.2265 (1.1); 4.2195 (1.0); 4.2050 (1.3); 4.1985 (0.8); 4.1836 (0.6); 4.1675 (0.5); 4.1527 (0.6); 4.1467 (0.5); 4.1318 (0.5); 3.8003 (0.4); 3.7906 (0.7); 3.7806 (1.1); 3.7709 (1.4); 3.7608 (1.2); 3.7502 (0.8); 3.7389 (0.4); 3.3617 (31.2); 3.1683 (2.1); 2.6743 (0.6); 2.6696 (0.8); 2.6650 (0.6); 2.6604 (0.4); 2.6315 (0.4); 2.6210 (0.5); 2.5958 (1.0); 2.5849 (1.4); 2.5742 (0.6); 2.5613 (1.1); 2.5507 (1.4); 2.5399 (1.2); 2.5232 (1.7); 2.5184 (2.7); 2.5098 (44.8); 2.5052 (98.6); 2.5006 (137.4); 2.4960 (99.7); 2.4914 (46.7); 2.4071 (0.5); 2.3998 (1.2); 2.3833 (0.8); 2.3784 (1.3); 2.3657 (2.0); 2.3447 (1.9); 2.3359 (1.4); 2.3322 (1.2); 2.3275 (1.3); 2.3229 (1.5); 2.3150 (1.1); 2.2934 (0.6); 2.2869 (0.5); 2.2786 (1.0); 2.2627 (1.1); 2.2540 (1.1); 2.2509 (1.1); 2.2412 (0.9); 2.2212 (0.5); 2.2096 (0.6); 2.1994 (0.5); 2.1249 (0.4); 2.1047 (0.9); 2.0927 (0.7); 2.0808 (0.9); 2.0723 (1.5); 2.0616 (0.5); 2.0524 (0.8); 2.0491 (0.9); 2.0295 (0.4); 1.8690 (0.6); 1.8571 (0.6); 1.8515 (0.7); 1.8399 (0.6); 1.8335 (0.5); 1.8224 (0.5); 1.8029 (0.6); 1.7945 (0.9); 1.7803 (1.0); 1.7709 (1.1); 1.7607 (1.1); 1.7533 (0.9); 1.7431 (0.8); 1.7294 (0.5); 1.3818 (0.5); 1.3644 (0.4); 1.3582 (0.3);

-continued 1.2949 (0.4); 1.2771 (0.6); 1.2600 (0.8); 1.2428 (0.9); 1.2249 (0.7); 1.2073 (0.4); 1.1887 (0.5); 1.1760 (0.5); 1.1694 (0.5); 1.1588 (0.8); 1.1540 (0.6); 1.1408 (0.9); 1.1354 (0.6); 1.1233 (0.7); 1.1066 (0.6); 1.0887 (0.4); 0.8483 (13.7); 0.8336 (16.0); 0.8313 (15.8); 0.8153 (4.9); 0.0082 (0.9)

I-006: $^1$H-NMR(400.0 MHz, $d_6$-DMSO):

δ = 7.3863 (1.5); 7.3823 (1.6); 7.3659 (3.0); 7.3617 (3.4); 7.3556 (1.7); 7.3461 (2.1); 7.3399 (3.3); 7.3357 (2.8); 7.3196 (1.8); 7.3156 (1.7); 7.2075 (1.8); 7.2037 (1.9); 7.1949 (1.9); 7.1911 (2.2); 7.1877 (3.4); 7.1840 (3.6); 7.1750 (3.4); 7.1715 (3.8); 7.1673 (2.3); 7.1635 (2.3); 7.1546 (2.0); 7.1512 (2.2); 7.1089 (3.6); 7.0930 (4.6); 7.0736 (2.3); 4.7514 (5.2); 4.7118 (6.0); 4.2748 (6.7); 4.2351 (5.7); 3.8544 (1.1); 3.8441 (2.1); 3.8339 (3.4); 3.8239 (4.0); 3.8138 (3.4); 3.8037 (2.6); 3.7930 (0.9); 3.4628 (15.4); 3.1689 (0.6); 2.8932 (5.3); 2.8829 (5.5); 2.8533 (7.2); 2.8431 (6.8); 2.6710 (0.5); 2.6664 (0.5); 2.6456 (7.4); 2.6245 (7.2); 2.6058 (5.8); 2.5847 (5.6); 2.5245 (1.2); 2.5197 (1.8); 2.5111 (30.4); 2.5065 (66.8); 2.5019 (93.7); 2.4972 (65.1); 2.4926 (28.7); 2.4590 (1.8); 2.4470 (4.5); 2.4406 (6.1); 2.4313 (9.6); 2.4180 (8.0); 2.4005 (3.4); 2.3949 (2.9); 2.3797 (1.5); 2.3648 (1.0); 2.3287 (0.6); 2.3004 (2.5); 2.2881 (2.8); 2.2758 (5.6); 2.2699 (7.5); 2.2637 (7.0); 2.2547 (10.3); 2.2383 (10.3); 2.2353 (10.2); 2.2289 (3.2); 2.2250 (4.9); 2.2156 (2.7); 2.2096 (2.1); 2.2045 (1.1); 2.1975 (3.3); 2.1912 (1.4); 2.1851 (1.1); 2.1782 (2.0); 2.1725 (1.8); 2.1537 (1.0); 2.0740 (3.4); 1.8160 (0.8); 1.7919 (3.1); 1.7803 (2.4); 1.7703 (2.8); 1.7626 (1.8); 1.7576 (1.8); 1.7535 (1.8); 1.7489 (2.0); 1.7381 (2.0); 1.7263 (1.3); 1.6501 (4.9); 1.5712 (13.8); 1.5641 (16.0); 1.5558 (11.3); −0.0002 (7.0)

I-009: $^1$H-NMR(400.1 MHz, $d_6$-DMSO):

δ = 7.3860 (0.3); 7.3818 (0.4); 7.3654 (0.8); 7.3615 (0.8); 7.3556 (0.4); 7.3456 (0.5); 7.3395 (0.8); 7.3356 (0.7); 7.3192 (0.4); 7.3153 (0.4); 7.2123 (0.4); 7.2086 (0.4); 7.1996 (0.5); 7.1957 (0.6); 7.1924 (0.8); 7.1888 (0.9); 7.1796 (0.8); 7.1764 (0.9); 7.1723 (0.6); 7.1684 (0.6); 7.1595 (0.5); 7.1559 (0.5); 7.0953 (0.9); 7.0793 (1.2); 7.0764 (1.1); 7.0600 (0.6); 4.7406 (1.3); 4.7009 (1.6); 4.3621 (2.5); 4.3560 (0.6); 4.3474 (5.0); 4.3389 (0.7); 4.3328 (2.8); 4.2515 (1.7); 4.2119 (1.5); 3.8177 (0.5); 3.8073 (0.8); 3.7971 (0.9); 3.7872 (0.9); 3.7768 (0.6); 3.4789 (2.0); 3.4645 (3.4); 3.4499 (1.9); 3.3678 (10.0); 3.1687 (0.4); 2.9991 (16.0); 2.8276 (1.2); 2.8176 (1.2); 2.7875 (1.6); 2.7774 (1.5); 2.5588 (1.6); 2.5370 (1.6); 2.5186 (1.8); 2.5099 (10.4); 2.5053 (23.0); 2.5007 (32.8); 2.4962 (24.9); 2.4916 (11.6); 2.4522 (0.4); 2.4349 (0.5); 2.4113 (1.0); 2.3936 (0.8); 2.3878 (0.7); 2.3809 (0.3); 2.3722 (0.4); 2.2921 (0.6); 2.2798 (0.6); 2.2677 (1.1); 2.2554 (1.1); 2.2263 (1.8); 2.2161 (1.1); 2.2060 (0.6); 2.2003 (0.5); 2.1878 (0.8); 2.1817 (0.4); 2.1686 (0.5); 2.1629 (0.5); 1.7810 (0.7); 1.7697 (0.6); 1.7594 (0.8); 1.7516 (0.4); 1.7467 (0.4); 1.7421 (0.4); 1.7380 (0.5); 1.7269 (0.5); 0.0000 (9.4)

I-011: $^1$H-NMR(400.1 MHz, $d_6$-DMSO):

δ = 19.7585 (0.3); 12.9496 (0.4); 12.6612 (0.4); 12.5714 (0.8); 12.5551 (0.6); 12.5285 (0.4); 8.1442 (0.6); 8.1255 (0.6); 8.1082 (0.4); 8.0797 (0.4); 8.0598 (1.4); 8.0365 (1.4); 7.9568 (0.6); 7.4617 (0.3); 7.3773 (0.7); 7.3549 (1.6); 7.3320 (1.6); 7.3094 (0.8); 7.2253 (0.4); 7.1847 (1.5); 7.1715 (1.6); 7.1543 (0.9); 7.0750 (1.9); 4.7539 (0.8); 4.7385 (1.7); 4.7121 (0.7); 4.6979 (1.9); 4.3971 (0.4); 4.3747 (0.4); 4.3452 (1.2); 4.3342 (1.3); 4.3244 (1.2); 4.3128 (1.1); 4.2488 (2.0); 4.2092 (2.0); 4.1683 (0.5); 4.1504 (0.6); 4.1304 (0.4); 4.0761 (0.6); 3.9659 (0.5); 3.9032 (0.3); 3.7811 (1.3); 3.7684 (1.7); 3.6533 (0.3); 3.6104 (0.4); 3.5831 (0.4); 3.5679 (0.5); 3.5390 (0.5); 3.5012 (0.6); 3.4888 (0.7); 3.4613 (0.8); 3.4216 (1.2); 3.3747 (2.8); 3.3178 (191.6); 3.2190 (1.5); 3.1907 (0.9); 3.1759 (2.8); 3.1633 (2.9); 3.1011 (0.3); 3.0923 (0.3); 3.0484 (0.3); 2.9989 (0.4); 2.8911 (4.6); 2.8794 (0.5); 2.8416 (0.4); 2.8290 (0.4); 2.7752 (0.4); 2.7315 (4.7); 2.6721 (3.3); 2.6460 (1.8); 2.6206 (2.3); 2.6130 (2.3); 2.5645 (2.6); 2.5030 (519.5); 2.3986 (2.3); 2.3764 (1.8); 2.3346 (4.2); 2.3020 (1.4); 2.2788 (1.8); 2.2605 (1.4); 2.2543 (1.4); 2.2229 (0.8); 2.1244 (0.5); 2.1025 (0.9); 2.0801 (1.2); 2.0721 (2.0); 2.0494 (1.0); 2.0274 (0.5); 1.8307 (1.2); 1.8156 (1.2); 1.7988 (1.3); 1.7776 (1.1); 1.7098 (0.3); 1.3822 (0.4); 1.3629 (0.4); 1.3493 (0.3); 1.2934 (0.5); 1.2783 (0.8); 1.2600 (0.9); 1.2433 (1.2); 1.2245 (0.8); 1.2092 (0.5); 1.1876 (0.4); 1.1534 (0.8); 1.1343 (1.1); 1.1167 (1.0); 1.0996 (0.8); 1.0820 (0.5); 0.8481 (12.7); 0.8318 (16.0); 0.8156 (4.6); 0.7823 (0.5); 0.1461 (0.5); 0.0081 (4.3); 0.0000 (107.5)

I-012: $^1$H-NMR(400.1 MHz, CDCl3):

δ = 7.5175 (0.6); 7.2750 (0.4); 7.2742 (0.4); 7.2725 (0.4); 7.2717 (0.5); 7.2708 (0.6); 7.2692 (0.8); 7.2684 (0.8); 7.2675 (1.0); 7.2598 (109.9); 7.2586 (104.9); 7.1390 (0.3); 7.1353 (0.3); 7.1256 (0.8); 7.1136 (0.6); 7.1072 (0.7); 7.1001 (1.1); 7.0924 (0.4); 7.0809 (2.0); 7.0741 (2.3); 7.0650 (2.5); 7.0564 (1.3); 7.0443 (0.3); 6.9959 (0.6); 4.8911 (1.2); 4.8510 (1.3); 4.2593 (1.6); 4.2207 (1.5); 3.9895 (0.4); 3.9803 (0.7); 3.9704 (0.9); 3.9598 (0.7); 3.9511 (0.5); 3.6684 (0.4); 3.4902 (1.4); 3.2842 (16.0); 2.7924 (1.0); 2.7801 (1.0); 2.7533 (1.3); 2.7411 (1.2); 2.5654 (0.4); 2.5431 (0.8); 2.5222 (1.0); 2.4998 (0.8); 2.4935 (0.8); 2.4802 (0.8); 2.4697 (1.0); 2.4566 (1.0); 2.4504 (0.4); 2.4259 (1.6); 2.4139 (0.5); 2.4057 (1.3); 2.3868 (1.0); 2.3669 (1.2); 2.3505 (0.7); 2.3376 (0.4); 2.3274 (0.5); 2.3175 (0.7); 2.2941 (0.5); 2.0982 (1.1); 1.8819 (0.3); 1.8698 (0.5); 1.8588 (0.6); 1.8488 (0.7); 1.8366 (0.7); 1.8261 (0.6); 1.8156 (0.4); 1.8032 (0.3); 1.5569 (1.4); 1.2547 (0.5); 0.0081 (1.3); 0.0069 (1.4)

I-013: $^1$H-NMR(400.0 MHz, $d_6$-DMSO):

δ = 3.4183 (16.0); 3.1685 (3.2); 2.5244 (0.4); 2.5197 (0.5); 2.5111 (9.3); 2.5064 (20.7); 2.5018 (29.1); 2.4972 (20.4); 2.4926 (9.0); 2.0734 (1.1)

I-014: $^1$H-NMR(400.0 MHz, $d_6$-DMSO):

δ = 12.3682 (1.9); 7.3838 (3.5); 7.3798 (3.8); 7.3634 (7.2); 7.3593 (8.0); 7.3532 (4.1); 7.3437 (5.1); 7.3373 (7.7); 7.3332 (6.6); 7.3173 (4.4); 7.3133 (4.1); 7.2101 (4.5); 7.2062 (4.6); 7.1974 (4.6); 7.1935 (5.5); 7.1902 (8.2); 7.1864 (8.7); 7.1776 (7.9); 7.1739 (9.0); 7.1699 (5.4); 7.1659 (5.4); 7.1572 (4.6); 7.1536 (4.9); 7.0954 (8.4); 7.0793 (11.4); 7.0598 (5.7); 4.7429 (12.5); 4.7028 (14.4); 4.2543 (16.0); 4.2147 (14.0); 3.7888 (2.8); 3.7783 (5.0); 3.7671 (7.2); 3.7574 (7.7); 3.7472 (7.1); 3.7368 (5.5); 3.7262 (2.2); 3.3181 (83.5); 2.7049 (13.3); 2.6947 (13.5); 2.6746 (2.9); 2.6702 (4.7); 2.6651 (18.9); 2.6548 (16.1); 2.5405 (1.3); 2.5238 (9.2); 2.5190 (13.3); 2.5104 (196.8); 2.5058 (432.4); 2.5012 (604.9); 2.4966 (419.9); 2.4920 (185.2); 2.4464 (4.5); 2.4293 (4.4); 2.4193 (2.7); 2.4049 (10.6); 2.3995 (19.2); 2.3879 (7.9); 2.3775 (18.6); 2.3652 (4.6); 2.3597 (14.8); 2.3500 (2.2); 2.3376 (15.2); 2.3280 (3.7); 2.3233 (2.9); 2.2890 (6.6); 2.2760 (7.2); 2.2645 (11.7); 2.2516 (11.2); 2.2231 (9.7); 2.2201 (9.8); 2.2117 (6.8); 2.2061 (6.5); 2.1959 (6.1); 2.1902 (4.8); 2.1780 (7.5); 2.1716 (3.8); 2.1655 (2.7); 2.1587 (5.0); 2.1525 (4.2); 2.1339 (2.4); 2.0734 (1.2); 1.7825 (1.1); 1.7604 (3.2); 1.7549 (7.3); 1.7435 (7.2); 1.7304 (7.2); 1.7256 (4.2); 1.7199 (4.1); 1.7142 (4.8); 1.7011 (4.4); 1.6885 (2.8); 0.1457 (0.9); 0.0080 (9.3); −0.0002 (333.6); −0.0060 (3.4); −0.0085 (9.7); −0.0338 (0.9); −0.1498 (0.9)

-continued

I-015: $^1$H-NMR(400.1 MHz, $d_6$-DMSO):
δ = 7.3621 (0.5); 7.3583 (0.6); 7.3425 (0.3); 7.3368 (0.6); 7.3325 (0.5); 7.1893 (0.6); 7.1858 (0.6); 7.1765 (0.6); 7.1734 (0.6); 7.1655 (0.4); 7.1532 (0.3); 7.0942 (0.6); 7.0781 (0.8); 7.0590 (0.4); 4.7306 (1.0); 4.6908 (1.1); 4.2636 (1.2); 4.2238 (1.0); 4.1134 (1.6); 4.1039 (1.7); 4.1016 (1.6); 4.0901 (1.9); 3.8187 (0.4); 3.8087 (0.6); 3.7985 (0.7); 3.7884 (0.6); 3.7783 (0.4); 3.5540 (0.3); 3.5057 (2.6); 3.4861 (3.3); 3.4809 (1.6); 3.4743 (2.9); 3.4628 (2.4); 3.2326 (16.0); 2.7929 (0.8); 2.7823 (0.8); 2.7530 (1.1); 2.7425 (1.1); 2.5512 (0.9); 2.5304 (1.2); 2.5235 (0.4); 2.5101 (7.8); 2.5055 (15.5); 2.5010 (21.5); 2.4965 (15.7); 2.4919 (8.0); 2.4384 (0.4); 2.4144 (0.7); 2.3970 (0.6); 2.3908 (0.5); 2.2923 (0.4); 2.2796 (0.4); 2.2678 (0.7); 2.2551 (0.8); 2.2254 (0.9); 2.2155 (0.7); 2.2116 (0.5); 2.2013 (0.4); 2.1957 (0.3); 2.1831 (0.5); 2.1583 (0.3); 1.7654 (0.5); 1.7542 (0.5); 1.7423 (0.6); 1.7247 (0.3); 1.7112 (0.4); 0.0007 (2.6); 0.0000 (2.7)
I-016: $^1$H-NMR(400.1 MHz, $d_6$-DMSO):
δ = 8.1813 (0.9); 8.1602 (0.9); 8.1024 (1.2); 8.0802 (1.2); 7.3760 (0.5); 7.3547 (1.2); 7.3328 (1.2); 7.3097 (0.6); 7.2067 (0.6); 7.1869 (1.3); 7.1744 (1.3); 7.1667 (0.8); 7.1541 (0.7); 7.0897 (1.0); 7.0739 (1.6); 7.0585 (0.8); 4.7547 (1.7); 4.7150 (2.0); 4.3988 (1.1); 4.3873 (1.2); 4.3766 (1.1); 4.3651 (1.2); 4.2672 (1.4); 4.2557 (1.1); 4.2276 (1.3); 4.2211 (1.3); 4.2168 (1.1); 4.2064 (1.2); 4.2000 (1.0); 4.1852 (0.9); 3.8011 (0.8); 3.7919 (1.1); 3.7826 (1.5); 3.7725 (1.8); 3.7626 (1.7); 3.7523 (1.4); 3.7412 (1.0); 2.5966 (0.9); 2.5858 (1.4); 2.5752 (0.7); 2.5624 (1.1); 2.5514 (1.9); 2.5408 (1.0); 2.5237 (0.4); 2.5190 (0.6); 2.5103 (12.4); 2.5058 (27.8); 2.5012 (39.6); 2.4966 (28.8); 2.4920 (13.8); 2.4567 (0.3); 2.4078 (0.6); 2.4012 (1.2); 2.3845 (0.9); 2.3799 (1.3); 2.3668 (2.2); 2.3461 (2.2); 2.3374 (1.0); 2.3236 (1.2); 2.3161 (0.8); 2.2785 (0.7); 2.2759 (0.7); 2.2656 (0.8); 2.2631 (0.8); 2.2546 (1.0); 2.2515 (0.9); 2.2415 (1.0); 2.2386 (1.0); 2.2241 (0.5); 2.2213 (0.4); 2.2128 (0.6); 2.2098 (0.5); 2.1999 (0.6); 2.1260 (0.4); 2.1058 (0.8); 2.0942 (0.6); 2.0849 (0.7); 2.0823 (0.7); 2.0745 (1.0); 2.0722 (1.1); 2.0625 (0.4); 2.0538 (0.8); 1.8697 (0.6); 1.8581 (0.6); 1.8523 (0.6); 1.8407 (0.6); 1.8353 (0.4); 1.8232 (0.4); 1.8097 (0.4); 1.8056 (0.5); 1.7966 (0.8); 1.7862 (0.8); 1.7827 (0.9); 1.7729 (1.1); 1.7633 (1.1); 1.7552 (1.0); 1.7517 (0.9); 1.7445 (0.8); 1.7408 (0.8); 1.7295 (0.5); 1.3826 (0.4); 1.3785 (0.4); 1.3672 (0.4); 1.3594 (0.4); 1.3490 (0.3); 1.2969 (0.3); 1.2789 (0.6); 1.2620 (0.7); 1.2446 (0.8); 1.2266 (0.6); 1.2107 (0.4); 1.1928 (0.4); 1.1893 (0.4); 1.1774 (0.4); 1.1705 (0.5); 1.1596 (0.8); 1.1416 (1.0); 1.1238 (0.8); 1.1074 (0.6); 1.0894 (0.4); 0.8493 (11.9); 0.8343 (16.0); 0.8161 (4.9)
I-017: $^1$H-NMR(400.0 MHz, $d_6$-DMSO):
δ = 7.3831 (2.0); 7.3792 (2.1); 7.3627 (4.0); 7.3586 (4.4); 7.3526 (2.3); 7.3429 (2.8); 7.3368 (4.3); 7.3325 (3.7); 7.3164 (2.3); 7.3124 (2.1); 7.2081 (2.6); 7.2041 (2.7); 7.1954 (2.6); 7.1914 (3.1); 7.1882 (4.6); 7.1844 (4.9); 7.1755 (4.5); 7.1719 (5.0); 7.1678 (3.0); 7.1638 (2.9); 7.1551 (2.5); 7.1514 (2.9); 7.0874 (4.7); 7.0715 (6.3); 7.0680 (5.7); 7.0520 (3.2); 6.1735 (0.9); 5.0416 (1.8); 5.0346 (3.7); 5.0254 (4.3); 5.0185 (5.9); 5.0117 (3.6); 5.0032 (3.4); 4.7163 (7.1); 4.6765 (8.3); 4.2594 (9.4); 4.2195 (8.0); 3.8187 (1.7); 3.8077 (3.2); 3.7985 (4.4); 3.7878 (6.2); 3.7778 (4.0); 3.7679 (3.4); 3.7570 (1.4); 3.5345 (16.0); 3.1684 (3.0); 2.7094 (7.7); 2.6986 (7.9); 2.6699 (12.2); 2.6591 (10.5); 2.6003 (0.5); 2.5956 (0.5); 2.5612 (0.8); 2.5567 (1.2); 2.5521 (1.3); 2.5474 (0.6); 2.5237 (2.5); 2.5189 (3.8); 2.5103 (67.7); 2.5057 (147.2); 2.5010 (206.5); 2.4964 (148.4); 2.4918 (69.8); 2.4738 (11.6); 2.4544 (6.4); 2.4344 (9.9); 2.4166 (2.2); 2.4078 (1.4); 2.3927 (5.3); 2.3751 (4.3); 2.3691 (3.8); 2.3532 (2.6); 2.3370 (0.6); 2.3325 (1.5); 2.3279 (1.4); 2.3232 (1.0); 2.2980 (3.9); 2.2846 (4.5); 2.2735 (6.8); 2.2602 (6.8); 2.2442 (0.7); 2.2320 (4.4); 2.2239 (6.7); 2.2200 (3.4); 2.2109 (2.9); 2.2080 (3.6); 2.1973 (3.5); 2.1914 (2.7); 2.1866 (1.6); 2.1834 (1.9); 2.1796 (3.9); 2.1728 (2.2); 2.1669 (1.6); 2.1598 (2.7); 2.1533 (2.4); 2.1353 (1.5); 2.0727 (1.1); 1.8271 (0.8); 1.8115 (2.1); 1.8020 (3.0); 1.7880 (5.5); 1.7768 (5.5); 1.7727 (5.8); 1.7651 (5.0); 1.7568 (7.5); 1.7451 (6.3); 1.7380 (3.6); 1.7340 (4.1); 1.7323 (4.1); 1.7287 (3.8); 1.7209 (2.7); 1.7144 (3.9); 1.7025 (2.6); 1.6892 (1.7); 1.6451 (0.6); 1.6320 (1.0); 1.6262 (1.4); 1.6152 (2.6); 1.6037 (4.2); 1.5947 (6.5); 1.5857 (4.9); 1.5832 (4.9); 1.5796 (4.5); 1.5732 (5.5); 1.5667 (4.3); 1.5637 (5.0); 1.5548 (7.4); 1.5442 (12.8); 1.5355 (8.9); 1.5300 (10.2); 1.5219 (9.2); 1.5174 (10.4); 1.5125 (9.2); 1.5072 (7.5); 1.5010 (5.7); 1.4967 (4.2); 1.4877 (2.7); 1.1950 (0.5); 1.1769 (1.1); 1.1586 (0.5); 0.0080 (1.4); −0.0002 (55.1); −0.0085 (1.7)
I-018: $^1$H-NMR(400.0 MHz, $d_6$-DMSO):
δ = 3.6978 (3.1); 3.4126 (2.5); 2.5189 (0.6); 2.5101 (3.6); 2.5055 (7.8); 2.5009 (10.7); 2.4963 (7.5); 2.4916 (3.3); 0.8652 (16.0); −0.0002 (2.3)
I-020: $^1$H-NMR(400.0 MHz, $d_6$-DMSO):
δ = 7.3835 (0.9); 7.3794 (0.9); 7.3630 (1.8); 7.3589 (2.0); 7.3529 (1.0); 7.3432 (1.2); 7.3370 (2.0); 7.3328 (1.7); 7.3168 (1.1); 7.3128 (1.0); 7.2114 (1.1); 7.2074 (1.2); 7.1987 (1.1); 7.1948 (1.3); 7.1915 (2.1); 7.1877 (2.2); 7.1788 (2.0); 7.1752 (2.2); 7.1711 (1.4); 7.1672 (1.4); 7.1584 (1.2); 7.1547 (1.3); 7.0971 (2.1); 7.0812 (2.8); 7.0777 (2.6); 7.0617 (1.5); 4.7325 (3.2); 4.6928 (3.8); 4.2733 (4.2); 4.2335 (3.6); 3.8378 (1.0); 3.8304 (15.1); 3.8123 (16.0); 3.7975 (2.0); 3.7873 (1.6); 3.7765 (0.6); 3.3106 (98.6); 3.2828 (0.6); 2.7797 (3.3); 2.7690 (3.3); 2.7400 (4.6); 2.7293 (4.4); 2.6700 (0.6); 2.5511 (0.6); 2.5454 (4.9); 2.5247 (5.3); 2.5189 (2.0); 2.5102 (31.1); 2.5056 (70.4); 2.5010 (92.7); 2.4963 (64.7); 2.4917 (29.4); 2.4852 (4.8); 2.4754 (0.5); 2.4569 (1.3); 2.4391 (0.9); 2.4295 (0.5); 2.4157 (2.4); 2.3983 (1.8); 2.3922 (1.6); 2.3836 (0.7); 2.3765 (0.8); 2.3278 (0.6); 2.2981 (1.7); 2.2853 (1.8); 2.2736 (3.0); 2.2609 (2.9); 2.2316 (3.5); 2.2219 (2.6); 2.2181 (1.9); 2.2084 (1.6); 2.2027 (1.3); 2.1976 (0.6); 2.1908 (1.9); 2.1838 (1.0); 2.1781 (0.7); 2.1712 (1.2); 2.1648 (1.0); 2.1466 (0.6); 2.0725 (0.6); 1.7778 (0.8); 1.7739 (1.9); 1.7628 (1.8); 1.7552 (1.2); 1.7513 (2.0); 1.7446 (1.1); 1.7391 (1.1); 1.7341 (1.2); 1.7314 (1.1); 1.7200 (1.2); 1.7075 (0.8); 1.0693 (0.6); 1.0629 (0.8); 1.0509 (1.6); 1.0494 (1.5); 1.0428 (1.4); 1.0391 (1.1); 1.0310 (3.0); 1.0229 (1.1); 1.0190 (1.5); 1.0126 (1.5); 1.0110 (1.8); 0.9991 (1.0); 0.9927 (0.7); 0.5139 (2.1); 0.5032 (6.3); 0.4987 (7.1); 0.4939 (2.8); 0.4881 (3.0); 0.4828 (7.2); 0.4785 (6.0); 0.4681 (2.6); 0.2467 (2.6); 0.2362 (7.3); 0.2322 (6.8); 0.2244 (6.2); 0.2205 (7.8); 0.2097 (1.8); −0.0002 (9.9)
I-021: $^1$H-NMR(400.0 MHz, $d_6$-DMSO):
δ = 7.3662 (0.7); 7.3621 (0.8); 7.3404 (0.8); 7.3360 (0.7); 7.1942 (0.5); 7.1909 (0.8); 7.1872 (0.8); 7.1782 (0.8); 7.1747 (0.9); 7.1706 (0.5); 7.1667 (0.5); 7.0968 (0.8); 7.0808 (1.1); 7.0775 (1.0); 7.0613 (0.6); 5.9130 (0.5); 5.8992 (1.1); 5.8866 (0.7); 5.8730 (1.3); 5.8700 (0.7); 5.8593 (0.6); 5.8561 (1.4); 5.8434 (0.8); 5.8427 (0.8); 5.8299 (1.4); 5.8162 (0.6); 5.3003 (0.7); 5.2962 (2.1); 5.2921 (2.2); 5.2880 (0.8); 5.2572 (0.6); 5.2531 (1.8); 5.2490 (1.9); 5.2449 (0.7); 5.2206 (0.8); 5.2172 (1.9); 5.2133 (1.8); 5.2099 (0.7); 5.1944 (0.7); 5.1910 (1.7); 5.1871 (1.7); 5.1837 (0.6); 4.7275 (1.2); 4.6877 (1.5); 4.5180 (2.3); 4.5143 (4.0); 4.5107 (2.4); 4.5042 (2.3); 4.5006 (3.9); 4.4969 (2.3); 4.2703 (1.6); 4.2305 (1.4); 3.8294 (0.5); 3.8192 (0.8); 3.8091 (1.0); 3.7991 (0.8); 3.7888 (0.6); 3.4612 (16.0); 2.8291 (1.3); 2.8185 (1.3); 2.7890 (1.7); 2.7784 (1.6); 2.5812 (1.8); 2.5602 (1.8); 2.5411 (1.4); 2.5202 (1.8); 2.5122 (10.8); 2.5077

-continued (23.1); 2.5030 (31.8); 2.4984 (22.5); 2.4939 (10.3); 2.4157 (1.0); 2.3981 (0.8); 2.3922 (0.7); 2.2979 (0.6); 2.2852 (0.7); 2.2734 (1.2); 2.2607 (1.1); 2.2302 (1.1); 2.2277 (1.0); 2.2207 (0.8); 2.2161 (0.7); 2.2060 (0.6); 2.1881 (0.8); 1.7633 (0.7); 1.7522 (0.7); 1.7396 (0.8); −0.0002 (3.0)

I-022: $^1$H-NMR(400.1 MHz, CDCl3):

δ = 7.5210 (0.4); 7.3865 (5.6); 7.3669 (8.7); 7.3136 (4.4); 7.2954 (8.2); 7.2754 (4.8); 7.2620 (76.5); 7.2333 (3.1); 7.2148 (4.0); 7.1968 (1.3); 7.1220 (0.5); 7.1099 (1.0); 7.0976 (1.9); 7.0867 (1.3); 7.0799 (1.9); 7.0718 (2.2); 7.0511 (5.0); 7.0477 (5.1); 7.0383 (6.7); 7.0281 (3.3); 7.0099 (0.4); 6.9980 (0.5); 4.8708 (3.2); 4.8318 (3.5); 4.2556 (5.6); 4.2388 (16.0); 4.2218 (6.2); 4.2007 (3.9); 3.8722 (0.6); 3.8621 (1.2); 3.8512 (1.9); 3.8409 (2.3); 3.8306 (2.0); 3.8198 (1.4); 3.8096 (0.7); 3.1305 (6.0); 3.1136 (12.0); 3.0967 (5.8); 2.6841 (2.6); 2.6742 (2.7); 2.6453 (3.3); 2.6353 (3.4); 2.5356 (0.7); 2.5178 (0.9); 2.5119 (0.9); 2.4930 (2.2); 2.4744 (1.9); 2.4692 (2.0); 2.4509 (1.8); 2.4237 (1.7); 2.4092 (1.9); 2.3992 (2.4); 2.3848 (2.6); 2.3779 (4.0); 2.3667 (1.0); 2.3558 (4.4); 2.3390 (3.1); 2.3168 (2.6); 2.2951 (1.0); 2.2760 (1.5); 2.2716 (1.0); 2.2628 (1.2); 2.2577 (1.1); 2.2517 (1.2); 2.2433 (1.7); 2.2387 (1.2); 2.2333 (0.8); 2.2246 (1.0); 2.2189 (1.3); 2.2002 (0.6); 1.8500 (0.8); 1.8371 (1.3); 1.8255 (1.5); 1.8155 (1.5); 1.8043 (1.4); 1.7931 (1.4); 1.7810 (1.0); 1.7679 (0.7); 1.5958 (37.9); 1.2550 (0.5)

I-023: $^1$H-NMR(400.0 MHz, $d_6$-DMSO):

δ = 7.3813 (0.9); 7.3773 (1.0); 7.3609 (1.9); 7.3568 (2.1); 7.3507 (1.1); 7.3411 (1.3); 7.3351 (2.1); 7.3307 (1.8); 7.3147 (1.1); 7.3106 (1.1); 7.2095 (1.2); 7.2055 (1.3); 7.1968 (1.2); 7.1929 (1.4); 7.1896 (2.2); 7.1858 (2.4); 7.1769 (2.2); 7.1733 (2.4); 7.1693 (1.5); 7.1653 (1.5); 7.1565 (1.3); 7.1529 (1.4); 7.0992 (2.2); 7.0834 (2.9); 7.0798 (2.7); 7.0639 (1.5); 4.7341 (3.2); 4.6941 (3.9); 4.6676 (15.7); 4.6668 (15.5); 4.6615 (15.9); 4.6606 (15.6); 4.2611 (4.4); 4.2213 (3.8); 4.0208 (1.0); 4.0031 (1.0); 3.8310 (0.9); 3.8206 (1.6); 3.8102 (2.4); 3.8001 (2.7); 3.7900 (2.4); 3.7797 (1.9); 3.7694 (1.0); 3.6357 (7.1); 3.5480 (7.2); 3.5418 (16.0); 3.5357 (6.8); 3.1674 (2.2); 2.8446 (3.4); 2.8344 (3.4); 2.8044 (4.6); 2.7942 (4.3); 2.6744 (0.7); 2.6698 (1.0); 2.6651 (0.8); 2.5908 (4.9); 2.5695 (4.8); 2.5507 (4.1); 2.5458 (0.6); 2.5400 (0.8); 2.5293 (4.0); 2.5233 (2.6); 2.5186 (3.5); 2.5099 (49.2); 2.5053 (105.4); 2.5007 (146.4); 2.4960 (102.8); 2.4915 (46.3); 2.4757 (0.6); 2.4646 (1.1); 2.4477 (1.1); 2.4385 (0.7); 2.4236 (2.5); 2.4059 (2.2); 2.4007 (2.0); 2.3922 (0.8); 2.3846 (1.0); 2.3692 (0.6); 2.3322 (0.8); 2.3275 (1.0); 2.3228 (0.7); 2.2919 (1.7); 2.2796 (1.8); 2.2673 (3.1); 2.2551 (3.1); 2.2259 (4.6); 2.2167 (2.7); 2.2137 (2.3); 2.2040 (1.8); 2.1980 (1.4); 2.1929 (0.8); 2.1859 (2.2); 2.1794 (1.1); 2.1734 (0.8); 2.1665 (1.4); 2.1606 (1.3); 2.1419 (0.8); 2.0720 (1.0); 1.7875 (0.5); 1.7619 (2.0); 1.7506 (1.6); 1.7399 (2.3); 1.7326 (1.2); 1.7276 (1.2); 1.7229 (1.2); 1.7186 (1.3); 1.7081 (1.3); 1.6960 (0.9); 1.1543 (1.3); 1.1365 (2.6); 1.1187 (1.2); 0.0080 (0.6); −0.0002 (22.9); −0.0085 (0.6)

I-024: $^1$H-NMR(400.0 MHz, $d_6$-DMSO):

δ = 7.3828 (2.8); 7.3788 (3.0); 7.3623 (5.7); 7.3582 (6.3); 7.3522 (3.3); 7.3425 (4.0); 7.3363 (6.2); 7.3321 (5.4); 7.3160 (3.4); 7.3121 (3.3); 7.2091 (3.6); 7.2051 (3.8); 7.1964 (3.8); 7.1924 (4.4); 7.1892 (6.6); 7.1854 (7.0); 7.1765 (6.5); 7.1729 (7.2); 7.1689 (4.4); 7.1649 (4.2); 7.1561 (3.7); 7.1524 (4.0); 7.0886 (6.8); 7.0727 (9.1); 7.0692 (8.3); 7.0531 (4.7); 4.8884 (2.2); 4.8863 (2.3); 4.8687 (8.7); 4.8510 (12.0); 4.8490 (12.2); 4.8313 (8.8); 4.8137 (2.3); 4.8114 (2.2); 4.7146 (10.2); 4.6748 (12.1); 4.2630 (13.4); 4.2231 (11.4); 3.8305 (0.9); 3.8233 (2.4); 3.8124 (5.2); 3.8029 (6.4); 3.7924 (8.6); 3.7825 (5.8); 3.7724 (4.7); 3.7616 (1.9); 3.3641 (1.6); 3.3429 (0.8); 3.3388 (1.2); 3.3339 (2.4); 3.3147 (672.4); 3.2910 (17.4); 3.2631 (0.7); 3.1761 (0.6); 3.1629 (0.6); 2.7359 (10.9); 2.7251 (11.0); 2.6960 (15.2); 2.6852 (14.5); 2.6749 (1.3); 2.6703 (1.5); 2.6657 (1.0); 2.5459 (0.8); 2.5405 (1.1); 2.5238 (3.8); 2.5191 (5.7); 2.5105 (82.5); 2.5058 (163.7); 2.5012 (225.8); 2.4966 (159.3); 2.4919 (85.2); 2.4797 (1.4); 2.4720 (11.9); 2.4516 (11.4); 2.4408 (3.1); 2.4316 (0.9); 2.4234 (3.5); 2.4141 (2.2); 2.3997 (7.8); 2.3821 (6.1); 2.3762 (5.5); 2.3650 (2.5); 2.3600 (2.9); 2.3435 (1.2); 2.3374 (0.6); 2.3326 (1.2); 2.3280 (1.8); 2.3234 (1.1); 2.3188 (0.5); 2.2958 (5.5); 2.2827 (6.1); 2.2712 (9.9); 2.2630 (5.6); 2.2582 (11.2); 2.2486 (4.3); 2.2450 (5.7); 2.2428 (7.6); 2.2385 (9.3); 2.2365 (9.1); 2.2323 (11.8); 2.2301 (13.6); 2.2255 (15.7); 2.2185 (15.1); 2.2145 (13.2); 2.2125 (16.0); 2.2081 (9.3); 2.2059 (8.0); 2.2024 (9.7); 2.1947 (8.7); 2.1880 (8.2); 2.1847 (6.8); 2.1781 (3.3); 2.1721 (2.3); 2.1651 (4.1); 2.1588 (3.5); 2.1405 (2.1); 2.0724 (0.7); 1.9896 (0.6); 1.9858 (2.2); 1.9800 (1.4); 1.9770 (2.7); 1.9700 (2.1); 1.9663 (3.1); 1.9608 (6.7); 1.9572 (4.7); 1.9551 (5.1); 1.9522 (7.9); 1.9452 (5.4); 1.9413 (6.6); 1.9359 (8.2); 1.9327 (9.2); 1.9302 (8.0); 1.9272 (8.3); 1.9214 (5.6); 1.9171 (5.3); 1.9106 (7.0); 1.9079 (6.8); 1.9058 (5.4); 1.9022 (5.4); 1.8967 (3.1); 1.8931 (2.2); 1.8859 (3.3); 1.8806 (1.1); 1.8773 (2.3); 1.8733 (0.6); 1.7838 (1.0); 1.7620 (2.9); 1.7562 (7.6); 1.7515 (3.9); 1.7492 (3.8); 1.7450 (7.9); 1.7374 (4.3); 1.7315 (9.9); 1.7269 (8.7); 1.7246 (9.8); 1.7219 (7.6); 1.7178 (5.8); 1.7155 (6.7); 1.7092 (2.9); 1.7067 (5.1); 1.7023 (7.0); 1.7000 (10.3); 1.6976 (7.2); 1.6932 (4.5); 1.6905 (4.8); 1.6821 (1.6); 1.6797 (1.6); 1.6753 (2.5); 1.6729 (2.5); 1.6685 (1.3); 1.6661 (1.2); 1.6268 (3.0); 1.6068 (5.3); 1.6018 (5.8); 1.5866 (3.4); 1.5816 (11.1); 1.5766 (4.0); 1.5749 (5.1); 1.5615 (5.5); 1.5597 (3.6); 1.5564 (6.0); 1.5547 (8.5); 1.5497 (2.4); 1.5362 (2.9); 1.5345 (3.9); 1.5295 (3.2); 1.5093 (1.5); 0.0079 (0.6); −0.0002 (19.9); −0.0085 (0.5)

I-025: $^1$H-NMR(400.0 MHz, $d_6$-DMSO):

δ = 7.3625 (1.0); 7.3584 (1.1); 7.3524 (0.6); 7.3427 (0.7); 7.3365 (1.0); 7.3324 (0.9); 7.3162 (0.6); 7.3123 (0.6); 7.2101 (0.6); 7.2061 (0.6); 7.1974 (0.6); 7.1934 (0.7); 7.1901 (1.1); 7.1863 (1.2); 7.1775 (1.1); 7.1738 (1.2); 7.1698 (0.8); 7.1658 (0.7); 7.1570 (0.6); 7.1533 (0.7); 7.0898 (1.1); 7.0739 (1.6); 7.0704 (1.4); 7.0544 (0.8); 4.8813 (0.9); 4.8657 (2.5); 4.8500 (3.5); 4.8344 (2.6); 4.8187 (1.0); 4.7207 (1.7); 4.6810 (2.0); 4.2640 (2.3); 4.2241 (1.9); 3.8189 (0.8); 3.8094 (1.1); 3.7989 (1.5); 3.7888 (1.0); 3.7789 (0.8); 3.4236 (20.1); 3.1686 (1.0); 2.7196 (2.0); 2.7088 (2.0); 2.6801 (2.8); 2.6749 (0.5); 2.6694 (2.8); 2.5237 (0.7); 2.5190 (1.1); 2.5104 (19.1); 2.5058 (41.5); 2.5012 (57.3); 2.4965 (40.0); 2.4919 (18.4); 2.4689 (2.9); 2.4498 (2.1); 2.4294 (2.1); 2.4242 (0.7); 2.4000 (1.4); 2.3821 (1.0); 2.3762 (0.9); 2.3599 (0.5); 2.2992 (1.0); 2.2859 (1.1); 2.2746 (1.7); 2.2615 (1.6); 2.2332 (1.2); 2.2292 (1.3); 2.2270 (1.3); 2.2216 (0.9); 2.2179 (0.8); 2.2145 (1.0); 2.2042 (0.9); 2.1984 (0.7); 2.1866 (1.0); 2.1797 (0.6); 2.1669 (0.7); 2.1603 (0.6); 1.7586 (1.1); 1.7473 (1.1); 1.7400 (0.6); 1.7339 (1.0); 1.7292 (0.6); 1.7233 (0.6); 1.7173 (0.8); 1.7047 (0.6); 1.1496 (16.0); 1.1465 (15.9); 1.1340 (15.8); 1.1309 (15.9); −0.0002 (1.0)

I-026: $^1$H-NMR(400.0 MHz, $d_6$-DMSO):

δ = 7.3813 (1.0); 7.3609 (2.1); 7.3383 (2.1); 7.3352 (2.0); 7.3147 (1.1); 7.2100 (1.1); 7.2064 (1.2); 7.1973 (1.2); 7.1898 (2.2); 7.1866 (2.3); 7.1770 (2.1); 7.1740 (2.4); 7.1661 (1.3); 7.1570 (1.1); 7.1536 (1.3); 7.0890 (2.3); 7.0730 (3.1); 7.0537 (1.5); 5.7926 (0.9); 5.7759 (1.9); 5.7670 (0.9); 5.7592 (0.9); 5.7501 (2.8); 5.7330 (2.8); 5.7239 (1.0); 5.7161 (1.0); 5.7072 (2.2); 5.6904 (1.0); 5.1063 (1.3); 5.1023 (3.2); 5.0974 (3.7); 5.0935 (1.5); 5.0632 (1.2); 5.0593 (2.9); 5.0543 (3.6); 5.0500 (4.2); 5.0470 (2.2); 5.0448 (2.8); 5.0418 (1.3); 5.0273 (1.4); 5.0242 (3.1); 5.0213 (2.0); 5.0192 (2.6); 5.0161 (1.1); 4.8686 (1.1);

-continued 4.8508 (1.5); 4.8488 (1.5); 4.8311 (1.1); 4.7250 (2.4); 4.7144 (1.3); 4.6854 (2.8); 4.6742 (1.6); 4.2566 (3.5); 4.2167 (3.0); 4.0464 (5.8); 4.0299 (13.0); 4.0134 (6.4); 3.8183 (0.8); 3.8119 (1.0); 3.8074 (1.4); 3.7976 (2.0); 3.7919 (1.8); 3.7874 (2.5); 3.7818 (1.5); 3.7774 (1.9); 3.7721 (1.3); 3.7673 (1.5); 3.7609 (0.8); 3.7568 (0.8); 3.5904 (16.0); 3.1680 (2.5); 2.7609 (2.4); 2.7502 (2.5); 2.7355 (1.3); 2.7245 (1.7); 2.7211 (3.5); 2.7105 (3.3); 2.6956 (2.0); 2.6848 (1.8); 2.6746 (0.7); 2.6700 (1.0); 2.6653 (0.8); 2.6000 (0.5); 2.5234 (2.1); 2.5206 (4.7); 2.5102 (54.9); 2.5056 (118.5); 2.5009 (165.6); 2.4963 (114.3); 2.4917 (53.2); 2.4810 (3.6); 2.4718 (1.4); 2.4601 (2.8); 2.4549 (1.3); 2.4507 (3.1); 2.4455 (2.5); 2.4415 (2.1); 2.4249 (1.4); 2.4164 (1.1); 2.4074 (0.8); 2.4011 (2.6); 2.3834 (2.0); 2.3790 (1.9); 2.3612 (1.2); 2.3324 (0.8); 2.3277 (1.0); 2.3230 (0.8); 2.3140 (1.2); 2.3105 (1.9); 2.3071 (1.2); 2.2974 (3.8); 2.2939 (7.0); 2.2906 (4.0); 2.2807 (4.9); 2.2774 (6.1); 2.2739 (3.8); 2.2686 (3.0); 2.2640 (1.8); 2.2606 (2.6); 2.2561 (3.7); 2.2428 (1.1); 2.2385 (1.3); 2.2365 (1.2); 2.2322 (1.5); 2.2267 (3.2); 2.2189 (3.7); 2.2152 (2.7); 2.2124 (2.4); 2.2076 (2.1); 2.1941 (2.1); 2.1878 (2.0); 2.1830 (1.4); 2.1758 (1.7); 2.1691 (1.0); 2.1642 (1.0); 2.1562 (1.2); 2.1499 (1.0); 2.1316 (0.6); 2.0721 (1.2); 1.9607 (0.8); 1.9549 (0.6); 1.9521 (1.0); 1.9451 (0.7); 1.9412 (0.8); 1.9358 (1.0); 1.9325 (1.1); 1.9301 (1.0); 1.9271 (1.0); 1.9213 (0.7); 1.9170 (0.7); 1.9104 (0.9); 1.9077 (0.8); 1.9021 (0.7); 1.7623 (1.0); 1.7553 (2.1); 1.7492 (0.7); 1.7437 (2.2); 1.7315 (2.4); 1.7270 (2.0); 1.7248 (2.1); 1.7200 (1.5); 1.7131 (1.7); 1.7067 (0.8); 1.7001 (2.2); 1.6932 (0.7); 1.6882 (0.9); 1.6067 (0.7); 1.6017 (0.7); 1.5815 (1.4); 1.5748 (0.6); 1.5614 (0.7); 1.5546 (1.1); 1.5345 (0.5); 0.0080 (0.6); 0.0023 (0.7); −0.0002 (20.5); −0.0085 (0.6)

I-027: $^{1}$H-NMR(400.1 MHz, CDCl3):

δ = 7.5188 (1.2); 7.3157 (1.4); 7.3097 (10.2); 7.3076 (4.4); 7.3043 (3.9); 7.2974 (2.1); 7.2913 (14.0); 7.2879 (13.8); 7.2820 (2.6); 7.2781 (1.3); 7.2745 (5.0); 7.2715 (6.0); 7.2694 (14.2); 7.2668 (3.9); 7.2659 (4.2); 7.2600 (208.0); 7.2535 (3.8); 7.2526 (3.2); 7.2510 (2.2); 7.2501 (1.9); 7.2493 (1.7); 7.2485 (1.5); 7.2476 (1.3); 7.2468 (1.3); 7.2461 (1.1); 7.2452 (1.0); 7.2444 (0.9); 7.2436 (0.9); 7.2428 (0.8); 7.2420 (0.7); 7.2411 (0.7); 7.2403 (0.7); 7.2395 (0.6); 7.2387 (0.5); 7.2379 (0.4); 7.2370 (0.4); 7.2362 (0.4); 7.2354 (0.4); 7.2338 (0.3); 7.1133 (1.1); 7.1030 (1.4); 7.0982 (1.9); 7.0957 (1.3); 7.0882 (3.6); 7.0783 (2.6); 7.0703 (4.1); 7.0641 (4.0); 7.0590 (4.0); 7.0472 (15.9); 7.0374 (15.1); 7.0324 (4.4); 7.0289 (5.9); 7.0220 (4.1); 7.0132 (0.6); 7.0025 (0.8); 6.9951 (3.3); 6.9925 (5.8); 6.9898 (3.5); 6.9762 (4.2); 6.9741 (9.8); 6.9720 (4.8); 6.9583 (2.5); 6.9556 (4.6); 6.9530 (2.7); 6.9098 (2.0); 6.9079 (2.4); 6.9044 (12.8); 6.9017 (16.0); 6.8997 (8.1); 6.8964 (4.4); 6.8874 (4.3); 6.8850 (7.2); 6.8824 (13.8); 6.8799 (11.8); 6.8735 (1.5); 4.8834 (4.9); 4.8796 (5.0); 4.8446 (5.6); 4.8407 (5.7); 4.4396 (9.1); 4.4333 (4.3); 4.4286 (10.7); 4.4247 (8.2); 4.4219 (4.6); 4.4161 (13.5); 4.2610 (8.0); 4.2221 (7.2); 4.1668 (14.2); 4.1617 (4.4); 4.1577 (8.4); 4.1548 (13.8); 4.1490 (4.2); 4.1434 (11.6); 3.9179 (1.2); 3.9070 (2.3); 3.8965 (3.4); 3.8861 (3.9); 3.8759 (3.4); 3.8655 (2.5); 3.8548 (1.3); 3.6679 (9.8); 3.4895 (0.4); 2.7731 (5.7); 2.7630 (5.8); 2.7342 (7.5); 2.7241 (7.3); 2.6981 (0.7); 2.6876 (0.7); 2.5477 (1.2); 2.5460 (1.2); 2.5299 (1.6); 2.5281 (1.6); 2.5234 (1.5); 2.5215 (1.5); 2.5048 (3.7); 2.4853 (3.6); 2.4802 (10.6); 2.4583 (8.3); 2.4412 (6.4); 2.4225 (4.3); 2.4194 (6.8); 2.4144 (1.9); 2.4082 (4.0); 2.3980 (5.6); 2.3837 (5.1); 2.3799 (2.2); 2.3759 (1.0); 2.3712 (0.5); 2.3656 (1.5); 2.3551 (2.8); 2.3412 (2.8); 2.3045 (2.2); 2.2850 (2.7); 2.2801 (1.7); 2.2723 (2.6); 2.2671 (2.2); 2.2605 (2.1); 2.2542 (3.0); 2.2526 (2.8); 2.2477 (2.1); 2.2427 (1.5); 2.2344 (2.1); 2.2279 (2.1); 2.2099 (1.4); 2.1326 (1.7); 2.0912 (2.6); 2.0041 (1.3); 1.8820 (1.8); 1.8707 (2.0); 1.8684 (2.3); 1.8575 (2.9); 1.8496 (2.3); 1.8469 (2.4); 1.8440 (2.2); 1.8380 (2.2); 1.8359 (2.4); 1.8326 (2.1); 1.8246 (2.5); 1.8140 (1.7); 1.8113 (1.6); 1.7997 (1.4); 1.5592 (12.2); 1.4369 (0.9); 1.4227 (0.9); 1.2845 (0.6); 1.2554 (2.0); 0.8800 (0.4); 0.8456 (0.4); 0.8358 (0.5); 0.0081 (1.1); 0.0061 (0.6); 0.0000 (36.6)

I-028: $^{1}$H-NMR(400.0 MHz, d$_6$-DMSO):

δ = 7.3630 (0.9); 7.3589 (1.0); 7.3528 (0.5); 7.3432 (0.6); 7.3370 (1.0); 7.3328 (0.9); 7.3168 (0.5); 7.3127 (0.5); 7.2091 (0.6); 7.2051 (0.6); 7.1964 (0.6); 7.1924 (0.7); 7.1892 (1.1); 7.1854 (1.1); 7.1765 (1.0); 7.1729 (1.2); 7.1688 (0.7); 7.1648 (0.7); 7.1561 (0.6); 7.1524 (0.6); 7.0919 (1.0); 7.0756 (1.4); 7.0566 (0.7); 4.8077 (0.5); 4.8010 (0.7); 4.7920 (0.8); 4.7897 (0.7); 4.7870 (0.7); 4.7846 (0.8); 4.7780 (0.7); 4.7757 (0.7); 4.7690 (0.5); 4.7311 (1.6); 4.6913 (1.9); 4.2601 (1.6); 4.2202 (1.3); 3.8119 (0.7); 3.8021 (1.0); 3.7918 (1.3); 3.7818 (1.0); 3.7717 (0.7); 3.4307 (10.7); 3.1680 (0.7); 2.7543 (1.0); 2.7474 (1.0); 2.7437 (1.1); 2.7369 (1.0); 2.7149 (1.3); 2.7080 (1.4); 2.7043 (1.3); 2.6976 (1.2); 2.5500 (0.6); 2.5454 (0.6); 2.5403 (0.6); 2.5236 (0.9); 2.5188 (1.2); 2.5102 (17.0); 2.5056 (36.3); 2.5010 (50.3); 2.4963 (35.4); 2.4918 (16.7); 2.4781 (1.4); 2.4717 (1.2); 2.4594 (0.8); 2.4533 (0.6); 2.4388 (1.3); 2.4322 (1.2); 2.4222 (0.5); 2.4061 (0.7); 2.3989 (0.6); 2.3815 (0.9); 2.3010 (0.6); 2.2881 (0.7); 2.2775 (1.0); 2.2761 (1.0); 2.2632 (1.2); 2.2347 (0.7); 2.2280 (1.4); 2.2153 (0.6); 2.2124 (0.8); 2.2018 (0.8); 2.1961 (0.6); 2.1838 (0.8); 2.1644 (0.6); 2.1581 (0.5); 1.7478 (0.7); 1.7456 (0.6); 1.7339 (0.8); 1.7233 (0.6); 1.7176 (0.8); 1.7034 (0.7); 1.4766 (0.6); 1.4665 (0.5); 1.4625 (0.8); 1.4575 (0.9); 1.4531 (0.8); 1.4480 (0.8); 1.4433 (1.1); 1.4389 (1.0); 1.4347 (0.9); 1.4307 (0.8); 1.4246 (1.1); 1.4203 (1.0); 1.4169 (0.6); 1.4118 (0.9); 1.4089 (0.9); 1.4049 (0.7); 1.3954 (0.7); 1.3912 (0.8); 1.2861 (0.6); 1.2757 (0.6); 1.2723 (0.7); 1.2675 (0.7); 1.2639 (0.9); 1.2574 (0.9); 1.2537 (0.9); 1.2489 (0.9); 1.2456 (0.9); 1.2395 (1.1); 1.2351 (0.8); 1.2309 (1.0); 1.2218 (1.0); 1.2133 (0.7); 1.2056 (0.5); 1.1247 (8.4); 1.1178 (8.5); 1.1091 (8.4); 1.1021 (8.4); 0.8641 (7.1); 0.8458 (16.0); 0.8275 (5.8); −0.0002 (12.0)

I-030: $^{1}$H-NMR(400.0 MHz, d$_6$-DMSO):

δ = 7.3833 (0.6); 7.3793 (0.6); 7.3629 (1.2); 7.3588 (1.4); 7.3527 (0.7); 7.3431 (0.9); 7.3370 (1.3); 7.3327 (1.2); 7.3166 (0.7); 7.3126 (0.7); 7.2098 (0.8); 7.2059 (0.8); 7.1972 (0.8); 7.1932 (0.9); 7.1899 (1.4); 7.1862 (1.5); 7.1773 (1.4); 7.1736 (1.5); 7.1696 (0.9); 7.1656 (0.9); 7.1569 (0.8); 7.1532 (0.9); 7.0943 (1.3); 7.0781 (1.8); 7.0598 (0.9); 4.7399 (1.6); 4.7332 (2.7); 4.7247 (2.0); 4.7173 (1.9); 4.7090 (1.9); 4.7014 (2.3); 4.6935 (3.0); 4.6861 (1.1); 4.2622 (2.8); 4.2224 (2.4); 3.8145 (0.9); 3.8046 (1.4); 3.7943 (1.7); 3.7843 (1.3); 3.7741 (1.0); 3.4668 (16.0); 3.1680 (1.2); 2.7597 (1.3); 2.7546 (1.4); 2.7492 (1.4); 2.7442 (1.3); 2.7203 (1.8); 2.7154 (1.8); 2.7098 (1.8); 2.7049 (1.7); 2.5235 (1.2); 2.5188 (1.7); 2.5102 (28.0); 2.5056 (61.7); 2.5010 (84.6); 2.4963 (57.8); 2.4917 (26.1); 2.4843 (2.6); 2.4798 (2.1); 2.4657 (1.5); 2.4613 (1.4); 2.4449 (1.5); 2.4404 (1.7); 2.4231 (0.6); 2.4066 (0.9); 2.3999 (0.9); 2.3890 (0.7); 2.3825 (1.2); 2.3766 (0.7); 2.3656 (0.6); 2.3278 (0.6); 2.3000 (0.8); 2.2868 (0.9); 2.2775 (1.3); 2.2753 (1.3); 2.2623 (1.5); 2.2338 (1.0); 2.2292 (1.7); 2.2177 (1.0); 2.2144 (1.1); 2.2039 (1.1); 2.1982 (0.8); 2.1865 (1.2); 2.1794 (0.7); 2.1667 (0.8); 2.1601 (0.7); 2.0722 (0.5); 1.7639 (0.7); 1.7531 (1.2); 1.7420 (1.2); 1.7348 (0.8); 1.7288 (0.9); 1.7232 (0.8); 1.7112 (0.8); 1.6975 (0.6); 1.5145 (1.1); 1.4958 (4.0); 1.4799 (4.5); 1.4773 (4.7); 1.4614 (4.4); 1.4429 (1.4); 1.1223 (12.5); 1.1159 (12.5); 1.1066 (12.4); 1.1002 (12.4); 0.8300 (5.2); 0.8261 (5.2); 0.8115 (11.2); 0.8076 (11.2); 0.7927 (4.8); 0.7889 (4.7); −0.0002 (15.5)

-continued

I-031: $^1$H-NMR(400.1 MHz, CDCl3):
δ = 7.2680 (0.4); 7.2603 (39.0); 7.0907 (0.4); 7.0728 (0.5); 7.0665 (0.5); 7.0597 (0.6); 7.0495 (1.9); 7.0401 (1.8); 7.0350 (0.6); 7.0316 (0.6); 7.0245 (0.4); 6.8313 (16.0); 4.8857 (0.6); 4.8816 (0.6); 4.8469 (0.7); 4.8429 (0.6); 4.4111 (1.0); 4.3996 (1.1); 4.3963 (0.8); 4.3876 (1.4); 4.2610 (1.0); 4.2222 (0.9); 4.1134 (1.5); 4.1081 (0.4); 4.1043 (0.9); 4.1015 (1.4); 4.0958 (0.4); 4.0900 (1.2); 3.8992 (0.4); 3.8890 (0.4); 3.8787 (0.4); 3.7686 (12.8); 3.6680 (2.6); 2.7755 (0.6); 2.7654 (0.6); 2.7366 (0.9); 2.7264 (0.9); 2.5062 (0.4); 2.4847 (1.1); 2.4629 (1.1); 2.4458 (0.7); 2.4240 (1.1); 2.4143 (0.4); 2.4098 (0.4); 2.3995 (0.7); 2.3852 (0.6); 2.3567 (0.4); 2.2548 (0.3); 1.8604 (0.4); 1.5522 (4.2)
I-032: $^1$H-NMR(400.1 MHz, CDCl3):
δ = 7.9307 (12.0); 7.9106 (13.3); 7.9065 (7.9); 7.7014 (2.1); 7.6982 (2.3); 7.6848 (4.4); 7.6802 (6.4); 7.6747 (1.8); 7.6642 (4.7); 7.6610 (4.7); 7.6578 (2.1); 7.6051 (9.0); 7.6002 (3.2); 7.5875 (11.4); 7.5846 (11.3); 7.5701 (4.4); 7.5664 (5.0); 7.5194 (1.0); 7.3621 (0.5); 7.3183 (0.7); 7.2675 (73.0); 7.2657 (73.4); 7.2606 (172.6); 7.2381 (0.6); 7.2185 (0.6); 7.1331 (1.1); 7.1262 (1.1); 7.1152 (3.0); 7.1090 (2.9); 7.0960 (4.3); 7.0900 (3.3); 7.0840 (3.7); 7.0784 (3.4); 7.0729 (3.1); 7.0658 (5.5); 7.0595 (7.1); 7.0479 (11.7); 7.0394 (9.2); 7.0351 (7.8); 7.0161 (1.3); 6.9966 (1.0); 4.8916 (1.1); 4.8402 (5.6); 4.8014 (6.3); 4.4350 (8.1); 4.4201 (16.0); 4.4050 (8.5); 4.2634 (1.3); 4.2238 (1.2); 4.1828 (6.4); 4.1441 (5.7); 3.8839 (0.9); 3.8741 (0.6); 3.8633 (0.4); 3.8159 (1.0); 3.8053 (1.9); 3.7944 (3.0); 3.7845 (3.4); 3.7739 (2.9); 3.7632 (2.0); 3.7530 (1.0); 3.6747 (5.3); 3.6682 (11.4); 3.4911 (0.6); 3.4383 (9.0); 3.4238 (15.1); 3.4084 (8.1); 2.7371 (0.8); 2.7271 (0.8); 2.6983 (1.0); 2.6883 (0.9); 2.5468 (3.9); 2.5370 (4.0); 2.5127 (4.2); 2.5074 (5.4); 2.4974 (6.1); 2.4704 (3.8); 2.4512 (4.1); 2.4462 (3.1); 2.4369 (1.8); 2.4278 (3.3); 2.4151 (4.2); 2.4002 (4.5); 2.3908 (3.6); 2.3764 (4.9); 2.3577 (1.4); 2.3480 (1.7); 2.3337 (1.6); 2.3168 (0.4); 2.2990 (0.6); 2.2761 (1.7); 2.2475 (6.5); 2.2384 (2.4); 2.2318 (4.7); 2.2255 (7.8); 2.2196 (2.3); 2.2078 (5.4); 2.2011 (2.2); 2.1861 (4.3); 2.1339 (1.2); 2.1014 (1.6); 2.0945 (3.8); 2.0048 (1.0); 1.8647 (0.5); 1.8514 (0.5); 1.8429 (0.6); 1.8325 (0.6); 1.8194 (0.4); 1.8083 (0.3); 1.7845 (1.3); 1.7731 (1.9); 1.7603 (2.4); 1.7517 (2.5); 1.7405 (2.4); 1.7280 (1.9); 1.7163 (1.6); 1.7021 (1.0); 1.6582 (0.3); 1.5562 (20.6); 1.4778 (0.4); 1.4380 (0.7); 1.4236 (0.9); 1.3335 (0.9); 1.3206 (0.6); 1.3094 (0.8); 1.2847 (1.6); 1.2607 (3.9); 1.1827 (0.4); 1.0873 (0.3); 1.0523 (0.4); 0.9215 (0.3); 0.8948 (0.7); 0.8820 (1.2); 0.8531 (2.0); 0.8367 (2.2); 0.0154 (0.4); 0.0069 (12.3); 0.0051 (12.5); 0.0000 (29.8)
I-033: $^1$H-NMR(400.1 MHz, CDCl3):
δ = 7.5192 (0.9); 7.2837 (0.4); 7.2828 (0.4); 7.2820 (0.4); 7.2812 (0.4); 7.2804 (0.5); 7.2797 (0.4); 7.2771 (0.7); 7.2763 (0.7); 7.2755 (0.8); 7.2747 (0.9); 7.2730 (1.2); 7.2722 (1.4); 7.2605 (167.0); 7.2517 (16.6); 7.2460 (5.3); 7.2402 (1.2); 7.2347 (5.7); 7.2290 (17.3); 7.2205 (1.7); 7.2102 (1.3); 7.1613 (0.3); 7.1173 (0.7); 7.1074 (0.7); 7.1024 (1.4); 7.0923 (2.2); 7.0825 (1.5); 7.0744 (2.7); 7.0681 (2.5); 7.0624 (2.1); 7.0594 (2.0); 7.0520 (9.4); 7.0507 (8.9); 7.0420 (9.5); 7.0369 (3.0); 7.0336 (3.7); 7.0265 (2.6); 7.0176 (0.4); 7.0071 (0.4); 6.9965 (0.9); 6.8412 (1.8); 6.8326 (16.0); 6.8269 (4.7); 6.8156 (4.9); 6.8099 (14.2); 6.8013 (1.3); 4.8846 (3.2); 4.8806 (3.0); 4.8458 (3.6); 4.8418 (3.4); 4.4266 (6.6); 4.4206 (3.1); 4.4151 (7.4); 4.4118 (5.0); 4.4085 (3.1); 4.4031 (8.3); 4.2569 (4.6); 4.2181 (4.2); 4.1316 (8.6); 4.1263 (3.1); 4.1227 (5.5); 4.1197 (8.2); 4.1138 (2.8); 4.1082 (7.0); 3.9164 (0.8); 3.9057 (1.5); 3.8954 (2.2); 3.8850 (2.7); 3.8747 (2.2); 3.8643 (1.6); 3.8538 (0.8); 3.6681 (7.0); 2.7712 (3.5); 2.7611 (3.5); 2.7323 (4.7); 2.7221 (4.5); 2.6982 (0.5); 2.6879 (0.5); 2.5475 (0.7); 2.5295 (1.0); 2.5276 (1.0); 2.5232 (0.9); 2.5211 (0.8); 2.5047 (2.4); 2.4927 (5.4); 2.4866 (2.3); 2.4804 (2.0); 2.4787 (2.0); 2.4712 (5.1); 2.4624 (2.0); 2.4537 (4.0); 2.4364 (1.1); 2.4322 (4.0); 2.4259 (2.4); 2.4116 (2.6); 2.4013 (3.3); 2.3871 (3.2); 2.3831 (1.3); 2.3759 (0.7); 2.3690 (1.0); 2.3584 (1.8); 2.3445 (1.7); 2.3043 (1.3); 2.2848 (1.8); 2.2798 (1.2); 2.2720 (1.7); 2.2667 (1.5); 2.2602 (1.4); 2.2539 (1.8); 2.2522 (1.8); 2.2474 (1.5); 2.2423 (1.0); 2.2340 (1.4); 2.2293 (1.2); 2.2276 (1.3); 2.2094 (0.8); 2.1335 (1.4); 2.0926 (1.2); 2.0047 (1.0); 1.8813 (1.1); 1.8701 (1.3); 1.8676 (1.4); 1.8569 (1.8); 1.8490 (1.4); 1.8462 (1.6); 1.8433 (1.5); 1.8375 (1.5); 1.8350 (1.5); 1.8319 (1.4); 1.8238 (1.6); 1.8134 (1.1); 1.8106 (1.0); 1.7990 (0.9); 1.5557 (14.2); 1.4376 (0.7); 1.4234 (0.7); 1.2846 (0.4); 1.2552 (1.1); 0.8362 (0.3); 0.8313 (0.3); 0.0082 (1.0)
I-034: $^1$H-NMR(400.1 MHz, CDCl3):
δ = 7.2694 (0.4); 7.2686 (0.4); 7.2600 (56.2); 7.1138 (0.4); 7.0988 (0.9); 7.0919 (3.4); 7.0903 (4.1); 7.0890 (3.6); 7.0757 (1.6); 7.0702 (5.4); 7.0687 (4.6); 7.0644 (2.0); 7.0590 (1.6); 7.0468 (5.0); 7.0369 (4.6); 7.0323 (1.5); 7.0286 (1.8); 7.0218 (1.3); 6.9961 (0.4); 6.8046 (0.6); 6.7972 (5.5); 6.7920 (1.9); 6.7809 (1.6); 6.7757 (4.9); 6.7684 (0.6); 4.8815 (1.4); 4.8778 (1.5); 4.8428 (1.6); 4.8390 (1.7); 4.4208 (2.8); 4.4145 (1.3); 4.4093 (3.2); 4.4061 (2.4); 4.4035 (1.5); 4.3974 (3.9); 4.2584 (2.3); 4.2196 (2.1); 4.1333 (3.9); 4.1280 (1.4); 4.1242 (2.4); 4.1213 (3.9); 4.1157 (1.4); 4.1098 (3.3); 3.9158 (0.4); 3.9050 (0.7); 3.8946 (1.0); 3.8841 (1.2); 3.8738 (1.1); 3.8633 (0.8); 3.8527 (0.4); 3.6678 (2.8); 2.7717 (1.6); 2.7616 (1.7); 2.7328 (2.1); 2.7227 (2.1); 2.5438 (0.4); 2.5262 (0.5); 2.5212 (0.4); 2.5191 (0.4); 2.5015 (1.1); 2.4828 (1.0); 2.4766 (3.1); 2.4593 (1.0); 2.4547 (2.3); 2.4377 (2.0); 2.4196 (1.2); 2.4158 (2.0); 2.4053 (1.2); 2.3951 (1.6); 2.3808 (1.5); 2.3769 (0.7); 2.3628 (0.5); 2.3523 (0.8); 2.3383 (0.9); 2.3013 (0.7); 2.2848 (16.0); 2.2690 (1.0); 2.2640 (0.8); 2.2574 (0.7); 2.2494 (0.9); 2.2444 (0.6); 2.2395 (0.5); 2.2312 (0.6); 2.2247 (0.6); 2.2066 (0.4); 2.1320 (0.4); 2.0040 (0.4); 1.8792 (0.5); 1.8678 (0.6); 1.8654 (0.7); 1.8546 (0.8); 1.8467 (0.6); 1.8440 (0.7); 1.8412 (0.7); 1.8354 (0.6); 1.8330 (0.7); 1.8297 (0.6); 1.8217 (0.7); 1.8112 (0.5); 1.8084 (0.5); 1.7969 (0.4); 1.5619 (6.3); 1.2553 (0.5)
I-036: $^1$H-NMR(400.0 MHz, $d_6$-DMSO):
δ = 7.3803 (0.5); 7.3639 (1.0); 7.3598 (1.1); 7.3537 (0.6); 7.3440 (0.7); 7.3380 (1.1); 7.3336 (1.0); 7.3176 (0.6); 7.3136 (0.6); 7.2100 (0.6); 7.2061 (0.7); 7.1973 (0.6); 7.1935 (0.8); 7.1902 (1.2); 7.1864 (1.3); 7.1775 (1.2); 7.1739 (1.3); 7.1698 (0.8); 7.1659 (0.8); 7.1571 (0.7); 7.1534 (0.8); 7.0994 (1.2); 7.0832 (1.6); 7.0639 (0.8); 4.7475 (1.3); 4.7079 (1.5); 4.6399 (1.2); 4.6290 (1.3); 4.6253 (1.5); 4.6144 (1.4); 4.6133 (1.4); 4.6096 (1.3); 4.5988 (1.2); 4.2576 (2.2); 4.2179 (1.9); 3.8070 (0.8); 3.7968 (1.2); 3.7868 (1.4); 3.7766 (1.1); 3.7664 (0.8); 3.4183 (25.7); 3.1677 (1.0); 2.7849 (1.0); 2.7745 (1.1); 2.7689 (1.1); 2.7587 (1.1); 2.7456 (1.4); 2.7352 (1.4); 2.7298 (1.4); 2.7197 (1.3); 2.6699 (0.6); 2.5233 (1.1); 2.5186 (1.7); 2.5100 (30.5); 2.5054 (66.0); 2.5007 (92.6); 2.4961 (65.3); 2.4915 (30.8); 2.4810 (2.2); 2.4741 (1.6); 2.4629 (1.4); 2.4530 (1.6); 2.4417 (1.4); 2.4248 (0.6); 2.4107 (0.8); 2.4001 (0.8); 2.3929 (0.6); 2.3841 (0.8); 2.3758 (0.6); 2.3275 (0.6); 2.3028 (0.6); 2.2999 (0.6); 2.2890 (0.7); 2.2866 (0.7); 2.2783 (1.0); 2.2751 (1.0); 2.2645 (1.1); 2.2620 (1.2); 2.2367 (0.7); 2.2337 (0.7); 2.2269 (1.7); 2.2135 (0.8); 2.2107 (0.9); 2.1999 (0.9); 2.1942 (0.7); 2.1859 (0.5); 2.1823 (1.0); 2.1754 (0.6); 2.1625 (0.7); 2.1562 (0.6); 1.7676 (0.5); 1.7565 (0.8); 1.7484 (0.8); 1.7373 (1.0); 1.7298 (0.6); 1.7254 (1.3); 1.7227 (1.5); 1.7123 (0.8); 1.7056 (2.1); 1.6912 (1.8); 1.6886 (1.4); 1.6741 (1.2); 1.0775 (10.2); 1.0693 (10.3); 1.0616 (10.3); 1.0533 (10.1); 0.8384 (8.8); 0.8341 (16.0); 0.8316 (10.6); 0.8214 (8.8); 0.8171 (15.3); 0.8146

-continued (10.4); 0.0079 (0.6); 0.0021 (0.8); −0.0002 (21.6); −0.0027 (1.2); −0.0085 (0.7)
I-037: $^{1}$H-NMR(400.0 MHz, $d_6$-DMSO):
δ = 8.9822 (0.9); 8.9751 (2.5); 8.9723 (2.4); 8.5699 (1.0); 8.5500 (1.0); 7.3976 (2.7); 7.3588 (0.8); 7.3362 (0.8); 7.1830 (0.8); 7.1703 (0.9); 7.0676 (0.7); 7.0480 (1.1); 7.0319 (0.6); 4.7177 (1.0); 4.6788 (1.3); 4.6586 (0.6); 4.6454 (0.6); 4.6384 (0.6); 4.1850 (1.2); 4.1450 (1.0); 3.7248 (0.7); 3.7144 (0.8); 3.7040 (0.7); 3.6433 (16.0); 3.6323 (5.2); 3.4005 (43.8); 3.1683 (1.9); 3.1533 (0.7); 3.1285 (0.9); 3.1152 (0.9); 3.0044 (0.9); 2.9808 (0.9); 2.9666 (0.7); 2.9433 (0.6); 2.6701 (0.7); 2.6654 (0.5); 2.5634 (0.8); 2.5523 (0.8); 2.5278 (1.3); 2.5236 (1.7); 2.5187 (2.7); 2.5102 (38.1); 2.5056 (83.0); 2.5010 (116.5); 2.4964 (81.0); 2.4918 (36.4); 2.3371 (0.6); 2.3326 (0.7); 2.3278 (0.8); 2.3231 (0.6); 2.3166 (0.8); 2.2955 (1.0); 2.2733 (0.7); 2.2567 (0.8); 2.2417 (1.4); 2.2323 (1.0); 2.2193 (1.7); 2.2058 (1.0); 2.2009 (0.7); 2.1845 (0.8); 2.0105 (0.5); 1.9785 (0.5); −0.0002 (1.4)
I-038: $^{1}$H-NMR(400.1 MHz, CDCl3):
δ = 7.5939 (0.3); 7.5408 (0.4); 7.5191 (1.0); 7.3295 (0.7); 7.3245 (5.0); 7.3186 (2.4); 7.3138 (0.4); 7.3083 (3.6); 7.3021 (16.0); 7.2973 (3.2); 7.2914 (0.7); 7.2869 (3.2); 7.2816 (16.7); 7.2759 (3.9); 7.2727 (1.0); 7.2719 (1.0); 7.2711 (1.0); 7.2703 (0.9); 7.2694 (1.0); 7.2686 (1.1); 7.2654 (4.2); 7.2645 (4.0); 7.2604 (153.4); 7.2553 (3.7); 7.2545 (3.1); 7.2537 (2.3); 7.2528 (1.9); 7.2520 (1.7); 7.2512 (1.5); 7.2504 (1.3); 7.2495 (1.1); 7.2487 (1.0); 7.2479 (0.8); 7.2471 (0.8); 7.2463 (0.7); 7.2454 (0.6); 7.2446 (0.6); 7.2438 (0.5); 7.2430 (0.5); 7.2422 (0.4); 7.2414 (0.4); 7.2405 (0.4); 7.2397 (0.4); 7.2389 (0.3); 7.2381 (0.3); 7.1274 (0.5); 7.1146 (1.2); 7.1098 (0.6); 7.1025 (2.2); 7.0917 (1.1); 7.0845 (1.9); 7.0777 (2.3); 7.0738 (1.2); 7.0673 (1.2); 7.0588 (7.1); 7.0524 (3.9); 7.0471 (6.2); 7.0399 (2.4); 7.0347 (2.8); 7.0275 (0.5); 6.9964 (0.8); 4.8845 (2.5); 4.8805 (2.5); 4.8457 (2.8); 4.8417 (2.7); 4.2610 (0.4); 4.2428 (3.8); 4.2360 (6.6); 4.2190 (13.7); 4.2022 (8.9); 3.8803 (0.6); 3.8696 (1.1); 3.8591 (1.7); 3.8489 (1.9); 3.8383 (1.6); 3.8279 (1.2); 3.8174 (0.6); 3.6680 (4.6); 3.1049 (6.9); 3.0880 (14.1); 3.0710 (6.5); 2.7004 (2.8); 2.6903 (2.8); 2.6615 (3.6); 2.6513 (3.4); 2.5420 (0.6); 2.5239 (0.7); 2.5193 (0.7); 2.4997 (1.8); 2.4809 (1.5); 2.4765 (1.4); 2.4576 (1.5); 2.4367 (0.6); 2.4311 (1.8); 2.4241 (0.4); 2.4165 (2.2); 2.4065 (2.7); 2.4019 (4.1); 2.3922 (2.6); 2.3882 (1.1); 2.3802 (3.8); 2.3739 (1.0); 2.3631 (4.0); 2.3495 (1.4); 2.3412 (2.9); 2.3002 (1.1); 2.2809 (1.3); 2.2760 (0.8); 2.2678 (1.2); 2.2625 (1.0); 2.2564 (1.0); 2.2482 (1.4); 2.2432 (1.1); 2.2381 (0.7); 2.2298 (1.0); 2.2237 (1.1); 2.2052 (0.6); 2.0945 (2.9); 2.0048 (0.9); 1.8549 (0.9); 1.8435 (1.0); 1.8410 (1.2); 1.8301 (1.4); 1.8222 (1.0); 1.8197 (1.2); 1.8170 (1.1); 1.8109 (1.0); 1.8083 (1.1); 1.8054 (1.0); 1.7971 (1.2); 1.7870 (0.8); 1.7842 (0.7); 1.7725 (0.7); 1.5518 (8.7); 1.2555 (1.0); 0.0083 (0.8); 0.0059 (0.4); 0.0051 (0.4); 0.0043 (0.6); 0.0034 (0.8); 0.0025 (1.4)
I-039: $^{1}$H-NMR(400.0 MHz, $d_6$-DMSO):
δ = 12.7567 (0.8); 8.3619 (3.9); 8.3516 (3.1); 8.3412 (3.9); 8.3310 (2.9); 7.3727 (1.3); 7.3473 (3.1); 7.3267 (3.3); 7.3062 (1.8); 7.2825 (3.5); 7.2643 (9.7); 7.2466 (14.1); 7.2294 (8.3); 7.2177 (14.3); 7.2114 (12.4); 7.2047 (9.5); 7.2001 (9.4); 7.1862 (8.9); 7.1690 (4.5); 7.0540 (2.1); 7.0381 (4.4); 7.0187 (3.5); 7.0020 (1.2); 4.6968 (3.4); 4.6775 (2.5); 4.6566 (3.8); 4.6384 (2.9); 4.4900 (1.5); 4.4786 (1.5); 4.4653 (2.2); 4.4546 (2.5); 4.4442 (2.5); 4.4331 (2.2); 4.4229 (1.5); 4.3971 (1.0); 4.1805 (4.0); 4.1404 (3.6); 4.1247 (2.8); 4.0835 (2.5); 3.9638 (2.9); 3.6687 (2.2); 3.6574 (2.8); 3.6472 (2.9); 3.6368 (2.6); 3.6242 (2.3); 3.6140 (1.9); 3.6026 (1.6); 3.4414 (69.2); 3.1663 (16.0); 3.0935 (2.3); 3.0824 (2.9); 3.0744 (1.9); 3.0592 (3.0); 3.0482 (3.4); 3.0402 (2.2); 2.8384 (3.1); 2.8128 (3.2); 2.8038 (2.9); 2.7783 (2.5); 2.6990 (1.6); 2.6790 (2.2); 2.6745 (4.8); 2.6699 (6.7); 2.6653 (4.8); 2.5568 (1.6); 2.5522 (1.6); 2.5471 (1.3); 2.5401 (3.9); 2.5363 (4.6); 2.5233 (18.8); 2.5186 (27.7); 2.5100 (388.7); 2.5054 (843.8); 2.5008 (1175.8); 2.4962 (827.4); 2.4916 (375.5); 2.4669 (3.8); 2.4568 (5.0); 2.4521 (3.3); 2.4468 (1.7); 2.3812 (1.3); 2.3369 (2.9); 2.3322 (5.5); 2.3276 (7.5); 2.3229 (5.4); 2.3181 (2.8); 2.2913 (2.0); 2.2695 (3.3); 2.2476 (4.0); 2.2270 (3.8); 2.1974 (2.3); 2.1880 (4.2); 2.1728 (5.5); 2.1654 (5.0); 2.1529 (4.8); 2.1377 (3.5); 2.1316 (3.5); 2.1158 (3.3); 2.0732 (1.8); 1.9407 (1.1); 1.9087 (1.3); 1.8851 (1.6); 1.8636 (1.8); 1.8513 (1.3); 1.8393 (1.6); 1.8316 (1.9); 1.8073 (1.7); 1.7879 (0.8); 1.6787 (1.0); 1.6661 (1.3); 1.6558 (1.3); 1.6449 (1.3); 1.4707 (1.2); 1.4600 (1.8); 1.4491 (1.6); 1.4377 (1.6); 1.4273 (1.6); 1.0281 (2.0); 0.1460 (1.2); 0.0080 (9.4); −0.0002 (340.8); −0.0086 (10.2); −0.1495 (1.0)
I-040: $^{1}$H-NMR(400.1 MHz, CDCl3):
δ = 7.3933 (0.3); 7.3855 (3.3); 7.3800 (1.1); 7.3688 (1.1); 7.3633 (3.7); 7.3555 (0.4); 7.2679 (0.3); 7.2670 (0.4); 7.2662 (0.6); 7.2653 (0.7); 7.2609 (28.8); 7.2514 (0.3); 7.0961 (0.6); 7.0857 (0.4); 7.0783 (0.6); 7.0712 (0.6); 7.0672 (0.5); 7.0599 (0.5); 7.0523 (2.3); 7.0459 (1.2); 7.0418 (2.1); 7.0339 (1.0); 7.0282 (0.8); 6.8670 (0.4); 6.8593 (3.4); 6.8538 (1.1); 6.8426 (1.0); 6.8372 (3.2); 6.8294 (0.4); 4.8816 (0.7); 4.8778 (0.8); 4.8429 (0.8); 4.8390 (0.8); 4.2401 (1.1); 4.1991 (2.5); 4.1820 (4.0); 4.1651 (2.0); 3.8721 (0.4); 3.8614 (1.0); 3.8513 (0.6); 3.8408 (0.5); 3.8303 (0.4); 3.7955 (16.0); 3.6680 (1.6); 3.0034 (2.0); 2.9865 (4.2); 2.9695 (1.9); 2.7015 (0.9); 2.6915 (0.9); 2.6627 (1.1); 2.6527 (1.0); 2.5003 (0.6); 2.4818 (0.5); 2.4773 (0.4); 2.4583 (0.5); 2.4281 (0.5); 2.4140 (0.7); 2.4036 (0.8); 2.3964 (1.3); 2.3893 (0.8); 2.3853 (0.4); 2.3744 (1.2); 2.3605 (0.5); 2.3576 (1.0); 2.3467 (0.4); 2.3356 (0.9); 2.3009 (0.3); 2.2817 (0.4); 2.2685 (0.4); 2.2633 (0.3); 2.2572 (0.3); 2.2491 (0.4); 2.2440 (0.3); 2.2245 (0.3); 2.0923 (1.1); 1.8509 (0.4); 1.8486 (0.4); 1.8377 (0.5); 1.8295 (0.4); 1.8272 (0.4); 1.8244 (0.3); 1.8184 (0.4); 1.8160 (0.4); 1.8047 (0.4); 1.5634 (1.2)
I-041: $^{1}$H-NMR(400.1 MHz, CDCl3):
δ = 7.5187 (0.4); 7.3014 (4.4); 7.2812 (5.5); 7.2755 (1.2); 7.2616 (58.1); 7.2599 (62.6); 7.2091 (0.8); 7.1221 (4.6); 7.1012 (3.6); 7.0874 (0.7); 7.0797 (1.1); 7.0721 (1.1); 7.0618 (0.7); 7.0518 (3.7); 7.0417 (3.7); 7.0332 (1.3); 7.0290 (1.3); 6.9961 (0.4); 4.8778 (1.6); 4.8392 (1.7); 4.2391 (2.4); 4.2249 (3.1); 4.2078 (6.4); 4.2007 (2.3); 4.1912 (3.2); 3.8783 (0.3); 3.8682 (0.7); 3.8574 (1.0); 3.8470 (1.2); 3.8366 (1.0); 3.8264 (0.7); 3.8157 (0.3); 3.0740 (3.2); 3.0570 (6.3); 3.0402 (3.0); 2.6982 (1.4); 2.6883 (1.4); 2.6594 (1.8); 2.6494 (1.7); 2.5387 (0.4); 2.5206 (0.5); 2.5144 (0.5); 2.4960 (1.2); 2.4776 (1.1); 2.4718 (0.9); 2.4537 (1.0); 2.4246 (1.2); 2.4106 (1.0); 2.4005 (1.2); 2.3869 (3.0); 2.3661 (2.0); 2.3580 (0.8); 2.3483 (1.6); 2.3439 (0.8); 2.3216 (16.0); 2.2966 (0.5); 2.2778 (0.7); 2.2710 (0.4); 2.2637 (0.6); 2.2589 (0.5); 2.2534 (0.6); 2.2451 (0.9); 2.2393 (0.5); 2.2346 (0.4); 2.2253 (0.5); 2.2207 (0.6); 2.2015 (0.3); 2.0046 (0.5); 1.8555 (0.4); 1.8434 (0.7); 1.8311 (0.8); 1.8218 (0.7); 1.8103 (0.7); 1.8081 (0.7); 1.7985 (0.7); 1.7868 (0.5); 1.5476 (23.8); 0.0018 (5.3)
I-042: $^{1}$H-NMR(400.0 MHz, CDCl3):
δ = 7.3483 (0.5); 7.3441 (0.6); 7.3275 (0.9); 7.3107 (0.6); 7.3065 (0.6); 7.2649 (8.0); 7.1927 (1.0); 7.1766 (0.6); 7.1726 (0.5); 7.0784 (0.9); 7.0759 (0.9); 7.0586 (1.3); 7.0562 (1.4); 7.0391 (0.6); 7.0365 (0.6); 5.3007 (1.1); 4.8692 (0.9); 4.8324 (1.0); 4.2589 (1.3); 4.2200 (1.2); 3.9037 (0.6); 3.8933 (0.8); 3.8830 (0.6); 3.6676 (16.0); 2.7314 (0.9); 2.7210 (1.0); 2.6924 (1.2); 2.6821 (1.2); 2.5138 (0.7); 2.4948 (0.6);

-continued 2.4901 (0.5); 2.4717 (0.6); 2.4429 (1.9); 2.4281 (0.8); 2.4214 (1.4); 2.4182 (1.1); 2.4040 (1.9); 2.3825 (1.0); 2.3751 (0.5); 2.3613 (0.5); 2.3035 (0.5); 2.2714 (0.6); 1.8554 (0.5); 1.2611 (0.5); 1.2544 (1.0); −0.0002 (4.9)

I-043: $^1$H-NMR(400.1 MHz, $d_6$-DMSO):

δ = 8.1400 (0.8); 8.1190 (0.8); 8.0535 (1.4); 8.0319 (1.4); 7.3771 (0.6); 7.3733 (0.6); 7.3525 (1.3); 7.3310 (1.4); 7.3106 (0.6); 7.2016 (0.7); 7.1828 (1.3); 7.1700 (1.4); 7.1502 (0.7); 7.0904 (1.0); 7.0715 (1.6); 7.0562 (0.8); 4.7376 (1.8); 4.6973 (2.0); 4.3465 (1.3); 4.3350 (1.4); 4.3245 (1.3); 4.3131 (1.4); 4.2479 (2.1); 4.2079 (1.8); 4.1679 (0.8); 4.1530 (0.8); 4.1472 (0.8); 4.1323 (0.8); 3.8020 (0.4); 3.7918 (0.8); 3.7808 (1.2); 3.7701 (1.5); 3.7599 (1.2); 3.7496 (0.9); 3.7390 (0.5); 3.4708 (0.3); 3.3853 (16.0); 2.6741 (0.6); 2.6692 (0.8); 2.6647 (0.6); 2.6570 (1.1); 2.6460 (1.0); 2.6312 (0.6); 2.6224 (1.5); 2.6114 (1.2); 2.5966 (0.8); 2.5856 (0.8); 2.5397 (0.5); 2.5227 (1.2); 2.5094 (40.5); 2.5048 (89.4); 2.5002 (126.9); 2.4956 (92.5); 2.4910 (44.2); 2.4498 (0.4); 2.4187 (0.4); 2.3957 (0.8); 2.3768 (1.2); 2.3545 (1.4); 2.3357 (2.2); 2.3274 (1.2); 2.3227 (0.9); 2.3138 (1.7); 2.3016 (1.2); 2.2936 (0.9); 2.2880 (1.1); 2.2792 (1.6); 2.2762 (1.4); 2.2636 (1.4); 2.2511 (1.3); 2.2332 (0.6); 2.2213 (0.7); 2.2094 (0.7); 2.1245 (0.5); 2.1047 (1.0); 2.0928 (0.8); 2.0808 (1.0); 2.0716 (1.7); 2.0616 (0.5); 2.0490 (1.0); 2.0296 (0.4); 1.8788 (0.4); 1.8617 (0.7); 1.8494 (0.8); 1.8438 (1.1); 1.8318 (1.3); 1.8205 (0.9); 1.8113 (1.0); 1.8023 (0.9); 1.7986 (0.9); 1.7889 (0.9); 1.7774 (0.8); 1.7721 (0.6); 1.7661 (0.6); 1.7481 (0.5); 1.3824 (0.4); 1.3717 (0.3); 1.3636 (0.3); 1.2960 (0.4); 1.2781 (0.7); 1.2615 (1.0); 1.2441 (1.0); 1.2260 (0.8); 1.2077 (0.5); 1.1896 (0.4); 1.1729 (0.5); 1.1669 (0.4); 1.1535 (0.8); 1.1347 (1.2); 1.1170 (0.9); 1.1004 (0.7); 1.0826 (0.4); 0.8484 (13.8); 0.8314 (15.4); 0.8156 (4.2); 0.0082 (0.4)

I-044: $^1$H-NMR(400.0 MHz, $d_6$-DMSO):

δ = 7.2642 (2.9); 7.2466 (4.4); 7.2114 (4.8); 3.3179 (1950.0); 3.2683 (4.4); 3.1666 (16.0); 2.6747 (5.7); 2.6699 (8.5); 2.6652 (5.5); 2.5402 (3.9); 2.5234 (18.8); 2.5186 (28.8); 2.5100 (477.4); 2.5054 (1050.3); 2.5008 (1468.1); 2.4962 (1027.3); 2.4916 (461.4); 2.4560 (4.0); 2.3323 (6.1); 2.3276 (8.3); 2.3228 (6.3); 2.1528 (2.0); 2.0729 (2.6); −0.0002 (69.2)

I-045: $^1$H-NMR(400.0 MHz, $d_6$-DMSO):

δ = 3.3177 (2918.2); 2.6699 (13.1); 2.6652 (10.2); 2.5234 (40.1); 2.5186 (61.2); 2.5100 (816.8); 2.5055 (1744.3); 2.5009 (2406.0); 2.4963 (1740.3); 2.4918 (848.3); 2.3324 (12.1); 2.3278 (15.4); 1.4880 (4.8); 0.8921 (15.7); 0.8754 (16.0); 0.8282 (13.0); 0.8128 (12.2); −0.0002 (106.8)

I-046: $^1$H-NMR(400.1 MHz, $d_6$-DMSO):

δ = 10.8047 (0.8); 7.3597 (0.5); 7.3554 (0.6); 7.3494 (0.4); 7.3393 (0.4); 7.3335 (0.6); 7.3292 (0.6); 7.3132 (0.3); 7.3092 (0.3); 7.1925 (0.6); 7.1891 (0.6); 7.1797 (0.6); 7.1764 (0.6); 7.1722 (0.5); 7.1684 (0.4); 7.1594 (0.4); 7.1559 (0.4); 7.0987 (0.6); 7.0825 (0.8); 7.0637 (0.4); 4.7545 (0.9); 4.7142 (1.0); 4.3051 (1.1); 4.2654 (1.0); 3.9296 (0.4); 3.9189 (0.5); 3.9091 (0.6); 3.8992 (0.5); 3.8886 (0.4); 3.3273 (29.0); 3.1686 (0.6); 2.9026 (0.6); 2.8921 (0.6); 2.8652 (0.7); 2.8547 (0.7); 2.6067 (0.7); 2.5852 (0.7); 2.5689 (0.6); 2.5472 (0.8); 2.5401 (0.4); 2.5233 (0.8); 2.5185 (1.2); 2.5100 (17.2); 2.5055 (37.2); 2.5008 (51.8); 2.4963 (37.8); 2.4918 (18.8); 2.4465 (0.5); 2.4223 (0.7); 2.4041 (0.6); 2.3994 (0.6); 2.3825 (0.4); 2.3321 (0.6); 2.3280 (0.4); 2.3190 (0.6); 2.3079 (0.8); 2.2951 (0.8); 2.2687 (16.0); 2.2564 (1.1); 2.2398 (0.6); 2.2279 (0.5); 2.2214 (0.4); 2.2093 (0.6); 2.1898 (0.4); 2.1847 (0.4); 1.8520 (0.4); 1.8404 (0.5); 1.8300 (0.4); 1.8225 (0.5); 1.8096 (0.4); 1.1588 (0.4)

I-047: $^1$H-NMR(400.1 MHz, $d_6$-DMSO):

δ = 7.5589 (2.7); 7.5544 (3.4); 7.5384 (4.3); 7.5334 (4.0); 7.3988 (4.8); 7.3785 (4.1); 7.3562 (1.0); 7.3360 (1.1); 7.3116 (0.8); 7.2081 (0.6); 7.1879 (1.1); 7.1764 (1.1); 7.1545 (0.6); 7.0864 (0.7); 7.0631 (1.2); 7.0577 (0.8); 4.7215 (0.8); 4.7116 (1.0); 4.6810 (1.0); 4.6709 (1.0); 4.3054 (0.3); 4.2746 (1.5); 4.2625 (2.1); 4.2557 (2.8); 4.2503 (1.9); 4.2446 (1.7); 4.2315 (1.8); 4.2204 (0.6); 4.1930 (1.3); 4.0877 (0.6); 4.0744 (0.6); 3.7487 (0.9); 3.7366 (0.9); 3.7194 (0.6); 3.4608 (0.9); 3.4103 (1.4); 3.3630 (9.7); 3.3123 (1240.8); 3.2884 (22.2); 3.2619 (8.4); 3.2432 (0.9); 3.2298 (1.2); 3.2139 (2.2); 3.2093 (0.6); 3.1956 (1.2); 3.1910 (0.9); 3.1753 (2.9); 3.1622 (2.3); 3.0761 (0.7); 3.0673 (1.2); 3.0544 (0.7); 3.0481 (0.8); 3.0412 (0.6); 3.0327 (0.8); 3.0134 (0.5); 2.9124 (0.4); 2.6973 (0.8); 2.6875 (1.4); 2.6787 (1.6); 2.6741 (2.1); 2.6697 (2.8); 2.6647 (2.1); 2.6574 (1.4); 2.6477 (2.0); 2.6375 (1.0); 2.5989 (0.7); 2.5948 (0.8); 2.5600 (2.4); 2.5558 (3.2); 2.5513 (3.4); 2.5466 (1.5); 2.5228 (4.0); 2.5182 (6.8); 2.5096 (153.0); 2.5051 (339.6); 2.5005 (481.2); 2.4959 (349.1); 2.4913 (165.5); 2.4592 (1.8); 2.4545 (2.7); 2.4501 (4.0); 2.4458 (3.5); 2.4410 (2.4); 2.4320 (2.1); 2.4201 (1.6); 2.4119 (2.1); 2.3986 (1.3); 2.3920 (1.4); 2.3793 (1.2); 2.3643 (16.0); 2.3492 (1.3); 2.3364 (1.1); 2.3320 (2.1); 2.3273 (2.9); 2.3229 (2.1); 2.2906 (0.8); 2.2778 (0.9); 2.2662 (1.3); 2.2536 (1.4); 2.2246 (0.9); 2.2136 (1.2); 2.1977 (0.7); 2.1852 (0.7); 2.1599 (0.8); 2.1408 (0.7); 2.1175 (0.4); 2.0722 (2.2); 1.7320 (0.6); 1.7230 (0.6); 1.7119 (0.8); 1.7010 (0.8); 1.6928 (0.8); 1.6804 (0.6); 1.6692 (0.6); 0.1456 (0.4); 0.0505 (0.8); 0.0080 (2.6); 0.0000 (84.3)

I-048: $^1$H-NMR(400.0 MHz, $d_6$-DMSO):

δ = 8.6522 (1.8); 7.3660 (0.5); 7.3440 (0.5); 7.1951 (0.6); 7.1916 (0.6); 7.1822 (0.5); 7.1791 (0.6); 7.0874 (0.6); 7.0714 (0.8); 4.7420 (0.8); 4.7023 (1.0); 4.2438 (1.1); 4.2040 (0.9); 3.7934 (0.6); 3.7833 (0.7); 3.7732 (0.6); 3.5596 (16.0); 2.5201 (0.8); 2.5114 (10.1); 2.5068 (20.3); 2.5023 (28.0); 2.4977 (19.8); 2.4932 (8.8); 2.4767 (1.0); 2.4654 (0.7); 2.3728 (0.6); 2.3527 (0.6); 2.3297 (0.6); 2.2782 (0.5); 2.2670 (0.6); 2.2542 (0.6); 2.1999 (0.9); 2.1782 (0.8); 2.1650 (0.8); 2.1431 (0.9); 1.3492 (1.4); 1.3385 (1.4); 1.3292 (1.3); 1.1744 (0.7); 0.9786 (0.7); 0.9733 (1.3); 0.9694 (1.8); 0.9612 (1.6); 0.9516 (0.5); −0.0002 (5.4)

I-049: $^1$H-NMR(400.0 MHz, $d_6$-DMSO):

δ = 7.9605 (3.6); 7.3729 (1.6); 7.3521 (3.5); 7.3305 (3.5); 7.3096 (1.9); 7.2064 (2.1); 7.2023 (2.2); 7.1936 (2.1); 7.1865 (3.8); 7.1826 (3.9); 7.1737 (3.7); 7.1701 (4.0); 7.1661 (2.5); 7.1620 (2.3); 7.1533 (2.1); 7.1495 (2.2); 7.0734 (3.7); 7.0576 (5.1); 7.0381 (2.7); 4.7356 (6.1); 4.6957 (7.1); 4.6274 (1.2); 4.2328 (7.4); 4.1925 (6.3); 3.8088 (1.2); 3.7985 (2.3); 3.7883 (3.5); 3.7780 (4.3); 3.7677 (3.6); 3.7572 (2.5); 3.7464 (1.3); 3.3775 (6.7); 3.3624 (14.5); 3.3474 (8.9); 3.3072 (176.5); 3.2559 (1.6); 3.1685 (0.8); 3.1067 (6.0); 3.0920 (16.0); 3.0774 (14.8); 3.0624 (4.8); 2.6739 (2.1); 2.6692 (3.0); 2.6646 (2.1); 2.5395 (2.4); 2.5229 (11.1); 2.5180 (10.8); 2.5094 (174.1); 2.5048 (381.4); 2.5001 (535.0); 2.4955 (370.0); 2.4909 (167.8); 2.4771 (8.4); 2.4502 (2.1); 2.4038 (1.4); 2.3992 (0.5); 2.3855 (2.4); 2.3620 (4.6); 2.3424 (4.2); 2.3316 (2.6); 2.3269 (3.6); 2.3193 (4.0); 2.2776 (3.3); 2.2645 (4.2); 2.2535 (5.2); 2.2406 (4.9); 2.2358 (2.3); 2.2229 (2.1); 2.2124 (8.5); 2.1989 (3.3); 2.1911 (6.4); 2.1779 (5.5); 2.1564 (5.3); 2.1397 (1.9); 2.1202 (3.2); 2.1158 (2.0); 2.1082 (2.3); 2.1010 (2.0); 2.0963 (2.8); 2.0887 (3.9); 2.0770 (1.5); 2.0689 (2.3); 2.0646 (3.0); 2.0451 (1.3); 1.7806 (1.6); 1.7684 (2.2); 1.7572 (3.2); 1.7474 (2.7); 1.7351 (2.7); 1.7253 (2.8); 1.7145 (1.8); 1.7019 (1.2); 0.0080 (1.6); −0.0002 (56.0); − 0.0086 (1.8)

I-050: $^1$H-NMR(400.0 MHz, $d_6$-DMSO):

-continued

δ = 8.9991 (2.5); 8.6323 (0.9); 8.6127 (0.9); 7.4148 (2.3); 7.3595 (0.7); 7.3369 (0.7); 7.1847 (0.7); 7.1725 (0.8); 7.0691 (0.7); 7.0525 (1.0); 4.7152 (1.0); 4.6759 (1.2); 4.6198 (0.5); 4.6103 (0.6); 4.6002 (0.6); 4.5906 (0.5); 4.1730 (1.2); 4.1329 (1.1); 3.7207 (0.6); 3.7100 (0.7); 3.6996 (0.6); 3.6313 (16.0); 3.3542 (134.1); 3.1857 (2.8); 3.1678 (3.3); 3.1510 (0.8); 3.1263 (1.0); 3.1128 (0.9); 3.0374 (1.0); 3.0141 (1.0); 3.0000 (0.7); 2.9763 (0.6); 2.6749 (0.6); 2.6703 (0.8); 2.6656 (0.6); 2.5407 (1.0); 2.5318 (1.2); 2.5238 (2.1); 2.5191 (3.0); 2.5104 (49.9); 2.5058 (108.6); 2.5012 (151.6); 2.4966 (106.3); 2.4920 (47.2); 2.3326 (0.7); 2.3279 (1.1); 2.3232 (1.3); 2.3027 (0.9); 2.2802 (0.7); 2.2720 (1.0); 2.2594 (0.6); 2.2499 (1.1); 2.2362 (1.3); 2.2226 (0.9); 2.2156 (1.0); 2.0292 (0.6); 1.7013 (0.5); 1.6913 (0.5); 0.0080 (0.5); −0.0002 (16.5)

I-051: $^1$H-NMR(400.0 MHz, $d_6$-DMSO):

δ = 8.3499 (4.6); 7.3263 (3.6); 7.2640 (9.4); 7.2465 (15.0); 7.2290 (11.4); 7.2168 (13.4); 7.2108 (16.0); 7.1858 (10.8); 7.0363 (4.8); 7.0215 (5.0); 4.6966 (3.6); 4.6769 (3.8); 4.6572 (4.0); 4.6371 (4.5); 4.1809 (3.8); 4.1394 (4.0); 4.1246 (4.5); 4.0843 (3.8); 3.6475 (3.2); 3.3671 (5.4); 3.3151 (6348.8); 3.2642 (17.1); 3.2158 (5.8); 3.1660 (9.5); 3.0520 (4.0); 2.8323 (3.3); 2.8073 (3.9); 2.6744 (25.2); 2.6697 (35.0); 2.6652 (25.8); 2.6607 (11.2); 2.5400 (23.0); 2.5232 (95.7); 2.5185 (141.3); 2.5098 (1948.2); 2.5053 (4233.3); 2.5007 (5926.9); 2.4960 (4148.6); 2.4915 (1849.1); 2.4552 (12.4); 2.4502 (15.1); 2.4457 (12.4); 2.4059 (5.9); 2.3368 (11.6); 2.3321 (24.8); 2.3275 (34.9); 2.3228 (25.0); 2.3185 (12.0); 2.2696 (4.0); 2.2469 (4.7); 2.2272 (4.7); 2.1878 (5.4); 2.1724 (6.5); 2.1649 (6.7); 2.1537 (6.4); 2.0730 (8.0); 0.0080 (20.9); −0.0002 (707.7); −0.0085 (19.0)

I-052: $^1$H-NMR(400.1 MHz, CDCl3):

δ = 10.3385 (0.3); 10.3199 (0.4); 7.5193 (1.3); 7.3089 (0.8); 7.2605 (246.9); 7.2126 (0.7); 7.1463 (2.1); 7.1417 (2.4); 7.1220 (7.3); 7.1076 (5.8); 7.1027 (9.1); 7.0973 (6.6); 7.0850 (8.0); 7.0764 (9.5); 7.0680 (9.5); 7.0562 (11.3); 7.0474 (6.5); 7.0363 (6.7); 7.0249 (8.1); 7.0092 (8.8); 6.9966 (4.3); 6.9921 (4.0); 6.7516 (0.5); 5.2983 (4.6); 4.9233 (0.5); 4.8772 (10.9); 4.8384 (12.5); 4.7961 (0.9); 4.3589 (0.4); 4.3341 (1.0); 4.2956 (1.0); 4.2232 (14.4); 4.2064 (1.3); 4.1846 (13.2); 4.1353 (0.9); 4.1194 (0.8); 4.0975 (0.8); 4.0467 (1.3); 4.0344 (1.4); 4.0260 (1.4); 4.0151 (1.4); 3.9968 (3.2); 3.9869 (5.4); 3.9768 (7.7); 3.9668 (9.7); 3.9566 (8.1); 3.9465 (5.9); 3.9367 (3.6); 3.9159 (1.7); 3.9051 (1.7); 3.8947 (1.8); 3.8870 (1.7); 3.8757 (1.7); 3.8439 (1.6); 3.8166 (1.5); 3.8102 (1.5); 3.7902 (1.5); 3.7877 (1.4); 3.7380 (1.3); 3.7195 (1.4); 3.6994 (1.5); 3.6715 (1.5); 3.6530 (1.3); 3.6347 (1.0); 3.6173 (0.8); 3.6084 (0.9); 3.5958 (0.8); 3.5761 (0.8); 3.5599 (0.8); 3.5008 (1.7); 3.4986 (1.7); 3.4934 (2.5); 3.4103 (0.5); 3.3407 (0.9); 3.3205 (0.9); 3.3031 (1.3); 3.2851 (1.9); 3.2672 (2.2); 3.2433 (1.6); 3.1611 (0.3); 3.1358 (1.1); 3.1129 (2.4); 3.1073 (2.3); 3.0368 (0.6); 3.0262 (0.6); 2.9948 (0.6); 2.9840 (0.6); 2.8921 (9.3); 2.8814 (12.8); 2.8768 (13.6); 2.8678 (13.0); 2.8518 (16.0); 2.8415 (12.0); 2.7276 (0.4); 2.7179 (0.8); 2.6992 (0.6); 2.6872 (0.8); 2.6773 (1.1); 2.6563 (11.2); 2.6360 (10.9); 2.6157 (8.6); 2.5955 (10.2); 2.5740 (4.2); 2.5532 (7.4); 2.5315 (8.1); 2.5098 (5.6); 2.4834 (5.0); 2.4711 (6.2); 2.4588 (7.7); 2.4467 (8.0); 2.4406 (3.6); 2.4280 (2.6); 2.4154 (4.0); 2.4036 (4.2); 2.3615 (3.1); 2.3414 (5.3); 2.3288 (3.9); 2.3172 (4.6); 2.3087 (6.2); 2.2971 (2.6); 2.2842 (4.8); 2.2637 (2.0); 2.1833 (0.3); 2.1053 (0.6); 2.0883 (1.7); 2.0689 (2.2); 2.0523 (1.9); 2.0358 (1.0); 2.0077 (1.2); 1.9291 (2.6); 1.9180 (4.4); 1.9066 (4.6); 1.8957 (5.8); 1.8845 (6.1); 1.8739 (4.1); 1.8616 (3.3); 1.8508 (2.2); 1.8346 (0.5); 1.8211 (0.4); 1.8151 (0.4); 1.8012 (0.3); 1.7888 (0.3); 1.3069 (0.6); 1.2888 (1.1); 1.2698 (0.9); 1.2520 (2.9); 1.2339 (4.4); 1.2167 (2.2); 1.1938 (2.2); 1.1757 (4.4); 1.1635 (0.4); 1.1574 (2.0); 1.1493 (0.5); 0.0082 (1.4)

I-054: $^1$H-NMR(400.1 MHz, $d_6$-DMSO):

δ = 7.8196 (0.5); 7.8124 (3.8); 7.8072 (1.1); 7.7951 (1.2); 7.7900 (4.2); 7.7827 (0.4); 7.3591 (0.5); 7.3374 (0.6); 7.3173 (0.4); 7.1875 (0.6); 7.1706 (0.9); 7.1641 (4.3); 7.1589 (1.2); 7.1470 (1.1); 7.1417 (3.7); 7.1341 (0.3); 7.0421 (0.6); 7.0285 (0.8); 7.0072 (0.4); 4.6716 (0.8); 4.6322 (1.1); 4.2422 (1.3); 4.2277 (2.7); 4.2137 (1.5); 4.1731 (1.2); 4.1319 (1.0); 4.0736 (0.3); 3.8581 (0.4); 3.8474 (16.0); 3.6939 (0.3); 3.6832 (0.4); 3.6731 (0.6); 3.6627 (0.8); 3.6537 (0.7); 3.6411 (0.5); 3.6304 (1.3); 3.6176 (1.9); 3.6135 (2.0); 3.6027 (0.9); 3.3624 (2.6); 3.3115 (801.9); 3.2877 (13.5); 3.2626 (2.3); 3.2118 (0.4); 3.1752 (1.4); 3.1621 (1.4); 2.6786 (0.7); 2.6741 (1.2); 2.6696 (1.8); 2.6649 (1.3); 2.6606 (0.7); 2.5622 (1.1); 2.5518 (1.9); 2.5399 (1.4); 2.5230 (4.1); 2.5183 (5.3); 2.5097 (103.1); 2.5051 (228.6); 2.5005 (323.1); 2.4959 (232.4); 2.4913 (109.4); 2.3902 (0.4); 2.3715 (0.4); 2.3480 (0.6); 2.3318 (1.5); 2.3275 (2.4); 2.3228 (1.8); 2.3055 (0.6); 2.2704 (1.1); 2.2652 (0.6); 2.2496 (1.2); 2.2410 (0.8); 2.2300 (1.2); 2.2096 (0.9); 2.1987 (0.4); 2.1859 (0.4); 2.1609 (0.4); 2.1419 (0.4); 2.1291 (0.3); 2.1172 (0.4); 2.1106 (0.5); 2.0911 (0.4); 2.0857 (0.4); 2.0720 (1.1); 1.6402 (0.4); 1.6295 (0.5); 1.6173 (0.5); 1.6068 (0.4); 1.5968 (0.4); 1.5839 (0.3); 0.0081 (1.8)

I-055: $^1$H-NMR(400.0 MHz, $d_6$-DMSO):

δ = 8.4699 (1.6); 8.4559 (3.0); 8.4411 (1.6); 7.3769 (1.1); 7.3560 (2.4); 7.3303 (4.7); 7.3282 (4.6); 7.3131 (6.4); 7.3089 (11.2); 7.2963 (3.3); 7.2916 (8.8); 7.2494 (3.7); 7.2465 (3.9); 7.2324 (16.0); 7.2124 (9.7); 7.1939 (1.4); 7.1867 (2.5); 7.1831 (2.6); 7.1706 (2.6); 7.1625 (1.5); 7.1536 (1.3); 7.1502 (1.4); 7.0799 (2.5); 7.0635 (3.4); 7.0444 (1.8); 4.7432 (3.9); 4.7038 (4.6); 4.2954 (1.0); 4.2805 (1.0); 4.2579 (4.8); 4.2411 (12.0); 4.2261 (5.0); 4.2003 (4.7); 4.1884 (1.1); 3.8472 (0.8); 3.8358 (1.6); 3.8257 (2.3); 3.8153 (2.8); 3.8055 (2.3); 3.7948 (1.7); 3.7840 (0.8); 3.3773 (0.6); 3.3248 (216.2); 3.2761 (1.0); 2.6743 (0.6); 2.6697 (0.9); 2.6650 (0.6); 2.6087 (3.2); 2.5975 (3.2); 2.5736 (3.9); 2.5624 (3.9); 2.5230 (2.3); 2.5097 (54.9); 2.5052 (116.5); 2.5006 (160.4); 2.4960 (112.7); 2.4915 (51.7); 2.4555 (0.8); 2.4024 (0.9); 2.3790 (1.3); 2.3597 (2.8); 2.3372 (2.8); 2.3275 (1.2); 2.3181 (2.5); 2.2862 (5.6); 2.2739 (2.7); 2.2637 (6.6); 2.2505 (6.1); 2.2292 (3.6); 2.2213 (1.8); 2.2085 (1.7); 2.1620 (1.2); 2.1429 (2.0); 2.1305 (1.4); 2.1235 (1.3); 2.1190 (1.7); 2.1114 (2.4); 2.0996 (0.9); 2.0918 (1.4); 2.0874 (1.8); 2.0675 (0.7); 1.7986 (1.0); 1.7867 (1.5); 1.7753 (2.0); 1.7652 (1.8); 1.7543 (1.7); 1.7436 (1.9); 1.7326 (1.1); 1.7199 (0.8); −0.0002 (13.6)

I-056: $^1$H-NMR(400.0 MHz, $d_6$-DMSO):

δ = 7.9206 (0.9); 7.3532 (0.9); 7.3373 (0.6); 7.3318 (0.9); 7.2077 (0.5); 7.2037 (0.6); 7.1949 (0.5); 7.1910 (0.6); 7.1878 (1.0); 7.1840 (1.0); 7.1751 (0.9); 7.1714 (1.0); 7.1675 (0.6); 7.1635 (0.6); 7.1546 (0.5); 7.1509 (0.6); 7.0766 (1.0); 7.0606 (1.3); 7.0574 (1.2); 7.0412 (0.7); 4.7386 (1.5); 4.6988 (1.7); 4.2400 (1.9); 4.2006 (1.6); 3.8045 (0.6); 3.7941 (0.8); 3.7838 (1.1); 3.7737 (0.8); 3.7633 (0.6); 3.3076 (49.6); 2.8956 (0.6); 2.8783 (1.6); 2.8613 (1.7); 2.8458 (1.5); 2.8284 (1.5); 2.8120 (1.4); 2.7942 (0.6); 2.5308 (1.4); 2.5229 (1.3); 2.5185 (2.5); 2.5096 (26.9); 2.5050 (59.5); 2.5004 (84.1); 2.4958 (59.9); 2.4912 (26.4); 2.3598 (1.1); 2.3406 (1.0); 2.3368 (1.1); 2.3272 (0.6); 2.3179 (1.0); 2.2882 (0.9); 2.2746 (1.1); 2.2641 (1.3); 2.2507 (1.3); 2.2465 (0.6); 2.2217 (2.1); 2.2090 (0.8); 2.1999 (1.6); 2.1867 (1.3); 2.1652 (1.3); 2.1271 (0.8); 2.1149 (0.6); 2.1032 (0.7); 2.0956 (0.9); 2.0910 (0.6); 2.0762 (0.5); 2.0714 (0.9); 1.7676 (0.6); 1.7566 (0.8); 1.7468 (0.6); 1.7355 (0.6); 1.7249 (0.7); 1.6672 (0.6); 1.6504 (1.2); 1.6336

-continued (1.5); 1.6169 (1.2); 1.6000 (0.6); 0.8217 (16.0); 0.8049 (15.4); −0.0002 (8.6)
I-057: $^{1}$H-NMR(400.1 MHz, $d_6$-DMSO):
δ = 7.3971 (7.6); 7.3790 (5.0); 7.3751 (4.6); 7.3584 (7.2); 7.3546 (7.8); 7.3484 (4.0); 7.3385 (4.9); 7.3330 (7.7); 7.3287 (6.4); 7.3122 (4.0); 7.3085 (3.7); 7.2099 (4.0); 7.2061 (4.0); 7.1972 (4.2); 7.1900 (7.8); 7.1864 (7.8); 7.1772 (7.6); 7.1739 (8.0); 7.1699 (4.9); 7.1660 (4.5); 7.1569 (4.1); 7.1536 (4.2); 7.0848 (7.8); 7.0687 (10.9); 7.0494 (5.5); 6.9468 (0.5); 6.8974 (7.5); 4.7474 (12.7); 4.7078 (14.6); 4.2404 (16.0); 4.2179 (0.4); 4.2007 (13.8); 3.8023 (2.5); 3.7915 (5.5); 3.7808 (7.4); 3.7706 (8.6); 3.7605 (7.5); 3.7498 (5.8); 3.7391 (2.8); 3.5598 (0.4); 3.5114 (0.4); 3.4589 (1.4); 3.4218 (1.6); 3.4080 (5.7); 3.3602 (1264.3); 3.3020 (0.4); 3.2922 (1.0); 3.2634 (1.2); 3.2470 (0.4); 3.2326 (0.3); 3.2116 (0.4); 3.1693 (2.2); 2.6794 (1.1); 2.6752 (2.3); 2.6707 (3.2); 2.6662 (2.4); 2.6618 (1.1); 2.6048 (0.4); 2.6001 (0.4); 2.5501 (1.4); 2.5455 (1.8); 2.5410 (2.0); 2.5240 (8.5); 2.5192 (12.0); 2.5106 (195.3); 2.5062 (398.9); 2.5016 (545.9); 2.4971 (389.8); 2.4926 (178.1); 2.4744 (16.3); 2.4633 (14.3); 2.4284 (0.4); 2.4105 (3.2); 2.3914 (4.0); 2.3876 (3.9); 2.3686 (9.0); 2.3494 (8.2); 2.3458 (7.5); 2.3379 (2.0); 2.3327 (3.4); 2.3274 (9.0); 2.3030 (0.4); 2.2872 (6.5); 2.2738 (7.6); 2.2631 (9.8); 2.2498 (9.8); 2.2321 (3.1); 2.2212 (5.4); 2.2083 (5.6); 2.1802 (12.7); 2.1658 (4.5); 2.1579 (12.8); 2.1452 (14.5); 2.1345 (5.2); 2.1227 (15.3); 2.1154 (8.3); 2.1107 (4.6); 2.1037 (2.8); 2.0958 (4.4); 2.0912 (5.6); 2.0716 (3.2); 1.7780 (3.3); 1.7662 (4.8); 1.7548 (6.8); 1.7444 (5.6); 1.7339 (5.5); 1.7231 (5.9); 1.7121 (3.8); 1.6993 (2.6)
I-058: $^{1}$H-NMR(400.0 MHz, $d_6$-DMSO):
δ = 9.5856 (2.2); 8.3724 (6.0); 7.3845 (3.1); 7.3633 (6.6); 7.3372 (6.3); 7.3175 (3.3); 7.2148 (3.8); 7.1953 (6.8); 7.1823 (6.8); 7.1618 (3.8); 7.0942 (2.6); 7.0802 (7.6); 7.0643 (7.4); 7.0453 (3.5); 4.7768 (3.5); 4.7369 (11.2); 4.6970 (8.8); 4.2390 (10.4); 4.1995 (9.5); 3.8528 (16.0); 3.8078 (14.7); 3.7971 (15.2); 3.7870 (15.8); 3.7764 (13.9); 3.1683 (6.6); 2.8096 (2.7); 2.7991 (2.9); 2.7719 (3.7); 2.7612 (3.8); 2.6747 (4.4); 2.6701 (6.0); 2.6658 (4.1); 2.5791 (115.5); 2.5404 (41.5); 2.5236 (16.2); 2.5189 (24.6); 2.5102 (357.0); 2.5057 (776.9); 2.5010 (1082.2); 2.4964 (752.8); 2.4919 (337.9); 2.4648 (7.9); 2.4539 (9.2); 2.4293 (9.1); 2.4186 (8.3); 2.4028 (6.4); 2.3865 (8.1); 2.3655 (14.1); 2.3543 (29.4); 2.3323 (7.1); 2.3276 (10.4); 2.2978 (4.6); 2.2845 (5.8); 2.2734 (8.1); 2.2606 (7.2); 2.2490 (3.8); 2.2318 (4.8); 2.2194 (4.2); 2.1713 (3.4); 2.1577 (7.3); 2.1368 (9.1); 2.1223 (9.1); 2.1010 (7.9); 2.0731 (2.6); 1.7782 (2.2); 1.7661 (2.9); 1.7541 (4.5); 1.7418 (4.2); 1.7222 (4.4); 0.0081 (7.5); −0.0002 (245.9); −0.0086 (6.7)
I-059: $^{1}$H-NMR(400.0 MHz, $d_6$-DMSO):
δ = 8.2264 (1.5); 8.1026 (5.0); 7.3780 (2.4); 7.3742 (2.4); 7.3577 (5.2); 7.3535 (5.7); 7.3321 (5.7); 7.3114 (2.9); 7.3077 (2.9); 7.2081 (3.3); 7.2041 (3.5); 7.1952 (3.4); 7.1882 (6.2); 7.1842 (6.4); 7.1755 (5.8); 7.1718 (6.5); 7.1677 (3.9); 7.1638 (3.8); 7.1551 (3.2); 7.1511 (3.4); 7.0772 (6.1); 7.0611 (8.3); 7.0419 (4.3); 5.8065 (3.2); 5.7932 (7.2); 5.7804 (5.9); 5.7675 (8.2); 5.7635 (4.0); 5.7543 (3.9); 5.7502 (8.7); 5.7373 (6.9); 5.7245 (8.7); 5.7112 (3.8); 5.1305 (4.3); 5.1261 (13.8); 5.1217 (14.7); 5.1173 (4.9); 5.0875 (4.0); 5.0831 (12.3); 5.0786 (12.9); 5.0742 (4.5); 5.0607 (5.2); 5.0567 (14.4); 5.0525 (13.4); 5.0485 (4.6); 5.0350 (4.8); 5.0310 (13.4); 5.0269 (12.8); 5.0229 (4.2); 4.7416 (9.7); 4.7019 (11.2); 4.2382 (12.1); 4.1985 (10.5); 3.8243 (2.0); 3.8132 (4.1); 3.8028 (5.8); 3.7926 (7.3); 3.7824 (5.8); 3.7722 (4.3); 3.7611 (2.0); 3.7060 (0.8); 3.6836 (3.4); 3.6792 (8.0); 3.6746 (9.0); 3.6698 (10.4); 3.6654 (16.0); 3.6609 (15.9); 3.6563 (10.8); 3.6517 (9.9); 3.6472 (8.5); 3.6428 (3.4); 3.6205 (0.9); 3.4150 (2.1); 3.3183 (241.7); 3.1678 (2.0); 2.6739 (2.0); 2.6694 (2.8); 2.6647 (2.1); 2.5597 (8.6); 2.5482 (8.7); 2.5244 (13.4); 2.5180 (10.9); 2.5095 (164.1); 2.5049 (354.0); 2.5003 (494.5); 2.4957 (343.6); 2.4911 (154.5); 2.4061 (2.6); 2.3871 (3.2); 2.3646 (7.2); 2.3449 (6.4); 2.3316 (2.7); 2.3269 (4.0); 2.3223 (7.4); 2.2878 (5.6); 2.2745 (6.7); 2.2637 (8.3); 2.2504 (9.2); 2.2462 (14.5); 2.2327 (3.4); 2.2246 (11.8); 2.2110 (10.6); 2.1896 (8.9); 2.1552 (3.0); 2.1359 (5.4); 2.1313 (2.9); 2.1237 (3.9); 2.1166 (3.1); 2.1119 (4.4); 2.1043 (6.1); 2.0999 (3.6); 2.0926 (2.4); 2.0849 (3.5); 2.0804 (4.6); 2.0712 (1.4); 2.0607 (2.1); 1.7829 (2.5); 1.7705 (3.8); 1.7596 (5.1); 1.7495 (4.3); 1.7386 (4.1); 1.7279 (4.5); 1.7165 (2.8); 1.7041 (2.0); 0.0080 (4.8); −0.0002 (171.8); −0.0085 (4.9); −0.1496 (0.6)
I-060: $^{1}$H-NMR(400.1 MHz, $d_6$-DMSO):
δ = 18.0164 (1.4); 13.3388 (1.8); 13.3093 (1.5); 7.8999 (16.0); 7.8951 (13.8); 7.8905 (8.8); 7.8828 (8.6); 7.7086 (4.5); 7.6871 (5.7); 7.6099 (1.4); 7.5926 (1.7); 7.5876 (1.9); 7.5620 (6.7); 7.5419 (10.4); 7.5217 (4.5); 7.3354 (1.4); 7.1419 (1.9); 7.1186 (1.5); 4.2575 (1.3); 4.2364 (1.7); 4.2203 (1.3); 4.0887 (1.6); 3.8133 (7.7); 3.5541 (9.2); 3.5127 (1.4); 3.4113 (2.2); 3.3672 (6.0); 3.3127 (3071.8); 3.2892 (66.0); 3.2581 (7.5); 3.2125 (2.2); 3.1757 (5.8); 3.1626 (6.1); 2.7009 (1.6); 2.6743 (7.0); 2.6700 (10.2); 2.6656 (7.9); 2.5995 (1.6); 2.5653 (2.4); 2.5232 (16.2); 2.5184 (27.4); 2.5100 (581.6); 2.5055 (1273.4); 2.5010 (1795.9); 2.4965 (1309.0); 2.4919 (630.4); 2.4379 (6.1); 2.4325 (5.1); 2.4073 (3.1); 2.3922 (2.7); 2.3518 (1.6); 2.3320 (8.0); 2.3279 (10.8); 2.3233 (7.8); 2.2795 (1.4); 2.2680 (1.7); 2.0730 (6.6); 0.0077 (3.3)
I-061: $^{1}$H-NMR(400.0 MHz, CDCl3):
δ = 7.5205 (0.6); 7.3304 (3.0); 7.3275 (5.3); 7.3236 (2.3); 7.3144 (3.3); 7.3101 (14.1); 7.3066 (7.6); 7.2947 (4.5); 7.2913 (11.2); 7.2616 (106.7); 7.2527 (5.8); 7.2493 (3.7); 7.2398 (1.9); 7.2343 (6.8); 7.2282 (1.6); 7.2193 (1.2); 7.2160 (2.1); 7.2119 (1.2); 7.1788 (9.8); 7.1750 (12.6); 7.1580 (9.3); 7.1173 (1.0); 7.1073 (1.5); 7.1021 (1.3); 7.0926 (3.5); 7.0801 (2.3); 7.0768 (2.4); 7.0740 (2.7); 7.0672 (3.0); 7.0646 (2.9); 7.0595 (1.6); 7.0496 (3.7); 7.0450 (7.6); 7.0380 (9.4); 7.0350 (6.1); 7.0294 (10.4); 7.0193 (4.9); 7.0085 (0.8); 7.0021 (0.7); 6.9976 (0.6); 5.4089 (2.2); 4.8403 (4.6); 4.8368 (4.5); 4.8016 (5.2); 4.7980 (5.1); 4.2210 (6.7); 4.1822 (6.0); 3.9311 (1.1); 3.9200 (2.3); 3.9090 (2.8); 3.8985 (3.2); 3.8890 (2.8); 3.8781 (2.3); 3.8670 (1.1); 3.5569 (0.9); 3.5405 (2.8); 3.5231 (5.7); 3.5112 (6.2); 3.5083 (6.2); 3.4964 (5.7); 3.4911 (3.1); 3.4795 (2.8); 3.4626 (0.9); 2.8151 (8.1); 2.7978 (16.0); 2.7805 (7.4); 2.5736 (4.6); 2.5627 (4.6); 2.5376 (5.4); 2.5267 (5.2); 2.5042 (1.0); 2.4846 (1.3); 2.4811 (1.2); 2.4610 (3.5); 2.4416 (3.2); 2.4380 (3.0); 2.4187 (3.0); 2.4067 (3.4); 2.3920 (3.8); 2.3826 (4.6); 2.3681 (4.6); 2.3640 (1.7); 2.3492 (1.2); 2.3397 (2.0); 2.3253 (2.0); 2.2579 (1.7); 2.2389 (2.8); 2.2341 (1.6); 2.2253 (2.0); 2.2198 (1.7); 2.2149 (2.3); 2.2063 (3.1); 2.2013 (1.8); 2.1960 (1.2); 2.1871 (1.8); 2.1821 (2.4); 2.1631 (1.2); 2.1082 (5.8); 2.0858 (5.7); 2.0722 (5.1); 2.0498 (4.9); 1.8087 (1.5); 1.7974 (1.7); 1.7946 (1.9); 1.7838 (2.2); 1.7741 (2.1); 1.7709 (1.8); 1.7647 (1.7); 1.7614 (2.1); 1.7504 (1.8); 1.7411 (1.5); 1.7381 (1.3); 1.7265 (1.2); 1.6036 (6.9); 0.0079 (1.1); −0.0002 (33.8); −0.0085 (0.9)
I-062: $^{1}$H-NMR(400.0 MHz, $d_6$-DMSO):
δ = 8.2750 (2.0); 8.2700 (2.5); 7.6771 (1.2); 7.6708 (1.4); 7.6565 (1.6); 7.6502 (1.8); 7.5218 (0.7); 7.5013 (0.6); 7.4833 (2.4); 7.4628 (2.0); 7.3544 (0.7); 7.3334 (0.8); 7.3127 (0.5); 7.1858 (0.7); 7.1728 (0.8); 7.1560 (0.5); 7.0954 (0.7); 7.0792 (0.9); 4.7492 (1.0); 4.7097 (1.2); 4.5538 (1.6); 4.5216 (0.6); 4.4838 (2.3); 4.4599 (2.4); 4.4220 (0.7); 4.2795 (1.2); 4.2402 (1.1); 3.8949 (0.6); 3.8855 (0.7); 3.8733 (0.6); 3.8641 (0.6); 3.5216 (4.3); 3.1666 (0.6); 2.8917 (16.0); 2.8742 (0.8); 2.8433 (1.0); 2.8333 (1.0); 2.7526

-continued (3.9); 2.6704 (0.6); 2.5962 (1.0); 2.5741 (1.0); 2.5552 (0.8); 2.5329 (0.8); 2.5238 (1.3); 2.5192 (1.9); 2.5105 (33.8); 2.5059 (74.9); 2.5013 (105.5); 2.4967 (74.0); 2.4921 (33.0); 2.4549 (0.5); 2.4312 (0.8); 2.4139 (0.7); 2.3281 (0.7); 2.3236 (0.6); 2.2685 (0.5); 2.2555 (0.9); 2.2437 (0.9); 2.2162 (1.4); 2.2074 (1.0); 2.1996 (0.9); 2.1813 (0.9); 1.7027 (0.6); 0.0080 (1.3); −0.0002 (48.4); −0.0085 (1.4)

I-063: $^1$H-NMR(400.0 MHz, $d_6$-DMSO):

δ = 7.9665 (0.6); 7.9501 (0.6); 7.3617 (0.6); 7.3579 (0.7); 7.3359 (0.7); 7.3317 (0.6); 7.1908 (0.7); 7.1872 (0.7); 7.1781 (0.7); 7.1747 (0.7); 7.0763 (0.5); 7.0600 (0.8); 4.7313 (0.7); 4.6909 (0.8); 4.2301 (1.4); 4.1901 (1.2); 4.0786 (0.6); 4.0619 (0.7); 4.0456 (0.6); 3.7653 (0.6); 3.7550 (0.5); 3.5995 (1.3); 3.5639 (16.0); 3.5626 (15.0); 2.5196 (0.6); 2.5109 (9.7); 2.5064 (21.4); 2.5017 (29.9); 2.4971 (20.7); 2.4925 (9.2); 2.4816 (1.0); 2.4754 (0.7); 2.4707 (0.7); 2.4644 (1.2); 2.4478 (1.0); 2.4432 (1.3); 2.4361 (0.8); 2.4272 (1.8); 2.4104 (1.0); 2.3955 (1.2); 2.3923 (1.3); 2.3784 (1.3); 2.3749 (1.4); 2.3544 (1.0); 2.3406 (0.5); 2.3369 (0.9); 2.3316 (0.7); 2.2648 (0.8); 2.2541 (0.6); 2.1673 (0.6); 2.1502 (0.7); 2.1460 (0.7); 2.1326 (0.8); 2.1287 (0.7); 2.1153 (0.9); 2.1114 (1.0); 2.0938 (0.8); 2.0804 (0.5); 1.7412 (0.5); 1.7306 (0.6); 1.0617 (6.8); 1.0450 (6.7); −0.0002 (6.2)

I-064: $^1$H-NMR(400.1 MHz, CDCl3):

δ = 7.5231 (0.6); 7.5199 (0.6); 7.2643 (96.1); 7.2611 (98.2); 7.1288 (0.4); 7.1156 (0.9); 7.1039 (1.4); 7.0955 (1.2); 7.0877 (1.6); 7.0791 (1.8); 7.0607 (6.4); 7.0531 (6.2); 7.0415 (2.5); 7.0002 (0.5); 6.9972 (0.6); 4.9006 (2.7); 4.8619 (3.0); 4.7252 (0.9); 4.7167 (1.0); 4.6977 (1.8); 4.6892 (2.0); 4.6711 (1.0); 4.6622 (1.0); 4.2537 (3.3); 4.2144 (3.0); 3.9096 (0.5); 3.8986 (0.9); 3.8881 (1.4); 3.8769 (1.7); 3.8671 (1.6); 3.8576 (1.1); 3.8466 (0.6); 2.7503 (1.7); 2.7432 (1.8); 2.7407 (1.7); 2.7121 (2.1); 2.7048 (2.1); 2.6878 (0.4); 2.5606 (0.6); 2.5439 (0.8); 2.5186 (1.9); 2.4974 (1.7); 2.4771 (1.5); 2.4433 (1.1); 2.4280 (1.4); 2.4189 (1.6); 2.4037 (2.3); 2.3879 (2.5); 2.3852 (2.6); 2.3792 (1.4); 2.3642 (2.9); 2.3495 (1.8); 2.3468 (1.8); 2.3268 (1.6); 2.3240 (1.6); 2.3076 (0.6); 2.2900 (1.0); 2.2826 (0.7); 2.2738 (1.2); 2.2693 (1.0); 2.2657 (1.0); 2.2573 (1.4); 2.2496 (1.0); 2.2362 (1.0); 2.2335 (1.0); 2.2159 (0.5); 1.9461 (1.5); 1.9169 (1.6); 1.8478 (0.7); 1.8366 (1.2); 1.8243 (1.5); 1.8123 (2.0); 1.8040 (2.1); 1.7920 (2.4); 1.7792 (1.7); 1.6939 (3.0); 1.6616 (3.0); 1.5546 (28.1); 1.5526 (28.0); 1.5217 (0.5); 1.4822 (1.1); 1.4749 (1.1); 1.4678 (1.1); 1.3812 (0.9); 1.3515 (1.8); 1.3233 (1.1); 1.0874 (0.6); 1.0567 (1.5); 1.0302 (1.7); 1.0226 (1.4); 0.9976 (0.8); 0.9920 (0.7); 0.9810 (1.0); 0.9683 (0.6); 0.9510 (2.6); 0.9106 (14.7); 0.9022 (16.0); 0.8970 (15.2); 0.8944 (14.7); 0.8872 (12.8); 0.8848 (13.2); 0.8449 (1.4); 0.8152 (0.5); 0.7507 (12.5); 0.7333 (12.2); 0.0032 (42.7)

I-065: $^1$H-NMR(400.0 MHz, $d_6$-DMSO):

δ = 12.3773 (1.5); 7.3837 (3.2); 7.3797 (3.5); 7.3633 (6.9); 7.3591 (7.6); 7.3531 (4.0); 7.3434 (4.9); 7.3372 (7.6); 7.3332 (6.5); 7.3171 (4.0); 7.3130 (3.9); 7.2100 (4.2); 7.2060 (4.4); 7.1973 (4.4); 7.1933 (5.3); 7.1901 (8.0); 7.1863 (8.4); 7.1773 (7.7); 7.1738 (8.5); 7.1698 (5.2); 7.1658 (5.1); 7.1570 (4.5); 7.1533 (4.8); 7.0952 (8.3); 7.0792 (11.0); 7.0598 (5.5); 4.7425 (12.4); 4.7031 (14.4); 4.2541 (16.0); 4.2145 (13.8); 3.7884 (2.7); 3.7780 (5.1); 3.7672 (7.1); 3.7579 (7.7); 3.7473 (6.9); 3.7367 (5.4); 3.7262 (2.2); 3.6385 (0.9); 3.3168 (89.6); 3.1651 (0.6); 2.7041 (12.6); 2.6939 (12.6); 2.6793 (1.6); 2.6747 (3.0); 2.6701 (4.8); 2.6644 (17.6); 2.6541 (15.4); 2.5618 (1.4); 2.5573 (1.7); 2.5528 (1.2); 2.5403 (1.6); 2.5236 (9.4); 2.5189 (14.8); 2.5102 (203.5); 2.5056 (437.7); 2.5010 (608.9); 2.4964 (428.8); 2.4919 (192.2); 2.4614 (2.0); 2.4563 (2.4); 2.4518 (2.2); 2.4469 (3.4); 2.4290 (4.0); 2.4192 (2.3); 2.4052 (10.4); 2.3986 (17.6); 2.3877 (7.9); 2.3805 (8.1); 2.3766 (17.3); 2.3650 (4.4); 2.3588 (13.7); 2.3498 (2.1); 2.3368 (14.3); 2.3279 (4.2); 2.3232 (2.8); 2.2887 (6.0); 2.2757 (6.7); 2.2642 (11.0); 2.2513 (10.8); 2.2363 (1.0); 2.2229 (9.2); 2.2199 (9.6); 2.2115 (6.8); 2.2059 (6.6); 2.1956 (5.9); 2.1900 (4.7); 2.1777 (7.1); 2.1712 (3.6); 2.1656 (2.7); 2.1584 (4.6); 2.1524 (4.1); 2.1340 (2.4); 2.0733 (1.0); 1.7823 (1.1); 1.7603 (3.1); 1.7547 (6.9); 1.7436 (7.0); 1.7307 (7.3); 1.7255 (4.2); 1.7198 (3.9); 1.7140 (4.9); 1.7008 (4.4); 1.6883 (2.8); 0.1461 (1.0); 0.0512 (0.6); 0.0080 (9.4); 0.0062 (3.6); −0.0002 (315.7); − 0.0060 (4.4); −0.0069 (3.9); −0.0085 (9.8); −0.0500 (1.2); −0.1495 (1.0)

I-066: $^1$H-NMR(400.1 MHZ, $d_6$-DMSO):

δ = 19.7654 (0.7); 19.7059 (0.7); 17.6711 (0.8); 17.1313 (0.7); 14.0023 (0.7); 12.6881 (0.7); 11.6932 (0.8); 8.3710 (7.3); 8.3494 (7.0); 7.4486 (0.7); 7.3835 (2.1); 7.3638 (4.8); 7.3410 (4.7); 7.3190 (2.7); 7.2892 (0.8); 7.2104 (2.6); 7.1910 (5.5); 7.1789 (6.0); 7.1607 (5.7); 7.1546 (6.4); 7.1441 (8.4); 7.1390 (12.3); 7.1300 (12.0); 7.1250 (11.6); 7.1018 (15.0); 7.0957 (16.0); 7.0781 (12.2); 7.0590 (3.6); 6.6020 (0.7); 4.9535 (3.4); 4.9384 (4.4); 4.7582 (7.4); 4.7184 (8.7); 4.2744 (4.6); 4.2540 (5.1); 4.2354 (4.1); 4.2140 (4.2); 3.8711 (1.9); 3.8605 (2.8); 3.8499 (3.7); 3.8371 (3.8); 3.8264 (3.4); 3.8173 (3.0); 3.8057 (1.6); 3.5814 (0.7); 3.5223 (0.7); 3.4939 (0.8); 3.4290 (1.7); 3.3282 (392.0); 3.2339 (1.8); 3.2191 (1.6); 3.1935 (1.2); 3.1687 (10.9); 2.8908 (2.3); 2.7728 (1.8); 2.7438 (3.8); 2.7307 (7.0); 2.7181 (6.0); 2.7034 (6.3); 2.6704 (6.4); 2.6468 (1.5); 2.6102 (0.9); 2.5963 (1.2); 2.5828 (3.6); 2.5732 (5.3); 2.5653 (5.2); 2.5497 (7.2); 2.5408 (10.4); 2.5061 (759.5); 2.5017 (1025.9); 2.4973 (785.6); 2.4215 (3.1); 2.3994 (3.1); 2.3813 (3.8); 2.3736 (4.1); 2.3555 (4.9); 2.3290 (7.1); 2.3245 (5.5); 2.3106 (2.9); 2.2989 (3.8); 2.2867 (5.8); 2.2815 (5.9); 2.2704 (6.1); 2.2609 (6.3); 2.2476 (7.6); 2.2348 (5.5); 2.2263 (4.3); 2.2145 (4.0); 2.1923 (2.1); 2.1687 (2.4); 2.1575 (3.1); 2.1395 (3.1); 2.1243 (2.4); 2.1006 (1.8); 2.0718 (3.2); 2.0201 (0.7); 1.9080 (0.7); 1.8353 (8.2); 1.8253 (9.3); 1.8157 (9.2); 1.7441 (1.9); 1.7206 (3.0); 1.7063 (4.1); 1.6799 (3.3); 1.6650 (3.2); 1.6491 (3.1); 1.6271 (3.9); 1.6062 (2.9); 0.1451 (0.8); 0.0082 (5.3)

I-067: $^1$H-NMR(400.1 MHz, CDCl3):

δ = 7.2620 (55.2); 7.2122 (0.6); 7.1295 (0.4); 7.1162 (0.8); 7.1047 (1.5); 7.0951 (0.9); 7.0869 (1.6); 7.0803 (1.6); 7.0760 (1.1); 7.0621 (6.5); 7.0523 (6.0); 7.0443 (2.1); 7.0383 (1.7); 4.9128 (1.9); 4.9094 (2.0); 4.9008 (0.5); 4.8741 (2.2); 4.8705 (2.2); 4.8622 (0.6); 4.8585 (0.5); 4.7174 (1.0); 4.7065 (1.0); 4.6968 (0.5); 4.6902 (2.0); 4.6793 (2.0); 4.6630 (1.1); 4.6520 (1.0); 4.2507 (0.7); 4.2430 (3.0); 4.2042 (2.7); 3.8924 (0.5); 3.8821 (0.9); 3.8716 (1.3); 3.8612 (1.4); 3.8499 (1.2); 3.8395 (0.9); 3.8293 (0.5); 2.7500 (0.4); 2.7401 (0.5); 2.7321 (2.0); 2.7227 (2.0); 2.7117 (0.5); 2.7016 (0.6); 2.6944 (2.6); 2.6850 (2.5); 2.5609 (0.6); 2.5425 (0.7); 2.5367 (0.7); 2.5180 (1.8); 2.4996 (1.4); 2.4940 (1.4); 2.4757 (1.4); 2.4378 (1.2); 2.4237 (1.4); 2.4183 (0.6); 2.4132 (1.7); 2.4018 (3.3); 2.3845 (0.8); 2.3794 (2.9); 2.3702 (1.1); 2.3642 (2.4); 2.3564 (1.0); 2.3465 (0.6); 2.3416 (2.1); 2.3239 (0.4); 2.2938 (0.7); 2.2746 (1.2); 2.2696 (0.7); 2.2614 (0.9); 2.2557 (0.8); 2.2499 (0.9); 2.2421 (1.2); 2.2368 (0.9); 2.2311 (0.6); 2.2229 (0.7); 2.2173 (0.9); 2.1985 (0.5); 1.9647 (0.5); 1.9530 (1.1); 1.9456 (0.9); 1.9349 (0.7); 1.9301 (0.8); 1.9228 (1.2); 1.9005 (0.7); 1.8872 (0.8); 1.8759 (1.2); 1.8655 (0.9); 1.8538 (0.9); 1.8431 (1.1); 1.8324 (0.8); 1.8240 (0.6); 1.8182 (0.9); 1.8073 (1.0); 1.8005 (1.1); 1.7896 (1.4); 1.7831 (1.3); 1.7722 (1.0); 1.7653 (1.0); 1.7547 (0.4); 1.7484 (0.4); 1.6921 (2.3); 1.6850 (1.9); 1.6660 (2.3); 1.6597 (2.4); 1.6516 (1.6); 1.6446 (0.6); 1.5676 (16.8); 1.5181 (0.4); 1.5113 (0.4); 1.5033 (0.5); 1.4953 (0.6); 1.4896 (0.7);

-continued 1.4816 (0.8); 1.4737 (0.8); 1.4654 (0.9); 1.4572 (0.7); 1.4510 (0.6); 1.4438 (0.6); 1.4357 (0.5); 1.3961 (0.5); 1.3883 (0.8); 1.3810 (0.6); 1.3583 (1.4); 1.3384 (0.6); 1.3303 (1.0); 1.3228 (0.7); 1.0850 (0.6); 1.0596 (1.1); 1.0531 (1.3); 1.0284 (1.6); 1.0206 (1.2); 0.9958 (1.6); 0.9893 (0.6); 0.9785 (0.3); 0.9657 (2.4); 0.9488 (0.6); 0.9376 (2.2); 0.9101 (16.0); 0.8988 (15.3); 0.8938 (15.8); 0.8814 (14.5); 0.8607 (0.4); 0.8484 (1.1); 0.8441 (1.1); 0.8186 (0.4); 0.7478 (13.9); 0.7304 (13.5); 0.0082 (0.7); 0.0000 (23.9)

I-068: $^1$H-NMR(400.0 MHz, $d_6$-DMSO):

δ = 10.8315 (1.3); 8.3271 (0.8); 8.3077 (1.5); 8.2885 (0.9); 7.5321 (0.9); 7.5210 (1.0); 7.5131 (1.0); 7.5019 (1.1); 7.3409 (0.9); 7.3286 (2.6); 7.3084 (3.1); 7.1670 (0.7); 7.1516 (0.8); 7.1346 (0.8); 7.1158 (2.7); 7.0659 (0.7); 7.0628 (0.7); 7.0482 (1.5); 7.0334 (1.2); 7.0303 (1.0); 7.0253 (0.8); 6.9860 (1.3); 6.9836 (1.4); 6.9666 (2.0); 6.9495 (1.6); 6.9326 (0.6); 6.9300 (0.6); 4.7106 (0.6); 4.6801 (0.8); 4.6716 (0.8); 4.6404 (0.8); 4.5032 (0.7); 4.4909 (0.7); 4.4827 (0.8); 4.4703 (0.7); 4.1974 (0.8); 4.1574 (0.7); 4.1352 (0.9); 4.0958 (0.8); 3.6900 (0.5); 3.6808 (0.7); 3.6703 (0.8); 3.6601 (0.8); 3.6508 (0.6); 3.4760 (16.0); 3.1850 (0.6); 3.1738 (0.6); 3.1679 (0.7); 3.1491 (0.9); 3.1384 (0.8); 3.0043 (1.1); 2.9815 (1.1); 2.9679 (0.8); 2.9455 (0.8); 2.6701 (0.6); 2.5341 (0.7); 2.5237 (1.5); 2.5189 (2.5); 2.5103 (33.0); 2.5057 (71.6); 2.5011 (99.7); 2.4965 (69.4); 2.4919 (31.1); 2.4730 (0.8); 2.3278 (0.6); 2.2630 (0.6); 2.2436 (0.9); 2.2244 (0.5); 2.2103 (0.7); 2.1970 (0.7); 2.1878 (1.3); 2.1754 (1.9); 2.1636 (1.4); 2.1518 (1.3); 2.1406 (0.6); 2.0727 (0.5); −0.0002 (5.4)

I-069: $^1$H-NMR(400.0 MHz, $d_6$-DMSO):

δ = 16.6531 (1.0); 16.4917 (1.2); 10.8380 (7.6); 8.3084 (7.5); 8.2888 (7.4); 7.5218 (8.8); 7.5025 (9.6); 7.3612 (2.6); 7.3371 (5.5); 7.3285 (13.2); 7.3083 (15.1); 7.2952 (2.2); 7.1709 (3.0); 7.1473 (4.9); 7.1350 (5.2); 7.1264 (3.7); 7.1167 (16.0); 7.1112 (12.4); 7.0658 (5.2); 7.0456 (9.4); 7.0281 (6.7); 7.0010 (4.2); 6.9845 (6.2); 6.9696 (9.2); 6.9671 (10.0); 6.9498 (11.2); 6.9324 (5.1); 6.9301 (4.5); 4.6804 (6.9); 4.6414 (7.6); 4.5027 (2.9); 4.4907 (3.8); 4.4816 (4.3); 4.4703 (4.2); 4.4612 (3.1); 4.4480 (2.3); 4.1353 (7.8); 4.0954 (7.4); 3.6820 (3.4); 3.6711 (4.3); 3.6609 (4.4); 3.6489 (3.8); 3.6396 (3.4); 3.4468 (130.7); 3.4028 (10.7); 3.3984 (10.2); 3.3937 (10.1); 3.3891 (9.3); 3.3843 (7.9); 3.3794 (5.9); 3.3739 (4.2); 3.3683 (3.6); 3.3634 (3.4); 3.3583 (3.8); 3.3542 (3.6); 3.3498 (3.4); 3.3244 (4.1); 3.3127 (2.1); 3.3078 (1.2); 3.3004 (1.2); 3.2956 (2.7); 3.2906 (3.3); 3.2855 (2.8); 3.2799 (2.2); 3.2338 (2.1); 3.2291 (2.1); 3.2236 (2.1); 3.2187 (2.8); 3.2143 (4.8); 3.2076 (3.4); 3.1850 (4.2); 3.1722 (5.5); 3.1678 (7.6); 3.1475 (6.0); 3.1365 (5.6); 3.1015 (1.3); 3.0458 (1.3); 3.0411 (1.4); 3.0048 (5.7); 2.9815 (5.6); 2.9676 (5.3); 2.9456 (4.1); 2.6705 (3.7); 2.6655 (2.5); 2.6364 (1.1); 2.5478 (1.9); 2.5103 (226.6); 2.5058 (476.1); 2.5012 (643.3); 2.4966 (445.4); 2.4920 (197.1); 2.4729 (9.5); 2.4609 (5.4); 2.4563 (7.0); 2.4518 (7.8); 2.4470 (5.2); 2.4426 (2.8); 2.4060 (1.9); 2.3817 (1.7); 2.3280 (3.9); 2.3233 (3.0); 2.3039 (2.5); 2.2817 (3.4); 2.2621 (4.9); 2.2411 (5.5); 2.2188 (4.4); 2.2100 (6.2); 2.1877 (9.8); 2.1757 (9.4); 2.1639 (5.8); 2.1523 (8.2); 2.1326 (2.3); 2.1217 (3.2); 2.1100 (2.3); 2.0729 (2.2); 2.0162 (1.3); 1.9686 (1.5); 1.9483 (3.3); 1.9348 (2.8); 1.9243 (2.8); 1.9158 (4.2); 1.8909 (3.6); 1.8859 (2.2); 1.8811 (1.8); 1.8721 (2.0); 1.8575 (1.2); 1.8273 (1.2); 1.8158 (1.2); 1.7611 (2.1); 1.7379 (1.4); 1.7304 (1.3); 1.7086 (3.0); 1.7038 (3.0); 1.6981 (3.3); 1.6875 (1.9); 1.6635 (5.3); 1.6538 (2.8); 1.6417 (2.7); 1.6305 (2.2); 1.6066 (2.5); 1.6019 (2.6); 1.5973 (2.6); 1.4791 (1.1); −0.0002 (19.8)

I-070: $^1$H-NMR(400.0 MHz, $d_6$-DMSO):

δ = 11.8093 (5.6); 7.5295 (2.0); 7.5212 (2.0); 7.5135 (3.2); 7.5050 (2.9); 7.5030 (3.0); 7.4960 (1.7); 7.4873 (2.2); 7.2311 (1.2); 7.2266 (1.1); 7.2153 (11.8); 7.2119 (6.5); 7.2060 (5.7); 7.1994 (7.2); 7.1964 (10.7); 7.1857 (0.6); 7.1800 (0.7); 7.0726 (2.1); 6.9448 (2.0); 4.7058 (3.8); 4.6662 (4.4); 4.2413 (4.7); 4.2012 (4.0); 3.9643 (4.0); 3.8630 (0.7); 3.8528 (1.5); 3.8422 (2.1); 3.8322 (2.4); 3.8220 (2.0); 3.8116 (1.5); 3.8020 (0.7); 3.3888 (70.2); 3.2101 (64.7); 3.1681 (16.0); 2.7502 (3.2); 2.7397 (3.2); 2.7120 (4.0); 2.7015 (3.8); 2.6788 (0.8); 2.6742 (1.6); 2.6695 (2.4); 2.6650 (1.6); 2.6602 (0.8); 2.5554 (0.5); 2.5507 (0.8); 2.5460 (0.8); 2.5398 (1.5); 2.5231 (6.2); 2.5183 (9.1); 2.5097 (130.5); 2.5052 (276.0); 2.5005 (376.9); 2.4959 (262.8); 2.4913 (118.3); 2.4408 (4.5); 2.4188 (4.7); 2.4022 (4.7); 2.3807 (5.7); 2.3597 (1.6); 2.3365 (0.9); 2.3319 (1.7); 2.3273 (2.3); 2.3227 (1.6); 2.3180 (0.8); 2.3083 (1.7); 2.2960 (2.0); 2.2842 (2.9); 2.2721 (2.8); 2.2553 (0.6); 2.2426 (1.9); 2.2319 (3.0); 2.2145 (2.2); 2.2028 (1.5); 2.1956 (1.2); 2.1904 (1.2); 2.1836 (2.3); 2.1715 (0.7); 2.1638 (1.3); 2.1593 (1.5); 2.1400 (0.6); 2.0719 (1.0); 1.7926 (0.8); 1.7841 (1.7); 1.7728 (1.6); 1.7622 (1.8); 1.7544 (1.9); 1.7423 (1.4); 1.7295 (1.2); 1.7181 (0.8); 0.0120 (0.6); 0.0080 (1.3); −0.0002 (46.8); −0.0085 (1.3)

I-071: $^1$H-NMR(400.0 MHz, $d_6$-DMSO):

δ = 7.3718 (1.6); 7.3679 (1.7); 7.3514 (3.5); 7.3476 (3.8); 7.3415 (2.0); 7.3316 (2.4); 7.3257 (3.9); 7.3050 (2.0); 7.3016 (1.9); 7.2046 (2.2); 7.2008 (2.3); 7.1919 (2.3); 7.1848 (4.1); 7.1810 (4.3); 7.1721 (4.0); 7.1685 (4.3); 7.1645 (2.6); 7.1605 (2.5); 7.1516 (2.2); 7.1482 (2.3); 7.0849 (4.2); 7.0690 (5.7); 7.0496 (2.8); 4.7002 (6.5); 4.6608 (7.8); 4.2973 (8.4); 4.2575 (7.0); 3.9112 (1.3); 3.8999 (2.5); 3.8912 (3.3); 3.8802 (4.7); 3.8711 (2.9); 3.8606 (2.5); 3.8492 (1.1); 3.4027 (98.0); 3.3419 (2.7); 3.3248 (4.7); 3.3164 (3.7); 3.3078 (3.4); 3.2998 (6.0); 3.2827 (3.4); 3.2515 (1.1); 3.2345 (2.0); 3.2221 (4.4); 3.2047 (13.6); 3.1875 (16.0); 3.1778 (3.8); 3.1703 (7.4); 3.1613 (5.2); 3.1444 (2.8); 2.6709 (5.0); 2.6594 (4.5); 2.6309 (5.8); 2.6190 (5.5); 2.5234 (3.1); 2.5187 (4.6); 2.5101 (70.3); 2.5055 (151.7); 2.5009 (210.5); 2.4963 (146.2); 2.4917 (65.3); 2.4619 (2.2); 2.4441 (2.5); 2.4354 (1.9); 2.4204 (5.1); 2.4040 (8.7); 2.3975 (4.0); 2.3841 (7.5); 2.3642 (4.8); 2.3438 (4.6); 2.3323 (1.0); 2.3277 (1.4); 2.3231 (1.0); 2.2797 (3.1); 2.2669 (3.4); 2.2555 (5.3); 2.2426 (5.3); 2.2269 (0.7); 2.2142 (4.1); 2.2071 (6.0); 2.1924 (3.2); 2.1811 (2.8); 2.1753 (2.3); 2.1629 (4.0); 2.1571 (1.9); 2.1511 (1.3); 2.1438 (2.3); 2.1385 (2.4); 2.1193 (1.2); 2.0717 (0.9); 1.8589 (0.6); 1.8458 (1.3); 1.8289 (3.7); 1.8174 (4.6); 1.8111 (5.8); 1.8009 (6.6); 1.7936 (4.8); 1.7848 (5.2); 1.7766 (2.6); 1.7690 (2.6); 1.7617 (1.4); 1.7479 (2.8); 1.7383 (2.7); 1.7319 (5.9); 1.7209 (8.6); 1.7177 (7.8); 1.7097 (5.3); 1.7003 (8.8); 1.6915 (4.0); 1.6861 (5.8); 1.6796 (3.4); 1.6677 (3.1); 1.6548 (2.0); −0.0002 (1.6)

I-072: $^1$H-NMR(400.1 MHz, $d_6$-DMSO):

δ = 11.7028 (3.9); 7.3857 (0.5); 7.3819 (0.6); 7.3615 (1.4); 7.3394 (1.4); 7.3190 (0.7); 7.3154 (0.7); 7.2125 (0.6); 7.2092 (0.7); 7.1926 (1.4); 7.1892 (1.5); 7.1770 (1.5); 7.1690 (0.9); 7.1595 (0.8); 7.1564 (0.8); 7.0754 (1.4); 7.0590 (2.0); 7.0403 (1.0); 4.7263 (2.3); 4.6864 (2.7); 4.2446 (2.8); 4.2045 (2.4); 3.8459 (0.4); 3.8360 (0.9); 3.8252 (1.3); 3.8151 (1.5); 3.8046 (1.3); 3.7948 (1.0); 3.7849 (0.5); 3.3584 (3.1); 3.3400 (10.5); 3.3219 (14.3); 3.3036 (4.2); 3.1691 (10.1); 2.7798 (1.8); 2.7697 (1.8); 2.7415 (2.2); 2.7313 (2.2); 2.5231 (0.4); 2.5098 (14.4); 2.5054 (31.9); 2.5009 (45.4); 2.4964 (33.9); 2.4919 (16.8); 2.4584 (2.4); 2.4364 (2.4); 2.4203 (2.4); 2.3983 (3.2); 2.3797 (1.5); 2.3584 (1.1); 2.3278 (0.3); 2.3045 (1.0); 2.2919 (1.2); 2.2802 (1.6); 2.2677 (1.6); 2.2511 (0.4); 2.2385 (1.0); 2.2276 (1.2); 2.2229 (1.0); 2.2046 (1.2); 2.1928 (0.8); 2.1857 (0.7); 2.1805 (0.8); 2.1736 (1.3); 2.1616 (0.5); 2.1539 (0.8); 2.1495

-continued (0.9); 2.1299 (0.4); 1.7782 (0.5); 1.7684 (1.0); 1.7570 (1.0); 1.7463 (1.1); 1.7383 (1.2); 1.7259 (0.9); 1.7143 (0.7); 1.7023 (0.4); 1.2086 (7.2); 1.1903 (16.0); 1.1719 (7.1); 0.0083 (0.3)

I-073: $^1$H-NMR(400.0 MHz, $d_6$-DMSO):

δ = 7.3683 (0.6); 7.3479 (1.4); 7.3258 (1.4); 7.3056 (0.6); 7.2030 (0.8); 7.1872 (1.5); 7.1832 (1.5); 7.1708 (1.6); 7.1626 (1.0); 7.1503 (0.9); 7.0857 (1.6); 7.0696 (2.1); 7.0501 (1.0); 4.7345 (2.2); 4.6951 (2.5); 4.6192 (0.6); 4.2853 (2.8); 4.2456 (2.4); 3.9014 (0.8); 3.8920 (1.2); 3.8815 (1.6); 3.8720 (1.2); 3.8615 (0.9); 3.3604 (1.6); 3.3239 (383.6); 3.2732 (0.9); 3.2547 (0.6); 3.2178 (4.1); 3.2098 (3.5); 3.2035 (3.9); 3.1999 (4.0); 3.1922 (3.5); 3.1784 (1.6); 3.1682 (1.7); 3.1587 (0.6); 2.7281 (1.8); 2.7166 (1.8); 2.6989 (2.8); 2.6881 (2.5); 2.6742 (3.8); 2.6694 (4.3); 2.6648 (3.0); 2.6603 (1.3); 2.5368 (1.7); 2.5229 (10.8); 2.5182 (16.4); 2.5095 (227.4); 2.5050 (496.0); 2.5003 (692.8); 2.4957 (481.1); 2.4911 (214.4); 2.4666 (2.4); 2.4506 (3.4); 2.4299 (2.8); 2.4254 (1.8); 2.4105 (2.4); 2.3898 (2.6); 2.3364 (1.5); 2.3318 (3.1); 2.3271 (4.3); 2.3225 (3.0); 2.3178 (1.4); 2.2761 (1.2); 2.2633 (1.2); 2.2517 (2.0); 2.2390 (1.8); 2.2106 (1.5); 2.2040 (2.1); 2.1897 (1.2); 2.1780 (1.0); 2.1723 (0.9); 2.1597 (1.4); 2.1401 (0.8); 2.1351 (0.9); 2.0722 (1.1); 1.6868 (1.2); 1.6756 (1.2); 1.6644 (1.0); 1.6460 (0.9); 1.6328 (0.8); 1.6204 (0.5); 1.1575 (0.8); 1.0315 (6.0); 1.0138 (14.6); 0.9960 (6.0); 0.9754 (7.1); 0.9577 (16.0); 0.9400 (6.9); 0.8308 (0.5); 0.0080 (5.1); −0.0002 (202.4); −0.0085 (6.1); −0.1497 (0.7)

I-074: $^1$H-NMR(400.1 MHz, $d_6$-DMSO):

δ = 7.3803 (2.0); 7.3765 (2.2); 7.3596 (4.3); 7.3560 (4.9); 7.3503 (2.7); 7.3400 (3.0); 7.3340 (4.9); 7.3303 (4.4); 7.3136 (2.5); 7.3101 (2.5); 7.2090 (2.5); 7.2052 (2.9); 7.1946 (9.0); 7.1894 (5.9); 7.1856 (5.6); 7.1761 (4.8); 7.1729 (5.4); 7.1690 (3.6); 7.1650 (3.2); 7.1559 (2.6); 7.1526 (2.8); 7.0723 (5.4); 7.0629 (16.0); 7.0566 (8.2); 7.0369 (3.8); 6.9312 (7.1); 4.7048 (8.2); 4.6648 (9.6); 4.4857 (0.3); 4.4346 (0.3); 4.3883 (0.3); 4.3790 (0.3); 4.3558 (0.3); 4.3214 (0.4); 4.3090 (0.4); 4.2590 (10.2); 4.2189 (8.7); 4.1710 (0.4); 4.1520 (0.4); 4.1467 (0.4); 4.1134 (0.4); 4.0808 (0.4); 4.0718 (0.4); 4.0420 (0.4); 4.0184 (0.4); 3.9887 (0.4); 3.9614 (0.3); 3.9413 (0.3); 3.9202 (0.4); 3.8772 (0.4); 3.8585 (1.8); 3.8483 (3.3); 3.8376 (4.6); 3.8273 (5.2); 3.8171 (4.5); 3.8069 (3.6); 3.7970 (1.7); 3.1694 (0.5); 2.8330 (6.0); 2.8230 (6.2); 2.7935 (7.6); 2.7835 (7.5); 2.6743 (0.7); 2.6696 (0.9); 2.6650 (0.7); 2.5567 (0.6); 2.5522 (0.9); 2.5495 (1.0); 2.5448 (0.8); 2.5230 (2.3); 2.5166 (9.3); 2.5098 (43.7); 2.5053 (97.0); 2.5007 (138.0); 2.4960 (106.3); 2.4916 (51.6); 2.4774 (7.1); 2.4552 (6.4); 2.4478 (2.8); 2.4286 (2.4); 2.4214 (2.2); 2.4054 (5.5); 2.3868 (4.7); 2.3829 (4.6); 2.3655 (3.1); 2.3433 (0.5); 2.3369 (0.4); 2.3322 (0.6); 2.3275 (1.0); 2.3228 (0.8); 2.3018 (3.4); 2.2894 (3.9); 2.2775 (5.8); 2.2651 (5.9); 2.2490 (0.8); 2.2359 (3.9); 2.2272 (6.8); 2.2110 (4.0); 2.1993 (3.1); 2.1927 (2.6); 2.1865 (2.3); 2.1805 (4.6); 2.1754 (2.5); 2.1684 (1.6); 2.1609 (2.6); 2.1561 (3.0); 2.1368 (1.3); 2.0710 (1.2); 1.7703 (1.8); 1.7623 (3.6); 1.7509 (3.5); 1.7401 (3.9); 1.7332 (3.8); 1.7281 (2.6); 1.7207 (3.0); 1.7080 (2.7); 1.6961 (1.5); 0.0082 (0.9)

I-075: $^1$H-NMR(400.0 MHz, $d_6$-DMSO):

δ = 10.6935 (0.5); 7.8181 (3.9); 7.3656 (0.9); 7.3437 (0.8); 7.1954 (0.9); 7.1826 (0.9); 7.1068 (0.8); 7.0899 (1.1); 7.0717 (0.6); 4.7752 (1.1); 4.7356 (1.3); 4.2913 (1.5); 4.2517 (1.4); 3.9036 (0.6); 3.8934 (0.8); 3.8842 (0.8); 3.8722 (0.7); 3.8621 (0.6); 3.5968 (16.0); 3.3206 (69.7); 3.1858 (0.9); 3.1343 (0.7); 3.1224 (0.8); 3.1161 (2.4); 3.1041 (2.2); 3.0979 (2.2); 3.0860 (2.2); 3.0798 (0.7); 3.0679 (0.7); 2.8861 (0.6); 2.8763 (0.6); 2.8491 (0.8); 2.8389 (0.7); 2.7694 (0.8); 2.7609 (0.8); 2.6746 (0.9); 2.6699 (1.2); 2.6653 (0.8); 2.5504 (1.4); 2.5459 (1.0); 2.5402 (1.3); 2.5234 (4.2); 2.5186 (6.2); 2.5100 (67.6); 2.5054 (143.4); 2.5008 (197.1); 2.4962 (137.3); 2.4916 (61.3); 2.4690 (0.6); 2.4264 (1.0); 2.4082 (0.8); 2.4040 (0.8); 2.3869 (0.7); 2.3369 (0.5); 2.3322 (1.0); 2.3276 (1.8); 2.3231 (1.0); 2.3150 (0.7); 2.3031 (1.0); 2.2904 (1.0); 2.2615 (0.7); 2.2508 (1.1); 2.2339 (0.8); 2.2219 (0.6); 2.2154 (0.5); 2.2034 (0.8); 2.1783 (0.6); 1.8628 (0.5); 1.8517 (0.6); 1.8405 (0.6); 1.8332 (0.6); 1.8209 (0.5); 1.1937 (5.4); 1.1755 (11.2); 1.1572 (5.2); 0.0079 (1.6); −0.0002 (51.9); −0.0086 (1.5)

I-076: $^1$H-NMR(400.1 MHz, $d_6$-DMSO):

δ = 11.6290 (3.4); 7.3855 (0.4); 7.3818 (0.5); 7.3649 (1.0); 7.3611 (1.1); 7.3553 (0.6); 7.3452 (0.7); 7.3391 (1.1); 7.3353 (1.0); 7.3189 (0.6); 7.3151 (0.5); 7.2120 (0.6); 7.2081 (0.6); 7.1992 (0.6); 7.1954 (0.8); 7.1920 (1.1); 7.1884 (1.2); 7.1792 (1.1); 7.1760 (1.2); 7.1720 (0.8); 7.1679 (0.8); 7.1589 (0.6); 7.1554 (0.7); 7.0760 (1.1); 7.0599 (1.6); 7.0569 (1.5); 7.0406 (0.8); 4.7255 (1.8); 4.6858 (2.1); 4.2447 (2.2); 4.2045 (1.9); 3.8415 (0.4); 3.8311 (0.7); 3.8205 (1.0); 3.8099 (1.1); 3.7996 (1.0); 3.7898 (0.8); 3.7800 (0.4); 3.5958 (0.7); 3.5787 (1.8); 3.5615 (2.6); 3.5443 (1.9); 3.5271 (0.7); 3.3514 (45.5); 3.1684 (5.7); 2.7907 (1.5); 2.7807 (1.5); 2.7524 (1.8); 2.7424 (1.8); 2.6742 (0.5); 2.6696 (0.7); 2.6650 (0.5); 2.5446 (0.4); 2.5400 (0.9); 2.5231 (1.6); 2.5184 (2.5); 2.5098 (38.6); 2.5052 (84.3); 2.5006 (118.7); 2.4960 (86.2); 2.4914 (41.1); 2.4656 (2.4); 2.4433 (2.0); 2.4272 (1.7); 2.4157 (0.7); 2.4051 (1.7); 2.3988 (1.4); 2.3796 (1.2); 2.3763 (1.1); 2.3578 (0.9); 2.3320 (0.5); 2.3274 (0.8); 2.3228 (0.6); 2.3040 (0.8); 2.2916 (1.0); 2.2798 (1.4); 2.2673 (1.4); 2.2380 (0.8); 2.2271 (1.0); 2.2219 (0.8); 2.2039 (0.9); 2.1978 (0.4); 2.1922 (0.7); 2.1850 (0.6); 2.1795 (0.6); 2.1730 (1.1); 2.1684 (0.6); 2.1608 (0.4); 2.1534 (0.6); 2.1488 (0.7); 2.0721 (0.7); 1.7729 (0.4); 1.7633 (0.8); 1.7520 (0.8); 1.7415 (0.9); 1.7332 (1.0); 1.7292 (0.6); 1.7213 (0.7); 1.7092 (0.6); 1.6974 (0.4); 1.2611 (15.5); 1.2593 (16.0); 1.2439 (15.5); 1.2422 (16.0); 0.0083 (0.5)

I-077: $^1$H-NMR(400.1 MHz, $d_6$-DMSO):

δ = 7.5844 (6.7); 7.5807 (7.4); 7.5644 (8.5); 7.5607 (8.7); 7.3707 (8.1); 7.3511 (16.0); 7.3313 (9.2); 7.2291 (7.7); 7.2273 (7.2); 7.2256 (8.2); 7.2098 (6.2); 7.2062 (6.2); 4.7040 (7.5); 4.6628 (9.2); 4.3067 (8.8); 4.2654 (7.4); 3.8384 (1.3); 3.8279 (2.5); 3.8173 (3.6); 3.8074 (4.1); 3.7979 (3.6); 3.7874 (2.9); 3.7769 (1.3); 3.7634 (0.4); 3.7424 (0.4); 3.5954 (1.0); 3.5574 (0.8); 3.5198 (0.6); 2.6743 (5.6); 2.6637 (5.7); 2.6344 (7.3); 2.6237 (7.2); 2.5507 (0.3); 2.5460 (0.3); 2.5407 (0.4); 2.5238 (0.7); 2.5191 (1.1); 2.5105 (21.2); 2.5059 (47.2); 2.5013 (67.0); 2.4966 (48.9); 2.4921 (23.6); 2.4808 (2.8); 2.4628 (2.5); 2.4516 (1.0); 2.4492 (1.0); 2.4391 (5.0); 2.4324 (8.3); 2.4224 (3.8); 2.4161 (4.4); 2.4109 (8.2); 2.3925 (6.3); 2.3709 (5.8); 2.3322 (2.8); 2.3198 (2.7); 2.3078 (5.0); 2.2958 (5.1); 2.2740 (3.6); 2.2701 (5.7); 2.2636 (4.9); 2.2613 (4.7); 2.2579 (3.9); 2.2525 (2.6); 2.2470 (1.5); 2.2402 (3.6); 2.2334 (1.5); 2.2280 (1.2); 2.2212 (2.2); 2.2155 (1.9); 2.1969 (1.0); 2.0720 (14.2); 1.8181 (0.9); 1.8127 (0.6); 1.7960 (1.8); 1.7906 (2.2); 1.7841 (3.3); 1.7768 (2.3); 1.7735 (3.0); 1.7668 (2.0); 1.7613 (2.8); 1.7541 (2.1); 1.7424 (2.4); 1.7305 (1.3); 0.0000 (8.9)

I-078: $^1$H-NMR(400.0 MHz, $d_6$-DMSO):

δ = 8.6528 (0.6); 8.6380 (1.2); 8.6238 (0.6); 8.5781 (1.1); 8.5760 (1.3); 8.5739 (1.3); 8.5718 (1.2); 8.5654 (1.2); 8.5634 (1.3); 8.5613 (1.3); 8.5591 (1.1); 7.9472 (0.5); 7.9318 (1.0); 7.9285 (1.0); 7.9123 (0.6); 7.9089 (0.6); 7.4323 (0.8); 7.4190 (0.9); 7.3988 (1.8); 7.3775 (1.6); 7.3603 (0.7); 7.3563 (0.8); 7.3501 (0.4); 7.3407 (0.5); 7.3344 (0.8); 7.3305 (0.7); 7.3142 (0.4); 7.3104 (0.4); 7.2071 (0.4); 7.2031 (0.5);

-continued 7.1942 (0.4); 7.1903 (0.6); 7.1873 (0.8); 7.1833 (0.9); 7.1745 (0.8); 7.1708 (0.9); 7.1668 (0.6); 7.1629 (0.6); 7.1541 (0.5); 7.1504 (0.5); 7.0785 (0.8); 7.0628 (1.1); 7.0593 (1.1); 7.0432 (0.6); 4.7472 (1.3); 4.7077 (1.5); 4.3997 (2.5); 4.3840 (2.4); 4.2485 (1.6); 4.2086 (1.4); 3.8481 (0.4); 3.8371 (0.6); 3.8266 (0.9); 3.8166 (1.1); 3.8067 (0.9); 3.7961 (0.7); 3.7848 (0.5); 3.7295 (0.4); 3.5405 (16.0); 3.1687 (4.8); 2.6757 (0.4); 2.6710 (0.5); 2.6664 (0.4); 2.6508 (1.1); 2.6396 (1.1); 2.6155 (1.4); 2.6042 (1.3); 2.5413 (0.4); 2.5244 (0.8); 2.5198 (1.2); 2.5111 (26.6); 2.5065 (60.5); 2.5019 (86.4); 2.4973 (61.2); 2.4926 (27.2); 2.4625 (0.4); 2.4577 (0.4); 2.4533 (0.4); 2.4114 (0.4); 2.3924 (0.5); 2.3886 (0.5); 2.3693 (1.0); 2.3449 (2.1); 2.3332 (0.6); 2.3282 (1.2); 2.3234 (1.9); 2.3094 (1.3); 2.2913 (0.9); 2.2878 (1.4); 2.2783 (0.9); 2.2674 (1.1); 2.2542 (1.1); 2.2498 (0.5); 2.2366 (0.4); 2.2255 (0.6); 2.2125 (0.6); 2.1656 (0.4); 2.1464 (0.7); 2.1419 (0.4); 2.1341 (0.5); 2.1270 (0.4); 2.1222 (0.6); 2.1148 (0.9); 2.1101 (0.5); 2.0954 (0.5); 2.0907 (0.6); 2.0735 (4.4); 1.8185 (0.4); 1.8059 (0.5); 1.7951 (0.7); 1.7847 (0.6); 1.7737 (0.6); 1.7634 (0.7); 1.7529 (0.4)

I-079: $^1$H-NMR(400.0 MHz, $d_6$-DMSO):

δ = 9.0177 (7.8); 9.0141 (8.9); 9.0070 (8.2); 9.0031 (8.7); 8.6645 (5.0); 8.6437 (5.5); 8.5983 (3.3); 8.5842 (6.2); 8.0113 (8.1); 7.9896 (10.5); 7.8133 (7.6); 7.7952 (9.4); 7.7741 (7.4); 7.6981 (5.9); 7.6869 (6.0); 7.6764 (5.6); 7.6656 (6.3); 7.5930 (9.0); 7.5756 (7.9); 7.3724 (2.3); 7.3522 (5.1); 7.3304 (4.8); 7.3059 (2.5); 7.1919 (2.8); 7.1723 (5.6); 7.1595 (5.2); 7.1428 (2.7); 7.0663 (4.3); 7.0513 (6.0); 7.0321 (3.8); 4.8225 (2.4); 4.8076 (2.5); 4.7849 (6.2); 4.7704 (6.5); 4.7398 (6.6); 4.7247 (8.7); 4.7017 (3.8); 4.6810 (7.9); 4.2205 (8.8); 4.1807 (7.9); 3.8393 (12.3); 3.8284 (14.2); 3.8170 (15.8); 3.8076 (16.0); 3.7981 (15.4); 3.2169 (2.0); 3.1660 (14.6); 2.7573 (2.0); 2.6750 (3.6); 2.6701 (5.2); 2.6655 (4.4); 2.6221 (5.0); 2.6112 (5.4); 2.5870 (6.2); 2.5760 (6.7); 2.5566 (2.5); 2.5237 (8.2); 2.5190 (14.1); 2.5103 (317.8); 2.5057 (712.5); 2.5011 (1013.9); 2.4965 (712.6); 2.4919 (319.1); 2.4557 (7.8); 2.4510 (10.0); 2.4464 (7.4); 2.4012 (2.7); 2.3753 (2.6); 2.3564 (3.2); 2.3325 (9.5); 2.3280 (7.1); 2.3232 (5.2); 2.3131 (5.7); 2.2975 (8.2); 2.2895 (5.6); 2.2755 (8.6); 2.2698 (5.8); 2.2624 (7.9); 2.2561 (6.1); 2.2455 (7.9); 2.2407 (7.7); 2.2324 (6.4); 2.2146 (3.2); 2.2038 (3.8); 2.1908 (3.9); 2.1485 (2.5); 2.1291 (3.9); 2.1050 (3.2); 2.0978 (4.9); 2.0734 (6.6); 2.0544 (1.7); 1.7691 (1.9); 1.7562 (3.2); 1.7457 (4.0); 1.7322 (3.6); 1.7138 (3.4); 1.7026 (2.6); 0.0505 (2.3); 0.0080 (18.1); 0.0063 (5.3); 0.0055 (5.9); 0.0047 (7.1); 0.0038 (9.5); −0.0002 (601.3); −0.0027 (33.5); −0.0051 (8.4); −0.0060 (5.9); − 0.0068 (5.3); −0.0085 (17.3); −0.0504 (4.4)

I-080: $^1$H-NMR(400.0 MHz, $d_6$-DMSO):

δ = 10.4881 (1.2); 8.1118 (0.9); 8.1095 (1.0); 8.0910 (1.0); 8.0887 (1.0); 7.8875 (1.0); 7.8838 (1.1); 7.8676 (1.1); 7.8640 (1.1); 7.6073 (0.6); 7.6032 (0.6); 7.5888 (0.7); 7.5852 (0.8); 7.5825 (0.6); 7.5681 (0.6); 7.5640 (0.6); 7.2204 (0.8); 7.2174 (0.8); 7.2019 (1.0); 7.2006 (1.0); 7.1991 (1.0); 7.1977 (1.0); 7.1823 (0.8); 7.1793 (0.8); 7.0880 (0.6); 4.7547 (0.7); 4.7150 (0.8); 4.3180 (0.9); 4.2781 (0.8); 3.9160 (0.5); 3.8292 (16.0); 3.3433 (14.2); 2.8442 (0.6); 2.8322 (0.6); 2.8069 (0.8); 2.7949 (0.7); 2.5970 (0.8); 2.5768 (0.7); 2.5596 (0.5); 2.5395 (0.7); 2.5240 (0.6); 2.5193 (0.8); 2.5106 (10.6); 2.5060 (22.8); 2.5014 (31.7); 2.4968 (22.1); 2.4922 (9.7); 2.4418 (0.7); 2.2978 (0.6); 2.2851 (0.6); 2.2484 (0.6); −0.0002 (2.8)

I-081: $^1$H-NMR(400.0 MHz, CDCl3):

δ = 7.5215 (0.9); 7.3826 (14.6); 7.3724 (0.5); 7.3621 (16.5); 7.2626 (183.5); 7.2570 (12.6); 7.1286 (1.1); 7.1191 (1.6); 7.1130 (1.6); 7.1039 (3.7); 7.0913 (2.6); 7.0888 (2.5); 7.0852 (2.9); 7.0772 (3.8); 7.0703 (1.8); 7.0651 (2.0); 7.0609 (4.2); 7.0573 (7.8); 7.0498 (11.2); 7.0472 (6.9); 7.0411 (10.1); 7.0338 (4.0); 7.0306 (6.0); 7.0272 (7.6); 7.0219 (7.4); 7.0127 (1.0); 7.0067 (6.4); 7.0015 (6.1); 5.4813 (2.4); 5.2999 (8.8); 4.8500 (4.8); 4.8464 (4.7); 4.8114 (5.4); 4.8076 (5.2); 4.2343 (7.0); 4.1957 (6.2); 3.9418 (1.1); 3.9306 (2.3); 3.9198 (2.9); 3.9095 (3.3); 3.8996 (2.9); 3.8888 (2.4); 3.8779 (1.1); 3.5433 (0.6); 3.5256 (1.3); 3.5092 (2.9); 3.4914 (5.9); 3.4761 (6.0); 3.4736 (6.2); 3.4715 (5.8); 3.4563 (5.8); 3.4390 (3.0); 3.4219 (1.3); 3.4049 (0.6); 2.7820 (8.4); 2.7644 (16.0); 2.7470 (7.1); 2.5969 (5.0); 2.5860 (5.0); 2.5607 (5.7); 2.5498 (5.6); 2.5240 (1.0); 2.5039 (1.3); 2.5005 (1.2); 2.4805 (3.6); 2.4609 (3.3); 2.4574 (3.1); 2.4380 (3.1); 2.4276 (3.6); 2.4129 (4.2); 2.4035 (5.0); 2.3890 (5.0); 2.3847 (1.8); 2.3701 (1.4); 2.3605 (2.3); 2.3462 (2.2); 2.2757 (2.0); 2.2565 (3.1); 2.2518 (1.9); 2.2430 (2.4); 2.2375 (2.0); 2.2325 (2.6); 2.2240 (3.3); 2.2190 (2.2); 2.2136 (1.5); 2.2048 (2.1); 2.1997 (2.6); 2.1808 (1.4); 2.1412 (6.3); 2.1189 (6.2); 2.1050 (5.4); 2.0827 (5.3); 1.8164 (1.6); 1.8051 (1.8); 1.8023 (2.0); 1.7913 (2.3); 1.7818 (2.2); 1.7785 (1.9); 1.7724 (1.8); 1.7692 (2.2); 1.7580 (2.0); 1.7488 (1.5); 1.7457 (1.4); 1.7342 (1.2); 0.0080 (1.5); −0.0002 (51.8); −0.0085 (1.4)

I-082: $^1$H-NMR(400.1 MHz, $d_6$-DMSO):

δ = 12.5995 (0.3); 12.5697 (0.4); 12.5511 (0.5); 12.5463 (0.4); 12.5223 (0.5); 12.4648 (0.4); 12.4379 (0.4); 7.3853 (1.4); 7.3652 (3.4); 7.3414 (3.4); 7.3197 (1.9); 7.2747 (0.7); 7.2564 (0.8); 7.2304 (1.0); 7.2122 (2.2); 7.1924 (3.7); 7.1797 (4.0); 7.1592 (2.1); 7.0754 (3.3); 7.0579 (5.0); 7.0392 (2.5); 4.7722 (3.3); 4.7485 (10.2); 4.7243 (16.0); 4.7001 (4.0); 4.6850 (6.7); 4.2406 (6.5); 4.2007 (5.7); 3.8510 (1.0); 3.8408 (2.0); 3.8308 (2.8); 3.8203 (3.4); 3.8107 (2.9); 3.7991 (2.2); 3.7910 (1.1); 3.5879 (0.4); 3.5774 (0.3); 3.5542 (0.6); 3.5450 (0.4); 3.3775 (42.3); 3.3101 (2.3); 3.2937 (1.6); 3.2848 (1.2); 3.2669 (1.0); 3.2543 (0.8); 3.2122 (0.5); 3.1963 (0.4); 3.1810 (0.4); 3.1719 (6.6); 3.1700 (6.3); 3.1686 (7.7); 2.8345 (0.5); 2.8151 (1.0); 2.8059 (3.6); 2.7964 (4.0); 2.7670 (4.4); 2.7575 (4.2); 2.6696 (1.4); 2.5478 (1.2); 2.5400 (0.7); 2.5040 (226.0); 2.5006 (244.5); 2.4646 (5.8); 2.4479 (5.0); 2.4250 (5.2); 2.4019 (3.8); 2.3827 (3.7); 2.3620 (2.5); 2.3271 (1.7); 2.3079 (2.2); 2.2959 (2.4); 2.2843 (3.2); 2.2715 (3.5); 2.2556 (0.8); 2.2421 (2.2); 2.2305 (3.1); 2.2099 (2.5); 2.1972 (2.0); 2.1779 (2.8); 2.1658 (1.2); 2.1571 (2.0); 2.1347 (0.8); 2.0751 (1.1); 2.0718 (1.2); 1.7679 (1.2); 1.7588 (2.3); 1.7472 (2.3); 1.7371 (2.7); 1.7282 (2.6); 1.7162 (2.1); 1.7045 (1.7); 1.6931 (1.0); 1.3458 (0.3); 1.3280 (0.6); 1.3112 (0.4); 1.2354 (0.3); 0.0082 (1.1); 0.0033 (24.6); 0.0013 (23.4)

I-083: $^1$H-NMR(400.1 MHz, $d_6$-DMSO):

δ = 11.4828 (0.9); 7.1786 (0.3); 7.0645 (0.4); 4.7372 (0.5); 4.6976 (0.6); 4.2484 (0.6); 4.2087 (0.5); 3.4007 (1.3); 2.7735 (16.0); 2.7376 (0.4); 2.7275 (0.4); 2.6998 (0.5); 2.6897 (0.5); 2.5098 (2.3); 2.5053 (5.1); 2.5007 (7.2); 2.4961 (5.3); 2.4916 (2.5); 2.4232 (0.5); 2.4012 (0.5); 2.3973 (0.4); 2.3857 (0.4); 2.3769 (0.3); 2.3637 (0.4); 2.2811 (0.4); 2.2687 (0.4)

I-084: $^1$H-NMR(400.1 MHz, CDCl3):

δ = 7.2638 (13.5); 7.0981 (0.6); 7.0862 (0.4); 7.0826 (0.4); 7.0795 (0.5); 7.0757 (0.6); 7.0731 (0.6); 7.0631 (0.4); 7.0566 (1.8); 7.0497 (1.8); 7.0462 (1.2); 7.0411 (1.9); 7.0329 (0.7); 7.0303 (0.7); 6.1081 (0.4); 4.8632 (0.9); 4.8597 (0.9); 4.8244 (1.0); 4.8208 (1.0); 4.2666 (1.3); 4.2278 (1.1); 3.9706 (0.4); 3.9601 (0.5); 3.9499 (0.7); 3.9398 (0.5); 3.9292 (0.4); 3.7080 (16.0); 3.5190 (0.5); 3.5143 (0.5); 3.5102 (0.3); 3.5019 (1.2); 3.4994 (1.1); 3.4947 (0.5); 3.4892 (1.2); 3.4862 (1.3); 3.4782 (0.3); 3.4741 (0.5); 3.4697 (0.5); 2.6137 (0.9); 2.6027 (0.9); 2.5775 (1.1); 2.5664 (1.1); 2.5387 (2.0); 2.5306 (0.8); 2.5240

-continued (2.2); 2.5179 (0.5); 2.5091 (2.4); 2.4888 (0.6); 2.4845 (0.5); 2.4657 (0.6); 2.4400 (0.6); 2.4254 (0.7); 2.4157 (0.8); 2.4013 (0.9); 2.3972 (0.4); 2.3728 (0.4); 2.3586 (0.5); 2.3027 (0.4); 2.2838 (0.7); 2.2787 (0.5); 2.2703 (0.6); 2.2650 (0.6); 2.2595 (0.6); 2.2513 (0.8); 2.2461 (0.6); 2.2409 (0.4); 2.2323 (0.5); 2.2269 (0.6); 2.2081 (0.3); 2.1913 (1.2); 2.1695 (1.1); 2.1551 (1.0); 2.1332 (1.0); 1.8559 (0.3); 1.8536 (0.4); 1.8427 (0.4); 1.8326 (0.4); 1.8297 (0.4); 1.8234 (0.3); 1.8207 (0.4); 1.8184 (0.3); 1.8097 (0.4)

I-085: $^1$H-NMR(400.0 MHz, $d_6$-DMSO):
δ = 8.2423 (0.5); 8.2285 (1.0); 8.2147 (0.5); 7.5641 (4.0); 7.3560 (0.8); 7.3402 (0.5); 7.3342 (0.8); 7.2872 (4.2); 7.2857 (4.3); 7.1856 (0.8); 7.1818 (0.8); 7.1727 (0.8); 7.1693 (0.8); 7.1654 (0.5); 7.0713 (0.8); 7.0553 (1.0); 7.0357 (0.5); 4.7306 (1.2); 4.6903 (1.4); 4.2163 (1.5); 4.1770 (1.3); 4.0842 (1.9); 4.0659 (7.0); 4.0568 (2.2); 4.0479 (7.0); 4.0437 (2.2); 4.0297 (1.9); 3.8004 (0.7); 3.7902 (0.9); 3.7804 (0.8); 3.7697 (0.5); 3.4701 (11.9); 3.1681 (0.6); 2.5323 (1.1); 2.5207 (1.6); 2.5104 (17.6); 2.5059 (39.0); 2.5012 (54.9); 2.4966 (39.0); 2.4920 (17.1); 2.3446 (0.9); 2.3235 (1.0); 2.3028 (0.7); 2.2754 (0.7); 2.2623 (0.8); 2.2514 (1.0); 2.2384 (1.0); 2.2176 (1.4); 2.2096 (0.6); 2.1961 (1.7); 2.1827 (1.1); 2.1611 (1.1); 2.1234 (0.6); 2.0995 (0.6); 2.0919 (0.8); 2.0732 (0.5); 2.0679 (0.6); 1.7485 (0.6); 1.7384 (0.6); 1.7274 (0.6); 1.7169 (0.6); 1.3358 (7.1); 1.3177 (16.0); 1.2995 (7.0); −0.0002 (2.5)

I-086: $^1$H-NMR(400.1 MHz, $d_6$-DMSO):
δ = 11.7696 (3.0); 7.3869 (0.4); 7.3831 (0.4); 7.3665 (0.8); 7.3625 (0.9); 7.3565 (0.5); 7.3468 (0.6); 7.3406 (0.9); 7.3365 (0.8); 7.3202 (0.5); 7.3164 (0.5); 7.2145 (0.5); 7.2108 (0.6); 7.2017 (0.5); 7.1979 (0.7); 7.1945 (1.0); 7.1910 (1.0); 7.1818 (0.9); 7.1785 (1.0); 7.1745 (0.6); 7.1705 (0.6); 7.1615 (0.6); 7.1581 (0.6); 7.0835 (1.0); 7.0674 (1.3); 7.0643 (1.3); 7.0480 (0.7); 4.7358 (1.5); 4.6962 (1.8); 4.2472 (1.9); 4.2073 (1.6); 3.8457 (0.6); 3.8353 (0.9); 3.8250 (1.0); 3.8148 (0.9); 3.8047 (0.6); 3.3984 (16.0); 3.3400 (0.4); 3.1687 (6.8); 2.9508 (0.4); 2.9367 (1.0); 2.9344 (0.8); 2.9261 (0.6); 2.9187 (1.7); 2.9129 (0.6); 2.9067 (0.7); 2.9026 (1.0); 2.8996 (0.6); 2.8871 (0.5); 2.7563 (1.3); 2.7458 (1.3); 2.7184 (1.6); 2.7080 (1.6); 2.6698 (0.4); 2.5401 (0.5); 2.5233 (0.8); 2.5185 (1.2); 2.5099 (19.4); 2.5053 (42.5); 2.5007 (59.8); 2.4961 (43.2); 2.4915 (20.3); 2.4465 (1.9); 2.4249 (2.1); 2.4087 (1.6); 2.4033 (1.2); 2.3866 (1.9); 2.3627 (0.7); 2.3277 (0.4); 2.3030 (0.7); 2.2908 (0.8); 2.2788 (1.2); 2.2667 (1.2); 2.2616 (0.5); 2.2371 (0.8); 2.2252 (1.0); 2.2067 (0.8); 2.1950 (0.6); 2.1877 (0.5); 2.1825 (0.5); 2.1758 (1.0); 2.1712 (0.5); 2.1560 (0.5); 2.1516 (0.6); 2.0721 (0.4); 1.7893 (0.4); 1.7803 (0.7); 1.7687 (0.7); 1.7587 (0.8); 1.7504 (0.8); 1.7467 (0.5); 1.7388 (0.6); 1.7259 (0.5); 1.0795 (0.9); 1.0683 (8.4); 1.0642 (3.5); 1.0541 (3.5); 1.0497 (4.4); 1.0447 (2.3)

I-087: $^1$H-NMR(400.0 MHz, $d_6$-DMSO):
δ = 11.8115 (2.9); 7.0842 (0.8); 7.0665 (1.7); 7.0473 (1.1); 6.9675 (1.1); 6.9643 (1.2); 6.9471 (1.8); 6.9303 (0.8); 6.9271 (0.8); 4.6937 (1.8); 4.6542 (2.1); 4.1785 (2.3); 4.1391 (2.0); 3.9644 (0.9); 3.8139 (0.8); 3.8034 (1.1); 3.7929 (1.3); 3.7827 (1.1); 3.7725 (0.8); 3.4807 (16.0); 3.2125 (36.5); 3.1689 (6.1); 2.7366 (1.7); 2.7262 (1.8); 2.6983 (2.2); 2.6879 (2.0); 2.5236 (1.2); 2.5189 (1.6); 2.5103 (22.0); 2.5057 (46.8); 2.5010 (64.2); 2.4964 (44.9); 2.4918 (20.1); 2.4242 (2.3); 2.4022 (2.7); 2.3858 (3.0); 2.3640 (2.8); 2.3434 (1.0); 2.2892 (1.0); 2.2767 (1.3); 2.2622 (10.2); 2.2575 (10.0); 2.2232 (0.9); 2.2118 (1.0); 2.1982 (0.7); 2.1795 (1.0); 2.1676 (0.7); 2.1603 (0.6); 2.1554 (0.7); 2.1482 (1.2); 2.1435 (0.6); 2.1284 (0.6); 2.1239 (0.8); 1.7645 (0.8); 1.7533 (0.9); 1.7430 (0.9); 1.7336 (1.0); 1.7222 (0.8); 1.7105 (0.6); −0.0002 (8.7)

I-088: $^1$H-NMR(400.0 MHz, $d_6$-DMSO):
δ = 7.5739 (0.6); 7.5701 (0.6); 7.5538 (0.7); 7.5501 (0.6); 7.3639 (0.7); 7.3443 (1.3); 7.3245 (0.8); 7.2132 (0.6); 7.2095 (0.6); 4.6726 (0.6); 4.6315 (0.7); 4.2824 (0.7); 4.2412 (0.5); 3.5781 (16.0); 3.1684 (0.7); 2.5307 (0.6); 2.5233 (0.8); 2.5186 (1.2); 2.5100 (16.6); 2.5054 (35.6); 2.5008 (48.4); 2.4961 (33.4); 2.4915 (15.0); 2.2233 (0.8); 2.2011 (0.5); 2.1868 (0.5); −0.0002 (3.0)

I-090: $^1$H-NMR(400.0 MHz, $d_6$-DMSO):
δ = 8.6552 (3.3); 8.6402 (6.1); 8.6239 (3.2); 7.3799 (2.4); 7.3761 (2.5); 7.3557 (5.5); 7.3340 (5.4); 7.3132 (2.9); 7.3094 (2.8); 7.2088 (3.2); 7.2047 (3.4); 7.1959 (3.3); 7.1887 (5.8); 7.1849 (6.2); 7.1761 (5.7); 7.1724 (6.2); 7.1685 (4.0); 7.1644 (3.7); 7.1556 (3.2); 7.1518 (3.4); 7.0798 (5.6); 7.0637 (7.7); 7.0444 (4.1); 4.7384 (8.9); 4.6989 (10.4); 4.2375 (11.5); 4.1977 (9.9); 3.9285 (2.6); 3.9067 (7.8); 3.9038 (7.8); 3.8879 (8.0); 3.8821 (8.2); 3.8790 (7.8); 3.8660 (7.6); 3.8631 (7.8); 3.8575 (3.4); 3.8383 (3.1); 3.8231 (4.0); 3.8123 (5.5); 3.8022 (6.9); 3.7921 (5.5); 3.7816 (3.9); 3.7713 (1.9); 3.3577 (1.2); 3.3081 (337.7); 3.2588 (2.5); 3.1685 (0.8); 2.6741 (2.9); 2.6693 (4.1); 2.6647 (2.8); 2.6377 (8.4); 2.6265 (8.6); 2.6022 (10.6); 2.5910 (10.0); 2.5502 (1.9); 2.5395 (2.6); 2.5228 (9.6); 2.5181 (13.9); 2.5095 (229.2); 2.5049 (503.0); 2.5002 (704.9); 2.4956 (486.0); 2.4910 (215.3); 2.4552 (3.4); 2.4504 (4.5); 2.4458 (3.2); 2.4106 (2.3); 2.3909 (3.2); 2.3686 (6.6); 2.3490 (6.2); 2.3315 (4.3); 2.3248 (15.4); 2.3027 (10.6); 2.2892 (11.2); 2.2776 (6.7); 2.2669 (16.0); 2.2535 (7.9); 2.2359 (2.9); 2.2248 (4.3); 2.2119 (4.1); 2.1591 (2.8); 2.1397 (4.8); 2.1352 (2.9); 2.1273 (3.5); 2.1203 (3.0); 2.1157 (4.2); 2.1080 (5.7); 2.1036 (3.3); 2.0966 (2.1); 2.0884 (3.2); 2.0839 (4.3); 2.0644 (2.0); 1.7623 (2.3); 1.7499 (3.5); 1.7388 (4.7); 1.7282 (4.0); 1.7174 (4.0); 1.7071 (4.0); 1.6961 (2.6); 1.6834 (1.7); 0.0081 (1.7); −0.0002 (63.7); −0.0085 (1.7)

I-091: $^1$H-NMR(400.0 MHz, $d_6$-DMSO):
δ = 8.0421 (3.8); 7.3784 (1.6); 7.3745 (1.7); 7.3583 (3.3); 7.3541 (3.6); 7.3481 (1.9); 7.3382 (2.2); 7.3319 (3.5); 7.3119 (1.9); 7.3081 (1.9); 7.2073 (2.1); 7.2033 (2.2); 7.1945 (2.1); 7.1875 (3.8); 7.1837 (4.0); 7.1747 (3.7); 7.1710 (4.1); 7.1672 (2.5); 7.1630 (2.4); 7.1543 (2.1); 7.1505 (2.3); 7.1265 (0.6); 7.1158 (0.8); 7.0740 (3.9); 7.0580 (5.2); 7.0385 (2.8); 4.7382 (6.0); 4.6989 (6.8); 4.2292 (7.5); 4.1894 (6.5); 3.8099 (1.2); 3.7986 (2.3); 3.7885 (3.6); 3.7783 (4.6); 3.7680 (3.6); 3.7582 (2.4); 3.7472 (1.3); 3.3987 (1.0); 3.3669 (1.3); 3.3169 (338.3); 3.3009 (29.3); 3.2875 (18.9); 3.2756 (1.7); 3.2691 (2.6); 3.2657 (2.4); 3.2524 (0.6); 3.2252 (183.9); 3.1996 (6.6); 3.1858 (16.0); 3.1718 (13.6); 3.1572 (4.0); 3.0471 (1.0); 2.6743 (1.6); 2.6696 (2.5); 2.6651 (1.6); 2.5505 (0.9); 2.5400 (1.5); 2.5231 (10.3); 2.5185 (8.7); 2.5098 (139.7); 2.5052 (300.9); 2.5006 (423.9); 2.4960 (294.5); 2.4914 (131.5); 2.4765 (8.2); 2.4558 (2.3); 2.4513 (2.8); 2.4467 (2.0); 2.4045 (1.7); 2.3815 (2.1); 2.3618 (4.4); 2.3420 (4.1); 2.3320 (2.2); 2.3274 (2.9); 2.3191 (3.9); 2.2787 (4.3); 2.2658 (4.3); 2.2547 (5.3); 2.2417 (5.2); 2.2371 (2.4); 2.2242 (8.8); 2.2128 (3.2); 2.2029 (7.6); 2.1894 (5.9); 2.1682 (5.6); 2.1407 (2.0); 2.1212 (3.3); 2.1168 (2.0); 2.1091 (2.3); 2.1019 (2.0); 2.0973 (2.9); 2.0896 (4.0); 2.0851 (2.4); 2.0775 (1.4); 2.0700 (2.2); 2.0654 (3.0); 2.0458 (1.3); 1.7752 (1.6); 1.7628 (2.4); 1.7520 (3.3); 1.7417 (2.8); 1.7308 (2.7); 1.7204 (3.0); 1.7095 (1.8); 1.6966 (1.3); 0.0080 (0.8); −0.0002 (33.1); −0.0086 (0.9)

I-092: $^1$H-NMR(400.0 MHz, $d_6$-DMSO):
δ = 8.4095 (4.9); 7.3744 (2.0); 7.3575 (4.0); 7.3538 (4.5); 7.3317 (4.4); 7.3112 (2.4); 7.2076 (2.6); 7.2037 (2.6); 7.1949 (2.6); 7.1877 (4.6); 7.1840 (5.0); 7.1750 (4.5); 7.1715 (4.9); 7.1673 (3.0); 7.1634 (2.9);

-continued 7.1546 (2.7); 7.1510 (2.8); 7.0804 (4.6); 7.0644 (6.4); 7.0449 (3.4); 4.7434 (7.4); 4.7041 (8.4); 4.2213 (9.2); 4.1818 (8.0); 3.8383 (15.1); 3.8320 (15.9); 3.8243 (16.0); 3.8181 (14.8); 3.8006 (3.0); 3.7903 (4.6); 3.7802 (5.6); 3.7698 (4.5); 3.7597 (3.0); 3.7490 (1.6); 3.4184 (0.8); 3.3165 (259.7); 3.2688 (2.2); 3.2161 (0.6); 3.1685 (3.5); 3.0919 (11.4); 2.6741 (1.9); 2.6695 (2.8); 2.6646 (2.0); 2.5476 (7.1); 2.5361 (7.4); 2.5229 (6.9); 2.5182 (10.8); 2.5096 (165.2); 2.5050 (354.4); 2.5003 (499.5); 2.4957 (342.2); 2.4911 (152.5); 2.4552 (2.5); 2.4508 (3.1); 2.4091 (2.2); 2.3865 (2.6); 2.3663 (5.4); 2.3464 (5.1); 2.3364 (1.6); 2.3319 (2.5); 2.3229 (5.6); 2.2790 (4.1); 2.2663 (5.0); 2.2549 (6.4); 2.2422 (6.4); 2.2353 (9.2); 2.2246 (2.7); 2.2135 (11.0); 2.2003 (10.0); 2.1786 (6.6); 2.1487 (2.4); 2.1292 (4.1); 2.1171 (2.9); 2.1098 (2.4); 2.1053 (3.4); 2.0977 (4.7); 2.0932 (2.7); 2.0856 (1.7); 2.0778 (2.7); 2.0735 (3.8); 2.0536 (1.5); 1.7651 (1.9); 1.7534 (2.9); 1.7422 (3.6); 1.7318 (3.5); 1.7206 (3.3); 1.7104 (3.3); 1.6990 (2.2); 1.6872 (1.5); 0.0080 (1.3); −0.0002 (45.0); −0.0085 (1.4)

I-093: $^1$H-NMR(400.0 MHz, $d_6$-DMSO):

δ = 8.3390 (0.7); 8.3253 (1.3); 8.3110 (0.7); 7.3583 (1.0); 7.3357 (1.0); 7.3156 (0.6); 7.2061 (1.8); 7.2014 (2.0); 7.1897 (5.0); 7.1870 (7.1); 7.1838 (4.8); 7.1730 (4.4); 7.1703 (4.5); 7.1599 (2.7); 7.1546 (2.2); 7.1451 (1.2); 7.1393 (1.2); 7.1345 (0.7); 7.1204 (0.6); 7.0765 (1.1); 7.0602 (1.5); 7.0410 (0.7); 4.7418 (1.4); 4.7013 (1.7); 4.2623 (2.5); 4.2542 (2.6); 4.2485 (2.7); 4.2401 (3.8); 4.2002 (1.6); 3.8266 (0.6); 3.8162 (0.8); 3.8060 (1.0); 3.7960 (0.9); 3.7857 (0.6); 3.3424 (236.4); 3.2908 (1.6); 3.1672 (2.3); 3.1529 (2.5); 2.6746 (1.3); 2.6700 (1.8); 2.6654 (1.3); 2.6229 (1.4); 2.6038 (5.3); 2.5907 (1.6); 2.5851 (5.0); 2.5665 (2.8); 2.5549 (0.9); 2.5495 (0.7); 2.5448 (1.0); 2.5402 (2.2); 2.5233 (5.0); 2.5187 (7.7); 2.5100 (103.3); 2.5055 (221.3); 2.5008 (305.4); 2.4962 (213.2); 2.4916 (94.7); 2.4596 (0.6); 2.4548 (1.0); 2.4501 (1.6); 2.4456 (1.4); 2.4018 (0.6); 2.3829 (0.7); 2.3599 (1.2); 2.3369 (1.7); 2.3324 (1.8); 2.3277 (2.1); 2.3229 (1.6); 2.3183 (1.5); 2.2834 (1.9); 2.2749 (1.6); 2.2617 (2.0); 2.2488 (2.0); 2.2265 (1.5); 2.2090 (0.7); 2.1616 (0.5); 2.1422 (0.8); 2.1300 (0.6); 2.1180 (0.7); 2.1106 (1.0); 2.0866 (0.8); 2.0730 (1.0); 1.7871 (0.6); 1.7766 (0.8); 1.7663 (0.7); 1.7550 (0.7); 1.7449 (0.8); 1.2098 (1.5); 1.1936 (1.5); 1.1566 (7.0); 1.1378 (16.0); 1.1189 (6.8); 0.0080 (1.2); −0.0002 (41.8); −0.0085 (1.2)

I-094: $^1$H-NMR(400.0 MHz, $d_6$-DMSO):

δ = 8.0946 (0.7); 7.4655 (3.6); 7.3567 (0.5); 7.3529 (0.6); 7.3307 (0.6); 7.1828 (0.6); 7.1790 (0.7); 7.1698 (0.6); 7.1665 (0.7); 7.0682 (0.6); 7.0520 (0.8); 4.7284 (0.9); 4.6890 (1.1); 4.2126 (1.2); 4.1730 (1.0); 4.0086 (1.9); 4.0026 (1.9); 3.9997 (2.2); 3.9958 (1.9); 3.9903 (2.0); 3.9815 (3.9); 3.9633 (4.0); 3.9452 (1.3); 3.7911 (0.6); 3.7811 (0.7); 3.7711 (0.6); 3.4698 (8.3); 2.5229 (1.4); 2.5185 (1.2); 2.5098 (16.8); 2.5052 (35.8); 2.5006 (50.3); 2.4960 (34.8); 2.4913 (15.5); 2.4763 (1.0); 2.3411 (0.7); 2.3224 (0.8); 2.2987 (0.5); 2.2722 (0.5); 2.2592 (0.6); 2.2482 (0.8); 2.2352 (0.8); 2.2118 (1.1); 2.2064 (0.5); 2.1902 (1.1); 2.1771 (0.9); 2.1694 (1.1); 2.1554 (0.8); 2.1195 (0.5); 2.0880 (0.6); 2.0638 (16.0); 1.7505 (0.5); 1.3113 (5.1); 1.2932 (11.7); 1.2750 (5.0); 1.2495 (0.7); −0.0002 (3.5)

I-095: $^1$H-NMR(400.6 MHz, $d_6$-DMSO):

δ = 7.5903 (6.8); 7.5867 (7.3); 7.5704 (8.7); 7.5667 (8.3); 7.3737 (8.6); 7.3541 (16.0); 7.3343 (9.2); 7.1940 (7.4); 7.1904 (7.7); 7.1746 (6.4); 7.1710 (6.2); 7.1587 (3.7); 7.0268 (7.6); 6.8950 (3.8); 4.6609 (6.9); 4.6192 (8.3); 4.2949 (8.1); 4.2532 (6.6); 3.8920 (1.6); 3.8824 (2.6); 3.8725 (3.4); 3.8630 (3.8); 3.8506 (3.4); 3.8410 (3.0); 3.4559 (5.6); 3.1673 (3.0); 2.7995 (4.0); 2.7899 (4.0); 2.7603 (5.0); 2.7507 (4.8); 2.6749 (1.5); 2.6703 (2.0); 2.6656 (1.6); 2.5238 (8.8); 2.5106 (101.5); 2.5060 (207.0); 2.5015 (282.6); 2.4969 (195.7); 2.4923 (88.3); 2.4775 (6.0); 2.4615 (3.1); 2.4547 (4.7); 2.4389 (4.6); 2.4209 (3.6); 2.4159 (3.5); 2.4014 (1.5); 2.3879 (1.4); 2.3391 (2.8); 2.3330 (2.1); 2.3282 (4.0); 2.3152 (4.7); 2.3037 (4.8); 2.2748 (5.9); 2.2692 (4.3); 2.2621 (3.0); 2.2560 (2.2); 2.2440 (3.5); 2.2314 (1.2); 2.2247 (2.0); 2.2196 (1.9); 2.2002 (1.0); 2.0857 (2.0); 2.0736 (3.2); 1.8267 (0.9); 1.8019 (2.3); 1.7934 (2.4); 1.7837 (2.8); 1.7765 (1.9); 1.7712 (2.0); 1.7632 (1.8); 1.7521 (2.0); 1.7408 (1.2); 1.3240 (0.5); 0.0080 (1.2); −0.0002 (31.2); −0.0085 (0.8)

I-096: $^1$H-NMR(400.0 MHz, $d_6$-DMSO):

δ = 7.8853 (0.8); 7.3594 (0.6); 7.3554 (0.7); 7.3334 (0.7); 7.3295 (0.6); 7.1881 (0.7); 7.1844 (0.8); 7.1754 (0.7); 7.1718 (0.8); 7.0705 (0.7); 7.0543 (1.0); 7.0511 (0.9); 7.0350 (0.5); 4.7320 (1.1); 4.6922 (1.3); 4.2348 (1.4); 4.1951 (1.2); 3.7968 (0.6); 3.7865 (0.9); 3.7764 (0.6); 3.0530 (0.5); 3.0460 (0.5); 3.0348 (1.3); 3.0277 (1.1); 3.0208 (1.2); 3.0140 (1.3); 3.0022 (0.6); 2.9960 (0.6); 2.5117 (5.5); 2.5072 (12.1); 2.5025 (17.0); 2.4979 (12.6); 2.4933 (5.4); 2.4853 (1.1); 2.4623 (1.2); 2.4504 (1.2); 2.3572 (0.8); 2.3381 (0.8); 2.3344 (0.8); 2.3152 (0.6); 2.2891 (0.6); 2.2755 (0.8); 2.2651 (1.0); 2.2516 (0.9); 2.1893 (1.2); 2.1682 (1.2); 2.1545 (1.1); 2.1334 (1.1); 2.1259 (0.6); 2.1019 (0.5); 2.0944 (0.7); 2.0703 (0.5); 1.7397 (0.6); 1.7293 (0.5); 1.7078 (0.6); 1.5512 (0.8); 1.5344 (1.1); 1.5176 (1.0); 1.5009 (0.5); 1.2729 (1.4); 1.2550 (3.4); 1.2372 (3.3); 1.2193 (1.1); 0.8541 (16.0); 0.8375 (15.3); −0.0002 (1.9)

I-097: $^1$H-NMR(400.0 MHz, CDCl3):

δ = 7.5560 (5.9); 7.5530 (6.1); 7.5360 (6.4); 7.5330 (6.6); 7.5212 (0.8); 7.2782 (2.7); 7.2751 (2.8); 7.2623 (132.8); 7.2565 (6.9); 7.2413 (5.8); 7.2381 (5.7); 7.2110 (6.1); 7.2064 (7.5); 7.1920 (3.7); 7.1873 (3.4); 7.1267 (4.2); 7.1219 (4.0); 7.1087 (5.2); 7.1068 (5.2); 7.1038 (4.8); 7.1021 (4.9); 7.0948 (3.4); 7.0887 (3.5); 7.0838 (4.3); 7.0789 (2.3); 7.0762 (2.5); 7.0693 (4.4); 7.0624 (1.3); 7.0578 (1.8); 7.0500 (8.0); 7.0431 (7.7); 7.0397 (5.8); 7.0348 (10.0); 7.0264 (4.3); 7.0241 (3.8); 7.0140 (0.8); 7.0073 (0.7); 6.9982 (0.7); 5.5102 (2.0); 5.2991 (0.7); 4.8492 (3.9); 4.8456 (3.9); 4.8104 (4.5); 4.8068 (4.4); 4.2368 (5.8); 4.1981 (5.1); 3.9487 (0.9); 3.9377 (2.0); 3.9267 (2.4); 3.9177 (2.5); 3.9154 (2.6); 3.9065 (2.4); 3.8955 (2.1); 3.8846 (1.0); 3.5526 (2.5); 3.5480 (2.4); 3.5348 (6.3); 3.5309 (5.6); 3.5199 (5.5); 3.5160 (6.9); 3.5024 (2.7); 3.4989 (2.8); 2.9729 (8.0); 2.9556 (16.0); 2.9382 (7.2); 2.6001 (4.1); 2.5894 (4.1); 2.5640 (4.7); 2.5532 (4.6); 2.5196 (0.9); 2.5010 (1.2); 2.4977 (1.1); 2.4771 (3.0); 2.4580 (2.7); 2.4547 (2.5); 2.4347 (2.5); 2.4174 (3.0); 2.4029 (3.6); 2.3933 (4.2); 2.3789 (4.2); 2.3746 (1.5); 2.3601 (1.3); 2.3503 (2.0); 2.3361 (1.9); 2.2634 (1.6); 2.2443 (2.5); 2.2394 (1.5); 2.2307 (2.0); 2.2252 (1.6); 2.2201 (2.1); 2.2116 (2.8); 2.2065 (1.8); 2.2012 (1.2); 2.1925 (1.7); 2.1873 (2.2); 2.1683 (1.2); 2.1321 (5.4); 2.1094 (5.3); 2.0959 (4.8); 2.0733 (4.7); 1.8186 (1.4); 1.8074 (1.5); 1.8046 (1.7); 1.7940 (2.1); 1.7840 (1.9); 1.7808 (1.6); 1.7746 (1.5); 1.7714 (1.9); 1.7605 (1.7); 1.7510 (1.3); 1.7480 (1.2); 1.7366 (1.1); 0.0080 (1.1); −0.0002 (37.7); −0.0085 (1.1)

I-098: $^1$H-NMR(400.0 MHz, $d_6$-DMSO):

δ = 7.9148 (1.0); 7.3566 (1.0); 7.3527 (1.0); 7.3467 (0.5); 7.3368 (0.6); 7.3309 (1.0); 7.3267 (0.9); 7.3105 (0.5); 7.2075 (0.6); 7.2034 (0.6); 7.1947 (0.6); 7.1875 (1.1); 7.1837 (1.1); 7.1747 (1.0); 7.1712 (1.1); 7.1673 (0.7); 7.1632 (0.6); 7.1543 (0.6); 7.1508 (0.6); 7.0711 (1.1); 7.0549 (1.5); 7.0358 (0.7); 4.7323 (1.7); 4.6926 (2.0); 4.2338 (2.2); 4.1940 (1.8); 3.8082 (0.7); 3.7979 (1.0); 3.7878 (1.3); 3.7775 (1.0); 3.7674 (0.7); 3.3174 (82.7); 3.0622 (0.8); 3.0441 (2.6); 3.0303 (2.8); 3.0261 (2.9); 3.0123 (2.7); 3.0082

-continued (1.1); 2.9943 (0.9); 2.5233 (1.0); 2.5186 (1.5); 2.5100 (21.1); 2.5054 (45.2); 2.5008 (62.5); 2.4962 (43.6); 2.4916 (19.9); 2.4772 (1.5); 2.4541 (1.7); 2.4421 (1.9); 2.3815 (0.6); 2.3587 (1.2); 2.3368 (1.2); 2.3167 (1.0); 2.2855 (1.0); 2.2719 (1.2); 2.2614 (1.4); 2.2480 (1.4); 2.2439 (0.6); 2.2195 (0.8); 2.2063 (0.8); 2.1793 (2.0); 2.1581 (1.9); 2.1488 (0.7); 2.1444 (1.7); 2.1295 (1.0); 2.1234 (1.8); 2.1173 (0.7); 2.1102 (0.6); 2.1056 (0.8); 2.0980 (1.1); 2.0934 (0.6); 2.0785 (0.6); 2.0739 (0.8); 1.7541 (0.7); 1.7434 (1.0); 1.7333 (0.8); 1.7221 (0.8); 1.7116 (0.8); 1.7010 (0.5); 0.9946 (7.5); 0.9765 (16.0); 0.9584 (7.2); −0.0002 (1.1)

I-099: $^1$H-NMR(400.0 MHz, CDCl3):
δ = 7.2624 (10.9); 7.0456 (0.6); 7.0382 (0.8); 7.0354 (0.5); 7.0294 (0.8); 6.3377 (0.8); 6.3324 (0.9); 6.3197 (2.4); 6.3142 (1.3); 5.2992 (0.7); 4.2308 (0.5); 3.7742 (16.0); 2.7484 (0.6); 2.7313 (1.3); 2.7141 (0.6); −0.0002 (3.1)

I-100: $^1$H-NMR(400.0 MHz, $d_6$-DMSO):
δ = 7.4139 (3.9); 7.3961 (10.3); 7.3770 (8.5); 7.3537 (3.3); 7.3337 (6.0); 7.3118 (4.7); 7.2911 (2.0); 7.2186 (11.3); 7.2152 (15.4); 7.1973 (11.5); 7.1268 (2.8); 7.1124 (2.7); 6.9103 (2.5); 4.5334 (2.0); 4.4962 (2.4); 4.1167 (2.4); 4.0751 (2.0); 3.8125 (2.4); 3.3769 (0.8); 3.3285 (209.0); 3.2797 (1.4); 3.2234 (0.6); 3.1689 (2.0); 3.1051 (16.0); 2.6747 (1.1); 2.6701 (1.5); 2.6654 (1.0); 2.6609 (0.6); 2.5401 (0.6); 2.5234 (3.4); 2.5187 (5.2); 2.5101 (89.3); 2.5055 (193.0); 2.5009 (268.9); 2.4963 (187.8); 2.4917 (84.6); 2.4517 (1.4); 2.4294 (1.8); 2.3901 (2.2); 2.3323 (1.4); 2.3277 (1.9); 2.3231 (1.4); 2.2402 (4.0); 2.2191 (4.6); 2.2051 (4.1); 2.1778 (3.2); 2.1425 (2.4); 2.1222 (1.9); 2.1008 (1.9); 2.0718 (2.4); 1.6628 (2.0); −0.0002 (1.3)

I-101: $^1$H-NMR(400.0 MHz, $d_6$-DMSO):
δ = 7.0772 (0.5); 4.7265 (0.6); 4.6868 (0.7); 4.2454 (0.7); 4.2058 (0.6); 3.3204 (27.1); 3.2966 (1.1); 2.6575 (14.5); 2.5190 (0.6); 2.5104 (9.0); 2.5058 (19.2); 2.5012 (26.3); 2.4965 (18.2); 2.4919 (8.1); 2.3812 (0.7); 2.3693 (0.8); 2.3500 (0.5); 2.3462 (0.8); 2.3341 (1.0); 2.3279 (0.5); 2.2205 (0.5); 1.9824 (0.8); 1.9602 (0.8); 1.9475 (0.7); 1.9252 (0.7); 1.7644 (0.5); 1.7551 (15.5); 1.7540 (16.0); 1.5963 (4.6); −0.0002 (1.0)

I-102: $^1$H-NMR(400.0 MHz, $d_6$-DMSO):
δ = 8.5561 (2.6); 8.5420 (4.8); 8.5278 (2.5); 8.2898 (11.9); 8.2884 (12.6); 8.2836 (12.5); 8.2821 (12.1); 7.7063 (8.7); 7.7000 (8.5); 7.6858 (10.7); 7.6795 (10.3); 7.4756 (15.5); 7.4552 (12.9); 7.3763 (1.7); 7.3727 (1.8); 7.3523 (4.0); 7.3361 (2.5); 7.3303 (4.0); 7.3098 (2.2); 7.3058 (2.0); 7.2025 (2.3); 7.1985 (2.4); 7.1896 (2.4); 7.1859 (2.9); 7.1824 (4.2); 7.1788 (4.6); 7.1698 (4.1); 7.1662 (4.6); 7.1622 (2.9); 7.1582 (2.8); 7.1493 (2.3); 7.1457 (2.5); 7.0695 (4.3); 7.0535 (5.9); 7.0501 (5.6); 7.0340 (3.1); 4.7262 (6.7); 4.6866 (7.8); 4.3084 (1.5); 4.2934 (1.5); 4.2700 (8.9); 4.2560 (16.0); 4.2423 (9.1); 4.2239 (8.6); 4.2042 (1.7); 4.1842 (7.3); 3.8354 (1.3); 3.8244 (2.8); 3.8139 (4.0); 3.8037 (4.7); 3.7936 (4.0); 3.7831 (2.9); 3.7724 (1.5); 3.3271 (164.8); 3.2779 (1.3); 3.1689 (0.7); 2.6747 (1.3); 2.6699 (1.8); 2.6654 (1.3); 2.6073 (5.9); 2.5962 (6.0); 2.5719 (7.1); 2.5608 (7.0); 2.5403 (1.1); 2.5235 (4.1); 2.5188 (6.0); 2.5102 (102.8); 2.5056 (226.1); 2.5009 (318.5); 2.4963 (221.4); 2.4917 (98.4); 2.4557 (1.5); 2.4513 (1.9); 2.4469 (1.5); 2.3916 (1.5); 2.3725 (2.0); 2.3684 (2.0); 2.3494 (4.9); 2.3276 (5.9); 2.3072 (4.0); 2.2818 (9.3); 2.2697 (5.1); 2.2594 (12.5); 2.2459 (11.4); 2.2243 (6.1); 2.2172 (3.2); 2.2041 (3.0); 2.1497 (2.0); 2.1303 (3.5); 2.1259 (2.0); 2.1181 (2.6); 2.1110 (2.1); 2.1064 (3.0); 2.0989 (4.1); 2.0942 (2.5); 2.0872 (1.6); 2.0794 (2.4); 2.0748 (3.1); 2.0628 (0.7); 2.0556 (1.3); 1.7673 (1.7); 1.7546 (2.5); 1.7435 (3.5); 1.7332 (2.9); 1.7224 (2.8); 1.7118 (3.1); 1.7011 (1.9); 1.6876 (1.3); 0.0080 (1.1); − 0.0002 (35.2); −0.0085 (0.9)

I-103: $^1$H-NMR(400.0 MHz, CDCl3):
δ = 7.5218 (1.1); 7.2628 (208.2); 7.1612 (2.9); 7.1452 (3.6); 7.1407 (6.8); 7.1249 (8.2); 7.1195 (4.4); 7.1147 (2.7); 7.1111 (2.1); 7.1077 (1.9); 7.1010 (6.4); 7.0917 (2.5); 7.0886 (3.3); 7.0846 (3.8); 7.0821 (4.2); 7.0752 (6.9); 7.0686 (2.1); 7.0636 (3.0); 7.0558 (13.8); 7.0491 (12.1); 7.0455 (9.5); 7.0410 (17.0); 7.0324 (7.1); 7.0303 (6.2); 7.0206 (1.2); 7.0134 (1.0); 6.9988 (1.2); 6.8491 (3.0); 6.8467 (2.8); 6.8426 (3.6); 6.8403 (3.9); 6.8283 (4.8); 6.8266 (4.6); 6.8199 (8.8); 6.8162 (5.9); 6.8080 (3.3); 6.7994 (4.8); 6.7938 (6.2); 6.7916 (6.3); 6.7884 (3.5); 6.7851 (4.2); 6.7693 (5.1); 6.7629 (3.8); 5.5040 (3.2); 5.2997 (3.6); 4.8528 (6.6); 4.8491 (6.6); 4.8141 (7.5); 4.8104 (7.4); 4.2353 (9.8); 4.1966 (8.8); 3.9365 (1.6); 3.9254 (3.3); 3.9145 (4.1); 3.9036 (4.3); 3.8943 (4.1); 3.8834 (3.4); 3.8725 (1.6); 3.5086 (0.8); 3.4922 (3.7); 3.4841 (3.4); 3.4747 (8.1); 3.4674 (8.1); 3.4594 (7.8); 3.4518 (8.5); 3.4421 (3.6); 3.4350 (3.9); 3.4174 (0.9); 2.8232 (8.3); 2.8060 (16.0); 2.7888 (7.5); 2.5970 (6.9); 2.5862 (6.9); 2.5608 (8.1); 2.5500 (7.9); 2.5223 (1.4); 2.5037 (1.9); 2.5002 (1.8); 2.4800 (5.0); 2.4607 (4.5); 2.4573 (4.3); 2.4374 (4.2); 2.4229 (5.0); 2.4084 (5.8); 2.3988 (6.9); 2.3844 (6.9); 2.3801 (2.5); 2.3655 (2.0); 2.3558 (3.1); 2.3415 (3.1); 2.2723 (2.7); 2.2531 (4.2); 2.2484 (2.4); 2.2396 (3.2); 2.2341 (2.7); 2.2290 (3.5); 2.2206 (4.7); 2.2155 (2.9); 2.2102 (2.0); 2.2014 (2.8); 2.1962 (3.7); 2.1773 (2.1); 2.1379 (9.3); 2.1154 (9.0); 2.1017 (8.0); 2.0792 (7.9); 1.8279 (2.3); 1.8166 (2.5); 1.8139 (2.9); 1.8031 (3.4); 1.7933 (3.2); 1.7900 (2.7); 1.7839 (2.5); 1.7807 (3.1); 1.7697 (2.8); 1.7603 (2.2); 1.7572 (2.0); 1.7458 (1.8); 0.0079 (1.8); −0.0002 (56.9); −0.0085 (1.6)

I-104: $^1$H-NMR(400.0 MHz, $d_6$-DMSO):
δ = 7.8495 (5.3); 7.3770 (3.1); 7.3732 (3.1); 7.3525 (7.5); 7.3309 (7.4); 7.3104 (4.0); 7.3064 (3.8); 7.2066 (4.2); 7.2027 (4.3); 7.1938 (4.3); 7.1866 (7.9); 7.1829 (8.2); 7.1738 (7.6); 7.1702 (8.5); 7.1664 (5.2); 7.1623 (4.8); 7.1535 (4.4); 7.1498 (4.7); 7.0695 (7.8); 7.0534 (10.9); 7.0342 (5.8); 4.7323 (12.7); 4.6930 (14.7); 4.2237 (16.0); 4.1841 (13.9); 3.8104 (2.6); 3.7998 (5.3); 3.7890 (7.3); 3.7790 (9.9); 3.7690 (7.4); 3.7586 (5.8); 3.7477 (2.6); 3.3210 (402.5); 3.1678 (1.1); 2.6741 (2.5); 2.6695 (3.6); 2.6650 (2.4); 2.5411 (80.2); 2.5296 (86.2); 2.5231 (10.4); 2.5183 (12.4); 2.5096 (208.9); 2.5051 (453.5); 2.5005 (641.2); 2.4959 (442.0); 2.4913 (200.8); 2.4649 (13.8); 2.4531 (13.1); 2.3966 (3.4); 2.3776 (4.3); 2.3549 (9.9); 2.3359 (9.2); 2.3320 (10.4); 2.3226 (3.3); 2.3128 (7.4); 2.2815 (7.5); 2.2680 (9.1); 2.2574 (11.2); 2.2441 (10.8); 2.2263 (3.7); 2.2154 (5.8); 2.2024 (5.9); 2.1860 (13.8); 2.1647 (13.5); 2.1509 (11.6); 2.1454 (5.0); 2.1294 (12.4); 2.1138 (5.2); 2.1067 (4.3); 2.1022 (5.9); 2.0945 (8.4); 2.0899 (4.9); 2.0828 (3.0); 2.0750 (4.7); 2.0705 (6.4); 2.0509 (2.8); 1.7555 (3.4); 1.7428 (5.0); 1.7320 (6.9); 1.7215 (5.5); 1.7108 (5.5); 1.7002 (6.1); 1.6896 (3.8); 1.6764 (2.6); 0.0080 (3.7); −0.0002 (124.4); −0.0086 (3.4)

I-105: $^1$H-NMR(400.0 MHz, $d_6$-DMSO):
δ = 11.7795 (1.4); 7.5926 (1.1); 7.5890 (1.1); 7.5726 (1.3); 7.5689 (1.2); 7.3775 (1.3); 7.3579 (2.5); 7.3381 (1.4); 7.1927 (1.1); 7.1892 (1.1); 7.1733 (1.0); 7.1697 (0.9); 4.6722 (1.1); 4.6304 (1.3); 4.2906 (1.2); 4.2489 (1.0); 3.8733 (0.6); 3.8627 (0.5); 3.3634 (36.0); 3.1854 (16.0); 3.1683 (5.1); 2.7287 (0.7); 2.7183 (0.7); 2.6905 (1.0); 2.6799 (1.0); 2.6697 (0.5); 2.5232 (1.1); 2.5184 (1.7); 2.5099 (27.0); 2.5053 (57.5); 2.5006 (78.5); 2.4960 (54.6); 2.4914 (24.6); 2.4601 (1.0); 2.4382 (1.2); 2.4219 (0.9); 2.4152 (0.7);

-continued 2.4002 (0.8); 2.3326 (0.6); 2.3274 (0.6); 2.3220 (0.9); 2.3100 (0.7); 2.2818 (1.0); 2.2727 (0.7); 2.2457 (0.6); −0.0002 (3.3)

I-106: $^{1}$H-NMR(400.1 MHz, $d_6$-DMSO):

δ = 8.2967 (1.1); 8.2902 (1.2); 8.2747 (1.2); 8.2688 (1.2); 7.3913 (0.4); 7.3861 (0.3); 7.3703 (1.0); 7.3654 (0.9); 7.3499 (1.0); 7.3453 (1.1); 7.3297 (0.4); 7.3246 (0.6); 7.2223 (0.6); 7.2025 (1.2); 7.1900 (1.3); 7.1862 (1.1); 7.1821 (0.9); 7.1697 (0.8); 7.1151 (0.8); 7.1036 (1.1); 7.0988 (1.2); 7.0946 (1.2); 7.0785 (2.0); 7.0588 (2.4); 6.9965 (2.2); 6.9775 (1.5); 6.8658 (1.9); 6.8477 (2.0); 4.8415 (0.8); 4.8195 (1.7); 4.7935 (2.4); 4.7526 (2.1); 4.2962 (1.2); 4.2812 (1.3); 4.2566 (1.1); 4.2410 (1.1); 3.8952 (0.4); 3.8852 (0.7); 3.8750 (1.0); 3.8654 (1.1); 3.8546 (1.0); 3.8454 (0.8); 3.8351 (0.5); 3.3681 (1.0); 3.3188 (110.0); 3.1684 (1.5); 2.9753 (1.1); 2.9560 (1.2); 2.9370 (1.4); 2.9174 (1.3); 2.6740 (0.5); 2.6695 (0.7); 2.6620 (1.0); 2.6512 (0.8); 2.6402 (0.8); 2.6285 (1.6); 2.6172 (1.0); 2.6057 (1.0); 2.5945 (0.9); 2.5547 (0.6); 2.5502 (0.9); 2.5456 (0.8); 2.5397 (0.9); 2.5229 (1.6); 2.5182 (2.3); 2.5097 (37.1); 2.5051 (81.0); 2.5005 (113.2); 2.4960 (84.2); 2.4915 (43.1); 2.4527 (1.1); 2.4481 (0.7); 2.4388 (0.9); 2.4158 (1.5); 2.4095 (1.6); 2.3970 (1.4); 2.3908 (1.1); 2.3778 (1.6); 2.3548 (0.8); 2.3446 (1.2); 2.3360 (0.9); 2.3322 (0.9); 2.3270 (1.2); 2.3229 (2.4); 2.3166 (1.6); 2.3103 (2.0); 2.2985 (1.9); 2.2942 (1.6); 2.2885 (1.4); 2.2823 (1.6); 2.2691 (0.9); 2.2521 (16.0); 2.2295 (1.0); 2.2180 (0.7); 2.2065 (0.8); 2.1985 (0.7); 2.1891 (1.0); 2.1742 (1.2); 2.1657 (1.1); 2.1543 (1.4); 2.1331 (1.1); 2.1139 (0.5); 2.0718 (0.4); 1.9069 (0.4); 1.8954 (0.5); 1.8766 (0.6); 1.8659 (0.7); 1.8553 (0.7); 1.8445 (0.6); 1.8241 (0.4); 1.1273 (6.0); 1.1215 (6.2); 1.1106 (6.2); 1.1048 (6.0)

I-107: $^{1}$H-NMR(400.0 MHz, CDCl3):

δ = 7.2626 (43.0); 7.0969 (1.1); 7.0845 (0.7); 7.0813 (0.7); 7.0783 (0.8); 7.0703 (1.2); 7.0583 (0.6); 7.0541 (1.3); 7.0505 (2.4); 7.0434 (2.9); 7.0403 (1.9); 7.0349 (3.1); 7.0245 (1.4); 6.7513 (3.3); 6.7316 (4.4); 6.6546 (3.1); 6.6508 (3.6); 6.6154 (2.2); 6.6111 (1.9); 6.5958 (1.7); 6.5914 (1.5); 5.9379 (2.2); 5.9339 (16.0); 5.9301 (2.2); 5.4159 (0.7); 5.2995 (3.0); 4.8498 (1.4); 4.8463 (1.3); 4.8111 (1.5); 4.8074 (1.5); 4.2272 (2.0); 4.1885 (1.7); 3.9359 (0.7); 3.9249 (0.8); 3.9146 (0.9); 3.9049 (0.8); 3.8940 (0.7); 3.4826 (0.8); 3.4654 (1.8); 3.4502 (2.8); 3.4350 (1.7); 3.4183 (0.8); 2.7252 (2.4); 2.7080 (4.8); 2.6908 (2.2); 2.5840 (1.4); 2.5730 (1.4); 2.5479 (1.6); 2.5369 (1.6); 2.4781 (1.0); 2.4589 (0.9); 2.4554 (0.8); 2.4358 (0.8); 2.4218 (1.0); 2.4072 (1.2); 2.3977 (1.4); 2.3833 (1.4); 2.3790 (0.5); 2.3547 (0.6); 2.3405 (0.6); 2.2785 (0.6); 2.2594 (0.8); 2.2546 (0.5); 2.2459 (0.6); 2.2404 (0.5); 2.2353 (0.7); 2.2269 (0.9); 2.2219 (0.6); 2.2077 (0.6); 2.2026 (0.7); 2.1274 (1.8); 2.1051 (1.8); 2.0913 (1.6); 2.0691 (1.5); 1.8164 (0.6); 1.8055 (0.7); 1.7958 (0.6); 1.7926 (0.5); 1.7865 (0.5); 1.7834 (0.6); 1.7723 (0.6); −0.0002 (12.1)

I-108: $^{1}$H-NMR(400.0 MHz, $d_6$-DMSO):

δ = 7.7544 (1.1); 7.7339 (1.2); 7.3757 (0.5); 7.3553 (1.2); 7.3338 (1.2); 7.3127 (0.6); 7.2094 (0.6); 7.2062 (0.6); 7.1895 (1.2); 7.1857 (1.2); 7.1735 (1.3); 7.1655 (0.7); 7.1533 (0.7); 7.0772 (1.2); 7.0611 (1.7); 7.0419 (0.9); 4.7378 (1.9); 4.6981 (2.2); 4.2415 (2.3); 4.2015 (1.9); 3.8041 (0.8); 3.7940 (1.1); 3.7838 (1.4); 3.7734 (1.1); 3.7636 (0.8); 3.6535 (0.6); 3.6441 (0.8); 3.6371 (0.8); 3.6238 (0.9); 3.6075 (0.7); 3.3135 (89.5); 3.2626 (0.7); 2.6698 (0.7); 2.5232 (1.8); 2.5185 (2.5); 2.5099 (41.1); 2.5053 (91.2); 2.5007 (127.6); 2.4960 (88.7); 2.4915 (40.6); 2.4804 (1.6); 2.4699 (1.5); 2.4579 (2.5); 2.4509 (1.2); 2.4461 (1.9); 2.4012 (0.5); 2.3799 (0.6); 2.3589 (1.4); 2.3365 (1.5); 2.3274 (0.9); 2.3227 (0.7); 2.3174 (1.3); 2.2917 (0.7); 2.2866 (0.7); 2.2784 (0.8); 2.2733 (0.9); 2.2679 (1.0); 2.2626 (1.0); 2.2544 (1.0); 2.2495 (1.2); 2.2259 (0.5); 2.2206 (0.6); 2.2126 (0.5); 2.1874 (1.3); 2.1837 (1.4); 2.1660 (1.4); 2.1624 (1.4); 2.1530 (1.2); 2.1491 (1.2); 2.1315 (1.2); 2.1274 (1.7); 2.1138 (0.7); 2.1020 (0.9); 2.0945 (1.2); 2.0707 (0.9); 1.7666 (0.5); 1.7585 (0.7); 1.7534 (0.7); 1.7453 (0.8); 1.7270 (0.7); 1.7217 (0.6); 1.3839 (0.8); 1.3651 (2.8); 1.3583 (1.2); 1.3467 (3.4); 1.3400 (1.8); 1.3299 (2.6); 1.3218 (1.3); 1.3116 (0.8); 0.9915 (16.0); 0.9749 (15.7); 0.8150 (4.3); 0.8118 (4.5); 0.7966 (9.0); 0.7934 (9.5); 0.7779 (3.8); 0.7747 (3.8); −0.0002 (12.0)

I-109: $^{1}$H-NMR(400.0 MHz, $d_6$-DMSO):

δ = 10.7955 (4.3); 8.0700 (2.2); 8.0560 (4.4); 8.0419 (2.1); 7.5174 (6.1); 7.4975 (6.5); 7.3808 (1.2); 7.3768 (1.3); 7.3603 (2.6); 7.3563 (2.9); 7.3502 (1.7); 7.3358 (10.9); 7.3338 (8.2); 7.3179 (6.5); 7.3157 (10.7); 7.3135 (7.3); 7.2085 (1.5); 7.2046 (1.7); 7.1958 (1.7); 7.1918 (2.0); 7.1885 (2.9); 7.1849 (3.1); 7.1757 (2.8); 7.1724 (3.2); 7.1683 (2.0); 7.1644 (1.9); 7.1555 (1.6); 7.1519 (1.7); 7.1238 (9.0); 7.1181 (8.7); 7.0747 (5.0); 7.0718 (6.0); 7.0571 (7.9); 7.0545 (11.1); 7.0519 (7.4); 7.0371 (6.2); 7.0343 (6.2); 6.9827 (5.5); 6.9800 (5.8); 6.9651 (5.0); 6.9628 (8.4); 6.9604 (6.2); 6.9455 (3.9); 6.9429 (3.7); 4.7400 (4.5); 4.7002 (5.2); 4.2323 (5.6); 4.1926 (4.9); 3.8159 (0.9); 3.8051 (1.8); 3.7946 (2.6); 3.7845 (3.3); 3.7745 (2.6); 3.7641 (1.8); 3.7534 (0.9); 3.4882 (16.0); 3.3360 (2.3); 3.3204 (5.3); 3.3028 (5.5); 3.2865 (2.8); 3.1700 (0.5); 2.8030 (5.9); 2.7837 (8.9); 2.7663 (5.1); 2.6704 (0.5); 2.5405 (0.6); 2.5190 (5.3); 2.5104 (30.4); 2.5059 (66.3); 2.5012 (90.3); 2.4966 (62.8); 2.4920 (28.2); 2.4843 (5.1); 2.4726 (4.3); 2.3874 (1.0); 2.3675 (1.5); 2.3644 (1.5); 2.3450 (3.2); 2.3256 (3.2); 2.3028 (2.5); 2.2718 (2.4); 2.2584 (2.9); 2.2477 (3.6); 2.2344 (3.5); 2.2166 (1.4); 2.2058 (2.1); 2.1980 (4.8); 2.1928 (2.4); 2.1765 (4.4); 2.1631 (3.8); 2.1416 (3.7); 2.1179 (1.2); 2.0984 (2.2); 2.0941 (1.4); 2.0862 (1.7); 2.0791 (1.5); 2.0744 (2.2); 2.0668 (2.7); 2.0623 (1.7); 2.0551 (1.0); 2.0472 (1.5); 2.0428 (2.1); 2.0232 (0.9); 1.7426 (1.2); 1.7299 (1.7); 1.7191 (2.4); 1.7089 (2.1); 1.6975 (2.1); 1.6872 (2.1); 1.6767 (1.2); 1.6636 (0.9); −0.0002 (8.2)

I-110: $^{1}$H-NMR(400.0 MHz, $d_6$-DMSO):

δ = 7.9121 (1.0); 7.3525 (1.0); 7.3309 (1.0); 7.3270 (0.9); 7.3107 (0.5); 7.3069 (0.5); 7.2071 (0.6); 7.2031 (0.6); 7.1945 (0.6); 7.1904 (0.7); 7.1872 (1.1); 7.1833 (1.2); 7.1744 (1.0); 7.1708 (1.2); 7.1668 (0.7); 7.1627 (0.7); 7.1540 (0.6); 7.1503 (0.6); 7.0730 (1.1); 7.0570 (1.5); 7.0376 (0.8); 4.7349 (1.7); 4.6950 (2.0); 4.2353 (2.1); 4.1954 (1.8); 3.8054 (0.7); 3.7953 (0.9); 3.7849 (1.3); 3.7747 (1.0); 3.7645 (0.7); 3.3070 (72.1); 3.2566 (0.6); 3.1685 (0.5); 2.9992 (1.0); 2.9817 (2.1); 2.9677 (2.2); 2.9560 (2.0); 2.9386 (1.0); 2.6695 (0.6); 2.5229 (1.7); 2.5182 (2.4); 2.5095 (38.6); 2.5050 (84.7); 2.5003 (118.4); 2.4957 (83.3); 2.4911 (36.6); 2.4723 (2.1); 2.4604 (2.2); 2.4552 (0.8); 2.4505 (0.9); 2.4459 (0.6); 2.3803 (0.6); 2.3578 (1.2); 2.3361 (1.3); 2.3271 (0.8); 2.3224 (0.6); 2.3161 (1.1); 2.2858 (1.0); 2.2723 (1.2); 2.2617 (1.5); 2.2483 (1.5); 2.2305 (0.5); 2.2198 (0.8); 2.2066 (0.8); 2.1970 (1.9); 2.1758 (1.8); 2.1622 (1.6); 2.1465 (0.7); 2.1409 (1.6); 2.1272 (1.0); 2.1227 (0.6); 2.1149 (0.7); 2.1079 (0.6); 2.1032 (0.8); 2.0956 (1.1); 2.0910 (0.7); 2.0763 (0.6); 2.0714 (1.3); 1.7588 (0.7); 1.7478 (0.9); 1.7378 (0.7); 1.7268 (0.7); 1.7160 (0.8); 1.3962 (2.0); 1.3781 (4.1); 1.3600 (4.5); 1.3420 (2.4); 1.3239 (0.5); 0.8362 (7.6); 0.8178 (16.0); 0.7991 (6.7); −0.0002 (9.2)

-continued

I-111: $^1$H-NMR(400.0 MHz, CDCl3):
δ = 7.5217 (1.2); 7.2627 (223.6); 7.2269 (2.2); 7.2106 (4.4); 7.2059 (3.8); 7.1942 (2.5); 7.1896 (8.4); 7.1850 (3.1); 7.1733 (3.8); 7.1687 (5.2); 7.1524 (2.5); 7.1168 (1.4); 7.1063 (2.2); 7.1022 (1.8); 7.0921 (5.0); 7.0800 (3.3); 7.0762 (3.6); 7.0735 (4.0); 7.0675 (7.0); 7.0601 (2.2); 7.0558 (3.2); 7.0486 (14.2); 7.0419 (12.2); 7.0380 (9.2); 7.0334 (16.0); 7.0250 (6.8); 7.0226 (5.7); 7.0129 (1.2); 7.0059 (1.1); 6.9987 (1.2); 6.9030 (1.2); 6.8986 (1.6); 6.8870 (10.5); 6.8780 (1.9); 6.8674 (14.1); 6.8566 (2.0); 6.8472 (9.2); 6.8352 (1.3); 6.8316 (1.0); 5.5095 (2.9); 5.2996 (0.8); 4.8468 (6.2); 4.8432 (6.2); 4.8080 (7.0); 4.8044 (7.0); 4.2270 (9.2); 4.1882 (8.1); 3.9262 (1.5); 3.9153 (3.1); 3.9041 (3.6); 3.8956 (3.8); 3.8926 (3.8); 3.8840 (3.6); 3.8727 (3.2); 3.8619 (1.5); 3.5525 (0.6); 3.5360 (1.6); 3.5189 (3.4); 3.5022 (7.1); 3.4859 (8.0); 3.4828 (8.0); 3.4669 (7.5); 3.4505 (3.3); 3.4330 (1.7); 3.4173 (0.6); 2.9016 (7.7); 2.8853 (14.6); 2.8689 (6.8); 2.5965 (6.4); 2.5860 (6.4); 2.5603 (7.4); 2.5498 (7.3); 2.5154 (1.3); 2.4954 (1.8); 2.4919 (1.7); 2.4716 (4.7); 2.4523 (4.2); 2.4490 (4.0); 2.4301 (3.9); 2.4118 (4.6); 2.3972 (5.4); 2.3876 (6.3); 2.3732 (6.4); 2.3689 (2.5); 2.3543 (2.0); 2.3446 (2.9); 2.3303 (2.9); 2.2516 (2.4); 2.2325 (3.8); 2.2276 (2.3); 2.2187 (2.9); 2.2135 (2.4); 2.2083 (3.2); 2.1998 (4.3); 2.1946 (2.8); 2.1895 (1.9); 2.1806 (2.6); 2.1754 (3.5); 2.1564 (1.8); 2.1158 (8.4); 2.0927 (8.3); 2.0797 (7.5); 2.0566 (7.4); 1.9860 (0.6); 1.8107 (2.2); 1.7994 (2.4); 1.7966 (2.8); 1.7858 (3.2); 1.7761 (3.1); 1.7728 (2.6); 1.7666 (2.5); 1.7632 (3.1); 1.7524 (2.8); 1.7429 (2.1); 1.7399 (1.9); 1.7284 (1.8); 0.0079 (1.8); −0.0002 (67.7); −0.0085 (2.2)
I-112: $^1$H-NMR(400.0 MHz, CDCl3):
δ = 7.2606 (70.3); 7.2152 (1.3); 7.1965 (3.2); 7.1777 (2.0); 7.1054 (0.6); 7.0917 (1.2); 7.0797 (0.7); 7.0733 (1.0); 7.0648 (1.9); 7.0596 (2.2); 7.0490 (1.5); 7.0456 (3.6); 7.0392 (3.8); 7.0357 (2.7); 7.0311 (4.0); 7.0222 (1.6); 6.9966 (0.6); 6.9864 (2.8); 6.9702 (1.7); 6.9512 (1.4); 5.3741 (0.8); 4.8420 (1.5); 4.8385 (1.6); 4.8033 (1.7); 4.7997 (1.7); 4.2253 (2.2); 4.1866 (2.0); 3.9306 (0.8); 3.9197 (0.9); 3.9091 (1.0); 3.8997 (0.9); 3.8887 (0.8); 3.5295 (0.9); 3.5123 (2.1); 3.4970 (3.3); 3.4817 (2.0); 3.4650 (1.0); 2.7739 (2.6); 2.7567 (5.3); 2.7395 (2.4); 2.5772 (1.6); 2.5663 (1.5); 2.5412 (1.8); 2.5303 (1.8); 2.4668 (1.2); 2.4475 (1.0); 2.4439 (1.0); 2.4244 (1.0); 2.4139 (1.2); 2.3992 (1.3); 2.3899 (1.6); 2.3754 (1.6); 2.3712 (0.6); 2.3469 (0.7); 2.3276 (16.0); 2.2669 (0.6); 2.2478 (1.0); 2.2431 (0.6); 2.2343 (0.7); 2.2288 (0.6); 2.2238 (0.8); 2.2152 (1.0); 2.2103 (0.6); 2.1961 (0.6); 2.1910 (0.8); 2.1057 (2.0); 2.0833 (1.9); 2.0697 (1.7); 2.0473 (1.7); 1.8160 (0.5); 1.8046 (0.6); 1.8019 (0.7); 1.7908 (0.8); 1.7813 (0.7); 1.7780 (0.6); 1.7719 (0.6); 1.7687 (0.7); 1.7576 (0.6); 1.7484 (0.5); 1.6474 (0.8); 0.0080 (0.6); −0.0002 (18.1)
I-113: $^1$H-NMR(400.1 MHz, CDCl3):
δ = 7.5201 (0.5); 7.5182 (0.5); 7.2613 (82.2); 7.2593 (80.8); 7.1275 (0.4); 7.1150 (0.9); 7.1029 (1.6); 7.0924 (1.1); 7.0849 (1.7); 7.0782 (1.7); 7.0692 (1.0); 7.0590 (6.4); 7.0487 (6.1); 7.0412 (2.1); 7.0363 (2.0); 6.9974 (0.5); 6.9955 (0.4); 4.8980 (2.5); 4.8595 (2.8); 4.7241 (1.1); 4.7131 (1.2); 4.6968 (2.2); 4.6859 (2.3); 4.6695 (1.2); 4.6584 (1.1); 4.2514 (3.7); 4.2126 (3.3); 3.9077 (0.5); 3.8965 (1.0); 3.8858 (1.5); 3.8754 (1.6); 3.8648 (1.5); 3.8541 (1.1); 3.8429 (0.6); 2.7495 (2.2); 2.7398 (2.2); 2.7112 (2.7); 2.7015 (2.7); 2.5585 (0.6); 2.5411 (0.8); 2.5341 (0.7); 2.5159 (1.9); 2.4981 (1.6); 2.4915 (1.5); 2.4741 (1.6); 2.4425 (1.3); 2.4272 (1.5); 2.4181 (1.9); 2.4021 (2.0); 2.3846 (3.2); 2.3752 (1.1); 2.3608 (3.5); 2.3463 (2.3); 2.3235 (2.2); 2.3064 (0.8); 2.2875 (1.2); 2.2730 (0.9); 2.2631 (0.9); 2.2549 (1.4); 2.2497 (0.9); 2.2355 (0.8); 2.2304 (1.0); 2.2121 (0.5); 1.9448 (1.3); 1.9154 (1.4); 1.8476 (0.7); 1.8342 (1.1); 1.8219 (1.5); 1.8098 (2.0); 1.8019 (2.0); 1.7911 (2.1); 1.7865 (1.9); 1.7754 (1.6); 1.7675 (1.2); 1.7571 (0.5); 1.7505 (0.5); 1.6912 (2.6); 1.6831 (2.1); 1.6643 (2.6); 1.6578 (2.6); 1.6497 (1.8); 1.6427 (0.7); 1.5553 (22.8); 1.5209 (0.3); 1.5111 (0.5); 1.5035 (0.5); 1.4900 (0.8); 1.4812 (0.9); 1.4736 (0.9); 1.4656 (1.0); 1.4578 (0.8); 1.4521 (0.7); 1.4440 (0.6); 1.4360 (0.5); 1.4274 (0.3); 1.3865 (0.6); 1.3789 (0.9); 1.3719 (0.6); 1.3496 (1.6); 1.3283 (0.7); 1.3210 (1.1); 1.3135 (0.6); 1.0953 (0.4); 1.0847 (0.6); 1.0590 (1.2); 1.0531 (1.3); 1.0281 (1.6); 1.0203 (1.3); 0.9964 (0.6); 0.9885 (0.6); 0.9779 (1.2); 0.9484 (2.9); 0.9192 (3.1); 0.9095 (15.0); 0.9013 (16.0); 0.8933 (15.0); 0.8839 (14.6); 0.8685 (1.8); 0.8448 (1.2); 0.8137 (0.5); 0.7498 (14.3); 0.7324 (14.0); 0.0061 (1.3)
I-114: $^1$H-NMR(400.0 MHz, CDCl3):
δ = 7.5212 (1.0); 7.3558 (5.6); 7.3360 (11.8); 7.3162 (7.9); 7.2729 (0.6); 7.2721 (0.7); 7.2713 (0.7); 7.2705 (0.8); 7.2697 (0.9); 7.2680 (1.4); 7.2622 (188.6); 7.1213 (6.8); 7.1103 (5.7); 7.1037 (9.1); 7.0965 (5.2); 7.0869 (5.2); 7.0840 (5.7); 7.0807 (4.5); 7.0779 (3.6); 7.0703 (4.9); 7.0640 (1.6); 7.0588 (2.0); 7.0535 (4.5); 7.0509 (9.6); 7.0440 (9.0); 7.0406 (7.1); 7.0359 (12.4); 7.0273 (6.4); 7.0248 (7.3); 7.0171 (7.6); 6.9982 (1.1); 5.4464 (2.4); 4.8443 (4.8); 4.8407 (4.8); 4.8056 (5.4); 4.8019 (5.4); 4.2387 (6.9); 4.1999 (6.2); 3.9469 (1.1); 3.9358 (2.3); 3.9250 (2.9); 3.9148 (3.2); 3.9049 (2.9); 3.8939 (2.4); 3.8829 (1.2); 3.5743 (0.6); 3.5566 (1.4); 3.5403 (3.0); 3.5226 (5.6); 3.5175 (2.6); 3.5074 (5.4); 3.5049 (4.1); 3.5002 (5.3); 3.4898 (2.9); 3.4851 (5.5); 3.4680 (3.0); 3.4510 (1.3); 3.4338 (0.6); 2.8432 (8.2); 2.8258 (16.0); 2.8083 (7.3); 2.5915 (4.9); 2.5806 (4.9); 2.5553 (5.7); 2.5444 (5.6); 2.5163 (1.0); 2.4963 (1.3); 2.4931 (1.2); 2.4734 (3.5); 2.4534 (3.2); 2.4500 (3.1); 2.4304 (3.1); 2.4201 (3.6); 2.4053 (4.2); 2.3960 (5.0); 2.3814 (5.0); 2.3773 (1.8); 2.3625 (1.4); 2.3530 (2.2); 2.3386 (2.1); 2.2718 (1.9); 2.2527 (2.9); 2.2480 (1.8); 2.2392 (2.3); 2.2338 (1.8); 2.2287 (2.4); 2.2203 (3.2); 2.2152 (2.1); 2.2098 (1.4); 2.2011 (2.0); 2.1959 (2.5); 2.1769 (1.3); 2.1280 (6.3); 2.1056 (6.2); 2.0918 (5.6); 2.0695 (5.6); 2.0061 (0.6); 1.8106 (1.6); 1.7992 (1.8); 1.7964 (2.1); 1.7852 (2.2); 1.7758 (2.2); 1.7727 (1.9); 1.7665 (1.9); 1.7633 (2.3); 1.7543 (1.7); 1.7520 (2.0); 1.7430 (1.6); 1.7399 (1.5); 1.7283 (1.3); 0.0080 (1.6); 0.0048 (0.6); −0.0002 (55.5); −0.0085 (1.6)
I-116: $^1$H-NMR(400.1 MHz, $d_6$-DMSO):
δ = 8.3599 (0.7); 8.3510 (1.1); 8.3400 (0.8); 8.3308 (1.0); 7.3878 (0.5); 7.3840 (0.5); 7.3672 (1.0); 7.3634 (1.1); 7.3575 (0.6); 7.3475 (0.7); 7.3415 (1.1); 7.3376 (1.0); 7.3211 (0.6); 7.3175 (0.6); 7.2526 (1.0); 7.2343 (2.3); 7.2285 (1.4); 7.2226 (1.4); 7.2170 (1.2); 7.2117 (1.6); 7.2056 (2.4); 7.2000 (1.8); 7.1931 (2.8); 7.1880 (2.4); 7.1833 (1.8); 7.1749 (2.7); 7.1713 (2.5); 7.1583 (1.7); 7.1537 (2.6); 7.1360 (1.3); 7.1226 (0.5); 7.1182 (0.4); 7.0947 (1.1); 7.0786 (1.5); 7.0595 (0.8); 5.2670 (0.8); 5.2492 (1.4); 5.2304 (1.2); 5.2116 (0.4); 4.7613 (1.8); 4.7216 (2.0); 4.2776 (1.4); 4.2673 (0.9); 4.2377 (1.2); 4.2275 (0.8); 3.8763 (0.5); 3.8657 (0.8); 3.8552 (1.1); 3.8451 (1.2); 3.8351 (0.9); 3.8246 (0.6); 3.4148 (16.0); 3.1685 (0.7); 2.9503 (0.3); 2.9406 (0.4); 2.9292 (0.4); 2.9193 (0.5); 2.9115 (0.7); 2.9017 (0.8); 2.8896 (0.7); 2.8799 (0.7); 2.8251 (0.6); 2.8045 (1.3); 2.7841 (1.0); 2.7746 (0.8); 2.7649 (0.7); 2.7449 (0.4); 2.6693 (0.4); 2.5985 (0.9); 2.5873 (1.0); 2.5823 (0.7); 2.5708 (0.7); 2.5639 (1.2); 2.5526 (1.3); 2.5480 (1.0); 2.5397 (0.7); 2.5363 (0.8); 2.5228 (0.8); 2.5180 (1.3); 2.5094 (22.6); 2.5049 (50.1); 2.5003 (70.6); 2.4957 (51.3); 2.4911 (24.5); 2.4246 (0.4); 2.4011 (0.9); 2.3913 (0.6); 2.3818 (1.8); 2.3702 (1.2); 2.3603 (1.8); 2.3502 (1.2); 2.3402 (1.6); 2.3310 (0.7); 2.3274 (0.8); 2.3180 (0.7); 2.3055 (0.8); 2.2929 (1.2); 2.2816 (1.3); 2.2765 (1.2); 2.2694 (2.0); 2.2548 (1.0); 2.2483 (1.4); 2.2406 (1.2); 2.2352 (1.2); 2.2274 (0.7);

-continued 2.2204 (0.9); 2.2136 (1.1); 2.2014 (0.4); 2.1911 (0.5); 2.1777 (0.4); 2.1716 (0.8); 2.1601 (0.6); 2.1483 (0.7); 2.1411 (0.7); 2.1366 (0.5); 2.1291 (0.3); 2.1217 (0.4); 2.1171 (0.5); 1.8401 (0.4); 1.8346 (0.4); 1.8282 (0.5); 1.8239 (0.5); 1.8169 (0.8); 1.8045 (0.8); 1.7970 (0.6); 1.7930 (0.7); 1.7857 (0.6); 1.7749 (0.4); 1.7659 (0.6); 1.7445 (1.2); 1.7343 (0.6); 1.7243 (1.1); 1.7131 (1.1); 1.7043 (0.5); 1.6928 (1.0); 1.6728 (0.3); 0.0082 (0.6)

I-117: $^{1}$H-NMR(400.0 MHz, $d_6$-DMSO):

δ = 8.9634 (3.8); 8.9592 (4.2); 8.9523 (4.1); 8.9481 (4.0); 8.6792 (1.2); 8.6644 (2.4); 8.6498 (1.2); 8.5056 (2.4); 8.4860 (2.5); 8.0392 (4.6); 8.0175 (5.3); 7.8521 (4.7); 7.8490 (4.9); 7.7265 (3.7); 7.7217 (3.4); 7.7047 (3.2); 7.6998 (3.0); 7.6571 (3.4); 7.6460 (3.4); 7.6363 (3.3); 7.6253 (3.3); 7.3786 (0.7); 7.3747 (0.8); 7.3581 (1.6); 7.3542 (1.7); 7.3480 (0.9); 7.3384 (1.2); 7.3324 (1.7); 7.3280 (1.4); 7.3119 (0.9); 7.3079 (0.9); 7.2057 (0.9); 7.2018 (1.0); 7.1929 (1.0); 7.1891 (1.2); 7.1857 (1.8); 7.1821 (1.9); 7.1730 (1.7); 7.1696 (2.0); 7.1655 (1.2); 7.1615 (1.2); 7.1526 (1.0); 7.1491 (1.0); 7.0861 (1.9); 7.0701 (2.5); 7.0668 (2.4); 7.0507 (1.3); 4.7617 (2.8); 4.7221 (3.2); 4.5217 (0.8); 4.5074 (0.8); 4.4832 (2.8); 4.4686 (2.9); 4.4590 (2.8); 4.4447 (2.9); 4.4201 (0.9); 4.4059 (0.9); 4.2547 (3.8); 4.2150 (3.4); 4.0404 (0.8); 3.8749 (1.0); 3.8643 (1.6); 3.8539 (2.1); 3.8437 (2.4); 3.8337 (2.0); 3.8234 (1.5); 3.8128 (0.9); 3.1679 (16.0); 3.1127 (0.8); 3.1007 (0.7); 3.0945 (0.8); 3.0825 (0.7); 2.7669 (1.3); 2.7553 (1.0); 2.6714 (0.6); 2.6668 (0.5); 2.6546 (2.2); 2.6435 (2.3); 2.6194 (2.8); 2.6083 (2.6); 2.5249 (1.0); 2.5202 (1.7); 2.5115 (31.3); 2.5069 (69.6); 2.5023 (97.9); 2.4977 (69.2); 2.4931 (31.2); 2.4155 (0.7); 2.3963 (1.0); 2.3919 (1.0); 2.3733 (1.9); 2.3547 (4.6); 2.3332 (4.3); 2.3245 (1.0); 2.3196 (2.7); 2.2979 (3.7); 2.2841 (1.9); 2.2733 (2.4); 2.2601 (2.3); 2.2558 (1.1); 2.2426 (0.9); 2.2314 (1.3); 2.2187 (1.3); 2.1855 (0.9); 2.1663 (1.4); 2.1617 (0.8); 2.1543 (1.1); 2.1472 (0.9); 2.1423 (1.2); 2.1351 (1.7); 2.1304 (1.0); 2.1232 (0.6); 2.1155 (1.0); 2.1108 (1.2); 2.0915 (0.6); 2.0746 (0.5); 1.8426 (0.8); 1.8305 (1.2); 1.8194 (1.6); 1.8091 (1.3); 1.7988 (1.3); 1.7879 (1.4); 1.7771 (0.9); 1.7642 (0.6); 1.1974 (1.6); 1.1792 (3.6); 1.1609 (1.6); 1.0511 (1.1); 1.0332 (0.5); 0.0080 (1.5); 0.0048 (0.5); 0.0040 (0.7); 0.0023 (2.0); −0.0002 (51.2); −0.0058 (0.6); −0.0067 (0.5); −0.0085 (1.4)

I-118: $^{1}$H-NMR(400.0 MHz, $d_6$-DMSO):

δ = 9.2012 (2.2); 9.1931 (2.2); 8.3078 (0.5); 6.9931 (1.3); 6.9901 (1.4); 6.9720 (1.6); 6.9690 (1.4); 6.6578 (1.5); 6.6497 (1.5); 6.6446 (0.5); 6.6415 (0.5); 6.6365 (1.4); 6.6284 (1.4); 3.3219 (22.1); 3.2981 (0.5); 2.8333 (0.6); 2.8182 (0.5); 2.5193 (0.5); 2.5108 (5.1); 2.5062 (10.9); 2.5016 (15.3); 2.4970 (10.7); 2.4924 (4.9); 2.2171 (0.8); 2.1965 (0.7); 2.1831 (0.6); 2.0857 (2.9); 1.3266 (16.0); 1.3198 (15.8)

I-119: $^{1}$H-NMR(400.0 MHz, CDCl3):

δ = 7.3405 (0.8); 7.3196 (1.0); 7.2610 (7.5); 7.1102 (0.9); 7.0893 (0.8); 7.0301 (0.6); 2.7640 (0.8); 1.3063 (16.0); −0.0002 (2.0)

I-120: $^{1}$H-NMR(400.0 MHz, $d_6$-DMSO):

δ = 9.2274 (0.5); 8.9569 (1.1); 7.3921 (0.6); 7.3724 (1.2); 7.3495 (1.2); 7.3252 (0.7); 7.2149 (0.6); 7.1946 (1.3); 7.1825 (1.4); 7.1645 (0.7); 7.0621 (1.1); 7.0468 (1.6); 7.0274 (0.8); 4.6753 (1.0); 4.6347 (1.2); 4.2501 (2.1); 4.2095 (1.9); 3.8530 (1.2); 3.5683 (4.2); 3.2012 (0.8); 3.1826 (2.3); 3.1666 (3.8); 3.1511 (2.4); 3.0606 (2.8); 2.9520 (9.6); 2.7495 (16.0); 2.7376 (14.6); 2.6877 (1.5); 2.6794 (1.7); 2.6700 (1.6); 2.6654 (1.1); 2.5235 (3.9); 2.5188 (5.7); 2.5101 (84.2); 2.5056 (183.0); 2.5010 (256.0); 2.4963 (179.1); 2.4918 (79.4); 2.4501 (0.8); 2.4270 (0.8); 2.4065 (1.5); 2.3836 (2.0); 2.3654 (1.8); 2.3424 (1.5); 2.3279 (1.6); 2.3003 (0.9); 2.2874 (1.1); 2.2760 (1.4); 2.2631 (1.4); 2.2338 (0.9); 2.2225 (0.9); 2.1583 (1.0); 2.0733 (0.7); 1.8751 (1.6); 1.8569 (2.0); 1.8374 (1.7); 1.8215 (1.2); 1.8104 (1.1); 1.7909 (1.0); 1.7796 (0.8); 1.0969 (5.9); 1.0787 (12.4); 1.0605 (5.5); 0.0081 (1.7); −0.0002 (57.4); −0.0086 (1.5)

I-121: $^{1}$H-NMR(400.1 MHz, CDCl3):

δ = 7.5235 (0.5); 7.5202 (0.6); 7.3105 (0.4); 7.2647 (84.8); 7.2614 (108.9); 7.1263 (0.9); 7.1132 (1.9); 7.1012 (3.7); 7.0931 (2.9); 7.0767 (5.6); 7.0705 (4.3); 7.0592 (16.0); 7.0489 (13.5); 7.0393 (4.9); 7.0199 (0.4); 7.0008 (0.4); 6.9974 (0.6); 5.7716 (0.7); 5.5327 (3.5); 5.3018 (1.7); 5.2985 (2.2); 4.8712 (1.1); 4.8405 (6.8); 4.8017 (7.5); 4.3545 (1.4); 4.3160 (1.2); 4.2790 (8.2); 4.2402 (7.1); 4.0405 (0.3); 4.0285 (0.5); 4.0196 (0.6); 4.0102 (0.5); 3.9891 (1.3); 3.9777 (2.3); 3.9687 (3.2); 3.9579 (4.3); 3.9472 (3.3); 3.9367 (2.4); 3.9262 (1.1); 3.2418 (0.4); 2.8976 (0.7); 2.8883 (0.7); 2.8575 (0.9); 2.8482 (0.9); 2.7045 (0.7); 2.6967 (1.7); 2.6870 (3.0); 2.6788 (4.0); 2.6695 (4.1); 2.6606 (3.0); 2.6519 (1.8); 2.6429 (0.7); 2.5719 (4.5); 2.5606 (4.5); 2.5494 (1.6); 2.5351 (6.1); 2.5250 (6.5); 2.5064 (5.2); 2.4855 (4.6); 2.4642 (4.9); 2.4425 (3.7); 2.4283 (3.5); 2.4186 (4.0); 2.4040 (5.1); 2.3880 (1.5); 2.3755 (2.4); 2.3617 (2.4); 2.3254 (1.8); 2.3064 (3.0); 2.2926 (2.3); 2.2867 (2.3); 2.2830 (2.2); 2.2739 (3.4); 2.2687 (2.0); 2.2535 (2.5); 2.2309 (1.3); 2.1439 (6.2); 2.1221 (6.5); 2.1076 (6.1); 2.0859 (5.9); 1.8772 (1.5); 1.8662 (2.6); 1.8537 (2.7); 1.8431 (3.0); 1.8325 (3.2); 1.8213 (2.7); 1.8098 (2.5); 1.7957 (1.4); 1.7767 (0.4); 0.8358 (0.3); 0.8164 (1.1); 0.7959 (3.3); 0.7818 (11.2); 0.7786 (10.4); 0.7671 (9.8); 0.7644 (11.0); 0.7609 (8.0); 0.7496 (3.0); 0.7236 (0.3); 0.5735 (0.3); 0.5480 (2.1); 0.5215 (0.5); 0.5116 (0.5); 0.4807 (2.9); 0.4665 (10.5); 0.4620 (9.6); 0.4574 (9.6); 0.4428 (2.5); 0.0117 (0.9); 0.0034 (31.3); 0.0000 (41.4)

I-122: $^{1}$H-NMR(400.0 MHz, $d_6$-DMSO):

δ = 7.8174 (0.6); 7.7987 (0.5); 7.3539 (0.6); 7.3317 (0.6); 7.1883 (0.6); 7.1846 (0.7); 7.1722 (0.7); 7.0709 (0.6); 7.0548 (0.9); 4.7290 (1.0); 4.6893 (1.2); 4.2374 (1.3); 4.1974 (1.1); 3.8137 (0.6); 3.8078 (0.5); 3.7974 (1.3); 3.7873 (0.9); 3.7785 (1.2); 3.7669 (0.6); 3.7624 (0.6); 3.3212 (46.0); 2.5232 (0.5); 2.5185 (0.8); 2.5098 (16.1); 2.5053 (35.6); 2.5007 (49.9); 2.4961 (35.5); 2.4916 (16.4); 2.4664 (1.1); 2.4543 (1.1); 2.4317 (1.2); 2.4197 (1.1); 2.3571 (0.8); 2.3372 (0.8); 2.3149 (0.6); 2.2867 (0.6); 2.2733 (0.7); 2.2628 (0.8); 2.2493 (0.8); 2.1643 (1.2); 2.1435 (1.3); 2.1295 (1.1); 2.1086 (1.2); 2.1026 (0.5); 2.0950 (0.7); 2.0710 (0.5); 1.7451 (0.5); 1.0207 (16.0); 1.0042 (15.9); −0.0002 (11.0)

I-123: $^{1}$H-NMR(400.0 MHz, $d_6$-DMSO):

δ = 7.3796 (0.9); 7.3589 (2.2); 7.3373 (2.2); 7.3163 (1.1); 7.2081 (1.1); 7.1992 (1.0); 7.1918 (2.0); 7.1883 (2.2); 7.1759 (2.2); 7.1718 (1.7); 7.1679 (1.6); 7.1555 (1.2); 7.0969 (1.2); 7.0810 (2.2); 7.0612 (1.6); 7.0452 (0.7); 5.0694 (1.0); 5.0605 (1.9); 5.0476 (1.1); 4.7892 (1.5); 4.7757 (1.2); 4.7526 (3.0); 4.7392 (1.2); 4.7151 (2.0); 4.3019 (0.7); 4.2884 (1.6); 4.2643 (2.0); 4.2487 (1.4); 4.2375 (1.0); 4.2240 (1.7); 4.1958 (0.9); 4.1811 (0.7); 4.1674 (1.5); 4.1500 (2.2); 4.1354 (1.5); 4.1327 (2.0); 4.1301 (2.4); 4.1230 (2.0); 4.1177 (1.6); 4.1123 (4.3); 4.1099 (3.6); 4.1052 (5.6); 4.0945 (3.7); 4.0921 (3.4); 4.0874 (5.6); 4.0766 (1.2); 4.0697 (1.8); 3.8576 (0.9); 3.8485 (1.0); 3.8383 (0.9); 3.8264 (0.9); 3.8153 (0.9); 3.8046 (0.9); 3.7932 (0.9); 3.7838 (1.2); 3.7744 (1.0); 3.7392 (1.0); 3.7061 (0.6); 3.3521 (0.9); 3.3172 (207.4); 3.2934 (5.9); 3.0627 (0.5); 3.0443 (0.6); 3.0371 (0.8); 3.0305 (0.8); 3.0197 (0.9); 3.0124 (0.9); 2.9876 (0.6); 2.9416 (6.9); 2.8973 (1.1); 2.8866 (0.9); 2.8652 (0.6); 2.8568 (1.4); 2.8461 (1.1); 2.8392 (0.9); 2.8289 (0.9); 2.7991 (1.1); 2.7894 (1.0); 2.6748 (0.8); 2.6701 (1.2); 2.6655 (0.9); 2.5986 (1.2); 2.5908

-continued (1.5); 2.5766 (1.8); 2.5588 (1.2); 2.5451 (0.8); 2.5404 (1.4); 2.5361 (1.3); 2.5236 (2.0); 2.5189 (3.7); 2.5102 (68.7); 2.5056 (152.9); 2.5010 (215.3); 2.4964 (151.0); 2.4918 (68.4); 2.4813 (3.5); 2.4730 (2.5); 2.4684 (2.0); 2.4633 (1.6); 2.4509 (0.7); 2.4409 (1.8); 2.4314 (1.4); 2.4183 (1.3); 2.4001 (2.0); 2.3778 (1.2); 2.3572 (0.8); 2.3374 (1.0); 2.3325 (1.3); 2.3278 (1.5); 2.3231 (1.3); 2.3188 (1.1); 2.3012 (0.7); 2.2777 (1.3); 2.2696 (0.9); 2.2652 (1.1); 2.2574 (1.0); 2.2533 (1.7); 2.2450 (1.4); 2.2412 (1.8); 2.2333 (1.3); 2.2119 (1.6); 2.2046 (1.9); 2.1925 (1.5); 2.1798 (0.8); 2.1708 (1.4); 2.1606 (1.4); 2.1471 (1.5); 2.1402 (1.6); 2.1158 (1.4); 2.0963 (1.5); 2.0734 (1.0); 2.0620 (1.3); 1.7125 (0.6); 1.7002 (0.6); 1.6875 (1.1); 1.6820 (1.0); 1.6576 (1.7); 1.6468 (2.1); 1.6148 (2.6); 1.6051 (2.5); 1.5825 (1.9); 1.5442 (0.8); 1.5292 (0.9); 1.5100 (1.1); 1.5010 (0.8); 1.4936 (0.8); 1.4776 (0.7); 1.4685 (0.5); 1.3801 (0.5); 1.3479 (0.6); 1.2847 (0.5); 1.2518 (0.9); 1.2432 (1.4); 1.2254 (2.3); 1.2148 (4.8); 1.2076 (1.8); 1.1970 (9.6); 1.1944 (8.8); 1.1889 (4.5); 1.1821 (8.5); 1.1793 (6.2); 1.1766 (16.0); 1.1712 (7.7); 1.1644 (15.5); 1.1588 (7.6); 1.1534 (3.7); 1.1466 (6.8); −0.0002 (2.2)

I-124: $^1$H-NMR(400.0 MHz, $d_6$-DMSO):

δ = 7.8237 (3.9); 7.3694 (0.8); 7.3653 (0.8); 7.3494 (0.6); 7.3435 (0.8); 7.1987 (0.8); 7.1952 (0.9); 7.1862 (0.8); 7.1829 (0.9); 7.1787 (0.6); 7.1749 (0.6); 7.1069 (0.7); 7.0906 (1.0); 7.0716 (0.6); 4.7754 (1.1); 4.7358 (1.3); 4.2921 (1.6); 4.2524 (1.5); 4.0350 (0.7); 3.9146 (0.6); 3.9045 (0.9); 3.8936 (1.1); 3.8843 (1.2); 3.8731 (1.0); 3.8630 (0.8); 3.5986 (16.0); 3.1667 (0.7); 2.8870 (0.6); 2.8770 (0.6); 2.8495 (0.7); 2.8398 (0.7); 2.7718 (0.5); 2.5541 (0.8); 2.5310 (1.0); 2.5236 (1.6); 2.5188 (2.6); 2.5102 (27.6); 2.5057 (58.6); 2.5011 (81.0); 2.4965 (57.0); 2.4919 (25.9); 2.4689 (0.6); 2.4270 (1.0); 2.4082 (0.9); 2.4043 (0.8); 2.3867 (0.6); 2.3279 (1.1); 2.3151 (0.7); 2.3035 (1.0); 2.2909 (1.0); 2.2618 (0.7); 2.2515 (1.1); 2.2347 (0.7); 2.2227 (0.6); 2.2038 (0.8); 2.1793 (0.5); 1.8635 (0.5); 1.8521 (0.6); 1.8414 (0.6); 1.8340 (0.6); 0.0080 (1.1); −0.0002 (35.3); −0.0085 (1.0)

I-125: $^1$H-NMR(400.0 MHz, CDCl3):

δ = 7.5204 (1.0); 7.2615 (178.9); 7.2514 (2.9); 7.2467 (2.4); 7.2382 (1.8); 7.2328 (4.2); 7.2278 (3.5); 7.2130 (4.7); 7.2081 (3.1); 7.1994 (2.4); 7.1946 (3.0); 7.1900 (3.0); 7.1854 (2.8); 7.1710 (6.9); 7.1665 (6.2); 7.1522 (4.7); 7.1476 (3.8); 7.1180 (1.4); 7.1022 (7.5); 7.0995 (8.0); 7.0932 (5.0); 7.0837 (10.5); 7.0810 (11.6); 7.0677 (6.4); 7.0622 (5.3); 7.0490 (15.2); 7.0426 (11.4); 7.0384 (8.2); 7.0337 (16.0); 7.0254 (10.9); 7.0148 (1.5); 7.0062 (4.7); 6.9976 (1.3); 5.4657 (3.0); 4.8462 (6.0); 4.8429 (6.1); 4.8075 (6.8); 4.8041 (6.9); 4.2303 (8.8); 4.1916 (7.7); 3.9338 (1.4); 3.9230 (2.9); 3.9120 (3.7); 3.9016 (4.0); 3.8918 (3.6); 3.8809 (3.0); 3.8699 (1.4); 3.5661 (0.5); 3.5490 (1.3); 3.5326 (3.5); 3.5156 (8.7); 3.4996 (12.2); 3.4835 (9.0); 3.4671 (3.5); 3.4499 (1.4); 3.4337 (0.5); 2.8632 (8.2); 2.8462 (15.7); 2.8292 (7.4); 2.5900 (5.8); 2.5792 (5.8); 2.5539 (6.8); 2.5431 (6.7); 2.5146 (1.3); 2.4955 (1.7); 2.4910 (1.6); 2.4715 (4.6); 2.4524 (4.0); 2.4483 (4.0); 2.4292 (3.9); 2.4132 (4.1); 2.3986 (4.6); 2.3890 (5.5); 2.3746 (5.6); 2.3559 (1.6); 2.3460 (2.5); 2.3318 (2.5); 2.2578 (2.1); 2.2386 (3.4); 2.2340 (1.9); 2.2250 (2.5); 2.2196 (2.1); 2.2146 (2.8); 2.2060 (3.9); 2.2010 (2.3); 2.1957 (1.6); 2.1867 (2.2); 2.1818 (3.0); 2.1626 (1.4); 2.1191 (7.2); 2.0965 (7.1); 2.0831 (6.3); 2.0604 (6.2); 1.8139 (2.2); 1.7998 (2.7); 1.7893 (3.4); 1.7796 (3.3); 1.7662 (3.4); 1.7560 (3.2); 1.7460 (2.8); 1.7317 (2.7); 0.0078 (1.5); − 0.0002 (46.8); −0.0084 (1.6)

I-126: $^1$H-NMR(400.0 MHz, $d_6$-DMSO):

δ = 7.3558 (0.8); 7.3347 (0.8); 7.1868 (0.8); 7.1740 (0.8); 7.1701 (0.7); 7.1663 (0.5); 7.0966 (0.6); 7.0806 (0.8); 4.7607 (0.9); 4.7213 (1.0); 4.7000 (0.5); 4.2677 (1.1); 4.2286 (1.0); 4.2047 (2.5); 4.1741 (0.5); 4.0381 (3.8); 4.0344 (3.7); 3.8308 (0.6); 3.8210 (0.7); 3.8112 (0.7); 3.8017 (0.6); 3.6734 (7.7); 3.6200 (16.0); 3.4115 (14.4); 3.1660 (1.4); 2.9682 (14.8); 2.8500 (0.6); 2.8396 (0.6); 2.8092 (0.9); 2.7991 (0.8); 2.7689 (5.6); 2.6743 (1.0); 2.6699 (1.2); 2.6652 (0.8); 2.5695 (1.0); 2.5554 (0.6); 2.5507 (0.8); 2.5469 (1.2); 2.5401 (0.8); 2.5286 (1.8); 2.5233 (3.2); 2.5186 (4.7); 2.5099 (61.2); 2.5053 (131.9); 2.5007 (182.5); 2.4961 (127.8); 2.4916 (57.4); 2.4327 (0.7); 2.4087 (0.8); 2.3961 (0.5); 2.3322 (0.9); 2.3275 (1.2); 2.3229 (0.8); 2.2562 (0.5); 2.2432 (0.8); 2.2316 (0.8); 2.2019 (0.6); 2.1948 (1.2); 2.1792 (0.6); 2.1479 (0.7); 0.0080 (2.4); −0.0002 (81.5); −0.0085 (2.4)

I-127: $^1$H-NMR(400.0 MHz, $d_6$-DMSO):

δ = 11.8166 (10.6); 8.0474 (2.6); 7.3838 (2.8); 7.3668 (5.4); 7.3424 (5.8); 7.3215 (3.5); 7.2101 (3.3); 7.1938 (5.9); 7.1782 (5.8); 7.1616 (3.6); 7.0731 (5.9); 7.0571 (7.6); 7.0409 (5.2); 7.0210 (2.4); 4.7204 (8.1); 4.6804 (9.2); 4.2464 (9.6); 4.2071 (8.5); 3.8462 (3.6); 3.8357 (4.9); 3.8259 (5.5); 3.8153 (4.6); 3.4014 (5.1); 3.3446 (566.1); 3.2334 (18.4); 3.2120 (111.6); 3.1658 (16.0); 2.7482 (7.1); 2.7376 (6.2); 2.7098 (7.4); 2.6993 (7.2); 2.6744 (15.0); 2.6698 (20.9); 2.6651 (14.7); 2.5623 (7.1); 2.5573 (5.4); 2.5232 (52.8); 2.5185 (81.7); 2.5098 (1173.9); 2.5053 (2552.9); 2.5007 (3561.7); 2.4961 (2494.2); 2.4915 (1123.6); 2.4606 (20.4); 2.4561 (23.2); 2.4514 (20.1); 2.4467 (9.1); 2.4375 (5.1); 2.4156 (10.0); 2.3988 (13.9); 2.3777 (12.1); 2.3564 (6.2); 2.3368 (8.4); 2.3322 (16.6); 2.3274 (22.3); 2.3229 (16.4); 2.3184 (8.5); 2.3038 (6.0); 2.2920 (5.8); 2.2800 (7.4); 2.2676 (7.2); 2.2381 (4.8); 2.2236 (5.9); 2.2047 (6.5); 2.1934 (4.4); 2.1741 (5.6); 2.1503 (4.3); 2.0732 (6.3); 1.7786 (3.5); 1.7677 (3.7); 1.7488 (4.5); 1.7241 (2.8); 1.1327 (2.5); 0.1461 (5.4); 0.0080 (44.0); −0.0002 (1593.3); − 0.0086 (48.3); −0.0496 (8.1); −0.1495 (5.3)

I-128: $^1$H-NMR(400.0 MHz, $d_6$-DMSO):

δ = 7.3794 (0.9); 7.3592 (1.9); 7.3374 (2.0); 7.3160 (0.9); 7.2080 (1.0); 7.1881 (2.0); 7.1756 (1.9); 7.1557 (1.0); 7.0970 (1.2); 7.0810 (1.8); 7.0623 (1.4); 5.0609 (1.7); 4.7885 (1.4); 4.7758 (1.1); 4.7522 (2.6); 4.7150 (1.7); 4.2886 (1.4); 4.2643 (1.8); 4.2493 (1.2); 4.2381 (0.8); 4.2230 (1.5); 4.1983 (0.7); 4.1804 (0.7); 4.1671 (1.3); 4.1498 (1.8); 4.1302 (2.2); 4.1228 (1.7); 4.1122 (3.7); 4.1050 (4.8); 4.0945 (3.2); 4.0873 (4.6); 4.0764 (1.0); 4.0694 (1.4); 3.8482 (1.0); 3.8147 (0.8); 3.7834 (1.1); 3.7395 (1.0); 3.7053 (0.6); 3.4581 (16.0); 3.1667 (1.2); 3.0383 (0.8); 3.0128 (0.8); 2.8972 (1.1); 2.8862 (0.8); 2.8567 (1.3); 2.8465 (1.0); 2.8293 (0.8); 2.7991 (1.0); 2.7893 (1.0); 2.6745 (1.0); 2.6700 (1.4); 2.6655 (0.9); 2.5981 (1.2); 2.5913 (1.4); 2.5760 (1.5); 2.5590 (0.6); 2.5368 (2.0); 2.5235 (4.2); 2.5188 (6.2); 2.5101 (83.2); 2.5056 (178.8); 2.5010 (248.2); 2.4963 (172.2); 2.4918 (75.6); 2.4622 (0.9); 2.4403 (1.3); 2.4001 (1.6); 2.3780 (1.0); 2.3324 (1.3); 2.3278 (1.6); 2.3231 (1.2); 2.3015 (0.5); 2.2781 (1.0); 2.2648 (1.0); 2.2531 (1.4); 2.2410 (1.4); 2.2043 (1.7); 2.1921 (1.4); 2.1708 (1.2); 2.1402 (1.3); 2.1158 (1.1); 2.0962 (1.2); 2.0608 (1.1); 1.6470 (1.9); 1.6141 (2.2); 1.5103 (0.8); 1.3485 (0.5); 1.2147 (4.0); 1.1970 (7.8); 1.1943 (7.2); 1.1888 (3.8); 1.1820 (6.9); 1.1765 (12.8); 1.1711 (6.1); 1.1643 (11.9); 1.1588 (5.9); 1.1534 (2.9); 1.1466 (5.2); 0.0080 (1.4); −0.0002 (47.2); −0.0086 (1.2)

I-129: $^1$H-NMR(400.0 MHz, $d_6$-DMSO):

δ = 8.9138 (2.4); 8.8925 (2.4); 7.3672 (0.6); 7.3634 (0.7); 7.3441 (4.2); 7.3408 (4.6); 7.3370 (2.2); 7.3280 (5.4); 7.3254 (7.4); 7.3225 (8.7); 7.3199 (7.9); 7.3063 (6.4); 7.3041 (7.4); 7.2603 (3.8); 7.2533 (16.0); 7.2451 (5.4); 7.2348 (9.3); 7.2312 (7.2); 7.2263 (2.0); 7.2221 (1.2); 7.2180 (1.2); 7.2146 (0.6); 7.1875

-continued (0.7); 7.1838 (0.8); 7.1749 (0.7); 7.1711 (0.9); 7.1676 (1.3); 7.1641 (1.4); 7.1548 (1.3); 7.1516 (1.4); 7.1476 (0.9); 7.1435 (0.9); 7.1346 (0.8); 7.1312 (0.8); 7.0655 (1.4); 7.0495 (1.9); 7.0301 (1.0); 6.1065 (3.0); 6.0853 (2.9); 4.7258 (2.1); 4.6859 (2.4); 4.2210 (2.6); 4.1813 (2.3); 3.8224 (0.8); 3.8119 (1.2); 3.8016 (1.5); 3.7917 (1.2); 3.7812 (0.9); 3.4995 (3.8); 3.1668 (1.2); 2.6716 (1.9); 2.6607 (1.9); 2.6369 (2.1); 2.6258 (1.9); 2.5232 (1.7); 2.5185 (2.5); 2.5099 (32.0); 2.5053 (69.1); 2.5007 (95.9); 2.4961 (67.1); 2.4915 (30.0); 2.3845 (2.3); 2.3627 (2.7); 2.3497 (1.8); 2.3391 (1.6); 2.3277 (2.4); 2.3187 (1.7); 2.2968 (1.2); 2.2678 (1.1); 2.2547 (1.3); 2.2438 (1.6); 2.2308 (1.6); 2.2130 (0.6); 2.2018 (0.8); 2.1891 (0.8); 2.1245 (0.6); 2.1049 (1.0); 2.0929 (0.8); 2.0854 (0.7); 2.0811 (0.9); 2.0732 (1.4); 2.0537 (0.7); 2.0494 (1.0); 1.7912 (0.5); 1.7789 (0.8); 1.7680 (1.1); 1.7579 (1.0); 1.7465 (1.0); 1.7364 (1.0); 1.7254 (0.6); 0.0080 (1.2); −0.0002 (40.1); −0.0086 (1.1)

I-131: $^1$H-NMR(400.0 MHz, $d_6$-DMSO):

δ = 7.4143 (3.5); 7.3966 (9.3); 7.3773 (7.7); 7.3360 (5.4); 7.3149 (4.4); 7.2941 (1.8); 7.2198 (10.3); 7.2165 (13.7); 7.1984 (10.2); 7.1280 (2.6); 7.1130 (2.5); 6.9106 (2.5); 4.5335 (2.1); 4.4938 (2.4); 4.1158 (2.5); 4.0738 (2.0); 3.8120 (2.3); 3.3795 (69.8); 3.1666 (4.9); 3.1037 (16.0); 2.6746 (1.9); 2.6700 (2.6); 2.6654 (1.8); 2.5546 (0.8); 2.5500 (1.0); 2.5404 (1.4); 2.5370 (0.7); 2.5234 (7.1); 2.5187 (11.0); 2.5101 (146.5); 2.5055 (316.7); 2.5009 (439.2); 2.4963 (307.5); 2.4917 (137.4); 2.4728 (2.3); 2.4679 (2.2); 2.4499 (0.8); 2.4273 (1.8); 2.3851 (2.0); 2.3808 (2.1); 2.3370 (1.2); 2.3323 (2.2); 2.3278 (2.8); 2.3231 (2.1); 2.2394 (3.8); 2.2185 (4.4); 2.2055 (3.8); 2.1769 (3.0); 2.1419 (2.2); 2.1213 (1.7); 2.0992 (1.8); 2.0733 (2.9); 2.0365 (1.2); 1.6575 (1.8); 0.0080 (3.2); −0.0002 (105.9); −0.0085 (3.0)

I-132: $^1$H-NMR(400.0 MHz, $d_6$-DMSO):

δ = 8.0055 (5.1); 7.9960 (5.0); 7.3809 (2.0); 7.3771 (2.1); 7.3604 (4.2); 7.3565 (4.6); 7.3505 (2.3); 7.3407 (3.0); 7.3347 (4.5); 7.3306 (3.9); 7.3141 (2.4); 7.3103 (2.3); 7.2073 (2.5); 7.2034 (2.7); 7.1945 (2.8); 7.1906 (3.4); 7.1874 (4.7); 7.1836 (5.0); 7.1746 (4.6); 7.1710 (5.1); 7.1672 (3.0); 7.1630 (2.9); 7.1542 (2.4); 7.1506 (2.6); 7.0670 (4.7); 7.0509 (6.4); 7.0315 (3.4); 4.7189 (7.5); 4.6791 (8.7); 4.2216 (9.4); 4.1817 (8.0); 3.8117 (1.5); 3.8006 (3.1); 3.7903 (4.2); 3.7802 (5.8); 3.7701 (4.3); 3.7599 (3.1); 3.7488 (1.6); 3.4239 (15.9); 3.1669 (0.9); 2.6750 (0.9); 2.6703 (1.2); 2.6658 (0.8); 2.6005 (1.0); 2.5906 (2.8); 2.5809 (4.0); 2.5724 (6.2); 2.5626 (6.6); 2.5539 (4.0); 2.5444 (3.2); 2.5342 (1.8); 2.5238 (4.0); 2.5191 (5.6); 2.5104 (75.1); 2.5059 (162.0); 2.5012 (225.4); 2.4967 (158.0); 2.4921 (71.3); 2.4711 (0.7); 2.4571 (7.3); 2.4453 (7.2); 2.4220 (8.3); 2.4102 (7.9); 2.3899 (1.8); 2.3703 (2.4); 2.3673 (2.3); 2.3478 (5.5); 2.3281 (6.5); 2.3056 (4.4); 2.2827 (4.4); 2.2692 (5.3); 2.2587 (6.5); 2.2453 (6.2); 2.2411 (2.6); 2.2274 (2.1); 2.2168 (3.3); 2.2037 (3.2); 2.1445 (8.8); 2.1296 (4.7); 2.1234 (9.5); 2.1175 (3.8); 2.1095 (9.2); 2.0982 (5.1); 2.0936 (3.5); 2.0881 (7.9); 2.0787 (2.9); 2.0741 (3.9); 2.0548 (1.5); 1.7474 (2.1); 1.7347 (3.0); 1.7240 (4.2); 1.7138 (3.4); 1.7025 (3.4); 1.6921 (3.8); 1.6816 (2.2); 1.6684 (1.6); 0.6075 (5.0); 0.5954 (12.4); 0.5904 (16.0); 0.5782 (15.3); 0.5725 (13.3); 0.5608 (5.8); 0.5390 (0.7); 0.5209 (0.6); 0.3885 (0.6); 0.3789 (0.6); 0.3484 (5.5); 0.3373 (14.4); 0.3313 (12.8); 0.3272 (12.7); 0.3217 (12.6); 0.3107 (4.2); 0.0080 (2.9); −0.0002 (93.3); −0.0085 (2.8)

I-133: $^1$H-NMR(400.0 MHz, $d_6$-DMSO):

δ = 7.9359 (3.3); 7.9214 (6.3); 7.9072 (3.3); 7.3843 (1.9); 7.3803 (2.1); 7.3636 (4.3); 7.3596 (4.6); 7.3538 (2.4); 7.3438 (3.0); 7.3377 (4.6); 7.3337 (4.0); 7.3175 (2.4); 7.3137 (2.3); 7.2093 (2.5); 7.2054 (2.6); 7.1966 (2.6); 7.1925 (3.3); 7.1890 (4.7); 7.1856 (5.0); 7.1765 (4.6); 7.1731 (5.1); 7.1691 (3.1); 7.1651 (3.0); 7.1562 (2.5); 7.1527 (2.7); 7.0727 (4.8); 7.0566 (6.5); 7.0372 (3.5); 4.7347 (7.5); 4.6948 (8.7); 4.2353 (9.3); 4.1954 (8.1); 3.8113 (3.1); 3.8002 (4.9); 3.7899 (6.5); 3.7798 (8.0); 3.7699 (6.8); 3.7596 (5.6); 3.7485 (3.8); 2.9174 (1.2); 2.9024 (1.8); 2.8849 (6.1); 2.8674 (11.6); 2.8523 (12.0); 2.8353 (5.9); 2.8174 (1.8); 2.8025 (1.3); 2.6770 (0.7); 2.6721 (1.0); 2.6674 (0.8); 2.5221 (7.9); 2.5121 (64.4); 2.5076 (133.3); 2.5030 (184.6); 2.4984 (130.0); 2.4938 (58.7); 2.4883 (11.4); 2.4762 (8.2); 2.4566 (0.9); 2.4004 (2.1); 2.3810 (2.4); 2.3585 (5.3); 2.3390 (5.4); 2.3355 (5.2); 2.3250 (1.4); 2.3162 (4.2); 2.2899 (4.0); 2.2764 (4.9); 2.2659 (6.0); 2.2525 (5.9); 2.2346 (2.2); 2.2240 (3.2); 2.2117 (9.7); 2.1907 (7.7); 2.1773 (6.5); 2.1559 (6.4); 2.1440 (2.2); 2.1245 (3.8); 2.1124 (2.8); 2.1052 (2.4); 2.1006 (3.5); 2.0931 (4.5); 2.0886 (2.9); 2.0813 (1.7); 2.0734 (2.7); 2.0689 (3.5); 2.0496 (1.5); 1.7686 (2.0); 1.7558 (2.8); 1.7451 (4.0); 1.7346 (3.4); 1.7237 (3.4); 1.7132 (3.6); 1.7027 (2.3); 1.6895 (2.0); 1.6558 (5.3); 1.6330 (16.0); 1.6060 (11.1); 1.3506 (1.7); 1.3411 (2.0); 1.3313 (2.5); 1.3235 (3.0); 1.3154 (2.6); 1.3045 (2.2); 1.2963 (2.0); 1.2783 (0.9); 1.1972 (1.3); 1.1666 (4.1); 1.1350 (8.7); 1.1196 (6.6); 1.1091 (6.2); 1.0787 (1.7); 1.0489 (0.6); 0.8691 (2.7); 0.8415 (5.9); 0.8164 (4.9); 0.7889 (1.7); 0.7801 (1.8); 0.0080 (1.0); −0.0002 (37.0); −0.0086 (1.1)

I-134: $^1$H-NMR(400.0 MHz, $d_6$-DMSO):

δ = 7.4143 (3.5); 7.3966 (9.3); 7.3774 (7.7); 7.3357 (5.3); 7.3144 (4.4); 7.2936 (1.8); 7.2198 (10.2); 7.2166 (13.7); 7.1986 (10.3); 7.1265 (2.6); 7.1137 (2.5); 6.9103 (2.5); 4.5349 (2.1); 4.4944 (2.4); 4.1148 (2.5); 4.0751 (2.1); 3.8108 (2.4); 3.5617 (9.8); 3.1666 (2.1); 3.1039 (16.0); 2.6794 (0.6); 2.6747 (1.3); 2.6701 (1.8); 2.6655 (1.3); 2.6609 (0.6); 2.5512 (0.6); 2.5404 (1.0); 2.5236 (4.8); 2.5189 (7.4); 2.5102 (101.8); 2.5057 (220.3); 2.5011 (306.7); 2.4965 (214.8); 2.4919 (96.8); 2.4243 (1.8); 2.3894 (2.1); 2.3372 (0.9); 2.3325 (1.6); 2.3279 (2.1); 2.3233 (1.6); 2.2399 (3.8); 2.2185 (4.4); 2.2049 (3.8); 2.1774 (2.9); 2.1419 (2.2); 2.1229 (1.7); 2.0992 (1.8); 2.0735 (2.1); 2.0586 (1.4); 2.0369 (1.2); 1.6579 (1.8); 0.0080 (4.3); −0.0002 (139.5); −0.0086 (4.0)

I-135: $^1$H-NMR(400.0 MHz, $d_6$-DMSO):

δ = 7.3557 (0.7); 7.3346 (0.8); 7.2064 (0.5); 7.1867 (0.9); 7.1741 (0.8); 7.1701 (0.6); 7.0964 (0.6); 7.0807 (0.8); 4.7602 (0.8); 4.7216 (1.0); 4.7007 (0.5); 4.2677 (1.1); 4.2288 (1.0); 4.2046 (2.5); 4.0381 (3.8); 4.0344 (3.7); 3.8314 (0.6); 3.8214 (0.7); 3.8116 (0.7); 3.8014 (0.6); 3.6734 (7.6); 3.6199 (16.0); 3.3789 (32.3); 3.1663 (1.6); 2.9682 (14.8); 2.8497 (0.6); 2.8394 (0.6); 2.8092 (0.9); 2.7989 (0.8); 2.7689 (5.6); 2.6791 (0.5); 2.6744 (1.0); 2.6699 (1.3); 2.6652 (0.9); 2.5693 (1.0); 2.5469 (1.5); 2.5401 (1.2); 2.5344 (0.9); 2.5290 (1.4); 2.5233 (3.0); 2.5186 (4.7); 2.5099 (69.4); 2.5054 (150.9); 2.5007 (209.7); 2.4961 (147.6); 2.4916 (66.4); 2.4326 (0.6); 2.4082 (0.8); 2.3322 (1.0); 2.3275 (1.3); 2.3230 (1.0); 2.2558 (0.5); 2.2431 (0.8); 2.2318 (0.7); 2.2018 (0.6); 2.1947 (1.2); 2.1795 (0.6); 2.1478 (0.7); 1.6716 (0.5); 0.0080 (1.5); −0.0002 (51.2); −0.0086 (1.5)

I-136: $^1$H-NMR(400.0 MHz, $d_6$-DMSO):

δ = 7.3790 (1.0); 7.3587 (2.4); 7.3373 (2.4); 7.3133 (1.2); 7.2083 (1.2); 7.1881 (2.4); 7.1758 (2.3); 7.1555 (1.2); 7.0974 (1.4); 7.0810 (2.4); 7.0613 (1.8); 5.0604 (2.1); 4.7896 (1.6); 4.7776 (1.3); 4.7532 (3.2); 4.7154 (2.2); 4.2889 (1.8); 4.2645 (2.1); 4.2490 (1.5); 4.2378 (1.1); 4.2237 (1.8); 4.1984 (0.9); 4.1817 (0.8); 4.1674 (1.5); 4.1501 (2.4); 4.1302 (2.6); 4.1231 (2.2); 4.1178 (1.8); 4.1124 (4.6); 4.1100 (4.0); 4.1052 (5.8); 4.0945 (3.8); 4.0922 (3.6); 4.0875 (5.7); 4.0766 (1.2); 4.0698 (1.8); 3.8478 (1.2); 3.8370

-continued (1.0); 3.8262 (1.0); 3.8149 (1.0); 3.8028 (1.0); 3.7943 (1.0); 3.7835 (1.2); 3.7373 (1.3); 3.7079 (0.8); 3.5386 (9.0); 3.1670 (1.4); 3.0621 (0.6); 3.0306 (0.9); 3.0202 (1.0); 3.0122 (1.0); 2.9884 (0.5); 2.8968 (1.2); 2.8868 (1.0); 2.8572 (1.5); 2.8464 (1.2); 2.8397 (1.0); 2.8291 (0.9); 2.7991 (1.2); 2.7893 (1.1); 2.6749 (0.8); 2.6704 (1.1); 2.6658 (0.8); 2.5986 (1.3); 2.5909 (1.7); 2.5767 (1.9); 2.5589 (0.8); 2.5367 (1.6); 2.5237 (3.4); 2.5190 (5.0); 2.5103 (68.7); 2.5057 (148.7); 2.5011 (207.4); 2.4965 (144.5); 2.4919 (63.9); 2.4622 (1.5); 2.4540 (0.5); 2.4408 (1.9); 2.4316 (1.4); 2.4177 (1.5); 2.4002 (2.0); 2.3780 (1.4); 2.3326 (1.3); 2.3280 (1.4); 2.3234 (1.3); 2.3013 (0.7); 2.2778 (1.3); 2.2653 (1.3); 2.2533 (1.8); 2.2411 (1.8); 2.2331 (1.4); 2.2120 (1.7); 2.2045 (2.0); 2.1926 (1.7); 2.1706 (1.6); 2.1607 (1.5); 2.1408 (1.6); 2.1173 (1.4); 2.0967 (1.5); 2.0629 (1.4); 1.7127 (0.6); 1.6878 (1.3); 1.6471 (2.3); 1.6150 (2.7); 1.5438 (0.9); 1.5288 (0.9); 1.5101 (0.9); 1.4921 (0.9); 1.3803 (0.5); 1.3487 (0.7); 1.2852 (0.6); 1.2149 (5.0); 1.1971 (9.6); 1.1945 (9.0); 1.1891 (4.7); 1.1822 (8.6); 1.1794 (6.6); 1.1767 (16.0); 1.1713 (7.6); 1.1645 (15.0); 1.1589 (7.6); 1.1536 (3.6); 1.1467 (6.5); 0.0080 (2.5); −0.0002 (80.2); −0.0086 (2.3)

I-137: $^1$H-NMR(400.0 MHz, $d_6$-DMSO):

δ = 8.9141 (1.9); 8.8929 (2.0); 7.3635 (0.5); 7.3443 (3.4); 7.3409 (3.7); 7.3371 (1.8); 7.3281 (4.4); 7.3254 (6.0); 7.3225 (7.0); 7.3199 (6.3); 7.3077 (5.1); 7.3064 (5.1); 7.3042 (6.0); 7.2603 (3.2); 7.2532 (12.8); 7.2450 (4.4); 7.2347 (7.2); 7.2332 (6.8); 7.2311 (5.7); 7.2264 (1.5); 7.2221 (0.9); 7.2180 (0.9); 7.1877 (0.6); 7.1839 (0.6); 7.1750 (0.6); 7.1712 (0.7); 7.1678 (1.0); 7.1642 (1.1); 7.1549 (1.0); 7.1517 (1.2); 7.1476 (0.7); 7.1437 (0.7); 7.1346 (0.6); 7.1313 (0.6); 7.0654 (1.1); 7.0494 (1.5); 7.0300 (0.8); 6.1062 (2.4); 6.0851 (2.4); 4.7257 (1.7); 4.6860 (2.0); 4.2208 (2.1); 4.1811 (1.8); 3.8225 (0.7); 3.8118 (1.0); 3.8016 (1.2); 3.7914 (1.0); 3.7810 (0.7); 3.3941 (5.4); 3.3384 (0.6); 3.1671 (16.0); 2.6715 (1.6); 2.6651 (0.7); 2.6606 (1.5); 2.6368 (1.7); 2.6258 (1.5); 2.5233 (1.9); 2.5186 (2.6); 2.5099 (29.6); 2.5054 (63.4); 2.5008 (87.9); 2.4962 (61.6); 2.4916 (27.1); 2.4554 (0.5); 2.4507 (0.6); 2.3843 (1.9); 2.3625 (2.1); 2.3495 (1.5); 2.3390 (1.3); 2.3276 (2.0); 2.3191 (1.4); 2.2967 (0.9); 2.2678 (0.9); 2.2547 (1.0); 2.2438 (1.3); 2.2308 (1.3); 2.2018 (0.6); 2.1891 (0.6); 2.1049 (0.8); 2.0930 (0.6); 2.0853 (0.5); 2.0811 (0.8); 2.0732 (1.2); 2.0536 (0.6); 2.0494 (0.8); 1.7786 (0.6); 1.7678 (0.9); 1.7578 (0.8); 1.7464 (0.8); 1.7362 (0.8); 0.0080 (0.8); −0.0002 (25.9); −0.0085 (0.7)

I-138: $^1$H-NMR(400.0 MHz, $d_6$-DMSO):

δ = 8.1476 (0.6); 8.1335 (1.1); 8.1193 (0.5); 7.3701 (0.7); 7.3660 (0.8); 7.3439 (0.7); 7.1960 (0.7); 7.1921 (0.8); 7.1795 (0.8); 7.0823 (0.7); 7.0664 (1.0); 7.0468 (0.5); 4.7458 (1.1); 4.7061 (1.3); 4.2400 (1.4); 4.2005 (1.3); 3.7998 (0.7); 3.7896 (0.9); 3.7795 (0.7); 3.7691 (0.5); 3.3360 (47.4); 3.1857 (0.5); 3.1333 (1.0); 3.1148 (2.7); 3.1036 (3.3); 3.0965 (3.0); 3.0854 (2.8); 3.0781 (1.8); 3.0670 (1.0); 3.0248 (0.7); 3.0116 (1.0); 2.9984 (1.0); 2.9842 (1.1); 2.9725 (0.7); 2.5314 (1.1); 2.5197 (1.9); 2.5109 (16.0); 2.5063 (35.2); 2.5017 (49.4); 2.4970 (35.0); 2.4924 (15.3); 2.4849 (1.5); 2.3681 (0.8); 2.3490 (0.8); 2.3261 (0.8); 2.3009 (0.6); 2.2873 (0.8); 2.2768 (1.0); 2.2634 (0.9); 2.2350 (1.6); 2.2215 (0.5); 2.2137 (1.2); 2.1998 (1.0); 2.1784 (1.0); 2.1454 (0.6); 2.1214 (0.5); 2.1141 (0.7); 2.0897 (0.5); 2.0735 (1.1); 1.7614 (0.7); 1.7518 (0.9); 1.7357 (1.2); 1.7297 (1.1); 1.7165 (1.2); 1.7073 (1.0); 1.6946 (0.9); 1.1858 (7.0); 1.1677 (16.0); 1.1495 (6.7); −0.0002 (1.4)

I-139: $^1$H-NMR(400.0 MHz, $d_6$-DMSO):

δ = 8.4942 (4.6); 8.4801 (9.1); 8.4658 (4.6); 7.3832 (2.4); 7.3792 (2.7); 7.3629 (9.3); 7.3527 (3.5); 7.3415 (12.6); 7.3327 (5.6); 7.3247 (10.1); 7.3197 (6.8); 7.3126 (3.3); 7.3030 (5.2); 7.2408 (6.2); 7.2344 (6.5); 7.2173 (7.2); 7.2146 (7.8); 7.2109 (8.0); 7.2082 (8.1); 7.2046 (4.1); 7.2005 (3.8); 7.1912 (9.3); 7.1846 (12.3); 7.1809 (6.8); 7.1716 (5.7); 7.1682 (6.4); 7.1643 (4.0); 7.1602 (3.7); 7.1512 (3.2); 7.1478 (3.4); 7.0717 (8.1); 7.0690 (10.1); 7.0655 (8.6); 7.0505 (15.9); 7.0481 (16.0); 7.0441 (10.6); 7.0417 (9.1); 7.0326 (4.9); 7.0292 (6.7); 7.0267 (5.3); 7.0226 (3.9); 7.0202 (3.8); 4.7280 (9.4); 4.6882 (10.8); 4.2834 (0.8); 4.2693 (1.0); 4.2412 (12.7); 4.2308 (13.0); 4.2180 (13.0); 4.2029 (1.3); 4.1780 (10.4); 3.8238 (3.0); 3.8131 (5.3); 3.8026 (7.3); 3.7924 (8.9); 3.7824 (8.3); 3.7719 (7.4); 3.7608 (6.2); 3.7323 (6.0); 2.6765 (1.3); 2.6719 (1.8); 2.6673 (1.3); 2.5923 (7.7); 2.5810 (7.7); 2.5573 (8.8); 2.5458 (8.3); 2.5254 (5.2); 2.5207 (7.8); 2.5119 (100.3); 2.5074 (218.4); 2.5028 (303.3); 2.4982 (214.5); 2.4936 (95.6); 2.4578 (1.7); 2.4532 (1.8); 2.4485 (1.1); 2.3866 (2.1); 2.3670 (2.9); 2.3444 (6.6); 2.3342 (2.0); 2.3249 (7.8); 2.3021 (5.3); 2.2789 (5.6); 2.2719 (10.6); 2.2657 (7.1); 2.2549 (8.9); 2.2503 (10.8); 2.2417 (8.7); 2.2369 (11.2); 2.2238 (3.0); 2.2148 (9.5); 2.2000 (3.8); 2.1410 (2.6); 2.1216 (4.7); 2.1174 (3.0); 2.1094 (3.5); 2.1021 (3.0); 2.0977 (4.3); 2.0900 (5.8); 2.0857 (3.6); 2.0783 (2.2); 2.0704 (3.2); 2.0660 (4.3); 2.0466 (1.8); 1.7666 (2.4); 1.7540 (3.6); 1.7432 (5.0); 1.7331 (4.3); 1.7217 (4.2); 1.7114 (4.4); 1.7009 (2.6); 1.6878 (1.9); 0.0080 (3.5); −0.0002 (114.0); −0.0085 (3.3); −0.0499 (0.6)

I-140: $^1$H-NMR(400.0 MHz, $d_6$-DMSO):

δ = 10.4717 (6.2); 10.4673 (6.3); 8.0564 (2.9); 8.0424 (6.0); 8.0283 (3.0); 7.3806 (1.5); 7.3767 (1.6); 7.3601 (3.2); 7.3561 (3.5); 7.3503 (1.9); 7.3404 (2.3); 7.3341 (3.5); 7.3302 (3.1); 7.3140 (1.9); 7.3101 (1.9); 7.2094 (1.9); 7.2055 (2.1); 7.1966 (2.0); 7.1929 (2.5); 7.1894 (3.6); 7.1858 (4.0); 7.1766 (3.5); 7.1733 (4.0); 7.1692 (2.4); 7.1652 (2.4); 7.1563 (2.0); 7.1528 (2.2); 7.1191 (14.0); 7.1181 (14.5); 7.0977 (15.2); 7.0966 (16.0); 7.0758 (3.8); 7.0597 (5.1); 7.0565 (4.9); 7.0403 (2.7); 7.0115 (10.8); 7.0060 (10.6); 6.8070 (12.8); 6.8013 (13.5); 6.5921 (8.9); 6.5864 (8.4); 6.5706 (8.2); 6.5650 (8.0); 4.7455 (5.8); 4.7058 (6.7); 4.2352 (7.3); 4.1955 (6.5); 3.8190 (9.1); 3.8084 (10.1); 3.7979 (10.6); 3.7878 (10.7); 3.7778 (9.2); 3.7673 (7.4); 3.7565 (5.4); 3.5746 (0.7); 3.3148 (0.8); 3.3007 (2.5); 3.2824 (5.1); 3.2689 (5.6); 3.2574 (5.1); 3.2397 (2.7); 3.2252 (0.8); 3.1692 (2.7); 2.7061 (6.9); 2.6876 (12.8); 2.6693 (6.5); 2.5408 (0.7); 2.5275 (4.9); 2.5244 (3.5); 2.5192 (4.6); 2.5108 (55.1); 2.5062 (120.4); 2.5016 (168.8); 2.4969 (119.4); 2.4924 (58.0); 2.4813 (6.4); 2.3951 (1.4); 2.3754 (1.9); 2.3722 (2.0); 2.3529 (4.1); 2.3331 (4.6); 2.3190 (0.9); 2.3106 (3.1); 2.2751 (3.0); 2.2618 (3.7); 2.2510 (4.6); 2.2378 (4.4); 2.2334 (2.2); 2.2200 (1.9); 2.2089 (3.0); 2.2036 (6.0); 2.1962 (2.9); 2.1820 (5.6); 2.1688 (4.8); 2.1472 (4.7); 2.1271 (1.6); 2.1076 (2.8); 2.1034 (1.9); 2.0953 (2.2); 2.0881 (1.9); 2.0836 (2.7); 2.0760 (3.6); 2.0730 (6.9); 2.0644 (1.4); 2.0564 (2.0); 2.0519 (2.6); 2.0324 (1.2); 1.7572 (1.5); 1.7447 (2.2); 1.7339 (3.0); 1.7235 (2.6); 1.7124 (2.6); 1.7020 (2.7); 1.6912 (1.6); 1.6784 (1.2); −0.0002 (6.7)

I-141: $^1$H-NMR(400.1 MHz, CDCl3):

δ = 7.5206 (1.2); 7.3094 (0.6); 7.2903 (0.4); 7.2618 (208.0); 7.2093 (0.4); 7.1312 (0.4); 7.1177 (0.8); 7.1064 (1.5); 7.0961 (1.0); 7.0888 (1.6); 7.0817 (1.7); 7.0728 (1.0); 7.0631 (6.2); 7.0529 (5.7); 7.0444 (2.2); 7.0395 (1.8); 6.9978 (1.2); 4.9135 (2.3); 4.8746 (2.5); 4.7178 (1.0); 4.7067 (1.0); 4.6906 (2.0); 4.6796 (2.0); 4.6635 (1.1); 4.6521 (1.0); 4.2430 (3.1); 4.2044 (2.9); 3.8931 (0.5); 3.8831 (0.9); 3.8726 (1.3); 3.8623 (1.5); 3.8510 (1.3); 3.8402 (0.9); 3.8304 (0.5); 2.7332 (2.0); 2.7239 (2.0); 2.6955 (2.5); 2.6862 (2.4); 2.5623 (0.5); 2.5439 (0.7); 2.5389 (0.7); 2.5202 (1.8); 2.5012 (1.5); 2.4963 (1.3); 2.4776 (1.4); 2.4394 (1.2); 2.4252 (1.4); 2.4149 (1.7); 2.4020 (4.0); 2.3796 (2.7); 2.3720 (1.2); 2.3647 (2.3);

-continued 2.3581 (1.1); 2.3420 (2.0); 2.2946 (0.7); 2.2754 (1.1); 2.2699 (0.7); 2.2623 (0.9); 2.2560 (0.8); 2.2515 (0.9); 2.2432 (1.2); 2.2376 (0.8); 2.2323 (0.5); 2.2234 (0.8); 2.2184 (0.9); 2.1989 (0.5); 1.9539 (1.2); 1.9239 (1.3); 1.9009 (0.6); 1.8883 (0.9); 1.8762 (1.2); 1.8663 (1.0); 1.8530 (1.0); 1.8429 (1.1); 1.8321 (0.8); 1.8185 (0.9); 1.8074 (1.0); 1.8008 (1.0); 1.7898 (1.4); 1.7837 (1.2); 1.7725 (1.0); 1.7654 (1.0); 1.7544 (0.4); 1.7487 (0.4); 1.6932 (2.4); 1.6669 (2.4); 1.6610 (2.5); 1.6525 (1.6); 1.6058 (0.5); 1.5582 (142.5); 1.5209 (0.4); 1.5050 (0.7); 1.4818 (1.0); 1.4741 (1.0); 1.4660 (0.9); 1.4361 (0.5); 1.4284 (0.4); 1.3964 (0.5); 1.3897 (0.9); 1.3819 (0.5); 1.3595 (1.5); 1.3388 (0.7); 1.3309 (1.0); 1.3237 (0.6); 1.0960 (0.4); 1.0857 (0.5); 1.0594 (1.1); 1.0533 (1.3); 1.0283 (1.5); 1.0213 (1.2); 0.9961 (1.6); 0.9665 (2.3); 0.9381 (2.5); 0.9105 (15.1); 0.8991 (16.0); 0.8943 (14.6); 0.8818 (14.2); 0.8477 (1.0); 0.8190 (0.5); 0.7477 (13.4); 0.7303 (12.9); 0.1460 (0.4); 0.0074 (4.4)

I-142: $^1$H-NMR(400.0 MHz, $d_6$-DMSO):

δ = 9.9728 (8.7); 7.5405 (10.7); 7.5377 (13.4); 7.5329 (4.1); 7.5188 (15.3); 7.5163 (13.5); 7.3672 (1.5); 7.3632 (1.6); 7.3467 (3.1); 7.3426 (3.5); 7.3366 (1.9); 7.3270 (2.3); 7.3207 (3.6); 7.3165 (3.3); 7.3089 (2.2); 7.3044 (12.7); 7.2995 (5.3); 7.2857 (16.0); 7.2835 (13.3); 7.2690 (4.2); 7.2645 (12.0); 7.2595 (1.5); 7.2069 (1.9); 7.2030 (2.0); 7.1942 (1.9); 7.1903 (2.3); 7.1870 (3.6); 7.1833 (3.8); 7.1742 (3.5); 7.1709 (3.9); 7.1666 (2.4); 7.1628 (2.3); 7.1538 (2.0); 7.1504 (2.2); 7.1247 (0.5); 7.0986 (3.6); 7.0826 (4.8); 7.0631 (2.7); 7.0569 (3.8); 7.0540 (6.0); 7.0511 (3.5); 7.0355 (9.6); 7.0199 (2.6); 7.0171 (4.4); 7.0142 (2.4); 4.7617 (5.5); 4.7220 (6.4); 4.2976 (7.0); 4.2577 (5.9); 3.9367 (1.1); 3.9255 (2.4); 3.9154 (3.2); 3.9052 (4.2); 3.8954 (3.2); 3.8852 (2.4); 3.8743 (1.1); 3.3566 (0.6); 3.3226 (130.9); 3.1676 (0.9); 2.7690 (4.9); 2.7574 (5.0); 2.7327 (6.1); 2.7211 (5.9); 2.6752 (0.8); 2.6705 (1.1); 2.6658 (0.8); 2.5448 (0.7); 2.5407 (1.2); 2.5356 (0.9); 2.5307 (0.8); 2.5240 (2.6); 2.5193 (4.1); 2.5106 (58.5); 2.5060 (126.9); 2.5014 (176.7); 2.4968 (123.5); 2.4922 (54.7); 2.4742 (0.9); 2.4643 (6.0); 2.4431 (6.2); 2.4281 (6.3); 2.4069 (8.7); 2.3879 (3.6); 2.3841 (3.3); 2.3655 (2.9); 2.3328 (1.0); 2.3280 (1.7); 2.3239 (3.5); 2.3110 (3.4); 2.3001 (4.6); 2.2871 (4.5); 2.2827 (1.9); 2.2700 (1.1); 2.2583 (2.6); 2.2462 (2.8); 2.2323 (2.1); 2.2139 (3.1); 2.2086 (1.4); 2.2018 (2.3); 2.1949 (1.9); 2.1898 (2.2); 2.1828 (3.6); 2.1778 (2.0); 2.1710 (1.2); 2.1633 (2.0); 2.1586 (2.5); 2.1393 (1.1); 2.0736 (2.2); 1.8493 (1.4); 1.8381 (2.3); 1.8269 (3.0); 1.8167 (2.5); 1.8073 (2.7); 1.7956 (2.6); 1.7844 (1.7); 1.7717 (1.1); 0.0079 (0.6); – 0.0002 (21.0); −0.0085 (0.6)

I-143: $^1$H-NMR(400.0 MHz, $d_6$-DMSO):

δ = 8.0190 (4.2); 8.0107 (4.1); 7.3768 (1.6); 7.3555 (3.4); 7.3353 (3.5); 7.3136 (1.8); 7.2048 (2.1); 7.1887 (3.4); 7.1851 (3.6); 7.1725 (3.7); 7.1522 (1.7); 7.0668 (3.4); 7.0512 (4.6); 7.0316 (2.5); 4.7196 (5.5); 4.6795 (6.3); 4.5964 (1.8); 4.2215 (7.1); 4.1818 (6.1); 4.0942 (1.0); 4.0309 (1.0); 3.9862 (1.0); 3.8929 (1.0); 3.8003 (2.4); 3.7911 (3.8); 3.7806 (4.6); 3.7702 (3.3); 3.7593 (2.7); 3.6865 (1.2); 3.5959 (3.2); 3.5560 (2.5); 3.5425 (2.1); 3.5259 (5.2); 3.5014 (2.1); 3.4917 (8.8); 3.4842 (9.0); 3.4456 (111.1); 3.4280 (96.8); 3.3529 (39.9); 3.3315 (6.4); 3.3131 (7.5); 3.2917 (13.7); 3.2753 (18.0); 3.2549 (3.8); 3.2479 (4.7); 3.1952 (5.0); 3.1853 (3.0); 3.1696 (16.0); 3.1419 (1.6); 3.0478 (0.9); 2.8950 (0.9); 2.7713 (2.1); 2.7590 (1.5); 2.6780 (5.8); 2.6734 (8.2); 2.6688 (6.0); 2.5906 (1.9); 2.5808 (2.7); 2.5723 (5.5); 2.5624 (9.0); 2.5595 (9.7); 2.5548 (11.9); 2.5504 (5.3); 2.5433 (5.4); 2.5377 (5.8); 2.5334 (5.9); 2.5267 (19.1); 2.5220 (28.5); 2.5134 (461.3); 2.5088 (1013.8); 2.5042 (1430.8); 2.4996 (1017.2); 2.4950 (462.7); 2.4676 (3.4); 2.4605 (3.6); 2.4568 (3.3); 2.4459 (1.9); 2.4224 (6.9); 2.4106 (6.3); 2.3923 (3.1); 2.3689 (2.2); 2.3504 (4.6); 2.3402 (3.6); 2.3356 (7.2); 2.3310 (12.5); 2.3265 (9.4); 2.3079 (3.7); 2.2841 (3.3); 2.2706 (3.6); 2.2599 (4.9); 2.2470 (4.4); 2.2286 (1.9); 2.2181 (2.4); 2.2050 (2.6); 2.1468 (6.6); 2.1257 (7.8); 2.1181 (3.0); 2.1115 (6.6); 2.0984 (3.7); 2.0905 (5.7); 2.0717 (4.9); 2.0555 (1.4); 1.7468 (1.4); 1.7345 (2.2); 1.7237 (3.0); 1.7105 (2.4); 1.7019 (2.5); 1.6917 (2.8); 1.6809 (1.7); 1.6677 (1.4); 1.1413 (1.0); 1.0689 (1.0); 1.0507 (1.7); 1.0303 (2.2); 0.6097 (3.2); 0.5973 (8.5); 0.5925 (11.0); 0.5804 (10.8); 0.5746 (9.4); 0.5630 (4.3); 0.3484 (3.7); 0.3376 (10.8); 0.3311 (8.9); 0.3276 (9.6); 0.3219 (9.2); 0.3107 (3.4); 0.1460 (1.2); 0.0503 (2.1); 0.0080 (8.6); −0.0002 (340.1); −0.0085 (11.2); −0.0486 (0.9); −0.1497 (1.1)

I-144: $^1$H-NMR(400.0 MHz, CDCl3):

δ = 7.5564 (0.5); 7.5203 (2.9); 7.5147 (3.6); 7.4955 (6.1); 7.4556 (4.1); 7.4367 (8.0); 7.4166 (12.5); 7.3808 (6.6); 7.3619 (3.7); 7.3118 (0.8); 7.3013 (0.5); 7.2798 (0.9); 7.2734 (1.3); 7.2726 (1.4); 7.2710 (1.8); 7.2702 (1.9); 7.2686 (2.7); 7.2678 (3.1); 7.2615 (294.4); 7.2573 (3.3); 7.2564 (2.0); 7.2556 (1.4); 7.2548 (0.8); 7.2540 (0.6); 7.2532 (0.6); 7.1258 (1.1); 7.1163 (1.7); 7.1098 (1.6); 7.1010 (4.0); 7.0884 (3.0); 7.0860 (2.8); 7.0823 (3.2); 7.0756 (4.0); 7.0661 (2.0); 7.0621 (2.4); 7.0580 (4.6); 7.0543 (8.4); 7.0468 (12.5); 7.0442 (7.7); 7.0381 (10.8); 7.0310 (4.2); 7.0276 (5.9); 7.0160 (1.0); 7.0097 (0.7); 6.9974 (1.6); 5.4611 (2.5); 4.8482 (5.3); 4.8445 (5.1); 4.8095 (6.0); 4.8058 (5.8); 4.2384 (7.4); 4.1997 (6.6); 3.9526 (1.2); 3.9416 (2.5); 3.9308 (3.2); 3.9203 (3.6); 3.9105 (3.2); 3.8996 (2.6); 3.8885 (1.3); 3.5985 (0.8); 3.5808 (1.9); 3.5646 (3.4); 3.5467 (5.9); 3.5316 (7.1); 3.5144 (6.8); 3.4997 (5.4); 3.4825 (3.3); 3.4656 (1.7); 3.4484 (0.8); 2.9086 (0.5); 2.8906 (8.7); 2.8730 (16.0); 2.8554 (7.1); 2.6016 (5.3); 2.5908 (5.3); 2.5654 (6.2); 2.5546 (6.0); 2.5311 (1.1); 2.5120 (1.4); 2.5089 (1.3); 2.4886 (3.8); 2.4691 (3.6); 2.4657 (3.4); 2.4458 (3.4); 2.4375 (3.9); 2.4228 (4.5); 2.4133 (5.2); 2.3988 (5.3); 2.3945 (1.9); 2.3797 (1.5); 2.3701 (2.2); 2.3557 (2.1); 2.2713 (1.9); 2.2521 (3.0); 2.2474 (1.9); 2.2385 (2.4); 2.2330 (2.0); 2.2280 (2.6); 2.2195 (3.4); 2.2144 (2.2); 2.2091 (1.5); 2.2002 (2.1); 2.1951 (2.6); 2.1761 (1.4); 2.1393 (6.7); 2.1170 (6.5); 2.1031 (5.9); 2.0808 (5.7); 2.0067 (1.1); 1.8070 (1.7); 1.7956 (1.9); 1.7927 (2.2); 1.7816 (2.4); 1.7722 (2.5); 1.7689 (2.1); 1.7627 (1.9); 1.7595 (2.5); 1.7484 (2.2); 1.7393 (1.7); 1.7361 (1.5); 1.7246 (1.3); 0.0079 (2.9); 0.0062 (1.0); −0.0002 (96.0); −0.0061 (0.7); −0.0069 (0.6); −0.0085 (2.6)

I-145: $^1$H-NMR(400.0 MHz, $d_6$-DMSO):

δ = 8.2689 (0.6); 8.2555 (1.2); 8.2411 (0.6); 7.3663 (0.8); 7.3443 (0.8); 7.1964 (0.8); 7.1928 (0.9); 7.1804 (0.9); 7.1724 (0.6); 7.1601 (0.5); 7.0780 (1.0); 7.0617 (1.2); 7.0427 (0.6); 4.7388 (1.3); 4.6990 (1.5); 4.2424 (1.6); 4.2027 (1.4); 3.8203 (0.5); 3.8098 (0.7); 3.8001 (0.9); 3.7900 (0.8); 3.7797 (0.6); 3.3844 (0.9); 3.3674 (2.2); 3.3329 (82.6); 3.2829 (0.9); 3.1617 (2.1); 3.1496 (2.4); 3.1441 (2.4); 3.1327 (2.2); 3.1149 (0.9); 3.0926 (0.9); 3.0766 (1.6); 3.0639 (1.7); 2.7819 (0.7); 2.6704 (0.5); 2.5621 (1.2); 2.5509 (1.0); 2.5241 (1.5); 2.5192 (1.8); 2.5105 (30.0); 2.5060 (66.1); 2.5013 (93.4); 2.4967 (65.1); 2.4921 (29.0); 2.4555 (0.5); 2.4509 (0.6); 2.3743 (1.0); 2.3555 (0.9); 2.3327 (1.1); 2.3235 (0.5); 2.3061 (0.8); 2.2925 (0.9); 2.2819 (1.2); 2.2683 (1.2); 2.2621 (1.6); 2.2506 (0.5); 2.2404 (1.8); 2.2263 (1.6); 2.2046 (1.1); 2.1575 (0.6); 2.1450 (0.5); 2.1333 (0.6); 2.1258 (0.8); 2.1016 (0.6); 2.0733 (0.9); 1.7658 (0.5); 1.7552 (0.7); 1.7444 (0.6); 1.7339 (0.6); 1.7234 (0.6); 1.1915 (7.2); 1.1734 (16.0); 1.1552 (6.8); 1.1419 (1.1); −0.0002 (2.7)

I-146: $^1$H-NMR(400.0 MHz, $d_6$-DMSO):

δ = 9.5994 (14.1); 8.6430 (14.2); 8.6273 (16.0); 8.6165 (2.6); 8.2522 (5.8); 8.2321 (6.6); 8.2187 (6.9); 8.2028 (6.4); 7.8746 (4.3); 7.8593 (7.6); 7.8239 (8.6); 7.8037 (8.4); 7.7858 (4.6); 7.3755 (1.4); 7.3715

-continued (1.5); 7.3550 (3.0); 7.3511 (3.2); 7.3451 (1.8); 7.3351 (2.3); 7.3289 (3.1); 7.3248 (2.7); 7.3087 (1.6); 7.3049 (1.6); 7.1952 (1.9); 7.1913 (2.1); 7.1824 (1.9); 7.1787 (2.4); 7.1753 (3.4); 7.1715 (3.7); 7.1624 (3.2); 7.1591 (3.7); 7.1550 (2.3); 7.1510 (2.1); 7.1421 (1.8); 7.1386 (2.0); 7.0662 (3.4); 7.0501 (4.6); 7.0308 (2.3); 4.8187 (2.0); 4.8043 (2.0); 4.7804 (5.0); 4.7659 (5.0); 4.7402 (5.1); 4.7267 (5.3); 4.7146 (5.6); 4.7024 (2.5); 4.6886 (2.4); 4.6750 (6.3); 4.2669 (2.0); 4.2195 (7.8); 4.1799 (7.0); 3.9648 (1.2); 3.8860 (1.1); 3.8516 (1.7); 3.8410 (2.7); 3.8305 (3.6); 3.8203 (4.2); 3.8101 (3.6); 3.7996 (2.7); 3.7890 (1.5); 3.6215 (0.6); 3.6027 (0.9); 3.5859 (0.8); 3.1666 (6.9); 3.1521 (0.6); 3.1341 (0.5); 3.0336 (0.7); 2.7710 (4.2); 2.7600 (3.2); 2.6799 (0.6); 2.6753 (1.3); 2.6707 (2.0); 2.6660 (1.5); 2.6614 (0.6); 2.6301 (3.8); 2.6192 (4.0); 2.5949 (4.6); 2.5839 (4.7); 2.5242 (3.7); 2.5195 (5.8); 2.5108 (103.8); 2.5062 (230.3); 2.5016 (323.4); 2.4970 (228.1); 2.4924 (102.3); 2.4219 (0.6); 2.4054 (0.8); 2.3713 (1.2); 2.3484 (1.6); 2.3286 (5.4); 2.3239 (2.3); 2.3131 (6.8); 2.2916 (6.0); 2.2782 (4.9); 2.2688 (3.2); 2.2560 (6.9); 2.2448 (4.6); 2.2315 (4.3); 2.2138 (1.4); 2.2029 (2.2); 2.1901 (2.2); 2.1517 (1.6); 2.1323 (2.6); 2.1202 (1.9); 2.1130 (1.7); 2.1085 (2.3); 2.1010 (3.1); 2.0965 (2.0); 2.0893 (1.2); 2.0811 (1.8); 2.0770 (2.3); 2.0739 (1.6); 2.0574 (1.0); 1.8103 (0.5); 1.7771 (1.4); 1.7648 (2.1); 1.7538 (2.8); 1.7434 (2.4); 1.7327 (2.4); 1.7220 (2.6); 1.7114 (1.5); 1.6983 (1.1); 1.0684 (1.7); 1.0504 (4.0); 1.0325 (1.8); 0.1460 (0.6); 0.0080 (6.2); −0.0002 (228.7); −0.0086 (6.4); −0.1494 (0.6)

I-147: $^{1}$H-NMR(400.0 MHz, $d_6$-DMSO):

δ = 7.3570 (0.9); 7.3344 (0.9); 7.1983 (0.6); 7.1903 (0.9); 7.1871 (0.9); 7.1785 (1.0); 7.1704 (0.7); 7.1667 (0.8); 7.1583 (0.5); 7.0993 (0.7); 7.0831 (0.9); 7.0642 (0.7); 4.7584 (1.3); 4.7187 (1.6); 4.2737 (1.3); 4.2341 (1.1); 4.1986 (0.7); 4.1597 (0.6); 4.0877 (2.2); 3.9436 (3.9); 3.9370 (3.8); 3.8362 (0.7); 3.8255 (0.9); 3.8158 (0.8); 3.8049 (0.6); 3.3304 (61.3); 2.9487 (16.0); 2.8403 (0.7); 2.8300 (0.7); 2.7997 (0.9); 2.7895 (1.0); 2.7633 (7.2); 2.6754 (0.6); 2.6708 (0.9); 2.6663 (0.6); 2.5293 (1.7); 2.5243 (3.2); 2.5196 (4.6); 2.5109 (49.9); 2.5064 (105.5); 2.5018 (145.5); 2.4972 (101.6); 2.4927 (44.8); 2.4726 (0.8); 2.4680 (1.1); 2.4634 (1.0); 2.4562 (1.0); 2.4513 (1.1); 2.4469 (0.9); 2.4334 (0.8); 2.4137 (0.7); 2.3999 (0.7); 2.3777 (0.6); 2.3374 (0.8); 2.3333 (0.8); 2.3286 (1.1); 2.3239 (0.8); 2.2660 (0.7); 2.2543 (0.7); 2.2416 (1.2); 2.2302 (1.1); 2.2004 (0.9); 2.1942 (1.4); 2.1795 (0.8); 2.1676 (0.6); 2.1605 (0.5); 2.1487 (0.9); 2.1286 (0.5); 2.1246 (0.6); 1.6732 (0.6); 0.0080 (1.6); −0.0002 (51.1); − 0.0086 (1.4)

I-148: $^{1}$H-NMR(400.0 MHz, $d_6$-DMSO):

δ = 8.9127 (2.5); 8.8915 (2.5); 7.3674 (0.7); 7.3631 (0.7); 7.3467 (2.9); 7.3441 (4.4); 7.3407 (4.8); 7.3369 (2.2); 7.3281 (5.6); 7.3253 (7.7); 7.3223 (9.0); 7.3197 (7.9); 7.3076 (6.5); 7.3061 (6.5); 7.3040 (7.8); 7.2602 (3.9); 7.2530 (16.0); 7.2446 (5.8); 7.2358 (9.1); 7.2342 (9.0); 7.2326 (8.8); 7.2306 (7.7); 7.2179 (1.2); 7.2146 (0.5); 7.1875 (0.7); 7.1838 (0.8); 7.1749 (0.8); 7.1710 (1.0); 7.1677 (1.4); 7.1641 (1.5); 7.1547 (1.4); 7.1516 (1.6); 7.1474 (0.9); 7.1434 (0.9); 7.1345 (0.8); 7.1312 (0.8); 7.0651 (1.4); 7.0491 (2.0); 7.0298 (1.0); 6.1058 (3.1); 6.0846 (3.1); 4.7250 (2.2); 4.6854 (2.5); 4.2205 (2.7); 4.1809 (2.3); 3.8221 (0.9); 3.8116 (1.3); 3.8012 (1.5); 3.7913 (1.3); 3.7807 (0.9); 3.3166 (219.2); 3.2928 (12.2); 3.2839 (0.6); 3.2654 (0.5); 2.6706 (2.3); 2.6651 (1.1); 2.6603 (2.1); 2.6364 (2.2); 2.6253 (2.0); 2.5492 (0.5); 2.5447 (0.8); 2.5400 (1.3); 2.5351 (0.9); 2.5304 (0.9); 2.5232 (2.7); 2.5185 (4.0); 2.5098 (54.1); 2.5052 (116.7); 2.5006 (162.6); 2.4960 (113.6); 2.4914 (50.3); 2.3839 (2.4); 2.3621 (2.8); 2.3492 (2.0); 2.3387 (1.7); 2.3320 (1.2); 2.3274 (2.9); 2.3187 (1.8); 2.2966 (1.2); 2.2676 (1.1); 2.2545 (1.4); 2.2436 (1.7); 2.2306 (1.7); 2.2127 (0.6); 2.2017 (0.9); 2.1888 (0.8); 2.1244 (0.6); 2.1047 (1.0); 2.0927 (0.8); 2.0809 (1.0); 2.0730 (1.6); 2.0613 (0.5); 2.0535 (0.8); 2.0492 (1.0); 1.7908 (0.6); 1.7783 (0.8); 1.7676 (1.1); 1.7577 (1.0); 1.7461 (1.0); 1.7358 (1.0); 1.7247 (0.6); 0.0080 (0.6); −0.0002 (18.5); −0.0086 (0.5)

I-149: $^{1}$H-NMR(400.0 MHz, CDCl3):

δ = 7.5189 (11.8); 7.3098 (3.4); 7.2977 (1.7); 7.2938 (1.5); 7.2913 (1.9); 7.2866 (2.1); 7.2850 (2.2); 7.2826 (2.5); 7.2802 (3.0); 7.2786 (2.6); 7.2770 (2.9); 7.2754 (3.2); 7.2746 (3.3); 7.2738 (3.7); 7.2730 (3.9); 7.2722 (4.3); 7.2706 (6.3); 7.2699 (6.5); 7.2691 (6.7); 7.2674 (10.4); 7.2666 (12.2); 7.2650 (19.2); 7.2600 (2279.1); 7.2095 (4.8); 7.1443 (5.4); 7.1388 (2.6); 7.1309 (5.6); 7.1224 (7.5); 7.1090 (7.3); 7.0998 (3.0); 7.0827 (2.2); 7.0733 (2.5); 7.0540 (8.4); 7.0439 (5.6); 7.0403 (8.6); 7.0296 (3.9); 7.0159 (9.1); 7.0104 (3.0); 6.9959 (16.0); 6.9941 (15.8); 6.9777 (2.3); 6.9723 (6.0); 5.3388 (1.7); 4.8461 (3.4); 4.8112 (3.9); 4.2304 (5.1); 4.1914 (4.6); 3.9189 (1.5); 3.9078 (2.2); 3.8983 (2.2); 3.8877 (2.2); 3.8767 (1.6); 3.7384 (3.2); 3.5069 (2.4); 3.5019 (2.2); 3.4890 (5.4); 3.4741 (4.7); 3.4699 (5.6); 3.4564 (2.4); 3.4528 (2.3); 2.7895 (5.4); 2.7716 (10.9); 2.7542 (5.0); 2.5815 (3.7); 2.5704 (3.7); 2.5453 (4.2); 2.5345 (4.2); 2.4752 (2.6); 2.4502 (2.2); 2.4334 (2.4); 2.4206 (2.5); 2.4057 (3.0); 2.3964 (3.9); 2.3819 (3.5); 2.3534 (1.6); 2.3390 (1.8); 2.2707 (1.3); 2.2513 (2.1); 2.2379 (1.8); 2.2273 (1.7); 2.2189 (2.1); 2.2009 (4.2); 2.1943 (1.9); 2.1236 (4.5); 2.1012 (4.7); 2.0874 (4.0); 2.0650 (3.8); 1.8074 (1.4); 1.7972 (1.8); 1.7886 (1.5); 1.7745 (1.6); 1.7631 (1.4); 1.7540 (1.3); 1.5442 (113.1); 1.4634 (2.2); 1.3860 (2.2); 0.0079 (4.9); −0.0002 (178.1); −0.0085 (5.8)

I-151: $^{1}$H-NMR(400.0 MHz, $d_6$-DMSO):

δ = 10.6262 (0.8); 8.0512 (0.7); 7.2229 (1.9); 7.2219 (1.9); 7.2012 (2.2); 7.2001 (2.2); 7.1827 (0.5); 7.1701 (0.5); 7.0787 (1.4); 7.0728 (1.5); 7.0515 (0.6); 6.9969 (1.6); 6.9908 (1.6); 6.7182 (1.2); 6.7123 (1.1); 6.6964 (1.0); 6.6905 (1.0); 4.7360 (0.7); 4.6960 (0.8); 4.2301 (0.9); 4.1903 (0.8); 3.7837 (0.5); 3.7457 (16.0); 3.3965 (17.0); 3.3117 (0.9); 3.2930 (0.9); 2.7656 (0.9); 2.7469 (1.4); 2.7290 (0.8); 2.5236 (0.5); 2.5103 (11.5); 2.5057 (25.4); 2.5011 (34.9); 2.4965 (24.5); 2.4919 (10.9); 2.4831 (1.0); 2.4713 (0.8); 2.3420 (0.5); 2.3231 (0.6); 2.2446 (0.6); 2.2313 (0.6); 2.1974 (0.8); 2.1759 (0.7); 2.1626 (0.6); 2.1411 (0.6); 2.0730 (0.7); −0.0002 (1.6)

I-152: $^{1}$H-NMR(400.0 MHz, $d_6$-DMSO):

δ = 7.3565 (1.0); 7.3349 (1.0); 7.1982 (0.6); 7.1870 (1.0); 7.1782 (1.0); 7.1702 (0.8); 7.1667 (0.8); 7.1581 (0.6); 7.0990 (0.7); 7.0828 (1.0); 7.0640 (0.8); 7.0508 (0.5); 4.7582 (1.4); 4.7182 (1.6); 4.2737 (1.3); 4.2339 (1.2); 4.1995 (0.7); 4.1596 (0.6); 4.0870 (2.3); 3.9436 (4.0); 3.9370 (3.9); 3.8356 (0.8); 3.8262 (0.9); 3.8157 (0.9); 3.8054 (0.7); 3.3316 (54.4); 2.9487 (16.0); 2.8403 (0.8); 2.8298 (0.8); 2.7997 (1.0); 2.7894 (1.0); 2.7633 (7.3); 2.6755 (0.6); 2.6709 (0.9); 2.6663 (0.6); 2.6555 (0.5); 2.6453 (0.6); 2.5533 (0.9); 2.5409 (0.7); 2.5363 (0.9); 2.5311 (1.4); 2.5243 (2.1); 2.5196 (3.4); 2.5109 (46.9); 2.5064 (99.8); 2.5018 (138.4); 2.4972 (98.6); 2.4927 (45.2); 2.4698 (0.8); 2.4560 (0.8); 2.4515 (0.8); 2.4330 (0.8); 2.4119 (0.7); 2.3994 (0.7); 2.3773 (0.6); 2.3333 (0.8); 2.3286 (1.0); 2.3240 (0.8); 2.2658 (0.7); 2.2542 (0.7); 2.2416 (1.2); 2.2299 (1.1); 2.2002 (1.0); 2.1942 (1.4); 2.1793 (0.9); 2.1676 (0.7); 2.1609 (0.6); 2.1485 (1.0); 2.1244 (0.6); 1.6949 (0.5); 1.6727 (0.6); 1.6556 (0.5); 0.0080 (1.3); −0.0002 (43.1); −0.0085 (1.4)

-continued

I-153: $^{1}$H-NMR(400.0 MHz, CDCl3):
δ = 7.5204 (1.4); 7.2615 (276.4); 7.2548 (0.8); 7.2539 (0.6); 7.2531 (0.6); 7.2114 (1.3); 7.2056 (7.2); 7.1997 (3.2); 7.1896 (5.0); 7.1834 (25.2); 7.1786 (4.8); 7.1650 (14.6); 7.1632 (14.4); 7.1427 (5.0); 7.1407 (4.3); 7.1244 (1.1); 7.1129 (2.0); 7.1067 (1.0); 7.0996 (3.9); 7.0910 (1.7); 7.0877 (2.2); 7.0831 (2.8); 7.0811 (2.9); 7.0732 (3.8); 7.0682 (1.4); 7.0618 (2.2); 7.0569 (4.0); 7.0540 (11.1); 7.0492 (7.2); 7.0472 (7.6); 7.0438 (7.0); 7.0398 (12.2); 7.0354 (3.8); 7.0291 (4.6); 7.0202 (0.8); 6.9974 (1.5); 5.4183 (2.3); 5.2994 (2.3); 4.8484 (4.6); 4.8447 (4.5); 4.8097 (5.2); 4.8060 (5.1); 4.2338 (6.7); 4.1951 (6.0); 3.9321 (1.1); 3.9210 (2.2); 3.9102 (2.8); 3.9002 (3.1); 3.8901 (2.8); 3.8792 (2.3); 3.8681 (1.1); 3.5481 (1.0); 3.5319 (2.7); 3.5140 (5.8); 3.5008 (6.6); 3.4993 (6.6); 3.4862 (5.6); 3.4691 (2.8); 3.4520 (0.9); 2.8266 (8.3); 2.8090 (16.0); 2.7915 (7.0); 2.5917 (4.8); 2.5809 (4.7); 2.5556 (5.5); 2.5447 (5.4); 2.5126 (0.9); 2.4942 (1.2); 2.4907 (1.2); 2.4704 (3.4); 2.4512 (3.1); 2.4477 (2.9); 2.4276 (2.9); 2.4178 (3.5); 2.4030 (4.1); 2.3937 (4.8); 2.3791 (4.8); 2.3749 (1.7); 2.3601 (1.4); 2.3507 (2.1); 2.3362 (2.0); 2.2599 (1.8); 2.2408 (2.7); 2.2361 (1.7); 2.2273 (2.2); 2.2218 (1.8); 2.2167 (2.3); 2.2084 (3.0); 2.2032 (2.0); 2.1979 (1.4); 2.1891 (1.9); 2.1838 (2.4); 2.1649 (1.3); 2.1346 (6.0); 2.1123 (5.9); 2.0984 (5.3); 2.0762 (5.2); 1.8064 (1.7); 1.7951 (1.8); 1.7922 (2.1); 1.7809 (2.3); 1.7716 (2.2); 1.7684 (1.9); 1.7623 (1.8); 1.7590 (2.2); 1.7477 (2.0); 1.7387 (1.6); 1.7356 (1.4); 1.7240 (1.3); 1.4557 (1.2); 0.0080 (2.5); −0.0002 (89.4); −0.0085 (2.5)
I-154: $^{1}$H-NMR(400.0 MHz, CDCl3):
δ = 7.5213 (1.0); 7.3828 (3.5); 7.3798 (4.2); 7.3779 (4.6); 7.3750 (4.3); 7.3631 (4.3); 7.3602 (4.9); 7.3582 (5.8); 7.3553 (5.1); 7.3210 (6.9); 7.3170 (11.2); 7.3129 (6.0); 7.2712 (1.0); 7.2696 (1.3); 7.2624 (175.4); 7.2566 (1.0); 7.2558 (0.8); 7.2550 (0.5); 7.2542 (0.5); 7.2001 (6.2); 7.1808 (13.4); 7.1614 (8.0); 7.1231 (1.3); 7.1149 (5.3); 7.1122 (8.6); 7.1110 (7.7); 7.1081 (6.1); 7.0981 (4.8); 7.0960 (4.2); 7.0929 (4.8); 7.0918 (5.0); 7.0891 (4.6); 7.0824 (2.9); 7.0797 (3.2); 7.0719 (4.7); 7.0659 (1.6); 7.0603 (2.0); 7.0557 (4.6); 7.0524 (9.6); 7.0455 (9.3); 7.0422 (7.1); 7.0374 (12.5); 7.0289 (5.3); 7.0267 (4.7); 7.0165 (0.9); 7.0099 (0.8); 6.9983 (1.0); 5.4452 (2.4); 4.8476 (4.9); 4.8439 (4.8); 4.8089 (5.5); 4.8051 (5.4); 4.2337 (7.1); 4.1949 (6.3); 3.9411 (1.2); 3.9300 (2.4); 3.9190 (2.9); 3.9084 (3.2); 3.8990 (2.9); 3.8880 (2.5); 3.8770 (1.2); 3.5608 (0.7); 3.5433 (1.7); 3.5267 (3.2); 3.5093 (5.5); 3.4941 (5.5); 3.4797 (5.3); 3.4770 (3.2); 3.4648 (5.3); 3.4478 (3.2); 3.4308 (1.6); 3.4137 (0.7); 2.7917 (8.3); 2.7744 (16.0); 2.7570 (7.1); 2.5937 (5.1); 2.5828 (5.0); 2.5576 (5.9); 2.5467 (5.7); 2.5197 (1.0); 2.5012 (1.4); 2.4977 (1.2); 2.4780 (3.6); 2.4582 (3.3); 2.4547 (3.0); 2.4349 (3.0); 2.4222 (3.7); 2.4075 (4.4); 2.3981 (5.2); 2.3836 (5.2); 2.3794 (1.8); 2.3647 (1.4); 2.3551 (2.3); 2.3408 (2.3); 2.2730 (1.9); 2.2539 (3.0); 2.2491 (1.8); 2.2404 (2.3); 2.2350 (1.9); 2.2298 (2.4); 2.2214 (3.2); 2.2163 (2.1); 2.2110 (1.4); 2.2023 (2.0); 2.1970 (2.5); 2.1782 (1.3); 2.1259 (6.5); 2.1034 (6.3); 2.0898 (5.6); 2.0673 (5.5); 2.0066 (1.4); 1.8159 (2.0); 1.8045 (2.3); 1.8017 (2.6); 1.7905 (3.1); 1.7810 (3.5); 1.7779 (3.3); 1.7718 (3.4); 1.7687 (3.9); 1.7667 (3.7); 1.7596 (3.3); 1.7574 (3.5); 1.7482 (2.7); 1.7451 (2.4); 1.7336 (2.0); 0.0080 (1.8); 0.0064 (0.6); 0.0056 (0.7); 0.0047 (0.8); 0.0039 (1.1); 0.0023 (2.6); −0.0002 (58.3); −0.0051 (0.7); −0.0059 (0.5); −0.0085 (1.6)
I-155: $^{1}$H-NMR(400.0 MHz, CDCl3):
δ = 7.5205 (0.8); 7.3114 (0.6); 7.3010 (8.5); 7.2802 (11.9); 7.2617 (146.4); 7.2117 (0.8); 7.1892 (6.7); 7.1833 (12.8); 7.1773 (10.3); 7.1710 (3.9); 7.1565 (6.0); 7.1502 (4.0); 7.1228 (0.8); 7.1107 (1.7); 7.0979 (3.1); 7.0866 (1.8); 7.0797 (2.6); 7.0737 (3.5); 7.0620 (1.9); 7.0553 (10.4); 7.0488 (6.8); 7.0447 (6.1); 7.0414 (10.1); 7.0367 (2.9); 7.0307 (3.6); 7.0221 (0.8); 6.9977 (0.9); 5.4829 (2.2); 4.8556 (4.1); 4.8522 (4.1); 4.8168 (4.6); 4.8134 (4.6); 4.2473 (6.0); 4.2086 (5.3); 3.9505 (1.0); 3.9395 (1.9); 3.9286 (2.4); 3.9172 (2.6); 3.9083 (2.4); 3.8973 (2.0); 3.8864 (1.0); 3.5808 (0.5); 3.5634 (1.2); 3.5469 (2.7); 3.5294 (4.7); 3.5209 (2.0); 3.5137 (4.5); 3.5039 (4.3); 3.4965 (2.2); 3.4884 (4.5); 3.4713 (2.6); 3.4543 (1.2); 3.4374 (0.5); 2.9322 (8.1); 2.9149 (16.0); 2.8976 (7.0); 2.6153 (4.1); 2.6047 (4.0); 2.5791 (4.7); 2.5685 (4.5); 2.5306 (0.9); 2.5115 (1.2); 2.5077 (1.1); 2.4878 (3.1); 2.4688 (2.8); 2.4645 (2.5); 2.4459 (2.6); 2.4299 (2.8); 2.4153 (3.3); 2.4058 (3.9); 2.3914 (4.0); 2.3872 (1.5); 2.3724 (1.1); 2.3628 (1.8); 2.3485 (1.8); 2.2856 (1.5); 2.2666 (2.4); 2.2618 (1.4); 2.2529 (1.8); 2.2476 (1.4); 2.2425 (1.9); 2.2340 (2.7); 2.2289 (1.6); 2.2237 (1.0); 2.2148 (1.5); 2.2097 (2.0); 2.1908 (1.0); 2.1331 (5.0); 2.1102 (4.9); 2.0970 (4.4); 2.0741 (4.2); 1.8267 (1.4); 1.8127 (1.8); 1.8022 (2.2); 1.7922 (2.1); 1.7795 (2.1); 1.7686 (2.0); 1.7590 (1.7); 1.7561 (1.6); 1.7444 (1.7); 1.7063 (1.9); 0.0079 (1.6); −0.0002 (46.6); −0.0085 (1.2)
I-157: $^{1}$H-NMR(400.0 MHz, CDCl3):
δ = 7.2635 (11.5); 7.2470 (0.6); 7.2426 (0.6); 7.2281 (0.8); 7.2267 (0.8); 7.2237 (0.9); 7.2079 (0.7); 7.2035 (0.7); 7.1060 (0.9); 7.1016 (0.9); 7.0873 (1.2); 7.0833 (1.5); 7.0711 (0.5); 7.0583 (1.0); 7.0389 (1.3); 7.0307 (2.0); 7.0286 (1.2); 7.0219 (1.5); 7.0204 (1.5); 7.0155 (0.6); 7.0113 (0.9); 6.9205 (0.8); 6.9178 (0.9); 6.9020 (1.3); 6.8993 (1.6); 6.8829 (1.7); 6.8808 (1.8); 6.8618 (1.2); 4.8305 (0.8); 4.8270 (0.8); 4.7917 (0.9); 4.7882 (0.8); 4.2146 (1.1); 4.1758 (1.0); 3.9003 (0.5); 3.8983 (0.5); 3.8297 (0.8); 3.8251 (16.0); 3.4764 (1.2); 3.4719 (0.9); 3.4629 (1.0); 3.4585 (1.2); 2.8261 (1.4); 2.8094 (2.7); 2.7927 (1.3); 2.5611 (0.8); 2.5500 (0.8); 2.5254 (0.9); 2.5143 (0.9); 2.4612 (0.6); 2.4418 (0.5); 2.4062 (0.6); 2.3916 (0.7); 2.3821 (0.8); 2.3676 (0.8); 2.1896 (0.5); 2.0897 (1.0); 2.0672 (1.0); 2.0540 (0.9); 2.0314 (0.8); −0.0002 (3.6)
I-158: $^{1}$H-NMR(400.0 MHz, CDCl3):
δ = 7.2619 (50.3); 7.0993 (0.6); 7.0723 (0.6); 7.0567 (0.7); 7.0528 (1.5); 7.0459 (1.4); 7.0426 (1.1); 7.0379 (1.9); 7.0294 (0.8); 7.0274 (0.7); 6.8156 (1.4); 6.7940 (2.1); 6.7121 (0.8); 6.7070 (1.5); 6.6996 (1.8); 6.6949 (1.9); 6.6906 (1.3); 4.8496 (0.8); 4.8461 (0.7); 4.8110 (0.8); 4.8073 (0.8); 4.2323 (1.1); 4.1936 (1.0); 3.9200 (0.6); 3.8672 (16.0); 3.8622 (16.0); 3.5004 (1.2); 3.4971 (1.0); 3.4860 (1.0); 3.4825 (1.2); 2.7612 (1.2); 2.7438 (2.5); 2.7264 (1.1); 2.5867 (0.8); 2.5756 (0.8); 2.5506 (0.9); 2.5395 (0.9); 2.4867 (0.6); 2.4668 (0.6); 2.4635 (0.5); 2.4442 (0.5); 2.4332 (0.6); 2.4185 (0.7); 2.4090 (0.8); 2.3946 (0.9); 2.2253 (0.5); 2.1335 (1.0); 2.1114 (0.9); 2.0975 (0.8); 2.0753 (0.8); 0.0079 (0.5); −0.0002 (16.3)
I-159: $^{1}$H-NMR(400.0 MHz, $d_6$-DMSO):
δ = 7.9699 (0.5); 7.0570 (0.6); 7.0536 (0.6); 4.7310 (0.7); 4.6912 (0.8); 4.2321 (0.9); 4.1924 (0.8); 3.7806 (0.5); 3.5759 (16.0); 3.3644 (17.6); 3.0358 (0.7); 3.0263 (0.8); 3.0216 (0.8); 3.0122 (0.7); 2.5108 (7.3); 2.5062 (14.7); 2.5016 (20.6); 2.4970 (14.4); 2.4924 (6.3); 2.4762 (0.8); 2.4646 (0.7); 2.3579 (0.5); 2.3383 (0.5); 2.3050 (1.4); 2.2865 (3.0); 2.2740 (0.6); 2.2676 (1.6); 2.2638 (0.8); 2.2501 (0.6); 2.1890 (0.8); 2.1676 (0.8); 2.1541 (0.7); 2.1325 (0.7); 1.6347 (1.2); 1.6164 (1.7); 1.5984 (1.0); −0.0002 (0.7)
I-167: $^{1}$H-NMR(400.0 MHz, CDCl3):
δ = 7.5189 (10.3); 7.3794 (6.3); 7.3746 (6.5); 7.3602 (7.2); 7.3554 (7.5); 7.3335 (1.2); 7.3088 (1.3); 7.2937 (2.1); 7.2898 (2.1); 7.2858 (2.5); 7.2600 (2050.6); 7.2533 (6.5); 7.2524 (5.5); 7.2516 (5.9); 7.2500 (2.9); 7.2492 (2.8); 7.2484 (2.1); 7.2477 (2.0); 7.2453 (1.5); 7.2445 (1.3); 7.2332 (1.5); 7.2317 (1.2);

-continued 7.2099 (3.8); 7.1729 (5.4); 7.1538 (14.4); 7.1347 (11.8); 7.1254 (8.6); 7.1206 (9.0); 7.1117 (2.5); 7.1063 (4.4); 7.0990 (3.6); 7.0872 (1.7); 7.0822 (2.4); 7.0746 (3.7); 7.0561 (11.8); 7.0495 (6.4); 7.0458 (6.9); 7.0430 (9.1); 7.0374 (3.0); 7.0317 (3.8); 6.9960 (10.6); 5.4251 (2.2); 4.8537 (3.7); 4.8112 (4.6); 4.2458 (5.6); 4.2078 (5.0); 3.9341 (1.8); 3.9228 (2.3); 3.9130 (2.5); 3.9032 (2.4); 3.8918 (1.9); 3.5566 (2.3); 3.5485 (2.0); 3.5387 (5.1); 3.5315 (4.9); 3.5236 (4.9); 3.5160 (5.1); 3.5059 (2.3); 3.4991 (2.5); 3.0103 (7.7); 2.9929 (16.0); 2.9755 (7.2); 2.6007 (3.8); 2.5901 (4.0); 2.5646 (4.6); 2.5537 (4.4); 2.5118 (1.2); 2.4887 (3.1); 2.4699 (2.5); 2.4454 (2.5); 2.4286 (2.9); 2.4141 (3.4); 2.4045 (4.0); 2.3901 (4.0); 2.3707 (1.2); 2.3616 (1.9); 2.3473 (2.1); 2.2673 (1.6); 2.2480 (2.3); 2.2346 (1.7); 2.2241 (1.9); 2.2153 (2.3); 2.2106 (1.7); 2.1967 (1.9); 2.1908 (2.0); 2.1720 (1.2); 2.1325 (5.0); 2.1099 (4.9); 2.0963 (4.3); 2.0737 (4.3); 1.8045 (1.8); 1.7949 (1.9); 1.7844 (2.0); 1.7692 (2.0); 1.7600 (1.9); 1.7505 (1.5); 1.5999 (9.2); 1.4632 (1.9); 0.1458 (2.2); 0.0110 (2.5); 0.0079 (19.2); 0.0062 (6.6); 0.0054 (7.6); 0.0046 (9.0); 0.0037 (12.3); −0.0002 (674.6); −0.0028 (35.2); −0.0044 (13.0); −0.0052 (7.7); −0.0061 (5.8); −0.0069 (5.0); −0.0085 (19.7); −0.0108 (2.6); −0.0117 (2.2); −0.0124 (2.1); −0.0132 (1.4); −0.0141 (1.3); −0.0148 (1.6); −0.0172 (1.1); −0.0196 (1.1); −0.0504 (1.7); −0.1495 (1.7)

I-168: $^1$H-NMR(400.0 MHz, CDCl3):

δ = 7.7604 (6.9); 7.6337 (16.0); 7.5227 (0.6); 7.2637 (122.0); 7.2603 (2.2); 7.2595 (1.6); 7.2586 (1.3); 7.2578 (1.0); 7.2570 (0.8); 7.2562 (0.7); 7.2554 (0.6); 7.2546 (0.5); 7.1244 (0.9); 7.1151 (1.3); 7.1086 (1.3); 7.0998 (3.1); 7.0873 (2.4); 7.0849 (2.2); 7.0810 (2.5); 7.0748 (5.1); 7.0665 (1.6); 7.0647 (1.6); 7.0630 (1.8); 7.0560 (7.6); 7.0480 (9.9); 7.0452 (6.2); 7.0392 (8.2); 7.0322 (3.1); 7.0286 (4.3); 7.0174 (0.8); 7.0109 (0.5); 6.9996 (0.6); 5.6265 (1.9); 4.8452 (4.1); 4.8416 (4.0); 4.8065 (4.6); 4.8029 (4.5); 4.2410 (5.8); 4.2023 (5.2); 3.9567 (0.9); 3.9456 (1.9); 3.9347 (2.4); 3.9240 (2.7); 3.9146 (2.5); 3.9037 (2.0); 3.8927 (1.0); 3.6128 (0.6); 3.5949 (1.6); 3.5790 (2.7); 3.5607 (4.2); 3.5452 (3.6); 3.5313 (1.7); 3.5272 (1.9); 3.5133 (3.0); 3.4980 (3.6); 3.4808 (2.6); 3.4637 (1.3); 3.4466 (0.7); 2.9777 (4.6); 2.9583 (7.7); 2.9435 (3.5); 2.9401 (3.6); 2.6155 (4.2); 2.6046 (4.2); 2.5792 (4.8); 2.5684 (4.7); 2.5128 (0.8); 2.4935 (1.0); 2.4900 (1.0); 2.4699 (3.0); 2.4504 (2.8); 2.4469 (2.7); 2.4274 (2.8); 2.4222 (3.1); 2.4074 (3.4); 2.3981 (4.1); 2.3836 (4.1); 2.3793 (1.4); 2.3645 (1.0); 2.3551 (1.8); 2.3408 (1.7); 2.2809 (1.6); 2.2618 (2.6); 2.2573 (1.6); 2.2484 (2.0); 2.2428 (1.6); 2.2379 (2.2); 2.2294 (2.9); 2.2244 (1.8); 2.2190 (1.2); 2.2102 (1.7); 2.2051 (2.3); 2.1862 (1.2); 2.1495 (5.4); 2.1270 (5.3); 2.1132 (4.7); 2.0908 (4.6); 1.8044 (1.3); 1.7931 (1.5); 1.7903 (1.7); 1.7793 (1.9); 1.7699 (1.9); 1.7666 (1.6); 1.7604 (1.5); 1.7572 (1.9); 1.7461 (1.7); 1.7370 (1.3); 1.7339 (1.2); 1.7224 (1.1); 0.0080 (1.1); 0.0023 (1.5); −0.0002 (38.7); −0.0050 (0.7); −0.0059 (0.6); −0.0067 (0.5); −0.0085 (1.2)

I-176: $^1$H-NMR(400.0 MHz, $d_6$-DMSO):

δ = 7.3806 (0.6); 7.3599 (2.0); 7.3360 (2.9); 7.3142 (2.3); 7.2944 (0.9); 7.2089 (0.8); 7.1890 (2.0); 7.1763 (2.5); 7.1726 (2.5); 7.1689 (2.4); 7.1561 (2.4); 7.0690 (1.7); 7.0507 (3.0); 7.0331 (2.6); 5.0988 (3.5); 4.7344 (1.6); 4.6938 (2.7); 4.6687 (1.0); 4.6500 (1.5); 4.2561 (0.7); 4.1967 (2.8); 4.1794 (2.0); 4.1567 (2.4); 4.1399 (1.5); 3.8167 (1.1); 3.7408 (1.6); 3.7034 (16.0); 3.6941 (15.9); 3.6686 (0.8); 3.6479 (4.0); 3.6129 (9.9); 3.5764 (3.5); 3.5635 (3.2); 3.5544 (3.4); 3.5263 (2.2); 3.4833 (10.3); 3.4605 (8.9); 3.3107 (60.2); 3.1517 (0.9); 3.1428 (0.9); 3.1062 (1.3); 3.0973 (1.2); 3.0196 (0.6); 3.0104 (0.5); 2.8979 (1.3); 2.8756 (1.3); 2.8525 (0.9); 2.8301 (0.9); 2.7827 (0.6); 2.7605 (0.5); 2.7377 (0.6); 2.7157 (0.5); 2.6746 (0.9); 2.6699 (1.2); 2.6650 (1.3); 2.6529 (1.5); 2.6179 (1.4); 2.5402 (0.5); 2.5234 (1.8); 2.5187 (2.6); 2.5101 (43.6); 2.5055 (94.5); 2.5009 (132.0); 2.4963 (91.8); 2.4917 (41.0); 2.4009 (1.1); 2.3843 (1.3); 2.3791 (1.3); 2.3611 (1.7); 2.3391 (1.3); 2.3323 (1.2); 2.3277 (1.4); 2.3230 (1.4); 2.2936 (1.5); 2.2800 (1.9); 2.2692 (2.0); 2.2639 (1.9); 2.2562 (2.4); 2.2517 (2.3); 2.2179 (2.6); 2.2006 (1.8); 2.1779 (1.9); 2.1698 (2.0); 2.1454 (1.7); 1.9592 (1.0); 1.7574 (1.1); 1.6840 (0.7); 1.6731 (0.7); 1.6640 (0.8); 1.6535 (0.8); 1.6421 (0.7); 1.6298 (0.6); 0.0080 (0.7); −0.0002 (24.2); −0.0086 (0.7)

I-177: $^1$H-NMR(400.0 MHz, $d_6$-DMSO):

δ = 7.3382 (1.1); 7.3140 (2.3); 7.2929 (2.3); 7.2720 (1.3); 7.1739 (1.5); 7.1542 (2.6); 7.1380 (2.5); 7.1180 (1.4); 7.0644 (2.4); 7.0468 (3.1); 7.0280 (1.8); 5.7516 (0.8); 4.7092 (3.7); 4.6697 (4.1); 4.2894 (4.6); 4.2498 (3.9); 3.9420 (1.9); 3.9314 (2.3); 3.9224 (1.9); 3.4272 (4.1); 3.3162 (118.5); 3.2037 (3.7); 3.1653 (4.0); 3.1534 (3.0); 2.9239 (2.2); 2.9017 (2.1); 2.8848 (1.7); 2.8637 (1.6); 2.6741 (2.7); 2.6694 (3.8); 2.6649 (2.8); 2.5229 (9.0); 2.5182 (13.4); 2.5096 (233.3); 2.5051 (506.2); 2.5004 (705.8); 2.4959 (492.9); 2.4913 (223.9); 2.4495 (1.9); 2.4328 (1.5); 2.4082 (1.7); 2.3907 (2.9); 2.3719 (2.4); 2.3494 (2.1); 2.3319 (3.2); 2.3272 (4.3); 2.3225 (3.2); 2.2879 (1.9); 2.2746 (2.3); 2.2635 (3.3); 2.2380 (16.0); 2.2221 (3.2); 2.2087 (2.2); 2.1789 (1.3); 2.1602 (1.6); 2.1473 (2.6); 2.0714 (4.0); 1.7472 (1.0); 1.7360 (1.4); 1.7242 (1.8); 1.7128 (1.9); 1.7045 (1.6); 1.6928 (1.7); 1.6821 (1.2); 1.2362 (2.4); 1.1945 (1.1); 1.1761 (2.2); 1.1580 (1.1); −0.0002 (4.4)

I-178: $^1$H-NMR(400.0 MHz, $d_6$-DMSO):

δ = 7.3599 (1.8); 7.3561 (1.8); 7.3354 (4.0); 7.3200 (2.5); 7.3139 (4.0); 7.2935 (2.0); 7.2895 (1.9); 7.1777 (2.2); 7.1738 (2.4); 7.1649 (2.4); 7.1577 (4.2); 7.1540 (4.3); 7.1449 (4.0); 7.1415 (4.4); 7.1334 (2.5); 7.1247 (2.2); 7.1210 (2.3); 7.0447 (4.2); 7.0285 (5.8); 7.0090 (2.9); 4.7055 (2.4); 4.6654 (3.0); 4.3087 (3.0); 4.2690 (2.4); 3.9621 (1.0); 3.8933 (1.8); 3.4410 (3.5); 3.3875 (121.8); 3.1682 (0.7); 3.0402 (2.0); 3.0200 (2.1); 3.0007 (1.7); 2.9810 (1.2); 2.6992 (4.8); 2.6831 (3.0); 2.6746 (2.3); 2.6699 (2.5); 2.6653 (1.7); 2.5232 (4.0); 2.5185 (5.7); 2.5099 (101.0); 2.5053 (220.7); 2.5007 (308.2); 2.4961 (216.6); 2.4915 (98.4); 2.4647 (2.3); 2.4454 (3.2); 2.4398 (3.4); 2.4224 (6.5); 2.4037 (5.6); 2.3812 (3.6); 2.3322 (1.4); 2.3274 (1.9); 2.3229 (1.5); 2.3016 (2.4); 2.2895 (2.7); 2.2774 (3.4); 2.2650 (3.6); 2.2483 (1.1); 2.2353 (2.3); 2.2240 (2.6); 2.2081 (1.2); 2.1892 (2.0); 2.1577 (2.1); 1.7374 (7.0); 1.7219 (8.3); 1.2220 (10.2); 1.0155 (16.0); 1.0014 (16.0); 0.0080 (1.6); −0.0002 (60.0); −0.0085 (1.9)

I-179: $^1$H-NMR(400.0 MHz, $d_6$-DMSO):

δ = 7.3428 (0.8); 7.3206 (0.8); 7.1597 (0.8); 7.1472 (0.8); 7.0543 (0.8); 7.0379 (1.1); 7.0193 (0.6); 4.6988 (1.3); 4.6591 (1.5); 4.3176 (1.6); 4.2780 (1.3); 3.9532 (0.6); 3.9436 (0.8); 3.9333 (1.0); 3.9236 (0.8); 3.9134 (0.5); 3.4618 (1.1); 3.4508 (1.1); 3.4207 (1.4); 3.4097 (1.3); 3.3233 (164.6); 3.0971 (1.3); 3.0766 (1.3); 3.0561 (1.1); 3.0356 (1.0); 2.6743 (0.5); 2.6698 (0.7); 2.6652 (0.6); 2.6086 (2.9); 2.5388 (0.6); 2.5232 (2.1); 2.5097 (42.4); 2.5052 (89.0); 2.5007 (121.7); 2.4961 (85.2); 2.4916 (38.8); 2.4602 (0.5); 2.4411 (0.7); 2.4188 (1.0); 2.3999 (1.0); 2.3780 (0.7); 2.3320 (0.6); 2.3275 (0.8); 2.3228 (0.6); 2.3023 (0.8); 2.2788 (3.2); 2.2658 (1.3); 2.2361 (0.7); 2.2252 (0.7); 2.2186 (0.6); 2.2007 (0.7); 2.1887 (0.5); 2.1698 (0.8); 2.1454 (0.5); 1.7589 (0.6); 1.7475 (0.6); 1.7375 (0.6); 1.7286 (0.7); 0.9731 (16.0); −0.0002 (3.7)

-continued

I-180: $^{1}$H-NMR(400.0 MHz, $d_6$-DMSO):
δ = 7.3645 (1.0); 7.3441 (2.2); 7.3213 (2.3); 7.3009 (1.1); 7.1816 (1.4); 7.1777 (1.4); 7.1614 (2.5); 7.1578 (2.5); 7.1453 (2.6); 7.1374 (1.5); 7.1284 (1.4); 7.0521 (2.4); 7.0359 (3.3); 7.0162 (1.6); 4.6822 (2.5); 4.6421 (3.1); 4.3262 (2.5); 4.2877 (2.0); 3.9618 (1.3); 3.9515 (2.0); 3.9417 (2.4); 3.9313 (2.0); 3.9218 (1.4); 3.4561 (3.4); 3.4448 (3.4); 3.4149 (4.4); 3.4037 (4.0); 3.3212 (380.2); 3.2892 (2.3); 3.2731 (1.3); 3.1683 (1.1); 3.0712 (4.2); 3.0507 (4.0); 3.0300 (3.4); 3.0095 (3.4); 2.6788 (1.6); 2.6741 (1.9); 2.6696 (2.5); 2.6648 (1.8); 2.6427 (1.9); 2.5398 (1.4); 2.5229 (5.8); 2.5183 (8.4); 2.5096 (121.2); 2.5050 (261.0); 2.5004 (362.6); 2.4959 (253.8); 2.4913 (114.7); 2.4615 (2.3); 2.4503 (2.1); 2.4409 (2.0); 2.4185 (2.9); 2.3987 (3.4); 2.3769 (2.5); 2.3573 (1.6); 2.3321 (1.7); 2.3272 (2.4); 2.3226 (1.7); 2.2998 (1.9); 2.2870 (2.2); 2.2752 (3.0); 2.2627 (3.0); 2.2463 (0.8); 2.2336 (2.1); 2.2223 (2.3); 2.2130 (1.8); 2.1951 (2.6); 2.1828 (2.2); 2.1760 (2.4); 2.1707 (2.5); 2.1637 (3.7); 2.1392 (3.8); 2.1204 (2.8); 2.0713 (0.6); 1.7614 (0.9); 1.7515 (1.7); 1.7400 (1.8); 1.7294 (1.8); 1.7208 (1.9); 1.7090 (1.6); 1.6963 (1.3); 1.6852 (0.8); 0.9875 (15.5); 0.9723 (16.0); −0.0002 (10.3)
I-181: $^{1}$H-NMR(400.0 MHz, $d_6$-DMSO):
δ = 8.9109 (4.4); 8.3477 (2.3); 7.7953 (2.4); 7.6126 (14.8); 7.3197 (0.9); 7.2974 (1.0); 7.1688 (2.6); 7.1668 (2.5); 7.1650 (2.4); 7.1630 (2.3); 7.1533 (1.1); 7.1371 (1.1); 7.1292 (0.6); 7.1205 (0.6); 7.0625 (1.1); 7.0470 (1.4); 7.0272 (0.7); 6.4529 (1.4); 6.4492 (2.9); 6.4454 (1.5); 4.7225 (1.6); 4.6829 (1.9); 4.2671 (2.0); 4.2275 (1.7); 3.8671 (0.9); 3.8558 (1.1); 3.8454 (1.4); 3.8357 (1.2); 3.8254 (1.0); 3.3525 (3.6); 3.1685 (2.0); 3.1477 (2.7); 3.1383 (3.5); 3.1348 (3.3); 3.1262 (2.5); 3.1221 (2.5); 3.1108 (4.2); 3.1005 (2.6); 3.0931 (1.8); 2.7986 (1.5); 2.7759 (1.5); 2.7624 (1.3); 2.7395 (1.2); 2.6743 (1.2); 2.6697 (1.7); 2.6649 (1.3); 2.5399 (0.7); 2.5232 (3.5); 2.5185 (5.0); 2.5098 (90.9); 2.5052 (202.8); 2.5006 (285.6); 2.4960 (197.8); 2.4914 (89.3); 2.4816 (4.9); 2.4552 (1.9); 2.4505 (2.6); 2.4460 (2.0); 2.4001 (0.9); 2.3793 (1.0); 2.3573 (1.4); 2.3368 (1.6); 2.3323 (2.0); 2.3274 (2.0); 2.3227 (1.4); 2.3152 (1.0); 2.2466 (0.9); 2.2340 (1.1); 2.2226 (1.4); 2.2099 (1.4); 2.1922 (0.7); 2.1803 (0.9); 2.1682 (1.3); 2.1552 (16.0); 2.1031 (0.6); 2.0831 (0.8); 2.0715 (1.1); 2.0591 (0.8); 2.0516 (1.0); 2.0278 (0.7); 1.7236 (0.7); 1.7124 (0.8); 1.7018 (0.8); 1.6909 (0.8); 1.6810 (0.7); 1.6690 (0.5); 1.1911 (0.9); 1.1729 (1.9); 1.1547 (0.9); −0.0002 (17.4)
I-182: $^{1}$H-NMR(400.0 MHz, $d_6$-DMSO):
δ = 7.0618 (0.6); 4.7373 (0.7); 4.6981 (0.8); 4.2026 (0.8); 4.1632 (0.7); 3.3102 (18.1); 3.1249 (0.7); 3.1123 (2.0); 3.0943 (2.0); 3.0766 (0.7); 2.5829 (0.7); 2.5720 (0.7); 2.5475 (0.9); 2.5366 (0.9); 2.5186 (0.6); 2.5100 (9.4); 2.5054 (20.2); 2.5008 (28.2); 2.4962 (19.6); 2.4916 (8.7); 2.3389 (0.5); 2.3309 (1.0); 2.3195 (0.5); 2.3084 (0.9); 2.2956 (1.0); 2.2729 (1.6); 2.2351 (0.6); 2.2218 (0.6); 1.1949 (7.7); 1.1768 (16.0); 1.1585 (7.5); −0.0002 (6.1)
I-183: $^{1}$H-NMR(400.0 MHz, $d_6$-DMSO):
δ = 7.3589 (3.6); 7.3384 (8.6); 7.3170 (7.8); 7.2952 (3.9); 7.1808 (4.5); 7.1612 (8.3); 7.1485 (8.8); 7.1280 (4.2); 7.0455 (7.9); 7.0285 (10.8); 7.0100 (5.2); 4.6945 (13.2); 4.6546 (16.0); 4.3150 (5.3); 4.2773 (4.4); 3.9061 (6.2); 3.4033 (8.0); 3.3330 (778.3); 3.1684 (9.5); 3.0577 (4.7); 3.0384 (4.2); 3.0187 (3.9); 2.9658 (7.3); 2.7823 (6.7); 2.6743 (4.8); 2.6697 (6.6); 2.6650 (4.7); 2.5398 (2.5); 2.5231 (15.0); 2.5184 (22.8); 2.5098 (394.0); 2.5052 (856.6); 2.5006 (1195.3); 2.4960 (832.2); 2.4914 (375.5); 2.4520 (6.9); 2.4338 (5.5); 2.4285 (5.4); 2.4104 (11.1); 2.3916 (9.5); 2.3693 (7.3); 2.3320 (5.4); 2.3273 (7.2); 2.3227 (5.4); 2.3015 (6.8); 2.2887 (7.9); 2.2772 (10.9); 2.2646 (10.4); 2.2477 (2.9); 2.2355 (7.0); 2.2238 (7.1); 2.2073 (3.5); 2.1889 (5.5); 2.1572 (7.0); 2.1331 (6.4); 2.0715 (12.4); 2.0258 (14.1); 1.9965 (13.6); 1.7603 (5.4); 1.7488 (8.2); 1.7376 (11.1); 1.7283 (9.6); 1.7184 (9.5); 1.7065 (8.2); 1.6949 (5.1); 1.6828 (3.2); 1.6486 (7.2); 1.6381 (13.6); 1.6273 (8.2); 1.6190 (7.3); 1.6082 (12.2); 1.5975 (6.2); 1.5056 (4.7); −0.0002 (4.2)
I-184: $^{1}$H-NMR(400.0 MHz, $d_6$-DMSO):
δ = 7.3704 (2.4); 7.3492 (5.5); 7.3279 (5.7); 7.3070 (2.9); 7.1913 (3.0); 7.1715 (6.1); 7.1590 (6.1); 7.1387 (3.6); 7.0715 (5.9); 7.0550 (8.0); 7.0360 (4.2); 4.7605 (9.4); 4.7205 (11.0); 4.3139 (11.8); 4.2743 (9.9); 3.9331 (3.7); 3.9229 (5.8); 3.9128 (7.0); 3.9031 (5.6); 3.8926 (4.0); 3.4897 (7.5); 3.4792 (7.8); 3.4496 (9.8); 3.4388 (9.6); 3.4012 (4.4); 3.3777 (19.0); 3.3394 (3342.2); 3.3062 (26.2); 3.2929 (3.9); 3.2837 (5.6); 3.2372 (2.5); 3.1671 (7.8); 3.0625 (9.6); 3.0414 (9.5); 3.0224 (8.2); 3.0013 (8.0); 2.6760 (8.3); 2.6714 (11.6); 2.6668 (8.1); 2.5417 (7.6); 2.5334 (2.4); 2.5247 (22.9); 2.5201 (35.8); 2.5114 (679.1); 2.5069 (1444.2); 2.5023 (1953.4); 2.4977 (1364.7); 2.4932 (619.9); 2.4686 (8.7); 2.4426 (7.0); 2.4234 (6.5); 2.4013 (5.1); 2.3336 (8.9); 2.3291 (12.2); 2.3244 (9.5); 2.3204 (8.1); 2.3085 (5.4); 2.2963 (7.4); 2.2844 (7.1); 2.2547 (4.9); 2.2437 (5.2); 2.2327 (3.7); 2.2145 (5.2); 2.2025 (3.8); 2.1902 (3.6); 2.1834 (5.8); 2.1592 (4.0); 2.1394 (2.0); 2.0753 (5.0); 1.8060 (2.4); 1.7963 (4.3); 1.7853 (4.1); 1.7740 (4.8); 1.7657 (4.9); 1.7540 (3.6); 1.7422 (3.2); 1.2968 (16.0); 0.0080 (2.9); −0.0002 (105.6); −0.0085 (3.1)
I-185: $^{1}$H-NMR(400.0 MHz, $d_6$-DMSO):
δ = 7.6344 (2.5); 7.3521 (1.0); 7.3281 (2.2); 7.3060 (2.3); 7.2859 (1.1); 7.1793 (1.2); 7.1626 (2.4); 7.1468 (2.4); 7.1260 (1.3); 7.0709 (2.3); 7.0548 (3.2); 7.0354 (1.7); 7.0107 (2.2); 4.7141 (3.6); 4.6749 (3.9); 4.1875 (4.2); 4.1478 (3.7); 4.1113 (0.7); 3.8270 (1.4); 3.8168 (2.0); 3.8072 (2.2); 3.7968 (1.9); 3.7862 (1.5); 3.7705 (1.0); 3.3315 (78.6); 3.1725 (2.5); 3.1621 (2.5); 3.0090 (2.6); 2.9982 (2.6); 2.9730 (3.5); 2.9621 (3.2); 2.7175 (3.7); 2.6955 (3.6); 2.6817 (3.4); 2.6757 (2.5); 2.6710 (3.1); 2.6664 (2.3); 2.6596 (3.2); 2.5409 (3.2); 2.5365 (3.0); 2.5317 (1.7); 2.5244 (6.0); 2.5197 (10.7); 2.5110 (169.4); 2.5065 (370.8); 2.5019 (515.0); 2.4973 (359.8); 2.4927 (160.7); 2.4744 (3.5); 2.4697 (1.9); 2.3671 (0.8); 2.3332 (2.3); 2.3285 (3.4); 2.3241 (4.2); 2.3026 (2.5); 2.2813 (1.7); 2.2083 (1.8); 2.1962 (2.1); 2.1843 (2.6); 2.1716 (2.4); 2.1540 (1.3); 2.1422 (1.4); 2.1305 (1.6); 2.0507 (9.1); 2.0350 (16.0); 2.0189 (11.7); 1.9951 (2.3); 1.9714 (1.7); 1.9511 (0.9); 1.7455 (1.5); 1.7341 (1.8); 1.7238 (1.8); 1.7127 (1.7); 1.7025 (1.5); 1.6923 (1.1); 1.6417 (1.4); 1.6245 (4.1); 1.6092 (5.4); 1.5926 (3.5); 1.2279 (1.2); 0.0343 (0.8); 0.0080 (4.3); −0.0002 (153.6); −0.0086 (4.7)
I-186: $^{1}$H-NMR(400.0 MHz, $d_6$-DMSO):
δ = 4.7271 (0.5); 4.6876 (0.6); 4.2208 (0.7); 4.1814 (0.6); 3.3573 (0.6); 3.3177 (8.9); 3.1244 (1.2); 3.1178 (0.9); 3.1060 (3.3); 3.0878 (3.5); 3.0696 (1.1); 2.7240 (0.6); 2.7012 (0.6); 2.6880 (0.5); 2.6652 (0.6); 2.5105 (5.6); 2.5059 (12.1); 2.5013 (16.8); 2.4967 (11.7); 2.4921 (5.2); 2.0350 (0.8); 1.4407 (16.0); 1.2316 (0.7); 1.1840 (7.4); 1.1658 (15.7); 1.1475 (7.1)
I-187: $^{1}$H-NMR(400.0 MHz, $d_6$-DMSO):
δ = 7.5026 (0.8); 7.3191 (0.8); 5.2964 (1.7); 4.7277 (0.5); 4.2838 (0.6); 4.2451 (0.5); 3.3730 (10.9); 3.3550 (10.4); 3.3393 (9.6); 3.1266 (2.1); 3.1083 (6.5); 3.0901 (6.6); 3.0719 (2.5); 3.0613 (0.5); 3.0350 (0.6); 3.0247 (0.6); 2.8877 (0.6); 2.8652 (0.6); 2.6698 (0.6); 2.5232 (1.7); 2.5185 (2.6); 2.5099 (38.8); 2.5053 (82.7); 2.5007 (114.3); 2.4961 (79.6); 2.4916 (35.8); 2.3322 (0.5); 2.3274 (0.7); 1.2496 (1.2);

-continued 1.2314 (2.6); 1.2133 (1.2); 1.1937 (7.6); 1.1755 (16.0); 1.1573 (7.3); −0.0002 (9.1)
I-188: $^1$H-NMR(400.0 MHz, $d_6$-DMSO):
δ = 7.3414 (1.8); 7.1968 (1.4); 7.1788 (2.3); 7.1653 (2.4); 7.1452 (1.1); 7.0786 (1.2); 7.0421 (1.3); 7.0262 (1.7); 4.7385 (2.1); 4.6990 (2.3); 4.2676 (2.6); 4.2532 (1.3); 4.2287 (2.2); 3.8650 (1.9); 3.7728 (6.6); 3.6480 (10.7); 3.5457 (16.0); 3.1677 (0.9); 3.1168 (1.2); 3.0948 (1.4); 2.9687 (0.7); 2.9176 (1.2); 2.8947 (1.3); 2.8608 (0.9); 2.7035 (0.9); 2.6930 (0.7); 2.6744 (1.5); 2.6698 (2.1); 2.6649 (2.0); 2.6536 (0.8); 2.5232 (5.1); 2.5185 (7.2); 2.5099 (118.0); 2.5053 (257.8); 2.5007 (361.0); 2.4960 (250.7); 2.4915 (111.7); 2.4007 (1.8); 2.3909 (1.8); 2.3789 (1.9); 2.3726 (1.9); 2.3319 (1.7); 2.3274 (2.4); 2.3227 (1.8); 2.2642 (1.7); 2.2511 (1.8); 2.2208 (1.2); 2.2070 (1.1); 2.0718 (1.1); 2.0418 (1.0); 1.7560 (1.2); 1.7338 (1.4); 0.0081 (2.7); −0.0002 (92.4); −0.0085 (2.5)
I-189: $^1$H-NMR(400.0 MHz, $d_6$-DMSO):
δ = 7.1881 (0.6); 7.1843 (0.5); 7.1754 (0.5); 7.1718 (0.5); 7.0513 (0.7); 4.7070 (0.8); 4.6670 (0.8); 4.1952 (0.9); 4.1553 (0.8); 3.6682 (1.0); 3.6121 (16.0); 3.5750 (3.3); 3.5622 (3.4); 3.5215 (0.5); 3.3018 (37.7); 3.0629 (0.6); 3.0534 (0.6); 3.0181 (0.9); 3.0086 (0.8); 2.7810 (0.9); 2.7589 (0.9); 2.7363 (0.7); 2.7141 (0.6); 2.5225 (1.1); 2.5177 (1.6); 2.5091 (25.6); 2.5046 (55.1); 2.4999 (76.5); 2.4953 (52.8); 2.4907 (23.5); 2.3772 (0.6); 2.2736 (0.7); 2.2623 (0.7); 2.2493 (0.7); 2.2106 (0.8); − 0.0002 (13.8)
I-190: $^1$H-NMR(400.0 MHz, $d_6$-DMSO):
δ = 17.2358 (3.1); 7.3395 (3.2); 7.3193 (4.9); 7.2456 (3.0); 7.2258 (1.9); 7.2027 (1.2); 7.1485 (3.8); 7.1280 (7.6); 7.1157 (7.7); 7.0948 (1.6); 7.0750 (1.2); 7.0457 (3.0); 7.0298 (4.2); 7.0109 (2.2); 6.4684 (4.5); 6.4612 (4.1); 6.4107 (4.0); 4.7283 (2.5); 4.6800 (4.1); 4.6402 (2.1); 4.3039 (5.3); 4.2638 (4.5); 4.0322 (1.8); 3.9921 (3.2); 3.9762 (1.9); 3.8529 (2.9); 3.8426 (3.2); 3.8319 (2.7); 3.3549 (215.6); 3.2703 (4.8); 3.2613 (4.6); 3.1676 (8.5); 2.9839 (3.0); 2.9642 (2.7); 2.9480 (2.6); 2.9277 (2.6); 2.6887 (1.5); 2.6791 (2.9); 2.6748 (3.1); 2.6699 (4.4); 2.6653 (2.9); 2.6495 (2.0); 2.6398 (1.6); 2.5598 (5.0); 2.5403 (4.1); 2.5316 (9.6); 2.5236 (10.8); 2.5188 (16.0); 2.5101 (256.0); 2.5056 (561.2); 2.5009 (788.3); 2.4963 (546.8); 2.4917 (241.0); 2.4325 (4.8); 2.4201 (6.9); 2.4092 (4.8); 2.3921 (6.7); 2.3803 (3.6); 2.3324 (3.6); 2.3276 (5.1); 2.3233 (3.7); 2.3135 (9.2); 2.3036 (2.8); 2.2921 (3.0); 2.2769 (16.0); 2.2681 (4.9); 2.2561 (4.3); 2.2408 (3.4); 2.2262 (2.5); 2.2140 (3.0); 2.1704 (1.4); 2.1496 (2.1); 2.1187 (3.2); 2.0939 (2.2); 1.7074 (2.3); 0.0081 (2.1); −0.0002 (95.6); −0.0085 (2.7)

The present invention furthermore provides the use of one or more compounds of the general formula (I) and/or salts thereof, as defined above, preferably in one of the embodiments identified as preferred or particularly preferred, in particular one or more compounds of the formulae (I-001) to (I-205) and/or salts thereof, in each case as defined above, as herbicide and/or plant growth regulator, preferably in crops of useful plants and/or ornamental plants.

The present invention furthermore provides a method for controlling harmful plants and/or for regulating the growth of plants, characterized in that an effective amount of one or more compounds of the general formula (I) and/or salts thereof, as defined above, preferably in one of the embodiments identified as preferred or particularly preferred, in particular one or more compounds of the formulae (I-001) to (I-205) and/or salts thereof, in each case as defined above, or of a composition according to the invention, as defined below, is applied to the (harmful) plants, seeds of (harmful) plants, the soil in which or on which the (harmful) plants grow or the area under cultivation.

The present invention also provides a method for controlling unwanted plants, preferably in crops of useful plants, characterized in that an effective amount of one or more compounds of the general formula (I) and/or salts thereof, as defined above, preferably in one of the embodiments identified as preferred or particularly preferred, in particular one or more compounds of the formulae (I-001) to (I-205) and/or salts thereof, in each case as defined above, or of a composition according to the invention, as defined below, is applied to unwanted plants (for example harmful plants such as mono- or dicotyledonous weeds or unwanted crop plants), the seed of the unwanted plants (i.e. plant seeds, for example grains, seeds or vegetative propagation organs such as tubers or shoot parts with buds), the soil in which or on which the unwanted plants grow (for example the soil of crop land or non-crop land) or the area under cultivation (i.e. the area on which the unwanted plants will grow).

The present invention furthermore also provides methods for regulating the growth of plants, preferably of useful plants, characterized in that an effective amount of one or more compounds of the general formula (I) and/or salts thereof, as defined above, preferably in one of the embodiments identified as preferred or particularly preferred, in particular one or more compounds of the formulae (1-001) to (1-205) and/or salts thereof, in each case as defined above, or of a composition according to the invention, as defined below, is applied to the plant, the seed of the plant (i.e. plant seed, for example grains, seeds or vegetative propagation organs such as tubers or shoot parts with buds), the soil in which or on which the plants grow (for example the soil of crop land or non-crop land) or the area under cultivation (i.e. the area on which the plants will grow).

In this context, the compounds according to the invention or the compositions according to the invention can be applied for example by pre-sowing (if appropriate also by incorporation into the soil), pre-emergence and/or post-emergence processes. Specific examples of some representatives of the monocotyledonous and dicotyledonous weed flora which can be controlled by the compounds according to the invention are as follows, though there is no intention to restrict the enumeration to particular species.

In a method according to the invention for controlling harmful plants or for regulating the growth of plants, one or more compounds of the general formula (I) and/or salts thereof are preferably employed for controlling harmful plants or for regulating growth in crops of useful plants or ornamental plants, where in a preferred embodiment the useful plants or ornamental plants are transgenic plants.

The compounds of the general formula (I) according to the invention and/or their salts are suitable for controlling the following genera of monocotyledonous and dicotyledonous harmful plants: Monocotyledonous harmful plants of the genera: *Aegilops, Agropyron, Agrostis, Alopecurus, Apera,*

*Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum.*

Dicotyledonous harmful plants of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the compounds according to the invention are applied to the soil surface before germination of the harmful plants (weed grasses and/or broad-leaved weeds) (pre-emergence method), either the seedlings of the weed grasses or broad-leaved weeds are prevented completely from emerging or they grow until they have reached the cotyledon stage, but then stop growing and eventually, after three to four weeks have elapsed, die completely.

If the active compounds are applied post-emergence to the green parts of the plants, growth stops after the treatment, and the harmful plants remain at the growth stage at the time of application, or they die completely after a certain time, so that in this manner competition by the weeds, which is harmful to the crop plants, is eliminated very early and in a sustained manner.

Although the compounds according to the invention display an outstanding herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Miscanthus, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum*, triticale, *triticum, Zea*, are damaged only to an insignificant extent, or not at all, depending on the structure of the respective compound according to the invention and its application rate. For these reasons, the present compounds are very suitable for selective control of unwanted plant growth in plant crops such as agriculturally useful plants or ornamental plants.

In addition, the compounds of the invention (depending on their particular structure and the application rate deployed) have outstanding growth-regulating properties in crop plants. They intervene in the plants' own metabolism with regulatory effect and can thus be used for the controlled influencing of plant constituents and to facilitate harvesting, for example by triggering desiccation and stunted growth. Furthermore, they are also suitable for the general control and inhibition of unwanted vegetative growth without killing the plants in the process. Inhibition of vegetative growth plays a major role for many mono- and dicotyledonous crops since, for example, this can reduce or completely prevent lodging.

By virtue of their herbicidal and plant growth regulatory properties, the active compounds can also be used to control harmful plants in crops of genetically modified plants or plants modified by conventional mutagenesis. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material.

It is preferred with a view to transgenic crops to use the compounds according to the invention and/or their salts in economically important transgenic crops of useful plants and ornamentals, for example of cereals such as wheat, barley, rye, oats, millet, rice and corn or else crops of sugar beet, cotton, soybean, oilseed rape, potato, tomato, peas and other vegetables.

It is preferred to employ the compounds according to the invention as herbicides in crops of useful plants which are resistant, or have been made resistant by recombinant means, to the phytotoxic effects of the herbicides.

By virtue of their herbicidal and plant growth regulatory properties, the active compounds can also be used to control harmful plants in crops of genetically modified plants which are known or are yet to be developed. In general, the transgenic plants are characterized by particular advantageous properties, for example by resistances to certain pesticides, in particular certain herbicides, resistances to plant diseases or pathogens of plant diseases, such as certain insects or microorganisms such as fungi, bacteria or viruses. Other specific characteristics relate, for example, to the harvested material with regard to quantity, quality, storability, composition and specific constituents. For instance, there are known transgenic plants with an elevated starch content or altered starch quality, or those with a different fatty acid composition in the harvested material. Further special properties may be tolerance or resistance to abiotic stressors, for example heat, cold, drought, salinity and ultraviolet radiation.

Preference is given to the use of the compounds of the general formula (I) according to the invention or salts thereof in economically important transgenic crops of useful plants and ornamental plants, for example of cereals such as wheat, barley, rye, oats, triticale, millet, rice, cassava and corn, or else crops of sugar beet, cotton, soybean, oilseed rape, potatoes, tomatoes, peas and other vegetables.

The compounds of the general formula (I) can preferably be used as herbicides in crops of useful plants which are resistant, or have been made resistant by recombinant means, to the phytotoxic effects of the herbicides.

Conventional ways of producing novel plants which have modified properties in comparison to existing plants consist, for example, in traditional cultivation methods and the generation of mutants. Alternatively, novel plants with altered properties can be generated with the aid of recombinant methods.

A large number of molecular-biological techniques by means of which novel transgenic plants with modified properties can be generated are known to the person skilled in the art. For such recombinant manipulations, nucleic acid molecules which allow mutagenesis or sequence alteration by recombination of DNA sequences can be introduced into plasmids. With the aid of standard methods, it is possible, for example, to undertake base exchanges, remove parts of sequences or add natural or synthetic sequences. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect, or by expressing at least one suitably constructed ribozyme which specifically cleaves transcripts of the abovementioned gene product.

To this end, it is firstly possible to use DNA molecules which encompass the entire coding sequence of a gene product inclusive of any flanking sequences which may be present, and also DNA molecules which only encompass portions of the coding sequence, in which case it is necessary for these portions to be long enough to have an antisense effect in the cells. It is also possible to use DNA sequences which have a high degree of homology to the coding sequences of a gene product, but are not completely identical to them.

When expressing nucleic acid molecules in plants, the protein synthesized may be localized in any desired compartment of the plant cell. However, to achieve localization in a particular compartment, it is possible, for example, to join the coding region to DNA sequences which ensure localization in a particular compartment. Such sequences are known to those skilled in the art (see, for example, Braun et al., EMBO J. 11 (1992), 3219-3227). The nucleic acid molecules can also be expressed in the organelles of the plant cells.

The transgenic plant cells can be regenerated by known techniques to give rise to entire plants. In principle, the transgenic plants may be plants of any desired plant species, i.e. not only monocotyledonous but also dicotyledonous plants.

Thus, transgenic plants can be obtained whose properties are altered by overexpression, suppression or inhibition of homologous (=natural) genes or gene sequences or expression of heterologous (=foreign) genes or gene sequences.

It is preferred to employ the compounds (I) according to the invention in transgenic crops which are resistant to growth regulators such as, for example, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, glyphosate, glufosinate or benzoylisoxazoles and analogous active compounds.

When the active compounds of the invention are employed in transgenic crops, not only do the effects toward harmful plants observed in other crops occur, but frequently also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also relates to the use of the compounds of the general formula (I) according to the invention and/or their salts as herbicides for controlling harmful plants in crops of useful plants or ornamentals, optionally in transgenic crop plants.

Preference is given to the use in cereals, here preferably corn, wheat, barley, rye, oats, millet or rice, by the pre- or post-emergence method.

Preference is also given to the use in soybeans by the pre- or post-emergence method.

The use according to the invention for the control of harmful plants or for growth regulation of plants also includes the case in which the active compound of the general formula (I) or its salt is not formed from a precursor substance ("prodrug") until after application on the plant, in the plant or in the soil.

The invention also provides for the use of one or more compounds of the general formula (I) or salts thereof or of a composition according to the invention (as defined below) (in a method) for controlling harmful plants or for regulating the growth of plants which comprises applying an effective amount of one or more compounds of the general formula (I) or salts thereof onto the plants (harmful plants, if appropriate together with the useful plants), plant seeds, the soil in which or on which the plants grow or the area under cultivation.

The invention also provides a herbicidal and/or plant growth-regulating composition, characterized in that the composition comprises (a) one or more compounds of the general formula (I) and/or salts thereof, as defined above, preferably in one of the embodiments identified as preferred or particularly preferred, in particular one or more compounds of the formulae (1-001) to (1-205) and/or salts thereof, in each case as defined above, and (b) one or more further substances selected from groups (i) and/or (ii):
    (i) one or more further agrochemically active substances, preferably selected from the group consisting of insecticides, acaricides, nematicides, further herbicides (i.e. those not corresponding to the general formula (I) defined above), fungicides, safeners, fertilizers and/or further growth regulators,
    (ii) one or more formulation auxiliaries customary in crop protection.

Here, the further agrochemically active substances of component (i) of a composition according to the invention are preferably selected from the group of substances mentioned in "The Pesticide Manual", 16th edition, The British Crop Protection Council and the Royal Soc. of Chemistry, 2012.

A herbicidal or plant growth-regulating composition according to the invention comprises preferably one, two, three or more formulation auxiliaries (ii) customary in crop protection selected from the group consisting of surfactants, emulsifiers, dispersants, film-formers, thickeners, inorganic salts, dusting agents, carriers solid at 25° C. and 1013 mbar, preferably adsorbent granulated inert materials, wetting agents, antioxidants, stabilizers, buffer substances, antifoam agents, water, organic solvents, preferably organic solvents miscible with water in any ratio at 25° C. and 1013 mbar.

The compounds of general formula (I) according to the invention can be used in the form of wettable powders, emulsifiable concentrates, sprayable solutions, dusting products or granules in the customary formulations. The invention therefore also provides herbicidal and plant growth-regulating compositions which comprise compounds of the general formula (I) and/or salts thereof.

The compounds of the general formula (I) and/or salts thereof can be formulated in various ways according to which biological and/or physicochemical parameters are required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), dispersions based on oil or water, oil-miscible solutions, capsule suspensions (CS), dusting products (DP), dressings, granules for scattering and soil application, granules (GR) in the form of microgranules, spray granules, absorption and adsorption granules, water-dispersible granules (WG), water-soluble granules (SG), ULV formulations, microcapsules and waxes.

These individual formulation types and the formulation assistants, such as inert materials, surfactants, solvents and further additives, are known to the person skilled in the art and are described, for example, in: Watkins, "Handbook of Insecticide Dust Diluents and Carriers", 2nd Ed., Darland Books, Caldwell N.J.; H.v. Olphen, "Introduction to Clay Colloid Chemistry", 2nd ed., J. Wiley & Sons, N.Y.; C. Marsden, "Solvents Guide", 2nd ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Interface-active Ethylene Oxide Adducts], Wiss. Verlagsgesellschaft, Stuttgart 1976; Winnacker-Küchler, "Chemische Technologie" [Chemical Technology], volume 7, C. Hanser Verlag Munich, 4th Ed. 1986.

Wettable powders are preparations which can be dispersed uniformly in water and, in addition to the active compound, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurate. To produce the wettable powders, the herbicidally active compounds are finely ground, for example in customary apparatuses such as hammer mills, blower mills and air-jet mills, and simultaneously or subsequently mixed with the formulation auxiliaries.

Emulsifiable concentrates are produced by dissolving the active compound in an organic solvent, for example butanol, cyclohexanone, dimethylformamide, xylene, or else relatively high-boiling aromatics or hydrocarbons or mixtures of the organic solvents, with addition of one or more ionic and/or nonionic surfactants (emulsifiers). Examples of emulsifiers which may be used are: calcium alkylarylsulfonates such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active compound with finely distributed solids, for example talc, natural clays, such as kaolin, bentonite and pyrophyllite, or diatomaceous earth.

Suspension concentrates may be water- or oil-based. They may be prepared, for example, by wet-grinding by means of commercial bead mills and optional addition of surfactants as have, for example, already been listed above for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active compound onto adsorptive granular inert material or by applying active compound concentrates to the surface of carriers, such as sand, kaolinites or granular inert material, by means of adhesives, for example polyvinyl alcohol, sodium polyacrylate or else mineral oils. Suitable active compounds can also be granulated in the manner customary for the production of fertilizer granules—if desired as a mixture with fertilizers.

Water-dispersible granules are produced generally by the customary processes such as spray-drying, fluidized-bed granulation, pan granulation, mixing with high-speed mixers and extrusion without solid inert material.

For the production of pan, fluidized-bed, extruder and spray granules, see e.g. processes in "Spray Drying Handbook" 3rd Ed. 1979, G. Goodwin Ltd., London, J. E. Browning, "Agglomeration", Chemical and Engineering 1967, pages 147 ff; "Perry's Chemical Engineer's Handbook", 5th Ed., McGraw Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical preparations, preferably herbicidal or plant growth-regulating compositions, of the present invention preferably comprise a total amount of from 0.1 to 99% by weight, preferably 0.5 to 95% by weight, particularly preferably 1 to 90% by weight, especially preferably 2 to 80% by weight, of active compounds of the general formula (I) and their salts.

In wettable powders, the active compound concentration is, for example, about 10 to 90% by weight, the remainder to 100% by weight consisting of customary formulation constituents. In emulsifiable concentrates, the active compound concentration may be about 1% to 90% and preferably 5% to 80% by weight. Formulations in the form of dusts comprise 1% to 30% by weight of active compound, preferably usually 5% to 20% by weight of active compound; sprayable solutions contain about 0.05% to 80% by weight, preferably 2% to 50% by weight of active compound. In the case of water-dispersible granules, the active compound content depends partially on whether the active compound is in liquid or solid form and on which granulation auxiliaries, fillers, etc., are used. In the water-dispersible granules, the content of active compound is, for example, between 1% and 95% by weight, preferably between 10% and 80% by weight.

In addition, the active compound formulations mentioned optionally comprise the respective customary stickers, wetters, dispersants, emulsifiers, penetrants, preservatives, antifreeze agents and solvents, fillers, carriers and dyes, defoamers, evaporation inhibitors and agents which influence the pH and the viscosity. Examples of formulation auxiliaries are described inter alia in "Chemistry and Technology of Agrochemical Formulations", ed. D. A. Knowles, Kluwer Academic Publishers (1998).

The compounds of the general formula (I) or salts thereof can be used as such or in the form of their preparations (formulations) in a combination with other pesticidally active substances, for example insecticides, acaricides, nematicides, herbicides, fungicides, safeners, fertilizers and/or growth regulators, for example in the form of a finished formulation or of a tank mix. The combination formulations can be prepared on the basis of the abovementioned formulations, while taking account of the physical properties and stabilities of the active compounds to be combined.

Active compounds which can be employed in combination with the compounds of general formula (I) according to the invention in mixture formulations or in a tank mix are, for example, known active compounds based on inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoendesaturase, photosystem I, photosystem II, protoporphyrinogen oxidase, as described, for example, in Weed Research 26 (1986) 441-445 or "The Pesticide Manual", 16th edition, The British Crop Protection Council and the Royal Soc. of Chemistry, 2012 and literature cited therein.

Of particular interest is the selective control of harmful plants in crops of useful plants and ornamentals. Although the compounds of general formula (I) according to the invention have already demonstrated very good to adequate selectivity in a large number of crops, in principle, in some crops and in particular also in the case of mixtures with other, less selective herbicides, phytotoxicities on the crop plants may occur. In this connection, combinations of compounds of general formula (I) according to the invention are of particular interest which comprise the compounds of general formula (I) or their combinations with other herbicides or pesticides and safeners. The safeners, which are used in an antidotically effective amount, reduce the phytotoxic side effects of the herbicides/pesticides employed, for example in economically important crops, such as cereals (wheat, barley, rye, corn, rice, millet), sugarbeet, sugarcane, oilseed rape, cotton and soybeans, preferably cereals.

The weight ratios of herbicide (mixture) to safener depend generally on the herbicide application rate and the efficacy of the safener in question and may vary within wide limits, for example in the range from 200:1 to 1:200, preferably 100:1 to 1:100, in particular 20:1 to 1:20. Analogously to the compounds (I) or mixtures thereof, the safeners can be formulated with further herbicides/pesticides and be provided and employed as a finished formulation or tank mix with the herbicides.

For application, the herbicide or herbicide/safener formulations present in commercial form are, if appropriate, diluted in a customary manner, for example in the case of wettable powders, emulsifiable concentrates, dispersions and water-dispersible granules with water. Dust-type preparations, granules for soil application or granules for scattering and sprayable solutions are not normally diluted further with other inert substances prior to application.

The application rate of the compounds of the general formula (I) and/or their salts is affected to a certain extent by external conditions such as temperature, humidity, etc. Here, the application rate may vary within wide limits. For the application as a herbicide for controlling harmful plants, the total amount of compounds of the general formula (I) and/or their salts is preferably in the range from 0.001 to 10.0 kg/ha, with preference in the range from 0.005 to 5 kg/ha, more preferably in the range from 0.01 to 1.5 kg/ha, in particular preferably in the range from 0.05 to 1 kg/ha. This applies both to the pre-emergence and the post-emergence application.

When the compounds of the general formula (I) and/or their salts are used as plant growth regulator, for example as culm stabilizer for crop plants like those mentioned above, preferably cereal plants, such as wheat, barley, rye, triticale, millet, rice or corn, the total application rate is preferably in the range of from 0.001 to 2 kg/ha, preferably in the range of from 0.005 to 1 kg/ha, in particular in the range of from 10 to 500 g/ha, very particularly in the range from 20 to 250 g/ha. This applies both to the pre-emergence and the post-emergence application.

The application as culm stabilizer may take place at various stages of the growth of the plants. Preferred is, for example, the application after the tilling phase, at the beginning of the longitudinal growth.

As an alternative, application as plant growth regulator is also possible by treating the seed, which includes various techniques for dressing and coating seed. Here, the application rate depends on the particular techniques and can be determined in preliminary tests.

Active compounds which can be employed in combination with the compounds of the general formula (I) according to the invention in compositions according to the invention (for example in mixed formulations or in the tank mix) are, for example, known active compounds which are based on the inhibition of, for example, acetolactate synthase, acetyl-CoA carboxylase, cellulose synthase, enolpyruvylshikimate-3-phosphate synthase, glutamine synthetase, p-hydroxyphenylpyruvate dioxygenase, phytoene desaturase, photosystem I, photosystem II, protoporphyrinogen oxidase, as are described in, for example, Weed Research 26 (1986) 441-445 or "The Pesticide Manual", 16th edition, The British Crop Protection Council and the Royal Soc. of Chemistry, 2012 and the literature cited therein. Known herbicides or plant growth regulators which can be combined with the compounds according to the invention are, for example, the following active compounds, where the compounds are designated either with the "common name" in accordance with the International Organization for Standardization (ISO) or with the chemical name or with the code number. They always encompass all of the application forms such as, for example, acids, salts, esters and also all isomeric forms such as stereoisomers and optical isomers, even if not explicitly mentioned.

Examples of Such Herbicidal Mixing Partners are:

acetochlor, acifluorfen, acifluorfen-methyl, acifluorfen-sodium, aclonifen, alachlor, allidochlor, alloxydim, alloxydim-sodium, ametryn, amicarbazone, amidochlor, amidosulfuron, 4-amino-3-chloro-6-(4-chloro-2-fluoro-3-methylphenyl)-5-fluoropyridine-2-carboxylic acid, aminocyclopyrachlor, aminocyclopyrachlor-potassium, aminocyclopyrachlor-methyl, aminopyralid, aminopyralid-dimethylammonium, aminopyralid-tripromine, amitrole, ammoniumsulfamate, anilofos, asulam, asulam-potassium, asulam sodium, atrazine, azafenidin, azimsulfuron, beflubutamid, (S)-(−)-beflubutamid, beflubutamid-M, benazolin, benazolin-ethyl, benazolin-dimethylammonium, benazolin-potassium, benfluralin, benfuresate, bensulfuron, bensulfuron-methyl, bensulide, bentazone, bentazone-sodium, benzobicyclon, benzofenap, bicyclopyrone, bifenox, bilanafos, bilanafos-sodium, bipyrazone, bispyribac, bispyribac-sodium, bixlozone, bromacil, bromacil-lithium, bromacil-sodium, bromobutide, bromofenoxim, bromoxynil, bromoxynil-butyrate, -potassium, -heptanoate und -octanoate, busoxinone, butachlor, butafenacil, butamifos, butenachlor, butralin, butroxydim, butylate, cafenstrole, cambendichlor, carbetamide, carfentrazone, carfentrazone-ethyl, chloramben, chloramben-ammonium, chloramben-diolamine, chlroamben-methyl, chloramben-methylammonium, chloramben-sodium, chlorbromuron, chlorfenac, chlorfenac-ammonium, chlorfenac-sodium, chlorfenprop, chlorfenprop-methyl, chlorflurenol, chlorflurenol-methyl, chloridazon, chlorimuron, chlorimuron-ethyl, chlorophthalim, chlorotoluron, chlorsulfuron, chlorthal, chlorthal-dimethyl, chlorthal-monomethyl, cinidon, cinidon-ethyl, cinmethylin, exo-(+)-cinmethylin, i.e. (1R,2S,4S)-4-isopropyl-1-methyl-2-[(2-methylbenzyl)oxy]-7-oxabicyclo[2.2.1] heptane, exo-(−)-cinmethylin, i.e. (1R,2S,4S)-4-isopropyl-1-methyl-2-[(2-methylbenzyl)oxy]-7-oxabicyclo[2.2.1] heptane, cinosulfuron, clacyfos, clethodim, clodinafop, clodinafop-ethyl, clodinafop-propargyl, clomazone, clomeprop, clopyralid, clopyralid-methyl, clopyralid-olamine, clopyralid-potassium, clopyralid-tripomine, cloransulam, cloransulam-methyl, cumyluron, cyanamide, cyanazine, cycloate, cyclopyranil, cyclopyrimorate, cyclosulfamuron, cycloxydim, cyhalofop, cyhalofop-butyl, cyprazine, 2,4-D (including the ammonium, butotyl, -butyl, choline, diethylammonium, -dimethylammonium, -diolamine, -doboxyl, -dodecylammonium, etexyl, ethyl, 2-ethylhexyl, heptylammonium, isobutyl, isooctyl, isopropyl, isopropylammonium, lithium, meptyl, methyl, potassium, tetradecylammonium, triethylammonium, triisopropanolammonium, tripromine and trolamine salt thereof), 2,4-DB, 2,4-DB-butyl, -dimethylammonium, isooctyl, -potassium und -sodium, daimuron (dymron), dalapon, dalapon-calcium, dalapon-magnesium, dalapon-sodium, dazomet, dazomet-sodium, n-decanol, 7-deoxy-D-sedoheptulose, desmedipham, detosyl-pyrazolate (DTP), dicamba and its salts, e.g. dicamba-biproamine, dicamba-N,N-Bis(3-aminopropyl)methylamine, dicamba-butotyl, dicamba-choline, dicamba-diglycolamine, dicamba-dimethylammonium, dicamba-diethanolamine ammonium, dicamba-diethylammonium, dicamba-isopropylammonium, dicamba-methyl, dicamba-monoethanolamine, dicamba-olamine, dicamba-potassium, dicamba-sodium, dicamba-triethanolamine, dichlobenil, 2-(2,4-dichlorobenzyl)-4,4-dimethyl-1,2-oxazolidin-3-one, 2-(2,5-dichlorobenzyl)-4,4-dimethyl-1,2-oxazolidin-3-one, dichlorprop, dichlorprop-butotyl, dichlorprop-dimethylammonium, dichhlorprop-etexyl, dichlorprop-ethylammonium, dichlorprop-isoctyl, dichlorprop-methyl, dichlorprop-potassium, dichlorprop-sodium, dichlorprop-P, dichlorprop-P-dimethylammonium, dichlorprop-P-etexyl, dichlorprop-P-potassium, dichlorprop-sodium, diclofop, diclofop-methyl, diclofop-P, diclofop-P-methyl, diclosulam, difenzoquat, difenzoquat-metilsulfate, diflufenican, diflufenzopyr, diflufenzopyr-sodium, dimefuron, dimepiperate, dimesulfazet, dimethachlor, dimethametryn, dimethenamid, dimethenamid-P, dimetrasulfuron, dinitramine, dinoterb, dinoterb-acetate, diphenamid, diquat, diquat-dibromid, diquat-dichloride, dithiopyr, diuron, DNOC, DNOC-ammonium, DNOC-potassium, DNOC-sodium, endothal, endothal-diammonium, endothal-dipotassium, endothal-disodium, Epyrifenacil (S-3100), EPTC, esprocarb, ethalfluralin, ethametsulfuron, ethametsulfuron-methyl, ethiozin, ethofumesate, ethoxyfen, ethoxyfen-ethyl, ethoxysulfuron, etobenzanid, F-5231, i.e. N-[2-Chlor-4-fluor-5-[4-(3-fluorpropyl)-4,5-dihydro-5-oxo-1H-tetrazol-1-yl]-phenyl]-ethansulfonamid, F-7967, i.e. 3-[7-Chlor-5-fluor-2-(trifluormethyl)-1H-benzimidazol-4-yl]-1-methyl-6-(trifluormethyl)pyrimidin-2,4(1H,3H)-dione, fenoxaprop, fenoxaprop-P, fenoxaprop-ethyl, fenoxaprop-P-ethyl, fenoxasulfone, fenpyrazone, fenquinotrione, fentrazamide, flamprop, flamprop-isoproyl, flamprop-methyl, flamprop-M-isopropyl, flamprop-M-methyl, flazasulfuron, florasulam, florpyrauxifen, florpyrauxifen-benzyl, fluazifop, fluazifop-butyl, fluazifop-methyl, fluazifop-P, fluazifop-P-butyl, flucarbazone, flucarbazone-sodium, flucetosulfuron, fluchloralin, flufenacet, flufenpyr, flufenpyr-ethyl, flumetsulam, flumiclorac, flumiclorac-pentyl, flumioxazin, fluometuron, flurenol, flurenol-butyl, -dimethylammonium und -methyl, fluoroglycofen, fluoroglycofen-ethyl, flupropanate, flupropanate-sdium, flupyrsulfuron, flupyrsulfuron-methyl, flupyrsulfuron-methyl-sodium, fluridone, flurochloridone, fluroxypyr, fluroxypyr-butometyl, fluroxypyr-meptyl, flurtamone, fluthiacet, fluthiacet-methyl, fomesafen, fomesafen-sodium, foramsulfuron, foramsulfuron sodium salt, fosamine, fosamine-ammonium, glufosinate, glufosinate-ammonium, glufosinate-sodium, L-glufosinate-ammonium, L-glufosiante-sodium, glufosinate-P-sodium, glufosinate-P-ammonium, glyphosate, glyphosate-ammonium, -isopropylammonium, -diammonium, -dimethylammonium, -potassium, -sodium, sesquisodium and -trimesium, H-9201, i.e. O-(2,4-Dimethyl-6-nitrophenyl)-O-ethyl-isopropylphosphoramidothioat, halauxifen, halauxifen-methyl, halosafen, halosulfuron, halosulfuron-methyl, haloxyfop, haloxyfop-P, haloxyfop-ethoxyethyl, haloxyfop-P-ethoxyethyl, haloxyfop-methyl, haloxyfop-P-methyl, haloxifop-sodium, hexazinone, HNPC-A8169, i.e. prop-2-yn-1-yl (2S)-2-{3-[(5-tert-butylpyridin-2-yl)oxy]phenoxy}propanoate, HW-02, i.e. 1-(Dimethoxyphosphoryl)-ethyl-(2,4-dichlorphenoxy)acetat, hydantocidin, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin.methyl, imazethapyr, imazethapyr-immonium, imazosulfuron, indanofan, indaziflam, iodosulfuron, iodosulfuron-methyl, iodosulfuron-methyl-sodium, ioxynil, ioxynil-lithium, -octanoate, -potassium und sodium, ipfencarbazone, isoproturon, isouron, isoxaben, isoxaflutole, karbutilate, KUH-043, i.e. 3-({[5-(Difluormethyl)-1-methyl-3-(trifluormethyl)-1H-pyrazol-4-yl]methyl}sulfonyl)-5,5-dimethyl-4,5-dihydro-1,2-oxazol, ketospiradox, ketospiradox-potassium, lactofen, lancotrione, lenacil, linuron, MCPA, MCPA-butotyl, -butyl, -dimethylammonium, -diolamine, -2-ethylhexyl, -ethyl, -isobutyl, isoctyl, -isopropyl, -isopropylammonium, -methyl, olamine, -potassium, -sodium and -trolamine, MCPB, MCPB-methyl, -ethyl und -sodium, mecoprop, mecoprop-butotyl, mecoprop-demethylammonium, mecoprop-diolamine, mecoprop-etexyl, mecoprop-ethadyl, mecoprop-isoctyl, mecoprop-methyl, mecoprop-potassium, mecoprop-sodium, and mecoprop-trolamine, mecoprop-P, mecoprop-P-butotyl, -dimethylammonium, -2-ethylhexyl and -potassium, mefenacet, mefluidide, mefluidide-diolamine, mefluidide-potassium, mesosulfuron, mesosulfuron-methyl, mesosulfuron sodium salt, mesotrione, methabenzthiazuron, metam, metamifop, metamitron, metazachlor, metazo-sulfuron, methabenzthiazuron, methiopyrsulfuron, methiozolin, methyl isothiocyanate, metobromuron, metolachlor, S-metolachlor, metosulam, metoxuron, metribuzin, metsulfuron, metsulfuron-methyl, molinate, monolinuron, monosulfuron, monosulfuron-methyl, MT-5950, i.e. N-[3-chlor-4-(1-methylethyl)-phenyl]-2-methylpentanamid, NGGC-011, napropamide, NC-310, i.e. 4-(2,4-Dichlorbenzoyl)-1-methyl-5-benzyloxypyrazol, NC-656, i.e. 3-[(isopropylsulfonyl)methyl]-N-(5-methyl-1,3,4-oxadiazol-2-yl)-5-(trifluoromethyl)[1,2,4]triazolo[4,3-a]pyridine-8-carboxamide, neburon, nicosulfuron, nonanoic acid (pelargonic acid), norflurazon, oleic acid (fatty acids), orbencarb, orthosulfamuron, oryzalin, oxadiargyl, oxadiazon, oxasulfuron, oxaziclomefone, oxyfluorfen, paraquat, paraquat-dichloride, paraquat-dimethylsulfate, pebulate, pendimethalin, penoxsulam, pentachlorphenol, pentoxazone, pethoxamid, petroleum oils, phenmedipham, phenmedipham-ethyl, picloram, picloram-dimethylammonium, picloram-etexyl, picloram-isoctyl, picloram-methyl, picloram-olamine, picloram-potassium, picloram-triethylammonium, picloram-tripromine, picloram-trolamine, picolinafen, pinoxaden, piperophos, pretilachlor, primisulfuron, primisulfuron-methyl, prodiamine, profoxydim, prometon, prometryn, propachlor, propanil, propaquizafop, propazine, propham, propisochlor, propoxycarbazone, propoxycarbazone-sodium, propyrisulfuron, propyzamide, prosulfocarb, prosulfuron, pyraclonil, pyraflufen, pyraflufen-ethyl, pyrasulfotole, pyrazolynate (pyrazolate), pyrazo-sulfuron, pyrazosulfuron-ethyl, pyrazoxyfen, pyribambenz, pyribambenz-isopropyl, pyribambenz-propyl, pyribenzoxim, pyributicarb, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinclorac-dimethylammonium, quinclorac-methyl, quinmerac, quinoclamine, quizalofop, quizalofop-ethyl, quizalofop-P, quizalofop-P-ethyl, quizalofop-P-tefuryl, QYM201, i.e. 1-{2-chloro-3-[(3-cyclopropyl-5-hydroxy-1-methyl-1H-pyrazol-4-yl)carbonyl]-6-(trifluoromethyl)phenyl}piperidin-2-one, rimsulfuron, saflufenacil, sethoxydim, siduron, simazine, simetryn, SL-261, sulcotrione, sulfentrazone, sulfometuron, sulfometuron-methyl, sulfosulfuron, SYP-249, i.e. 1-Ethoxy-3-methyl-1-oxobut-3-en-2-yl-5-[2-chlor-4-(trifluormethyl)phenoxy]-2-nitrobenzoat, SYP-300, i.e. 1-[7-Fluor-3-oxo-4-(prop-2-in-1-yl)-3,4-dihydro-2H-1,4-benzoxazin-6-yl]-3-propyl-2-thioxoimidazolidin-4,5-dion, 2,3,6-TBA, TCA (trichloro acetic acid) and its salts, e.g. TCA-ammonium, TCA-calcium, TCA-ethyl, TCA-magnesium, TCA-sodium, tebuthiuron, tefuryltrione, tembotrione, tepraloxydim, terbacil, terbucarb, terbumeton, terbuthylazine, terbutryn, tetflupyrolimet, thaxtomin, thenylchlor, thiazopyr, thiencarbazone, thiencarbazone-methyl, thifensulfuron, thifensulfuron-methyl, thiobencarb, tiafenacil, tolpyralate, topramezone, tralkoxydim, triafamone, tri-allate, triasulfuron, triaziflam, tribenuron, tribenuron-methyl, triclopyr, triclopyr-butotyl, triclopyr-choline, triclopyr-ethyl, triclopyr-triethylammonium, trietazine, trifloxysulfuron, trifloxysulfuron-sodium, trifludimoxazin, trifluralin, triflusulfuron, triflusulfuron-methyl, tritosulfuron, urea sulfate, vernolate, XDE-848, ZJ-0862, i.e. 3,4-Dichlor-N-{2-[(4,6-dimethoxypyrimidin-2-yl)oxy]benzyl}anilin, 3-(2-chloro-4-fluoro-5-(3-methyl-2,6-dioxo-4-trifluoromethyl-3,6-dihydropyrimidin-1 (2H)-yl)phenyl)-5-methyl-4,5-dihydroisoxazole-5-carboxylic acid ethyl ester, ethyl-[(3-{2-chlor-4-fluor-5-[3-methyl-2,6-dioxo-4-(trifluormethyl)-3,6-dihydropyrimidin-1(2H)-yl]phenoxy}pyridin-2-yl)oxy] acetate, 3-chloro-2-[3-(difluoromethyl)isoxazolyl-5-yl] phenyl-5-chloropyrimidin-2-yl ether, 2-(3,4-dimethoxyphenyl)-4-[(2-hydroxy-6-oxocyclohex-1-en-1-yl) carbonyl]-6-methylpyridazine-3(2H)-one, 2-({2-[(2-methoxyethoxy)methyl]-6-methylpyridin-3-yl}carbonyl) cyclohexane-1,3-dione, (5-hydroxy-1-methyl-1H-pyrazol-4-yl)(3,3,4-trimethyl-1,1-dioxido-2,3-dihydro-1-benzothiophen-5-yl)methanone, 1-methyl-4-[(3,3,4-trimethyl-1,1-dioxido-2,3-dihydro-1-benzothiophen-5-yl) carbonyl]-1H-pyrazol-5-yl propane-1-sulfonate, 4-{2-chloro-3-[(3,5-dimethyl-1H-pyrazol-1-yl)methyl]-4-(methylsulfonyl)benzoyl}-1-methyl-1H-pyrazol-5-yl-1,3-dimethyl-1H-pyrazole-4-carboxylate; cyanomethyl 4-amino-3-chloro-5-fluoro-6-(7-fluoro-1H-indol-6-yl)pyridine-2-carboxylate, prop-2-yn-1-yl 4-amino-3-chloro-5-fluoro-6-(7-fluoro-1H-indol-6-yl)pyridine-2-carboxylate, methyl 4-amino-3-chloro-5-fluoro-6-(7-fluoro-1H-indol-6-yl)pyridine-2-carboxylate, 4-amino-3-chloro-5-fluoro-6-(7-fluoro-1H-indol-6-yl)pyridine-2-carboxylic acid, benzyl 4-amino-3-chloro-5-fluoro-6-(7-fluoro-1H-indol-6-yl)pyridine-2-carboxylate, ethyl 4-amino-3-chloro-5-fluoro-6-(7-fluoro-1H-indol-6-yl)pyridine-2-carboxylate, methyl 4-amino-3-chloro-5-fluoro-6-(7-fluoro-1-isobutyryl-1H-indol-6-yl)pyridine-2-carboxylate, methyl 6-(1-acetyl-7-fluoro-1H-indol-6-yl)-4-amino-3-chloro-5-fluoropyridine-2-carboxylate, methyl 4-amino-3-chloro-6-[1-(2,2-dimethylpropanoyl)-7-fluoro-1H-indol-6-yl]-5-fluoropyridine-2-carboxylate, methyl 4-amino-3-chloro-5-fluoro-6-[7-fluoro-1-(methoxyacetyl)-1H-indol-6-yl] pyridine-2-carboxylate, potassium 4-amino-3-chloro-5-fluoro-6-(7-fluoro-1H-indol-6-yl)pyridine-2-carboxylate, sodium 4-amino-3-chloro-5-fluoro-6-(7-fluoro-1H-indol-6-yl)pyridine-2-carboxylate, butyl 4-amino-3-chloro-5-fluoro-6-(7-fluoro-1H-indol-6-yl)pyridine-2-carboxylate, 4-hydroxy-1-methyl-3-[4-(trifluoromethyl)pyridin-2-yl] imidazolidin-2-one, 3-(5-tert-butyl-1,2-oxazol-3-yl)-4-hydroxy-1-methylimidazolidin-2-one, 3-[5-chloro-4-(trifluormethyl)pyridin-2-yl]-4-hydroxy-1-methylimidazolidin-2-one, 4-hydroxy-1-methoxy-5-methyl-3-[4-(trifluormethyl)pyridin-2-yl]imidazolidin-2-one, 6-[(2-hydroxy-6-oxocyclohex-1-en-1-yl)carbonyl]-1,5-dimethyl-3-(2-methylphenyl)quinazolin-2,4(1H,3H)-dione, 3-(2,6-dimethylphenyl)-6-[(2-hydroxy-6-oxocyclohex-1-en-1-yl) carbonyl]-1-methylquinazolin-2,4(1H,3H)-dione, 2-[2-chloro-4-(methylsulfonyl)-3-(morpholin-4-ylmethyl) benzoyl]-3-hydroxycyclohex-2-en-1-one, 1-(2-carboxyethyl)-4-(pyrimidin-2-yl)pyridazin-1-ium salt (with anions such as chloride, acetate or trifluoroacetate), 1-(2-carboxyethyl)-4-(pyridazin-3-yl)pyridazin-1-ium salt (with anions such as chloride, acetate or trifluoroacetate), 4-(pyrimidin-2-yl)-1-(2-sulfoethyl)pyridazin-1-ium salt (with anions such as chloride, acetate or trifluoroacetate), 4-(pyridazin-3-yl)-1-(2-sulfoethyl)pyridazin-1-ium salt (with anions such as chloride, acetate or trifluoroacetate).

Examples of Plant Growth Regulators as Possible Mixing Partners are:

Abscisic acid, acibenzolar, acibenzolar-S-methyl, 1-aminocyclopro-1-yl carboxylic acid and derivatives thereof, 5-Aminolavulinsaure, ancymidol, 6-benzylaminopurine, bikinin, brassinolide, brassinolide-ethyl, catechin, chitooligosaccharides (CO; COs differ from LCOs in that they lack the pendant fatty acid chain that is characteristic of LCOs. COs, sometimes referred to as N-acetylchitooligosaccharides, are also composed of GlcNAc residues but have side chain decorations that make them different from chitin molecules [$(C_8H_{13}NO_5)_n$, CAS No. 1398-61-4] and chitosan molecules [$(C_5H_{11}NO_4)_n$, CAS No. 9012-76-4]), chitinous compounds, chlormequat chloride, cloprop, cyclanilide, 3-(Cycloprop-1-enyl)propionic acid, daminozide, dazomet, dazomet-sodium, n-decanol, dikegulac, dikegulac-sodium, endothal, endothal-dipotassium, -disodium, and mono(N,N-dimethylalkylammonium), ethephon, flumetralin, flurenol, flurenol-butyl, flurenol-methyl, flurprimidol, forchlorfenuron, gibberellic acid, inabenfide, indol-3-acetic acid (IAA), 4-indol-3-ylbutyric acid, isoprothiolane, probenazole, jasmonic acid, Jasmonic acid or derivatives thereof (e.g. Jasmonic acid methyl ester), lipo-chitooligosaccharides (LCO, sometimes referred to as symbiotic nodulation (Nod) signals (or Nod factors) or as Myc factors, consist of an oligosaccharide backbone of β-1,4-linked N-acetyl-D-glucosamine (“GlcNAc”) residues with an N-linked fatty acyl chain condensed at the non-reducing end. As understood in the art, LCOs differ in the number of GlcNAc residues in the backbone, in the length and degree of saturation of the fatty acyl chain and in the substitutions of reducing and non-reducing sugar residues), linoleic acid or derivatives thereof, linolenic acid or derivatives thereof, maleic hydrazide, mepiquat chloride, mepiquat pentaborate, 1-methylcyclopropene, 3'-methyl abscisic acid, 2-(1-naphthyl)acetamide, 1-naphthylacetic acid, 2-naphthyloxyacetic acid, nitrophenolate-mixture, 4-Oxo-4[(2-phenylethyl)amino]butyric acid, paclobutrazol, 4-phenylbutyric acid, N-phenylphthalamic acid, prohexadione, prohexadione-calcium, prohydrojasmon, salicylic acid, salicylic acid methyl ester, strigolacton, tecnazene, thidiazuron, triacontanol, trinexapac, trinexapac-ethyl, tsitodef, uniconazole, uniconazole-P, 2-fluoro-N-(3-methoxyphenyl)-9H-purin-6-amine.

Suitable combination partners for the compounds of the general formula (I) according to the invention also include, for example, the following safeners:

S1) Compounds from the group of heterocyclic carboxylic acid derivatives (formula S1)

(S1)

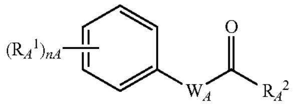

wherein symbols and indices are defined as follows:

$n_A$ is an integer value in the range of 0 to 5, preferably 0 to 3;

$R_A^1$ is halogen, $(C_1-C_4)$alkyl, $(C_1-C_4)$alkoxy, nitro or $(C_1-C_4)$haloalkyl;

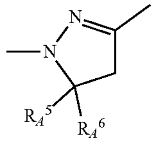

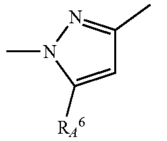

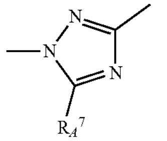

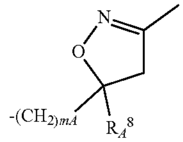

$W_A$ is an unsubstituted or substituted divalent heterocyclic moiety selected from the group of partially unsaturated or aromatic five-membered heterocycles carrying 1 to 3 hetero ring atoms selected from the group of nitrogen (N) und oxygen (O), and carrying at least one N-atom and not more than one O-atom in the ring, preferably a five-membered heterocyclic moiety selected from the group $(W_A^1)$ to $(W_A^4)$, $m_A$ is 0 or 1;

$R_A^2$ is $OR_A^3$, $SR_A^3$ or $NR_A^3R_A^4$ or a saturated or unsaturated 3- to 7-membered heterocycle containing at least one N-atom and up to 3 heteroatoms, preferably combined with other heteroatoms from the group of O (oxygen) and S (sulfur), and which is linked to the carbonyl group in (S1) via a nitrogen atom, and which is unsubstituted or substituted by moieties selected from the group of $(C_1-C_4)$alkyl, $(C_1-C_4)$alkoxy or possibly substituted phenyl, preferably $OR_A^3$, $NHR_A^4$ order $N(CH_3)_2$, particularly $OR_A^3$ $R_A^3$ is hydrogen or an unsubstituted or substituted aliphatic hydrocarbon moiety, preferably containing 1 to 18 C-atoms;

$R_A^4$ is hydrogen, $(C_1-C_6)$alkyl, $(C_1-C_6)$alkoxy or substituted or unsubstituted phenyl;

$R_A^5$ is hydrogen, $(C_1-C_8)$alkyl, $(C_1-C_8)$haloalkyl, $(C_1-C_4)$alkoxy$(C_1-C_5)$alkyl, cyano or $COOR_A^9$, wherein $R_A^9$ is hydrogen, $(C_1-C_8)$alkyl, $(C_1-C_8)$haloalkyl, $(C_1-C_4)$alkoxy-$(C_1-C_4)$alkyl, $(C_1-C_6)$hydroxyalkyl, $(C_3-C_{12})$cycloalkyl order tris-$(C_1-C_4)$-alkylsilyl;

$R_A^6$, $R_A^7$, $R_A^8$ are independently hydrogen, $(C_1-C_8)$alkyl, $(C_1-C_8)$haloalkyl, $(C_3-C_{12})$cycloalkyl or substituted or unsubstituted phenyl;

$S1^a$) Compounds of the dichlorophenylpyrazoline-3-carboxylic acid type ($S1^a$), preferably compounds such as 1-(2,4-dichlorophenyl)-5-(ethoxycarbonyl)-5-methyl-2-pyrazoline-3-carboxylic acid, ethyl 1-(2,4-dichlorophenyl)-5-(ethoxycarbonyl)-5-methyl-2-pyrazoline-3-carboxylate (S1-1) ("mefenpyr-diethyl"), and related compounds as described in WO-A-91/07874;

$S1^b$) Derivatives of dichlorophenylpyrazolecarboxylic acid ($S1^b$), preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4) and related compounds as described in EP-A-333131 131 and EP-A-269806;

$S1^c$) Derivatives of 1,5-diphenylpyrazole-3-carboxylic acid ($S1^c$), preferably compounds such as ethyl 1-(2,4-dichlorophenyl)-5-phenylpyrazole-3-carboxylate (S1-5), methyl 1-(2-chlorophenyl)-5-phenylpyrazole-3-carboxylate (51-6) and related compounds as described, for example, in EP-A-268554;

$S1^d$) Compounds of the triazolecarboxylic acid type ($S1^d$), preferably compounds such as fenchlorazole (ethyl ester), i.e. ethyl 1-(2,4-dichlorophenyl)-5-trichloromethyl-1H-1,2,4-triazole-3-carboxylate (S1-7), and related compounds, as described in EP-A-174562 and EP-A-346620;

$S1^e$) Compounds of the 5-benzyl- or 5-phenyl-2-isoxazoline-3-carboxylic acid or of the 5,5-diphenyl-2-isoxazoline-3-carboxylic acid type ($S1^e$), preferably compounds such as ethyl 5-(2,4-dichlorobenzyl)-2-isoxazoline-3-carboxylate (S1-8) or ethyl 5-phenyl-2-isoxazoline-3-carboxylate (S1-9) and related compounds as described in WO-A-91/08202, or 5,5-diphenyl-2-isoxazolinecarboxylic acid (S1-10) or ethyl 5,5-diphenyl-2-isoxazoline-3-carboxylate (S1-11) ("isoxadifen-ethyl") or n-propyl 5,5-diphenyl-2-isoxazoline-3-carboxylate (S1-12) or ethyl 5-(4-fluorophenyl)-5-phenyl-2-isoxazoline-3-carboxylate (S1-13), as described in patent application WO-A-95/07897.

S2) Compounds from the group of the 8-quinolinoxy derivatives (S2):

$S2^a$) Compounds of the 8-quinolinoxyacetic acid type (S2a), preferably 1-methylhexyl (5-chloro-8-quinolinoxy)acetate ("cloquintocet-mexyl") (52-1), 1,3-dimethylbut-1-yl (5-chloro-8-quinolinoxy)acetate (S2-2), 4-allyloxybutyl (5-chloro-8-quinolinoxy)acetate (S2-3), 1-allyloxyprop-2-yl (5-chloro-8-quinolinoxy)acetate (S2-4), ethyl (5-chloro-8-quinolinoxy)acetate (S2-5), methyl 5-chloro-8-quinolinoxyacetate (S2-6), allyl (5-chloro-8-quinolinoxy)acetate (S2-7), 2-(2-propylideneiminoxy)-1-ethyl (5-chloro-8-quinolinoxy)acetate (S2-8), 2-oxoprop-1-yl (5-chloro-8-quinolinoxy) acetate (S2-9) and related compounds, as described in EP-A-86750, EP-A-94349 and EP-A-191736 or EP-A-0 492 366, and also (5-chloro-8-quinolinoxy)acetic acid (S2-10), hydrates and salts thereof, for example the lithium, sodium, potassium, calcium, magnesium, aluminum, iron, ammonium, quaternary ammonium, sulfonium or phosphonium salts thereof, as described in WO-A-2002/34048;

S2$^{b}$) Compounds of the (5-chloro-8-quinolinoxy)malonic acid type (S2$^{b}$), preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds, as described in EP-A-0 582 198.

S3) Active compounds of the dichloroacetamide type (S3), which are frequently used as pre-emergence safeners (soil-acting safeners), for example "dichlormid" (N,N-diallyl-2,2-dichloroacetamide) (S3-1), "R-29148" (3-dichloroacetyl-2,2,5-trimethyl-1,3-oxazolidine) from Stauffer (S3-2), "R-28725" (3-dichloroacetyl-2,2-dimethyl-1,3-oxazolidine) from Stauffer (S3-3), "benoxacor" (4-dichloroacetyl-3,4-dihydro-3-methyl-2H-1,4-benzoxazine) (S3-4), "PPG-1292" (N-allyl-N-[(1,3-dioxolan-2-yl)methyl]dichloroacetamide) from PPG Industries (S3-5), "DKA-24" (N-allyl-N-[(allylaminocarbonyl)methyl]dichloroacetamide) from Sagro-Chem (S3-6), "AD-67" or "MON 4660" (3-dichloroacetyl-1-oxa-3-azaspiro[4.5]decane) from Nitrokemia or Monsanto (S3-7), "TI-35" (1-dichloroacetylazepane) from TRI-Chemical RT (S3-8), "Diclonon" (Dicyclonon) or "BAS145138" or "LAB145138" (S3-9)

((RS)-1-dichloroacetyl-3,3,8a-trimethylperhydropyrrolo [1,2-a]pyrimidin-6-one) from BASF, "furilazole" or "MON 13900" ((RS)-3-dichloroacetyl-5-(2-furyl)-2,2-dimethyloxazolidine) (S3-10), and the (R) isomer thereof (S3-11).

S4) Compounds from the class of the acylsulfonamides (S4):

S4$^{a}$) N-Acylsulfonamides of the formula (S4a) and salts thereof, as described in WO-A-97/45016, (S4$^{a}$)

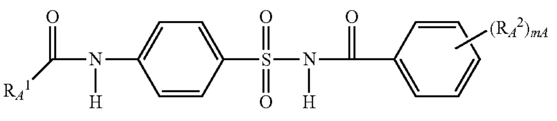

in which $R_A^1$ is $(C_1-C_6)$-alkyl, $(C_3-C_6)$-cycloalkyl, where the 2 latter radicals are substituted by $v_A$ substituents from the group of halogen, $(C_1-C_4)$-alkoxy, $(C_1-C_6)$-haloalkoxy and $(C_1-C_4)$-alkylthio and, in the case of cyclic radicals, also by $(C_1-C_4)$-alkyl and $(C_1-C_4)$-haloalkyl;

$R_A^2$ is halogen, $(C_1-C_4)$-alkyl, $(C_1-C_4)$-alkoxy, $CF_3$;

$m_A$ is 1 or 2;

$v_A$ is 0, 1, 2 or 3;

S4$^{b}$) Compounds of the 4-(benzoylsulfamoyl)benzamide type of the formula (S4$^{b}$) and salts thereof, as described in WO-A-99/16744, (S4$^{b}$)

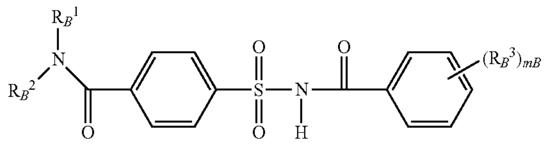

in which $R_B^1$, $R_B^2$ are independently hydrogen, $(C_1-C_6)$-alkyl, $(C_3-C_6)$-cycloalkyl, $(C_3-C_6)$-alkenyl, $(C_3-C_6)$-alkynyl, $R_B^3$ is halogen, $(C_1-C_4)$-alkyl, $(C_1-C_4)$-haloalkyl or $(C_1-C_4)$-alkoxy and $m_B$ is 1 or 2, for example those in which $R_B^1$=cyclopropyl, $R_B^2$=hydrogen and $(R_B^3)$=2-OMe ("cyprosulfamide", S4-1), $R_B^1$=cyclopropyl, $R_B^2$=hydrogen and $(R_B^3)$=5-Cl-2-OMe (S4-2), $R_B^1$=ethyl, $R_B^2$=hydrogen and $(R_B^3)$=2-OMe (S4-3), $R_B^1$=isopropyl, $R_B^2$=hydrogen and $(R_B^3)$=5-Cl-2-OMe (S4-4) and $R_B^1$=isopropyl, $R_B^2$=hydrogen and $(R_B^3)$=2-OMe (S4-5);

S4$^{c}$) Compounds from the class of the benzoylsulfamoylphenylureas of the formula (S4$^{c}$), as described in EP-A-365484, (S4$^{c}$)

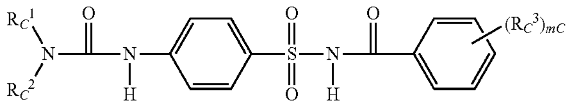

in which $R_C^1$, $R_C^2$ are independently hydrogen, $(C_1-C_8)$-alkyl, $(C_3-C_8)$-cycloalkyl, $(C_3-C_6)$-alkenyl, $(C_3-C_6)$-alkynyl, $R_C^3$ is halogen, $(C_1-C_4)$-alkyl, $(C_1-C_4)$-alkoxy, $CF_3$ and $m_C$ is 1 or 2;

for example

1-[4-(N-2-methoxybenzoylsulfamoyl)phenyl]-3-methylurea,

1-[4-(N-2-methoxybenzoylsulfamoyl)phenyl]-3,3-dimethylurea,

1-[4-(N-4,5-dimethylbenzoylsulfamoyl)phenyl]-3-methylurea;

S4$^{d}$) Compounds of the N-phenylsulfonylterephthalamide type of the formula (S4$^{d}$) and salts thereof, which are known, for example, from CN 101838227, (S4$^{d}$)

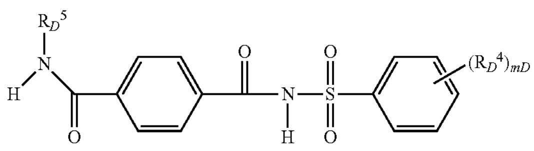

in which $R_D^4$ is halogen, $(C_1-C_4)$-alkyl, $(C_1-C_4)$-alkoxy, $CF_3$;

$m_D$ is 1 or 2;

$R_D^5$ is hydrogen, $(C_1-C_6)$-alkyl, $(C_3-C_6)$-cycloalkyl, $(C_2-C_6)$-alkenyl, $(C_2-C_6)$-alkynyl or $(C_5-C_6)$-cycloalkenyl.

S5) Active compounds from the class of the hydroxyaromatics and the aromatic-aliphatic carboxylic acid derivatives (S5), for example ethyl 3,4,5-triacetoxybenzoate, 3,5-dimethoxy-4-hydroxybenzoic acid, 3,5-dihydroxybenzoic acid, 4-hydroxysalicylic acid, 4-fluorosalicyclic acid, 2-hydroxycinnamic acid, 2,4-dichlorocinnamic acid, as described in WO-A-2004/084631, WO-A-2005/015994, WO-A-2005/016001.

S6) Active compounds from the class of the 1,2-dihydroquinoxalin-2-ones (S6), for example 1-methyl-3-(2-thienyl)-1,2-dihydroquinoxalin-2-one, 1-methyl-3-(2-thienyl)-1,2-dihydroquinoxaline-2-thione, 1-(2-aminoethyl)-3-(2-thienyl)-1,2-dihydroquinoxalin-2-one hydrochloride, 1-(2-methylsulfonylaminoethyl)-3-(2-thienyl)-1,2-dihydroquinoxalin-2-one, as described in WO-A-2005/112630.

S7) Compounds from the class of the diphenylmethoxyacetic acid derivatives (S7), e.g. methyl diphenylmethoxyacetate (CAS Reg. No. 41858-19-9) (S7-1), ethyl diphenylmethoxyacetate or diphenylmethoxyacetic acid, as described in WO-A-98/38856.

S8) Compounds of the formula (S8), as described in WO-A-98/27049, (S8)

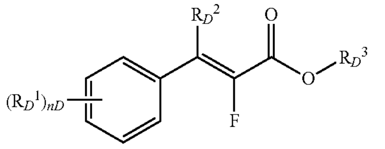

in which the symbols and indices are defined as follows:

$R_D^1$ is halogen, $(C_1-C_4)$-alkyl, $(C_1-C_4)$-haloalkyl, $(C_1-C_4)$-alkoxy, $(C_1-C_4)$-haloalkoxy, $R_D^2$ is hydrogen or $(C_1-C_4)$-alkyl, $R_D^3$ is hydrogen, $(C_1-C_5)$-alkyl, $(C_2-C_4)$-alkenyl, $(C_2-C_4)$-alkynyl or aryl, where each of the aforementioned carbon-containing radicals is unsubstituted or substituted by one or more, preferably up to three identical or different radicals from the group consisting of halogen and alkoxy; or salts thereof, $n_D$ is an integer from 0 to 2.

S9) active compounds from the class of the 3-(5-tetrazolylcarbonyl)-2-quinolones (S9), for example 1,2-dihydro-4-hydroxy-1-ethyl-3-(5-tetrazolylcarbonyl)-2-quinolone (CAS Reg. No. 219479-18-2), 1,2-dihydro-4-hydroxy-1-methyl-3-(5-tetrazolylcarbonyl)-2-quinolone (CAS Reg. No. 95855-00-8), as described in WO-A-199/000020;

S10) Compounds of the formula ($S10^a$) or ($S10^b$)

as described in WO-A-2007/023719 and WO-A-2007/023764

($S10^a$)

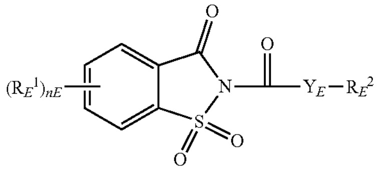

-continued ($S10^b$)

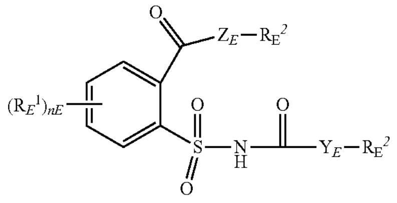

in which $R_E^1$ is halogen, $(C_1-C_4)$-alkyl, methoxy, nitro, cyano, $CF_3$, $OCF_3$ $Y_E$, $Z_E$ are independently O or S, $n_E$ is an integer from 0 to 4, $R_E^2$ is $(C_1-C_{16})$-alkyl, $(C_2-C_6)$-alkenyl, $(C_3-C_6)$-cycloalkyl, aryl; benzyl, halobenzyl, $R_E^3$ is hydrogen or $(C_1-C_6)$-alkyl.

S11) Active compounds of the oxyimino compound type (S11), which are known as seed-dressing agents, for example "oxabetrinil" ((Z)-1,3-dioxolan-2-ylmethoxyimino(phenyl)acetonitrile) (S11-1), which is known as a seed-dressing safener for millet/sorghum against metolachlor damage, "fluxofenim" (1-(4-chlorophenyl)-2,2,2-trifluoro-1-ethanone O-(1,3-dioxolan-2-ylmethyl)oxime) (S11-2), which is known as a seed-dressing safener for millet/sorghum against metolachlor damage, and "cyometrinil" or "CGA-43089" ((Z)-cyanomethoxyimino (phenyl)acetonitrile) (S11-3), which is known as a seed-dressing safener for millet/sorghum against metolachlor damage.

S12) active compounds from the class of the isothiochromanones (S12), for example methyl [(3-oxo-1H-2-benzothiopyran-4(3H)-ylidene)methoxy]acetate (CAS Reg. No. 205121-04-6) (S12-1) and related compounds from WO-A-1998/13361.

S13) One or more compounds from group (S13):

"naphthalic anhydride" (1,8-naphthalenedicarboxylic anhydride) (S13-1), which is known as a seed-dressing safener for corn against thiocarbamate herbicide damage, "fenclorim" (4,6-dichloro-2-phenylpyrimidine) (S13-2), which is known as a safener for pretilachlor in sown rice, "flurazole" (benzyl 2-chloro-4-trifluoromethyl-1,3-thiazole-5-carboxylate) (S13-3), which is known as a seed-dressing safener for millet/sorghum against alachlor and metolachlor damage, "CL 304415" (CAS Reg. No. 31541-57-8) (4-carboxy-3,4-dihydro-2H-1-benzopyran-4-acetic acid) (S13-4) from American Cyanamid, which is known as a safener for corn against damage by imidazolinones, "MG 191" (CAS Reg. No. 96420-72-3) (2-dichloromethyl-2-methyl-1,3-dioxolane) (S13-5) from Nitrokemia, which is known as a safener for corn, "MG 838" (CAS Reg. No. 133993-74-5) (2-propenyl 1-oxa-4-azaspiro[4.5]decane-4-carbodithioate) (S13-6) from Nitrokemia "disulfoton" (0,0-diethyl S-2-ethylthioethyl phosphorodithioate) (S13-7), "dietholate" (0,0-diethyl O-phenyl phosphorothioate) (S13-8), "mephenate" (4-chlorophenyl methylcarbamate) (S13-9).

S14) active compounds which, in addition to herbicidal action against weeds, also have safener action on crop plants such as rice, for example "dimepiperate" or "MY-93" (S-1-methyl 1-phenylethylpiperidine-1-carbothioate), which is known as a safener for rice against damage by the herbicide molinate, "daimuron" or "SK 23" (1-(1-methyl-1-phenylethyl)-3-p-tolylurea), which is known as safener for rice against imazosulfuron herbicide damage, "cumyluron"="JC-940" (3-(2-chlorophenylmethyl)-1-(1-methyl-1-phenylethyl)urea, see JP-A-60087254), which is known as safener for rice against damage by some herbicides, "methoxyphenone" or "NK 049" (3,3'-dimethyl-4-methoxybenzophenone), which is known as a safener for rice against damage by some herbicides, "CSB" (1-bromo-4-(chloromethylsulfonyl)benzene) from Kumiai, (CAS Reg. No. 54091-06-4), which is known as a safener against damage by some herbicides in rice.

S15) Compounds of the formula (S15) or tautomers thereof

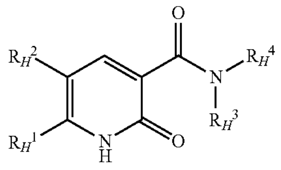

(S15)

as described in WO-A-2008/131861 and WO-A-2008/131860 in which $R_H^1$ is a $(C_1-C_6)$-haloalkyl radical and $R_H^2$ is hydrogen or halogen and $R_H^3$, $R_H^4$ are each independently hydrogen, $(C_1-C_{16})$-alkyl, $(C_2-C_{16})$-alkenyl or $(C_2-C_{16})$-alkynyl, where each of the 3 latter radicals is unsubstituted or substituted by one or more radicals from the group of halogen, hydroxyl, cyano, $(C_1-C_4)$-alkoxy, $(C_1-C_4)$-haloalkoxy, $(C_1-C_4)$-alkylthio, $(C_1-C_4)$-alkylamino, di[$(C_1-C_4)$-alkyl]amino, [$(C_1-C_4)$-alkoxy]carbonyl, [$(C_1-C_4)$-haloalkoxy]carbonyl, $(C_3-C_6)$-cycloalkyl which is unsubstituted or substituted, phenyl which is unsubstituted or substituted, and heterocyclyl which is unsubstituted or substituted, or $(C_3-C_6)$-cycloalkyl, $(C_4-C_6)$-cycloalkenyl, $(C_3-C_6)$-cycloalkyl fused on one side of the ring to a 4 to 6-membered saturated or unsaturated carbocyclic ring, or $(C_4-C_6)$-cycloalkenyl fused on one side of the ring to a 4 to 6-membered saturated or unsaturated carbocyclic ring, where each of the 4 latter radicals is unsubstituted or substituted by one or more radicals from the group of halogen, hydroxyl, cyano, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylamino, di[$(C_1-C_4)$alkyl]amino, [$(C_1-C_4)$alkoxy]carbonyl, [$(C_1-C_4)$haloalkoxy]carbonyl, $(C_3-C_6)$cycloalkyl which is unsubstituted or substituted, phenyl which is unsubstituted or substituted, and heterocyclyl which is unsubstituted or substituted, or $R_H^3$ is $(C_1-C_4)$-alkoxy, $(C_2-C_4)$-alkenyloxy, $(C_2-C_6)$-alkynyloxy or $(C_2-C_4)$-haloalkoxy and $R_H^4$ is hydrogen or $(C_1-C_4)$-alkyl or $R_H^3$ and $R_H^4$ together with the directly bonded nitrogen atom are a four- to eight-membered heterocyclic ring which, as well as the nitrogen atom, may also contain further ring heteroatoms, preferably up to two further ring heteroatoms from the group of N, O and S, and which is unsubstituted or substituted by one or more radicals from the group of halogen, cyano, nitro, $(C_1-C_4)$-alkyl, $(C_1-C_4)$-haloalkyl, $(C_1-C_4)$-alkoxy, $(C_1-C_4)$-haloalkoxy and $(C_1-C_4)$-alkylthio.

S16) Active compounds which are used primarily as herbicides but also have safener action on crop plants, for example (2,4-dichlorophenoxy)acetic acid (2,4-D), (4-chlorophenoxy)acetic acid, (R,S)-2-(4-chloro-o-tolyloxy)propionic acid (mecoprop), 4-(2,4-dichlorophenoxy)butyric acid (2,4-DB), (4-chloro-o-tolyloxy)acetic acid (MCPA), 4-(4-chloro-o-tolyloxy)butyric acid, 4-(4-chlorophenoxy)butyric acid, 3,6-dichloro-2-methoxybenzoic acid (dicamba), 1-(ethoxycarbonyl)ethyl 3,6-dichloro-2-methoxybenzoate (lactidichlor-ethyl).

Preferred safeners in combination with the compounds of the general formula (I) according to the invention and/or salts thereof, in particular with the compounds of the formulae (I-001) to (I-211) and and/or salts thereof, are: cloquintocet-mexyl, cyprosulfamide, fenchlorazole-ethyl, isoxadifen-ethyl, mefenpyr-diethyl, fenclorim, cumyluron, 54-1 and S4-5, and particularly preferred safeners are: cloquintocet-mexyl, cyprosulfamide, isoxadifen-ethyl and mefenpyr-diethyl.

Biological Examples

The following abbreviations are used in the examples and tables below:

| Tested harmful plants: | |
|---|---|
| ABUTH: | Abutilon theophrasti |
| AGSTE: | Agrostis tenuis |
| ALOMY: | Alopecurus myosuroides |
| AVEFA: | Avena fatua, |
| AMARE | Amaranthus retroflexus |
| CYPES: | Cyperus esculentus |
| DIGSA: | Digitaria sanguinalis |
| ECHCG: | Echinochloa crus-galli |
| KCHSC: | Kochia scoparia |
| LOLMU: | Lolium multiflorum |
| LOLRI | Lolium rigidum |
| MATIN: | Matricaria inodora |
| PHBPU: | Pharbitis purpurea |
| POAAN: | Poa annua |
| POLCO: | Polygonum convolvulus |
| SETVI: | Setaria viridis |
| STEME: | Stellaria media |
| VERPE: | Veronica persica |
| VIOTR: | Viola tricolor |

A. Herbicidal Pre-Emergence Action

Seeds of mono- and dicotyledonous weed plants and crop plants were sown, in plastic or organic planting pots, in sandy loam and covered with soil. The compounds according to the invention, formulated in the form of wettable powders (WP) or as emulsifiable concentrates (EC), were applied to the surface of the covering soil as aqueous suspension or emulsion, with the addition of 0.5% of an additive, at an application rate of 600 1 of water/ha (converted).

Following treatment, the pots were placed in a greenhouse and kept under optimum growth conditions for the test plants. The visual grading of the damage to the test plants was carried out after ca. 3 weeks in comparison to untreated controls (herbicidal effect in percent (%): 100% effect=plants have died off, 0% effect=as control plants).

Tables A1 to A16, below, show the effects of selected compounds of the general formula (I) according to table 1 on various harmful plants and an application rate corresponding to 1280 g/ha or lower obtained by the experimental procedure mentioned above.

TABLE A1a

| Pre-emergence activity at 320 g/ha against ALOMY in % | | |
|---|---|---|
| Example number | Dosage [g/ha] | ALOMY |
| I-027 | 320 | 80 |
| I-041 | 320 | 80 |
| I-002 | 320 | 100 |
| I-201 | 320 | 100 |
| I-001 | 320 | 80 |

TABLE A1b

| Pre-emergence activity at 1280 g/ha against ALOMY in % | | |
|---|---|---|
| Example number | Dosage [g/ha] | ALOMY |
| I-003 | 1280 | 90 |
| I-022 | 1280 | 90 |
| I-084 | 1280 | 80 |
| I-057 | 1280 | 90 |
| I-012 | 1280 | 90 |
| I-010 | 1280 | 80 |
| I-015 | 1280 | 90 |
| I-031 | 1280 | 90 |
| I-040 | 1280 | 90 |
| I-034 | 1280 | 90 |
| I-032 | 1280 | 90 |
| I-033 | 1280 | 90 |
| I-029 | 1280 | 80 |
| I-007 | 1280 | 90 |
| I-013 | 1280 | 90 |
| I-043 | 1280 | 90 |
| I-009 | 1280 | 90 |
| I-004 | 1280 | 90 |
| I-011 | 1280 | 80 |
| I-005 | 1280 | 90 |
| I-001 | 1280 | 90 |
| I-008 | 1280 | 90 |
| I-019 | 1280 | 90 |
| I-018 | 1280 | 90 |
| I-036 | 1280 | 90 |
| I-023 | 1280 | 90 |
| I-030 | 1280 | 90 |
| I-028 | 1280 | 80 |
| I-017 | 1280 | 90 |
| I-026 | 1280 | 90 |
| I-087 | 1280 | 90 |
| I-025 | 1280 | 90 |
| I-020 | 1280 | 80 |
| I-024 | 1280 | 90 |
| I-176 | 1280 | 90 |
| I-059 | 1280 | 80 |
| I-053 | 1280 | 90 |
| I-178 | 1280 | 90 |
| I-037 | 1280 | 90 |
| I-180 | 1280 | 80 |
| I-100 | 1280 | 90 |
| I-071 | 1280 | 80 |
| I-056 | 1280 | 80 |
| I-091 | 1280 | 90 |
| I-049 | 1280 | 90 |
| I-021 | 1280 | 90 |
| I-068 | 1280 | 80 |
| I-044 | 1280 | 80 |
| I-006 | 1280 | 90 |

TABLE A1b-continued

| Pre-emergence activity at 1280 g/ha against ALOMY in % | | |
|---|---|---|
| Example number | Dosage [g/ha] | ALOMY |
| I-061 | 1280 | 80 |
| I-014 | 1280 | 100 |
| I-048 | 1280 | 80 |
| I-058 | 1280 | 90 |
| I-192 | 1280 | 90 |

TABLE A2

| Pre-emergence activity at 1280 g/ha against AMARE in % | | |
|---|---|---|
| Example number | Dosage [g/ha] | AMARE |
| I-055 | 1280 | 100 |
| I-048 | 1280 | 90 |

TABLE A3a

| Pre-emergence activity at 320 g/ha against AVEFA in % | | |
|---|---|---|
| Example number | Dosage [g/ha] | AVEFA |
| I-027 | 320 | 90 |
| I-041 | 320 | 90 |
| I-002 | 320 | 100 |
| I-200 | 320 | 100 |
| I-203 | 320 | 100 |
| I-191 | 320 | 100 |
| I-201 | 320 | 100 |
| I-001 | 320 | 100 |
| I-080 | 320 | 80 |
| I-075 | 320 | 90 |

TABLE A3b

| Pre-emergence activity at 1280 g/ha against AVEFA in % | | |
|---|---|---|
| Example number | Dosage [g/ha] | AVEFA |
| I-003 | 1280 | 90 |
| I-022 | 1280 | 90 |
| I-057 | 1280 | 80 |
| I-052 | 1280 | 90 |
| I-012 | 1280 | 90 |
| I-010 | 1280 | 100 |
| I-015 | 1280 | 100 |
| I-031 | 1280 | 100 |
| I-040 | 1280 | 90 |
| I-034 | 1280 | 100 |
| I-032 | 1280 | 100 |
| I-033 | 1280 | 100 |
| I-029 | 1280 | 100 |
| I-007 | 1280 | 100 |
| I-013 | 1280 | 100 |
| I-043 | 1280 | 100 |
| I-009 | 1280 | 100 |
| I-004 | 1280 | 100 |
| I-046 | 1280 | 100 |
| I-076 | 1280 | 80 |
| I-072 | 1280 | 80 |
| I-011 | 1280 | 90 |
| I-005 | 1280 | 100 |
| I-001 | 1280 | 100 |
| I-035 | 1280 | 100 |
| I-008 | 1280 | 100 |
| I-019 | 1280 | 100 |
| I-018 | 1280 | 100 |
| I-036 | 1280 | 100 |
| I-023 | 1280 | 100 |
| I-030 | 1280 | 100 |

TABLE A3b-continued

| Pre-emergence activity at 1280 g/ha against AVEFA in % | | |
|---|---|---|
| Example number | Dosage [g/ha] | AVEFA |
| I-028 | 1280 | 100 |
| I-017 | 1280 | 100 |
| I-026 | 1280 | 100 |
| I-025 | 1280 | 100 |
| I-020 | 1280 | 100 |
| I-024 | 1280 | 100 |
| I-176 | 1280 | 100 |
| I-059 | 1280 | 80 |
| I-053 | 1280 | 90 |
| I-178 | 1280 | 90 |
| I-055 | 1280 | 80 |
| I-037 | 1280 | 100 |
| I-179 | 1280 | 90 |
| I-180 | 1280 | 90 |
| I-071 | 1280 | 90 |
| I-049 | 1280 | 100 |
| I-092 | 1280 | 80 |
| I-021 | 1280 | 100 |
| I-068 | 1280 | 80 |
| I-045 | 1280 | 90 |
| I-044 | 1280 | 90 |
| I-006 | 1280 | 100 |
| I-061 | 1280 | 90 |
| I-065 | 1280 | 80 |
| I-014 | 1280 | 100 |
| I-048 | 1280 | 90 |
| I-058 | 1280 | 100 |

TABLE A4a

| Pre-emergence activity at 320 g/ha against CYPES in % | | |
|---|---|---|
| Example number | Dosage [g/ha] | CYPES |
| I-027 | 320 | 80 |

TABLE A4b

| Pre-emergence activity at 1280 g/ha against CYPES in % | | |
|---|---|---|
| Example number | Dosage [g/ha] | CYPES |
| I-057 | 1280 | 100 |
| I-012 | 1280 | 80 |
| I-015 | 1280 | 80 |
| I-031 | 1280 | 80 |
| I-040 | 1280 | 80 |
| I-032 | 1280 | 80 |
| I-033 | 1280 | 80 |
| I-007 | 1280 | 90 |
| I-009 | 1280 | 80 |
| I-004 | 1280 | 100 |
| I-046 | 1280 | 100 |
| I-001 | 1280 | 80 |
| I-019 | 1280 | 80 |
| I-018 | 1280 | 80 |
| I-023 | 1280 | 80 |
| I-028 | 1280 | 80 |
| I-026 | 1280 | 90 |
| I-024 | 1280 | 90 |
| I-055 | 1280 | 100 |
| I-037 | 1280 | 100 |
| I-006 | 1280 | 90 |

TABLE A5

| Pre-emergence activity at 320 or 1280 g/ha against ECHCG in % | | |
|---|---|---|
| Example number | Dosage [g/ha] | ECHCG |
| I-003 | 1280 | 80 |
| I-012 | 1280 | 80 |
| I-015 | 1280 | 90 |
| I-031 | 1280 | 80 |
| I-040 | 1280 | 80 |
| I-034 | 1280 | 80 |
| I-032 | 1280 | 80 |
| I-033 | 1280 | 80 |
| I-029 | 1280 | 90 |
| I-007 | 1280 | 90 |
| I-013 | 1280 | 90 |
| I-043 | 1280 | 90 |
| I-009 | 1280 | 90 |
| I-004 | 1280 | 80 |
| I-005 | 1280 | 80 |
| I-001 | 1280 | 80 |
| I-035 | 1280 | 80 |
| I-008 | 1280 | 90 |
| I-019 | 1280 | 90 |
| I-018 | 1280 | 90 |
| I-036 | 1280 | 80 |
| I-023 | 1280 | 80 |
| I-030 | 1280 | 80 |
| I-028 | 1280 | 80 |
| I-017 | 1280 | 90 |
| I-026 | 1280 | 90 |
| I-025 | 1280 | 90 |
| I-020 | 1280 | 80 |
| I-024 | 1280 | 80 |
| I-176 | 1280 | 90 |
| I-178 | 1280 | 90 |
| I-037 | 1280 | 90 |
| I-180 | 1280 | 90 |
| I-049 | 1280 | 80 |
| I-021 | 1280 | 80 |
| I-045 | 1280 | 80 |
| I-044 | 1280 | 80 |
| I-006 | 1280 | 90 |
| I-014 | 1280 | 80 |
| I-192 | 1280 | 80 |
| I-201 | 320 | 100 |

TABLE A6

| Pre-emergence activity at 1280 g/ha against LOLMU in % | | |
|---|---|---|
| Example number | Dosage [g/ha] | LOLMU |
| I-003 | 1280 | 90 |
| I-012 | 1280 | 90 |
| I-015 | 1280 | 80 |
| I-029 | 1280 | 80 |
| I-007 | 1280 | 90 |
| I-013 | 1280 | 90 |
| I-043 | 1280 | 80 |
| I-009 | 1280 | 80 |
| I-004 | 1280 | 90 |
| I-011 | 1280 | 80 |
| I-005 | 1280 | 80 |
| I-001 | 1280 | 90 |
| I-008 | 1280 | 80 |
| I-019 | 1280 | 90 |
| I-018 | 1280 | 90 |
| I-036 | 1280 | 80 |
| I-023 | 1280 | 80 |
| I-030 | 1280 | 80 |
| I-028 | 1280 | 90 |
| I-017 | 1280 | 80 |
| I-026 | 1280 | 90 |
| I-025 | 1280 | 90 |
| I-020 | 1280 | 80 |
| I-024 | 1280 | 90 |
| I-176 | 1280 | 90 |

TABLE A6-continued

| Pre-emergence activity at 1280 g/ha against LOLMU in % | | |
|---|---|---|
| Example number | Dosage [g/ha] | LOLMU |
| I-037 | 1280 | 90 |
| I-049 | 1280 | 80 |
| I-021 | 1280 | 90 |
| I-006 | 1280 | 90 |
| I-014 | 1280 | 90 |
| I-048 | 1280 | 80 |
| I-058 | 1280 | 80 |

TABLE A7

| Pre-emergence activity at 1280 g/ha against MATIN in % | | |
|---|---|---|
| Example number | Dosage [g/ha] | MATIN |
| I-033 | 1280 | 80 |
| I-184 | 1280 | 80 |

TABLE A8

| Pre-emergence activity at 1280 g/ha against PHBPU in % | | |
|---|---|---|
| Example number | Dosage [g/ha] | PHBPU |
| I-033 | 1280 | 80 |
| I-007 | 1280 | 80 |
| I-178 | 1280 | 90 |
| I-090 | 1280 | 100 |

TABLE A9

| Pre-emergence activity at 320 and 1280 g/ha against SETVI in % | | |
|---|---|---|
| Example number | Dosage [g/ha] | SETVI |
| I-003 | 1280 | 80 |
| I-022 | 1280 | 80 |
| I-057 | 1280 | 80 |
| I-012 | 1280 | 90 |
| I-015 | 1280 | 90 |
| I-033 | 1280 | 80 |
| I-029 | 1280 | 80 |
| I-007 | 1280 | 90 |
| I-013 | 1280 | 90 |
| I-043 | 1280 | 90 |
| I-009 | 1280 | 80 |
| I-004 | 1280 | 80 |
| I-001 | 320 | 100 |
| I-008 | 1280 | 90 |
| I-019 | 1280 | 90 |
| I-018 | 1280 | 90 |
| I-036 | 1280 | 100 |
| I-023 | 1280 | 90 |
| I-030 | 1280 | 80 |
| I-028 | 1280 | 80 |
| I-017 | 1280 | 90 |
| I-026 | 1280 | 80 |
| I-025 | 1280 | 80 |
| I-024 | 1280 | 80 |
| I-037 | 1280 | 90 |
| I-021 | 1280 | 80 |
| I-192 | 1280 | 90 |
| I-201 | 320 | 100 |
| I-014 | 320 | 90 |
| I-080 | 320 | 90 |

TABLE A10

| Pre-emergence activity at 1280 g/ha against STEME in % | | |
|---|---|---|
| Example number | Dosage [g/ha] | STEME |
| I-007 | 1280 | 80 |
| I-179 | 1280 | 80 |

TABLE A11

| Pre-emergence activity at 320 and 1280 g/ha against VIOTR in % | | |
|---|---|---|
| Example number | Dosage [g/ha] | VIOTR |
| I-003 | 1280 | 90 |
| I-065 | 1280 | 100 |
| I-200 | 320 | 80 |
| I-195 | 320 | 80 |
| I-014 | 320 | 90 |
| I-009 | 320 | 100 |
| I-013 | 320 | 90 |
| I-007 | 320 | 90 |
| I-015 | 320 | 90 |

TABLE A12

| Pre-emergence activity at 320 and 1280 g/ha against POLCO in % | | |
|---|---|---|
| Example number | Dosage [g/ha] | POLCO |
| I-003 | 1280 | 90 |
| I-057 | 1280 | 80 |
| I-015 | 1280 | 80 |
| I-031 | 1280 | 80 |
| I-007 | 1280 | 90 |
| I-013 | 1280 | 90 |
| I-004 | 1280 | 80 |
| I-005 | 1280 | 80 |
| I-008 | 1280 | 90 |
| I-019 | 1280 | 90 |
| I-018 | 1280 | 80 |
| I-036 | 1280 | 80 |
| I-030 | 1280 | 80 |
| I-017 | 1280 | 80 |
| I-025 | 1280 | 80 |
| I-024 | 1280 | 80 |
| I-176 | 1280 | 80 |
| I-104 | 1280 | 90 |
| I-178 | 1280 | 90 |
| I-071 | 1280 | 80 |
| I-186 | 1280 | 100 |
| I-102 | 1280 | 80 |
| I-049 | 1280 | 90 |
| I-021 | 1280 | 80 |
| I-044 | 1280 | 90 |
| I-006 | 1280 | 90 |
| I-065 | 1280 | 100 |
| I-200 | 320 | 90 |
| I-203 | 320 | 80 |
| I-001 | 320 | 80 |
| I-014 | 320 | 90 |
| I-009 | 320 | 80 |

TABLE A13a

| Pre-emergence activity at 320 g/ha against VERPE in % | | |
|---|---|---|
| Example number | Dosage [g/ha] | VERPE |
| I-041 | 320 | 90 |

TABLE A13b

| Pre-emergence activity at 1280 g/ha against VERPE in % | | |
|---|---|---|
| Example number | Dosage [g/ha] | VERPE |
| I-040 | 1280 | 90 |
| I-034 | 1280 | 100 |
| I-032 | 1280 | 80 |
| I-033 | 1280 | 90 |
| I-007 | 1280 | 90 |
| I-106 | 1280 | 80 |
| I-046 | 1280 | 100 |
| I-001 | 1280 | 90 |
| I-018 | 1280 | 90 |
| I-036 | 1280 | 90 |
| I-023 | 1280 | 80 |
| I-030 | 1280 | 90 |
| I-028 | 1280 | 80 |
| I-088 | 1280 | 90 |
| I-087 | 1280 | 100 |
| I-105 | 1280 | 90 |
| I-020 | 1280 | 80 |
| I-095 | 1280 | 80 |
| I-056 | 1280 | 100 |
| I-102 | 1280 | 90 |

TABLE A14a

| Pre-emergence activity at 320 g/ha against DIGSA in % | | |
|---|---|---|
| Example number | Dosage [g/ha] | DIGSA |
| I-192 | 320 | 90 |
| I-200 | 320 | 80 |
| I-201 | 320 | 90 |
| I-001 | 320 | 100 |
| I-014 | 320 | 100 |
| I-080 | 320 | 80 |
| I-002 | 320 | 80 |
| I-009 | 320 | 90 |
| I-013 | 320 | 90 |
| I-007 | 320 | 90 |
| I-015 | 320 | 100 |
| I-003 | 320 | 90 |

TABLE A14b

| Pre-emergence activity at 1280 g/ha against DIGSA in % | | |
|---|---|---|
| Example number | Dosage [g/ha] | DIGSA |
| I-192 | 1280 | 90 |

TABLE A15a

| Pre-emergence activity at 320 g/ha against POAAN in % | | |
|---|---|---|
| Example number | Dosage [g/ha] | POAAN |
| I-192 | 320 | 100 |

TABLE A15b

| Pre-emergence activity at 1280 g/ha against POAAN in % | | |
|---|---|---|
| Example number | Dosage [g/ha] | POAAN |
| I-192 | 1280 | 100 |
| I-193 | 1280 | 90 |

TABLE A16

| Pre-emergence activity at 320 g/ha against LOLRI in % | | |
|---|---|---|
| Example number | Dosage [g/ha] | LOLRI |
| I-192 | 320 | 90 |
| I-201 | 320 | 80 |
| I-001 | 320 | 90 |
| I-014 | 320 | 90 |
| I-009 | 320 | 80 |
| I-013 | 320 | 80 |
| I-015 | 320 | 80 |
| I-003 | 320 | 80 |

As the results show, compounds according to the invention have very good herbicidal pre-emergence effectiveness against a broad spectrum of mono- and dicotyledonous weeds such as *Abutilon theophrasti, Alopecurus myosuroides, Amaranthus retroflexus, Avena fatua, Cyperus esculentus, Echinochloa crus-galli, Lolium rigidum, Matricaria inodora, Polygonum convolvulus, Setaria viridis, Stellaria media, Veronica persica* and Viola tricolor at an application rate of 320 g and 1280 g of active substance per hectare, respectively.

B. Herbicidal Post-Emergence Action

Seeds of mono- and dicotyledonous weed plants and crop plants were sown, in plastic or organic planting pots, in sandy loam, covered with soil and grown in a greenhouse under controlled growth conditions. 2 to 3 weeks after sowing, the test plants were sprayed in the single-leaf stage. The compounds according to the invention, formulated in form of wettable powders (WP) or as emulsifiable concentrates (EC), were sprayed onto the green plant parts as aqueous suspension or emulsion, with the addition of 0.5% of an additive, at an application rate of 600 l of water/ha (converted). The test plants were placed in the greenhouse for ca. 3 weeks under optimum growth conditions, and then the effect of the preparations was assessed visually in comparison with untreated controls (herbicidal effect in percent (%): 100% effect=plants have died off, 0% effect=as control plants).

Tables B1 to B16 below show the effects of selected compounds of the general formula (I) according to table 1 on various harmful plants and an application rate corresponding to 1280 g/ha or 320 g/ha obtained by the experimental procedure mentioned above.

TABLE B1a

| Post-emergence activity at 320 g/ha against ALOMY in % | | |
|---|---|---|
| Example number | Dosage [g/ha] | ALOMY |
| I-041 | 320 | 80 |
| I-002 | 320 | 80 |
| I-200 | 320 | 80 |
| I-201 | 320 | 90 |

TABLE B1b

| Post-emergence activity at 1280 g/ha against ALOMY in % | | |
|---|---|---|
| Example number | Dosage [g/ha] | ALOMY |
| I-003 | 1280 | 90 |
| I-012 | 1280 | 80 |
| I-010 | 1280 | 80 |
| I-038 | 1280 | 80 |
| I-031 | 1280 | 90 |

TABLE B1b-continued

| Post-emergence activity at 1280 g/ha against ALOMY in % | | |
|---|---|---|
| Example number | Dosage [g/ha] | ALOMY |
| I-040 | 1280 | 90 |
| I-034 | 1280 | 80 |
| I-032 | 1280 | 80 |
| I-033 | 1280 | 80 |
| I-029 | 1280 | 80 |
| I-007 | 1280 | 80 |
| I-013 | 1280 | 80 |
| I-043 | 1280 | 80 |
| I-009 | 1280 | 80 |
| I-004 | 1280 | 90 |
| I-005 | 1280 | 90 |
| I-001 | 1280 | 90 |
| I-035 | 1280 | 80 |
| I-008 | 1280 | 80 |
| I-019 | 1280 | 80 |
| I-018 | 1280 | 80 |
| I-036 | 1280 | 80 |
| I-023 | 1280 | 80 |
| I-030 | 1280 | 80 |
| I-028 | 1280 | 80 |
| I-017 | 1280 | 80 |
| I-026 | 1280 | 80 |
| I-025 | 1280 | 80 |
| I-020 | 1280 | 80 |
| I-024 | 1280 | 90 |
| I-053 | 1280 | 80 |
| I-049 | 1280 | 80 |
| I-021 | 1280 | 80 |
| I-184 | 1280 | 80 |
| I-045 | 1280 | 80 |
| I-006 | 1280 | 90 |
| I-061 | 1280 | 90 |
| I-014 | 1280 | 80 |
| I-058 | 1280 | 80 |
| I-176 | 1280 | 90 |
| I-037 | 1280 | 80 |

TABLE B2

| Post-emergence activity at 1280 g/ha against AMARE in % | | |
|---|---|---|
| Example number | Dosage [g/ha] | AMARE |
| I-066 | 1280 | 100 |
| I-178 | 1280 | 100 |
| I-180 | 1280 | 90 |
| I-184 | 1280 | 80 |

TABLE B3a

| Post-emergence activity at 320 g/ha against AVEFA in % | | |
|---|---|---|
| Example number | Dosage [g/ha] | AVEFA |
| I-002 | 320 | 80 |
| I-200 | 320 | 80 |
| I-201 | 320 | 100 |

TABLE B3b

| Post-emergence activity at 1280 g/ha against AVEFA in % | | |
|---|---|---|
| Example number | Dosage [g/ha] | AVEFA |
| I-003 | 1280 | 90 |
| I-022 | 1280 | 90 |
| I-012 | 1280 | 90 |
| I-010 | 1280 | 90 |
| I-015 | 1280 | 90 |

TABLE B3b-continued

| Post-emergence activity at 1280 g/ha against AVEFA in % | | |
|---|---|---|
| Example number | Dosage [g/ha] | AVEFA |
| I-029 | 1280 | 90 |
| I-007 | 1280 | 90 |
| I-013 | 1280 | 80 |
| I-043 | 1280 | 80 |
| I-009 | 1280 | 90 |
| I-004 | 1280 | 100 |
| I-046 | 1280 | 90 |
| I-076 | 1280 | 80 |
| I-072 | 1280 | 80 |
| I-011 | 1280 | 90 |
| I-005 | 1280 | 90 |
| I-001 | 1280 | 90 |
| I-035 | 1280 | 90 |
| I-008 | 1280 | 90 |
| I-019 | 1280 | 100 |
| I-018 | 1280 | 80 |
| I-036 | 1280 | 90 |
| I-023 | 1280 | 80 |
| I-030 | 1280 | 80 |
| I-028 | 1280 | 80 |
| I-017 | 1280 | 90 |
| I-026 | 1280 | 90 |
| I-070 | 1280 | 80 |
| I-025 | 1280 | 80 |
| I-020 | 1280 | 90 |
| I-024 | 1280 | 90 |
| I-176 | 1280 | 80 |
| I-059 | 1280 | 80 |
| I-053 | 1280 | 80 |
| I-178 | 1280 | 80 |
| I-098 | 1280 | 80 |
| I-037 | 1280 | 90 |
| I-179 | 1280 | 90 |
| I-180 | 1280 | 80 |
| I-071 | 1280 | 80 |
| I-021 | 1280 | 80 |
| I-184 | 1280 | 80 |
| I-085 | 1280 | 90 |
| I-006 | 1280 | 100 |
| I-061 | 1280 | 90 |
| I-079 | 1280 | 90 |
| I-065 | 1280 | 90 |
| I-014 | 1280 | 80 |
| I-075 | 1280 | 100 |
| I-058 | 1280 | 80 |

TABLE B4

| Post-emergence activity at 1280 g/ha against CYPES in % | | |
|---|---|---|
| Example number | Dosage [g/ha] | CYPES |
| I-012 | 1280 | 80 |
| I-005 | 1280 | 90 |
| I-056 | 1280 | 80 |
| I-021 | 1280 | 80 |
| I-006 | 1280 | 80 |
| I-014 | 1280 | 80 |

TABLE B5a

| Post-emergence activity at 320 g/ha against ECHCG in % | | |
|---|---|---|
| Example number | Dosage [g/ha] | ECHCG |
| I-027 | 320 | 90 |
| I-041 | 320 | 90 |
| I-002 | 320 | 90 |
| I-201 | 320 | 90 |

TABLE B5b

| Post-emergence activity at 1280 g/ha against ECHCG in % | | |
|---|---|---|
| Example number | Dosage [g/ha] | ECHCG |
| I-003 | 1280 | 90 |
| I-022 | 1280 | 90 |
| I-052 | 1280 | 80 |
| I-012 | 1280 | 90 |
| I-074 | 1280 | 80 |
| I-010 | 1280 | 100 |
| I-015 | 1280 | 100 |
| I-038 | 1280 | 90 |
| I-031 | 1280 | 90 |
| I-040 | 1280 | 80 |
| I-034 | 1280 | 90 |
| I-032 | 1280 | 90 |
| I-033 | 1280 | 80 |
| I-029 | 1280 | 90 |
| I-007 | 1280 | 90 |
| I-013 | 1280 | 80 |
| I-043 | 1280 | 80 |
| I-009 | 1280 | 100 |
| I-004 | 1280 | 100 |
| I-072 | 1280 | 80 |
| I-086 | 1280 | 80 |
| I-011 | 1280 | 80 |
| I-005 | 1280 | 100 |
| I-001 | 1280 | 90 |
| I-035 | 1280 | 90 |
| I-008 | 1280 | 90 |
| I-019 | 1280 | 80 |
| I-018 | 1280 | 90 |
| I-036 | 1280 | 90 |
| I-023 | 1280 | 90 |
| I-030 | 1280 | 80 |
| I-028 | 1280 | 80 |
| I-101 | 1280 | 80 |
| I-017 | 1280 | 90 |
| I-026 | 1280 | 80 |
| I-070 | 1280 | 80 |
| I-025 | 1280 | 90 |
| I-020 | 1280 | 90 |
| I-024 | 1280 | 90 |
| I-176 | 1280 | 90 |
| I-059 | 1280 | 80 |
| I-053 | 1280 | 80 |
| I-178 | 1280 | 90 |
| I-050 | 1280 | 80 |
| I-179 | 1280 | 90 |
| I-180 | 1280 | 90 |
| I-186 | 1280 | 80 |
| I-021 | 1280 | 90 |
| I-044 | 1280 | 90 |
| I-006 | 1280 | 100 |
| I-061 | 1280 | 80 |
| I-014 | 1280 | 90 |
| I-058 | 1280 | 80 |
| I-192 | 1280 | 90 |

TABLE B6a

| Post-emergence activity at 320 g/ha against LOLMU in % | | |
|---|---|---|
| Example number | Dosage [g/ha] | LOLMU |
| I-027 | 320 | 80 |
| I-041 | 320 | 80 |
| I-002 | 320 | 80 |

TABLE B6b

| Post-emergence activity at 1280 g/ha against LOLMU in % | | |
|---|---|---|
| Example number | Dosage [g/ha] | LOLMU |
| I-003 | 1280 | 90 |
| I-022 | 1280 | 80 |
| I-052 | 1280 | 80 |
| I-012 | 1280 | 90 |
| I-010 | 1280 | 90 |
| I-015 | 1280 | 80 |
| I-038 | 1280 | 80 |
| I-031 | 1280 | 90 |
| I-040 | 1280 | 80 |
| I-034 | 1280 | 90 |
| I-032 | 1280 | 90 |
| I-029 | 1280 | 80 |
| I-043 | 1280 | 80 |
| I-009 | 1280 | 90 |
| I-004 | 1280 | 90 |
| I-046 | 1280 | 80 |
| I-011 | 1280 | 90 |
| I-005 | 1280 | 90 |
| I-001 | 1280 | 100 |
| I-035 | 1280 | 80 |
| I-008 | 1280 | 80 |
| I-019 | 1280 | 90 |
| I-018 | 1280 | 80 |
| I-023 | 1280 | 80 |
| I-030 | 1280 | 80 |
| I-028 | 1280 | 80 |
| I-026 | 1280 | 80 |
| I-025 | 1280 | 80 |
| I-020 | 1280 | 80 |
| I-024 | 1280 | 90 |
| I-176 | 1280 | 80 |
| I-021 | 1280 | 90 |
| I-184 | 1280 | 80 |
| I-045 | 1280 | 80 |
| I-006 | 1280 | 80 |
| I-014 | 1280 | 80 |

TABLE B7

| Post-emergence activity at 1280 g/ha against MATIN in % | | |
|---|---|---|
| Example number | Dosage [g/ha] | MATIN |
| I-184 | 1280 | 90 |

TABLE B8

| Post-emergence activity at 1280 g/ha against PHBPU in % | | |
|---|---|---|
| Example number | Dosage [g/ha] | PHBPU |
| I-184 | 1280 | 90 |
| I-065 | 1280 | 80 |

TABLE B9

| Post-emergence activity at 1280 g/ha and 320 g/ha against SETVI in % | | |
|---|---|---|
| Example number | Dosage [g/ha] | SETVI |
| I-022 | 1280 | 90 |
| I-012 | 1280 | 90 |
| I-010 | 1280 | 90 |
| I-015 | 1280 | 90 |
| I-038 | 1280 | 80 |
| I-031 | 1280 | 80 |
| I-034 | 1280 | 80 |
| I-043 | 1280 | 80 |

TABLE B9-continued

| Post-emergence activity at 1280 g/ha and 320 g/ha against SETVI in % | | |
|---|---|---|
| Example number | Dosage [g/ha] | SETVI |
| I-009 | 1280 | 80 |
| I-005 | 1280 | 90 |
| I-001 | 1280 | 80 |
| I-035 | 1280 | 100 |
| I-008 | 1280 | 80 |
| I-023 | 1280 | 80 |
| I-024 | 1280 | 80 |
| I-176 | 1280 | 80 |
| I-179 | 1280 | 80 |
| I-021 | 1280 | 90 |
| I-045 | 1280 | 80 |
| I-044 | 1280 | 80 |
| I-006 | 1280 | 80 |
| I-014 | 1280 | 90 |
| I-003 | 1280 | 80 |

TABLE B10

| Post-emergence activity at 1280 g/ha against STEME in % | | |
|---|---|---|
| Example number | Dosage [g/ha] | STEME |
| I-015 | 1280 | 90 |
| I-004 | 1280 | 80 |
| I-178 | 1280 | 80 |
| I-179 | 1280 | 80 |
| I-180 | 1280 | 90 |
| I-184 | 1280 | 80 |

TABLE B11

| Post-emergence activity at 1280 g/ha against VIOTR in % | | |
|---|---|---|
| Example number | Dosage [g/ha] | VIOTR |
| I-180 | 1280 | 80 |

TABLE B12a

| Post-emergence activity at 320 g/ha against POLCO in % | | |
|---|---|---|
| Example number | Dosage [g/ha] | POLCO |
| I-027 | 320 | 80 |
| I-041 | 320 | 80 |

TABLE B12b

| Post-emergence activity at 1280 g/ha against POLCO in % | | |
|---|---|---|
| Example number | Dosage [g/ha] | POLCO |
| I-003 | 1280 | 80 |
| I-015 | 1280 | 80 |
| I-040 | 1280 | 80 |
| I-034 | 1280 | 80 |
| I-005 | 1280 | 80 |
| I-017 | 1280 | 80 |
| I-026 | 1280 | 80 |
| I-176 | 1280 | 90 |
| I-037 | 1280 | 80 |
| I-180 | 1280 | 80 |
| I-071 | 1280 | 80 |
| I-110 | 1280 | 80 |
| I-021 | 1280 | 80 |

TABLE B13

| Post-emergence activity at 1280 g/ha against VERPE in % | | |
|---|---|---|
| Example number | Dosage [g/ha] | VERPE |
| I-004 | 1280 | 80 |
| I-184 | 1280 | 80 |

TABLE B14a

| Post-emergence activity at 320 g/ha against DIGSA in % | | |
|---|---|---|
| Example number | Dosage [g/ha] | DIGSA |
| I-194 | 320 | 90 |
| I-200 | 320 | 80 |
| I-201 | 320 | 90 |
| I-001 | 320 | 90 |
| I-014 | 320 | 80 |
| I-002 | 320 | 80 |
| I-009 | 320 | 80 |
| I-013 | 320 | 80 |
| I-007 | 320 | 90 |
| I-015 | 320 | 80 |

TABLE B14b

| Post-emergence activity at 1280 g/ha against DIGSA in % | | |
|---|---|---|
| Example number | Dosage [g/ha] | DIGSA |
| I-192 | 1280 | 90 |

TABLE B15a

| Post-emergence activity at 320 g/ha against POAAN in % | | |
|---|---|---|
| Example number | Dosage [g/ha] | POAAN |
| I-192 | 320 | 100 |

TABLE B15b

| Post-emergence activity at 1280 g/ha against POAAN in % | | |
|---|---|---|
| Example number | Dosage [g/ha] | POAAN |
| I-192 | 1280 | 100 |
| I-193 | 1280 | 90 |

TABLE B16

| Post-emergence activity at 320 g/ha against LOLRI in % | | |
|---|---|---|
| Example number | Dosage [g/ha] | LOLRI |
| I-001 | 320 | 80 |
| I-014 | 320 | 80 |
| I-007 | 320 | 80 |
| I-015 | 320 | 80 |

As the results show, compounds according to the invention have good herbicidal post-emergence effectiveness against a broad spectrum of mono- and dicotyledonous weeds such as *Abutilon theophrasti, Alopecurus myosuroides, Amaranthus retroflexus, Avena fatua, Cyperus esculentus, Echinochloa crus-galli, Lolium rigidum, Matricaria inodora, Polygonum convolvulus, Setaria viridis, Stellaria*

*media, Veronica persica* and Viola tricolor at an application rate of 1280 g and less of active ingredient per hectare.

C. Pre-Emergence Effects on Crop Plants

Tables C1 to C3 below show the effects of selected compounds of the general formula (I) according to table 1 on various crop plants and an application rate corresponding to 320 g/ha or below obtained by the experimental procedure mentioned above in biology section A.

TABLE C1

| pre-emergence activity at 320 g/ha and 80 g/ha against ZEAMX in % | | |
|---|---|---|
| Example number | application rate [g/ha] | ZEAMX |
| I-001 | 80 | 0 |
| I-192 | 80 | 20 |
| I-201 | 80 | 0 |
| I-075 | 320 | 0 |
| I-014 | 80 | 0 |
| I-080 | 320 | 0 |
| I-002 | 320 | 0 |
| I-002 | 320 | 20 |
| I-013 | 320 | 0 |
| I-007 | 320 | 0 |
| I-015 | 320 | 0 |
| I-003 | 80 | 0 |

TABLE C2

| pre-emergence activity at 320 g/ha and 80 g/ha against GLXMA in % | | |
|---|---|---|
| Example number | application rate [g/ha] | GLXMA |
| I-001 | 320 | 0 |
| I-201 | 320 | 0 |
| I-075 | 320 | 0 |
| I-014 | 320 | 0 |
| I-080 | 320 | 0 |
| I-002 | 320 | 0 |
| I-009 | 80 | 20 |
| I-013 | 80 | 0 |
| I-007 | 320 | 0 |
| I-015 | 320 | 0 |
| I-003 | 320 | 0 |

TABLE C3

| pre-emergence activity at 320 g/ha and 80 g/ha against BRSNW in % | | |
|---|---|---|
| Example number | application rate [g/ha] | BRSNW |
| I-001 | 320 | 0 |
| I-192 | 320 | 0 |
| I-075 | 320 | 0 |
| I-014 | 320 | 0 |
| I-080 | 320 | 0 |
| I-002 | 320 | 0 |
| I-009 | 320 | 0 |
| I-013 | 320 | 0 |
| I-007 | 320 | 0 |
| I-015 | 320 | 20 |
| I-003 | 320 | 0 |

As the results in tables C1 to C3 show, compounds according to the invention show only low or no damaging effects in crop plants such as *Zea Mays, Glycine max* and *Brassica napus.*

D. Post-Emergence Effects on Crop Plants

Tables D1 to D3 below show the effects of selected compounds of the general formula (I) according to table 1 on various crop plants and an application rate corresponding to 320 g/ha or below obtained by the experimental procedure mentioned above in biology section B.

TABLE D1

| post-emergence activity at 320 g/ha and 80 g/ha against ZEAMX in % | | |
|---|---|---|
| Example number | application rate [g/ha] | ZEAMX |
| I-001 | 320 | 20 |
| I-192 | 80 | 20 |
| I-201 | 80 | 0 |
| I-075 | 320 | 0 |
| I-014 | 80 | 0 |
| I-080 | 320 | 0 |
| I-002 | 80 | 0 |
| I-002 | 320 | 0 |
| I-013 | 320 | 0 |
| I-007 | 320 | 0 |
| I-015 | 320 | 0 |
| I-003 | 320 | 0 |

TABLE D2

| post-emergence activity at 320 g/ha and 80 g/ha against GLXMA in % | | |
|---|---|---|
| Example number | application rate [g/ha] | GLXMA |
| I-001 | 320 | 0 |
| I-201 | 320 | 0 |
| I-192 | 320 | 0 |
| I-075 | 320 | 0 |
| I-014 | 320 | 0 |
| I-080 | 320 | 0 |
| I-002 | 80 | 0 |
| I-009 | 320 | 0 |
| I-013 | 320 | 0 |
| I-007 | 320 | 0 |
| I-015 | 320 | 0 |
| I-003 | 320 | 0 |

TABLE D3

| post-emergence activity at 320 g/ha and 80 g/ha against BRSNW in % | | |
|---|---|---|
| Example number | application rate [g/ha] | BRSNW |
| I-001 | 320 | 0 |
| I-192 | 320 | 0 |
| I-075 | 320 | 0 |
| I-014 | 80 | 0 |
| I-080 | 320 | 0 |
| I-002 | 320 | 0 |
| I-009 | 320 | 20 |
| I-013 | 320 | 0 |
| I-007 | 320 | 0 |
| I-015 | 80 | 0 |
| I-003 | 320 | 0 |

As the results in tables D1 to D3 show, compounds according to the invention show only low or no damaging effects in crop plants such as *Zea Mays* (ZEAMX), *Glycine max* (GLXMA) and *Brassica napus* (BRSNW).

The invention claimed is:

1. A substituted pyrrolidin-2-one compound of general formula (I) or salts thereof

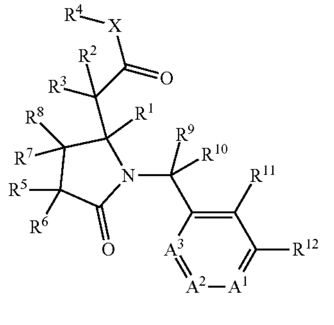

(I)

wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen, ($C_1$-$C_8$)-alkyl, ($C_1$-$C_{10}$)-haloalkyl, ($C_2$-$C_8$)-alkenyl, ($C_2$-$C_8$)-alkynyl, ($C_3$-$C_8$)-cycloalkyl, ($C_3$-$C_8$)-cycloalkyl-($C_1$-$C_8$)-alkyl, aryl-($C_1$-$C_8$)-alkyl, $R^{19}$—O—($C_1$-$C_8$)-alkyl, heteroaryl-($C_1$-$C_8$)-alkyl, or heterocyclyl-($C_1$-$C_8$)-alkyl;

$R^2$ and $R^3$ are each independently hydrogen, halogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, $OR^{19}$, $R^{17}R^{18}$N—($C_1$-$C_8$)-alkyl, ($C_3$-$C_{10}$)-cycloalkyl-($C_1$-$C_8$)-alkyl, C(═O) $R^{19}$, C(═O) $OR^{19}$, C(═O) $NR^{17}R^{18}$, or $R^{20}S(O)_m$—($C_1$-$C_8$)-alkyl;

$R^4$ is hydrogen, ($C_1$-$C_8$)-alkyl, ($C_1$-$C_{10}$)-haloalkyl, cyano-($C_1$-$C_8$)-alkyl, nitro-($C_1$-$C_8$)-alkyl, ($C_3$-$C_8$)-cycloalkyl, ($C_3$-$C_8$)-cycloalkyl-($C_1$-$C_8$)-alkyl, ($C_2$-$C_8$)-alkenyl, ($C_2$-$C_8$)-alkynyl, ($C_2$-$C_8$)-haloalkenyl, ($C_2$-$C_8$)-haloalkynyl, ($C_3$-$C_{10}$)-halocycloalkyl, ($C_4$-$C_{10}$)-cycloalkenyl, ($C_4$-$C_{10}$)-halocycloalkenyl, aryl-($C_1$-$C_8$)-alkyl, $R^{19}$O—($C_1$-$C_8$)-alkyl, $R^{19}$O—($C_1$-$C_8$)-alkoxy-($C_1$-$C_8$)-alkyl, $R^{20}$S(O)m-($C_1$-$C_8$)-alkyl, $R^{17}R^{18}$N—($C_1$-$C_8$)-alkyl, $R^{19}$O(O)C—($C_1$-$C_8$)-alkyl, $R^{19}$(O═)C—($C_1$-$C_8$)-Alkyl, $R^{17}R^{18}$N(O)C—($C_1$-$C_8$)-alkyl, heteroaryl-($C_1$-$C_8$)-alkyl, heterocyclyl-($C_1$-$C_8$)-alkyl, aryl, heteroaryl, heterocyclyl, ($C_1$-$C_8$)-alkoxy-($C_1$-$C_8$)-haloalkyl, ($C_1$-$C_8$)-alkylthio-($C_1$-$C_8$)-haloalkyl, or tris-[($C_1$-$C_8$)-alkyl]silyl-($C_1$-$C_8$)-alkyl;

$R^5$, $R^6$, $R^7$ and $R^8$ are each independently hydrogen, halogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, $OR^{19}$, $NR^{17}R^{18}$, $R^{17}R^{18}$N—($C_1$-$C_8$)-alkyl, ($C_3$-$C_{10}$)-cycloalkyl-($C_1$-$C_8$)-alkyl, C(═O) $R^{19}$, C(═O) $OR^{19}$, C(═O) $NR^{17}$R 18 $S(O)_mR^{20}$, or $R^{20}S(O)_m$—($C_1$-$C_8$)-alkyl;

$R^9$ and $R^{10}$ are each independently hydrogen, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, ($C_3$-$C_{10}$)-cycloalkyl-($C_1$-$C_8$)-alkyl, or $R^{20}S(O)_m$—($C_1$-$C_8$)-alkyl;

$R^{11}$ and $R^{12}$ are each independently halogen, cyano, nitro, thiocyanato, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, cyano-($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, $NR^{17}R^{18}$, $S(O)_mR^{20}$, N—O—$R^{19}$, C(═N—O—$R^{19}$) H, C(═O) H, C(═O) $R^{19}$, C(═O) $OR^{19}$, C(═O) $NR^{17}R^{18}$, tris-[($C_1$-$C_8$)-alkyl]silyl, ($C_1$-$C_8$)-alkoxy-($C_1$-$C_8$)-haloalkyl, or ($C_1$-$C_8$)-alkylthio-($C_1$-$C_8$)-haloalkyl;

m is 0, 1, or 2;

X is O (oxygen), S (sulfur), $NR^{13}$, or a group $CR^{14}R^{15}$;

$R^{13}$ is hydrogen, amino, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, $R^{19}$O—($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, $NR^{17}R^{18}$, $S(O)_mR^{20}$, C(═O) $R^{19}$, C(═O) $OR^{19}$, C(—O) $NR^{17}R^{18}$, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, heterocyclyl, heterocyclyl-($C_1$-$C_8$)-alkyl, or $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution;

$R^{14}$ and $R^{15}$ are equal or different and each independently ($C_1$-$C_8$)-alkyl, ($C_1$-$C_{10}$)-haloalkyl, ($C_3$-$C_8$)-cycloalkyl, ($C_3$-$C_8$)-cycloalkyl-($C_1$-$C_8$)-alkyl, aryl, heteroaryl, heterocyclyl, aryl-($C_1$-$C_8$)-alkyl, $R^{19}$—O—($C_1$-$C_8$)-alkyl, heteroaryl-($C_1$-$C_8$)-alkyl, heterocyclyl-($C_1$-$C_8$)-alkyl, C(═O) $R^{19}$, C(═O) $OR^{19}$, C(═O) $NR^{17}R^{18}$, $R^{19}$O(O)C—($C_1$-$C_8$)-alkyl, $R^{19}$ (O═)C—($C_1$-$C_8$)-Alkyl, $R^{17}R^{18}$N(O)C—($C_1$-$C_8$)-alkyl, cyano-($C_1$-$C_8$)-alkyl, or $R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution, or $R^{14}$ and $R^{15}$ together with the carbon atom to which they are bonded form an unsaturated 5- to 6-membered heteroaromatic or aromatic ring optionally having further substituents;

$R^{16}$ is hydrogen, halogen, cyano, nitro, ($C_1$-$C_8$)-alkyl, ($C_2$-$C_8$)-alkenyl, ($C_2$-$C_8$)-alkynyl, ($C_1$-$C_{10}$)-haloalkyl, ($C_3$-$C_{10}$)-cycloalkyl, aryl-($C_1$-$C_8$)-alkyl, aryl, heteroaryl, heteroaryl-($C_1$-$C_8$)-alkyl, heterocyclyl, heterocyclyl-($C_1$-$C_8$)-alkyl, $R^{19}$O—($C_1$-$C_8$)-alkyl, ($C_3$-$C_{10}$)-cycloalkyl-($C_1$-$C_8$)-alkyl, $R^{20}S(O)_m$—($C_1$-$C_8$)-alkyl, $R^{17}R^{18}$N—($C_1$-$C_8$)-alkyl, $OR^{19}$, $NR^{17}R^{18}$, $S(O)_mR^{20}$, C(═O) $R^{19}$, C(═N—O—$R^{19}$) H, C(═O) H, C(═O) $OR^{19}$, C(═O) $NR^{17}R^{18}$, ($C_1$-$C_8$)-alkoxy-($C_1$-$C_8$)-haloalkyl, or ($C_1$-$C_8$)-alkylthio-($C_1$-$C_8$)-haloalkyl;

$R^{17}$ and $R^{18}$ are equal or different and each independently hydrogen, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkyl, ($C_1$-$C_8$)-haloalkoxy-($C_1$-

$C_8$)-alkyl, ($C_1$-$C_8$)-alkylthio-($C_1$-$C_8$)-alkyl, ($C_1$-$C_8$)-haloalkylthio-($C_1$-$C_8$)-alkyl, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, $COR^{19}$, $SO_2R^{20}$, heterocyclyl, ($C_1$-$C_8$)-alkoxycarbonyl, bis-[($C_1$-$C_8$)-alkyl]aminocarbonyl-($C_1$-$C_8$)-alkyl, ($C_1$-$C_8$)-alkyl-aminocarbonyl-($C_1$-$C_8$)-alkyl, aryl-($C_1$-$C_8$)-alkyl-aminocarbonyl-($C_1$-$C_8$)-alkyl, ($C_1$-$C_8$)-alkoxycarbonyl-($C_1$-$C_8$)-alkyl, ($C_2$-$C_8$)-alkenyloxycarbonyl-($C_1$-$C_8$)-alkyl, ($C_2$-$C_8$)-alkynyloxycarbonyl-($C_1$-$C_8$)-alkyl, aryl-($C_1$-$C_8$)-alkoxycarbonyl-($C_1$-$C_8$)-alkyl, heteroaryl-($C_1$-$C_8$)-alkoxycarbonyl-($C_1$-$C_8$)-alkyl, heterocyclyl-($C_1$-$C_8$)-alkoxycarbonyl-($C_1$-$C_8$)-alkyl, aryl-($C_1$-$C_8$)-alkoxycarbonyl, heteroaryl-($C_1$-$C_8$)-alkoxycarbonyl, ($C_2$-$C_8$)-alkenyloxycarbonyl, ($C_2$-$C_8$)-alkynyloxycarbonyl, heterocyclyl-($C_1$-$C_8$)-alkyl, or $R^{17}$ and $R^{18}$ together with the nitrogen atom to which they are bonded form a fully saturated or partly saturated 3- to 10-membered monocyclic or bicyclic ring optionally interrupted by heteroatoms and optionally having further substitution;

$R^{19}$ is hydrogen, ($C_1$-$C_8$)-alkyl, ($C_2$-$C_8$)-alkenyl, ($C_2$-$C_8$)-alkinyl, ($C_1$-$C_8$)-cyanoalkyl, ($C_1$-$C_{10}$)-haloalkyl, ($C_2$-$C_8$)-haloalkenyl, ($C_3$-$C_8$)-haloalkinyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-haloalkoxy-($C_1$-$C_8$)-alkyl, ($C_1$-$C_8$)-alkoxy-($C_1$-$C_8$)-haloalkyl, ($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkyl, ($C_1$-$C_8$)-alkoxy-($C_1$-$C_8$)-alkoxy-($C_1$-$C_8$)-alkoxy-($C_1$-$C_8$)-alkoxy-($C_1$-$C_8$)-alkyl, aryl, aryl-($C_1$-$C_8$)-alkyl, aryl-($C_1$-$C_8$)-alkoxy-($C_1$-$C_8$)-alkyl, aryloxy-($C_1$-$C_8$)-alkyl, heteroaryl-($C_1$-$C_8$)-alkoxy-($C_1$-$C_8$)-alkyl, heteroaryloxy-($C_1$-$C_8$)-alkyl, heteroaryl, heteroaryl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, bis-[($C_1$-$C_8$)-alkyl]aminocarbonyl-($C_1$-$C_8$)-alkyl, ($C_1$-$C_8$)-alkyl-aminocarbonyl-($C_1$-$C_8$)-alkyl, aryl-($C_1$-$C_8$)-alkyl-aminocarbonyl-($C_1$-$C_8$)-alkyl, bis-[($C_1$-$C_8$)-alkyl]amino-($C_2$-$C_6$)-alkyl, ($C_1$-$C_8$)-alkyl-amino-($C_2$-$C_6$)-alkyl, aryl-($C_1$-$C_8$)-alkylamino-($C_2$-$C_6$)-alkyl, $R^{20}(O)_m$S-($C_1$-$C_8$)-alkyl, hydroxycarbonyl-($C_1$-$C_8$)-alkyl, heterocyclyl, heterocyclyl-($C_1$-$C_8$)-alkyl, heterocyclyl-($C_1$-$C_8$)-alkoxy-($C_1$-$C_8$)-alkyl, heterocyclyloxy-($C_1$-$C_8$)-alkyl, tris-[($C_1$-$C_8$)-alkyl]silyl-($C_1$-$C_8$)-alkyl, bis-[($C_1$-$C_8$)-alkyl](aryl) silyl ($C_1$-$C_8$)-alkyl, [($C_1$-$C_8$)-alkyl]-bis-(aryl) silyl-($C_1$-$C_8$)-alkyl, ($C_1$-$C_8$)-alkylcarbonyloxy-($C_1$-$C_8$)-alkyl, ($C_3$-$C_8$)-cycloalkylcarbonyloxy-($C_1$-$C_8$)-alkyl, arylcarbonyloxy-($C_1$-$C_8$)-alkyl, heteroarylcarbonyloxy-($C_1$-$C_8$)-alkyl, Heterocyclylcarbonyloxy-($C_1$-$C_8$)-alkyl, ($C_1$-$C_8$)-alkoxycarbonyl, ($C_1$-$C_8$)-alkoxycarbonyl-($C_1$-$C_8$)-alkyl, ($C_2$-$C_8$)-alkenyloxycarbonyl-($C_1$-$C_8$)-alkyl, ($C_2$-$C_8$)-alkynyloxycarbonyl-($C_1$-$C_8$)-alkyl, aryl-($C_1$-$C_8$)-alkoxycarbonyl-($C_1$-$C_8$)-alkyl, heteroaryl-($C_1$-$C_8$)-alkoxycarbonyl-($C_1$-$C_8$)-alkyl, or heterocyclyl-($C_1$-$C_8$)-alkoxycarbonyl-($C_1$-$C_8$)-alkyl; and $R^{20}$ is hydrogen, ($C_1$-$C_8$)-alkyl, ($C_2$-$C_8$)-alkenyl, ($C_2$-$C_8$)-alkynyl, ($C_1$-$C_8$)-cyanoalkyl, ($C_1$-$C_{10}$)-haloalkyl, ($C_2$-$C_8$)-haloalkenyl, ($C_3$-$C_8$)-haloalkynyl, ($C_3$-$C_{10}$)-cycloalkyl, ($C_3$-$C_{10}$)-halocycloalkyl, ($C_4$-$C_{10}$)-cycloalkenyl, ($C_4$-$C_{10}$)-halocycloalkenyl, ($C_1$-$C_8$)-alkoxy-($C_1$-$C_8$)-alkyl, ($C_1$-$C_8$)-alkoxy-($C_1$-$C_8$)-haloalkyl, aryl, aryl-($C_1$-$C_8$)-alkyl, heteroaryl, heteroaryl-($C_1$-$C_8$)-alkyl, heterocyclyl-($C_1$-$C_8$)-alkyl, ($C_3$-$C_8$)-cycloalkyl-($C_1$-$C_8$)-alkyl, ($C_4$-$C_{10}$)-cycloalkenyl-($C_1$-$C_8$)-alkyl, bis-[($C_1$-$C_8$)-alkyl]amino, ($C_1$-$C_8$)-alkyl-amino, aryl-($C_1$-$C_8$)-amino, aryl-($C_1$-$C_6$)-alkyl-amino, aryl-[($C_1$-$C_8$)-alkyl]amino; heteroaryl-($C_1$-$C_8$)-amino, heteroaryl-($C_1$-$C_6$)-alkyl-amino, heteroaryl-[($C_1$-$C_8$)-alkyl]amino, heterocyclyl-($C_1$-$C_8$)-amino, heterocyclyl-($C_1$-$C_6$)-alkyl-amino, heterocyclyl-[($C_1$-$C_8$)-alkyl]amino; ($C_3$-$C_8$)-cycloalkyl-amino, ($C_3$-$C_8$)-cycloalkyl-[($C_1$-$C_8$)-alkyl]amino; N-azetidinyl, N-pyrrolidinyl, N-piperidinyl, or N-morpholinyl.

2. The compound of the general formula (I) or salts thereof according to claim 1, wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen, ($C_1$-$C_7$)-alkyl, ($C_1$-$C_7$)-haloalkyl, ($C_3$-$C_7$)-cycloalkyl, ($C_3$-$C_7$)-cycloalkyl-($C_1$-$C_7$)-alkyl, aryl-($C_1$-$C_7$)-alkyl, $R^{19}$—O—($C_1$-$C_7$)-alkyl, heteroaryl-($C_1$-$C_7$)-alkyl, or heterocyclyl-($C_1$-$C_7$)-alkyl;

$R^2$ and $R^3$ are each independently hydrogen, halogen, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}$O—($C_1$-$C_7$)-alkyl, $OR^{19}$, $R^{17}R^{18}$N—($C_1$-$C_7$)-alkyl, ($C_3$-$C_7$)-cycloalkyl-($C_1$-$C_7$)-alkyl, C(═O) $R^{19}$, C(═O) $OR^{19}$, C(═O) $NR^{17}R^{18}$, or $R^{20}S(O)_m$—($C_1$-$C_7$)-alkyl;

$R^4$ is hydrogen, ($C_1$-$C_7$)-alkyl, ($C_1$-$C_7$)-haloalkyl, cyano-($C_1$-$C_7$)-alkyl, nitro-($C_1$-$C_7$)-alkyl, ($C_3$-$C_7$)-cycloalkyl, ($C_3$-$C_7$)-cycloalkyl-($C_1$-$C_7$)-alkyl, ($C_2$-$C_7$)-alkenyl, ($C_2$-$C_7$)-alkynyl, ($C_2$-$C_7$)-haloalkenyl, ($C_2$-$C_7$)-haloalkynyl, ($C_3$-$C_7$)-halocycloalkyl, ($C_4$-$C_7$)-cycloalkenyl, ($C_4$-$C_7$)-halocycloalkenyl, aryl-($C_1$-$C_7$)-alkyl, $R^{19}$O—($C_1$-$C_7$)-alkyl, $R^{19}$O—($C_1$-$C_7$)-alkoxy-($C_1$-$C_7$)-alkyl, $R^{20}S(O)_m$—($C_1$-$C_7$)-alkyl, $R^{17}R^{18}$N—($C_1$-$C_7$)-alkyl, $R^{19}$O(O)C—($C_1$-$C_7$)-alkyl, $R^{19}$ (O═)C—($C_1$-$C_7$)-Alkyl, $R^{17}R^{18}$N(O)C—($C_1$-$C_7$)-alkyl, heteroaryl-($C_1$-$C_7$)-alkyl, heterocyclyl-($C_1$-$C_7$)-alkyl, aryl, heteroaryl, heterocyclyl, ($C_1$-$C_7$)-alkoxy-($C_1$-$C_7$)-haloalkyl, ($C_1$-$C_7$)-alkylthio-($C_1$-$C_7$)-haloalkyl, or tris-[($C_1$-$C_7$)-alkyl]silyl-($C_1$-$C_7$)-alkyl;

$R^5$, $R^6$, $R^7$ and $R^8$ are each independently hydrogen, halogen, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}$O—($C_1$-$C_7$)-alkyl, $OR^{19}$, $NR^{17}R^{18}$, $R^{17}R^{18}$N—($C_1$-$C_7$)-alkyl, ($C_3$-$C_7$)-cycloalkyl-($C_1$-$C_7$)-alkyl, C(═O) $R^{19}$, C(═O) $OR^{19}$, C(═O) $NR^{17}R^{18}$, $S(O)_mR^{20}$, or $R^{20}S(O)_m$—($C_1$-$C_7$)-alkyl;

$R^9$ and $R^{10}$ are each independently hydrogen, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}$O—($C_1$-$C_7$)-alkyl, ($C_3$-$C_{10}$)-cycloalkyl-($C_1$-$C_7$)-alkyl, or $R^{20}S(O)_m$—($C_1$-$C_7$)-alkyl;

$R^{11}$ and $R^{12}$ are each independently halogen, cyano, nitro, thiocyanato, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}$O—($C_1$-$C_7$)-alkyl, cyano-($C_1$-$C_7$)-alkyl, ($C_3$-$C_7$)-cycloalkyl-($C_1$-$C_7$)-alkyl, $R^{20}S(O)_m$—($C_1$-$C_7$)-alkyl, $R^{17}R^{18}N$—($C_1$-$C_7$)-alkyl, $OR^{19}$, $NR^{17}R^{18}$, $S(O)_mR^{20}$, C(=O) $R^{19}$, C(=O) $OR^{19}$, C(=O) $NR^{17}R^{18}$, tris-[($C_1$-$C_7$)-alkyl] silyl, ($C_1$-$C_7$)-alkoxy-($C_1$-$C_7$)-haloalkyl, or ($C_1$-$C_7$)-alkylthio-($C_1$-$C_7$)-haloalkyl;

m is 0, 1, or 2;

X is O (oxygen), S (sulfur), $NR^{13}$, or a group $CR^{14}R^{15}$;

$R^{13}$ is hydrogen, amino, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_7$)-haloalkyl, ($C_2$-$C_7$)-haloalkenyl, ($C_3$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, $R^{19}O$—($C_1$-$C_7$)-alkyl, ($C_3$-$C_7$)-cycloalkyl-($C_1$-$C_7$)-alkyl, $R^{20}S(O)_m$—($C_1$-$C_7$)-alkyl, $R^{17}R^{18}N$—($C_1$-$C_7$)-alkyl, $OR^{19}$, $NR^{17}R^{18}$, $S(O)_mR^{20}$, C(=O) $R^{19}$, C(=O) $OR^{19}$, C(=O) $NR^{17}R^{18}$, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, heterocyclyl, heterocyclyl-($C_1$-$C_7$)-alkyl, or $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution;

$R^{14}$ and $R^{15}$ are equal or different and each independently ($C_1$-$C_7$)-alkyl, ($C_1$-$C_7$)-haloalkyl, ($C_3$-$C_7$)-cycloalkyl, ($C_3$-$C_7$)-cycloalkyl-($C_1$-$C_7$)-alkyl, aryl, heteroaryl, heterocyclyl, aryl-($C_1$-$C_7$)-alkyl, $R^{19}$—O—($C_1$-$C_7$)-alkyl, heteroaryl-($C_1$-$C_7$)-alkyl, heterocyclyl-($C_1$-$C_7$)-alkyl, C(=O) $R^{19}$, C(=O) $OR^{19}$, C(=O) $NR^{17}R^{18}$, $R^{19}O(O)C$—($C_1$-$C_7$)-alkyl, $R^{19}$ (O=)C—($C_1$-$C_7$)-Alkyl, $R^{17}R^{18}N(O)C$—($C_1$-$C_7$)-alkyl, cyano-($C_1$-$C_7$)-alkyl, or $R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution, or $R^{14}$ and $R^{15}$ together with the carbon atom to which they are bonded form an unsaturated 5- to 6-membered heteroaromatic or aromatic ring optionally having further substituents;

$R^{16}$ is hydrogen, halogen, cyano, nitro, ($C_1$-$C_7$)-alkyl, ($C_2$-$C_7$)-alkenyl, ($C_2$-$C_7$)-alkynyl, ($C_1$-$C_7$)-haloalkyl, ($C_3$-$C_7$)-cycloalkyl, aryl-($C_1$-$C_7$)-alkyl, aryl, heteroaryl, heteroaryl-($C_1$-$C_7$)-alkyl, heterocyclyl, heterocyclyl-($C_1$-$C_7$)-alkyl, $R^{19}O$—($C_1$-$C_7$)-alkyl, ($C_3$-$C_{10}$)-cycloalkyl-($C_1$-$C_7$)-alkyl, $R^{20}S(O)_m$—($C_1$-$C_7$)-alkyl, $R^{17}R^{18}N$—($C_1$-$C_8$)-alkyl, $OR^{19}$, $NR^{17}R^{18}$, $S(O)_mR^{20}$, C(=O) $R^{19}$, C(=O) $OR^{19}$, C(=O) $NR^{17}R^{18}$, ($C_1$-$C_7$)-alkoxy-($C_1$-$C_7$)-haloalkyl, or ($C_1$-$C_7$)-alkylthio-($C_1$-$C_7$)-haloalkyl;

$R^{17}$ and $R^{18}$ are equal or different and each independently hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_7$)-haloalkyl, ($C_2$-$C_7$)-haloalkenyl, ($C_3$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkoxy-($C_1$-$C_7$)-alkyl, ($C_1$-$C_7$)-haloalkoxy-($C_1$-$C_7$)-alkyl, ($C_1$-$C_7$)-alkylthio-($C_1$-$C_7$)-alkyl, ($C_1$-$C_7$)-haloalkylthio-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, $COR^{19}$, $SO_2R^{20}$, heterocyclyl, ($C_1$-$C_7$)-alkoxycarbonyl, bis-[($C_1$-$C_7$)-alkyl]aminocarbonyl-($C_1$-$C_7$)-alkyl, ($C_1$-$C_7$)-alkyl-aminocarbonyl-($C_1$-$C_7$)-alkyl, aryl-($C_1$-$C_7$)-alkyl-aminocarbonyl-($C_1$-$C_7$)-alkyl, ($C_1$-$C_7$)-alkoxycarbonyl-($C_1$-$C_7$)-alkyl, ($C_2$-$C_7$)-alkenyloxycarbonyl-($C_1$-$C_7$)-alkyl, ($C_2$-$C_7$)-alkynyloxycarbonyl-($C_1$-$C_7$)-alkyl, aryl-($C_1$-$C_7$)-alkoxycarbonyl-($C_1$-$C_7$)-alkyl, heteroaryl-($C_1$-$C_7$)-alkoxycarbonyl-($C_1$-$C_7$)-alkyl, heterocyclyl-($C_1$-$C_7$)-alkoxycarbonyl-($C_1$-$C_7$)-alkyl, aryl-($C_1$-$C_7$)-alkoxycarbonyl, heteroaryl-($C_1$-$C_7$)-alkoxycarbonyl, ($C_2$-$C_7$)-alkenyloxycarbonyl, ($C_2$-$C_7$)-alkynyloxycarbonyl, heterocyclyl-($C_1$-$C_7$)-alkyl, or $R^{17}$ and $R^{18}$ together with the nitrogen atom to which they are bonded form a fully saturated or partly saturated 3- to 10-membered monocyclic or bicyclic ring optionally interrupted by heteroatoms and optionally having further substitution;

$R^{19}$ is hydrogen, ($C_1$-$C_7$)-alkyl, ($C_2$-$C_7$)-alkenyl, ($C_2$-$C_7$)-alkinyl, ($C_1$-$C_7$)-cyanoalkyl, ($C_1$-$C_7$)-haloalkyl, ($C_2$-$C_7$)-haloalkenyl, ($C_3$-$C_7$)-haloalkinyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-haloalkoxy-($C_1$-$C_7$)-alkyl, ($C_1$-$C_7$)-alkoxy-($C_1$-$C_7$)-haloalkyl, ($C_1$-$C_7$)-alkoxy-($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkoxy-($C_1$-$C_7$)-alkyl, ($C_1$-$C_7$)-alkoxy-($C_1$-$C_7$)-alkoxy-($C_1$-$C_7$)-alkoxy-($C_1$-$C_7$)-alkoxy-($C_1$-$C_7$)-alkyl, aryl, aryl-($C_1$-$C_7$)-alkyl, aryl-($C_1$-$C_7$)-alkoxy-($C_1$-$C_7$)-alkyl, aryloxy-($C_1$-$C_7$)-alkyl, heteroaryl-($C_1$-$C_7$)-alkoxy-($C_1$-$C_7$)-alkyl, heteroaryloxy-($C_1$-$C_7$)-alkyl, heteroaryl, heteroaryl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, bis-[($C_1$-$C_7$)-alkyl]aminocarbonyl-($C_1$-$C_7$)-alkyl, ($C_1$-$C_7$)-alkyl-aminocarbonyl-($C_1$-$C_7$)-alkyl, aryl-($C_1$-$C_7$)-alkyl-aminocarbonyl-($C_1$-$C_7$)-alkyl, bis-[($C_1$-$C_7$)-alkyl]amino-($C_2$-$C_6$)-alkyl, ($C_1$-$C_7$)-alkyl-amino-($C_2$-$C_6$)-alkyl, aryl-($C_1$-$C_7$)-alkylamino-($C_2$-$C_6$)-alkyl, $R^{20}(O)_mS$-($C_1$-$C_7$)-alkyl, hydroxycarbonyl-($C_1$-$C_7$)-alkyl, heterocyclyl, heterocyclyl-($C_1$-$C_7$)-alkyl, heterocyclyl-($C_1$-$C_7$)-alkoxy-($C_1$-$C_7$)-alkyl, heterocyclyloxy-($C_1$-$C_7$)-alkyl, tris-[($C_1$-$C_7$)-alkyl]silyl-($C_1$-$C_7$)-alkyl, bis-[($C_1$-$C_7$)-alkyl](aryl) silyl ($C_1$-$C_7$)-alkyl, [($C_1$-$C_7$)-alkyl]-bis-(aryl) silyl-($C_1$-$C_7$)-alkyl, ($C_1$-$C_7$)-alkylcarbonyloxy-($C_1$-$C_7$)-alkyl, ($C_3$-$C_7$)-cycloalkylcarbonyloxy-($C_1$-$C_7$)-alkyl, arylcarbonyloxy-($C_1$-$C_7$)-alkyl, heteroarylcarbonyloxy-($C_1$-$C_7$)-alkyl, Heterocyclylcarbonyloxy-($C_1$-$C_7$)-alkyl, ($C_1$-$C_7$)-alkoxycarbonyl, ($C_1$-$C_7$)-alkoxycarbonyl-($C_1$-$C_7$)-alkyl, ($C_2$-$C_7$)-alkenyloxycarbonyl-($C_1$-$C_7$)-alkyl, ($C_2$-$C_7$)-alkynyloxycarbonyl-($C_1$-$C_7$)-alkyl, aryl-($C_1$-$C_7$)-alkoxycarbonyl-($C_1$-$C_7$)-alkyl, heteroaryl-($C_1$-$C_7$)-alkoxycarbonyl-($C_1$-$C_7$)-alkyl, or heterocyclyl-($C_1$-$C_7$)-alkoxycarbonyl-($C_1$-$C_7$)-alkyl; and $R^{20}$ is hydrogen, ($C_1$-$C_7$)-alkyl, ($C_2$-$C_7$)-alkenyl, ($C_2$-$C_7$)-alkynyl, ($C_1$-$C_7$)-cyanoalkyl, ($C_1$-$C_{10}$)-haloalkyl, ($C_2$-$C_7$)-haloalkenyl, ($C_3$-$C_7$)-haloalkynyl, ($C_3$-$C_7$)-cycloalkyl, ($C_3$-$C_7$)-halocycloalkyl, ($C_4$-$C_7$)-cycloalkenyl, ($C_4$-$C_7$)-halocycloalkenyl, ($C_1$-$C_7$)-alkoxy-($C_1$-$C_7$)-alkyl, ($C_1$-$C_7$)-alkoxy-($C_1$-$C_7$)-haloalkyl, aryl, aryl-($C_1$-$C_7$)-alkyl, heteroaryl, heteroaryl-($C_1$-$C_7$)-alkyl, heterocyclyl-($C_1$-$C_7$)-alkyl, ($C_3$-$C_7$)-cycloalkyl-($C_1$-$C_7$)-alkyl, ($C_4$-$C_7$)-cycloalkenyl-($C_1$-$C_7$)-alkyl, bis-[($C_1$-$C_7$)-alkyl]amino, ($C_1$-$C_7$)-alkyl-amino, aryl-($C_1$-$C_7$)-amino, aryl-($C_1$-$C_6$)-alkyl-amino, aryl-[($C_1$-$C_7$)-alkyl]amino; heteroaryl-($C_1$-$C_7$)-amino, heteroaryl-($C_1$-$C_6$)-alkyl-amino, heteroaryl-[($C_1$-$C_7$)-alkyl]amino, heterocyclyl-($C_1$-$C_7$)-amino, heterocyclyl-($C_1$-$C_6$)-alkyl-amino, heterocyclyl-[($C_1$-$C_7$)-alkyl]amino; ($C_3$-$C_7$)-cycloalkyl-amino, ($C_3$-$C_7$)- cycloalkyl-[($C_1$-$C_7$)-alkyl]amino; N-azetidinyl, N-pyrrolidinyl, N-piperidinyl, or N-morpholinyl.

3. A method for controlling unwanted plants or for regulating the growth of plants comprising applying a composition comprising one or more compounds of the general formula (I) and/or salts thereof according to claim 2 or dilution thereof to the plants, seeds of the plants, soil in which or on which the plants grow, and/or an area under cultivation.

4. The compound of the general formula (I) salts thereof according to claim 1, wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen, ($C_1$-$C_6$)-alkyl, ($C_1$-$C_6$)-haloalkyl, ($C_3$-$C_6$)-cycloalkyl, $R^{19}$—O—($C_1$-$C_6$)-alkyl, or heterocyclyl-($C_1$-$C_6$)-alkyl;

$R^2$ and $R^3$ are each independently hydrogen, fluorine, chlorine, bromine, iodine, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, $OR^{19}$, $R^{17}R^{18}$N—($C_1$-$C_6$)-alkyl, ($C_3$-$C_6$)-cycloalkyl-($C_1$-$C_6$)-alkyl, C(═O) $R^{19}$, C(═O) $OR^{19}$, C(═O) $NR^{17}R^{18}$, or $R^{20}$S(O)$_m$—($C_1$-$C_6$)-alkyl;

$R^4$ is hydrogen, ($C_1$-$C_6$)-alkyl, ($C_1$-$C_6$)-haloalkyl, cyano-($C_1$-$C_6$)-alkyl, nitro-($C_1$-$C_6$)-alkyl, ($C_3$-$C_6$)-cycloalkyl, ($C_3$-$C_6$)-cycloalkyl-($C_1$-$C_6$)-alkyl, ($C_2$-$C_6$)-alkenyl, ($C_2$-$C_6$)-alkynyl, ($C_2$-$C_6$)-haloalkenyl, ($C_2$-$C_6$)-haloalkynyl, ($C_3$-$C_6$)-halocycloalkyl, ($C_4$-$C_6$)-cycloalkenyl, ($C_4$-$C_6$)-halocycloalkenyl, aryl-($C_1$-$C_6$)-alkyl, $R^{19}$O—($C_1$-$C_6$)-alkyl, $R^{19}$O—($C_1$-$C_6$)-alkoxy-($C_1$-$C_6$)-alkyl, $R^{20}$S(O)$_m$—($C_1$-$C_6$)-alkyl, $R^{17}R^{18}$N—($C_1$-$C_6$)-alkyl, $R^{19}$% (O)C—($C_1$-$C_6$)-alkyl, $R^{19}$ (O═)C—($C_1$-$C_6$)-Alkyl, $R^{17}R^{18}$N(O)C—($C_1$-$C_6$)-alkyl, heteroaryl-($C_1$-$C_6$)-alkyl, heterocyclyl-($C_1$-$C_6$)-alkyl, aryl, heteroaryl, heterocyclyl, ($C_1$-$C_6$)-alkoxy-($C_1$-$C_6$)-haloalkyl, ($C_1$-$C_6$)-alkylthio-($C_1$-$C_6$)-haloalkyl, or tris-[($C_1$-$C_6$)-alkyl]silyl-($C_1$-$C_6$)-alkyl;

$R^5$, $R^6$, $R^7$ and $R^8$ are each independently hydrogen, fluorine, chlorine, bromine, iodine, ($C_1$-$C_6$)-alkyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, $OR^{19}$, $NR^{17}R^{18}$, $R^{17}R^{18}$N—($C_1$-$C_6$)-alkyl, ($C_3$-$C_6$)-cycloalkyl-($C_1$-$C_6$)-alkyl, C(═O) $R^{19}$, C(═O) $OR^{19}$, C(═O) $NR^{17}R^{18}$, S(O)$_m$$R^{20}$, or $R^{20}$S(O)$_m$—($C_1$-$C_6$)-alkyl;

$R^9$ and $R^{10}$ are each independently hydrogen, ($C_1$-$C_6$)-alkyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, or $R^{19}$O—($C_1$-$C_6$)-alkyl;

$R^{11}$ and $R^{12}$ are each independently fluorine, chlorine, bromine, iodine, cyano, nitro, thiocyanato, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, cyano-($C_1$-$C_6$)-alkyl, ($C_3$-$C_6$)-cycloalkyl-($C_1$-$C_6$)-alkyl, $R^{20}$S(O)$_m$—($C_1$-$C_6$)-alkyl, $R^{17}R^{18}$N—($C_1$-$C_6$)-alkyl, $OR^{19}$, $NR^{17}R^{18}$, S(O)$_m$$R^{20}$, C(═O) $R^{19}$, C(═O) $OR^{19}$, C(═O) $NR^{17}R^{18}$, ($C_1$-$C_6$)-alkoxy-($C_1$-$C_6$)-haloalkyl, or ($C_1$-$C_6$)-alkylthio-($C_1$-$C_6$)-haloalkyl;

m is 0, 1, or 2;

X is O (oxygen), S (sulfur), $NR^{13}$, or a group $CR^{14}R^{15}$;

$R^{13}$ is hydrogen, amino, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_6$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, $R^{19}$O—($C_1$-$C_6$)-alkyl, ($C_3$-$C_6$)-cycloalkyl-($C_1$-$C_6$)-alkyl, $R^{20}$S(O)$_m$—($C_1$-$C_6$)-alkyl, $R^{17}R^{18}$N—($C_1$-$C_6$)-alkyl, $OR^{19}$, NR 17R 18, S(O)$_m$$R^{20}$, C(═O) $R^{19}$, C(═O) $OR^{19}$, C(═O) $NR^{17}R^{18}$, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, heterocyclyl, heterocyclyl-($C_1$-$C_6$)-alkyl, or $R^4$ and $R^{13}$ together with the nitrogen atom to which they are bonded form a fully saturated or partly saturated 3- to 10-membered monocyclic or bicyclic ring optionally interrupted by heteroatoms and optionally having further substitution;

$R^{14}$ and $R^{15}$ are equal or different and each independently ($C_1$-$C_6$)-alkyl, ($C_1$-$C_6$)-haloalkyl, ($C_3$-$C_6$)-cycloalkyl, ($C_3$-$C_6$)-cycloalkyl-($C_1$-$C_6$)-alkyl, aryl, heteroaryl, heterocyclyl, aryl-($C_1$-$C_6$)-alkyl, $R^{19}$—O—($C_1$-$C_6$)-alkyl, heteroaryl-($C_1$-$C_6$)-alkyl, heterocyclyl-($C_1$-$C_6$)-alkyl, C(═O) $R^{19}$, C(═O) $OR^{19}$, C(═O) $NR^{17}R^{18}$, $R^{19}$O(O)C—($C_1$-$C_6$)-alkyl, $R^{19}$ (O═)C—($C_1$-$C_6$)-Alkyl, $R^{17}R^{18}$N(O)C—($C_1$-$C_6$)-alkyl, or cyano-($C_1$-$C_6$)-alkyl, or $R^{14}$ and $R^{15}$ together with the carbon atom to which they are bonded form a fully saturated, or partly saturated 3- to 10-membered monocyclic or bicyclic ring optionally interrupted by heteroatoms and optionally having further substitution, or $R^{14}$ and $R^{15}$ together with the carbon atom to which they are bonded form an unsaturated 5- to 6-membered heteroaromatic or aromatic ring optionally having further substituents:

$R^{16}$ is hydrogen, fluorine, chlorine, bromine, iodine, cyano, nitro, ($C_1$-$C_6$)-alkyl, ($C_2$-$C_6$)-alkenyl, ($C_2$-$C_6$)-alkynyl, ($C_1$-$C_6$)-haloalkyl, ($C_3$-$C_6$)-cycloalkyl, aryl-($C_1$-$C_6$)-alkyl, aryl, heteroaryl, heteroaryl-($C_1$-$C_6$)-alkyl, heterocyclyl, heterocyclyl-($C_1$-$C_6$)-alkyl, $R^{19}$O—($C_1$-$C_6$)-alkyl, ($C_3$-$C_{10}$)-cycloalkyl-($C_1$-$C_6$)-alkyl, $R^{20}$S(O)$_m$—($C_1$-$C_6$)-alkyl, $R^{17}R^{18}$N—($C_1$-$C_8$)-alkyl, $OR^{19}$, $NR^{17}R^{18}$, S(O)$_m$$R^{20}$, C(═O) $R^{19}$, C(═O) $OR^{19}$, C(═O) $NR^{17}R^{18}$, ($C_1$-$C_6$)-alkoxy-($C_1$-$C_6$)-haloalkyl, or ($C_1$-$C_6$)-alkylthio-($C_1$-$C_6$)-haloalkyl;

$R^{17}$ and $R^{18}$ are equal or different and each independently hydrogen, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_6$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkyl, ($C_1$-$C_6$)-haloalkoxy-($C_1$-$C_6$)-alkyl, ($C_1$-$C_6$)-alkylthio-($C_1$-$C_6$)-alkyl, ($C_1$-$C_6$)-haloalkylthio-($C_1$-$C_6$)-alkyl, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, $COR^{19}$, $SO^2R^{20}$, heterocyclyl, ($C_1$-$C_6$)-alkoxycarbonyl, bis-[($C_1$-$C_6$)-alkyl]aminocarbonyl-($C_1$-$C_6$)-alkyl, ($C_1$-$C_6$)-alkyl-aminocarbonyl-($C_1$-$C_6$)-alkyl, aryl-($C_1$-$C_6$)-alkyl-aminocarbonyl-($C_1$-$C_6$)-alkyl, ($C_1$-$C_6$)-alkoxycarbonyl-($C_1$-$C_6$)-alkyl, ($C_2$-$C_6$)-alkenyloxycarbonyl-($C_1$-$C_6$)-alkyl, ($C_2$-$C_6$)-alkynyloxycarbonyl-($C_1$-$C_6$)-alkyl, aryl-($C_1$-$C_6$)-alkoxycarbonyl-($C_1$-$C_6$)-alkyl, heteroaryl-($C_1$-$C_6$)- alkoxycarbonyl-($C_1$-$C_6$)-alkyl, heterocyclyl-($C_1$-$C_6$)-alkoxycarbonyl-($C_1$-$C_6$)-alkyl, aryl-($C_1$-$C_6$)-alkoxycarbonyl, heteroaryl-($C_1$-$C_6$)-alkoxycarbonyl, ($C_2$-$C_6$)-alkenyloxycarbonyl, ($C_2$-$C_6$)-alkynyloxycarbonyl, or heterocyclyl-($C_1$-$C_6$)-alkyl, or $R^{17}$ and $R^{18}$ together with the nitrogen atom to which they are bonded form a fully saturated or partly saturated 3- to 10-membered monocyclic or bicyclic ring optionally interrupted by heteroatoms and optionally having further substitution;

$R^{19}$ is hydrogen, ($C_1$-$C_6$)-alkyl, ($C_2$-$C_6$)-alkenyl, ($C_2$-$C_6$)-alkinyl, ($C_1$-$C_6$)-cyanoalkyl, ($C_1$-$C_6$)-haloalkyl, ($C_2$-$C_6$)-haloalkenyl, ($C_3$-$C_6$)-haloalkinyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-haloalkoxy-($C_1$-$C_6$)-alkyl, ($C_1$-$C_6$)-alkoxy-($C_1$-$C_6$)-haloalkyl, ($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkyl, ($C_1$-$C_6$)-alkoxy-($C_1$-$C_6$)-alkoxy-($C_1$-$C_6$)-alkoxy-($C_1$-$C_6$)-alkoxy-($C_1$-$C_6$)-alkyl, aryl, aryl-($C_1$-$C_6$)-alkyl, aryl-($C_1$-$C_6$)-alkoxy-($C_1$-$C_6$)-alkyl, aryloxy-($C_1$-$C_6$)-alkyl, heteroaryl-($C_1$-$C_6$)-alkoxy-($C_1$-$C_6$)-alkyl, R 19 heteroaryloxy-($C_1$-$C_6$)-alkyl, heteroaryl, heteroaryl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, bis-[($C_1$-$C_6$)-alkyl]aminocarbonyl-($C_1$-$C_6$)-alkyl, ($C_1$-$C_6$)-alkyl-aminocarbonyl-($C_1$-$C_6$)-alkyl, aryl-($C_1$-$C_6$)-alkyl-aminocarbonyl-($C_1$-$C_6$)-alkyl, bis-[($C_1$-$C_6$)-alkyl]amino-($C_2$-$C_6$)-alkyl, ($C_1$-$C_6$)-alkyl-amino-($C_2$-$C_6$)-alkyl, aryl-($C_1$-$C_6$)-alkylamino-($C_2$-$C_6$)-alkyl, $R^{20}(O)_mS$-($C_1$-$C_6$)-alkyl, hydroxycarbonyl-($C_1$-$C_6$)-alkyl, heterocyclyl, heterocyclyl-($C_1$-$C_6$)-alkyl, heterocyclyl-($C_1$-$C_6$)-alkoxy-($C_1$-$C_6$)-alkyl, heterocyclyloxy-($C_1$-$C_6$)-alkyl, tris-[($C_1$-$C_6$)-alkyl]silyl-($C_1$-$C_6$)-alkyl, bis-[($C_1$-$C_6$)-alkyl](aryl) silyl ($C_1$-$C_6$)-alkyl, [($C_1$-$C_6$)-alkyl]-bis-(aryl) silyl-($C_1$-$C_6$)-alkyl, ($C_1$-$C_6$)-alkylcarbonyloxy-($C_1$-$C_6$)-alkyl, ($C_3$-$C_6$)-cycloalkylcarbonyloxy-($C_1$-$C_6$)-alkyl, arylcarbonyloxy-($C_1$-$C_6$)-alkyl, heteroarylcarbonyloxy-($C_1$-$C_6$)-alkyl, Heterocyclylcarbonyloxy-($C_1$-$C_6$)-alkyl, ($C_1$-$C_6$)-alkoxycarbonyl, ($C_1$-$C_6$)-alkoxycarbonyl-($C_1$-$C_6$)-alkyl, ($C_2$-$C_6$)-alkenyloxycarbonyl-($C_1$-$C_6$)-alkyl, ($C_2$-$C_6$)-alkynyloxycarbonyl-($C_1$-$C_6$)-alkyl, aryl-($C_1$-$C_6$)-alkoxycarbonyl-($C_1$-$C_6$)-alkyl, heteroaryl-($C_1$-$C_6$)-alkoxycarbonyl-($C_1$-$C_6$)-alkyl, or heterocyclyl-($C_1$-$C_6$)-alkoxycarbonyl-($C_1$-$C_6$)-alkyl; and is $R^{20}$ hydrogen, ($C_1$-$C_6$)-alkyl, ($C_2$-$C_6$)-alkenyl, ($C_2$-$C_6$)-alkynyl, ($C_1$-$C_6$)-cyanoalkyl, ($C_1$-$C_{10}$)-haloalkyl, ($C_2$-$C_6$)-haloalkenyl, ($C_3$-$C_6$)-haloalkynyl, ($C_3$-$C_6$)-cycloalkyl, ($C_3$-$C_6$)-halocycloalkyl, ($C_4$-$C_6$)-cycloalkenyl, ($C_4$-$C_6$)-halocycloalkenyl, ($C_1$-$C_6$)-alkoxy-($C_1$-$C_6$)-alkyl, ($C_1$-$C_6$)-alkoxy-($C_1$-$C_6$)-haloalkyl, aryl, aryl-($C_1$-$C_6$)-alkyl, heteroaryl, heteroaryl-($C_1$-$C_6$)-alkyl, heterocyclyl-($C_1$-$C_6$)-alkyl, ($C_3$-$C_6$)-cycloalkyl-($C_1$-$C_6$)-alkyl, ($C_4$-$C_6$)-cycloalkenyl-($C_1$-$C_6$)-alkyl, bis-[($C_1$-$C_6$)-alkyl]amino, ($C_1$-$C_6$)-alkyl-amino, aryl-($C_1$-$C_6$)-amino, aryl-($C_1$-$C_6$)-alkyl-amino, aryl-[($C_1$-$C_6$)-alkyl]amino; heteroaryl-($C_1$-$C_6$)-amino, heteroaryl-($C_1$-$C_6$)-alkyl-amino, heteroaryl-[($C_1$-$C_6$)-alkyl]amino; heterocyclyl-($C_1$-$C_6$)-amino, heterocyclyl-($C_1$-$C_6$)-alkyl-amino, heterocyclyl-[($C_1$-$C_6$)-alkyl]amino; ($C_3$-$C_6$)-cycloalkyl-amino, ($C_3$-$C_6$)-cycloalkyl-[($C_1$-$C_6$)-alkyl]amino; N-azetidinyl, N-pyrrolidinyl, N-piperidinyl, or N-morpholinyl.

5. A method for controlling unwanted plants or for regulating the growth of plants comprising applying a composition comprising one or more compounds of the general formula (I) and/or salts thereof according to claim 4 or dilution thereof to the plants, seeds of the plants, soil in which or on which the plants grow, and/or an area under cultivation.

6. The compound of the general formula (I) or salts thereof according to claim 1, wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen, methyl, ethyl, prop-1-yl, prop-2-yl, but-1-yl, difluoromethyl, trifluoromethyl, 2,2-difluoroethyl, 2,2,2-trifluoroethyl, cyclopropyl, cyclobutyl, cyclopentyl, cyclohexyl, methoxymethyl, methoxyethyl, ethoxymethyl, or ethoxyethyl;

$R^2$ and $R^3$ are each independently hydrogen, fluorine, chlorine, bromine, iodine, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl, 1-ethyl-2-methylprop-1-yl, cyclopropylmethyl, cyclobutylmethyl, cyclopentylmethyl, cyclohexylmethyl, ethenyl, prop-1-en-1-yl, prop-2-en-1-yl, 1-methyl-eth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-1-yl, 1-ethylprop-2-en-1-yl, hexen-1-yl, hexen-2-yl, hexen-3-yl, hexen-4-yl, hexen-5-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, cyclopropyl, cyclobutyl, cyclopentyl, cyclohexyl, cyclopropylmethyl, cyclobutylmethyl, cyclopentylmethyl, cyclohexylmethyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, 3,3,3-trifluoro-n-propyl, methoxymethyl, ethoxymethyl, ethoxyethyl, methoxyethyl, methoxy-n-propyl, ethoxy-n-propyl, methoxybutyl, methoxyisopropyl, isopropoxymethyl, isopropoxyethyl, trifluoromethoxymethyl, methoxy, ethoxy, 1-methylethoxy, benzyloxy, methylcarbonyloxy, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 4-Cl-phenyl, 3-Cl-phenyl, 2-Cl-phenyl, methylthiomethyl, trifluoromethylthiomethyl, pyridin-2-yl, pyridin-3-yl, pyridin-4-yl, pyridin-2-ylmethyl, pyridin-3-ylmethyl, pyridin-4-ylmethyl, hydroxycarbonyl, methoxycarbonyl, ethoxycarbonyl, 1-methylethoxycarbonyl, or 1,1-dimethylethoxycarbonyl;

$R^5$, $R^6$, $R^7$ and $R^8$ are each independently hydrogen, fluorine, chlorine, bromine, iodine, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl, 1-ethyl-2-methylprop-1-yl, cyclopropyl, cyclobutyl, cyclopentyl, cyclohexyl, cyclopropylmethyl, cyclobutylmethyl, cyclopentylmethyl, cyclohexylmethyl, difluoromethyl, trifluoromethyl, 2,2-difluoroethyl, 2,2,2-trifluoroethyl, pentafluorethyl, methoxy, ethoxy, trifluoromethoxy, 2,2-difluoroethoxy, 2,2,2-trifluoroethoxy, methoxymethyl, ethoxymethyl, methoxyethyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 4-Cl-phenyl, 3-Cl-phenyl, 2-Cl-phenyl, methylthiomethyl, trifluoromethylthiomethyl, pyridin-2-yl, pyridin-3-yl, pyridin-4-yl, pyridin-2-ylmethyl, pyridin-3-ylmethyl, or pyridin-4-ylmethyl;

$R^9$ and $R^{10}$ are each independently hydrogen, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, cyclopropyl, cyclobutyl, cyclopentyl, cyclohexyl, difluoromethyl, trifluoromethyl, 2,2-difluoroethyl, 2,2,2-trifluoroethyl, pentafluorethyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, thiophen-3-yl, methoxymethyl, ethoxymethyl, methoxyethyl, or ethoxyethyl;

$R^{11}$ and $R^{12}$ are each independently fluorine, chlorine, bromine, iodine, cyano, nitro, thiocyanato, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl, 1-ethyl-2-methylprop-1-yl, cyclopropylmethyl, cyclobutylmethyl, cyclopentylmethyl, cyclohexylmethyl, ethenyl, prop-1-en-1-yl, prop-2-en-1-yl, 1-methyleth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, 1-methylbut-1-en-1-yl, 2-methylbut-1-en-1-yl, 3-methylbut-1-en-1-yl, 1-methylbut-2-en-1-yl, 2-methylbut-2-en-1-yl, 3-methylbut-2-en-1-yl, 1-methylbut-3-en-1-yl, 2-methylbut-3-en-1-yl, 3-methylbut-3-en-1-yl, 1,1-dimethylprop-2-en-1-yl, 1,2-dimethylprop-1-en-1-yl, 1,2-dimethylprop-2-en-1-yl, 1-ethylprop-1-en-1-yl, 1-ethylprop-2-en-1-yl, hexen-1-yl, hexen-2-yl, hexen-3-yl, hexen-4-yl, hexen-5-yl, 1-methylpent-1-en-1-yl, 2-methylpent-1-en-1-yl, 3-methylpent-1-en-1-yl, 4-methylpent-1-en-1-yl, 1-methylpent-2-en-1-yl, 2-methylpent-2-en-1-yl, 3-methylpent-2-en-1-yl, 4-methylpent-2-en-1-yl, 1-methylpent-3-en-1-yl, 2-methylpent-3-en-1-yl, 3-methylpent-3-en-1-yl, 4-methylpent-3-en-1-yl, 1-methylpent-4-en-1-yl, 2-methylpent-4-en-1-yl, 3-methylpent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl- 2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl, methoxymethyl, ethoxymethyl, ethoxyethyl, methoxyethyl, methoxy-n-propyl, ethoxy-n-propyl, methoxy-n-butyl, iso-propoxymethyl, iso-propoxyethyl, trifluoromethyl, pentafluoroethyl, 1,1,2,2-tetrafluoroethyl, heptafluoropropyl, nonafluorobutyl, chlorodifluoromethyl, bromodifluoromethyl, dichlorofluoromethyl, iododifluoromethyl, bromofluoromethyl, 1-fluoroethyl, 2-fluoroethyl, fluoromethyl, difluoromethyl, 2,2-difluoroethyl, 2,2,2-trifluoroethyl, difluoro-tert-butyl, trifluoromethoxymethyl, trifluoromethoxyethyl, trifluoromethoxy-n-propyl, difluoromethoxymethyl, difluoromethoxyethyl, difluoromethoxy-n-propyl, 2,2-difluoroethoxymethyl, 2,2-difluoroethoxyethyl, 2,2-difluoroethoxy-n-propyl, 2,2,2-trifluoroethoxymethyl, 2,2,2-trifluoroethoxyethyl, 2,2,2-trifluoroethoxy-n-propyl, pentafluoroethoxymethyl, pentafluoroethoxyethyl, pentafluoroethoxy-n-propyl, methylthiomethyl, methylthioethyl, ethylthioethyl, methylthio-n-propyl, ethylthio-n-propyl, trifluoromethylthiomethyl, trifluoromethylthioethyl, trifluoromethylthio-n-propyl, methoxymethoxymethyl, methoxyethoxymethyl, methoxyethoxyethyl, methoxymethoxyethyl, ethoxy-n-propoxymethyl, ethoxy-n-propoxyethyl, ethoxyethoxymethyl, ethoxyethoxyethyl, hydroxymethyl, methylcarbonyloxymethyl, hydroxyethyl, hydroxyethoxy, hydroxy, methoxy, ethoxy, 1-methylethoxy, 1,1-dimethylethoxy, benzyloxy, phenoxy, methylcarbonyloxy, hydrothio, methylthio, ethylthio, difluoromethoxy, trifluoromethoxy, 2,2-difluoroethoxy, 2,2,2-trifluoroethoxy, trifluoromethylthio, cyclopropyl, cyclobutyl, cyclopentyl, cyclohexyl, cyclopropylmethyl, cyclobutylmethyl, cyclopentylmethyl, cyclohexylmethyl, 1-methylcycloprop-1-yl, 2-methylcycloprop-1-yl, 2,2-dimethylcycloprop-1-yl, 2,3-dimethylcycloprop-1-yl, 1,1'-bi (cyclopropyl)-1-yl, 1,1'-bi (cyclopropyl)-2-yl, 2'-methyl-1, l'-bi (cyclopropyl)-2-yl, 1-cyanocycloprop-1-yl, 2-cyanocycloprop-1-yl, methylamino, ethylamino, dimethylamino, diethylamino, methyl(ethyl)amino, methoxycarbonylamino, ethoxycarbonylamino, 1,1-dimethylethoxycarbonylamino, N-azetidinyl, N-pyrrolidinyl, N-piperidinyl, N-morpholinyl, dimethylaminomethyl, diethylaminomethyl, hydroxycarbonyl, methoxycarbonyl, ethoxycarbonyl, 1-methylethoxycarbonyl, 1,1-dimethylethoxycarbonyl, aminocarbonyl, methylaminocarbonyl, ethylaminocarbonyl, cyclopropylaminocarbonyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, or thiophen-3-yl;

$R^{16}$ is hydrogen, fluorine, chlorine, bromine, iodine, cyano, nitro, methyl, ethyl, n-propyl, 1-methylethyl, n-butyl, 1-methylprop-1-yl, 2-methylprop-1-yl, 1,1-dimethylethyl, pent-1-yl, 1-methylbut-1-yl, 2-methylbut-1-yl, 3-methylbut-1-yl, 1,1-dimethylprop-1-yl, 1,2-dimethylprop-1-yl, 2,2-dimethylprop-1-yl, 1-ethylprop-1-yl, hex-1-yl, 1-methylpent-1-yl, 2-methylpent-1-yl, 3-methylpent-1-yl, 4-methylpent-1-yl, 1,1-dimethylbut-1-yl, 1,2-dimethylbut-1-yl, 1,3-dimethylbut-1-yl, 2,2-dimethylbut-1-yl, 2,3-dimethylbut-1-yl, 3,3-dimethylbut-1-yl, 1-ethylbut-1-yl, 2-ethylbut-1-yl, 1,1,2-trimethylprop-1-yl, 1,2,2-trimethylprop-1-yl, 1-ethyl-1-methylprop-1-yl, 1-ethyl-2-methylprop-1-yl, cyclopropyl, cyclobutyl, cyclopentyl, cyclohexyl, cyclopropylmethyl, cyclobutylmethyl, cyclopentylmethyl, cyclohexylmethyl, hydroxy, methoxy, ethoxy, 1-methylethoxy, 1,1-dimethylethoxy, benzyloxy, phenoxy, methylcarbonyloxy, hydrothio, methylthio, ethylthio, difluoromethoxy, trifluoromethoxy, 2,2-difluoroethoxy, 2,2,2-trifluoroethoxy, trifluoromethylthio, ethenyl, prop-1-en-1-yl, prop-2-en-1-yl, 1-methyleth-1-en-1-yl, but-1-en-1-yl, but-2-en-1-yl, but-3-en-1-yl, 1-methylprop-1-en-1-yl, 2-methylprop-1-en-1-yl, 1-methylprop-2-en-1-yl, 2-methylprop-2-en-1-yl, pent-1-en-1-yl, pent-2-en-1-yl, pent-3-en-1-yl, pent-4-en-1-yl, ethynyl, prop-1-yn-1-yl, prop-2-yn-1-yl, but-1-yn-1-yl, but-2-yn-1-yl, but-3-yn-1-yl, 1-methyl-2-propynyl, 1-pentynyl, difluoromethyl, trifluoromethyl, 2,2-difluoroethyl, 2,2,2-trifluoroethyl, pentafluoroethyl, methoxymethyl, ethoxymethyl, ethoxyethyl, hydroxymethyl, methylamino, ethylamino, dimethylamino, diethylamino, methyl(ethyl)amino, methoxycarbonylamino, ethoxycarbonylamino, 1,1-dimethylethoxycarbonylamino, N-azetidinyl, N-pyrrolidinyl, N-piperidinyl, N-morpholinyl, dimethylaminomethyl, diethylaminomethyl, hydroxycarbonyl, methoxycarbonyl, ethoxycarbonyl, 1-methylethoxycarbonyl, 1,1-dimethylethoxycarbonyl, aminocarbonyl, methylaminocarbonyl, ethylaminocarbonyl, cyclopropylaminocarbonyl, benzyl, 4-F-benzyl, 3-F-benzyl, 2-F-benzyl, 4-Cl-benzyl, 3-Cl-benzyl, 2-Cl-benzyl, phenyl, 4-F-phenyl, 3-F-phenyl, 2-F-phenyl, 2,3-difluorophenyl, 2-fluoro-3-chlorophenyl, 4-Me-phenyl, 4-Cl-phenyl, 3-Cl-phenyl, 2-Cl-phenyl, pyridin-2-yl, pyridin-3-yl, pyridin-4-yl, pyridin-2-ylmethyl, pyridin-3-ylmethyl, pyridin-4-ylmethyl, thiophen-2-yl, or thiophen-3-yl; and $R^4$—X is OH, (1-methyl-1H-1,2,4-triazol-5-yl)amino, (1-ethyl-1H-1,2,4-triazol-5-yl)amino, (1-methyl-1H-tetrazol-5-yl)amino, (1-ethyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl]amino, [(1R,2R)-1-carboxy-2-methylbutyl] amino, [(1S,2R)-1-carboxy-2-methylbutyl]amino, (5-methoxy-2,5-dioxopentyl)amino, 2-(4-fluorophenoxy) ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl) sulfinylethoxy, butan-2-yloxy, 2-(4-methoxyphenoxy) ethoxy, 2-(benzenesulfonyl) ethoxy, 2-(4-chlorophenoxy) ethoxy, 2-(4-methylphenoxy) ethoxy, 3-methylbutan-2-yloxy, [3-(1H-imidazol-4-yl)-1-methoxy-1-oxopropan-2-yl]amino, [(2R)-3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl]amino, [(1R)-1-carboxy-2-phenylethyl]amino, [(1S)-1-carboxy-2-phenylethyl]amino, [1-carboxy-2-(4-hydroxyphenyl)ethyl]amino, [(1R)-1-carboxy-2-(4-hydroxyphenyl)ethyl]amino, [(1S)-1-carboxy-2-(4-hydroxyphenyl)ethyl]amino, [1-carboxy-2-(4-methoxyphenyl)ethyl]amino, [(1R)-1-carboxy-2-(4-methoxyphenyl)ethyl]amino, [(1S)-1-carboxy-2-(4-methoxyphenyl)ethyl]amino, 2-[(4-methoxyphenyl)thio]ethoxy, 2-[(4-methylphenyl)thio]ethoxy, [1-carboxy-3-methylbutyl]amino, [(1R)-1-carboxy-3-methylbutyl]amino, [(1S)-1-carboxy-3-methylbutyl]amino, (4-methyl-1,2,5-oxadiazol-3-yl)amino, 2-(4-methylphenyl) sulfinylethoxy, [1-(methoxycarbonyl)cyclopropyl]amino, 2-hydroxyethylamino, [3-(1H-imidazol-4-yl)-1-methoxy-1-oxopropan-2-yl]amino, [(2S)-3-(1H-imidazol-4-yl)-1-methoxy-1-oxopropan-2-yl]amino, [(2R)-3-(1H-imidazol-4-yl)-1-methoxy-1-oxopropan-2-yl]amino, [1-carboxy-2-methoxyethyl]amino, [(1R)-1-carboxy-2-methoxyethyl]amino, [(1S)-1-carboxy-2-methoxyethyl]amino, [1-carboxy-2-methylthioethyl]amino, [(1R)-1-carboxy-2-methylthioethyl]amino, [(1S)-1-carboxy-2-methylthioethyl]amino, [1-carboxyethyl]amino, [(1R)-1-carboxyethyl]amino, [(1S)-1-carboxyethyl]amino, [1-carboxy-2-methylpropyl]amino, [(1R)-1-carboxy-2-methylpropyl]amino, [(1S)-1-carboxy-2-methylpropyl]amino, trifluoromethylsulfonylamino, (2-methoxy-2-oxoethyl)-methylamino, 2-(4-methoxyphenyl)sulfonylethoxy, benzylamino, 2-methylpropylamino, amino, 2,2-dimethylhydrazino, hydrazino, prop-2-en-1-ylamino, 2-(4-methoxyphenyl) sulfinylethoxy, 2-phenylethylamino, (6-chloropyridin-3-yl)methyl-methylamino, (4-methoxy-4-oxobutan-2-yl)amino, [(2S)-4-methoxy-4-oxobutan-2-yl)]amino, [(2R)-4-methoxy-4-oxobutan-2-yl)]amino, [2-isopropyl-5-methylcyclohexyl]oxy, [(1S,2R,5S)-2-isopropyl-5-methylcyclohexyl]oxy, [(1S,2R,5R)-2-isopropyl-5-methylcyclohexyl]oxy, [(1R,2R,5S)-2-isopropyl-5-methylcyclohexyl]oxy, [(1R,2R,5R)-2-isopropyl-5-methylcyclohexyl]oxy, [(1S,2S,5S)-2-isopropyl-5-methylcyclohexyl]oxy, [(1S,2S,5R)-2-isopropyl-5-methylcyclohexyl]oxy, [(1R,2S,5S)-2-isopropyl-5-methylcyclohexyl]oxy, [(1R,2S,5R)-2-isopropyl-5-methylcyclohexyl]oxy, 1,2,3,4-tetrahydronaphthalen-1-ylamino, [1-carboxy-2-(1H-indol-3-yl)ethyl]amino, [(1S)-1-carboxy-2-(1H-indol-3-yl)ethyl]amino, [(1R)-1-carboxy-2-(1H-indol-3-yl)ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl) anilino, 2-(3,4-dichlorophenyl)ethylamino, 2,2,2-trifluoroethylsulfonylamino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, ethoxyethylamino, prop-2-yn-1-ylamino, (2-ethylphenyl)methylamino, (1-ethyl-3-methyl-1H-pyrazol-4-yl)methylamino, 3-methylbutylamino, 2-(2-bromophenyl)ethylamino, ethylamino, 2-(3,5-dimethoxyphenyl)ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, [(1R,2R)-2,6-dimethylindan-1-yl]amino, [(1S,2S)-2,6-dimethylindan-1-yl]amino, [(1S,2R)-2,6-dimethylindan-1-yl]amino, 2-(1,3-benzodioxol-5-yl)ethylamino, butan-2-ylamino, 2-(1H-indol-3-yl)ethylamino, propylamino, 2-(2,6-difluorophenyl)ethylamino, 2-(3-methylphenyl)ethylamino, 2-[3-(trifluoromethoxy)phenyl]ethylamino, indan-1-ylamino, quinolin-6-ylmethylamino, [1-tert-butoxy-3-(4-hydroxyphenyl)-1-oxopropan-2-yl]amino, [(2S)-1-tert-butoxy-3-(4-hydroxyphenyl)-1-oxopropan-2-yl]amino, [(2R)-1-tert-butoxy-3-(4-hydroxyphenyl)-1-oxopropan-2-yl]amino, [1-methoxy-3-(4-hydroxyphenyl)-1-oxopropan-2-yl]amino, [(2S)-1-methoxy-3-(4-hydroxyphenyl)-1-oxopropan-2-yl]amino, [(2R)-1-methoxy-3-(4-hydroxyphenyl)-1-oxopropan-2-yl]amino, [1-tert-butoxy-3-phenyl-1-oxopropan-2-yl]amino, [(2S)-1-tert-butoxy-3-phenyl-1-oxopropan-2-yl]amino, [(2R)-1-tert-butoxy-3-phenyl-1-oxopropan-2-yl]amino, [1-methoxy-3-phenyl-1-oxopropan-2-yl]amino, [(2S)-1-methoxy-3-phenyl-1-oxopropan-2-yl]amino, [(2R)-1-methoxy-3-(4-hydroxyphenyl)-1-oxopropan-2-yl]amino, 2-(4-tert-butylphenyl)ethylamino, cyclopropylamino, isopropylamino, 2-(ethoxycarbonyl) piperidin-1-yl, (1-n-propyl-1H-1,2,4-triazol-5-yl)amino, 2-(2-fluorophenyl)ethylamino, (2-methoxy-2-oxoethyl)-methylamino, 2-(ethoxycarbonyl) piperidin-1-yl, benzhydrylamino, N-propylanilino, cyclobutylamino, cyclohexylmethylamino, N-ethylanilino, (2-methoxy-2-oxoethyl)-methylamino, 2-(ethoxycarbonyl) piperidin-1-yl, 3-(diethylamino) propylamino, (2,4-difluorophenyl)methylamino, 2-(5-hydroxy-1H-indol-3-yl)ethylamino, anilino, cyclopentylamino, cyclohexylamino, 2-[3-(trifluoromethyl)phenyl]ethylamino, 2-(diethylamino)ethylamino, isoquinolin-5-ylmethylamino, carboxymethyl(methyl)amino, 2-(4-fluorophenyl)ethylamino, 2-(5-methoxy-1H-indol-3-yl)ethylamino, carboxymethyl(ethyl)amino, 2-[4-(trifluoromethoxy)phenyl]ethylamino, 2-(3-bromophenyl)ethylamino, 2-(2,5-dichlorophenyl)ethylamino, 2-thiophen-2-ylethylamino, 2-(2-methoxyphenyl)ethylamino, 2-(3,4-dimethoxyphenyl)ethylamino, (4-methoxy-4-oxobutyl)amino, 2-(4-chlorophenyl)ethylamino, 2-pyridin-3-ylethylamino, 2-[3-chloro-5-(trifluoromethyl)pyridin-2-yl]ethylamino, cyclopentylsulfonylamino, 2-(4-methoxyphenyl)ethylamino, 2-(3-methoxyphenyl)ethylamino, 2-(2,3-dichlorophenyl)ethylamino, 2-[3,5-bis(trifluoromethyl)phenyl]ethylamino, 2-(4-methylphenyl)ethylamino, 2-(3-chlorophenyl)ethylamino, 2-(2-chlorophenyl)ethylamino, 2-pyridin-2-ylethylamino, 2-(2,4-dichlorophenyl)ethylamino, 2-(3-fluorophenyl)ethylamino, 2,2-difluoroethylamino, 1,3-dimethoxy-1,3-dioxopropan-2-yl, 5-hydroxy-1,3-dimethyl-1H-pyrazol-4-yl, 3,3-dimethyl-2,6-dioxocyclohexyl, 4,4-dimethyl-2,6-dioxocyclohexyl, 4-methyl-2,6-dioxocyclohexyl, 2,5-dioxocyclopentyl, dicyanomethyl, 2,4-dioxo-3-bicyclo[3.2.1]octanyl, 3,3,5,5-tetramethyl-2,4,6-trioxocyclohexyl, 2,6-dioxocyclohexyl, 2,2-dimethyl-4,6-dioxo-1,3-dioxan-5-yl, 5-hydroxy-1-methyl-1H-pyrazol-4-yl, 1-cyano-2-methoxy-2-oxoethyl, 1-methoxy-1,3-dioxobutan-2-yl, 2,4-dioxo-3-bicyclo[3.2.1]oct-6-enyl, phenylsulfonyl, ethoxyethoxy, methoxyethoxyethoxy, hydroxyethoxy, hydroxyethoxyethoxy, hydroxyethoxyethoxyethoxy, cyclopropylmethoxy, cyclobutylmethoxy, cyclopentylmethoxy, cyclohexylmethoxy, cyclopropylmethylamino, cyclobutylmethylamino, cyclopentylmethylamino, cyclohexylmethylamino, oxetan-3-yloxy, oxetan-3-ylamino, tetrahydrofuran-2-yloxy, tetrahydrofuran-3-yloxy, tetrahydrofuran-2-ylmethoxy, tetrahydrofuran-3-ylmethoxy, tetrahydrofuran-2-ylamino, tetrahydrofuran-3-ylamino, tetrahydrofuran-2-ylmethylamino, tetrahydrofuran-3-ylmethylamino, benzyloxy, 4-fluorobenzyloxy, 4-chlorobenzyloxy, 3-fluorobenzyloxy, 3-chlorobenzyloxy, 2-fluorobenzyloxy, 2-chlorobenzyloxy, 4-fluorobenzylamino, 4-chlorobenzylamino, 3-fluorobenzylamino, 3-chlorobenzylamino, 2-fluorobenzylamino, 2-chlorobenzylamino, pyridin-3-ylmethylamino, pyridin-4-ylmethylamino, 4-chloro-pyridin-2-ylmethylamino, 4-chloro-pyridin-3-ylmethylamino, 4-trifluoromethyl-pyridin-3-ylmethylamino, pyridin-2-ylmethoxy, pyridin-3-ylmethoxy, pyridin-4-ylmethoxy, 4-chloro-pyridin-2-ylmethoxy, 4-chloro-pyridin-3-ylmethoxy, cyanomethylamino, cyanomethoxy, cyanoethoxy, hydroxycarbonylmethylamino, hydroxycarbonylmethoxy, hydroxycarbonylethoxy, hydroxycarbonylethylamino, methoxycarbonylmethylamino, ethoxycarbonylmethylamino, azetidin-1-yl-amino, pyrrolidin-1-ylamino, piperidin-1-ylamino, ethylthioethoxy, 1,2,4-thiadiazol-5-ylamino, 5-(difluoromethyl)-1,3,4-thiadiazol-2-ylamino, 5-tert-butyl-1,2-oxazol-3-ylamino, 4-(trifluoromethyl)pyridin-2-ylamino, 5-chloro-4-(trifluoromethyl)pyridin-2-ylamino, (pyridin-4-ylmethoxy)amino, hydroxyamino, methoxyamino, ethoxyamino, benzyloxyamino, methyl(methoxy)amino, methoxycarbonylmethoxyamino, ethoxycarbonylmethoxyamino, methoxycarbonylethoxyamino, ethoxycarbonylethoxyamino, hydroxycarbonylmethoxyamino, hydroxycarbonylethoxyamino, benzyloxycarbonylmethoxyamino, benzyloxycarbonylmethoxyamino, (1,1-dimethyleth-1-yl)oxycarbonylmethoxyamino, or (1,1-dimethyleth-1-yl)oxycarbonylmethoxyamino.

7. A method for controlling unwanted plants or for regulating the growth of plants comprising applying a composition comprising one or more compounds of the general formula (I) and/or salts thereof according to claim 6 or dilution thereof to the plants, seeds of the plants, soil in which or on which the plants grow, and/or an area under cultivation.

8. The compound of the general formula (I) salts thereof according to claim 1, wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen or methyl;

$R^2$ and $R^3$ are each independently hydrogen or methyl;

$R^5$, $R^6$, $R^7$ and $R^8$ are each independently hydrogen, methyl or phenyl;

$R^9$ and $R^{10}$ are each independently hydrogen or methyl;

$R^{11}$ and $R^{12}$ are each independently fluorine, chlorine, bromine, iodine, cyano, methyl, ethyl, 1-methylethyl, trifluoromethyl, difluoromethyl, ethenyl, 1-methylethenyl, ethynyl, hydroxy, methoxy, ethoxy, benzyloxy, phenoxy, methylthio, difluoromethoxy, trifluoromethoxy, trifluoromethylthio, or cyclopropyl;

$R^{16}$ is hydrogen, fluorine, chlorine, bromine, iodine, cyano, methyl, ethyl, 1-methylethyl, hydroxy, methoxy, ethoxy, methylthio, difluoromethoxy, trifluoromethoxy, trifluoromethylthio, ethenyl, 1-methyleth-1-en-1-yl, ethynyl, difluoromethyl, or trifluoromethyl; and $R^4$ is OH, (1-methyl-1H-1,2,4-triazol-5-yl)amino, (1-ethyl-1H-1,2,4-triazol-5-yl)amino, (1-methyl-1H-tetrazol-5-yl)amino, (1-ethyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl]amino, [(1R,2R)-1-carboxy-2-methylbutyl]amino, [(1S,2R)-1-carboxy-2-methylbutyl]amino, (5-methoxy-2,5-dioxopentyl)amino, 2-(4-fluorophenoxy) ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl) sulfinylethoxy, butan-2-yloxy, 2-(4-methoxyphenoxy) ethoxy, 2-(benzenesulfonyl) ethoxy, 2-(4-chlorophenoxy) ethoxy, 2-(4-methylphenoxy) ethoxy, 3-methylbutan-2-yloxy, [3-(1H-imidazol-4-yl)-1-methoxy-1-oxopropan-2-yl]amino, [(2R)-3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl]amino, [(1R)-1-carboxy-2-phenylethyl]amino, [(1S)-1-carboxy-2-phenylethyl]amino, [1-carboxy-2-(4-hydroxyphenyl)ethyl]amino, [(1R)-1-carboxy-2-(4-hydroxyphenyl)ethyl]amino, [(1S)-1-carboxy-2-(4-hydroxyphenyl)ethyl]amino, [1-carboxy-2-(4-methoxyphenyl)ethyl]amino, [(1R)-1-carboxy-2-(4-methoxyphenyl)ethyl]amino, [(1S)-1-carboxy-2-(4-methoxyphenyl)ethyl]amino, 2-[(4-methoxyphenyl) thio]ethoxy, 2-[(4-methylphenyl)thio]ethoxy, [1-carboxy-3-methylbutyl]amino, [(1R)-1-carboxy-3-methylbutyl]amino, [(1S)-1-carboxy-3-methylbutyl] amino, (4-methyl-1,2,5-oxadiazol-3-yl)amino, 2-(4-methylphenyl) sulfinylethoxy, [1-(methoxycarbonyl) cyclopropyl]amino, 2-hydroxyethylamino, [3-(1H-imidazol-4-yl)-1-methoxy-1-oxopropan-2-yl]amino, [(2S)-3-(1H-imidazol-4-yl)-1-methoxy-1-oxopropan-2-yl]amino, [(2R)-3-(1H-imidazol-4-yl)-1-methoxy-1-oxopropan-2-yl]amino, [1-carboxy-2-methoxyethyl] amino, [(1R)-1-carboxy-2-methoxyethyl]amino, [(1S)-1-carboxy-2-methoxyethyl]amino, [1-carboxy-2-methylthioethyl]amino, [(1R)-1-carboxy-2-methylthioethyl]amino, [(1S)-1-carboxy-2-methylthioethyl]amino, [1-carboxyethyl]amino, [(1R)-1-carboxyethyl]amino, [(1S)-1-carboxyethyl]amino, [1-carboxy-2-methylpropyl]amino, [(1R)-1-carboxy-2-methylpropyl]amino, [(1S)-1-carboxy-2-methylpropyl] amino, trifluoromethylsulfonylamino, (2-methoxy-2-oxoethyl)-methylamino, 2-(4-methoxyphenyl) sulfonylethoxy, benzylamino, 2-methylpropylamino, amino, 2,2-dimethylhydrazino, hydrazino, prop-2-en-1-ylamino, 2-(4-methoxyphenyl) sulfinylethoxy, 2-phenylethylamino, (6-chloropyridin-3-yl)methyl-methylamino, (4-methoxy-4-oxobutan-2-yl)amino, [(2S)-4-methoxy-4-oxobutan-2-yl)]amino, [(2R)-4-methoxy-4-oxobutan-2-yl)]amino, [2-isopropyl-5-methylcyclohexyl]oxy, [(1S,2R,5S)-2-isopropyl-5-methylcyclohexyl]oxy, [(1S,2R,5R)-2-isopropyl-5-methylcyclohexyl]oxy, [(1R,2R,5S)-2-isopropyl-5-methylcyclohexyl]oxy, [(1R,2R,5R)-2-isopropyl-5-methylcyclohexyl]oxy, [(1S,2S,5S)-2-isopropyl-5-methylcyclohexyl]oxy, [(1S,2S,5R)-2-isopropyl-5-methylcyclohexyl]oxy, [(1R,2S,5S)-2-isopropyl-5-methylcyclohexyl]oxy, [(1R,2S,5R)-2-isopropyl-5-methylcyclohexyl]oxy, 1,2,3,4-tetrahydronaphthalen-1-ylamino, [1-carboxy-2-(1H-indol-3-yl)ethyl]amino, [(1S)-1-carboxy-2-(1H-indol-3-yl)ethyl]amino, [(1R)-1-carboxy-2-(1H-indol-3-yl)ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl) anilino, 2-(3,4-dichlorophenyl) ethylamino, 2,2,2-trifluoroethylsulfonylamino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, ethoxyethylamino, prop-2-yn-1-ylamino, (2-ethylphenyl)methylamino, (1-ethyl-3-methyl-1H-pyrazol-4-yl)methylamino, 3-methylbutylamino, 2-(2-bromophenyl)ethylamino, ethylamino, 2-(3,5-dimethoxyphenyl)ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, [(1R,2R)-2,6-dimethylindan-1-yl]amino, [(1S,2S)-2,6-dimethylindan-1-yl]amino, [(1S,2R)-2,6-dimethylindan-1-yl]amino, 2-(1,3-benzodioxol-5-yl) ethylamino, butan-2-ylamino, 2-(1H-indol-3-yl) ethylamino, propylamino, 2-(2,6-difluorophenyl) ethylamino, 2-(3-methylphenyl)ethylamino, 2-[3-(trifluoromethoxy)phenyl]ethylamino, indan-1-ylamino, quinolin-6-ylmethylamino, [1-tert-butoxy-3-(4-hydroxyphenyl)-1-oxopropan-2-yl]amino, [(2S)-1-tert-butoxy-3-(4-hydroxyphenyl)-1-oxopropan-2-yl] amino, [(2R)-1-tert-butoxy-3-(4-hydroxyphenyl)-1-oxopropan-2-yl]amino, [1-methoxy-3-(4-hydroxyphenyl)-1-oxopropan-2-yl]amino, [(2S)-1-methoxy-3-(4-hydroxyphenyl)-1-oxopropan-2-yl] amino, [(2R)-1-methoxy-3-(4-hydroxyphenyl)-1-oxopropan-2-yl]amino, [1-tert-butoxy-3-phenyl-1-oxopropan-2-yl]amino, [(2S)-1-tert-butoxy-3-phenyl-1-oxopropan-2-yl]amino, [(2R)-1-tert-butoxy-3-phenyl-1-oxopropan-2-yl]amino, [1-methoxy-3-phenyl-1-oxopropan-2-yl]amino, [(2S)-1-methoxy-3-phenyl-1-oxopropan-2-yl]amino, [(2R)-1-methoxy-3-(4-hydroxyphenyl)-1-oxopropan-2-yl]amino, 2-(4-tert-butylphenyl)ethylamino, cyclopropylamino, isopropylamino, 2-(ethoxycarbonyl) piperidin-1-yl, (1-n-propyl-1H-1,2,4-triazol-5-yl)amino, 2-(2-fluorophenyl)ethylamino, (2-methoxy-2-oxoethyl)-methylamino, 2-(ethoxycarbonyl) piperidin-1-yl, benzhydrylamino, N-propylanilino, cyclobutylamino, cyclohexylmethylamino, N-ethylanilino, (2-methoxy-2-oxoethyl)-methylamino, 2-(ethoxycarbonyl) piperidin-1-yl, 3-(diethylamino) propylamino, (2,4-difluorophenyl)methylamino, 2-(5-hydroxy-1H-indol-3-yl) ethylamino, anilino, cyclopentylamino, cyclohexylamino, 2-[3-(trifluoromethyl)phenyl]ethylamino, 2-(diethylamino)ethylamino, isoquinolin-5-ylmethylamino, carboxymethyl(methyl)amino, 2-(4-fluorophenyl)ethylamino, 2-(5-methoxy-1H-indol-3-yl)ethylamino, carboxymethyl(ethyl)amino, 2-[4-(trifluoromethoxy)phenyl]ethylamino, 2-(3-bromophenyl)ethylamino, 2-(2,5-dichlorophenyl) ethylamino, 2-thiophen-2-ylethylamino, 2-(2-methoxyphenyl)ethylamino, 2-(3,4-dimethoxyphenyl) ethylamino, (4-methoxy-4-oxobutyl)amino, 2-(4-chlorophenyl)ethylamino, 2-pyridin-3-ylethylamino, 2-[3-chloro-5-(trifluoromethyl)pyridin-2-yl]ethylamino, cyclopentylsulfonylamino, 2-(4-methoxyphenyl)ethylamino, 2-(3-methoxyphenyl)ethylamino, 2-(2,3-dichlorophenyl)ethylamino, 2-[3,5-bis (trifluoromethyl)phenyl]ethylamino, 2-(4-methylphenyl)ethylamino, 2-(3-chlorophenyl) ethylamino, 2-(2-chlorophenyl)ethylamino, 2-pyridin-2-ylethylamino, 2-(2,4-dichlorophenyl)ethylamino, 2-(3-fluorophenyl)ethylamino, 2,2-difluoroethylamino, 1,3-dimethoxy-1,3-dioxopropan-2-yl, 5-hydroxy-1,3-dimethyl-1H-pyrazol-4-yl, 3,3-dimethyl-2,6-dioxocyclohexyl, 4,4-dimethyl-2,6-dioxocyclohexyl, 4-methyl-2,6-dioxocyclohexyl, 2,5-dioxocyclopentyl, dicyanomethyl, 2,4-dioxo-3-bicyclo[3.2.1]octanyl, 3,3,5,5-tetramethyl-2,4,6-trioxocyclohexyl, 2,6-dioxocyclohexyl, 2,2-dimethyl-4,6-dioxo-1,3-dioxan-5-yl, 5-hydroxy-1-methyl-1H-pyrazol-4-yl, 1-cyano-2-methoxy-2-oxoethyl, 1-methoxy-1,3-dioxobutan-2-yl, 2,4-dioxo-3-bicyclo[3.2.1]oct-6-enyl, phenylsulfonyl, ethoxyethoxy, methoxyethoxyethoxy, hydroxyethoxy, hydroxyethoxyethoxy, hydroxyethoxyethoxyethoxy, cyclopropylmethoxy, cyclobutylmethoxy, cyclopentylmethoxy, cyclohexylmethoxy, cyclopropylmethylamino, cyclobutylmethylamino, cyclopentylmethylamino, cyclohexylmethylamino, oxetan-3-yloxy, oxetan-3-ylamino, tetrahydrofuran-2-yloxy, tetrahydrofuran-3-yloxy, tetrahydrofuran-2-ylmethoxy, tetrahydrofuran-3-ylmethoxy, tetrahydrofuran-2-ylamino, tetrahydrofuran-3-ylamino, tetrahydrofuran-2-ylmethylamino, tetrahydrofuran-3-ylmethylamino, benzyloxy, 4-fluorobenzyloxy, 4-chlorobenzyloxy, 3-fluorobenzyloxy, 3-chlorobenzyloxy, 2-fluorobenzyloxy, 2-chlorobenzyloxy, 4-fluorobenzylamino, 4-chlorobenzylamino, 3-fluorobenzylamino, 3-chlorobenzylamino, 2-fluorobenzylamino, 2-chlorobenzylamino, pyridin-3-ylmethylamino, pyridin-4-ylmethylamino, 4-chloro-pyridin-2-ylmethylamino, 4-chloro-pyridin-3-ylmethylamino, 4-trifluoromethyl-pyridin-3-ylmethylamino, pyridin-2-ylmethoxy, pyridin-3-ylmethoxy, pyridin-4-ylmethoxy, 4-chloro-pyridin-2-ylmethoxy, 4-chloro-pyridin-3-ylmethoxy, cyanomethylamino, cyanomethoxy, cyanoethoxy, hydroxycarbonylmethylamino, hydroxycarbonylmethoxy, hydroxycarbonylethoxy, hydroxycarbonylethylamino, methoxycarbonylmethylamino, ethoxycarbonylmethylamino, azetidin-1-yl-amino, pyrrolidin-1-ylamino, piperidin, -1-ylamino, ethylthioethoxy, 1,2,4-thiadiazol-5-ylamino, 5-(difluoromethyl)-1,3,4-thiadiazol-2-ylamino, 5-tert-butyl-1,2-oxazol-3-ylamino, 4-(trifluoromethyl)pyridin-2-ylamino, 5-chloro-4-(trifluoromethyl)pyridin-2-ylamino, (pyridin-4-ylmethoxy)amino, hydroxyamino, methoxyamino, ethoxyamino, benzyloxyamino, methyl(methoxy)amino, methoxycarbonylmethoxyamino, ethoxycarbonylmethoxyamino, methoxycarbonylethoxyamino, ethoxycarbonylethoxyamino, hydroxycarbonylmethoxyamino, hydroxycarbonylethoxyamino, benzyloxycarbonylmethoxyamino, benzyloxycarbonylmethoxyamino, (1,1-dimethyleth-1-yl)oxycarbonylmethoxyamino, or (1,1-dimethyleth-1-yl)oxycarbonylmethoxyamino.

9. A method for controlling unwanted plants or for regulating the growth of plants comprising applying a composition comprising one or more compounds of the general formula (I) and/or salts thereof according to claim 8 or dilution thereof to the plants, seeds of the plants, soil in which or on which the plants grow, and/or an area under cultivation.

10. The compound of the general formula (I) salts thereof according to claim 1, wherein:

$A^1$, $A^2$, and $A^3$ are the same or different and each independently N (nitrogen) or the C—$R^{16}$ moiety, with a maximum of two adjacent nitrogen atoms, and where $R^{16}$ in each C—$R^{16}$ moiety is the same or different as defined below;

$R^1$ is hydrogen;

$R^2$ and $R^3$ are each independently hydrogen;

$R^5$, $R^6$, $R^7$ and $R^8$ are each independently hydrogen;

$R^9$ and $R^{10}$ are each independently hydrogen;

$R^{11}$ and $R^{12}$ are each independently fluorine, chlorine, or methyl;

$R^{16}$ is hydrogen, fluorine, chlorine, or methyl; and $R^4$ is-OH, (1-methyl-1H-1,2,4-triazol-5-yl)amino, (1-methyl-1H-tetrazol-5-yl)amino, [1-carboxy-2-methylbutyl]amino, [(1S,2S)-1-carboxy-2-methylbutyl]amino, [(1R,2S)-1-carboxy-2-methylbutyl]amino, [(1R,2R)-1-carboxy-2-methylbutyl]amino, [(1S,2R)-1-carboxy-2-methylbutyl]amino, (5-methoxy-2,5-dioxopentyl)amino, 2-(4-fluorophenoxy) ethoxy; methoxy; 2-methylsulfonylethoxy; 2-methylsulfanylethoxy; methanesulfonamido; 2-carboxypyrrolidin-1-yl, 2-methoxyethoxy, cyclopentyloxy, 2,2-dimethylpropoxy, ethoxy, cyclopropylmethoxy, prop-2-ene-1-yloxy, 2-phenylsulfanylethoxy, prop-2-yne-1-yloxy, cyclobutyloxy, isopropyloxy, but-3-enoxy, 2-phenoxyethoxy, pentan-2-yloxy, 2-(4-chlorophenyl) sulfinylethoxy, butan-2-yloxy, 2-(4-methoxyphenoxy) ethoxy, 2-(benzenesulfonyl) ethoxy, 2-(4-chlorophenoxy) ethoxy, 2-(4-methylphenoxy) ethoxy, 3-methylbutan-2-yloxy, [3-(1H-imidazol-4-yl)-1-methoxy-1-oxopropan-2-yl]amino, [(2S)-3-(1H-imidazol-4-yl)-1-methoxy-1-oxopropan-2-yl]amino, 2-[(4-chlorophenyl)thio]ethoxy, [1-carboxy-2-phenylethyl]amino, [(1R)-1-carboxy-2-phenylethyl]amino, [(1S)-1-carboxy-2-phenylethyl]amino, [1-carboxy-3-methylbutyl]amino, [(1R)-1-carboxy-3-methylbutyl]amino, 2-[(4-methoxyphenyl)thio]ethoxy, 2-[(4-methylphenyl)thio]ethoxy, (4-methyl-1,2,5-oxadiazol-3-yl)amino, 2-(4-methylphenyl) sulfinylethoxy, [1-(methoxycarbonyl)cyclopropyl]amino, 2-hydroxyethylamino, trifluoromethylsulfonylamino, (2-methoxy-2-oxoethyl)-methylamino, 2-(4-methoxyphenyl) sulfonylethoxy, benzylamino, 2-methylpropylamino, amino, 2,2-dimethylhydrazino, hydrazino, prop-2-en-1-ylamino, 2-(4-methoxyphenyl) sulfinylethoxy, 2-phenylethylamino, [1-carboxy-2-(1H-indol-3-yl)ethyl]amino, [(1S)-1-carboxy-2-(1H-indol-3-yl)ethyl]amino, pyrrolidin-1-yl, ethylsulfonylamino, diethylamino, difluoromethylsulfonylamino, isopropylsulfonylamino, pyridin-2-ylmethylamino, quinolin-5-ylmethylamino, 2-(methoxycarbonyl) anilino, dimethylsulfamoylamino, (3-methoxy-3-oxopropyl)amino, (1-ethyl-1H-pyrazol-3-yl)methylamino, cyclopropylsulfonylamino, tert-butoxy, 2,2,2-trifluoroethylamino, 2-methoxyethylamino, prop-2-yn-1-ylamino, ethylamino, N-methylanilino, methylsulfonylazanidyl, (6-chloropyridin-3-yl)methylamino, 2-(2,4-difluorophenyl)ethylamino, methylamino, [2,6-dimethylindan-1-yl]amino, [(1R,2S)-2,6-dimethylindan-1-yl]amino, propylamino, 2-[3-(trifluoromethyl)phenyl]ethylamino, 2-pyridin-2-ylethylamino, 2,2-difluoroethylamino, 1,3-dimethoxy-1,3-dioxopropan-2-yl, 3,3-dimethyl-2,6-dioxocyclohexyl, 4,4-dimethyl-2,6-dioxocyclohexyl, 4-methyl-2,6-dioxocyclohexyl, 3,3,5,5-tetramethyl-2,4,6-trioxocyclohexyl, 2,2-dimethyl-4,6-dioxo-1,3-dioxan-5-yl, pyrrolidin-1-ylamino, piperidin, -1-ylamino, or 1,2,4-thiadiazol-5-ylamino.

11. A method for controlling unwanted plants or for regulating the growth of plants comprising applying a composition comprising one or more compounds of the general formula (I) and/or salts thereof according to claim 10 or dilution thereof to the plants, seeds of the plants, soil in which or on which the plants grow, and/or an area under cultivation.

12. The compound of the general formula (I) or salts thereof according to claim 6, wherein:

$A^1$, $A^2$, and $A^3$ are each independently C—$R^{16}$ where $R^{16}$ in each C—$R^{16}$ moiety is the same or different as defined below;

$R^1$ is hydrogen;

$R^2$ and $R^3$ are each independently hydrogen;

$R^5$, $R^6$, $R^7$ and $R^8$ are each independently hydrogen;

$R^9$ and $R^{10}$ are each independently hydrogen;

$R^{11}$ and $R^{12}$ are each independently fluorine, chlorine, or methyl; and $R^{16}$ is hydrogen, fluorine, chlorine, or methyl.

13. A method for controlling unwanted plants or for regulating the growth of plants comprising applying a composition comprising one or more compounds of the general formula (I) and/or salts thereof according to claim 12 or dilution thereof to the plants, seeds of the plants, soil in which or on which the plants grow, and/or an area under cultivation.

14. A herbicidal and/or plant growth-regulating composition, comprising one or more compounds of the general formula (I) and/or salts thereof according to claim 1, and one or more further substances selected from groups (i) and/or (ii), with (i) one or more further agrochemically active substances, selected from the group consisting of insecticides, acaricides, nematicides, further herbicides, fungicides, safeners, fertilizers and further growth regulators, (ii) one or more crop protection formulation auxiliaries.

15. A method for controlling unwanted plants or for regulating the growth of plants, comprising applying an effective amount of the composition of claim 14, to the plants, seeds of the plants, soil in which or on which the plants grow or an area under cultivation.

16. A herbicidal and/or plant growth-regulating composition, comprising one or more compounds of the general formula (I) and/or salts thereof according to claim 1, and a safener.

17. The herbicidal and/or plant growth-regulating composition of claim 16, wherein the safener comprises at least one compound selected from the group consisting of cloquintocet-mexyl, cyprosulfamide, fenchlorazole-ethyl, isoxadifen-ethyl, mefenpyr-diethyl, fenclorim, and cumyluron.

18. A method for controlling unwanted plants or for regulating the growth of plants, comprising applying an effective amount of the composition of claim 16 to the plants, seeds of the plants, soil in which or on which the plants grow, and/or an area under cultivation.

19. A method for controlling unwanted plants or for regulating the growth of plants, wherein an effective amount of one or more compounds of the general formula (I) and/or salts thereof, according to claim 1, is applied to the plants, seeds of the plants, soil in which or on which the plants grow or an area under cultivation.

20. A method for controlling unwanted plants or for regulating the growth of plants comprising applying a composition comprising one or more compounds of the general formula (I) and/or salts thereof according to claim 1 or dilution thereof to the plants, seeds of the plants, soil in which or on which the plants grow, and/or an area under cultivation.

* * * * *